(12) United States Patent
Chen et al.

(10) Patent No.: US 7,495,007 B2
(45) Date of Patent: Feb. 24, 2009

(54) SPIROINDOLINONE DERIVATIVES

(75) Inventors: Li Chen, Shanghai (CN); Qingjie Ding, Bridgewater, NJ (US); Jin-Jun Liu, Warren Township, NJ (US); Song Yang, Shanghai (CN); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/846,597

(22) Filed: Aug. 29, 2007

(65) Prior Publication Data
US 2008/0009486 A1 Jan. 10, 2008

Related U.S. Application Data

(63) Continuation-in-part of application No. 11/712,883, filed on Mar. 1, 2007, now abandoned.

(60) Provisional application No. 60/881,756, filed on Jan. 22, 2007, provisional application No. 60/781,958, filed on Mar. 13, 2006.

(51) Int. Cl.
*A61K 31/438* (2006.01)
*C07D 471/10* (2006.01)

(52) U.S. Cl. .......................... 514/278; 546/17; 544/62; 544/124; 544/360; 514/228.2; 514/232.8; 514/253

(58) Field of Classification Search ................ 514/278, 514/253, 232.8, 228.2; 546/17; 544/124, 544/360, 62
See application file for complete search history.

(56) References Cited

U.S. PATENT DOCUMENTS 6,774,132 B1 * 8/2004 Claesson et al. ............ 514/278

FOREIGN PATENT DOCUMENTS

WO WO 01/05790 1/2001

OTHER PUBLICATIONS

*J. Amer. Chem. Soc.* (2005) 127 p. 10130.

* cited by examiner

*Primary Examiner*—Charanjit S Aulakh
(74) *Attorney, Agent, or Firm*—George W. Johnston; Patricia S. Rocha-Tramaloni

(57) ABSTRACT

The present invention relates to spiroindolinone derivatives of the formula

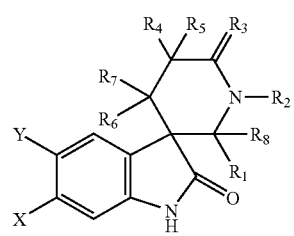

and their enantiomers and pharmaceutically acceptable salts and esters thereof wherein $R_1$, $R_2$, $R_3$, $R_4$, $R_5$, $R_6$, $R_7$ and $R_8$, are as herein described.

The compounds have utility as antiproliferative agents, especially, as anticancer agents.

45 Claims, No Drawings

SPIROINDOLINONE DERIVATIVES

PRIORITY TO RELATED APPLICATIONS

This application is a continuation-in-part of U.S. application Ser. No. 11/712,883, filed Mar. 1, 2007, now pending which claims the benefit of U.S. Provisional Application No. 60/881,756, filed Jan. 22, 2007 and U.S. Provisional Application No. 60/781,958, filed Mar. 13, 2006, which is hereby incorporated by reference in its entirety.

SUMMARY OF THE INVENTION

The present invention relates to spiroindolinone derivatives of the formula

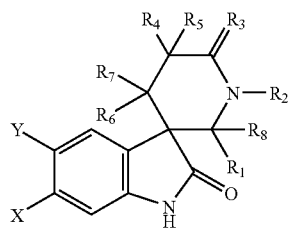

I and pharmaceutically acceptable salts and esters thereof wherein $R_1$, $R_2$, $R_3$, $R_4$, $R_5$, $R_6$, $R_7$ and $R_8$, are as herein described.

The compounds have utility as antiproliferative agents, especially, as anticancer agents.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am. Chem. Soc., 2005, 127, 10130.

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

DETAILED DESCRIPTION OF THE INVENTION

The present invention relates to 3,3'-spiroindolinones of the formula

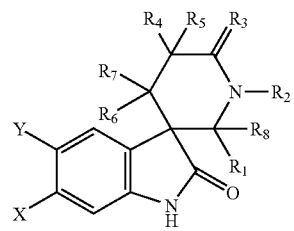

I wherein
X is selected from the group consisting of hydrogen, halogen, cyano, nitro, ethynyl, cyclopropyl, methyl, ethyl, isopropyl, methoxy and vinyl,
Y is hydrogen or fluorine,
$R_4$ and $R_5$ are hydrogen or lower alkyl,
one of $R_1$ and $R_8$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen,
one of $R_6$ and $R_7$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, cyano or lower alkyl,
$R_2$ is selected from the group consisting of hydrogen, lower alkyl and substituted lower alkyl,
$R_3$ is selected from the group consisting of oxygen, sulfur and $NNH(C=O)OR_9$,
$R_9$ is lower alkyl or substituted lower alkyl, and the pharmaceutically acceptable salts and esters thereof.
Preferred are compounds of formula I having a stereochemical structure as shown as formula II

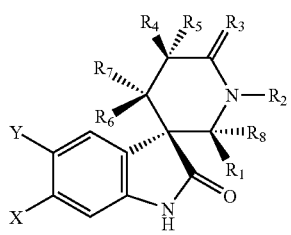

wherein
X is hydrogen, halogen, cyano, nitro, ethynyl, cyclopropyl, methyl, ethyl, isopropyl, methoxy, and vinyl,
Y is hydrogen or fluorine,
$R_1$ is hydrogen,
$R_2$ is hydrogen, lower alkyl or substituted lower alkyl,
$R_4$ and $R_5$ are hydrogen or lower alkyl,
$R_6$ is hydrogen, cyano, or lower alkyl,
$R_3$ is O, S or NNH(C=O)$R_9$,
$R_7/R_8$ is independently selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl,
$R_9$ is lower alkyl or substituted lower alkyl.

Further preferred are compounds of formula II wherein
X is chlorine or bromine,
Y is hydrogen,
$R_1$ is hydrogen,
$R_4$ and $R_5$ are both hydrogen,
$R_6$ is hydrogen,
$R_3$ is O,
$R_7$ is a substituted phenyl or substituted heteroaryl with the substituted phenyl or substituted heteroaryl selected from group consisting of:

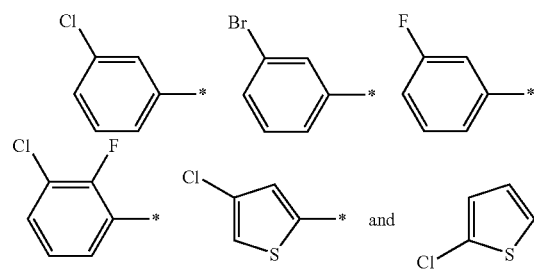

$R_8$ is independently selected from the group consisting of lower alkyl, substituted lower alkyl, lower alkenyl, substituted lower alkenyl, aryl, substituted aryl, heteroaryl, substituted heteroaryl, cycloalkyl, substituted cycloalkyl, cycloalkenyl and substituted cycloalkenyl and
$R_2$ is hydrogen, lower alkyl or substituted lower alkyl,
with the proviso that when $R_2$ is lower alkyl or substituted lower alkyl, $R_8$ is selected from lower alkenyl, substituted lower alkenyl, aryl, substituted aryl, heteroaryl, substituted heteroaryl, cycloalkyl, substituted cycloalkyl, cycloalkenyl or substituted cycloalkenyl.

Also further preferred are compounds of formula II wherein
X is Cl or Br,
Y is hydrogen,
$R_1$ is hydrogen,
$R_4$ and $R_5$ are both hydrogen,
$R_6$ is hydrogen,
$R_3$ is O,
$R_7$ is a substituted phenyl or substituted heteroaryl with the substituted phenyl or substituted heteroaryl selected from group consisting of:

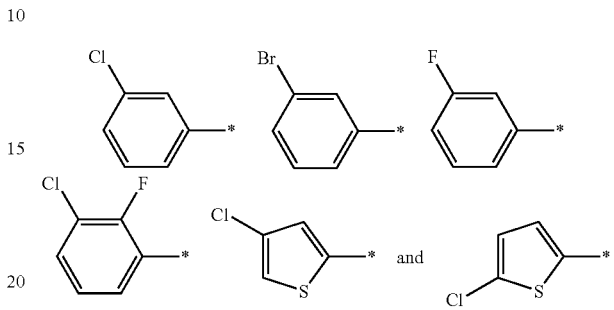

and
$R_8$ is selected from the group consisting of:

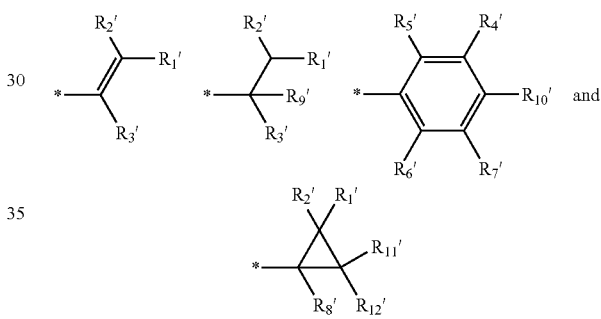

wherein
$R_1'$ is hydrogen, methyl, ethyl, propyl, isopropyl, $CF_3$, F, $CHF_2$, or $CH_2F$,
$R_2'$ is hydrogen, methyl, ethyl, propyl, isopropyl, $CF_3$, F, $CHF_2$, or $CH_2F$,
$R_3'$ is hydrogen, F, $CF_3$, $CH_2F$, methyl, ethyl, propyl, isopropyl, cyclopropyl, tert-butyl or sec-butyl,
$R_4'$ is hydrogen, F, Cl, Br, I, methyl, ethyl, cyclopropyl, cyano, methoxy, or ethynyl,
$R_5'$ is hydrogen, F or methyl,
$R_6'$ is selected from the group consisting of hydrogen, halogen, hydroxy, cyano lower alkyl, substituted lower alkyl, lower alkoxy, substituted lower alkoxy, lower alkynyl, substituted lower alkynyl
$R_7'$ is hydrogen, F or methyl,
$R_8'$ is hydrogen, F, methyl, ethyl, propyl, isopropyl, tert-butyl or sec-butyl,
$R_9'$ is hydrogen, hydroxyl, or F,
$R_{10}'$ is hydrogen or F,
$R_{11}'$ is hydrogen or methyl,
$R_{12}'$ is hydrogen or methyl,
$R_2$ is hydrogen, lower alkyl or substituted lower alkyl
with the proviso that when $R_2$ is lower alkyl or substituted lower alkyl, $R_8$ is selected from:

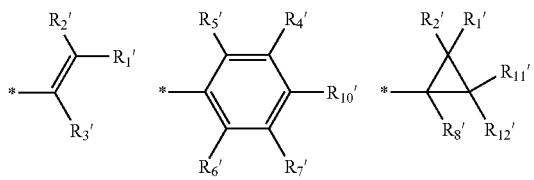

Also preferred are compounds of formula I having a stereochemical structure as shown in structure III

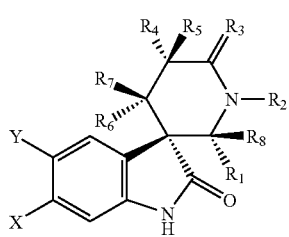

wherein
X is selected from the group consisting of hydrogen, halogen, cyano, nitro, ethynyl, cyclopropyl, methyl, ethyl, isopropyl, methoxy, and vinyl,
Y is hydrogen or fluorine,
$R_1$ is hydrogen,
$R_2$ is hydrogen, lower alkyl or substituted lower alkyl,
$R_4$ and $R_5$ are hydrogen or lower alkyl,
$R_6$ is hydrogen, cyano or lower alkyl,
$R_3$ is O, S or NNH(C=O)$OR_9$,
$R_7$/$R_8$ is independently selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl and
$R_9$ is lower alkyl or substituted lower alkyl.
Further preferred are compounds of formula III wherein
X is Cl or Br,
Y is hydrogen,
$R_1$ is hydrogen,
$R_2$ is hydrogen, lower alkyl or substituted lower alkyl,
$R_4$ and $R_5$ are both hydrogen,
$R_6$ is hydrogen,
$R_3$ is O,
$R_8$ is a substituted phenyl with the substituted phenyl selected from group consisting of

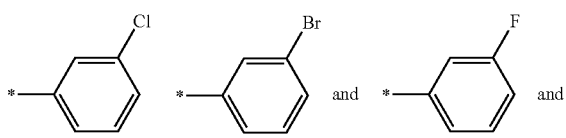

$R_7$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl.

In particular, preferred compounds are those of the formula
racemic (2'S,3S,4'S)-6-chloro-2'-(3-chlorophenyl)-4'-(2,2-dimethylpropyl)spiro[3H-indole-3,3'-piperidine]-2,6'(1H)-dione,
racemic (2'S/R,3S,4'R)-4'-(tert-butyl)-6-chloro-2'-(3-chlorophenyl)spiro[3H-indole-3,3'-piperidine]-2,6'(1H)-dione,
racemic (2'S,3S,4'R)-6-chloro-2'-(3-chlorophenyl)-4'-isopropylspiro[3H-indole-3,3'-piperidine]-2,6'(1H)-dione,
racemic (2'R,3R,4'S)-6-chloro-2',4'-bis(3-chlorophenyl)spiro[3H-indole-3,3'-piperidine]-2,6'(1H)-dione,
chiral (2'R,3R,4'S)-6-chloro-2',4'-bis(3-chlorophenyl)spiro[3H-indole-3,3'-piperidine]-2,6'(1H)-dione,
racemic (2'S,3S,4'R)-6-chloro-2'-(3-chlorophenyl)-4'-cyclopentylspiro[3H-indole-3,3'-piperidine]-2,6'(1H)-dione,
racemic (2'S,3S,4'R)-6-chloro-2'-(3-chlorophenyl)-4'-cyclohexylspiro[3H-indole-3,3'-piperidine]-2,6'(1H)-dione,
racemic (2'S,3S,4'R)-6-chloro-2'-(4-chlorophenyl)-4'-cyclohexylspiro[3H-indole-3,3'-piperidine]-2,6'(1H)-dione,
racemic (2'R,3R,4'S)-6-chloro-2'-(4-chlorophenyl)-4'-(3-chlorophenyl)spiro[3H-indole-3,3'-piperidine]-2,6'(1H)-dione,
racemic (2'S,3S,4'R)-6-chloro-2'-(3-chlorophenyl)-4'-(4-chlorophenyl)spiro[3H-indole-3,3'-piperidine]-2,6'(1H)-dione,
racemic (2'R,3R,4'S)-6-chloro-4'-(3-chlorophenyl)-2'-(3-methylphenyl)spiro[3H-indole-3,3'-piperidine]-2,6'(1H)-dione,
racemic (2'R,3R,4'S)-6-chloro-4'-(3-chlorophenyl)-2'-(3-fluorophenyl)spiro[3H-indole-3,3'-piperidine]-2,6'(1H)-dione,
racemic (2'S,3S,4'R)-6-chloro-2'-(3-chlorophenyl)-4'-phenylspiro[3H-indole-3,3'-piperidine]-2,6'(1H)-dione,
racemic (2'S,3S,4'R,5'R)-6-chloro-2'-(3-chlorophenyl)-5'-methyl-4'-phenylspiro[3H-indole-3,3'-piperidine]-2,6'(1H)-dione,
racemic (2'R,3R,4'S)-6-chloro-4'-(3-chlorophenyl)-2'-phenylspiro[3H-indole-3,3'-piperidine]-2,6'(1H)-dione,
chiral (2'R,3R,4'S)-6-chloro-4'-(3-chlorophenyl)-2'-phenylspiro[3H-indole-3,3'-piperidine]-2,6'(1H)-dione,
racemic (2'R,3R,4'S)-6-chloro-4'-(3-chlorophenyl)-2'-(3-methoxyphenyl)spiro[3H-indole-3,3'-piperidine]-2,6'(1H)-dione,
racemic (2'R,3R,4'S)-6-chloro-2'-(2-chlorophenyl)-4'-(3-chlorophenyl)spiro[3H-indole-3,3'-piperidine]-2,6'(1H)-dione,
chiral (2'R,3R,4'S)-6-chloro-2'-(2-chlorophenyl)-4'-(3-chlorophenyl)spiro[3H-indole-3,3'-piperidine]-2,6'(1H)-dione,
racemic (2'R,3R,4'S)-6-chloro-4'-(3-chlorophenyl)-2'-(2-methylphenyl)spiro[3H-indole-3,3'-piperidine]-2,6'(1H)-dione,
chiral (2'R,3R,4'S)-6-chloro-4'-(3-chlorophenyl)-2'-(2-methylphenyl)spiro[3H-indole-3,3'-piperidine]-2,6'(1H)-dione,
racemic (2'R,3R,4'S)-6-chloro-4'-(3-chlorophenyl)-2'-(2-ethylphenyl)spiro[3H-indole-3,3'-piperidine]-2,6'(1H)-dione,
chiral (2'R,3R,4'S)-6-chloro-4'-(3-chlorophenyl)-2'-(2-ethylphenyl)spiro[3H-indole-3,3'-piperidine]-2,6'(1H)-dione,
racemic (2'R,3R,4'S,5'S)-6-chloro-4'-(3-chlorophenyl)-5'-methyl-2'-(2-methylphenyl)spiro[3H-indole-3,3'-piperidine]-2,6'(1H)-dione,
racemic (2'R,3R,4'S,5'S)-6-chloro-2',4'-bis(3-chlorophenyl)-5'-methylspiro[3H-indole-3,3'-piperidine]-2,6'(1H)-dione, racemic (2'R,3R,4'S)-6-chloro-4'-(3-chlorophenyl)-2'-(2-isopropylphenyl)spiro[3H-indole-3,3'-piperidine]-2,6'(1H)-dione, chiral (2'R,3R,4'S)-6-chloro-4'-(3-chlorophenyl)-2'-(2-isopropylphenyl)spiro[3H-indole-3,3'-piperidine]-2,6'(1H)-dione, racemic (2'R,3R,4'S)-2'-(2-bromophenyl)-6-chloro-4'-(3-chlorophenyl)spiro[3H-indole-3,3'-piperidine]-2,6'(1H)-dione, chiral (2'R,3R,4'S)-2'-(2-bromophenyl)-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-(3-cyanophenyl)spiro[3H-indole-3,3'-piperidine]-2,6'(1H)-dione, racemic (2'R,3R,4'S)-6-chloro-4'-(3-chlorophenyl)-1'-methyl-2'-(2-methylphenyl)spiro[3H-indole-3,3'-piperidine]-2,6'(1H)-dione, chiral (2'R,3R,4'S)-6-chloro-4'-(3-chlorophenyl)-1'-methyl-2'-(2-methylphenyl)spiro[3H-indole-3,3'-piperidine]-2,6'(1H)-dione, racemic (2'R,3R,4'S)-6-chloro-4'-(3-chlorophenyl)-2'-(3-fluoro-2-methyl-phenyl)spiro[3H-indole-3,3'-piperidine]-2,6'(1H)-dione, chiral (2'R,3R,4'S)-6-chloro-4'-(3-chlorophenyl)-2'-(3-fluoro-2-methyl-phenyl)spiro[3H-indole-3,3'-piperidine]-2,6'(1H)-dione, racemic (2'R,3R,4'S)-6-chloro-4'-(3-chlorophenyl)-1'-ethyl-2'-(2-methylphenyl)spiro[3H-indole-3,3'-piperidine]-2,6'(1H)-dione, chiral (2'R,3R,4'S)-6-chloro-4'-(3-chlorophenyl)-1'-ethyl-2'-(2-methylphenyl)spiro[3H-indole-3,3'-piperidine]-2,6'(1H)-dione, racemic (2'R,3R,4'S)-6-chloro-4'-(3-chlorophenyl)-2'-(2,6-dimethylphenyl)spiro[3H-indole-3,3'-piperidine]-2,6'(1H)-dione, racemic (2'R,3R,4'S)-6-chloro-4'-(3-chlorophenyl)-2'-(2,3-dimethylphenyl)spiro[3H-indole-3,3'-piperidine]-2,6'(1H)-dione, racemic (2'R,3R,4'S)-6-chloro-4'-(3-chlorophenyl)-1'-[(methoxycarbonyl)methyl]-2'-(2-methylphenyl)spiro[3H-indole-3,3'-piperidine]-2,6'(1H)-dione, racemic (2'S,3R,4'R)-6-chloro-2'-(3-chlorophenyl)-4'-isopropyl-6'-thioxospiro[3H-indole-3,3'-piperidine]-2(1H)-one, racemic (2'R,3R,4'S)-6-chloro-4'-(3-chlorophenyl)-1'-[(hydroxycarbonyl)-methyl]-2'-(2-methylphenyl)spiro[3H-indole-3,3'-piperidine]-2,6'(1H)-dione, racemic (2'R,3R,4'S)-6-chloro-4'-(3-chlorophenyl)-2'-[2-(trifluoromethyl)-phenyl]spiro[3H-indole-3,3'-piperidine]-2,6'(1H)-dione, racemic (2'R,3R,4'S)-6-chloro-4'-(3-chlorophenyl)-6'-thioxo-2'-[2-(trifluoromethyl)-phenyl]spiro[3H-indole-3,3'-piperidine]-2(1H)-one, racemic (2'R,3R,4'S)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione, chiral (2'R,3R,4'S)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione, racemic (2'R,3R,4'S)-6-chloro-4'-(3-chlorophenyl)-2'-[5-fluoro-2-(trifluoromethyl)-phenyl]spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-1'-[(cyclopropylamino)-carbonyl-methyl]-2'-(2-methylphenyl)spiro[3H-indole-3,3'-piperidine]-2,6'(1H)-dione, racemic (2'R,3R,4'S)-6-chloro-[[2-[6-chloro-4'-(3-chlorophenyl)-2,3-dihydro-2'-(2-methylphenyl)-2,6-dioxospiro[3H-indole-3,3'-piperidin]-1-yl]-1-oxoethyl]-amino]-piperidine carboxylic acid tert-butyl ester, racemic (2'R,3R,4'S)-6-chloro-4'-(3-chlorophenyl)-2'-(5-fluoro-2-methylphenyl)-6'-thioxospiro[3H-indole-3,3'-piperidine]-2(1H)-one, racemic (2'R,3R,4'S)-[6-chloro-4'-(3-chlorophenyl)-2,3-dihydro-2'-[2-(trifluoromethyl)phenyl]]-2-oxospiro[3H-indole-3,3'-piperidin-6-ylene]-hydrazine carboxylic acid ethyl ester, racemic (2'R,3R,4'S)-6-chloro-4'-(3-chlorophenyl)-2'-(2,4-difluorophenyl)spiro[3H-indole-3,3'-piperidine]-2,6'(1H)-dione, racemic (2'R,3R,4'S)-6-chloro-4'-(3-chlorophenyl)-2'-(5-fluoro-2-methoxyphenyl)spiro[3H-indole-3,3'-piperidine]-2,6'(1H)-dione, racemic (2'R,3R,4'S)-6-chloro-4'-(3-chlorophenyl)-2'-(1-naphthalenyl)spiro[3H-indole-3,3'-piperidine]-2,6'(1H)-dione, racemic (2'R,3R,4'S)-6-chloro-4'-(3-chlorophenyl)-2'-(3-pyridinyl)spiro[3H-indole-3,3'-piperidine]-2,6'(1H)-dione, racemic (2'R,3R,4'S)-6-chloro-4'-(3-chlorophenyl)-2'-(2,3-difluoro-6-methoxyphenyl)spiro[3H-indole-3,3'-piperidine]-2,6'(1H)-dione, racemic (2'R,3R,4'S)-6-chloro-4'-(3-chlorophenyl)-2'-(3,4-difluorophenyl)spiro[3H-indole-3,3'-piperidine]-2,6'(1H)-dione, racemic (2'R,3R,4'S)-6-chloro-4'-(3-chlorophenyl)-2'-(1-cyclohexenyl)spiro[3H-indole-3,3'-piperidine]-2,6'(1H)-dione, racemic (2'R,3R,4'S)-6-chloro-4'-(3-chlorophenyl)-2'-(3,4-difluorophenyl)-6'-thioxospiro[3H-indole-3,3'-piperidine]-2(1H)-one, racemic (2'R,3R,4'S)-[6-chloro-4'-(3-chlorophenyl)-2'-(3,4-difluorophenyl)-2,3-dihydro-2-oxospiro[3H-indole-3,3'-piperidin]-6-ylene]hydrazine carboxylic acid ethyl ester, racemic (2'R,3R,4'S)-2'-(1,3-benzodioxol-4-yl)-6-chloro-4'-(3-chlorophenyl)spiro[3H-indole-3,3'-piperidine]-2,6'(1H)-dione, racemic (2'R,3R,4'S)-[6-chloro-4'-(3-chlorophenyl)-2'-(5-fluoro-2-methylphenyl)-2,3-dihydro-2-oxospiro[3H-indole-3,3'-piperidin]-6-ylene]hydrazine carboxylic acid ethyl ester, racemic (2'R,3R,4'S)-6-chloro-4'-(3-chlorophenyl)-2'-(2,3-difluoro-6-methylphenyl)spiro[3H-indole-3,3'-piperidine]-2,6'(1H)-dione, racemic (2'R,3R,4'S)-6-chloro-4'-(3-chlorophenyl)-5-fluoro-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-2'-(2,3-difluoro-6-methylphenyl)-6'-thioxospiro[3H-indole-3,3'-piperidine]-2(1H)-one, racemic (2'R,3R,4'S)-6-chloro-4'-(3-chlorophenyl)-2'-(5-fluoro-2-methylphenyl)-1'-hydroxycarbonylmethylspiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione, racemic (2'R,3R,4'S)-6-chloro-4'-(3-chlorophenyl)-1'-fluorocarbonylmethyl-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione, racemic (2'R,3R,4'S)-1'-[1-tert-butoxycarbonyl-piperidin-4-yl)aminocarbonylmethyl]-6-chloro-4'-(3-chlorophenyl)-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione, racemic (2'R,3R,4'S)-6-chloro-4'-(3-chlorophenyl)-2'-(1-isopropyl-4-methyl-pent-1-enyl)spiro[3H-indole-3,3'-piperidine]-2,6'(1H)-dione, racemic (2'R,3R,4'S)-6-chloro-4'-(3-chlorophenyl)-2'-(2,3-difluoro-6-isopropoxyphenyl)spiro[3H-indole-3,3'-piperidine]-2,6'(1H)-dione, chiral (2'R,3R,4'S)-6-chloro-4'-(3-chlorophenyl)-2'-(2,3-difluoro-6-isopropoxyphenyl)spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-(3-pyrrolidin-1-yl-propyl)spiro[3H-indole-3,3'-piperidine]-2,6'(1H)-dione, racemic (2'R,3R,4'S)-6-chloro-4'-(3-chlorophenyl)-2'-(3-methoxycarbonyl-phenyl)spiro[3H-indole-3,3'-piperidine]-2,6'(1H)-dione, racemic (2'R,3R,4'S)-1'-[3-(4-acetyl-piperazin-1-yl)-propyl]-6-chloro-4'-(3-chlorophenyl)-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-2'-(1-ethyl-propenyl)spiro[3H-indole-3,3'-piperidine]-2,6'(1H)-dione, chiral (2'R,3R,4'S)-6-chloro-4'-(3-chlorophenyl)-2'-(1-ethyl-propenyl)spiro[3H-indole-3,3'-piperidine]-2,6'(1H)-dione, racemic (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione, chiral (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione, racemic (2'R,3R,4'S)-6-chloro-4'-(3-chlorophenyl)-2'-(2,5-dimethyl-phenyl)spiro[3H-indole-3,3'-piperidine]-2,6'(1H)-dione, chiral (2'R,3R,4'S)-6-chloro-4'-(3-chlorophenyl)-2'-(2,5-dimethyl-phenyl)spiro[3H-indole-3,3'-piperidine]-2,6'(1H)-dione, racemic (2'R,3R,4'S)-6-chloro-4'-(3-chlorophenyl)-2'-(2,5-dimethyl-2H-pyrazole-3-yl)spiro[3H-indole-3,3'-piperidine]-2,6'(1H)-dione, racemic (2'R,3R,4'S)-6-chloro-4'-(3-chlorophenyl)-2'-(1-methyl-propenyl)spiro[3H-indole-3,3'-piperidine]-2,6'(1H)-dione, racemic (2'R,3R,4'S)-6-chloro-4'-(3-chlorophenyl)-2'-(1-methyl-but-1-enyl)spiro[3H-indole-3,3'-piperidine]-2,6'(1H)-dione, racemic (2'R,3R,4'S)-6-chloro-4'-(3-chlorophenyl)-2'-(1-ethyl-propyl)spiro[3H-indole-3,3'-piperidine]-2,6'(1H)-dione, chiral (2'R,3R,4'S)-6-chloro-4'-(3-chlorophenyl)-2'-(1-ethyl-propyl)spiro[3H-indole-3,3'-piperidine]-2,6'(1H)-dione, racemic (2'R,3R,4'S)-6-chloro-4'-(3-chlorophenyl)-2'-(2,3-difluoro-6-isopropoxyphenyl)-1'-(3-morpholin-4-yl-propyl)spiro[3H-indole-3,3'-piperidine]-2,6'(1H)-dione, chiral (2'R,3R,4'S)-6-chloro-4'-(3-chlorophenyl)-2'-(2,3-difluoro-6-isopropoxyphenyl)-1'-(3-morpholin-4-yl-propyl)spiro[3H-indole-3,3'-piperidine]-2,6'(1H)-dione, racemic (2'R,3R,4'S)-6-chloro-4'-(3-chlorophenyl)-2'-(1-ethylidene-pentyl)spiro[3H-indole-3,3'-piperidine]-2,6'(1H)-dione, racemic (2'R,3R,4'S)-6-chloro-4'-(3-chlorophenyl)-2'-(2,3-difluoro-6-isopropoxyphenyl)-6'-thioxospiro[3H-indole-3,3'-piperidine]-2(1H)-one, racemic (2'R,3R,4'S)-[6-chloro-4'-(3-chlorophenyl)-2'-(2,3-difluoro-6-isopropoxyphenyl)-2,3-dihydro-2-oxospiro[3H-indole-3,3'-piperidin]-6-ylene]hydrazine carboxylic acid ethyl ester, racemic (2'R,3R,4'S)-6-chloro-4'-(3-chlorophenyl)-2'-(cyclopent-1-enyl)spiro[3H-indole-3,3'-piperidine]-2,6'(1H)-dione, racemic (2'R,3R,4'S)-6-chloro-4'-(3-chlorophenyl)-2'-cyclopentylspiro[3H-indole-3,3'-piperidine]-2,6'(1H)-dione, chiral (2'R,3R,4'S)-6-chloro-4'-(3-chlorophenyl)-2'-cyclopentylspiro[3H-indole-3,3'-piperidine]-2,6'(1H)-dione, racemic (2'R,3R,4'S)-6-chloro-4'-(3-chlorophenyl)-2'-(1-isopropyl-propenyl)spiro[3H-indole-3,3'-piperidine]-2,6'(1H)-dione, chiral (2'R,3R,4'S)-6-chloro-4'-(3-chlorophenyl)-2'-(1-isopropyl-propenyl)spiro[3H-indole-3,3'-piperidine]-2,6'(1H)-dione, racemic (2'R,3R,4'S)-6-chloro-4'-(3-chlorophenyl)-2'-(1-methylene-propyl)spiro[3H-indole-3,3'-piperidine]-2,6'(1H)-dione, chiral (2'R,3R,4'S)-6-chloro-4'-(3-chlorophenyl)-2'-(1-methylene-propyl)spiro[3H-indole-3,3'-piperidine]-2,6'(1H)-dione, racemic (2'R,3R,4'S)-6-chloro-4'-(3-chlorophenyl)-2'-(1-ethyl-propenyl)-1'-hydroxycarbonylmethyl-spiro[3H-indole-3,3'-piperidine]-2,6'(1H)-dione, racemic (2'R,3R,4'S)-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione, chiral (2'R,3R,4'S)-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione, racemic (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione,
chiral (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione,
racemic (2'R,3R,4'S)-6-chloro-4'-(3-chlorophenyl)-2'-(2-methyl-1-methylene-propyl)spiro[3H-indole-3,3'-piperidine]-2,6'(1H)-dione,
racemic (2'R,3R,4'S)-6-chloro-4'-(3-chlorophenyl)-2'-(2,2-dimethyl-1-methylene-propyl)spiro[3H-indole-3,3'-piperidine]-2,6'(1H)-dione,
racemic (2'R,3R,4'S)-6-chloro-4'-(3-chlorophenyl)-2'-(1-ethyl-propenyl)-1'-[(2-morpholin-4-yl-ethyl)aminocarbonyl-methyl]spiro[3H-indole-3,3'-piperidine]-2,6'(1H)-dione,
racemic (2'R,3R,4'S)-6-chloro-4'-(3-chlorophenyl)-2'-isopropenylspiro[3H-indole-3,3'-piperidine]-2,6'(1H)-dione,
chiral (2'R,3R,4'S)-6-chloro-4'-(3-chlorophenyl)-2'-isopropenylspiro[3H-indole-3,3'-piperidine]-2,6'(1H)-dione,
racemic (2'R,3R,4'S)-6-chloro-4'-(3-chlorophenyl)-2'-(1-methylene-butyl)spiro[3H-indole-3,3'-piperidine]-2,6'(1H)-dione,
chiral (2'R,3R,4'S)-6-chloro-4'-(3-chlorophenyl)-2'-(1-methylene-butyl)spiro[3H-indole-3,3'-piperidine]-2,6'(1H)-dione,
racemic (2'R,3R,4'S)-6-chloro-4'-(3-chlorophenyl)-2'-(3-methyl-1-methylene-butyl)spiro[3H-indole-3,3'-piperidine]-2,6'(1H)-dione,
chiral (2'R,3R,4'S)-6-chloro-4'-(3-chlorophenyl)-2'-(3-methyl-1-methylene-butyl)spiro[3H-indole-3,3'-piperidine]-2,6'(1H)-dione,
racemic (2'R,3R,4'S)-6-chloro-4'-(3-chlorophenyl)-2'-(1-methylene-butyl)-6'-thioxospiro[3H-indole-3,3'-piperidine]-2(1H)-one,
racemic (2'R,3R,4'S)-6-chloro-4'-(3-chlorophenyl)-2'-(4-ethoxy-1,2-difluorophenyl)spiro[3H-indole-3,3'-piperidine]-2,6'(1H)-dione,
chiral (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione,
racemic (2'R,3R,4'S)-6-chloro-4'-(3-chloro-5-methoxycarbonyl-phenyl)-2'-(1-methylene-propyl)spiro[3H-indole-3,3'-piperidine]-2,6'(1H)-dione,
racemic (2'R,3R,4'S)-6-chloro-4'-(3-chloro-5-hydroxycarbonyl-phenyl)-2'-(1-methylene-propyl)spiro[3H-indole-3,3'-piperidine]-2,6'(1H)-dione,
racemic (2'R,3R,4'S)-6-chloro-4'-(3-chloro-5-fluorocarbonyl-phenyl)-2'-(1-methylene-propyl)spiro[3H-indole-3,3'-piperidine]-2,6'(1H)-dione,
racemic (2'R,3R,4'S)-6-chloro-4'-[3-chloro-5-(4-methanesulfonyl-piperazine-1-carbonyl)-phenyl]-2'-(1-methylene-propyl)spiro[3H-indole-3,3'-piperidine]-2,6'(1H)-dione,
racemic (2'R,3R,4'S)-6-chloro-4'-(3-chlorophenyl)-2'-(1-ethyl-propenyl)-1'-methylspiro[3H-indole-3,3'-piperidine]-2,6'(1H)-dione,
chiral (2'R,3R,4'S)-6-chloro-4'-(3-chlorophenyl)-2'-(1-ethyl-propenyl)-1'-methylspiro[3H-indole-3,3'-piperidine]-2,6'(1H)-dione,
racemic (2'R,3R,4'S)-6-chloro-4'-(3-chlorophenyl)-2'-isopropylspiro[3H-indole-3,3'-piperidine]-2,6'(1H)-dione,
chiral (2'R,3R,4'S)-6-chloro-4'-(3-chlorophenyl)-2'-isopropylspiro[3H-indole-3,3'-piperidine]-2,6'(1H)-dione,
racemic (2'R,3R,4'S)-6-chloro-4'-(3-chlorophenyl)-2'-(1-methylene-propyl)-1'-methylspiro[3H-indole-3,3'-piperidine]-2,6'(1H)-dione,
chiral (2'R,3R,4'S)-6-chloro-4'-(3-chlorophenyl)-2'-(1-methylene-propyl)-1'-methylspiro[3H-indole-3,3'-piperidine]-2,6'(1H)-dione,
racemic (2'R,3R,4'S)-2'-sec-Butyl-6-chloro-4'-(3-chlorophenyl)spiro[3H-indole-3,3'-piperidine]-2,6'(1H)-dione,
racemic (2'R,3R,4'S)-6-chloro-4'-(3-chlorophenyl)-2'-(1-hydroxymethyl-vinyl)spiro[3H-indole-3,3'-piperidine]-2,6'(1H)-dione,
racemic (2'R,3R,4'S)-6-chloro-4'-(3-chlorophenyl)-2'-(1-methoxymethyl-vinyl)spiro[3H-indole-3,3'-piperidine]-2,6'(1H)-dione,
racemic (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione,
chiral (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione,
racemic (2'R,3R,4'S)-6-chloro-4'-(3-chlorophenyl)-2'-(1,2-dimethyl-propenyl)spiro[3H-indole-3,3'-piperidine]-2,6'(1H)-dione,
racemic (2'R,3R,4'S)-6-chloro-4'-(3-chlorophenyl)-2'-propionylspiro[3H-indole-3,3'-piperidine]-2,6'(1H)-dione,
racemic (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione,
chiral (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione,
racemic (2'R,3R,4'S)-6-chloro-4'-(3-chlorophenyl)-2'-(1-cyclopropyl-vinyl)spiro[3H-indole-3,3'-piperidine]-2,6'(1H)-dione,
racemic (2'R,3R,4'S)-6-chloro-4'-(3-chlorophenyl)-1'-hydroxycarbonylmethyl-2'-(1-methylene-propyl)spiro[3H-indole-3,3'-piperidine]-2,6'(1H)-dione,
racemic (2'R,3R,4'S)-6-chloro-4'-(3-chlorophenyl)-2'-(1-methylene-propyl)-1'-[(1-methanesulfonyl-piperidin-4-yl)aminocarbonyl-methyl]spiro[3H-indole-3,3'-piperidine]-2,6'(1H)-dione,
racemic (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione,
chiral (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione,
racemic (2'R,3R,4'S)-6-chloro-4'-(3-chlorophenyl)-2'-(1-ethyl-2-methyl-propenyl)spiro[3H-indole-3,3'-piperidine]-2,6'(1H)-dione,
racemic (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione,
chiral (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione,
racemic (2'R,3R,4'S)-6-chloro-4'-(3-chlorophenyl)-2'-(2,3-difluoro-6-hydroxy-phenyl)spiro[3H-indole-3,3'-piperidine]-2,6'(1H)-dione,
racemic (2'R,3R,4'S)-6-chloro-4'-(3-chlorophenyl)-2'-(1-ethyl-1-hydroxy-propyl)spiro[3H-indole-3,3'-piperidine]-2,6'(1H)-dione,
racemic (2'R,3R,4'S)-6-chloro-4'-(3-chlorophenyl)-2'-(1-ethyl-3-methyl-oxiranyl)spiro[3H-indole-3,3'-piperidine]-2,6'(1H)-dione,
racemic (2'R,3R,4'S)-6-chloro-4'-(3-chlorophenyl)-2'-(1-fluoro-2-methyl-propenyl)spiro[3H-indole-3,3'-piperidine]-2,6'(1H)-dione,
racemic (2'R,3R,4'S)-6-chloro-4'-(3-chlorophenyl)-2'-isobutyrylspiro[3H-indole-3,3'-piperidine]-2,6'(1H)-dione, racemic (2'R,3R,4'S)-6-chloro-4'-(3-chlorophenyl)-2'-isopropenyl-1'-hydroxycarbonylmethylspiro[3H-indole-3,3'-piperidine]-2,6'(1H)-dione, racemic (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione, racemic (2'R,3R,4'S)-6-chloro-4'-(3-chlorophenyl)-1'-(cyclopropylaminocarbonyl-methyl)-2'-isopropenylspiro[3H-indole-3,3'-piperidine]-2,6'(1H)-dione, racemic (2'R,3R,4'S)-6-chloro-4'-(3-chlorophenyl)-2'-isopropenyl-1'-[(1-methyl-piperidin-4-yl)aminocarbonylmethyl]spiro[3H-indole-3,3' piperidine]-2,6'(1H)-dione, racemic (2'R,3R,4'S)-6-chloro-4'-(3-chlorophenyl)-2'-isopropenyl-1'-[(1-methylsulfonyl-piperidin-4-yl)aminocarbonyl-methyl]spiro[3H-indole-3,3'-piperidine]-2,6'(1H)-dione, racemic (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione, racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione, racemic (2'R,3S,4'R)-6-chloro-4'-(3-chloro-phenyl)-4'-cyano-2'-(1-methylene-propyl)spiro[3H-indole-3,3'-piperidine]-2,6'(1H)-dione, racemic (2'R,3R,4'S)-1'-[3-(4-acetylamino-piperidin-1-yl)-propyl]-6-chloro-4'-(3-chlorophenyl)-2'-isopropenylspiro[3H-indole-3,3' piperidine]-2,6'(1H)-dione, racemic (2'R,3R,4'S)-4'-(3-chloro-phenyl)-6'-cyano-2'-(1-methylene-propyl)spiro[3H-indole-3,3'-piperidine]-2,6'(1H)-dione, racemic (2'R,3R,4'S)-4'-(3-chloro-phenyl)-6-cyano-2'-(5-fluoro-2-methyl-phenyl)spiro[3H-indole-3,3'-piperidine]-2,6'(1H)-dione, racemic (2'R,3R,4'S)-1'-[3-(4-acetyl-piperazin-1-yl)-propyl]-6-chloro-4'-(3-chlorophenyl)-2'-isopropenylspiro[3H-indole-3,3'-piperidine]-2,6'(1H)-dione, racemic (2'R,3R,4'S)-6-chloro-4'-(3-chlorophenyl)-2'-isopropenyl-1'-(3-piperidin-1-yl-propyl)spiro[3H-indole-3,3' piperidine]-2,6'(1H)-dione, racemic (2'R,3R,4'S)-2'-[2-(2-acetoxy-ethoxy)-5-methyl-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[6-(2-hydroxy-ethoxy)-3-methyl-phenyl]spiro[3H-indole-3,3'-piperidine]-2,6'(1H)-dione, racemic (2'R,3R,4'S)-6-chloro-4'-(3-chlorophenyl)-2'-[5-cyclopropyl-2-(2-hydroxy-ethoxy)-phenyl]spiro[3H-indole-3,3'-piperidine]-2,6'(1H)-dione, racemic (2'R,3R,4'S)-6-chloro-2'-[5-chloro-2-(2-hydroxy-ethoxy)-phenyl]-4'-(3-chlorophenyl)spiro[3H-indole-3,3'-piperidine]-2,6'(1H)-dione, racemic (2'R,3R,4'S)-6-chloro-2'-[3-chloro-2-fluoro-6-(2-hydroxy-ethoxy)-phenyl]-4'-(3-chlorophenyl)spiro[3H-indole-3,3'-piperidine]-2,6'(1H)-dione, racemic (2'R,3R,4'S)-6-chloro-4'-(3,5-difluoro-phenyl)-2'-(1-methylene-propyl)spiro[3H-indole-3,3'-piperidine]-2,6'(1H)-dione, racemic (2'R,3R,4'S)-6-chloro-4'-(3-cyano-phenyl)-2'-(1-methylene-propyl)spiro[3H-indole-3,3'-piperidine]-2,6'(1H)-dione, racemic (2'R,3R,4'S)-4'-(3-bromo-phenyl)-6-chloro-2'-(1-methylene-propyl)spiro[3H-indole-3,3'-piperidine]-2,6'(1H)-dione, racemic (2'R,3R,4'S)-6-chloro-4'-(3-methoxy-phenyl)-2'-(1-methylene-propyl)spiro[3H-indole-3,3'-piperidine]-2,6'(1H)-dione, racemic (2'R,3R,4'S)-6-chloro-4'-(5-fluoro-2-methyl-phenyl)-2'-(1-methylene-propyl)spiro[3H-indole-3,3'-piperidine]-2,6'(1H)-dione, racemic (2'R,3R,4'S)-6-chloro-4'-(3-fluoro-phenyl)-2'-(1-methylene-propyl)spiro[3H-indole-3,3'-piperidine]-2,6'(1H)-dione, racemic (2'R,3R,4'S)-6-chloro-2'-(1-methylene-propyl)-4'-m-tolylspiro[3H-indole-3,3'-piperidine]-2,6'(1H)-dione, racemic (2'R,3R,4'S)-6-chloro-2'-(1-methylene-propyl)-4'-o-tolylspiro[3H-indole-3,3'-piperidine]-2,6'(1H)-dione, racemic (2'R,3R,4'R)-6-chloro-2'-(1-methylene-propyl)-4'-thiophen-3-ylspiro[3H-indole-3,3'-piperidine]-2,6'(1H)-dione, racemic (2'R,3R,4'S)-6-chloro-4'-(3,5-dichloro-phenyl)-2'-(1-methylene-propyl)spiro[3H-indole-3,3'-piperidine]-2,6'(1H)-dione, racemic (2'R,3R,4'S)-6-chloro-4'-(5-chloro-2-trifluoromethyl-phenyl)-2'-(1-methylene-propyl)spiro[3H-indole-3,3'-piperidine]-2,6'(1H)-dione, racemic (2'R,3R,4'S)-4'-(3-Bromo-phenyl)-6-chloro-2'-isopropenylspiro[3H-indole-3,3'-piperidine]-2,6'(1H)-dione, racemic (2'S,3S,4'R)-6-chloro-2'-(3-chlorophenyl)-4'-(5-fluoro-2-methyl-phenyl)-spiro[3H-indole-3,3'-piperidine]-2,6'(1H)-dione, racemic (2'S,3S,4'R)-6-chloro-2'-(3-chlorophenyl)-4'-(5-fluoro-2-methyl-phenyl)-1'-hydroxycarbonylmethyl-spiro[3H-indole-3,3'-piperidine]-2,6'(1H)-dione, racemic (2'S,3S,4'R)-6-chloro-2'-(3-chlorophenyl)-4'-(5-fluoro-2-methyl-phenyl)-1'-(methylamino-carbonyl-methyl)spiro[3H-indole-3,3'-piperidine]-2,6'(1H)-dione, racemic (2'S,3S,4'R)-6-chloro-2'-(3-chlorophenyl)-1'-(dimethylamino-carbonyl-methyl)-4'-(5-fluoro-2-methyl-phenyl)-spiro[3H-indole-3,3'-piperidine]-2,6'(1H)-dione, racemic (2'S,3S,4'R)-1'-[(4-aminocarbonyl-piperidin-1-yl) carbonyl-methyl]-6-chloro-2'-(3-chlorophenyl)-4'-(5-fluoro-2-methyl-phenyl)spiro[3H-indole-3,3'-piperidine]-2,6'(1H)-dione, racemic (2'S,3S,4'R)-1'-[(3-aminocarbonyl-piperidin-1-yl) carbonyl-methyl]-6-chloro-2'-(3-chlorophenyl)-4'-(5-fluoro-2-methyl-phenyl)-spiro[3H-indole-3,3'-piperidine]-2,6'(1H)-dione, racemic (2'S,3S,4'R)-1'-(aminocarbonyl-methyl)-6-chloro-2'-(3-chlorophenyl)-4'-(5-fluoro-2-methyl-phenyl)spiro[3H-indole-3,3'-piperidine]-2,6'(1H)-dione, racemic (2'S,3S,4'R)-6-chloro-2'-(3-chlorophenyl)-1'-(dimethylamino-propyl)-4'-(5-fluoro-2-methyl-phenyl)-spiro[3H-indole-3,3'-piperidine]-2,6'(1H)-dione, racemic (2'S,3S,4'R)-6-chloro-4'-(3-chlorophenyl)-2'-(5-fluoro-2-methylphenyl)-1'-[(1-methanesulfonyl-piperidine-4-yl)carbonylamino-ethyl]spiro[3H-indole-3,3'-piperidine]-2,6'(1H)-dione, racemic (2'R,3R,4'R)-6-chloro-4'-[2-(4-chloro-2-thiophenyl)]-2'-(5-fluoro-2-methylphenyl)-spiro[3H-indole-3,3'-piperidine]-2,6'(1H)-dione, racemic (2'R,3R,4'R)-6-chloro-4'-[2-(5-chloro-2-thiophenyl)]-2'-(5-fluoro-2-methylphenyl)-spiro[3H-indole-3,3'-piperidine]-2,6'(1H)-dione, racemic (2'R,3R,4'S)-6-chloro-4'-(2,2-dimethylpropyl)-2'-(5-fluoro-2-methylphenyl)-spiro[3H-indole-3,3'-piperidine]-2,6'(1H)-dione, racemic (2'R,3R,4'S)-6-bromo-4'-(3-chlorophenyl)-2'-(2-methylphenyl)spiro[3H-indole-3,3'-piperidine]-2,6'(1H)-dione, racemic (2'R,3R,4'S)-6-bromo-4'-(3-chlorophenyl)-2'-(5-fluoro-2-methylphenyl)spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)spiro[3H-indole-3,3'-piperidine]-2,6'(1H)-dione, racemic (2'R,3R,4'S)-6-bromo-4'-(3-chlorophenyl)-2'-(2,5-dichlorophenyl)spiro[3H-indole-3,3'-piperidine]-2,6'(1H)-dione, racemic (2'R,3R,4'S)-6-bromo-4'-(3-chlorophenyl)-2'-(5-chloro-2-methylphenyl)spiro[3H-indole-3,3'-piperidine]-2,6'(1H)-dione, racemic (2'R,3R,4'S)-6-bromo-4'-(3-chlorophenyl)-2'-(1-methylene-propyl)-spiro[3H-indole-3,3'-piperidine]-2,6'(1H)-dione, chiral (2'R,3R,4'S)-6-bromo-4'-(3-chlorophenyl)-2'-(1-methylene-propyl)-spiro[3H-indole-3,3'-piperidine]-2,6'(1H)-dione, chiral (2'R,3R,4'S)-6-bromo-4'-(3-chlorophenyl)-2'-(1-ethyl-cyclopropyl)-spiro[3H-indole-3,3'-piperidine]-2,6'(1H)-dione, racemic (2'R,3R,4'S)-6-cyclopropyl-4'-(3-chlorophenyl)-2'-(1-ethyl-cyclopropyl)-spiro[3H-indole-3,3'-piperidine]-2,6'(1H)-dione, racemic (2'R,3R,4'S)-2'-[2-(4-aminocarbonyl-piperidin-1-yl)methyl-5-fluoro-phenyl)-6-chloro-4'-(3-chlorophenyl)-spiro[3H-indole-3,3'-piperidine]-2,6'(1H)-dione, racemic (2'R,3R,4'S)-6-chloro-4'-(3-chlorophenyl)-2'-[5-fluoro-2-(4-methanesulfonyl-piperazin-1-yl)methyl-phenyl]-spiro[3H-indole-3,3'-piperidine]-2,6'(1H)-dione, racemic (2'R,3R,4'S)-6-chloro-4'-(3-chlorophenyl)-2'-{5-fluoro-2-[(1-methanesulfonyl-piperidin-4-yl)carbonylamino-methyl]-phenyl}-spiro[3H-indole-3,3'-piperidine]-2,6'(1H)-dione, chiral (2'R,3R,4'S)-4'-(3-chlorophenyl)-6-fluoro-2'-(5-fluoro-2-methylphenyl)spiro[3H-indole-3,3'-piperidine]-2,6'(1H)-dione, racemic (2'R,3R,4'S)-4'-(3-chlorophenyl)-2'-(5-fluoro-2-methylphenyl)-6-methoxyspiro[3H-indole-3,3'-piperidine]-2,6'(1H)-dione, racemic (2'R,3R,4'S)-4'-(3-chlorophenyl)-2'-(5-fluoro-2-methylphenyl)spiro[3H-indole-3,3'-piperidine]-2,6'(1H)-dione, racemic (2'R,3R,4'S)-4'-(3-chlorophenyl)-5-fluoro-2'-(5-fluoro-2-methylphenyl)spiro[3H-indole-3,3'-piperidine]-2,6'(1H)-dione, chiral (2'R,3R,4'S)-6-chloro-4'-(3-chloro-phenyl)-2'-(1-methyl-cyclopropyl)spiro[3H-indole-3,3'-piperidine]-2,6'(1H)-dione, racemic (2'R,3R,4'S)-6-bromo-4'-(3-chlorophenyl)-2'-isopropenylspiro[3H-indole-3,3'-piperidine]-2,6'(1H)-dione, chiral (2'R,3R,4'S)-6-bromo-4'-(3-chloro-phenyl)-2'-(1-methyl-cyclopropyl)spiro[3H-indole-3,3'-piperidine]-2,6'(1H)-dione, racemic (2'R,3R,4'S)-4'-(3-chlorophenyl)-6-ethynyl-2'-isopropenylspiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-[(1-methylsulphonyl-4-piperidinyl)aminocarbonyl-methyl]spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-{[4-(1,1-dioxido-2-isothiazolidinyl)ethyl]piperazinyl-carbonyl-methyl}spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-{[3-(methylsulphonyl)propyl]piperazinyl-carbonyl-methyl}spiro[3H-indole-3,3'-piperidine]-2,6'(1H)-dione, racemic (2'R,3R,4'S)-2'-(2-bromo-5-fluorophenyl)-6-chloro-4'-(3-chlorophenyl)spiro[3H-indole-3,3'-piperidine]-2,6'(1H)-dione, racemic (2'R,3R,4'S)-2'-6-chloro-4'-(3-chlorophenyl)-(2-ethynyl-5-fluorophenyl)spiro[3H-indole-3,3'-piperidine]-2,6'(1H)-dione, racemic (2'R,3R,4'S)-2'-6-chloro-4'-(3-chlorophenyl)-{5-fluoro-2-[3-(methanesulfonyl-methyl-amino)-prop-1-ynyl-phenyl]spiro[3H-indole-3,3'-piperidine]-2,6'(1H)-dione, racemic (2'R,3R,4'S)-2'-[5-bromo-2-(2-hydroxy-ethoxy)-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione, chiral (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione, racemic (2'R,3R,4'S)-2'-[3-bromo-2-fluoro-6-(2-hydroxy-ethoxy)-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[2-fluoro-6-(2-hydroxy-ethoxy)-3-trimethylsilanylethynyl-phenyl]spiro[3H-indole-3,3'-piperidine]-2,6'(1H)-dione, racemic (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-ethyl-2-(2-hydroxy-ethoxy)-phenyl]spiro[3H-indole-3,3'-piperidine]-2,6'(1H)-dione, chiral (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione, chiral (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione, chiral (2'R,3R,4'S)-6-chloro-4'-(3-chlorophenyl)-1'-(cyclopropylaminocarbonyl-methyl)-2'-isopropenylspiro[3H-indole-3,3'piperidine]-2,6'(1H)-dione, racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione, racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-cyano-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-(3-iodophenyl)spiro[3H-indole-3,3'-piperidine]-2,6'(1H)-dione, racemic (2'R,3R,4'S)-6-chloro-4'-(3-chlorophenyl)-2'-(3-ethynyl-phenyl)spiro[3H-indole-3,3'-piperidine]-2,6'(1H)-dione, racemic (2'R,3R,4'S)-6-chloro-4'-(3-chlorophenyl)-2'-(2-fluoro-5-iodophenyl)spiro[3H-indole-3,3'-piperidine]-2,6'(1H)-dione, racemic (2'R,3R,4'S)-6-chloro-4'-(3-chlorophenyl)-2'-(5-ethynyl-2-fluoro-phenyl)spiro[3H-indole-3,3'-piperidine]-2,6'(1H)-dione, racemic (2'R,3R,4'S)-6-chloro-4'-(3-chlorophenyl)-2'-[2-(2-hydroxy-ethoxy)-5-iodo-3-methoxy-phenyl]spiro[3H-indole-3,3'-piperidine]-2,6'(1H)-dione, racemic (2'R,3R,4'S)-6-chloro-4'-(3-chlorophenyl)-2'-[5-ethynyl-2-(2-hydroxy-ethoxy)-3-methoxy-phenyl]spiro[3H-indole-3,3'-piperidine]-2,6'(1H)-dione, racemic (2'R,3R,4'S)-6-chloro-4'-(3-chlorophenyl)-2'-(5-iodo-2-methylphenyl)spiro[3H-indole-3,3'-piperidine]-2,6'(1H)-dione, racemic (2'R,3R,4'S)-6-chloro-4'-(3-chlorophenyl)-2'-(5-ethynyl-2-methylphenyl)spiro[3H-indole-3,3'-piperidine]-2,6'(1H)-dione, chiral (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-(5-iodo-2-nitrophenyl)spiro[3H-indole-3,3'-piperidine]-2,6'(1H)-dione, racemic (2'R,3R,4'S)-6-chloro-4'-(3-chlorophenyl)-2'-(5-ethynyl-2-nitrophenyl)spiro[3H-indole-3,3'-piperidine]-2,6'(1H)-dione, racemic (2'R,3R,4'S)-2'-(2-amino-5-iodophenyl)-6-chloro-4'-(3-chlorophenyl)spiro[3H-indole-3,3'-piperidine]-2,6'(1H)-dione, racemic (2'R,3R,4'S)-2'-(2-amino-5-ethynylphenyl)-6-chloro-4'-(3-chlorophenyl)spiro[3H-indole-3,3'-piperidine]-2,6'(1H)-dione, racemic (2'R,3R,4'S)-2'-(3-bromo-4-fluoro-phenyl)-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-(3-ethynyl-4-fluoro-phenyl)spiro[3H-indole-3,3'-piperidine]-2,6'(1H)-dione, racemic (2'R,3R,4'S)-2'-(1-benzofuran-5-yl)-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-(5-chloro-2-iodophenyl)spiro[3H-indole-3,3'-piperidine]-2,6'(1H)-dione, racemic (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione, chiral (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione, racemic (2'R,3R,4'S)-6-chloro-4'-(3-chlorophenyl)-2'-[5-(3,3-dimethyl-1-butynyl)-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-(3-cyclopropyl-1-butynyl)-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-(3-methyl-1-butynyl)-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[2-(2-hydroxy-ethoxy)-5-vinyl-phenyl]spiro[3H-indole-3,3'-piperidine]-2,6'(1H)-dione, racemic (2'R,3R,4'S)-6-chloro-4'-(3-chlorophenyl)-2'-[5-ethynyl-2-hydroxy-phenyl]spiro[3H-indole-3,3'-piperidine]-2,6'-dione, chiral (2'R,3R,4'S)-6-chloro-4'-(3-chlorophenyl)-2'-[5-ethynyl-2-hydroxy-phenyl]spiro[3H-indole-3,3'-piperidine]-2,6'-dione, racemic (2'R,3R,4'S)-6-chloro-4'-(3-chlorophenyl)-2'-[5-ethynyl-2-(2,3-dihydroxy-propoxy)-phenyl]-spiro[3H-indole-3,3'-piperidine]-2,6'(1H)-dione, racemic (2'R,3R,4'S)-2'-[5-bromo-2-methylsulfanyl-phenyl]-6-chloro-4'-(3-chlorophenyl)spiro[3H-indole-3,3'-piperidine]-2,6'-dione, racemic (2'R,3R,4'S)-2'-[5-bromo-2-methylsulfonyl-phenyl]-6-chloro-4'-(3-chlorophenyl)spiro[3H-indole-3,3'-piperidine]-2,6'-dione, racemic (2'R,3R,4'S)-6-chloro-4'-(3-chlorophenyl)-2'-[5-ethynyl-2-methylsulfonyl-phenyl]spiro[3H-indole-3,3'-piperidine]-2,6'-dione, racemic (2'R,3R,4'S)-2'-[5-bromo-2-methoxy-phenyl]-6-chloro-4'-(3-chlorophenyl)spiro[3H-indole-3,3'-piperidine]-2,6'-dione, racemic (2'R,3R,4'S)-6-chloro-4'-(3-chlorophenyl)-2'-[5-ethynyl-2-methoxy-phenyl]-spiro[3H-indole-3,3'-piperidine]-2,6'-dione, chiral (2'R,3R,4'S)-6-chloro-4'-(3-chlorophenyl)-2'-[2-(2-hydroxy-ethoxy)-5-(3-trifluoroprop-1-ynyl)-phenyl]spiro[3H-indole-3,3'-piperidine]-2,6'-dione, racemic (2'R,3R,4'S)-6-chloro-4'-(3-chlorophenyl)-2'-{5-ethynyl-2-[2-(1-piperidinyl)-ethoxy]-phenyl}spiro[3H-indole-3,3'-piperidine]-2,6'-dione, racemic (2'R,3R,4'S)-2'-[2-(2-azido-ethoxy)-5-ethynyl-phenyl]-6-chloro-4'-(3-chlorophenyl)spiro[3H-indole-3,3'-piperidine]-2,6'-dione, racemic (2'R,3R,4'S)-2'-[2-(2-aminoethyl)-5-ethynyl-phenyl]-6-chloro-4'-(3-chlorophenyl)spiro[3H-indole-3,3'-piperidine]-2,6'-dione, racemic (2'R,3R,4'S)-1'-(aminocarbonyl-methyl)-6-bromo-4'-(3-chlorophenyl)-2'-(1-methylene-propyl)spiro[3H-indole-3,3'-piperidine]-2,6'(1H)-dione, chiral (2'R,3R,4'S)-1'-(aminocarbonyl-methyl)-6-bromo-4'-(3-chlorophenyl)-2'-(1-methylene-propyl)-spiro[3H-indole-3,3'-piperidine]-2,6'(1H)-dione, racemic (2'R,3R,4'S)-6-chloro-4'-(3-chloro-phenyl)-2'-((R)-2,2-difluoro-1-methyl-cyclopropyl)spiro[3H-indole-3,3'-piperidine]-2,6'(1H)-dione, racemic (2'R,3R,4'S)-6-chloro-4'-(3-chloro-phenyl)-2'-((S)-2,2-difluoro-1-methyl-cyclopropyl)spiro[3H-indole-3,3'-piperidine]-2,6'(1H)-dione, racemic (2'R,3R,4'S)-6-chloro-4'-(5-chloro-2-isopropoxy-phenyl)-2'-isopropenylspiro[3H-indole-3,3'-piperidine]-2,6'(1H)-dione, racemic (2'S,3S,4'R)-6-chloro-4'-[5-chloro-2-(2-hydroxy-ethoxy)-phenyl]-2'-[5-fluoro-2-methyl-phenyl]spiro[3H-indole-3,3'-piperidine]-2,6'(1H)-dione, chiral (2'S,3S,4'R)-6-chloro-4'-[5-chloro-2-(2-hydroxy-ethoxy)-phenyl]-2'-[5-fluoro-2-methylphenyl]spiro[3H-indole-3,3'-piperidine]-2,6'(1H)-dione, racemic (2'S,3S,4'R)-6-chloro-4'-[5-chloro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione, racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2-hydroxy-1,1-dimethyl-ethoxy)-phenyl]-2'-[5-fluoro-2-methylphenyl]spiro[3H-indole-3,3'-piperidine]-2,6'(1H)-dione, racemic (2'R,3R,4'S)-2'-[5-bromo-2-(2,2,2-trifluoro-ethoxy)phenyl]-6-chloro-4'-(3-chlorophenylspiro[3H-indole-3,3'-piperidine]-2,6'(1H)-dione, racemic (2'R,3R,4'S)-6-chloro-4'-(5-chloro-2-methoxycarbonylmethoxy-phenyl)-2'-isopropenylspiro[3H-indole-3,3'-piperidine]-2,6'(1H)-dione, racemic (2'R,3R,4'S)-6-chloro-4'-(5-chloro-2-hydroxycarbonylmethoxy-phenyl)-2'-isopropenylspiro[3H-indole-3,3'-piperidine]-2,6'(1H)-dione, racemic (2'R,3S,4'R)-6-chloro-4'-[5-chloro-2-(1-ethoxycarbonyl-1-methyl-ethoxy)-phenyl]-2'-(2,5-difluoro phenyl)spiro[3H-indole-3,3'-piperidine]-2,6'(1H)-dione, racemic (2'R,3S,4'R)-6-chloro-4'-[5-chloro-2-(1-hydroxycarbonyl-1-methyl-ethoxy)-phenyl]-2'-(2,5-difluoro phenyl)spiro[3H-indole-3,3'-piperidine]-2,6'(1H)-dione, racemic (2'R,3S,4'R)-6-chloro-4'-[5-chloro-2-(2-hydroxy-1,1-dimethyl-ethoxy)-phenyl]-2'-(2,5-difluorophenyl)spiro[3H-indole-3,3'-piperidine]-2,6'(1H)-dione, racemic (2'R,3S,4'R)-4'-[5-bromo-2-(2-methoxycarbonyl-2-methyl-propoxy)-phenyl]-6-chloro 2'-(2,5-dichlorophenyl)spiro[3H-indole-3,3'-piperidine]-2,6'(1H)-dione, racemic (2'R,3S,4'R)-4'-[5-bromo-2-(3-hydroxy-2,2-dimethyl-propoxy)-phenyl]-6-chloro-2'-(2,5-dichlorophenyl)spiro[3H-indole-3,3'-piperidine]-2,6'(1H)-dione, racemic (2'S,3S,4'R)-4'-[5-bromo-2-(2-methoxycarbonyl-2-methyl-propoxy)-phenyl]-6-chloro-2'-(5-fluoro-2-methyl phenyl)spiro[3H-indole-3,3'-piperidine]-2,6'(1H)-dione, racemic (2'S,3S,4'R)-4'-[5-bromo-2-(3-hydroxy-2,2-dimethyl-propoxy)phenyl]-6-chloro-2'-(5-fluoro-2-methyl phenyl)spiro[3H-indole-3,3'-piperidine]-2,6'(1H)-dione, racemic (2'R,3S,4'R)-4'-[5-bromo-2-(2-ethoxycarbonyl-2-methyl-ethoxy)-phenyl]-6-chloro-2'-(2,5-dichloro phenyl)spiro[3H-indole-3,3'-piperidine]-2,6'(1H)-dione, racemic (2'R,3S,4'R)-4'-[5-bromo-2-(2-hydroxycarbonyl-2-methyl-ethoxy)-phenyl]-6-chloro-2'-(2,5-dichloro phenyl)spiro[3H-indole-3,3'-piperidine]-2,6'(1H)-dione, racemic (2'R,3R,4'S)-2'-[5-bromo-2-(2-methoxycarbonyl-2-methyl-propoxy)-phenyl]-6-chloro-4'-(2,5-dichlorophenyl)spiro[3H-indole-3,3'-piperidine]-2,6'(1H)-dione, racemic (2'R,3R,4'S)-2'-[5-bromo-2-(2,2-dimethyl-3-hydroxy propoxy)-phenyl]-6-chloro-4'-(2,5-dichlorophenyl)spiro[3H-indole-3,3'-piperidine]-2,6'(1H)-dione, racemic (2'R,3R,4'S) 4'-[2-(2-amino-ethoxy)-5-chloro-phenyl]-6-chloro-2'-(5-fluoro-2-methyl-phenyl)spiro[3H-indole-3,3'-piperidine]-2,6'(1H)-dione, racemic (2'R,3R,4'S)-4'-(3-chlorophenyl)-6-cyclopropyl-2'-isopropenylspiro[3H-indole-3,3'-piperidine]-2,6'(1H)-dione, chiral (2'R,3R,4'S)-6-chloro-4'-(5-chloro-3-pyridinyl)-2'-isopropenylspiro[3H-indole-3,3'-piperidine]-2,6'(1H)-dione, racemic (2'R,3R,4'S)-6-chloro-4'-(5-chloro-2-nitro-phenyl)-2'-isopropenylspiro[3H-indole-3,3'-piperidine]-2,6'(1H)-dione, racemic (2'R,3R,4'S)-4'-(2-amino-5-chloro-phenyl)-6-chloro-2'-isopropenylspiro[3H-indole-3,3'-piperidine]-2,6'(1H)-dione, racemic (2'R,3R,4'S)-4'-(2-acetylamino-5-chloro-phenyl)-6-chloro-2'-isopropenylspiro[3H-indole-3,3'-piperidine]-2,6'(1H)-dione, racemic (2'R,3R,4'S)-6-chloro-4'-(5-chloro-2-methanesulfonylamino-phenyl)-2'-isopropenylspiro[3H-indole-3,3'-piperidine]-2,6'(1H)-dione, racemic (2'R,3R,4'S)-6-chloro-4'-(5-chloro-2-iodophenyl)-2'-(5-fluoro-2-methylphenyl)spiro[3H-indole-3,3'-piperidine]-2,6'(1H)-dione, racemic (2'S,3S,4'R)-6-chloro-4'-[5-chloro-2-(3-hydroxy-2,2-dimethyl-propoxy)-phenyl]-2'-(5-fluoro-2-methyl phenyl)-spiro[3H-indole-3,3'-piperidine]-2,6'(1H)-dione, racemic (2'S,3S,4'R)-6-chloro-4'-(5-chloro-2-(2,2,2-trifluoro-ethoxy)hydroxy-phenyl)-2'-(5-fluoro-2-methylphenyl)spiro[3H-indole-3,3'-piperidine]-2,6'(1H)-dione, racemic (2'S,3S,4'R)-6-chloro-4'-[5-chloro-2-(2-methoxycarbonyl-2-methyl-propoxy)-phenyl]-2'-(5-fluoro-2-methylphenyl)spiro[3H-indole-3,3'-piperidine]-2,6'(1H)-dione, racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione, chiral (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione, racemic (2'R,3R,4'S)-6-chloro-4'-[5-chloro-2-(3-hydroxypropoxyl)-phenyl]-2'-[5-fluoro-2-methylphenyl]spiro[3H-indole-3,3'-piperidine]-2,6'(1H)-dione, racemic (2'R,3S,4'R)-6-chloro-4'-[5-chloro-2-(2-methoxycarbonyl-methoxy)-phenyl]-2'-(2,5-difluorophenyl)spiro[3H-indole-3,3'-piperidine]-2,6'(1H)-dione, racemic (2'R,3S,4'R)-6-chloro-4'-[5-chloro-2-(2-hydroxycarbonyl-methoxy)-phenyl]-2'-(2,5-difluorophenyl)spiro[3H-indole-3,3'-piperidine]-2,6'(1H)-dione, racemic (2'R,3R,4'S)-2'-[5-bromo-2-(2-methoxycarbonyl-2-methyl-propoxy)-phenyl]-6-chloro-4'-(5-chloro-2-methyl-phenyl)spiro[3H-indole-3,3'-piperidine]-2,6'(1H)-dione, racemic (2'R,3R,4'S)-2'-[5-bromo-2-(2-hydroxycarbonyl-2-methyl-propoxy)-phenyl]-6-chloro-4'-(5-chloro-2-methyl-phenyl)spiro[3H-indole-3,3'-piperidine]-2,6'(1H)-dione, racemic (2'S,3S,4'R)-4'-[5-bromo-2-(1-ethoxycarbonyl-1-methyl-ethoxy)-phenyl]-6-chloro-2'-(5-chloro-2-methyl-phenyl)spiro[3H-indole-3,3'-piperidine]-2,6'(1H)-dione, racemic (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione, racemic (2'R,3R,4'S)-2'-[5-bromo-2-(3-hydroxy-2,2-dimethyl-propoxy)-phenyl]-6-chloro-4'-(5-chloro-2-methyl-phenyl)spiro[3H-indole-3,3'-piperidine]-2,6'(1H)-dione, chiral (2'R,3R,4'S)-6-bromo-4'-(3-chlorophenyl)-1'-(2-hydroxy ethyl-2'-isopropenylspiro[3H-indole-3,3'-piperidine]-2,6'(1H)-dione, chiral (2'R,3R,4'S)-1'-(aminocarbonyl-methyl)-6-bromo-4'-(3-chlorophenyl)-2'-isopropenylspiro[3H-indole-3,3'-piperidine]-2,6'(1H)-dione, chiral (2'R,3R,4'S)-1'-(aminocarbonyl-methyl)-6-bromo-4'-(3-chlorophenyl)-2'-(1-methyl cyclopropyl)-spiro[3H-indole-3,3'-piperidine]-2,6'(1H)-dione, racemic (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione, chiral (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione, racemic (2'R,3R,4'S)-2'-(1-bromo-vinyl)-6-chloro-4'-(3-chlorophenyl)spiro[3H-indole-3,3'-piperidine]-2,6'(1H)-dione, chiral (2'R,3R,4'S)-2'-(1-bromo-vinyl)-6-chloro-4'-(3-chlorophenyl)spiro[3H-indole-3,3'-piperidine]-2,6'(1H)-dione, racemic (2'R,3R,4'S)-6-chloro-4'-(5-chloro-2-methoxycarbonyl-phenyl)-2'-isopropenylspiro[3H-indole-3,3'-piperidine]-2,6'(1H)-dione, racemic (2'R,3R,4'S)-6-chloro-4'-(5-chloro-2-hydroxycarbonyl-phenyl)-2'-isopropenylspiro[3H-indole-3,3'-piperidine]-2,6'(1H)-dione,
racemic (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione,
chiral (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione,
racemic (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione,
chiral (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione,
racemic (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione,
chiral (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione,
racemic (2'R,3R,4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione,
racemic (2'R,3R,4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione,
racemic (2'R,3R,4'S)-6-chloro-4'-(3-chlorophenyl)-2'-[5-bromo-2-(2-hydroxy-1,1-dimethyl-ethoxy)phenyl]spiro[3H-indole-3,3'-piperidine]-2,6'(1H)-dione,
racemic (2'S,3S,4'R)-4'-[5-bromo-2-(1-ethoxycarbonyl-1-methyl-ethoxy)-phenyl]-6-chloro-2'-(5-fluoro-2-methyl-phenyl)spiro[3H-indole-3,3'-piperidine]-2,6'(1H)-dione,
racemic (2'S,3S,4'R)-4'-[5-bromo-2-(1-hydroxycarbonyl-1-methyl-ethoxy)-phenyl]-6-chloro-2'-(5-fluoro-2-methyl-phenyl)spiro[3H-indole-3,3'-piperidine]-2,6'(1H)-dione,
racemic (2'R,3S,4'R)-4'-[5-bromo-2-(1-ethoxycarbonyl-1-methyl-ethoxy)-phenyl]-6-chloro-2'-(2,5-difluorophenyl)spiro[3H-indole-3,3'-piperidine]-2,6'(1H)-dione,
racemic (2'R,3S,4'R)-4'-[5-bromo-2-(1-hydroxycarbonyl-1-methyl-ethoxy)-phenyl]-6-chloro-2'-(2,5-difluorophenyl)spiro[3H-indole-3,3'-piperidine]-2,6'(1H)-dione,
racemic (2'S,3S,4'R)-6-chloro-4'-[5-chloro-2-(1-methoxycarbonyl-cyclobutoxy)-phenyl]-2'-(5-fluoro-2-methyl-phenyl)spiro[3H-indole-3,3'-piperidine]-2,6'(1H)-dione,
racemic (2'S,3S,4'R)-6-chloro-4'-[5-chloro-2-(1-hydroxycarbonyl-cyclobutoxy)-phenyl]-2'-(5-fluoro-2-methyl-phenyl)spiro[3H-indole-3,3'-piperidine]-2,6'(1H)-dione,
racemic (2'R,3R,4'S)-6-chloro-4'-[5-chloro-2-(1-hydroxymethyl-cyclobutoxy)-phenyl]-2'-(5-fluoro-2-methyl phenyl)spiro[3H-indole-3,3'-piperidine]-2,6'(1H)-dione,
racemic (2'R,3R,4'S)-6-chloro-4'-(5-chloro-2-hydroxy-phenyl)-2'-isopropenylspiro[3H-indole-3,3'-piperidine]-2,6'(1H)-dione,
racemic (2'R,3R,4'S)-6-chloro-4'-[5-chloro-2-(2-methoxycarbonyl-2-methyl-propoxy)-phenyl]-2'-isopropenylspiro[3H-indole-3,3'-piperidine]-2,6'(1H)-dione,
racemic (2'R,3R,4'S)-6-chloro-4'-[5-chloro-2-(2-hydroxycarbonyl-2-methyl-propoxy)-phenyl]-2'-isopropenylspiro[3H-indole-3,3'-piperidine]-2,6'(1H)-dione,
racemic (2'R,3R,4'S)-2'-[5-bromo-2-(2-methoxycarbonyl-2-methyl-propoxy)-phenyl]-6-chloro-4'-[5-chloro-2-(methoxycarbonyl-methoxy)-phenyl]spiro[3H-indole-3,3'-piperidine]-2,6'(1H)-dione,
racemic (2'R,3R,4'S)-6-chloro-4'-[5-chloro-2-hydroxyethoxy)-phenyl]-2'-[5-bromo-2-(3-hydroxy-2,2-dimethyl-propoxy)-phenyl]spiro[3H-indole-3,3'-piperidine]-2,6'(1H)-dione,
racemic (2'S,3S,4'R)-6-chloro-4'-[5-chloro-2-(methoxycarbonyl-methoxy)-phenyl]-2'-(5-fluoro-2-methyl-phenyl)spiro[3H-indole-3,3'-piperidine]-2,6'(1H)-dione,
racemic (2'S,3S,4'R)-6-chloro-4'-[5-chloro-2-(hydroxycarbonyl-methoxy)-phenyl]-2'-(5-fluoro-2-methyl-phenyl)spiro[3H-indole-3,3'-piperidine]-2,6'(1H)-dione,
racemic (2'S,3S,4'R)-4'-[5-bromo-2-(2,2,2-trifluoro-ethoxy)-phenyl]-6-chloro-2'-(5-fluoro-2-methylphenyl)spiro[3H-indole-3,3'-piperidine]-2,6'(1H)-dione,
racemic (2'R,3S,4'R)-4'-[5-bromo-2-(2,2,2-trifluoro-ethoxy)-phenyl]-6-chloro-2'-(2,5-dichlorophenyl)spiro[3H-indole-3,3'-piperidine]-2,6'(1H)-dione,
racemic (2'R,3S,4'R)-6-chloro-4'-[5-chloro-2-(1-ethoxycarbonyl-1-methyl-ethoxy)-phenyl]-2'-(5-chloro-2-fluoro-phenyl)spiro[3H-indole-3,3'-piperidine]-2,6'(1H)-dione,
racemic (2'R,3S,4'R)-6-chloro-4'-[5-chloro-2-(1-hydroxycarbonyl-1-methyl-ethoxy)-phenyl]-2'-(5-chloro-2-fluoro-phenyl)spiro[3H-indole-3,3'-piperidine]-2,6'(1H)-dione,
chiral (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione,
racemic (2'R,3S,4'R)-6-chloro-4'-[5-chloro-2-(1-ethoxycarbonyl-1-methyl-ethoxy)-phenyl]-2'-(2-chloro-5-fluoro-phenyl)spiro[3H-indole-3,3'-piperidine]-2,6'(1H)-dione,
racemic (2'S,3S,4'R)-6-chloro-4'-[5-fluoro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione,
racemic (2'S,3S,4'R)-6-chloro-4'-[5-fluoro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione,
racemic (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione,
chiral (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione and
racemic (2'R,3R,4'R)-6-chloro-4'-(3-chloro-2-fluoro-phenyl)-2'-(5-fluoro-2-methyl-phenyl)spiro[3H-indole-3,3'-piperidine]-2,6'(1H)-dione.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formulas I or II or III as well as their salts have at least one asymmetric carbon atom and therefore may be present as racemic mixtures or different stereoisomers. The various isomers can be isolated by known separation methods, e.g., chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formulas I or II or III having a carboxyl group or hydroxy group, which esters retain the biological effectiveness and properties of the compounds of formulas I and are cleaved in vivo (in the organism) to the corresponding active carboxylic acid or alcohol respectively.

Synthesis

Compounds of this invention in formula I or II or III can be synthesized according to the following general schemes. It will be readily apparent to those of ordinary skill in the art that compounds in formula I-III can be prepared by substitution of the reagents or agents in the general synthesis routes. The starting materials are either commercially available or can be synthesized by well-established literature methods known to those of ordinary skill in the art. The key step of the transformation is a convergent [4+2] cycloaddition utilizing aza Diels-Alder reaction to generate a racemic mixture of spiroindolinone compounds in formula I in a stereoselective and efficient manner. By using purification of chiral chromatography, compounds in formula II or formula III can be obtained as an optically pure or enriched enantiomers.

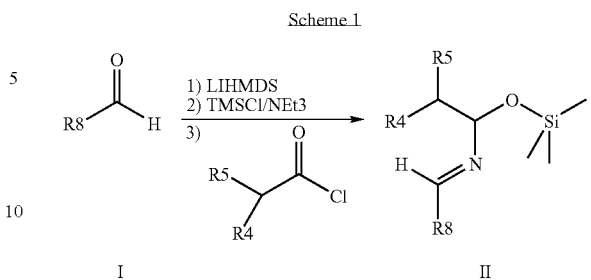

In general an appropriately selected aldehyde I can be reacted with lithium hexamethyldisilamide, chlorotrialkylsilane and a selectively substituted acyl chloride in a one-pot, multi-steps manner to generate 2-aza-1,3-butadiene II (Scheme I) and can be used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited therein). The appropriately selected aldehyde I are either commercially available or can be synthesized by well-established multiple literature methods.

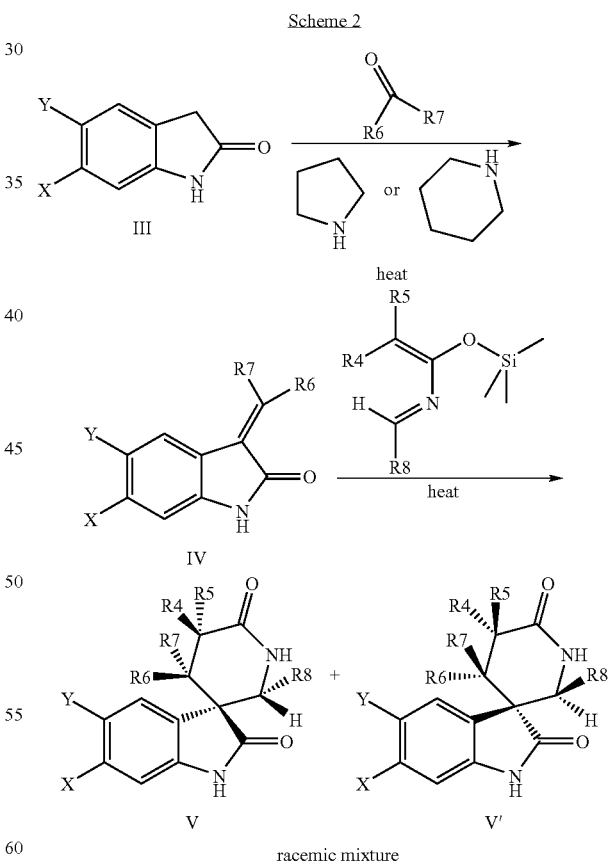

Oxindole III can be reacted with an appropriately substituted aldehyde or ketone in the presence of base under heated condition in either a protic like methanol, ethanol or an aprotic solvent like toluene, o-xylene to give intermediate IV. The commonly used base is either pyrrolidine or piperidine. Intermediate IV can then be reacted with 2-aza-1,3-butadiene II in toluene or o-xylene under heating from about 110° C. to 160° C. and anhydrous condition to afford a racemic mixture of spiroindolinone V and V' as the major products shown together with other minor stereoisomers. 6-substituted or 5,6-disubstituted oxindole III starting materials are either commercially available or prepared according to literature methods, for examples, Kraynack, E. A.; Dalgard, J. E.; Gaeta, F. C. A. *Tetrahedron Letters,* 1998, 39, 7679-7682, EP153818 for 5-fluoro-6-chlorooxindole, etc Scheme 3

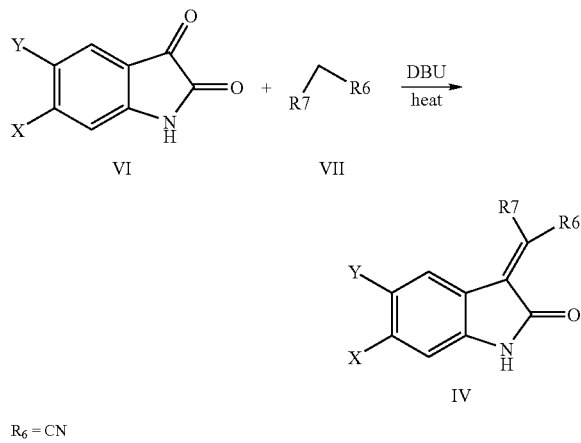

$R_6 = CN$

When $R_6$ is a strong electron withdrawing group in reagent VII, intermediate IV can be prepared alternatively from Isatin VI and reagent VII. For example, when $R_6$ is cyano and $R_7$ is a substituted aryl, hetereoaryl, Isatin VI can react with various $R_7$ substituted cyanide VII in the presence of a base like DBU in methanol under heated condition to form IV (Scheme 3). 6-substituted or 5,6-disubstituted isatin VI starting materials are either commercially available or prepared according to literature methods Scheme 4

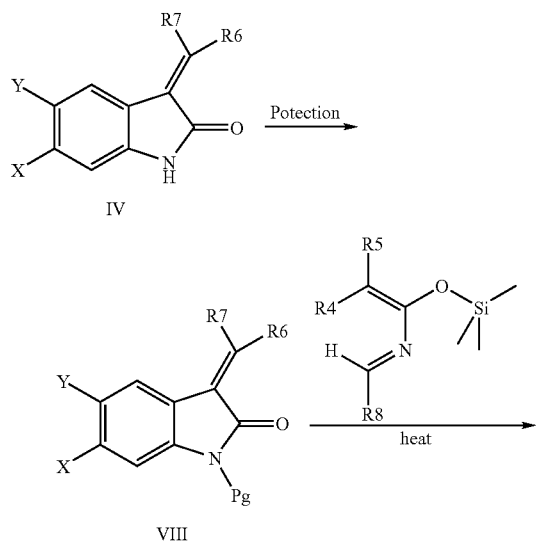

-continued

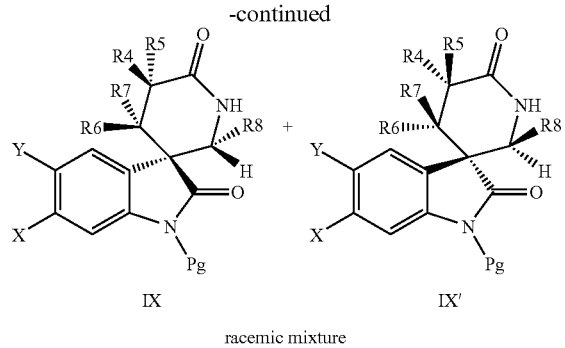

racemic mixture

Intermediate IV can be protected to give intermediate VIII. The protective group can be attached by using ethyl chloroformate, di-tert-butyl dicarbonate, SEM-Cl, benzyl bromide, and a base like 4-(dimethylamine)pyridine (DMAP), triethylamine, NaH, or LiH according to well established literature procedures. Examples of protective group formation and their deprotection have been described and reviewed comprehensively by Greene, T. W. et al in "Protective Groups in Organic Synthesis, $2^{nd}$ Edition. John Wiley & Sons Inc. In a similar manner intermediate VIII can be reacted with a selected 2-aza-butadiene II prepared in Scheme 1 in toluene or o-xylene under heating from 110° C. to 160° C. and anhydrous condition to form intermediate IX and IX' as the major products shown as a racemic mixture of two enantiomers together with other minor stereoisomers (Scheme 4). Intermediate IX can be converted into V by a deprotection reaction (Scheme 5). A useful Pg can be ethyl carbamate, tert-butyl carbamate (BOC), or trimethylsilylethoxymethyl (SEM). Ethyl carbamate can be removed easily by treatment of IX with a base like NaOH in methanol or ethanol at room temperature. tert-butyl carbamate (BOC) can be readily removed by treatment of IX with trifluoroacetic acid at room temperature. Deprotection of trimethylsilylethoxymethyl (SEM) can be achieved by treatment with trifluoroacetic acid in dichloromethane at room temperature first, followed by heating with diisopropylethylamine in methanol.

Scheme 5

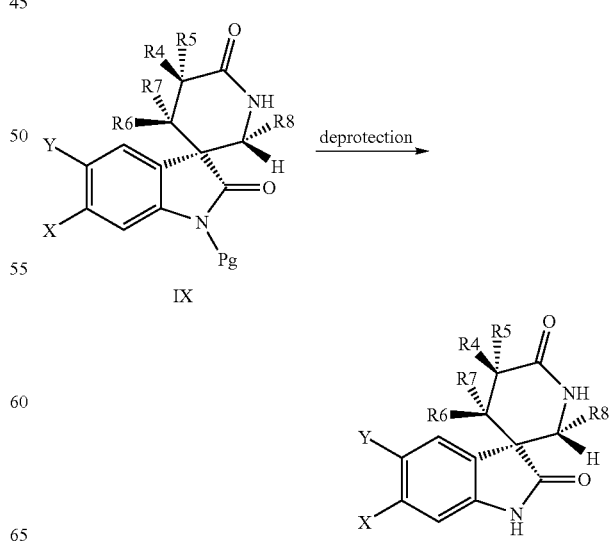

When $R_8$ is selected from a certain group such as lower alkyl, substituted lower alkyl, cycloalkyl, substituted cycloalkyl, alternative synthetic methods can be used to gain access to compounds V or intermediate IX. Typically, the compounds of V or intermediate IX with $R_8$ selected from a related lower alkenyl, or substituted alkenyl, or cycloalkenyl, or substituted cycloalkenyl, would be prepared first according to the methods in scheme 2 or scheme 4, followed by a catalytic hydrogenation reaction to give those V or IX with a $R_8$ as the corresponding lower alkyl, or substituted lower alkyl, or cycloalkyl, or substituted cycloalkyl. Treatment of the compounds of V or intermediate IX with $R_8$ selected from a related lower alkenyl, or substituted alkenyl with Simmons-Smith reagent ($CH_2I_2$-$Et_2Zn$) will lead to those V or IX with a $R_8$ as the corresponding substituted cyclopropyl group.

V can be selectively protected to give IX under controlled conditions. In this case, a useful protective group Pg here can be ethyl carbamate, or tert-butyl carbamate (BOC) (Scheme 6). The protective group can be attached by using ethyl chloroformate, or di-tert-butyl dicarbonate, and a base like 4-(dimethylamine)pyridine (DMAP) in dichloromethane at room or lowered temperature similar to the transformation from IV to VIII in Scheme 4.

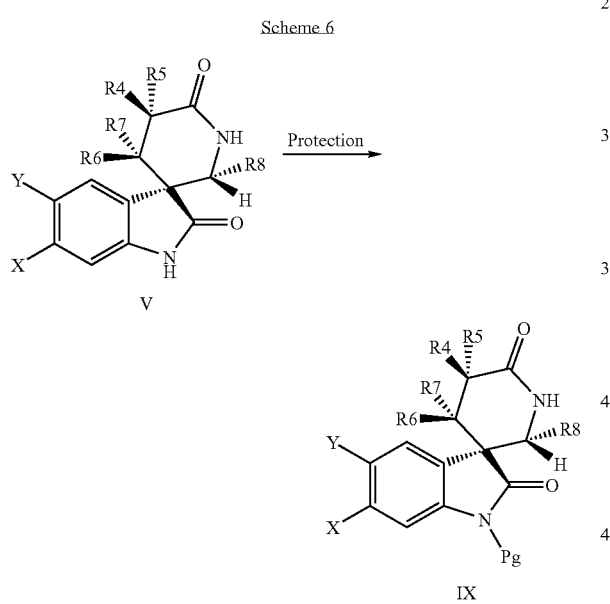

By using either an organic base diisopropylethyl amine or an inorganic base like $Cs_2CO_3$, LiH or NaH, and an appropriately selected alkylation reagent, N-alkylate intermediate X can be prepared from IX. A subsequent reaction to remove protective group (Pg) leads to various $R_2$ derivatized compound XI (Scheme 7).

When Pg is trimethylsiloxyethoxymethyl (SEM) group and $R_2$ is —$(CH_2)_nCl$, $R_2$ can be functionalized with other substituting group. For example, intermediate X with —$(CH_2)_nCl$ can be reacted with $HNR_{10}R_{11}$ in neat or a solvent like isopropanol under heated condition, followed by treatment of trifluoroacetic acid and diisopropylamine to give compounds XI with $R_2$ as —$(CH_2)_nNR_{10}R_{11}$.

When $R_2$ group is —$(CH_2)_mC(=O)OR'$, in which R' is hydrogen or a lower alkyl group, compound XI can be converted to give compounds XI with $R_2$ as $(CH_2)_mC(=O)NR_{10}R_{11}$ by using well-known methods for carboxamide formation.

$R_{10}$ or $R_{11}$ is independently selected from the group consisting of hydrogen, lower alkyl, substituted lower alkyl, lower alkoxy, substituted lower alkoxy, cycloalkyl, substituted cycloalkyl, heterocycle, substituted heterocycle, or $R_{10}$ and $R_{11}$ may be linked to form a heterocycle, substituted heterocycle, heteroaryl, or substituted heteroaryl.

n=2, 3, 4 m=1, 2, 3

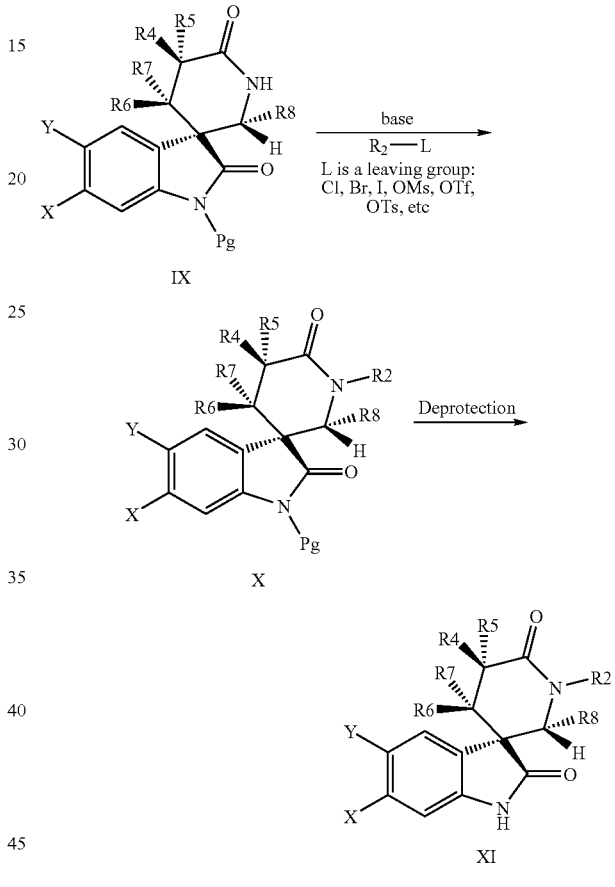

In one step compound XI can be selectively converted into thioamide analogue XII by using Lawesson reagent or other similarly related reagents (Scheme 8)

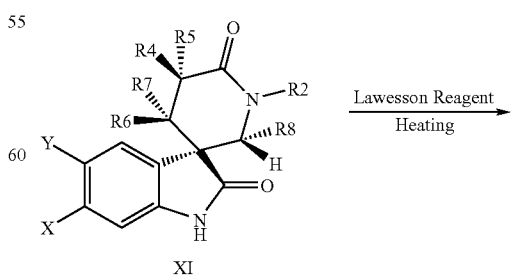

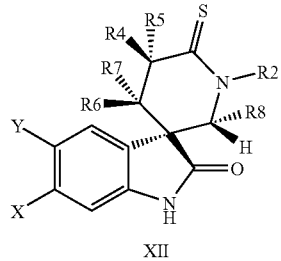

When R$_2$ is hydrogen, thioamide compound XIII can also be a useful intermediate to prepare various R$_3$ derivatized analogues. For example, compound XIII can be reacted with active nucleophilic, appropriately substituted hydrazide R$_9$—O(O═C)NHNH2, and a mercuric reagent like HgCl$_2$ or Hg(OAc)$_2$ to form analogues XIV (Scheme 9). R$_9$ is lower alkyl or substituted lower alkyl.

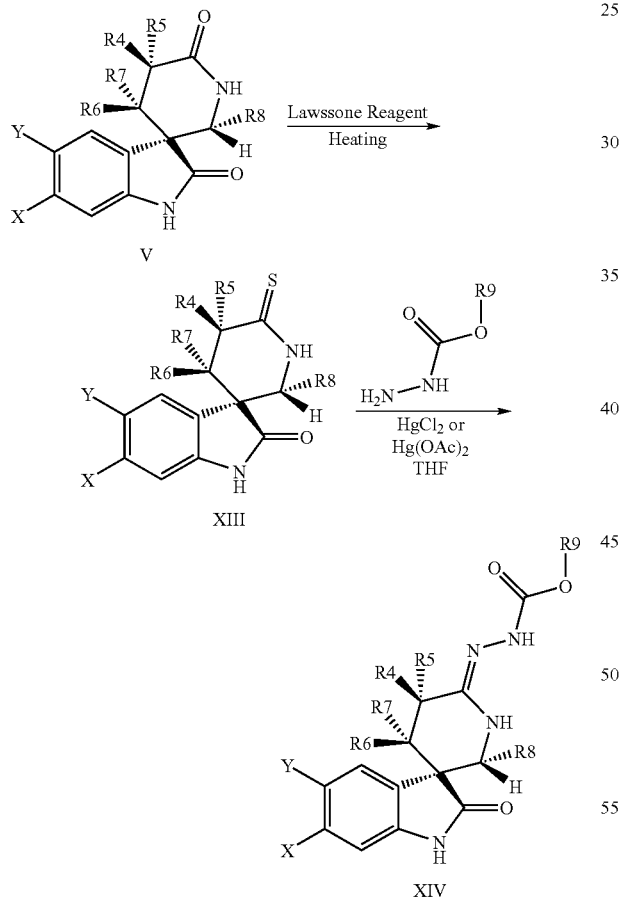

Compound V and V' can be readily resolved into two optically pure or enriched chiral enantiomers by separation using chiral Super Fluid Chromatography (SFC) or chiral HPLC or chiral column chromatography (Scheme 10). In a similar manner to the methods in the reaction schemes above, the chiral enantiomer of intermediate X and compounds XI, XII, XIII, XIV can be prepared by substitution of V with its enantiomer V', or substitution of IX with IX'. The compounds V and V', intermediates IX and IX' were generated initially as a racemic mixture and subsequently reacted without chiral separation to give the corresponding racemic mixture of X, XI, XII, XIII, or XIV together with their enantiomers. All these racemic mixture of IX, X, XI, XII, XIII, XIV and their enantiomers in the reaction schemes above can also be readily separated into optically pure or enriched chiral enantiomeric pairs in a similar manner as scheme 10.

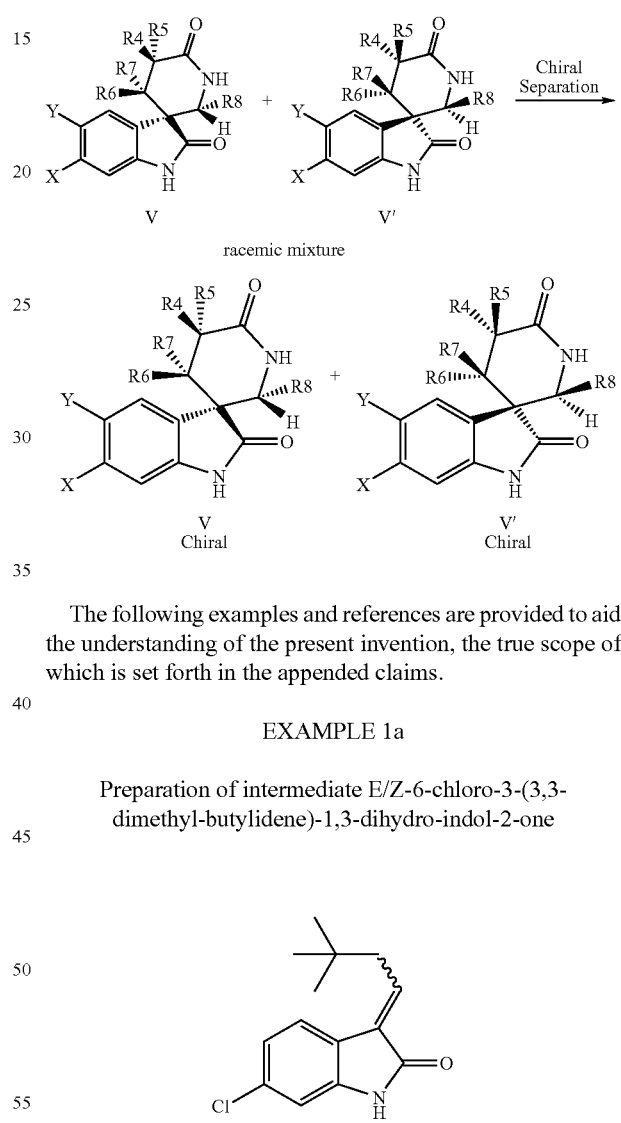

The following examples and references are provided to aid the understanding of the present invention, the true scope of which is set forth in the appended claims.

EXAMPLE 1a

Preparation of intermediate E/Z-6-chloro-3-(3,3-dimethyl-butylidene)-1,3-dihydro-indol-2-one

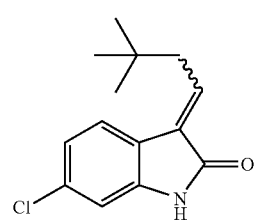

M. W. 249.74 C$_{14}$H$_{16}$ClNO

To the mixture of 6-chlorooxindole (0.26 g, 1.49 mmol) (Crescent) and 3,3-dimethyl-butyraldehyde (0.21 g, 2.09 mmol) (Aldrich) in methanol (20 mL) was added pyrrolidine (0.15 g, 2.09 mmol) (Aldrich) dropwise. The mixture was then heated at 100° C. for 1 h. The mixture was concentrated, and the residue was partitioned between ethyl acetate and water. The organic layer was separated, dried over Na$_2$SO$_4$, concentrated, and dried in vacuo to give the crude E/Z-6- chloro-3-(3,3-dimethyl-butylidene)-1,3-dihydro-indol-2-one as a white solid (Yield 0.37 g, 100%).

EXAMPLE 1b

Preparation of intermediate 1-(3-chlorophenyl)-3-trimethylsilyoxy-2-aza-1,3-butadiene

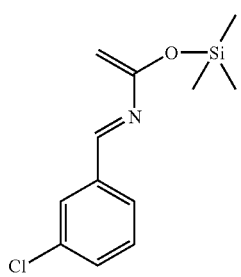

M. W. 253.81 C$_{12}$H$_{16}$ClNOSi

To 1,1,3,3,3-hexamethyldisilazane (2.18 mL, 10.5 mmol) (Aldrich) under nitrogen at room temperature was added n-butyllithium (2.5 M, 4.2 mL, 10.5 mmol) (Aldrich). The reaction mixture was stirred at room temperature for 10 minutes. Then dry tetrahydrofuran (30 mL) was added, followed by the addition of 3-chloro-benzaldehyde (1.19 mL, 10.5 mmol) (Aldrich). After the mixture was stirred at room temperature for 0.5 h, trimethylsilyl chloride (1.33 mL, 10.5 mmol) (Aldrich) was added dropwise. Then the temperature of the mixture was lowered to 0° C. on a cooling ice bath. To this mixture was added triethylamine (1.9 mL, 13.6 mmol) in one portion, followed by the dropwise addition of a solution of acetyl chloride (0.97 mL, 13.6 mmol) in diethyl ether (50 mL). The cooling bath was removed, and the mixture was stirred at room temperature for 1 h. The mixture was quickly filtered on celite under nitrogen, and filtrate was concentrated under reduced pressure to give crude 1-(3-chlorophenyl)-3-trimethylsilyloxy-2-aza-1,3-butadiene as a yellow gum and used for the next step without further purification.

Similar transformation has been reported by Ghosez, L., Bayard, Ph., Nshimyumukiza, P., Gouverneur, V., Sainte, F., Beaudegnies, R., Rivers, M., Frique-Hesbain, A.-M. and Wynants, C. in *Tetrahedron* 1995, 11021-11042.

EXAMPLE 1c

Preparation of racemic (2'S,3S,4'S)-6-chloro-2'-(3-chlorophenyl)-4'-(2,2-dimethylpropyl)spiro[3H-indole-3,3'-piperidine]-2,6'(1H)-dione

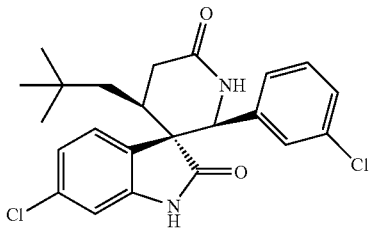

M. W. 431.36 C$_{23}$H$_{24}$Cl$_2$N$_2$O$_2$

To a mixture of 1-(3-chlorophenyl)-3-trimethylsilyoxy-2-aza-1,3-butadiene (0.25 g, 1 mmol) prepared in example 1b, and toluene (4 mL) was added E/Z-6-chloro-3-(3,3-dimethyl-butylidene)-1,3-dihydro-indol-2-one (0.25 g, 1 mmol) prepared in example 1a. The reaction mixture was heated in a sealed tube under nitrogen at 110° C. for 18 h. The mixture was cooled to room temperature, and methanol (10 mL) was added. The mixture was concentrated and the residue was purified by chromatography (EtOAc/hexanes=2:1) to give racemic (2'S,3S,4'S)-6-chloro-2'-(3-chlorophenyl)-4'-(2,2-dimethylpropyl)spiro[3H-indole-3,3'-piperidine]-2,6'(1H)-dione as a brown solid (Yield 0.15 g, 35%).

HRMS (ES$^+$) m/z Calcd for C$_{23}$H$_{24}$Cl$_2$N$_2$O$_2$+H [(M+H)$^+$]: 431.1288. Found: 431.1285

Similar transformation has been reported by Ghosez, L. and Jnoff, E. in *J. Am. Chem. Soc* 1999, 2617-2618.

EXAMPLE 2a

Preparation of intermediate E-6-chloro-3-(2,2-dimethyl-propylidene)-1,3-dihydro-indol-2-one

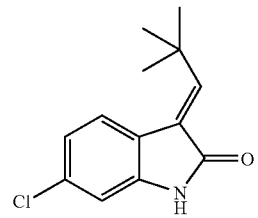

M. W. 235.72 C$_{13}$H$_{14}$ClNO

In a manner similar to the method described in example 1a, 6-chlorooxindole (0.88 g, 5 mmol) was reacted with 2,2-dimethyl-propionaldehyde (0.43 g, 5 mmol) (Aldrich), pyrrolidine (0.36 g, 5 mmol) in methanol to give a mixture of E- and Z-6-Chloro-3-(2,2-dimethyl-propylidene)-1,3-dihydro-indol-2-one. Purification by chromatography (EtOAc:hexanes=1:2) led to E-6-chloro-3-(2,2-dimethyl-propylidene)-1,3-dihydro-indol-2-one as an off-white foam (Yield 0.82 g, 70%).

EXAMPLE 2b

Preparation of racemic (2'SR,3S,4'R)-4'-(tert-butyl)-6-chloro-2'-(3-chlorophenyl)spiro[3H-indole-3,3'-piperidine]-2,6'(1H)-dione

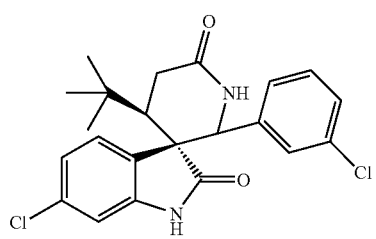

M. W. 417.34 C$_{22}$H$_{22}$Cl$_2$N$_2$O$_2$

In a manner similar to the method described in example 1c, E-6-chloro-3-(2,2-dimethyl-propylidene)-1,3-dihydro-indol-2-one (0.23 g, 1 mmol) was reacted with 1-(3-chlorophenyl)-3-trimethylsilyoxy-2-aza-1,3-butadiene (0.63 g, 2.5 mmol) prepared in example 1b, in toluene to give racemic (2'SR,3S,4'R)-4'-(tert-butyl)-6-chloro-2'-(3-chlorophenyl) spiro[3H-indole-3,3'-piperidine]-2,6'(1H)-dione as a mixture of two sets of diastereomers (Yield 0.21 g, 50%).

HRMS (ES$^+$) m/z Calcd for $C_{22}H_{22}Cl_2N_2O_2$+H [(M+H)$^+$]: 417.1131. Found: 417.1129

EXAMPLE 3a

Preparation of intermediate E/Z-6-chloro-3-isobutyl-idene-1,3-dihydro-indol-2-one

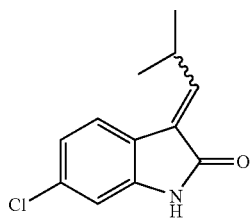

M. W. 221.69 $C_{12}H_{12}ClNO$

In a manner similar to the method described in example 1a, 6-chlorooxindole (0.85 g, 4.8 mmol) was reacted with 2-methyl-propionaldehyde (0.42 g, 5.8 mmol) (Aldrich), pyrrolidine (0.41 g, 5.8 mmol) in methanol (40 mL) to give a mixture of E/Z-6-chloro-3-isobutylidene-1,3-dihydro-indol-2-one as a brown foam (Yield 1.0 g, 100%).

EXAMPLE 3b

Preparation of racemic (2'S,3S,4'R)-6-chloro-2'-(3-chlorophenyl)-4'-isopropylspiro[3H-indole-3,3'-piperidine]-2,6'(1H)-dione

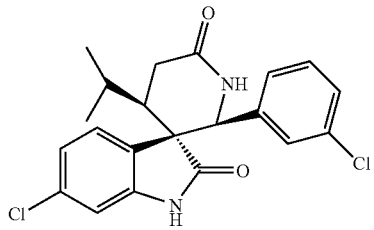

M. W. 403.31 $C_{21}H_{20}Cl_2N_2O_2$

In a manner similar to the method described in example 1c, E/Z-6-chloro-3-isobutylidene-1,3-dihydro-indol-2-one (0.25 g, 1.1 mmol) was reacted with 1-(3-chlorophenyl)-3-trimethylsilyoxy-2-aza-1,3-butadiene (1.2 g, 4.7 mmol) prepared in example 1b, in toluene to give racemic (2'S,3S,4'R)-6-chloro-2'-(3-chlorophenyl)-4'-isopropylspiro[3H-indole-3,3'-piperidine]-2,6'(1H)-dione as a white solid (Yield 0.25 g, 56%).

HRMS (ES$^+$) m/z Calcd for $C_{21}H_{20}Cl_2N_2O_2$+H [(M+H)$^+$]: 403.0975. Found: 403.0975.

EXAMPLE 4a

Preparation of intermediate E/Z-6-chloro-3-(3-chloro-benzylidene)-1,3-dihydro-indol-2-one

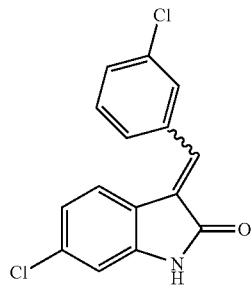

M. W. 290.15 $C_{15}H_9Cl_2NO$

To the mixture of 6-chlorooxindole (16.2 g, 92 mmol) (Crescent) and 3-chloro-benzaldehyde (12.9 g, 92 mmol) (Aldrich) in methanol (109 mL) was added pyrrolidine (6.55 g, 92 mmol) (Aldrich) dropwise. The mixture was then heated at 70° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 25.2 g, 95%).

EXAMPLE 4b

Preparation of intermediate E/Z-6-chloro-3-(3-chloro-benzylidene)-2-oxo-2,3-dihydro-indole-1-carboxylic acid ethyl ester

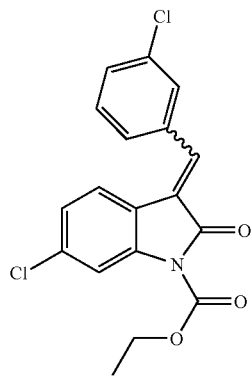

M. W. 362.22 $C_{18}H_{13}Cl_2NO_3$

To a solution of E/Z-6-chloro-3-(3-chloro-benzylidene)-1,3-dihydro-indol-2-one prepared in example 4a (1.33 g, 4.6 mmol) in dichloromethane (50 mL) at 0° C. was added ethyl chloroformate (0.66 mL, 6.9 mmol) (Aldrich), followed by the addition of triethylamine (0.93 g, 9.2 mmol). The reaction mixture was stirred at 0° C. for 30 minutes. The mixture was then poured into aqueous HCl solution (1 N). The organic layer was separated and the aqueous layer was extracted with ethyl acetate. The organic layers were combined and dried over $Na_2SO_4$, and concentrated to give E/Z-6-chloro-3-(3-chloro-benzyl indene)-2-oxo-2,3-dihydro-indole-1-carboxylic acid ethyl ester as a yellow solid and used for the next step without further purification (Yield 1.7 g, 100%).

EXAMPLE 4c

Preparation of intermediate racemic (2'R,3R,4'S)-6-chloro-2',4'-bis(3-chlorophenyl)-2,3-dihydro-2,6'-dioxospiro[indole-3,3'-piperidine]-1-carboxylic acid ethyl ester

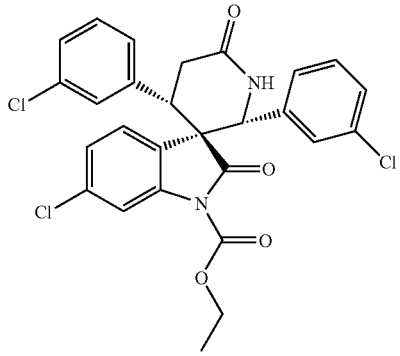

M. W. 543.84 $C_{27}H_{21}Cl_3N_2O_4$

To a solution of 1-(3-chlorophenyl)-3-trimethylsilyoxy-2-aza-1,3-butadiene prepared in example 1b in toluene (20 mL) was added E/Z-6-chloro-3-(3-chloro-benzylidene)-2-oxo-2,3-dihydro-indole-1-carboxylic acid ethyl ester prepared in example 6b (0.3 g, 0.83 mmol). The reaction mixture was stirred under nitrogen in a sealed tube at 135° C. for 1 h. After the solution was cooled to room temperature, methanol (50 mL) was added, and then the mixture was concentrated. The residue was purified by chromatography (EtOAc:CH$_2$Cl$_2$=1:3) to give racemic (2'R,3R,4'S)-6-chloro-2',4'-bis(3-chlorophenyl)-2,3-dihydro-2,6'-dioxospiro[indole-3,3'-piperidine]-1-carboxylic acid ethyl ester as a yellow oil (Yield 0.45 g, 100%).

EXAMPLE 4d

Preparation of racemic (2'R,3R,4'S)-6-chloro-2',4'-bis(3-chlorophenyl)spiro[3H-indole-3,3'-piperidine]-2,6'(1H)-dione

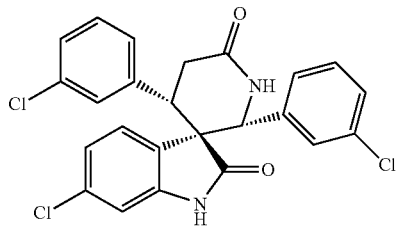

M. W. 471.77 $C_{24}H_{17}Cl_3N_2O_2$

To a solution of racemic (2'R,3R,4'S)-6-chloro-2',4'-bis(3-chlorophenyl)-2,3-dihydro-2,6'-dioxospiro[indole-3,3'-piperidine]-1-carboxylic acid ethyl ester prepared in example 4c (0.45 g, 0.92 mmol) in methanol (30 mL) was added NaOH (66 mg, 1.65 mmol). The mixture was stirred at room temperature for 0.5 h. The solvent was removed and the residue was partitioned between ethyl acetate and aqueous HCl solution (1 N). The aqueous layer was extracted with ethyl acetate. The organic layers were combined and then concentrated. The residue was purified with chromatography (EtOAc:CH$_2$Cl$_2$=1:3) to give racemic (2'R,3R,4'S)-6-chloro-2',4'-bis(3-chlorophenyl)spiro[3H-indole-3,3'-piperidine]-2,6'-dione as a white solid (Yield 0.2 g, 51%).

HRMS (ES$^+$) m/z Calcd for $C_{24}H_{17}Cl_3N_2O_2$+H [(M+H)$^+$]: 471.0429. Found: 471.0431.0.

EXAMPLE 4e

Preparation of chiral (2'R,3R,4'S)-6-chloro-2',4'-bis(3-chlorophenyl)spiro[3H-indole-3,3'-piperidine]-2,6'(1H)-dione

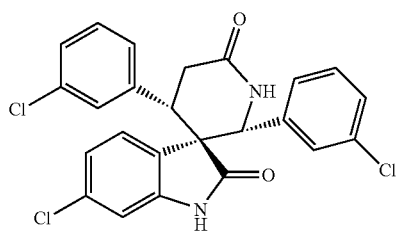

M. W. 471.77 $C_{24}H_{17}Cl_3N_2O_2$

Separation of the two enantiomers from racemic (2'R,3R,4'S)-6-chloro-2',4'-bis(3-chlorophenyl)spiro[3H-indole-3,3'-piperidine]-2,6'(1H)-dione (84 mg) prepared in example 4d was conducted by chiral SFC to provide chiral (2'R,3R,4'S)-6-chloro-2',4'-bis(3-chlorophenyl)spiro[3H-indole-3,3'-piperidine]-2,6'(1H)-dione as a white solid (Yield 10 mg, 12%). HRMS (ES$^+$) m/z Calcd for $C_{24}H_{17}Cl_3N_2O_2$+H [(M+H)$^+$]: 471.0429. Found: 471.0431 and chiral (2'S,3S,4'R)-6-chloro-2',4'-bis(3-chlorophenyl)spiro[3H-indole-3,3'-piperidine]-2,6'(1H)-dione as a white solid (Yield 17 mg, 20%). HRMS (ES$^+$) m/z Calcd for $C_{24}H_{17}Cl_3N_2O_2$+H [(M+H)$^+$]: 471.0429. Found: 471.0428.

EXAMPLE 5a

Preparation of intermediate E/Z-6-chloro-3-cyclopentylmethylene-1,3-dihydro-indol-2-one

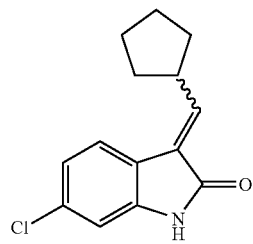

M. W. 247.73 $C_{14}H_{14}ClNO$

In a manner similar to the method described in example 1a, 6-chlorooxindole (1.16 g, 6.59 mmol) was reacted with cyclopentanecarbaldehyde (0.77 g, 7.85 mmol) (Wiley) and piperidine (0.67 g, 7.85 mmol) in methanol to give a mixture of E- and Z-6-Chloro-3-cyclopentylmethylene-1,3-dihydro-indol-2-one as a brown oil (Yield 0.8 g, 49%).

EXAMPLE 5b

Preparation of intermediate E/Z-6-chloro-3-cyclopentylmethylene-2-oxo-2,3-dihydro-indole-1-carboxylic acid ethyl ester

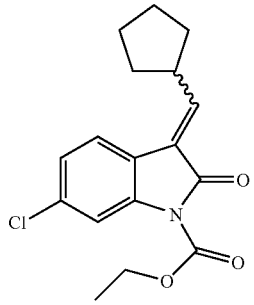

M. W. 319.79 $C_{17}H_{18}ClNO_3$

In a manner similar to the method described in example 4b, E/Z-6-chloro-3-cyclopentylmethylene-1,3-dihydro-indol-2-one (0.8 g, 3.2 mmol) was reacted with ethyl chloroformate (0.46 mL, 4.9 mmol) and triethylamine (0.9 mL, 6.4 mmol) in dichloromethane to give E/Z-6-chloro-3-cyclopentylmethylene-2-oxo-2,3-dihydro-indole-1-carboxylic acid ethyl ester as brown oil (Yield 0.6 g, 58%).

EXAMPLE 5c

Preparation of intermediate racemic (2'S,3S,4'R)-6-chloro-2'-(3-chlorophenyl)-4'-cyclopentyl-2,3-dihydro-2,6'-dioxospiro[indole-3,3'-piperidine]-1-carboxylic acid ethyl ester

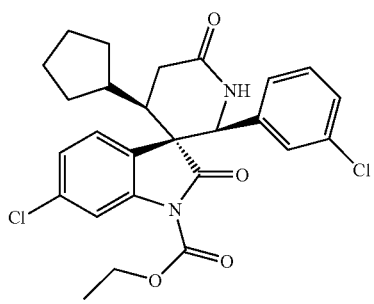

M. W. 501.41 $C_{26}H_{26}Cl_2N_2O_4$

In a manner similar to the method described in example 4c, E/Z-6-chloro-3-cyclopentylmethylene-2-oxo-2,3-dihydro-indole-1-carboxylic acid ethyl ester (0.32 g, 1.00 mmol) was reacted with 1-(3-chlorophenyl)-3-trimethylsilyoxy-2-aza-1,3-butadiene prepared in example 1b, in toluene to give racemic (2'S,3S,4'R)-6-chloro-2'-(3-chlorophenyl)-4'-cyclopentyl-2,3-dihydro-2,6'-dioxospiro[indole-3,3'-piperidine]-1-carboxylic acid ethyl ester as an off-white foam (Yield 0.26 g, 52%).

EXAMPLE 5d

Preparation of racemic (2'S,3S,4'R)-6-chloro-2'-(3-chlorophenyl)-4'-cyclopentylspiro[3H-indole-3,3'-piperidine]-2,6'(1H)-dione

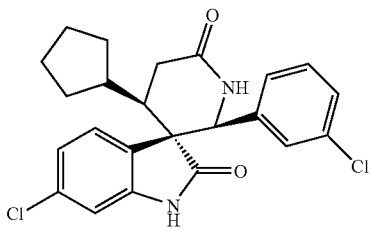

M. W. 429.35 $C_{23}H_{22}Cl_2N_2O_2$

In a manner similar to the method described in example 4d, racemic (2'S,3S,4'R)-6-chloro-2'-(3-chlorophenyl)-4'-cyclopentyl-2,3-dihydro-2,6'-dioxospiro[indole-3,3'-piperidine]-1-carboxylic acid ethyl ester (0.26 g, 0.52 mmol) was reacted with NaOH (37 mg, 0.93 mmol) in methanol to give racemic (2'S,3S,4'R)-6-chloro-2'-(3-chlorophenyl)-4'-cyclopentylspiro[3H-indole-3,3'-piperidine]-2,6'(1H)-dione as a white solid (Yield 0.13 g, 59%).

HRMS (ES$^+$) m/z Calcd for $C_{23}H_{22}Cl_2N_2O_2$+H [(M+H)$^+$]: 429.1131. Found: 429.1121.

EXAMPLE 6a

Preparation of intermediate E/Z-6-chloro-3-cyclohexylmethylene-1,3-dihydro-indol-2-one

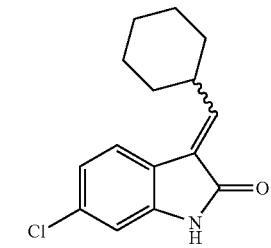

M. W. 261.75 $C_{15}H_{16}ClNO$

In a manner similar to the method described in example 1a, 6-chlorooxindole (2 g, 11.4 mmol) was reacted with cyclohexanecarbaldehyde (1.53 g, 13.6 mmol) (Aldrich) and piperidine (1.35 mL, 13.6 mmol) in methanol to give a mixture of E- and Z-6-chloro-3-cyclohexylmethylene-1,3-dihydro-indol-2-one as a brown solid (Yield 2.71 g, 91%).

EXAMPLE 6b

Preparation of intermediate E/Z-6-chloro-3-cyclohexylmethylene-2-oxo-2,3-dihydro-indole-1-carboxylic acid ethyl ester

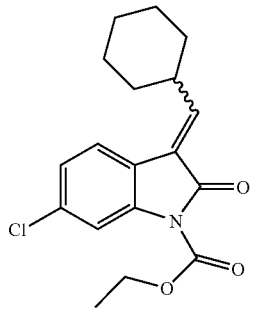

M. W. 333.82 $C_{18}H_{20}ClNO_3$

In a manner similar to the method described in example 4b, E/Z-6-chloro-3-cyclohexylmethylene-1,3-dihydro-indol-2-one (2.71 g, 10.4 mmol) was reacted with ethyl chloroformate (1.47 mL, 15.6 mmol) and triethylamine (2.89 mL, 20.7 mmol) in dichloromethane to give E/Z-6-chloro-3-cyclohexylmethylene-2-oxo-2,3-dihydro-indole-1-carboxylic acid ethyl ester as a brown solid (Yield 3.3 g, 95%).

EXAMPLE 6c

Preparation of intermediate racemic (2'S,3S,4'R)-6-chloro-2'-(3-chlorophenyl)-4'-cyclohexyl-2,3-dihydro-2,6'-dioxospiro[indole-3,3'-piperidine]-1-carboxylic acid ethyl ester

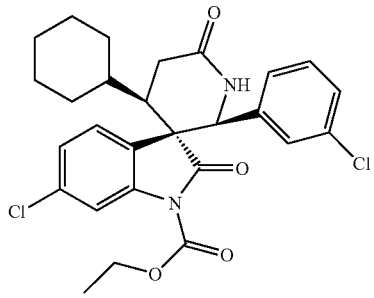

M. W. 515.44 $C_{27}H_{28}Cl_2N_2O_4$

In a manner similar to the method described in example 4c, E/Z-6-chloro-3-cyclohexylmethylene-2-oxo-2,3-dihydro-indole-1-carboxylic acid ethyl ester (0.40 g, 1.20 mmol) was reacted with 1-(3-chlorophenyl)-3-trimethylsilyoxy-2-aza-1,3-butadiene prepared in example 1b, in toluene to give racemic ((2'S,3S,4'R)-6-chloro-2'-(3-chlorophenyl)-4'-cyclohexyl-2,3-dihydro-2,6'-dioxospiro[indole-3,3'-piperidine]-1-carboxylic acid ethyl ester as a yellow oil (Yield 0.2 g, 32%).

EXAMPLE 6d

Preparation of racemic (2'S,3S,4'R)-6-chloro-2'-(3-chlorophenyl)-4'-cyclohexylspiro[3H-indole-3,3'-piperidine]-2,6'(1H)-dione

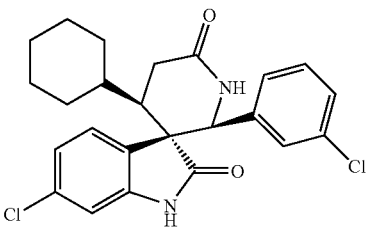

M. W. 443.38 $C_{24}H_{24}Cl_2N_2O_2$

In a manner similar to the method described in example 4d, racemic (2'S,3S,4'R)-6-chloro-2'-(3-chlorophenyl)-4'-cyclohexyl-2,3-dihydro-2,6'-dioxospiro[indole-3,3'-piperidine]-1-carboxylic acid ethyl ester (0.2 g, 0.39 mmol) was reacted with NaOH (28 mg, 0.70 mmol) in methanol to give racemic (2'S,3S,4'R)-6-chloro-2'-(3-chlorophenyl)-4'-cyclohexyl-spiro[3H-indole-3,3'-piperidine]-2,6'(1H)-dione as a white solid (Yield 0.05 g, 29%).

HRMS (ES$^+$) m/z Calcd for $C_{24}H_{24}Cl_2N_2O_2$+H [(M+H)$^+$]: 443.1288. Found: 443.1288.

EXAMPLE 7a

Preparation of intermediate 1-(4-chlorophenyl)-3-trimethylsilyoxy-2-aza-1,3-butadiene

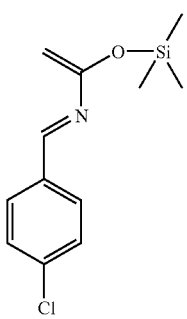

M. W. 253.81 $C_{12}H_{16}ClNOSi$

In a manner similar to the method described in example 1b, 4-chloro-benzaldehyde (1.48 g, 10.5 mmol) (Aldrich) was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(4-chlorophenyl)-3-trimethylsilyoxy-2-aza-1,3-butadiene as a yellow gum and used for the next step without further purification.

EXAMPLE 7b

Preparation of intermediate racemic (2'S,3S,4'R)-6-chloro-2'-(4-chlorophenyl)-4'-cyclohexyl-2,3-dihydro-2,6'-dioxospiro[indole-3,3'-piperidine]-1-carboxylic acid ethyl ester

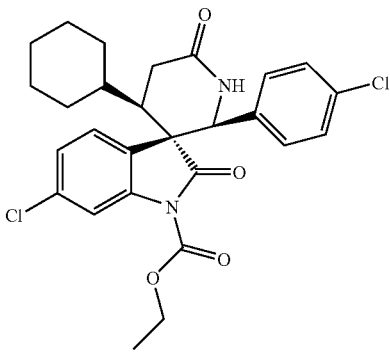

M. W. 515.44 $C_{27}H_{28}Cl_2N_2O_4$

In a manner similar to the method described in example 4c, E/Z-6-chloro-3-cyclohexylmethylene-2-oxo-2,3-dihydro-indole-1-carboxylic acid ethyl ester (0.40 g, 1.20 mmol) prepared in example 6b was reacted with 1-(4-chlorophenyl)-3-trimethylsilyoxy-2-aza-1,3-butadiene prepared in example 7a, in toluene to give racemic (2'S,3S,4'R)-6-chloro-2'-(4-chlorophenyl)-4'-cyclohexyl-2,3-dihydro-2,6'-dioxospiro[indole-3,3'-piperidine]-1-carboxylic acid ethyl ester as a white solid (Yield 0.45 g, 72%).

EXAMPLE 7c

Preparation of racemic (2'S,3S,4'R)-6-chloro-2'-(4-chlorophenyl)-4'-cyclohexylspiro[3H-indole-3,3'-piperidine]-2,6'(1H)-dione

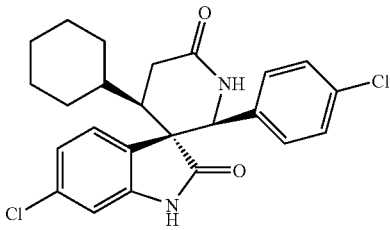

M. W. 443.38 $C_{24}H_{24}Cl_2N_2O_2$

In a manner similar to the method described in example 4d, racemic (2'S,3S,4'R)-6-chloro-2'-(4-chlorophenyl)-4'-cyclohexyl-2,3-dihydro-2,6'-dioxospiro[indole-3,3'-piperidine]-1-carboxylic acid ethyl ester (0.4 g, 0.78 mmol) was reacted with NaOH (56 mg, 1.4 mmol) in methanol to give racemic (2'S,3S,4'R)-6-chloro-2'-(4-chlorophenyl)-4'-cyclohexylspiro[3H-indole-3,3'-piperidine]-2,6'(1H)-dione as a white solid (Yield 0.15 g, 44%).

HRMS (ES$^+$) m/z Calcd for $C_{24}H_{24}Cl_2N_2O_2$+H [(M+H)$^+$]: 443.1288. Found: 443.1287.

EXAMPLE 8a

Preparation of intermediate racemic (2'R,3R,4'S)-6-chloro-2'-(4-chlorophenyl)-4'-(3-chlorophenyl)-2,3-dihydro-2,6'-dioxospiro[indole-3,3'-piperidine]-1-carboxylic acid ethyl ester

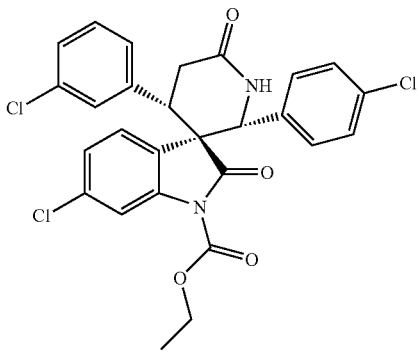

M. W. 543.84 $C_{27}H_{21}Cl_3N_2O_4$

In a manner similar to the method described in example 4c, E/Z-6-chloro-3-(3-chloro-benzylidene)-2-oxo-2,3-dihydro-indole-1-carboxylic acid ethyl ester (0.3 g, 0.83 mmol) prepared in example 4b was reacted with 1-(4-chlorophenyl)-3-trimethylsilyoxy-2-aza-1,3-butadiene prepared in example 7a, in toluene to give racemic (2'R,3R,4'S)-6-chloro-2'-(4-chlorophenyl)-4'-(3-chlorophenyl)-2,3-dihydro-2,6'-dioxospiro[indole-3,3'-piperidine]-1-carboxylic acid ethyl ester as a yellow solid (Yield 0.45 g, 72%).

EXAMPLE 8b

Preparation of racemic (2'R,3R,4'S)-6-chloro-2'-(4-chlorophenyl)-4'-(3-chlorophenyl)spiro[3H-indole-3,3'-piperidine]-2,6'(1H)-dione

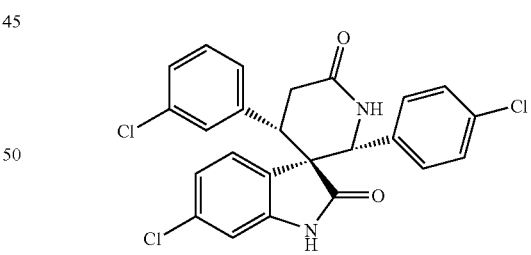

M. W. 471.77 $C_{24}H_{17}Cl_3N_2O_2$

In a manner similar to the method described in example 4d, racemic (2'R,3R,4'S)-6-chloro-2'-(4-chlorophenyl)-4'-(3-chlorophenyl)-2,3-dihydro-2,6'-dioxospiro[indole-3,3'-piperidine]-1-carboxylic acid ethyl ester (0.45 g, 0.83 mmol) was reacted with NaOH (60 mg, 1.49 mmol) in methanol to give racemic (2'R,3R,4'S)-6-chloro-2'-(4-chlorophenyl)-4'-(3-chlorophenyl)spiro[3H-indole-3,3'-piperidine]-2,6'(1H)-dione as a white solid (Yield 0.2 g, 51%).

HRMS (ES$^+$) m/z Calcd for $C_{24}H_{17}Cl_3N_2O_2$+H [(M+H)$^+$]: 471.0429. Found: 471.0427.

EXAMPLE 9a

Preparation of intermediate E/Z-6-chloro-3-(4-chloro-benzylidene)-1,3-dihydro-indol-2-one

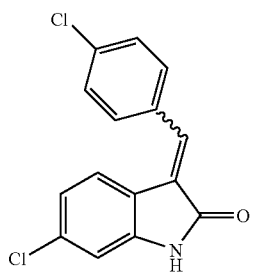

M. W. 290.15 $C_{15}H_9Cl_2NO$

In a manner similar to the method described in example 1a, 6-chlorooxindole (2 g, 11.4 mmol) was reacted with 4-chloro-benzaldehyde (1.91 g, 13.6 mmol) (1.53 g, 13.6 mmol) (Aldrich) and piperidine (1.34 mL, 13.6 mmol) in methanol to give a mixture of E- and Z-6-chloro-3-(4-chloro-benzylidene)-1,3-dihydro-indol-2-one as a yellow solid (Yield: 3.3 g, 100%).

EXAMPLE 9b

Preparation of intermediate E/Z 6-chloro-3-(4-chloro-benzylidene)-2-oxo-2,3-dihydro-indole-1-carboxylic acid ethyl ester

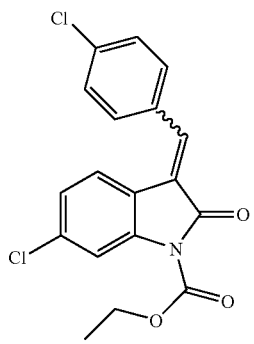

M. W. 362.22 $C_{18}H_{13}Cl_2NO_3$

In a manner similar to the method described in example 4b, E/Z-6-chloro-3-(4-chloro-benzylidene)-1,3-dihydro-indol-2-one (3.3 g, 11.3 mmol) was reacted with ethyl chloroformate (1.62 mL, 17.0 mmol) and triethylamine (3.16 mL, 22.6 mmol) in dichloromethane to give E/Z-6-chloro-3-(4-chloro-benzylidene)-2-oxo-2,3-dihydro-indole-1-carboxylic acid ethyl ester as a yellow solid (Yield 3.0 g, 73%).

EXAMPLE 9c

Preparation of intermediate racemic (2'S,3S,4'R)-6-chloro-2'-(3-chlorophenyl)-4'-(4-chlorophenyl)-2,3-dihydro-2,6'-dioxospiro[indole-3,3'-piperidine]-1-carboxylic acid ethyl ester

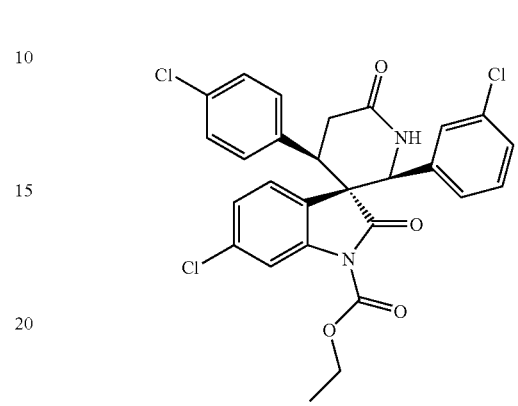

M. W. 543.84 $C_{27}H_{21}Cl_3N_2O_4$

In a manner similar to the method described in example 4c, E/Z-6-chloro-3-(4-chloro-benzylidene)-2-oxo-2,3-dihydro-indole-1-carboxylic acid ethyl ester (0.35 g, 0.97 mmol) prepared in example 9b was reacted with 1-(3-chlorophenyl)-3-trimethylsilyoxy-2-aza-1,3-butadiene prepared in example 1b, in toluene to give racemic (2'S,3S,4'R)-6-chloro-2'-(3-chlorophenyl)-4'-(4-chlorophenyl)-2,3-dihydro-2,6'-dioxospiro[indole-3,3'-piperidine]-1-carboxylic acid ethyl ester as a yellow solid (Yield 0.5 g, 95%).

EXAMPLE 9d

Preparation of racemic (2'S,3S,4'R)-6-chloro-2'-(3-chlorophenyl)-4'-(4-chlorophenyl)spiro[3H-indole-3,3'-piperidine]-2,6'(1H)-dione

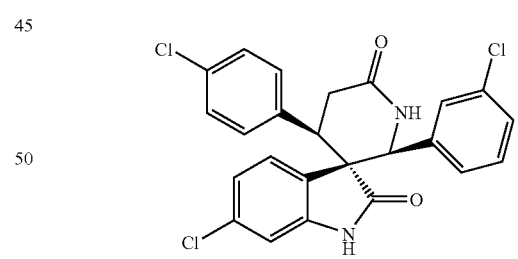

M. W. 471.77 $C_{24}H_{17}Cl_3N_2O_2$

In a manner similar to the method described in example 4d, racemic (2'S,3S,4'R)-6-chloro-2'-(3-chlorophenyl)-4'-(4-chlorophenyl)-2,3-dihydro-2,6'-dioxospiro[indole-3,3'-piperidine]-1-carboxylic acid ethyl ester (0.5 g, 0.92 mmol) was reacted with NaOH (67 mg, 1.67 mmol) in methanol to give racemic (2'S,3S,4'R)-6-chloro-2'-(3-chlorophenyl)-4'-(4-chlorophenyl)spiro[3H-indole-3,3'-piperidine]-2,6'(1H)-dione as a white solid (Yield 0.08 g, 18%).

HRMS (ES$^+$) m/z Calcd for $C_{24}H_{17}Cl_3N_2O_2$+H [(M+H)$^+$]: 471.0429. Found: 471.0427.

EXAMPLE 10a

Preparation of intermediate 1-(3-methylphenyl)-3-trimethylsilyoxy-2-aza-1,3-butadiene

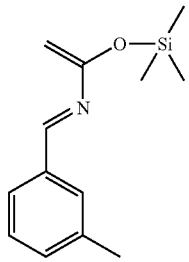

M. W. 233.39 C$_{13}$H$_{19}$NOSi

In a manner similar to the method described in example 1b, 3-methyl-benzaldehyde (1.30 g, 10.5 mmol) (Matrix) was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(3-methylphenyl)-3-trimethylsilyoxy-2-aza-1,3-butadiene as a yellow gum and used for the next step without further purification.

EXAMPLE 10b

Preparation of intermediate racemic (2'R,3R,4'S)-6-chloro-4'-(3-chlorophenyl)-2,3-dihydro-2'-(3-methylphenyl)-2,6'-dioxospiro[indole-3,3'-piperidine]-1-carboxylic acid ethyl ester

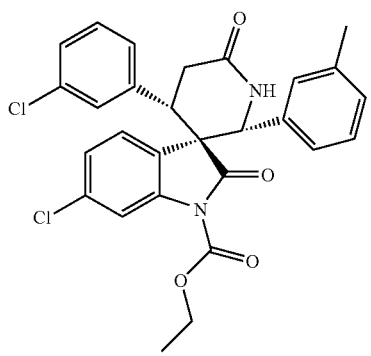

M. W. 523.42 C$_{28}$H$_{24}$Cl$_2$N$_2$O$_4$

In a manner similar to the method described in example 4c, E/Z-6-chloro-3-(3-chloro-benzylidene)-2-oxo-2,3-dihydro-indole-1-carboxylic acid ethyl ester (0.4 g, 1.10 mmol) prepared in example 4b was reacted with 1-(3-methylphenyl)-3-trimethylsilyoxy-2-aza-1,3-butadiene prepared in example 10a, in toluene to give racemic (2'R,3R,4'S)-6-chloro-4'-(3-chlorophenyl)-2,3-dihydro-2'-(3-methylphenyl)-2,6'-dioxospiro[indole-3,3'-piperidine]-1-carboxylic acid ethyl ester as a yellow oil (Yield 0.5 g, 86%).

EXAMPLE 10c

Preparation of racemic (2'R,3R,4'S)-6-chloro-4'-(3-chlorophenyl)-2'-(3-methylphenyl)spiro[3H-indole-3,3'-piperidine]-2,6'(1H)-dione

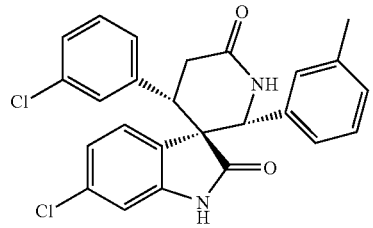

M. W. 451.35 C$_{25}$H$_{20}$Cl$_2$N$_2$O$_2$

In a manner similar to the method described in example 4d, racemic (2'R,3R,4'S)-6-chloro-4'-(3-chlorophenyl)-2,3-dihydro-2'-(3-methylphenyl)-2,6'-dioxospiro[indole-3,3'-piperidine]-1-carboxylic acid ethyl ester (0.5 g, 0.96 mmol) was reacted with NaOH (69 mg, 1.72 mmol) in methanol to give racemic (2'R,3R,4'S)-6-chloro-4'-(3-chlorophenyl)-2'-(3-methylphenyl)spiro[3H-indole-3,3'-piperidine]-2,6'(1H)-dione as a white solid (Yield 0.15 g, 35%).

HRMS (ES$^+$) m/z Calcd for C$_{25}$H$_{20}$Cl$_2$N$_2$O$_2$+H [(M+H)$^+$]: 451.0975. Found: 451.0976.

EXAMPLE 11a

Preparation of intermediate 1-(3-fluorophenyl)-3-trimethylsilyoxy-2-aza-1,3-butadiene

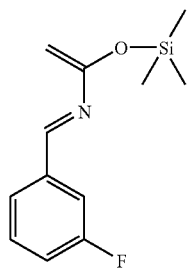

M. W. 237.35 C$_{12}$H$_{16}$FNOSi

In a manner similar to the method described in example 1b, 3-fluoro-benzaldehyde (1.11 mL, 10.5 mmol) (Fluka) was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(3-fluorophenyl)-3-trimethylsilyoxy-2-aza-1,3-butadiene as a yellow gum and used for the next step without further purification.

EXAMPLE 11b

Preparation of intermediate racemic (2'R,3R,4'S)-6-chloro-4'-(3-chlorophenyl)-2'-(3-fluorophenyl)-2,3-dihydro-2,6'-dioxospiro[indole-3,3'-piperidine]-1-carboxylic acid ethyl ester

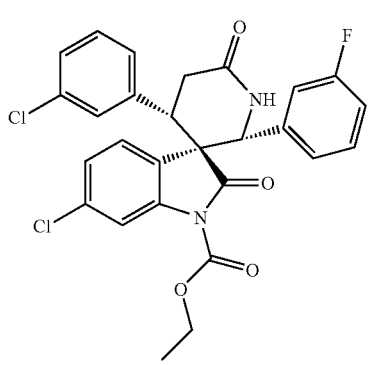

M. W. 527.38 $C_{27}H_{21}Cl_2FN_2O_4$

In a manner similar to the method described in example 4c, E/Z-6-chloro-3-(3-chloro-benzylidene)-2-oxo-2,3-dihydro-indole-1-carboxylic acid ethyl ester (0.25 g, 0.69 mmol) prepared in example 4b was reacted with 1-(3-fluorophenyl)-3-trimethylsilyoxy-2-aza-1,3-butadiene prepared in example 11a, in toluene to give racemic (2'R,3R,4'S)-6-chloro-4'-(3-chlorophenyl)-2'-(3-fluorophenyl)-2,3-dihydro-2,6'-dioxospiro[indole-3,3'-piperidine]-1-carboxylic acid ethyl ester as a yellow oil (Yield 0.35 g, 97%).

EXAMPLE 11c

Preparation of racemic (2'R,3R,4'S)-6-chloro-4'-(3-chlorophenyl)-2'-(3-fluorophenyl)spiro[3H-indole-3,3'-piperidine]-2,6'(1H)-dione

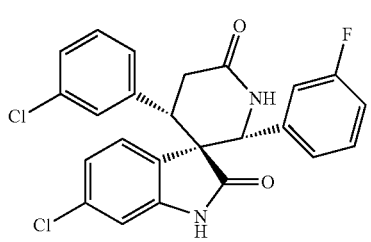

M. W. 455.314 $C_{24}H_{17}Cl_2FN_2O_2$

In a manner similar to the method described in example 4d, racemic (2'R,3R,4'S)-6-chloro-4'-(3-chlorophenyl)-2'-(3-fluorophenyl)-2,3-dihydro-2,6'-dioxospiro[indole-3,3'-piperidine]-1-carboxylic acid ethyl ester (0.35 g, 0.66 mmol) was reacted with NaOH (48 mg, 1.19 mmol) to give racemic (2'R,3R,4'S)-6-chloro-4'-(3-chlorophenyl)-2'-(3-fluorophenyl)spiro[3H-indole-3,3'-piperidine]-2,6'(1H)-dione as a white solid (Yield 0.15 g, 50%).

HRMS (ES+) m/z Calcd for $C_{24}H_{17}Cl_2FN_2O_2$+H [(M+H)+]: 451.0975. Found: 451.0976.

EXAMPLE 12a

Preparation of intermediate E/Z-3-benzylidene-6-chloro-1,3-dihydro-indol-2-one

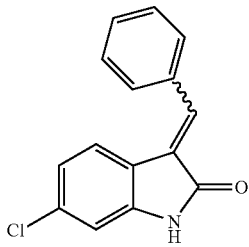

M. W. 255.71 $C_{15}H_{10}ClNO$

In a manner similar to the method described in example 1a, 6-chlorooxindole (1.0 g, 5.7 mmol) was reacted with benzaldehyde (0.6 g, 5.7 mmol) (Aldrich) and pyrrolidine (0.4 g, 5.7 mmol) in methanol to give a mixture of E- and Z-3-benzylidene-6-chloro-1,3-dihydro-indol-2-one as a yellow solid (Yield 1.5 g, 100%).

EXAMPLE 12b

Preparation of intermediate E/Z-3-benzylidene-6-chloro-2-oxo-2,3-dihydro-indole-1-carboxylic acid ethyl ester

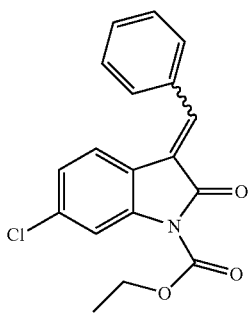

M. W. 327.77 $C_{18}H_{14}ClNO_3$

In a manner similar to the method described in example 4b, E/Z-3-benzylidene-6-chloro-1,3-dihydro-indol-2-one (1.5 g, 5.87 mmol) was reacted with ethyl chloroformate (0.83 mL, 8.8 mmol) and triethylamine (1.64 mL, 12 mmol) in dichloromethane to give E/Z-3-benzylidene-6-chloro-2-oxo-2,3-dihydro-indole-1-carboxylic acid ethyl ester as a yellow solid (Yield 2.0 g, 100%).

EXAMPLE 12c

Preparation of racemic (2'S,3S,4'R)-6-chloro-2'-(3-chlorophenyl)-4'-phenylspiro[3H-indole-3,3'-piperidine]-2,6'(1H)-dione

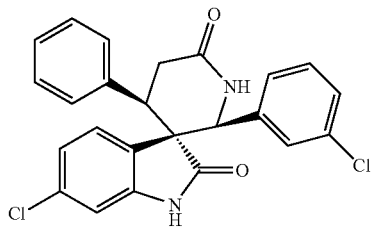

M. W. 437.33 $C_{24}H_{18}Cl_2N_2O_2$

To a solution of 1-(3-chlorophenyl)-3-trimethylsilyoxy-2-aza-1,3-butadiene prepared in example 1c in toluene (30 mL) was added E/Z-3-benzylidene-6-chloro-2-oxo-2,3-dihydro-indole-1-carboxylic acid ethyl ester prepared in Example 12b (0.4 g, 1.22 mmol). The reaction mixture was stirred under nitrogen in a sealed tube at 140° C. for 1 h. After the solution was cooled to room temperature, methanol (40 mL) was added. The reaction mixture was filtered through a short pad of celite gel and washed with ethyl acetate. The filtrate was concentrated. The residue was dissolved in methanol (30 mL) and 1N of NaOH solution (5 mL, 5 mmol) was added. The reaction mixture was stirred at room temperature for 0.5 h, then the mixture was concentrated. The residue was purified by chromatography (EtOAc:$CH_2Cl_2$=1:4) to give racemic (2'S,3S,4'R)-6-chloro-2'-(3-chlorophenyl)-4'-phenylspiro[3H-indole-3,3'-piperidine]-2,6'(1H)-dione as a yellow oil (Yield 0.5 g, 100%).

HRMS (ES$^+$) m/z Calcd for $C_{24}H_{18}Cl_2N_2O_2$+H [(M+H)$^+$]: 437.0818. Found: 437.0817.

EXAMPLE 13a

Preparation of intermediate 1-(3-chlorophenyl)-4-methyl-3-trimethylsilyoxy-2-aza-1,3-butadiene

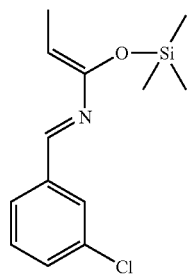

M. W. 267.83 $C_{13}H_{18}ClNOSi$

In a manner similar to the method described in example 1b, propionyl chloride (1.2 g, 13.mmol) (Aldrich) was used as the starting material in place of acetyl chloride to react with 1,1,3,3,3-hexamethyldisilazane (1.61 g, 10 mmol), n-butyllithium (2.5 M, 4 mL, 10 mmol), 3-chloro-benzaldehyde (1.4 g, 10 mmol) (Aldrich), trimethylsilyl chloride (1.1 g, 10 mmol) and triethylamine (1.36 g, 13 mmol) to give 1-(3-chlorophenyl)-4-methyl-3-trimethylsilyoxy-2-aza-1,3-butadiene as a yellow gum and used for the next step without further purification.

EXAMPLE 13b

Preparation of racemic (2'S,3S,4'R,5'R)-6-chloro-2'-(3-chlorophenyl)-5'-methyl-4'-phenylspiro[3H-indole-3,3'-piperidine]-2,6'(1H)-dione

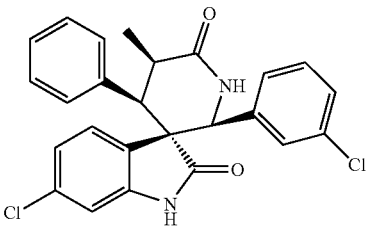

M. W. 451.36 $C_{25}H_{20}Cl_2N_2O_2$

In a manner similar to the method described in example 12c, E/Z-3-benzylidene-6-chloro-2-oxo-2,3-dihydro-indole-1-carboxylic acid ethyl ester (0.32 g, 0.98 mmol) prepared in example 12b was reacted with 1-(3-chlorophenyl)-4-methyl-3-trimethylsilyoxy-2-aza-1,3-butadiene (1.5 g, 5.6 mmol) prepared in example 13a in toluene and then 2 N of NaOH solution (4 mL, 8 mmol) in methanol to give racemic (2'S,3S, 4'R,5'R)-6-chloro-2'-(3-chlorophenyl)-5'-methyl-4'-phenylspiro[3H-indole-3,3'-piperidine]-2,6'(1H)-dione as a white foam (Yield 0.21 g, 48%).

HRMS (ES$^+$) m/z Calcd for $C_{25}H_{20}Cl_2N_2O_2$+H [(M+H)$^+$]: 451.0975. Found: 451.0972.

EXAMPLE 14a

Preparation of intermediate 1-phenyl-3-trimethylsilyoxy-2-aza-1,3-butadiene

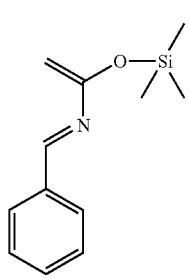

M. W. 219.36 $C_{12}H_{17}NOSi$

In a manner similar to the method described in example 1b, benzaldehyde (1.06 g, 10 mmol) (Aldrich) was used as the starting material in place of 3-chlorobenzaldehyde to react with 1,1,3,3,3-hexamethyldisilazane (1.6 mL, 10 mmol), n-butyllithium (2.5 M, 4 mL, 10 mmol), trimethylsilyl chloride (1.08 mL, 10 mmol), triethylamine (1.31 mL, 13 mmol) and acetyl chloride (1.02 g, 13 mmol) to give 1-phenyl-3-trimethylsilyoxy-2-aza-1,3-butadiene as a yellow gum and used for the next step without further purification.

EXAMPLE 14b

Preparation of racemic (2'R,3R,4'S)-6-chloro-4'-(3-chlorophenyl)-2'-phenylspiro[3H-indole-3,3'-piperidine]-2,6'(1H)-dione

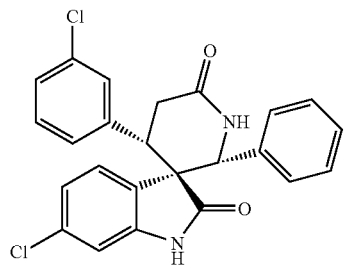

M. W. 437.33 $C_{24}H_{18}Cl_2N_2O_2$

To a solution of 1-phenyl-3-trimethylsilyoxy-2-aza-1,3-butadiene (1.5 g, 6.8 mmol) prepared in example 14a in toluene (30 mL) was added E/Z-3-benzylidene-6-chloro-2-oxo-2,3-dihydro-indole-1-carboxylic acid ethyl ester (0.22 g, 0.61 mmol) prepared in example 4b. The reaction mixture was stirred under nitrogen in a sealed tube at 150° C. for 1.5 h. After the solution was cooled to room temperature, methanol (40 mL) was added. The reaction mixture was filtered through a short pad of celite gel and washed with ethyl acetate. The filtrate was concentrated. The residue was dissolved in ethanol (20 mL) and NaOH (0.2 g, 5 mmol) was added, followed by the addition of a couple drops of $H_2O$. After the reaction mixture was stirred at room temperature for 1 h, the mixture was concentrated. The residue was partitioned between ethyl acetate and 1N of HCl solution. The organic layer was separated and concentrated. The residue was purified by chromatography (EtOAc:hexanes=2:1) to give racemic (2'R,3R,4'S)-6-chloro-4'-(3-chlorophenyl)-2'-phenylspiro[3H-indole-3,3'-piperidine]-2,6'(1H)-dione as a yellow solid (Yield 0.14 g, 52%).

HRMS (ES$^+$) m/z Calcd for $C_{24}H_{18}Cl_2N_2O_2$+H [(M+H)$^+$]: 437.0818. Found: 437.0816.

EXAMPLE 14c

Preparation of chiral (2'R,3R,4'S)-6-chloro-4'-(3-chlorophenyl)-2'-phenylspiro[3H-indole-3,3'-piperidine]-2,6'(1H)-dione

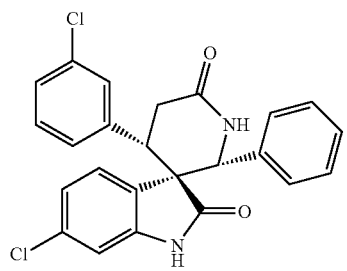

M. W. 437.33 $C_{24}H_{18}Cl_2N_2O_2$

Separation of the two enantiomers from racemic (2'R,3R,4'S)-6-chloro-4'-(3-chlorophenyl)-2'-phenylspiro[3H-indole-3,3'-piperidine]-2,6'(1H)-dione prepared in example 14b was conducted by chiral SFC to provide chiral (2'R,3R,4'S)-6-chloro-4'-(3-chlorophenyl)-2'-phenylspiro[3H-indole-3,3'-piperidine]-2,6'(1H)-dione as a yellow solid (25 mg) and chiral (2'S,3S,4'R)-6-chloro-4'-(3-chlorophenyl)-2'-phenylspiro[3H-indole-3,3'-piperidine]-2,6'(1H)-dione as a yellow solid (27 mg).

EXAMPLE 15a

Preparation of intermediate 1-(3-methoxyphenyl)-3-trimethylsilyoxy-2-aza-1,3-butadiene

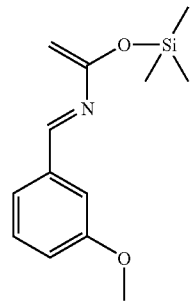

M. W. 249.39 $C_{13}H_{19}NO_2Si$

In a manner similar to the method described in example 1b, 3-methoxy-benzaldehyde (1.3 g, 9.5 mmol) (Aldrich) was used as the starting material in place of 3-chloro-benzaldehyde to react with 1,1,1,3,3,3-hexamethyldisilazane (1.53 g, 9.5 mmol), n-butyllithium (2.5 M, 3.8 mL, 9.5 mmol), trimethylsilyl chloride (1.2 mL, 9.5 mmol), triethylamine (1.72 mL, 12.4 mmol) and acetyl chloride (0.88 mL, 12.4 mmol) to give 1-(3-methoxyphenyl)-3-trimethylsilyoxy-2-aza-1,3-butadiene as a yellow gum and used for the next step without further purification.

EXAMPLE 15b

Preparation of racemic (2'R,3R,4'S)-6-chloro-4'-(3-chlorophenyl)-2'-(3-methoxyphenyl)spiro[3H-indole-3,3'-piperidine]-2,6'(1H)-dione

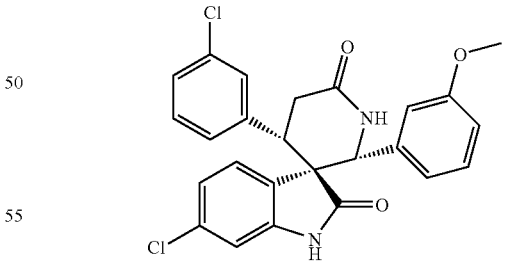

M. W. 467.36 $C_{25}H_{20}Cl_2N_2O_3$

In a manner similar to the method described in example 14b, E/Z-6-chloro-3-(3-chloro-benzylidene)-2-oxo-2,3-dihydro-indole-1-carboxylic acid ethyl ester (0.23 g, 0.63 mmol) prepared in example 4b was reacted with 1-(3-methoxyphenyl)-3-trimethylsilyoxy-4-methyl-2-aza-1,3-butadiene (2 g, 8.0 mmol) prepared in example 15a in toluene and then 2 N of NaOH solution (4 mL, 8 mmol) in methanol to give racemic (2'R,3R,4'S)-6-chloro-4'-(3-chlorophenyl)-2'-

(3-methoxyphenyl)spiro[3H-indole-3,3'-piperidine]-2,6'(1H)-dione (Yield 0.2 g, 69%).

HRMS (ES$^+$) m/z Calcd for $C_{25}H_{20}Cl_2N_2O_3$+H [(M+H)$^+$]: 467.0924. Found: 467.0925.

EXAMPLE 16a

Preparation of intermediate 1-(2-chlorophenyl)-3-trimethylsilyoxy-2-aza-1,3-butadiene

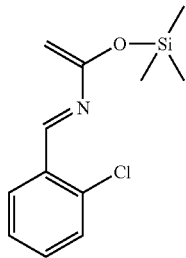

M. W. 253.81 $C_{12}H_{16}ClNOSi$

In a manner similar to the method described in example 1b, 2-chloro-benzaldehyde (1.3 g, 9.25 mmol) (Aldrich) was used as the starting material in place of 3-chloro-benzaldehyde to react with 1,1,1,3,3,3-hexamethyldisilazane (1.49 g, 9.25 mmol), n-butyllithium (2.5 M, 3.7 mL, 9.25 mmol), trimethylsilyl chloride (1.2 mL, 9.25 mmol), triethylamine (1.7 mL, 12.0 mmol) and acetyl chloride (0.85 mL, 12.0 mmol) to give 1-(2-chlorophenyl)-3-trimethylsilyoxy-2-aza-1,3-butadiene as a yellow gum and used for the next step without further purification.

EXAMPLE 16b

Preparation of intermediate racemic (2'R,3R,4'S)-6-chloro-2'-(2-chlorophenyl)-4'-(3-chlorophenyl)-2,3-dihydro-2,6'-dioxospiro[indole-3,3'-piperidine]-1-carboxylic acid ethyl ester

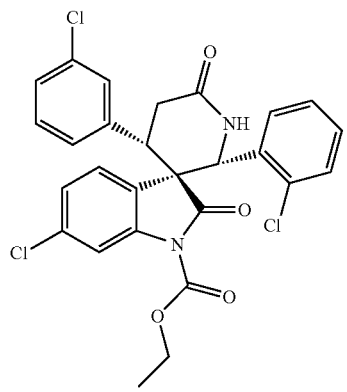

M. W. 543.84 $C_{27}H_{21}Cl_3N_2O_4$

In a manner similar to the method described in example 4c, E/Z-6-chloro-3-(3-chloro-benzylidene)-2-oxo-2,3-dihydro-indole-1-carboxylic acid ethyl ester (0.31 g, 0.85 mmol) prepared in example 4b was reacted with 1-(2-chlorophenyl)-3-trimethylsilyoxy-2-aza-1,3-butadiene (2.1 g, 8.27 mmol) prepared in example 16a, in toluene to give racemic (2'R,3R,4'S)-6-chloro-2'-(2-chlorophenyl)-4'-(3-chlorophenyl)-2,3-dihydro-2,6'-dioxospiro[indole-3,3'-piperidine]-1-carboxylic acid ethyl ester as a yellow gum (Yield 0.31 g, 67%).

EXAMPLE 16c

Preparation of racemic (2'R,3R,4'S)-6-chloro-2'-(2-chlorophenyl)-4'-(3-chlorophenyl)spiro[3H-indole-3,3'-piperidine]-2,6'(1H)-dione

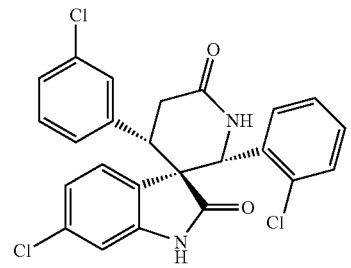

M. W. 471.77 $C_{24}H_{17}Cl_3N_2O_2$

In a manner similar to the method described in example 4d, racemic (2'R,3R,4'S)-6-chloro-2'-(2-chlorophenyl)-4'-(3-chlorophenyl)-2,3-dihydro-2,6'-dioxospiro[indole-3,3'-piperidine]-1-carboxylic acid ethyl ester (0.3 g, 0.55 mmol) was reacted with NaOH (2N, 5 mL, 10 mmol) in methanol to give racemic (2'R,3R,4'S)-6-chloro-2'-(2-chlorophenyl)-4'-(3-chlorophenyl)spiro[3H-indole-3,3'-piperidine]-2,6'(1H)-dione as a white solid (Yield: 0.21 g, 81%).

HRMS (ES$^+$) m/z Calcd for $C_{24}H_{17}Cl_3N_2O_2$+H [(M+H)$^+$]: 471.0429. Found: 471.0430.

EXAMPLE 16d

Preparation of chiral (2'R,3R,4'S)-6-chloro-2'-(2-chlorophenyl)-4'-(3-chlorophenyl)spiro[3H-indole-3,3'-piperidine]-2,6'(1H)-dione

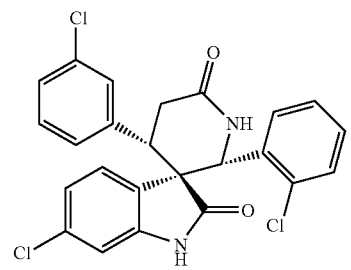

M. W. 471.77 $C_{24}H_{17}Cl_3N_2O_2$

Separation of the two enantiomers from racemic (2'R,3R,4'S)-6-chloro-2'-(2-chlorophenyl)-4'-(3-chlorophenyl)spiro[3H-indole-3,3'-piperidine]-2,6'(1H)-dione prepared in example 16c was conducted by chiral SFC to provide chiral (2'R,3R,4'S)-6-chloro-2'-(2-chlorophenyl)-4'-(3-chlorophenyl)spiro[3H-indole-3,3'-piperidine]-2,6'(1H)-dione as a white solid (53 mg) and (2'S,3S,4'R)-6-chloro-2'-(2-chlorophenyl)-4'-(3-chlorophenyl)spiro[3H-indole-3,3'-piperidine]-2,6'(1H)-dione as a white solid (51 mg).

EXAMPLE 17a

Preparation of intermediate 1-(2-methylphenyl)-3-trimethylsilyoxy-2-aza-1,3-butadiene

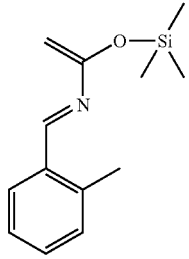

M. W. 233.39 C$_{13}$H$_{19}$NOSi

In a manner similar to the method described in example 1b, 2-methyl-benzaldehyde (1.2 g, 10 mmol) (Aldrich) was used as the starting material in place of 3-chloro-benzaldehyde to react with 1,1,1,3,3,3-hexamethyldisilazane (1.62 g, 10 mmol), n-butyllithium (2.5 M, 4 mL, 10 mmol), trimethylsilyl chloride (1.1 g, 10 mmol), triethylamine (1.3 g, 13 mmol) and acetyl chloride (1.0 g, 13 mmol) to give 1-(2-methylphenyl)-3-trimethylsilyoxy-2-aza-1,3-butadiene as a yellow gum and used for the next step without further purification.

EXAMPLE 17b

Preparation of intermediate racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid ethyl ester

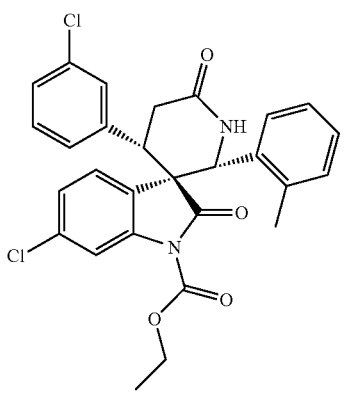

M. W. 523.42 C$_{28}$H$_{24}$Cl$_2$N$_2$O$_4$

In a manner similar to the method described in example 4c, E/Z-6-chloro-3-(3-chloro-benzylidene)-2-oxo-2,3-dihydro-indole-1-carboxylic acid ethyl ester (0.32 g, 0.88 mmol) prepared in example 4b was reacted with 1-(2-methylphenyl)-3-trimethylsilyoxy-2-aza-1,3-butadiene (2.4 g, 1.71 mmol) prepared in example 17a, in toluene to give racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid ethyl ester (Yield 0.4 g, 87%).

EXAMPLE 17c

Preparation of racemic (2'R,3R,4'S)-6-chloro-4'-(3-chlorophenyl)-2'-(2-methylphenyl)spiro[3H-indole-3,3'-piperidine]-2,6'(1H)-dione

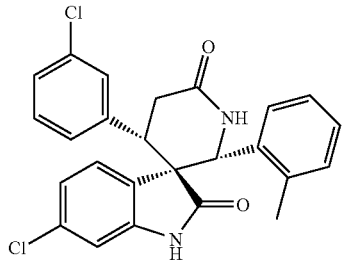

M. W. 451.36 C$_{25}$H$_{20}$Cl$_2$N$_2$O$_2$

In a manner similar to the method described in example 4d, racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid ethyl ester (0.4 g, 0.76 mmol) was reacted with 2 N of NaOH solution (10 mL, 20 mmol) in methanol to give racemic (2'R,3R,4'S)-6-chloro-4'-(3-chlorophenyl)-2'-(2-methylphenyl)spiro[3H-indole-3,3'-piperidine]-2,6'(1H)-dione (Yield 0.24 g, 70%).

HRMS (ES$^+$) m/z Calcd for C$_{25}$H$_{20}$Cl$_2$N$_2$O$_2$+H [(M+H)$^+$]: 451.0975. Found: 451.0972.

EXAMPLE 17d

Preparation of chiral (2'R,3R,4'S)-6-chloro-4'-(3-chlorophenyl)-2'-(2-methylphenyl)spiro[3H-indole-3,3'-piperidine]-2,6'(1H)-dione

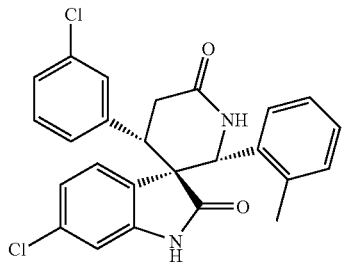

M. W. 451.36 C$_{25}$H$_{20}$Cl$_2$N$_2$O$_2$

Separation of the two enantiomers from racemic (2'R,3R,4'S)-6-chloro-4'-(3-chlorophenyl)-2'-(2-methylphenyl)spiro[3H-indole-3,3'-piperidine]-2,6'(1H)-dione prepared in example 23c was conducted by chiral SFC to provide chiral (2'R,3R,4'S)-6-chloro-4'-(3-chlorophenyl)-2'-(2-methylphenyl)spiro[3H-indole-3,3'-piperidine]-2,6'(1H)-dione as a white solid (52 mg) and chiral (2'S,3S,4'R)-6-chloro-4'-(3-chlorophenyl)-2'-(2-methylphenyl)spiro[3H-indole-3,3'-piperidine]-2,6'(1H)-dione as a white solid (52 mg).

EXAMPLE 18a

Preparation of intermediate 1-(2-ethylphenyl)-3-trimethylsilyoxy-2-aza-1,3-butadiene

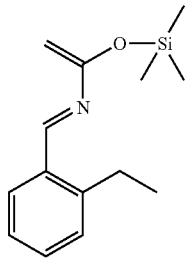

M. W. 247.42 $C_{14}H_{21}NOSi$

In a manner similar to the method described in example 1b, 2-ethyl-benzaldehyde (1.6 g, 11.8 mmol) (Aldrich) was used as the starting material in place of 3-chloro-benzaldehyde to react with 1,1,1,3,3,3-hexamethyldisilazane (1.96 g, 11.8 mmol), n-butyllithium (2.5 M, 4.7 mL, 11.8 mmol), trimethylsilyl chloride (1.50 mL, 11.8 mmol), triethylamine (2.13 mL, 15.3 mmol) and acetyl chloride (1.09 mL, 15.3 mmol) to give 1-(2-ethylphenyl)-3-trimethylsilyoxy-2-aza-1,3-butadiene as a yellow gum and used for the next step without further purification.

EXAMPLE 18b

Preparation of racemic (2'R,3R,4'S)-6-chloro-4'-(3-chlorophenyl)-2'-(2-ethylphenyl)spiro[3H-indole-3,3'-piperidine]-2,6'(1H)-dione

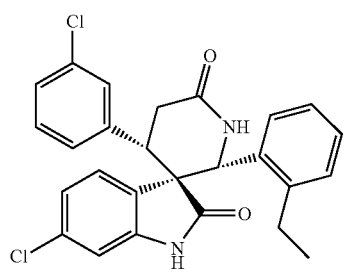

M. W. 465.38 $C_{26}H_{22}Cl_2N_2O_2$

In a manner similar to the method described in example 14b, E/Z-6-chloro-3-(3-chloro-benzylidene)-2-oxo-2,3-dihydro-indole-1-carboxylic acid ethyl ester (0.4 g, 1.1 mmol) prepared in example 4b was reacted with 1-(2-ethylphenyl)-3-trimethylsilyoxy-4-methyl-2-aza-1,3-butadiene (3.2 g, 12.9 mmol) prepared in example 18a in toluene and then 2 N of NaOH solution (5 mL, 10 mmol) in methanol to give racemic (2'R,3R,4'S)-6-chloro-4'-(3-chlorophenyl)-2'-(2-ethylphenyl)spiro[3H-indole-3,3'-piperidine]-2,6'(1H)-dione (Yield 0.085 g, 17%).

HRMS (ES$^+$) m/z Calcd for $C_{26}H_{22}Cl_2N_2O_2$+H [(M+H)$^+$]: 465.1131. Found: 465.1132.

EXAMPLE 18c

Preparation of chiral (2'R,3R,4'S)-6-chloro-4'-(3-chlorophenyl)-2'-(2-ethylphenyl)spiro[3H-indole-3,3'-piperidine]-2,6'(1H)-dione

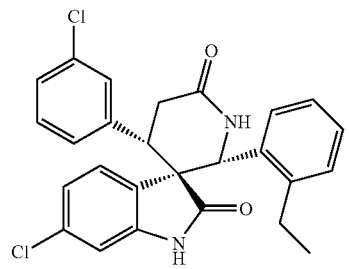

M. W. 465.38 $C_{26}H_{22}Cl_2N_2O_2$

Separation of the two enantiomers from racemic (2'R,3R,4'S)-6-chloro-4'-(3-chlorophenyl)-2'-(2-ethylphenyl)spiro[3H-indole-3,3'-piperidine]-2,6'(1H)-dione prepared in example 17b was conducted by chiral SFC to provide chiral (2'R,3R,4'S)-6-chloro-4'-(3-chlorophenyl)-2'-(2-ethylphenyl)spiro[3H-indole-3,3'-piperidine]-2,6'(1H)-dione as an off-white solid (25 mg) and chiral (2'S,3S,4'R)-6-chloro-4'-(3-chlorophenyl)-2'-(2-ethylphenyl)spiro[3H-indole-3,3'-piperidine]-2,6'(1H)-dione as an off-white solid (27 mg).

EXAMPLE 19a

Preparation of intermediate 4-methyl-1-(2-methylphenyl)-3-trimethylsilyoxy-2-aza-1,3-butadiene

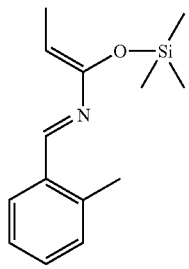

M. W. 247.42 $C_{14}H_{21}NOSi$

In a manner similar to the method described in example 13a, 2-methyl-benzaldehyde (1.2 g, 10 mmol) (Aldrich) was used as the starting material in place of 3-chloro-benzaldehyde to react with 1,1,1,3,3,3-hexamethyldisilazane (1.61 g, 10 mmol), n-butyllithium (2.5 M, 4 mL, 10 mmol), trimethylsilyl chloride (1.1 g, 10 mmol), triethylamine (1.4 g, 13 mmol) and propionyl chloride (1.2 g, 13 mmol) to give 4-methyl-1-(2-methyl phenyl)-3-trimethylsilyoxy-2-aza-1,3-butadiene as a yellow gum and used for the next step without further purification

EXAMPLE 19b

Preparation of racemic (2'R,3R,4'S,5'S)-6-chloro-4'-(3-chlorophenyl)-5'-methyl-2'-(2-methylphenyl)spiro[3H-indole-3,3'-piperidine]-2,6'(1H)-dione

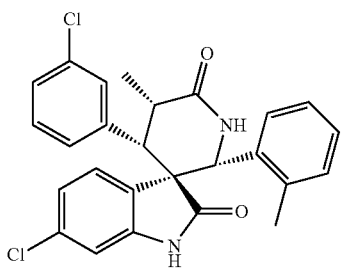

M. W. 465.38 $C_{26}H_{22}Cl_2N_2O_2$

In a manner similar to the method described in example 14b, E/Z-6-chloro-3-(3-chloro-benzylidene)-2-oxo-2,3-dihydro-indole-1-carboxylic acid ethyl ester (0.36 g, 0.99 mmol) prepared in example 4b was reacted with 4-methyl-1-(2-methylphenyl)-3-trimethylsilyoxy-2-aza-1,3-butadiene) prepared in example 19a in toluene and then 2 N of NaOH solution (4 mL, 8 mmol) in methanol to give racemic (2'R,3R,4'S,5'S)-6-chloro-4'-(3-chlorophenyl)-5'-methyl-2'-(2-methylphenyl)spiro[3H-indole-3,3'-piperidine]-2,6'(1H)-dione as a white solid (Yield 0.26 g, 56%).

HRMS (ES$^+$) m/z Calcd for $C_{26}H_{22}Cl_2N_2O_2$+H [(M+H)$^+$]: 465.1131. Found: 465.1132.

EXAMPLE 20

Preparation of racemic (2'R,3R,4'S,5'S)-6-chloro-2',4'-bis(3-chlorophenyl)-5'-methylspiro[3H-indole-3,3'-piperidine]-2,6'(1H)-dione

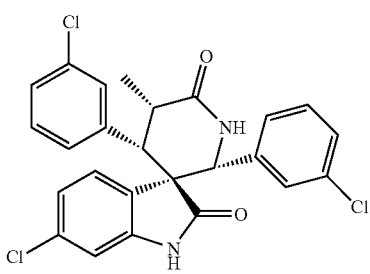

M. W. 485.80 $C_{25}H_{19}Cl_3N_2O_2$

In a manner similar to the method described in example 14b, E/Z-6-chloro-3-(3-chloro-benzylidene)-2-oxo-2,3-dihydro-indole-1-carboxylic acid ethyl ester (0.36 g, 0.99 mmol) prepared in example 4b was reacted with 1-(3-chlorophenyl)-4-methyl-3-trimethylsilyoxy-2-aza-1,3-butadiene (2.2 g, 8.9 mmol) prepared in example 13a in toluene and then 2 N of NaOH solution (4 mL, 8 mmol) in methanol to give racemic (2'R,3R,4'S,5'S)-6-chloro-2',4'-bis(3-chlorophenyl)-5'-methylspiro[3H-indole-3,3'-piperidine]-2,6'(1H)-dione (Yield 0.26 g, 57%).

HRMS (ES$^+$) m/z Calcd for $C_{25}H_{19}Cl_3N_2O_2$+H [(M+H)$^+$]: 485.0585. Found: 485.0583

EXAMPLE 21a

Preparation of intermediate 1-(2-isopropylphenyl)-3-trimethylsilyoxy-2-aza-1,3-butadiene

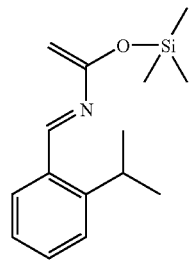

M. W. 261.44 $C_{15}H_{23}NOSi$

In a manner similar to the method described in example 1b, 2-isopropyl-benzaldehyde (1.5 g, 10 mmol) (Aldrich) was used as the starting material in place of 3-chloro-benzaldehyde to react with 1,1,1,3,3,3-hexamethyldisilazane (1.61 g, 10 mmol), n-butyllithium (2.5 M, 4 mL, 10 mmol), trimethylsilyl chloride (1.1 g, 10 mmol), triethylamine (1.3 g, 13 mmol) and acetyl chloride (1.0 g, 13 mmol) to give 1-(2-isopropylphenyl)-3-trimethylsilyoxy-2-aza-1,3-butadiene as a yellow gum and used for the next step without further purification.

EXAMPLE 21b

Preparation of racemic (2'R,3R,4'S)-6-chloro-4'-(3-chlorophenyl)-2'-(2-isopropylphenyl)spiro[3H-indole-3,3'-piperidine]-2,6'(1H)-dione

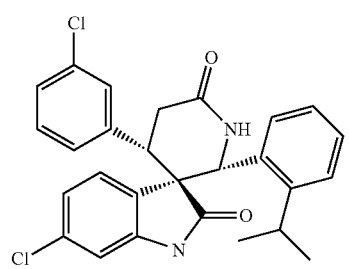

M. W. 479.41 $C_{27}H_{24}Cl_2N_2O_2$

In a manner similar to the method described in example 14b, E/Z-6-chloro-3-(3-chloro-benzylidene)-2-oxo-2,3-dihydro-indole-1-carboxylic acid ethyl ester (0.38 g, 1.05 mmol) prepared in example 4b was reacted with 1-(2-isopropylphenyl)-3-trimethylsilyoxy-2-aza-1,3-butadiene (2.7 g, 10.3 mmol) prepared in example 21a in toluene and then 2 N of NaOH solution (5 mL, 10 mmol) in methanol to give racemic (2'R,3R,4'S)-6-chloro-4'-(3-chlorophenyl)-2'-(2-isopropylphenyl)spiro[3H-indole-3,3'-piperidine]-2,6'(1H)-dione as a white solid (Yield 0.26 g, 52%).

HRMS (ES$^+$) m/z Calcd for $C_{27}H_{24}Cl_2N_2O_2$+H [(M+H)$^+$]: 479.1288. Found: 479.1289.

EXAMPLE 21c

Preparation of chiral (2'R,3R,4'S)-6-chloro-4'-(3-chlorophenyl)-2'-(2-isopropylphenyl)spiro[3H-indole-3,3'-piperidine]-2,6'(1H)-dione

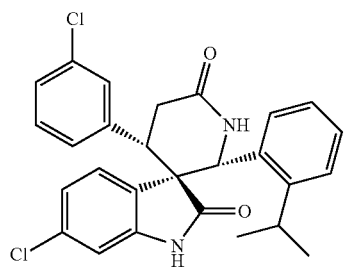

M. W. 479.41 $C_{27}H_{24}Cl_2N_2O_2$

Separation of the two enantiomers from racemic (2'R,3R,4'S)-6-chloro-4'-(3-chlorophenyl)-2'-(2-isopropylphenyl)spiro[3H-indole-3,3'-piperidine]-2,6'(1H)-dione prepared in example 21b was conducted by chiral SFC to provide chiral (2'R,3R,4'S)-6-chloro-4'-(3-chlorophenyl)-2'-(2-isopropylphenyl)spiro[3H-indole-3,3'-piperidine]-2,6'(1H)-dione as a white solid (61 mg) and (2'S,3S,4'R)-6-chloro-4'-(3-chlorophenyl)-2'-(2-isopropylphenyl)spiro[3H-indole-3,3'-piperidine]-2,6'(1H)-dione as a white solid (66 mg).

EXAMPLE 22a

Preparation of intermediate 1-(2-bromophenyl)-3-trimethylsilyoxy-2-aza-1,3-butadiene

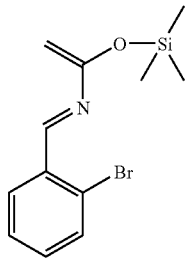

M. W. 298.26 $C_{12}H_{16}BrNOSi$

In a manner similar to the method described in example 1b, 2-bromo-benzaldehyde (1.85 g, 10 mmol) (Aldrich) was used as the starting material in place of 3-chloro-benzaldehyde to react with 1,1,1,3,3,3-hexamethyldisilazane (1.62 g, 10 mmol), n-butyllithium (2.5 M, 4 mL, 10 mmol), trimethylsilyl chloride (1.1 g, 10 mmol), triethylamine (1.3 g, 13 mmol) and acetyl chloride (1.0 g, 13 mmol) to give 1-(2-bromophenyl)-3-trimethylsilyoxy-2-aza-1,3-butadiene as a yellow gum and used for the next step without further purification.

EXAMPLE 22b

Preparation of intermediate racemic (2'R,3R,4'S)-2'-(2-bromophenyl)-6-chloro-4'-(3-chlorophenyl)-2,3-dihydro-2,6'-dioxospiro[indole-3,3'-piperidine]-1-carboxylic acid ethyl ester

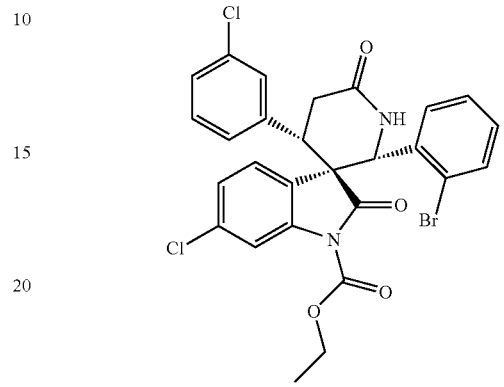

M. W. 588.29 $C_{27}H_{21}BrCl_2N_2O_4$

In a manner similar to the method described in example 4c, E/Z-6-chloro-3-(3-chloro-benzylidene)-2-oxo-2,3-dihydro-indole-1-carboxylic acid ethyl ester (0.4 g, 1.1 mmol) prepared in example 4b was reacted with 1-(2-bromophenyl)-3-trimethylsilyoxy-2-aza-1,3-butadiene (3.0 g, 10 mmol) prepared in example 22a, in toluene to give racemic (2'R,3R,4'S)-2'-(2-bromophenyl)-6-chloro-4'-(3-chlorophenyl)-2,3-dihydro-2,6'-dioxospiro[indole-3,3'-piperidine]-1-carboxylic acid ethyl ester (0.45 g, 69%).

EXAMPLE 22c

Preparation of racemic (2'R,3R,4'S)-2'-(2-bromophenyl)-6-chloro-4'-(3-chlorophenyl)spiro[3H-indole-3,3'-piperidine]-2,6'(1H)-dione

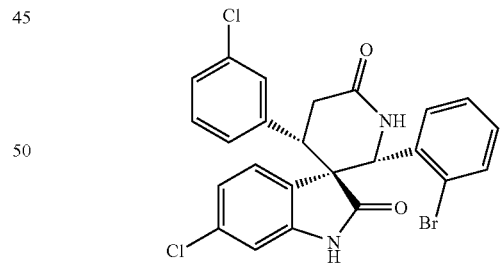

M. W. 516.23 $C_{24}H_{17}BrCl_2N_2O_2$

In a manner similar to the method described in example 4d, racemic (2'S,3R,4'S)-2'-(2-bromophenyl)-6-chloro-4'-(3-chlorophenyl)-2,3-dihydro-2,6'-dioxospiro[indole-3,3'-piperidine]-1-carboxylic acid ethyl ester (0.45 g, 0.76 mmol) was reacted with NaOH in methanol (2N, 5 mL, 10 mmol) to give racemic (2'R,3R,4'S)-2'-(2-bromophenyl)-6-chloro-4'-(3-chlorophenyl)spiro[3H-indole-3,3'-piperidine]-2,6'(1H)-dione as a white solid (Yield 0.25 g, 64%).

HRMS (ES$^+$) m/z Calcd for $C_{24}H_{17}BrCl_2N_2O_2$+H [(M+H)$^+$]: 514.9923. Found: 514.9926.

EXAMPLE 22d

Preparation of chiral (2'R,3R,4'S)-2'-(2-bromophenyl)-6-chloro-4'-(3-chlorophenyl)spiro[3H-indole-3,3'-piperidine]-2,6'(1H)-dione

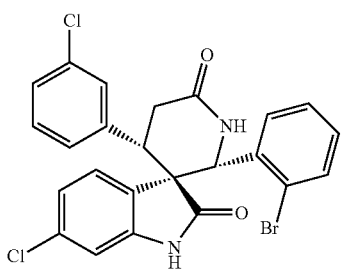

M. W. 516.23 C$_{24}$H$_{17}$BrCl$_2$N$_2$O$_2$

Separation of the two enantiomers from racemic (2'R,3R,4'S)-2'-(2-bromophenyl)-6-chloro-4'-(3-chlorophenyl)spiro[3H-indole-3,3'-piperidine]-2,6'(1H)-dione prepared in example 22c was conducted by chiral SFC to provide chiral (2'S,3R,4'S)-2'-(2-bromophenyl)-6-chloro-4'-(2-chlorophenyl)spiro[3H-indole-3,3'-piperidine]-2,6'(1H)-dione as a white solid (86 mg) and chiral (2'R,3S,4'R)-2'-(2-bromophenyl)-6-chloro-4'-(3-chlorophenyl)spiro[3H-indole-3,3'-piperidine]-2,6'(1H)-dione as a white solid (76 mg).

EXAMPLE 23a

Preparation of intermediate 1-(3-cyanophenyl)-3-trimethylsilyoxy-2-aza-1,3-butadiene

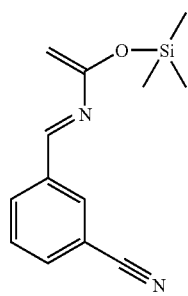

M. W. 244.37 C$_{13}$H$_{16}$N$_2$OSi

In a manner similar to the method described in example 1b, 3-cyano-benzaldehyde (1.2 g, 10 mmol) (Aldrich) was used as the starting material in place of 3-chloro-benzaldehyde to react with 1,1,1,3,3,3-hexamethyldisilazane (1.62 g, 10 mmol), n-butyllithium (2.5 M, 4 mL, 10 mmol), trimethylsilyl chloride (1.1 g, 10 mmol), triethylamine (1.3 g, 13 mmol) and acetyl chloride (1.0 g, 13 mmol) to give 1-(3-cyanophenyl)-3-trimethylsilyoxy-2-aza-1,3-butadiene as a yellow gum and used for the next step without further purification.

EXAMPLE 23b

Preparation of racemic (2'R,3R,4'S)-6-chloro-4'-(3-chlorophenyl)-2'-(3-cyanophenyl)spiro[3H-indole-3,3'-piperidine]-2,6'(1H)-dione

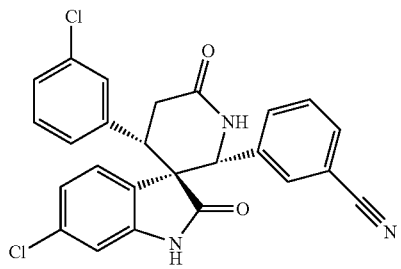

M. W. 462.34 C$_{25}$H$_{17}$Cl$_2$N$_3$O$_2$

In a manner similar to the method described in example 14b, E/Z-6-chloro-3-(3-chloro-benzylidene)-2-oxo-2,3-dihydro-indole-1-carboxylic acid ethyl ester (0.42 g, 1.2 mmol) prepared in example 4b was reacted with 1-(3-cyanophenyl)-3-trimethylsilyoxy-2-aza-1,3-butadiene (2.0 g, 8.18 mmol) prepared in example 23a in toluene and then 2 N of NaOH solution (5 mL, 10 mmol) in methanol to give racemic (2'R,3R,4'S)-6-chloro-4'-(3-chlorophenyl)-2'-(3-cyanophenyl)spiro[3H-indole-3,3'-piperidine]-2,6'(1H)-dione as a white foam (Yield 0.11 g, 20%).

HRMS (ES$^+$) m/z Calcd for C$_{25}$H$_{17}$Cl$_2$N$_3$O$_2$+H [(M+H)$^+$]: 462.0771 Found: 462.0771.

EXAMPLE 24a

Preparation of intermediate E/Z-6-chloro-3-(3-chloro-benzylidene)-2-oxo-2,3-dihydro-indole-1-carboxylic acid tert-butyl ester

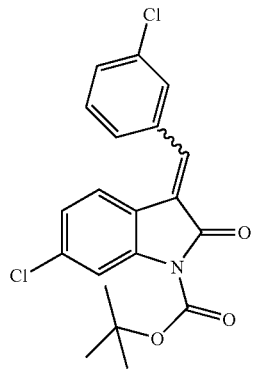

M. W. 390.27 C$_{20}$H$_{17}$Cl$_2$NO$_3$

To a solution of E/Z-6-chloro-3-(3-chloro-benzylidene)-1,3-dihydro-indol-2-one prepared in example 4a (1 g, 3.4 mmol) in dichloromethane (50 mL) at room temperature was added Di-tert-butyl-dicarbonate (1.5 g, 6.9 mmol) (Aldrich), followed by the addition of 4-dimethylaminopyridine (1 g, 8.2 mmol). The reaction mixture was stirred at room temperature for 1 h. The mixture was then concentrated and the residue was purified by chromatography to give E/Z-6-chloro-3-(3-chloro-benzylidene)-2-oxo-2,3-dihydro-indole-1-carboxylic acid tert-butyl ester as an orange solid (Yield 1.3 g, 96%).

EXAMPLE 24b

Preparation of intermediate racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid tert-butyl ester

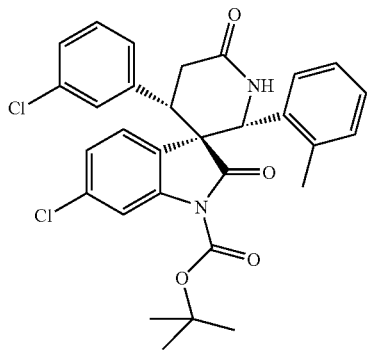

M. W. 551.47 C$_{30}$H$_{28}$Cl$_2$N$_2$O$_4$

In a manner similar to the method described in example 4c, E/Z-6-chloro-3-(3-chloro-benzylidene)-2-oxo-2,3-dihydroindole-1-carboxylic acid tert-butyl ester (1 g, 2.6 mmol) prepared in example 24a was reacted with 1-(2-methylphenyl)-3-trimethylsilyoxy-2-aza-1,3-butadiene (3.3 g, 14.1 mmol) prepared in example 17a, in toluene to give racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid tert-butyl ester as a white foam (Yield: 0.92 g, 65%).

EXAMPLE 24c

Preparation of intermediate racemic (2'R,3R,4'S)-6-chloro-4'-(3-chlorophenyl)-2,3-dihydro-1'-methyl-2'-(2-methylphenyl)-2,6'-dioxospiro[indole-3,3'-piperidine]-1-carboxylic acid tert-butyl ester

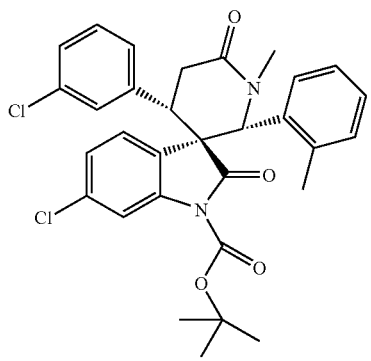

M. W. 565.50 C$_{31}$H$_{30}$Cl$_2$N$_2$O$_4$

To a solution of racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid tert-butyl ester (0.25 g, 0.45 mmol) in N,N-dimethyl-formamide (20 mL) at 0° C. was added LiH (90 mg, 11.2 mmol) (Aldrich), followed by the addition of iodomethane (0.39 g, 2.74 mmol). The reaction mixture was warmed up to room temperature and stirred at room temperature for 3 h. The mixture was diluted with ethyl acetate, and then washed with saturated NH$_4$Cl solution. The aqueous layer was extracted with ethyl acetate and the combined organic layer was dried over MgSO$_4$. The solvent was removed and the residue was purified by chromatography (EtOAc:hexanes=1:2) to give racemic (2'R,3R,4'S)-6-chloro-4'-(3-chlorophenyl)-2,3-dihydro-1'-methyl-2'-(2-methylphenyl)-2,6'-dioxospiro[indole-3,3'-piperidine]-1-carboxylic acid tert-butyl ester (Yield 0.20 g, 77%).

EXAMPLE 24d

Preparation of racemic (2'R,3R,4'S)-6-chloro-4'-(3-chlorophenyl)-1'-methyl-2'-(2-methylphenyl)spiro[3H-indole-3,3'-piperidine]-2,6'(1H)-dione

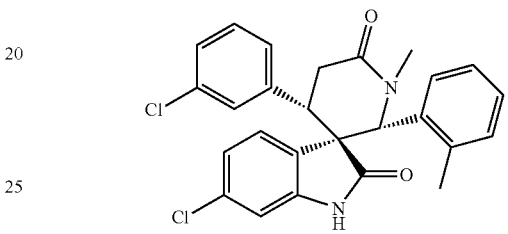

M. W. 465.38 C$_{26}$H$_{22}$Cl$_2$N$_2$O$_2$

Trifluoroacetic acid (5 mL) was added to a solution of racemic (2'R,3R,4'S)-6-chloro-4'-(3-chlorophenyl)-2,3-dihydro-1'-methyl-2'-(2-methylphenyl)-2,6'-dioxospiro[indole-3,3'-piperidine]-1-carboxylic acid tert-butyl ester (0.20 g, 0.35 mmol) prepared in example 24c in dichloromethane (10 mL). The mixture was stirred at room temperature for 1 h. The solvent was evaporated in vacuo. To this residue was added saturated NaHCO$_3$ solution, and extracted with ethyl acetate. The organic layers were combined, washed with water and brine, dried over MgSO$_4$. The solvent was removed and the residue was purified by chromatography (EtOAc:CH$_2$Cl$_2$=1:4) to give racemic (2'R,3R,4'S)-6-chloro-4'-(3-chlorophenyl)-1'-methyl-2'-(2-methylphenyl)spiro[3H-indole-3,3'-piperidine]-2,6'(1H)-dione as a white solid (Yield: 0.075 g, 46%).

HRMS (ES$^+$) m/z Calcd for C$_{26}$H$_{22}$Cl$_2$N$_2$O$_2$+H [(M+H)$^+$]: 465.1131. Found: 465.1132.

EXAMPLE 24e

Preparation of chiral (2'R,3R,4'S)-6-chloro-4'-(3-chlorophenyl)-1'-methyl-2'-(2-methylphenyl)spiro[3H-indole-3,3'-piperidine]-2,6'(1H)-dione

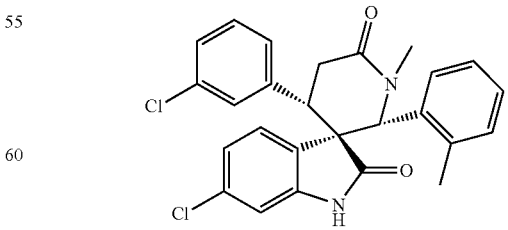

M. W. 465.38 C$_{26}$H$_{22}$Cl$_2$N$_2$O$_2$

Separation of the two enantiomers from racemic (2'R,3R,4'S)-6-chloro-4'-(3-chlorophenyl)-1'-methyl-2'-(2-methylphenyl)spiro[3H-indole-3,3'-piperidine]-2,6'(1H)-dione prepared in example 24d was conducted by chiral SFC to provide chiral (2'R,3R,4'S)-6-chloro-4'-(3-chlorophenyl)-1'-methyl-2'-(2-methylphenyl)spiro[3H-indole-3,3'-piperidine]-2,6'(1H)-dione as a white solid (24 mg) and chiral (2'S,3S,4'R)-6-chloro-4'-(3-chlorophenyl)-1'-methyl-2'-(2-methylphenyl)spiro[3H-indole-3,3'-piperidine]-2,6'(1H)-dione as a white solid (23 mg).

EXAMPLE 25a

Preparation of intermediate 1-(3-fluoro-2-methyl-phenyl)-3-trimethylsilyoxy-2-aza-1,3-butadiene

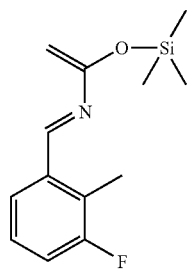

M. W. 251.38 C$_{13}$H$_{18}$FNOSi

In a manner similar to the method described in example 1b, 3-fluoro-2-methyl-benzaldehyde (1.4 g, 10 mmol) (Aldrich) was used as the starting material in place of 3-chloro-benzaldehyde to react with 1,1,3,3,3-hexamethyldisilazane (1.62 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(3-fluoro-2-methyl-phenyl)-3-trimethylsilyoxy-2-aza-1,3-butadiene as a yellow gum and used for the next step without further purification.

EXAMPLE 25b

Preparation of intermediate racemic (2'R,3R,4'S)-6-chloro-4'-(3-chlorophenyl)-2'-(3-fluoro-2-methyl-phenyl)-2,3-dihydro-2,6'-dioxospiro[indole-3,3'-piperidine]-1-carboxylic acid ethyl ester

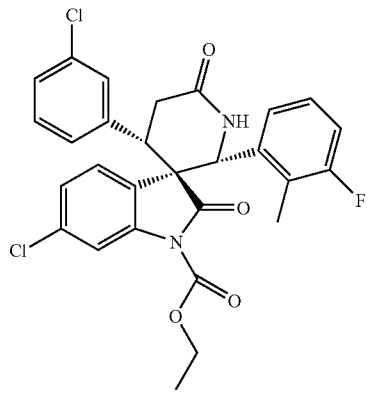

M. W. 541.41 C$_{28}$H$_{23}$Cl$_2$FN$_2$O$_4$

In a manner similar to the method described in example 4c, E/Z-6-chloro-3-(3-chloro-benzylidene)-2-oxo-2,3-dihydroindole-1-carboxylic acid ethyl ester (0.39 g, 1.08 mmol) prepared in example 4b was reacted with 1-(3-fluoro-phenyl-2-methyl)-3-trimethylsilyoxy-2-aza-1,3-butadiene (2.6 g, 10.3 mmol) prepared in example 31a, in toluene to give racemic (2'R,3R,4'S)-6-chloro-4'-(3-chlorophenyl)-2'-(3-fluoro-2-methyl-phenyl)-2,3-dihydro-2,6'-dioxospiro[indole-3,3'-piperidine]-1-carboxylic acid ethyl ester (Yield 0.35 g, 60%).

EXAMPLE 25c

Preparation of racemic (2'R,3R,4'S)-6-chloro-4'-(3-chlorophenyl)-2'-(3-fluoro-2-methyl-phenyl)spiro[3H-indole-3,3'-piperidine]-2,6'(1H)-dione

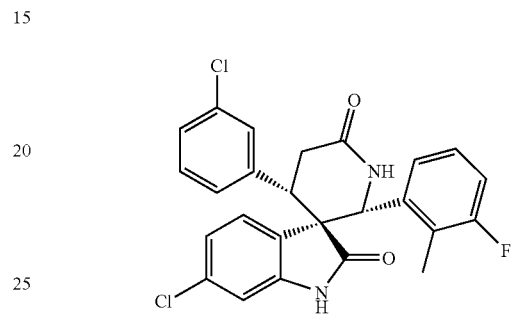

M. W. 469.35 C$_{25}$H$_{19}$Cl$_2$FN$_2$O$_2$

In a manner similar to the method described in example 4d, racemic (2'R,3R,4'S)-6-chloro-4'-(3-chlorophenyl)-2'-(3-fluoro-2-methyl-phenyl)-2,3-dihydro-2,6'-dioxospiro[indole-3,3'-piperidine]-1-carboxylic acid ethyl ester (0.35 g, 0.65 mmol) was reacted with NaOH (2N, 5 mL, 10 mmol) in methanol to give racemic (2'R,3R,4'S)-6-chloro-4'-(3-chlorophenyl)-2'-(3-fluoro-2-methyl-phenyl)spiro[3H-indole-3,3'-piperidine]-2,6'(1H)-dione as a white solid (Yield 0.25 g, 83%).

HRMS (ES$^+$) m/z Calcd for C$_{25}$H$_{19}$Cl$_2$FN$_2$O$_2$+H [(M+H)$^+$]: 469.0881. Found: 469.0885.

EXAMPLE 25d

Preparation of chiral (2'R,3R,4'S)-6-chloro-4'-(3-chlorophenyl)-2'-(3-fluoro-2-methyl-phenyl)spiro[3H-indole-3,3'-piperidine]-2,6'(1H)-dione

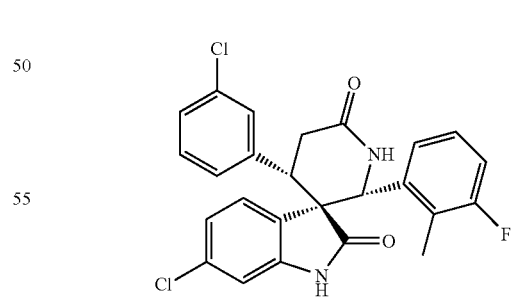

M. W. 469.35 C$_{25}$H$_{19}$Cl$_2$FN$_2$O$_2$

Separation of the two enantiomers from racemic (2'R,3R,4'S)-6-chloro-4'-(3-chlorophenyl)-2'-(3-fluoro-2-methyl-phenyl)spiro[3H-indole-3,3'-piperidine]-2,6'(1H)-dione prepared in example 25c was conducted by chiral SFC to provide chiral (2'R,3R,4'S)-6-chloro-4'-(3-chlorophenyl)-2'-(3-fluoro-2-methyl-phenyl)spiro[3H-indole-3,3'-piperidine]-2, 6'(1H)-dione as a white solid (71 mg) and chiral (2'S,3S,4'R)-6-chloro-4'-(3-chlorophenyl)-2'-(3-fluoro-2-methyl-phenyl)spiro[3H-indole-3,3'-piperidine]-2,6'(1H)-dione as a white solid (74 mg).

EXAMPLE 26a

Preparation of intermediate racemic (2'R,3R,4'S)-6-chloro-4'-(3-chlorophenyl)-1'-ethyl-2,3-dihydro-2'-(2-methylphenyl)-2,6'-dioxospiro[indole-3,3'-piperidine]-1-carboxylic acid tert-butyl ester

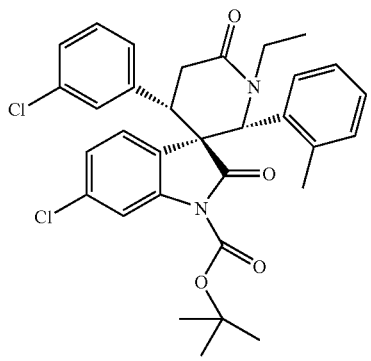

M. W. 579.53 $C_{32}H_{32}Cl_2N_2O_4$

In a manner similar to the method described in example 24c, racemic (2'R,3R,4'S)-6-chloro-4'-(3-chlorophenyl)-2,3-dihydro-2'-(2-methylphenyl-2,6'-dioxospiro[indole-3,3'-piperidine]-1-carboxylic acid tert-butyl ester (0.3 g, 0.54 mmol) prepared in example 24b was reacted with LiH (86 mg, 10.9 mmol) (Aldrich) and iodoethane (2 mL, 25 mmol) in N,N-dimethyl-formamide to give racemic (2'R,3R,4'S)-6-chloro-4'-(3-chlorophenyl)-1'-ethyl-2,3-dihydro-2'-(2-methylphenyl)-2,6'-dioxospiro[indole-3,3'-piperidine]-1-carboxylic acid tert-butyl ester as a white foam (Yield: 0.2 g, 63%).

EXAMPLE 26b

Preparation of racemic (2'R,3R,4'S)-6-chloro-4'-(3-chlorophenyl)-1'-ethyl-2'-(2-methylphenyl)spiro[3H-indole-3,3'-piperidine]-2,6'(1H)-dione

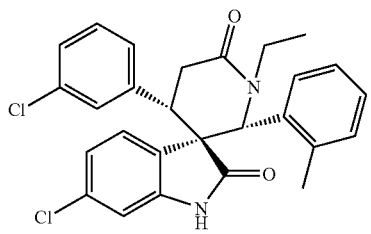

M. W. 479.41 $C_{27}H_{24}Cl_2N_2O_2$

In a manner similar to the method described in example 24d, racemic (2'R,3R,4'S)-6-chloro-4'-(3-chlorophenyl)-1'-ethyl-2,3-dihydro-2'-(2-methylphenyl)-2,6'-dioxospiro[indole-3,3'-piperidine]-1-carboxylic acid tert-butyl ester (0.2 g, 0.34 mmol) prepared in example 26a was reacted with trifluoroacetic acid in dichlormethane to give racemic (2'R,3R,4'S)-6-chloro-4'-(3-chlorophenyl)-1'-ethyl-2'-(2-methylphenyl)spiro[3H-indole-3,3'-piperidine]-2,6'(1H)-dione as an off-white foam (Yield: 0.11 g, 69%).

HRMS (ES+) m/z Calcd for $C_{27}H_{24}Cl_2N_2O_2$+H [(M+H)+]: 479.1288. Found: 479.1284.

EXAMPLE 26c

Preparation of chiral (2'R,3R,4'S)-6-chloro-4'-(3-chlorophenyl)-1'-ethyl-2'-(2-methylphenyl)spiro[3H-indole-3,3'-piperidine]-2,6'(1H)-dione

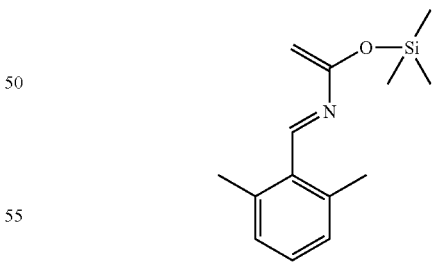

M. W. 479.41 $C_{27}H_{24}Cl_2N_2O_2$

Separation of the two enantiomers from racemic (2'R,3R,4'S)-6-chloro-4'-(3-chlorophenyl)-1'-ethyl-2'-(2-methylphenyl)spiro[3H-indole-3,3'-piperidine]-2,6'(1H)-dione prepared in 26b was conducted by chiral SFC to provide chiral (2'R,3R,4'S)-6-chloro-4'-(3-chlorophenyl)-1'-ethyl-2'-(2-methylphenyl)spiro[3H-indole-3,3'-piperidine]-2,6'(1H)-dione as a white solid (29 mg) and chiral (2'S,3S,4'R)-6-chloro-4'-(3-chlorophenyl)-1'-ethyl-2'-(2-methylphenyl)spiro[3H-indole-3,3'-piperidine]-2,6'(1H)-dione as a white solid (27 mg).

EXAMPLE 27a

Preparation of intermediate 1-(2,6-dimethylphenyl)-3-trimethylsilyoxy-2-aza-1,3-butadiene M. W. 247.42 $C_{14}H_{21}NOSi$ In a manner similar to the method described in example 1b, 2,6-dimethyl-benzaldehyde (1.3 g, 10 mmol) (Aldrich) was used as the starting material in place of 3-chloro-benzaldehyde to react with 1,1,3,3,3-hexamethyldisilazane (1.61 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,6-dimethylphenyl)-3-trimethylsilyoxy-2-aza-1,3-butadiene as an orange oil and used for the next step without further purification.

EXAMPLE 27b

Preparation of intermediate racemic (2'R,3R,4'S)-6-chloro-4'-(3-chlorophenyl)-2'-(2,6-dimethylphenyl)-2,3-dihydro-2,6'-dioxospiro[indole-3,3'-piperidine]-1-carboxylic acid ethyl ester

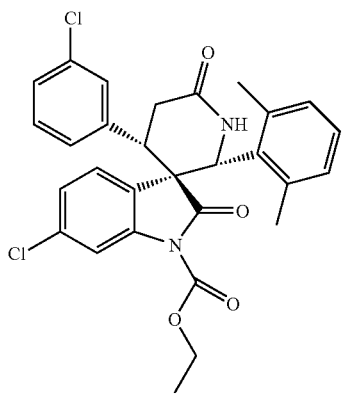

M. W. 537.45 $C_{29}H_{26}Cl_2N_2O_4$

In a manner similar to the method described in example 4c, E/Z-6-chloro-3-(3-chloro-benzylidene)-2-oxo-2,3-dihydro-indole-1-carboxylic acid ethyl ester (0.4 g, 1.08 mmol) prepared in example 4b was reacted with 1-(2,6-dimethylphenyl)-3-trimethylsilyoxy-2-aza-1,3-butadiene (2.9 g, 11.7 mmol) prepared in example 27a, in toluene to give racemic (2'R,3R,4'S)-6-chloro-4'-(3-chlorophenyl)-2'-(2,6-dimethylphenyl)-2,3-dihydro-2,6'-dioxospiro[indole-3,3'-piperidine]-1-carboxylic acid ethyl ester (Yield 0.41 g, 71%).

EXAMPLE 27c

Preparation of racemic (2'R,3R,4'S)-6-chloro-4'-(3-chlorophenyl)-2'-(2,6-dimethylphenyl)spiro[3H-indole-3,3'-piperidine]-2,6'(1H)-dione

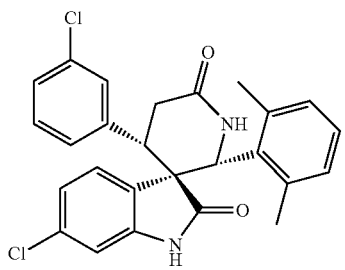

M. W. 465.38 $C_{26}H_{22}Cl_2N_2O_2$

In a manner similar to the method described in example 4d, (2'R,3R,4'S)-6-chloro-4'-(3-chlorophenyl)-2'-(2,6-dimethylphenyl)-2,3-dihydro-2,6'-dioxospiro[indole-3,3'-piperidine]-1-carboxylic acid ethyl ester (0.41 g, 0.76 mmol) was reacted with NaOH (0.4 g, 10 mmol) in methanol to give racemic (2'R,3R,4'S)-6-chloro-4'-(3-chlorophenyl)-2'-(2,6-dimethylphenyl)spiro[3H-indole-3,3'-piperidine]-2,6'(1H)-dione (Yield 0.25 g, 71%).

HRMS (ES$^+$) m/z Calcd for $C_{26}H_{22}Cl_2N_2O_2$+H [(M+H)$^+$]: 465.1131. Found: 465.1131.

EXAMPLE 28a

Preparation of intermediate 1-(2,3-dimethylphenyl)-3-trimethylsilyoxy-2-aza-1,3-butadiene

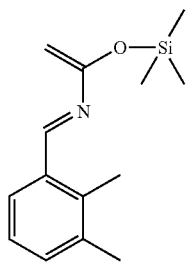

M. W. 247.42 $C_{14}H_{21}NOSi$

In a manner similar to the method described in example 1b, 2,3-dimethyl-benzaldehyde (1.34 g, 10 mmol) (Aldrich) was used as the starting material in place of 3-chloro-benzaldehyde to react with 1,1,3,3,3-hexamethyldisilazane (1.61 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,3-dimethylphenyl)-3-trimethylsilyoxy-2-aza-1,3-butadiene as a yellow gum and used for the next step without further purification.

EXAMPLE 28b

Preparation of racemic (2'R,3R,4'S)-6-chloro-4'-(3-chlorophenyl)-2'-(2,3-dimethylphenyl)spiro[3H-indole-3,3'-piperidine]-2,6'(1H)-dione

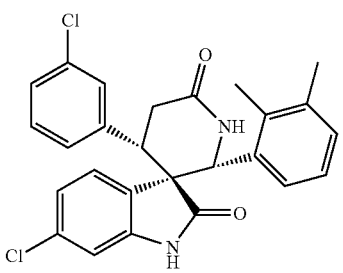

M. W. 465.38 $C_{26}H_{22}Cl_2N_2O_2$

In a manner similar to the method described in example 14b, E/Z-6-chloro-3-(3-chloro-benzylidene)-2-oxo-2,3-dihydro-indole-1-carboxylic acid ethyl ester (0.3 g, 0.83 mmol) prepared in example 4b was reacted with 1-(2,3-dimethylphenyl)-3-trimethylsilyoxy-2-aza-1,3-butadiene (2.4 g, 9.72 mmol) prepared in example 28a in toluene and then NaOH (0.2 g, 5 mmol) in methanol to give racemic (2'R,3R,4'S)-6-chloro-4'-(3-chlorophenyl)-2'-(2,3-dimethylphenyl)spiro[3H-indole-3,3'-piperidine]-2,6'(1H)-dione (Yield 0.20 g, 53%).

HRMS (ES+) m/z Calcd for C26H22Cl2N2O2+H [(M+H)+]: 465.1131. Found: 465.1131.

EXAMPLE 29a

Preparation of intermediate racemic (2'R,3R,4'S)-6-chloro-4'-(3-chlorophenyl)-2,3-dihydro-1'-[(methoxycarbonyl)-methyl]-2'-(2-methylphenyl)-2,6'-dioxospiro[indole-3,3'-piperidine]-1-carboxylic acid tert-butyl ester

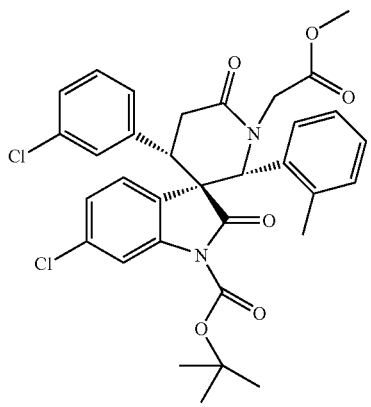

M. W. 623.54 C33H32Cl2N2O6

In a manner similar to the method described in example 24c, racemic (2'R,3R,4'S)-6-chloro-4'-(3-chlorophenyl)-2,3-dihydro-2'-(2-methylphenyl)-2,6'-dioxospiro[indole-3,3'-piperidine]-1-carboxylic acid tert-butyl ester (1.02 g, 1.86 mmol) prepared in example 24b was reacted with LiH (86 mg, 10.9 mmol) (Aldrich) and methyl bromoacetate (0.57 g, 3.72 mmol) (Aldrich) to give racemic 2'R,3R,4'S)-6-chloro-4'-(3-chlorophenyl)-2,3-dihydro-1'-[(methoxycarbonyl)-methyl]-2'-(2-methylphenyl)-2,6'-dioxospiro[indole-3,3'-piperidine]-1-carboxylic acid tert-butyl ester as a white solid (Yield: 0.37 g, 32%).

EXAMPLE 29b

Preparation of racemic (2'R,3R,4'S)-6-chloro-4'-(3-chlorophenyl)-1'-[(methoxycarbonyl)methyl]-2'-(2-methylphenyl)spiro[3H-indole-3,3'-piperidine]-2,6'(1H)-dione

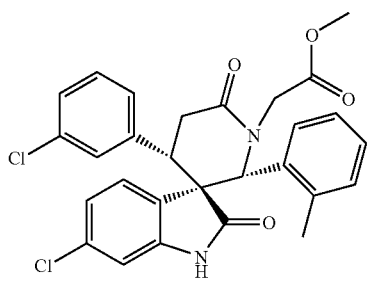

M. W. 523.42 C28H24Cl2N2O4

In a manner similar to the method described in example 24d, racemic 2'R,3R,4'S)-6-chloro-4'-(3-chlorophenyl)-2,3-dihydro-1'-[(methoxycarbonyl)-methyl]-2'-(2-methylphenyl)-2,6'-dioxospiro[indole-3,3'-piperidine]-1-carboxylic acid tert-butyl ester (0.37 g, 0.59 mmol) prepared in example 29a was reacted with trifluoroacetic acid (20 mL) in dichloromethane to give racemic (2'R,3R,4'S)-6-chloro-4'-(3-chlorophenyl)-1'-[(methoxycarbonyl)-methyl]-2'-(2-methylphenyl)spiro[3H-indole-3,3'-piperidine]-2,6'(1H)-dione as a white solid (Yield: 0.21 g, 67%).

HRMS (ES+) m/z Calcd for C28H24Cl2N2O4+H [(M+H)+]: 523.1186. Found: 523.1183.

EXAMPLE 30

Preparation of racemic (2'S,3R,4R)-6-chloro-2'-(3-chlorophenyl)-4'-isopropyl-6'-thioxospiro[3H-indole-3,3'-piperidine]-2(1H)-one

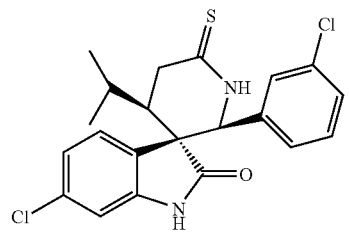

M. W. 419.38 C21H20Cl2N2OS

The mixture of racemic (2'S,3R)-6-chloro-2'-(3-chlorophenyl)-4',4'-isopropylspiro[3H-indole-3,3'-piperidine]-2,6'(1H)-dione (60 mg, 0.15 mmol) prepared in example 3b and 2,4-bis-(4-methoxyphenyl)-1,3-dithia-2,4-diphosphetane 2,4-disulfide (100 mg, 0.25 mmol) (Aldrich) in toluene (20 mL) was heated at 120° C. for 0.5 h. The mixture was cooled to room temperature and then concentrated. The residue was purified by chromatography (EtOAc:hexanes=1:1) to give racemic (2'S,3R)-6-chloro-2'-(3-chlorophenyl)-4'-isopropyl-6'-thioxospiro[3H-indole-3,3'-piperidine]-2(1H)-one as a white solid (Yield 60 mg, 92%).

HRMS (ES+) m/z Calcd for C21H20Cl2N2OS+H [(M+H)+]: 419.0746. Found: 419.0744.

EXAMPLE 31

Preparation of racemic (2'R,3R,4'S)-6-chloro-4'-(3-chlorophenyl)-1'-[(hydroxycarbonyl)-methyl]-2'-(2-methylphenyl)spiro[3H-indole-3,3'-piperidine]-2,6'(1H)-dione

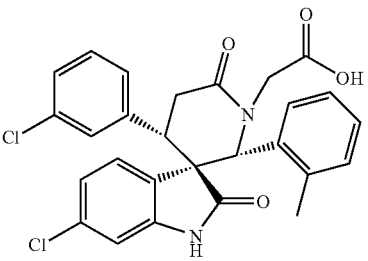

M. W. 509.39 C27H22Cl2N2O4

To the solution of racemic (2'R,3R,4'S)-6-chloro-4'-(3-chlorophenyl)-1'-[(methoxycarbonyl)-methyl]-2'-(2-methylphenyl)spiro[3H-indole-3,3'-piperidine]-2,6'(1H)-dione (0.21 g, 0.4 mmol) prepared in 29b in the mixture of methanol (10 mL) and tetrahydrofuran (20 mL) was added aqueous NaOH solution (1N, 10 mL, 10 mmol). The reaction mixture was stirred at room temperature for overnight and then concentrated. The residue was neutralized to "pH" ~7, then extracted with ethyl acetate. The organic layer was separated, washed with $H_2O$, brine, dried over $MgSO_4$ and concentrated to give racemic (2'R,3R,4'S)-6-chloro-4'-(3-chlorophenyl)-1'-[(hydroxycarbonyl)-methyl]-2'-(2-methylphenyl)spiro[3H-indole-3,3'-piperidine]-2,6'(1H)-dione as a white foam.

HRMS (ES$^+$) m/z Calcd for $C_{27}H_{22}Cl_2N_2O_4$+H [(M+H)$^+$]: 509.1030. Found: 509.1028.

EXAMPLE 32a

Preparation of intermediate 1-[2-(trifluoromethyl)-phenyl]-3-trimethylsilyoxy-2-aza-1,3-butadiene

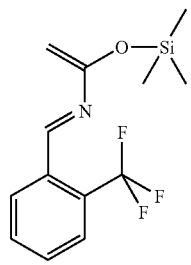

M. W. 287.36 $C_{13}H_{16}F_3NOSi$

In a manner similar to the method described in example 1b, 2-(trifluoromethyl)-benzaldehyde (1.75 g, 10 mmol) (Aldrich) was used as the starting material in place of 3-chloro-benzaldehyde to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-[2-(trifluoromethyl)-phenyl]-3-trimethylsilyoxy-2-aza-1,3-butadiene as a yellow gum and used for the next step without further purification.

EXAMPLE 32b

Preparation of racemic (2'R,3R,4'S)-6-chloro-4'-(3-chlorophenyl)-2'-[2-(trifluoromethyl)-phenyl]spiro[3H-indole-3,3'-piperidine]-2,6'(1H)-dione

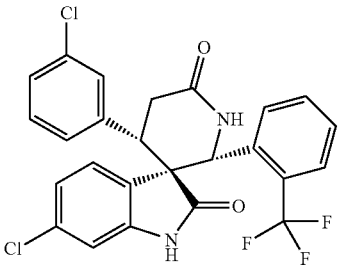

M. W. 505.33 $C_{25}H_{17}Cl_2F_3N_2O_2$

In a manner similar to the method described in example 14b, E/Z-6-chloro-3-(3-chloro-benzylidene)-2-oxo-2,3-dihydro-indole-1-carboxylic acid ethyl ester (0.5 g, 1.38 mmol) prepared in example 4b was reacted with 1-[2-(trifluoromethyl)-phenyl]-3-trimethylsilyoxy-2-aza-1,3-butadiene (3.2 g, 11.1 mmol) prepared in example 32a in toluene and then NaOH (0.2 g, 5 mmol) in methanol to give racemic (2'R,3R,4'S)-6-chloro-4'-(3-chlorophenyl)-2'-[2-(trifluoromethyl)-phenyl]spiro[3H-indole-3,3'-piperidine]-2,6'(1H)-dione as an off-white solid (Yield 0.45 g, 64%).

HRMS (ES$^+$) m/z Calcd for $C_{25}H_{17}Cl_2F_3N_2O_2$+H [(M+H)$^+$]: 505.0692. Found: 505.0688.

EXAMPLE 33

Preparation of racemic (2'R,3R,4'S)-6-chloro-4'-(3-chlorophenyl)-6'-thioxo-2'-[2-(trifluoromethyl)-phenyl]spiro[3H-indole-3,3'-piperidine]-2(1H)-one

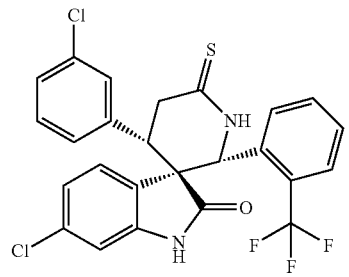

M. W. 521.39 $C_{25}H_{17}Cl_2F_3N_2OS$

In a manner similar to the method described in example 30, racemic (2'R,3R,4'S)-6-chloro-4'-(3-chlorophenyl)-2'-[2-(trifluoromethyl)-phenyl]spiro[3H-indole-3,3'-piperidine]-2,6'(1H)-dione (0.4 g, 0.79 mmol) prepared in example 32b was reacted with 2,4-bis-(4-methoxyphenyl)-1,3-dithia-2,4-diphosphetane 2,4-disulfide (0.4 g, 0.99 mmol) in toluene to give racemic (2'R,3R,4'S)-6-chloro-4'-(3-chlorophenyl)-6'-thioxo-2'-[2-(trifluoromethyl)-phenyl]spiro[3H-indole-3,3'-piperidine]-2(1H)-one (Yield 0.15 g, 36%).

HRMS (ES$^+$) m/z Calcd for $C_{25}H_{17}Cl_2F_3N_2OS$+H [(M+H)$^+$]: 521.0464. Found: 521.0458.

EXAMPLE 34a

Preparation of intermediate racemic (2'R,3R,4'S)-6-chloro-4'-(3-chlorophenyl)-1'-[(fluorocarbonyl)-methyl]-2'-(2-methylphenyl)spiro[3H-indole-3,3'-piperidine]-2,6'(1H)-dione

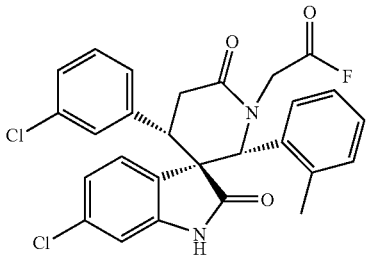

M. W. 511.38 $C_{27}H_{21}Cl_2FN_2O_3$

To the solution of (2'R,3R,4'S)-6-chloro-4'-(3-chlorophenyl)-1'-[(hydroxycarbonyl)-methyl]-2'-(2-methylphenyl)spiro[3H-indole-3,3'-piperidine]-2,6'(1H)-dione (0.12 g, 0.24 mmol) prepared in example 31 in dichloromethane (40 mL) at 0° C. was added cyanuric fluoride (48 mg, 0.35 mmol) (Alfa) and pyridine (37 mg, 0.48 mmol). After the mixture was stirred at 0° C. for 2 h, the mixture was partitioned between H$_2$O and dichloromethane. The organic layer was separated and the aqueous layer was extracted with dichloromethane. The organic layers were combined, dried over MgSO$_4$, concentrated to give racemic (2'R,3R,4'S)-6-chloro-4'-(3-chlorophenyl)-1'-[(fluorocarbonyl)-methyl]-2'-(2-methylphenyl)spiro[3H-indole-3,3'-piperidine]-2,6'(1H)-dione as a yellow gum and used for the next step without further purification (Yield: 0.12 g, 98%).

EXAMPLE 34b

Preparation of racemic (2'R,3R,4'S)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione

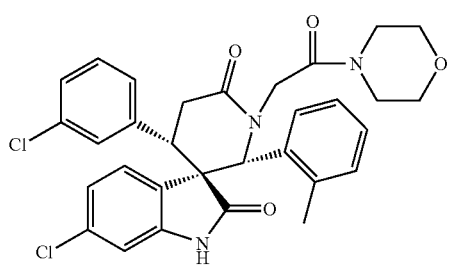

M. W. 578.50 C$_{31}$H$_{29}$Cl$_2$N$_3$O$_4$

To a solution of racemic (2'R,3R,4'S)-6-chloro-4'-(3-chlorophenyl)-1'-[(fluorocarbonyl)-methyl]-2'-(2-methylphenyl) spiro[3H-indole-3,3'-piperidine]-2,6'(1H)-dione (0.12 g, 0.23 mmol) prepared in 34a in tetrahydrofuran (10 mL) in a sealed tube was added morpholine (41 mg, 0.47 mmol), N-methylmorpholine (47 mg, 0.47 mmol) and 4-dimethylaminopyridine (3 mg, 0.025 mmol). After the mixture was heated under microwave irradiation at 100° C. for 10 min, the mixture was diluted with ethyl acetate, washed with 1N of HCl aqueous solution and H$_2$O. The organic layer was separated, dried over Na$_2$SO$_4$ and concentrated. The residue was purified by chromatography (MeOH:EtOAc=1:19) to give racemic (2'R,3R,4'S)-6-chloro-4'-(3-chlorophenyl)-2'-(2-methylphenyl)-1'-[2-(4-morpholinyl)-carbonyl-methyl] spiro[3H-indole-3,3'-piperidine]-2,6'(1H)-dione as a white solid (Yield: 0.11 g, 85%).

HRMS (ES$^+$) m/z Calcd for C$_{31}$H$_{29}$Cl$_2$N$_3$O$_4$+H [(M+H)$^+$]: 578.1608. Found: 578.1600.

EXAMPLE 34c

Preparation of chiral (2'R,3R,4'S)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione

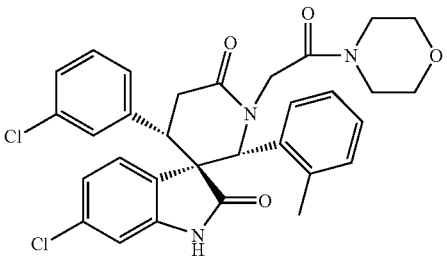

M. W. 578.50 C$_{31}$H$_{29}$Cl$_2$N$_3$O$_4$

Separation of the two enantiomers from racemic (2'R,3R,4'S)-6-chloro-4'-(3-chlorophenyl)-2'-(2-methylphenyl)-1'-[2-(4-morpholinyl)-2-oxoethyl]spiro[3H-indole-3,3'-piperidine]-2,6'(1H)-dione (51 mg) prepared in example 34b was conducted by chiral SFC to provide chiral (2'R,3R,4'S)-6-chloro-4'-(3-chlorophenyl)-2'-(2-methylphenyl)-1'-[2-(4-morpholinyl)-2-oxoethyl]spiro[3H-indole-3,3'-piperidine]-2,6'(1H)-dione as a white solid (Yield: 15 mg, 29%) and chiral (2'S,3S,4'R)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione as a white solid (Yield: 14 mg, 27%).

EXAMPLE 35a

Preparation of intermediate 1-[5-fluoro-2-(trifluoromethyl)-phenyl]-3-trimethylsilyoxy-2-aza-1,3-butadiene

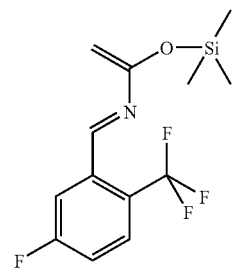

M. W. 305.35 C$_{13}$H$_{15}$F$_4$NOSi

In a manner similar to the method described in example 1b, 5-fluoro-2-(trifluoromethyl)-benzaldehyde (1.9 g, 10 mmol) (Matrix) was used as the starting material in place of 3-chloro-benzaldehyde to react with 1,1,3,3,3-hexamethyldisilazane (1.61 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-[5-fluoro-2-(trifluoromethyl)-phenyl]-3-trimethylsilyoxy-2-aza-1,3-butadiene as a yellow gum and used for the next step without further purification.

EXAMPLE 35b

Preparation of racemic (2'R,3R,4'S)-6-chloro-4'-(3-chlorophenyl)-2'-[5-fluoro-2-(trifluoromethyl)-phenyl]spiro[3H-indole-3,3'-piperidine]-2,6'(1H)-dione

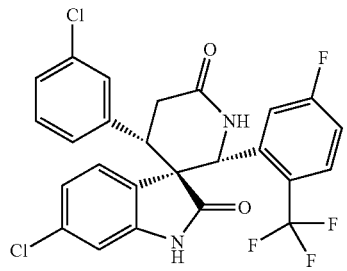

M. W. 523.32 $C_{25}H_{16}Cl_2F_4N_2O_2$

In a manner similar to the method described in example 14b, E/Z-6-chloro-3-(3-chloro-benzylidene)-2-oxo-2,3-dihydro-indole-1-carboxylic acid ethyl ester (0.41 g, 1.13 mmol) prepared in example 4b was reacted 1-[5-fluoro-2-(trifluoromethyl)-phenyl]-3-trimethylsilyoxy-2-aza-1,3-butadiene (2.9 g, 9.5 mmol) prepared in example 35a in toluene and then NaOH (0.2 g, 5 mmol) in methanol to give racemic (2'R,3R,4'S)-6-chloro-4'-(3-chlorophenyl)-2'-[5-fluoro-2-(trifluoromethyl)-phenyl]spiro[3H-indole-3,3'-piperidine]-2,6'(1H)-dione as an off-white solid (Yield 0.31 g, 52%).

HRMS (ES$^+$) m/z Calcd for $C_{25}H_{16}Cl_2F_4N_2O_2$+H [(M+H)$^+$]: 523.0598. Found: 523.0593.

EXAMPLE 36a

Preparation of intermediate 1-(5-fluoro-2-methylphenyl)-3-trimethylsilyoxy-2-aza-1,3-butadiene

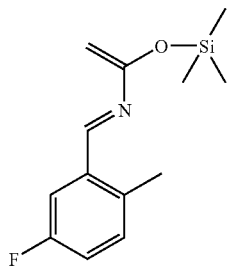

M. W. 251.38 $C_{13}H_{18}FNOSi$

In a manner similar to the method described in example 1b, 5-fluoro-2-methyl-benzaldehyde (1.38 g, 10 mmol) (Platte) was used as the starting material in place of 3-chloro-benzaldehyde to react with 1,1,1,3,3,3-hexamethyldisilazane (1.61 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(5-fluoro-2-methylphenyl)-3-trimethylsilyoxy-2-aza-1,3-butadiene as a yellow gum and used for the next step without further purification.

EXAMPLE 36b

Preparation of racemic (2'R,3R,4'S)-6-chloro-4'-(3-chlorophenyl)-2'-(5-fluoro-2-methylphenyl)spiro[3H-indole-3,3'-piperidine]-2,6'(1H)-dione

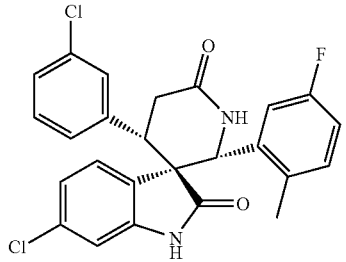

M. W. 469.35 $C_{25}H_{19}Cl_2FN_2O_2$

In a manner similar to the method described in example 14b, E/Z-6-chloro-3-(3-chloro-benzylidene)-2-oxo-2,3-dihydro-indole-1-carboxylic acid ethyl ester (0.25 g, 0.69 mmol) prepared in example 4b was reacted with 1-(5-fluoro-2-methylphenyl)-3-trimethylsilyoxy-2-aza-1,3-butadiene (2.5 g, 9.9 mmol) prepared in example 36a in toluene and then NaOH (1N, 5 mL, 5 mmol) in methanol to give racemic (2'R,3R,4'S)-6-chloro-4'-(3-chlorophenyl)-2'-(5-fluoro-2-methylphenyl)spiro[3H-indole-3,3'-piperidine]-2,6'(1H)-dione (Yield 0.13 g, 41%).

HRMS (ES$^+$) m/z Calcd for $C_{25}H_{19}Cl_2FN_2O_2$+H [(M+H)$^+$]: 469.0881. Found: 469.0881.

EXAMPLE 36c

Preparation of chiral (2'R,3R,4'S)-6-chloro-4'-(3-chlorophenyl)-2'-(5-fluoro-2-methylphenyl)spiro[3H-indole-3,3'-piperidine]-2,6'(1H)-dione

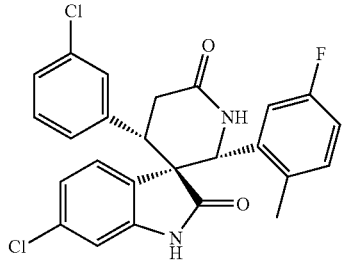

M. W. 469.35 $C_{25}H_{19}Cl_2FN_2O_2$

Separation of the two enantiomers (35 mg) from racemic (2'R,3R,4'S)-6-chloro-4'-(3-chlorophenyl)-2'-(5-fluoro-2-methylphenyl)spiro[3H-indole-3,3'-piperidine]-2,6'(1H)-dione prepared in example 36b was conducted by chiral SFC to provide chiral (2'R,3R,4'S)-6-chloro-4'-(3-chlorophenyl)-2'-(5-fluoro-2-methylphenyl)spiro[3H-indole-3,3'-piperidine]-2,6'(1H)-dione as a white solid (Yield: 10.7 mg, 30%) and chiral (2'S,3S,4'R)-6-chloro-4'-(3-chlorophenyl)-2'-(5-fluoro-2-methylphenyl)spiro[3H-indole-3,3'-piperidine]-2,6'(1H)-dione as a white solid (Yield: 11 mg, 31%).

EXAMPLE 37

Preparation of racemic (2'R,3R,4'S)-6-chloro-4'-(3-chlorophenyl)-1'-[(cyclopropylamino)-carbonyl-methyl]-2'-(2-methylphenyl)spiro[3H-indole-3,3'-piperidine]-2,6'(1H)-dione

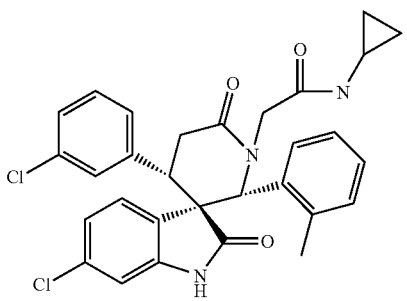

M. W. 548.47 $C_{30}H_{27}Cl_2N_3O_3$

In a manner similar to the method described in example 34b, racemic (2'R,3R,4'S)-6-chloro-4'-(3-chlorophenyl)-1'-[(fluorocarbonyl)-methyl]-2'-(2-methylphenyl)spiro[3H-indole-3,3'-piperidine]-2,6'(1H)-dione (0.12 g, 0.23 mmol) prepared in example 34a was reacted with cyclopropylamine (0.1 g, 1.8 mmol) (Aldrich), N-methylmorpholine (48 mg, 0.47 mmol) and 4-dimethylaminopyridine (2 mg, 0.017 mmol) in tetrahydrofuran to give racemic (2'R,3R,4'S)-6-chloro-4'-(3-chlorophenyl)-1'-[(cyclopropylamino)-carbonyl-methyl]-2'-(2-methylphenyl)spiro[3H-indole-3,3'-piperidine]-2,6'(1H)-dione as an off-white solid (Yield 0.039 g, 30%).

HRMS (ES$^+$) m/z Calcd for $C_{30}H_{27}Cl_2N_3O_3$ [(M+H)$^+$]: 548.1502. Found: 548.1501.

EXAMPLE 38

Preparation of racemic (2'R,3R,4'S)-6-chloro-[[2-[6-chloro-4'-(3-chlorophenyl)-2,3-dihydro-2'-(2-methylphenyl)-2,6-dioxospiro[3H-indole-3,3'-piperidin]-1-yl]-1-oxoethyl]-amino]-piperidine carboxylic acid tert-butyl ester

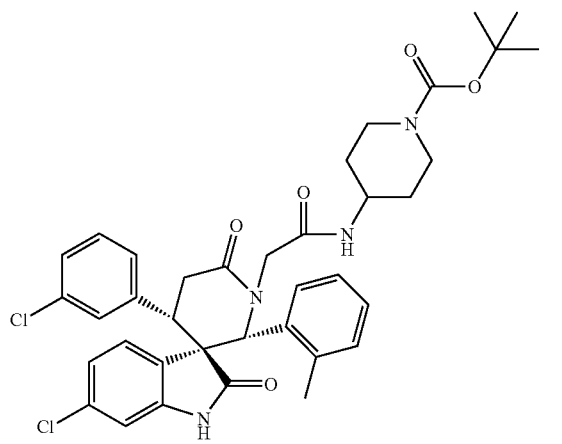

M. W. 691.66 $C_{37}H_{40}Cl_2N_4O_5$

In a manner similar to the method described in example 34b, racemic (2'R,3R,4'S)-6-chloro-4'-(3-chlorophenyl)-1'-[(fluorocarbonyl)-methyl]-2'-(2-methylphenyl)spiro[3H-indole-3,3'-piperidine]-2,6'(1H)-dione (0.12 g, 0.23 mmol) prepared in example 34a was reacted with 4-amino-piperidine-1-carboxylic acid tert-butyl ester (0.1 g, 0.5 mmol) (Aldrich), N-methylmorpholine (48 mg, 0.47 mmol) and 4-dimethylaminopyridine (2 mg, 0.017 mmol) in tetrahydrofuran to give racemic (2'R,3R,4'S)-6-chloro-[[2-[6-chloro-4'-(3-chlorophenyl)-2,3-dihydro-2'-(2-methylphenyl)-2,6-dioxospiro[3H-indole-3,3'-piperidin]-1-yl]-1-oxoethyl]-amino]-piperidine carboxylic acid tert-butyl ester as an off-white solid (Yield 0.036 g, 22%).

HRMS (ES$^+$) m/z Calcd for $C_{37}H_{40}Cl_2N_4O_5$ [(M+H)$^+$]: 691.2449. Found: 691.2441.

EXAMPLE 39

Preparation of racemic (2'R,3R,4'S)-6-chloro-4'-(3-chlorophenyl)-2'-(5-fluoro-2-methylphenyl)-6'-thioxospiro[3H-indole-3,3'-piperidine]-2(1H)-one

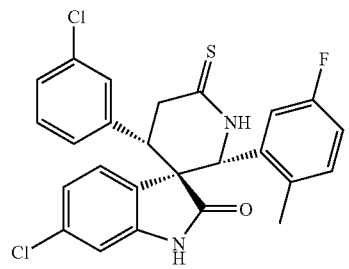

M. W. 485.41 $C_{25}H_{19}Cl_2FN_2OS$

In a manner similar to the method described in example 30, racemic (2'R,3R,4'S)-6-chloro-4'-(3-chlorophenyl)-2'-(5-fluoro-2-methylphenyl)spiro[3H-indole-3,3'-piperidine]-2,6'(1H)-dione (0.1 g, 0.21 mmol) prepared in example 36b was reacted with 2,4-bis-(4-methoxyphenyl)-1,3-dithia-2,4-diphosphetane 2,4-disulfide (0.2 g, 0.49 mmol) in toluene to give racemic (2'R,3R,4'S)-6-chloro-4'-(3-chlorophenyl)-2'-(5-fluoro-2-methylphenyl)-6'-thioxospiro[3H-indole-3,3'-piperidine]-2(1H)-one as a white solid (Yield 0.095 g, 92%).

HRMS (ES$^+$) m/z Calcd for $C_{25}H_{19}Cl_2FN_2OS$+H [(M+H)$^+$]: 485.0652. Found: 485.0648.

EXAMPLE 40

Preparation of racemic (2'R,3R,4'S)-[6-chloro-4'-(3-chlorophenyl)-2,3-dihydro-2'-[2-(trifluoromethyl)phenyl)]-2-oxospiro[3H-indole-3,3'-piperidin]-6-ylene]-hydrazine carboxylic acid ethyl ester

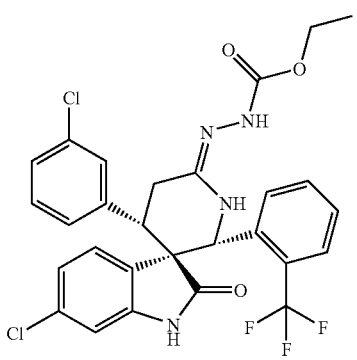

M. W. 591.42 $C_{28}H_{23}Cl_2F_3N_4O_3$

To a solution of racemic (2'R,3R,4'S)-6-chloro-4'-(3-chlorophenyl)-6'-thioxo-2'-[2-(trifluoromethyl)-phenyl]spiro[3H-indole-3,3'-piperidine]-2(1H)-one (0.035 g, 0.067 mmol) prepared in example 33 in tetrahydrofuran (30 mL) was added ethyl carbazate (0.019 g, 0.134 mmol) (Aldrich) and mercuric acetate (0.042 g, 0.134 mmol). After the reaction mixture was stirred at room temperature for 2 h, the reaction mixture was filtered through a short pad of celite. The filtrate was concentrated and the residue was purified by chromatography (EtOAc) to give racemic (2'R,3R,4'S)-[6-chloro-4'-(3-chlorophenyl)-2,3-dihydro-2'-[2-(trifluoromethyl)-phenyl)]-2-oxospiro[3H-indole-3,3'-piperidin]-6-ylene]-hydrazinecarboxylic acid ethyl ester as a white solid (Yield: 0.036 g, 91%).

HRMS (ES+) m/z Calcd for $C_{28}H_{23}Cl_2F_3N_4O_3$+H [(M+H)+]: 591.1172. Found: 591.1168

EXAMPLE 41a

Preparation of intermediate 1-(2,4-difluorophenyl)-3-trimethylsilyoxy-2-aza-1,3-butadiene

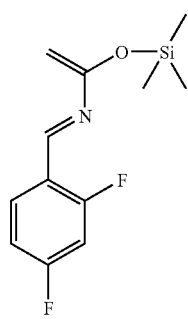

M. W. 255.34 $C_{12}H_{15}F_2NOSi$

In a manner similar to the method described in example 1b, 2,4-difluoro-benzaldehyde (1.4 g, 10 mmol) (Aldrich) was used as the starting material in place of 3-chloroben-zaldehyde to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,4-difluorophenyl)-3-trimethylsilyoxy-2-aza-1,3-butadiene as a yellow gum and used for the next step without further purification.

EXAMPLE 41b

Preparation of racemic (2'R,3R,4'S)-6-chloro-4'-(3-chlorophenyl)-2'-(2,4-difluorophenyl)spiro[3H-indole-3,3'-piperidine]-2,6'(1H)-dione

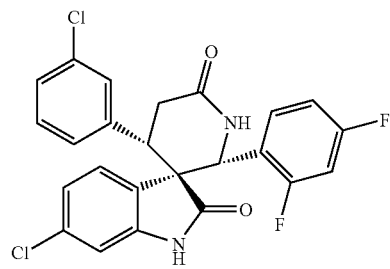

M. W. 473.31 $C_{24}H_{16}Cl_2F_2N_2O_2$

To a solution of 1-(2,4-difluorophenyl)-3-trimethylsilyoxy-2-aza-1,3-butadiene prepared in example 41a (2.4 g, 9.40 mmol) in toluene (30 mL) was added E/Z-6-chloro-3-(3-chlorobenzylidene)-2-oxo-2,3-dihydro-indole-1-carboxylic acid tert-butyl ester prepared in Example 24a (0.3 g, 0.77 mmol). The reaction mixture was stirred under nitrogen in a sealed tube at 140° C. for 0.5 h. After the solution was cooled to room temperature, methanol (10 mL) was added. The reaction mixture was filtered through a short pad of celite gel and washed with ethyl acetate. The filtrate was concentrated. The residue was dissolved in dichloromethane (20 mL) and trifluoroactic acid (15 mL) was added. After the reaction mixture was stirred at room temperature for 1 h, the mixture was concentrated. The residue was partitioned between saturated NaHCO3 solution and ethyl acetate. The aqueous layer was extracted with ethyl acetate. The combined organic layer was dried over Na2SO4 and concentrated. The residue was purified by chromatography (EtOAc:hexanes=2:1) to give racemic (2'R,3R,4'S)-6-chloro-4'-(3-chlorophenyl)-2'-(2,4-difluorophenyl)spiro[3H-indole-3,3'-piperidine]-2,6'(1H)-dione as an off-white solid (Yield 0.23 g, 63.9%).

HRMS (ES+) m/z Calcd for $C_{24}H_{16}Cl_2F_2N_2O_2$+H [(M+H)+]: 473.0630. Found: 473.0630.

EXAMPLE 42a

Preparation of intermediate 1-(5-fluoro-2-methoxyphenyl)-3-trimethylsilyoxy-2-aza-1,3-butadiene

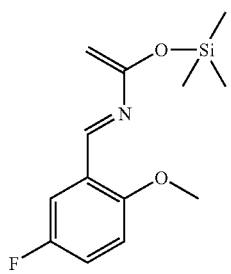

M. W. 267.38 $C_{13}H_{18}FNO_2Si$

In a manner similar to the method described in example 1b, 5-fluoro-2-methoxy-benzaldehyde (1.5 g, 10 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(5-fluoro-2-methoxyphenyl)-3-trimethylsilyoxy-2-aza-1,3-butadiene as a yellow gum and used for the next step without further purification.

EXAMPLE 42b

Preparation of racemic (2'R,3R,4'S)-6-chloro-4'-(3-chlorophenyl)-2'-(5-fluoro-2-methoxyphenyl)spiro[3H-indole-3,3'-piperidine]-2,6'(1H)-dione

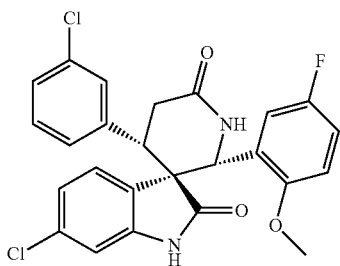

M. W. 485.36 $C_{25}H_{19}Cl_2FN_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.3 g, 0.77 mmol) was reacted with 1-(5-fluoro-2-methoxyphenyl)-3-trimethylsilyoxy-2-aza-1,3-butadiene (2.4 g, 9.0 mmol) prepared in example 42a in toluene and then trifluoroacetic acid (15 mL) in dichloromethane to give racemic (2'R,3R,4'S)-6-chloro-4'-(3-chlorophenyl)-2'-(5-fluoro-2-methoxyphenyl)spiro[3H-indole-3,3'-piperidine]-2,6'(1H)-dione (Yield 0.18 g, 49%).

HRMS (ES$^+$) m/z Calcd for $C_{25}H_{19}Cl_2FN_2O_3$+H [(M+H)$^+$]: 485.0830. Found: 485.0827.

EXAMPLE 43a

Preparation of intermediate 1-(1-naphthalenyl)-3-trimethylsilyoxy-2-aza-1,3-butadiene

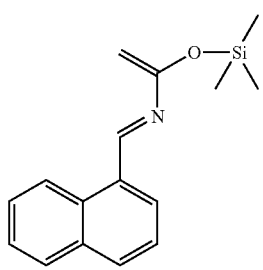

M. W. 269.42 $C_{16}H_{19}NOSi$

In a manner similar to the method described in example 1b, naphthalene-1-carbaldehyde (1.6 g, 10 mmol) (Lancaster) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(1-naphthalenyl)-3-trimethylsilyoxy-2-aza-1,3-butadiene as a yellow gum and used for the next step without further purification.

EXAMPLE 43b

Preparation of racemic (2'R,3R,4'S)-6-chloro-4'-(3-chlorophenyl)-2'-(1-naphthalenyl)spiro[3H-indole-3,3'-piperidine]-2,6'(1H)-dione

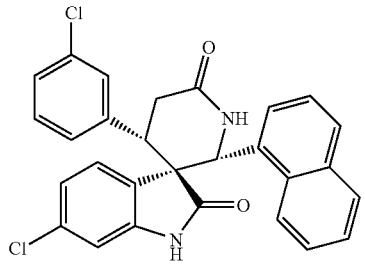

M. W. 487.39 $C_{28}H_{10}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.3 g, 0.77 mmol) was reacted with 1-(1-naphthalenyl)-3-trimethylsilyoxy-2-aza-1,3-butadiene (2.7 g, 10.0 mmol) prepared in example 43a in toluene and then trifluoroacetic acid (15 mL) in dichloromethane to give racemic (2'R,3R,4'S)-6-chloro-4'-(3-chlorophenyl)-2'-(1-naphthalenyl)spiro[3H-indole-3,3'-piperidine]-2,6'(1H)-dione (Yield 0.21 g, 57%).

HRMS (ES$^+$) m/z Calcd for $C_{28}H_{10}Cl_2N_2O_2$+H [(M+H)$^+$]: 487.0975. Found: 487.0975.

EXAMPLE 44a

Preparation of intermediate 1-(3-pyridinyl)-3-trimethylsilyoxy-2-aza-1,3-butadiene

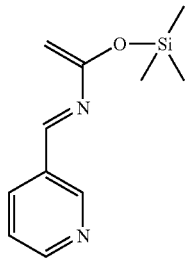

M. W. 220.35 $C_{11}H_{16}N_2OSi$

In a manner similar to the method described in example 1b, pyridine-3-carbaldehyde (1.1 g, 10 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(3-pyridinyl)-3-trimethylsilyoxy-2-aza-1,3-butadiene as a yellow gum and used for the next step without further purification.

EXAMPLE 44b

Preparation of racemic (2'R,3R,4'S)-6-chloro-4'-(3-chlorophenyl)-2'-(3-pyridinyl)spiro[3H-indole-3,3'-piperidine]-2,6'(1H)-dione

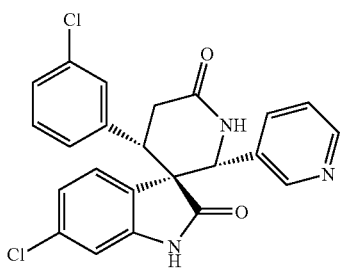

M. W. 438.32 $C_{23}H_{17}Cl_2N_3O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.3 g, 0.77 mmol) was reacted with 1-(3-pyridinyl)-3-trimethylsilyoxy-2-aza-1,3-butadiene (2.1 g, 9.5 mmol) prepared in example 44a in toluene and then trifluoroacetic acid (10 mL) in dichloromethane to give racemic (2'R,3R,4'S)-6-chloro-4'-(3-chlorophenyl)-2'-(3-pyridinyl)spiro[3H-indole-3,3'-piperidine]-2,6'(1H)-dione (0.21 g, 62%).

HRMS (ES$^+$) m/z Calcd for $C_{23}H_{17}Cl_2N_3O_2$+H [(M+H)$^+$]: 438.0771. Found: 438.0771.

EXAMPLE 45a

Preparation of intermediate 1-(2,3-difluoro-6-methoxyphenyl)-3-trimethylsilyoxy-2-aza-1,3-butadiene

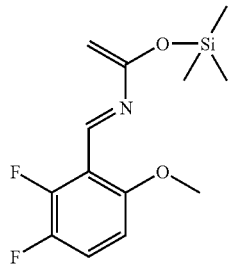

M. W. 285.37 $C_{13}H_{17}F_2NO_2Si$

In a manner similar to the method described in example 1b, 2,3-difluoro-6-methoxy-benzaldehyde (1.8 g, 10 mmol) (Apollo) was used as the starting material in place of 3-chloro-benzaldehyde to react with 1,1,1,3,3,3-hexamethyl-disilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,3-difluoro-6-methoxyphenyl)-3-trimethylsilyoxy-2-aza-1,3-butadiene as an orange gum and used for the next step without further purification.

EXAMPLE 45b

Preparation of racemic (2'R,3R,4'S)-6-chloro-4'-(3-chlorophenyl)-2'-(2,3-difluoro-6-methoxyphenyl)spiro[3H-indole-3,3'-piperidine]-2,6'(1H)-dione

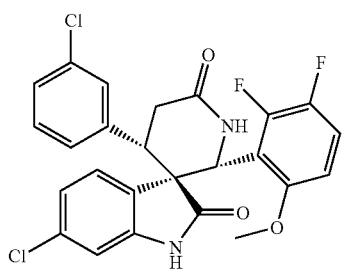

M. W. 503.34 $C_{25}H_{18}Cl_2F_2N_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.3 g, 0.77 mmol) was reacted with 1-(2,3-difluoro-6-methoxyphenyl)-3-trimethylsilyoxy-2-aza-1,3-butadiene (2.5 g, 8.8 mmol) prepared in example 45a in toluene and then trifluoroacetic acid (15 mL) in dichloromethane to give racemic (2'R,3R,4'S)-6-chloro-4'-(3-chlorophenyl)-2'-(2,3-difluoro-6-methoxyphenyl)spiro[3H-indole-3,3'-piperidine]-2,6'(1H)-dione (0.22 g, 56%).

HRMS (ES$^+$) m/z Calcd for $C_{25}H_{18}Cl_2F_2N_2O_3$+H [(M+H)$^+$]: 503.0736. Found: 503.0735.

EXAMPLE 46a

Preparation of intermediate 1-(3,4-difluorophenyl)-3-trimethylsilyoxy-2-aza-1,3-butadiene

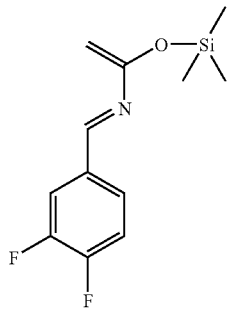

M. W. 255.34 $C_{12}H_{15}F_2NOSi$

In a manner similar to the method described in example 1b, 3,4-difluoro-benzaldehyde (1.4 g, 10 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(3,4-difluorophenyl)-3-trimethylsilyoxy-2-aza-1,3-butadiene as an orange gum and used for the next step without further purification.

EXAMPLE 46b

Preparation of racemic (2'R,3R,4'S)-6-chloro-4'-(3-chlorophenyl)-2'-(3,4-difluorophenyl)spiro[3H-indole-3,3'-piperidine]-2,6'(1H)-dione

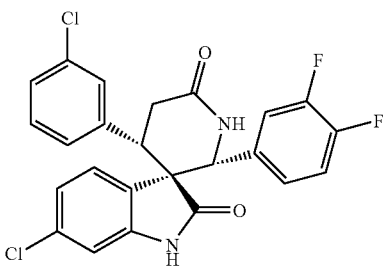

M. W. 473.31 $C_{24}H_{16}Cl_2F_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.3 g, 0.77 mmol) was reacted with 1-(3,4-difluorophenyl)-3-trimethylsilyoxy-2-aza-1,3-butadiene (2.1 g, 8.2 mmol) prepared in example 46a in toluene and then trifluoroacetic acid (10 mL) in dichloromethane to give racemic (2'R,3R,4'S)-6-chloro-4'-(3-chlorophenyl)-2'-(3,4-difluorophenyl)spiro[3H-indole-3,3'-piperidine]-2,6'(1H)-dione (0.4 g, 100%).

HRMS (ES$^+$) m/z Calcd for $C_{24}H_{16}Cl_2F_2N_2O_2$+H [(M+H)$^+$]: 473.0630. Found: 473.0631.

EXAMPLE 47a

Preparation of intermediate 1-(1-cyclohexenyl)-3-trimethylsilyoxy-2-aza-1,3-butadiene

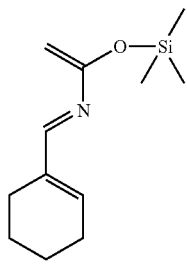

M. W. 223.39 $C_{12}H_{21}NOSi$

In a manner similar to the method described in example 1b, 1-cyclohexene-1-carboxaldehyde (1.1 g, 10 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(1-cyclohexenyl)-3-trimethylsilyoxy-2-aza-1,3-butadiene as an off-white gum and used for the next step without further purification.

EXAMPLE 47b

Preparation of racemic (2'R,3R,4'S)-6-chloro-4'-(3-chlorophenyl)-2'-(1-cyclohexenyl)spiro[3H-indole-3,3'-piperidine]-2,6'(1H)-dione

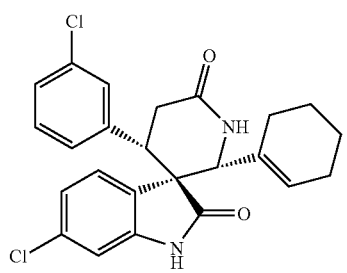

M. W. 441.36 $C_{24}H_{22}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.26 g, 0.67 mmol) was reacted with 1-(1-cyclohexenyl)-3-trimethylsilyoxy-2-aza-1,3-butadiene (2.1 g, 9.42 mmol) prepared in example 47a in toluene and then trifluoroacetic acid (10 mL) in dichloromethane to give racemic (2'R,3R,4'S)-6-chloro-4'-(3-chlorophenyl)-2'-(1-cyclohexenyl)spiro[3H-indole-3,3'-piperidine]-2,6'(1H)-dione as an off-white solid (0.14 g, 48%).

HRMS (ES$^+$) m/z Calcd for $C_{24}H_{22}Cl_2N_2O_2$+H [(M+H)$^+$]: 441.1131. Found: 441.1131.

EXAMPLE 48

Preparation of racemic (2'R,3R,4'S)-6-chloro-4'-(3-chlorophenyl)-2'-(3,4-difluorophenyl)-6'-thioxospiro[3H-indole-3,3'-piperidine]-2(1H)-one

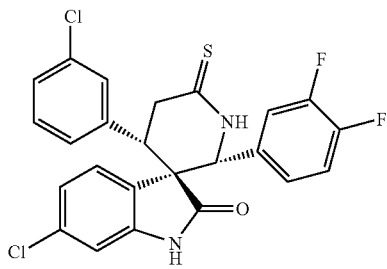

M. W. 489.37 $C_{24}H_{16}Cl_2F_2N_2OS$

In a manner similar to the method described in example 30, racemic (2'R,3R,4'S)-6-chloro-4'-(3-chlorophenyl)-2'-(3,4-difluorophenyl)spiro[3H-indole-3,3'-piperidine]-2,6'(1H)-dione (0.3 g, 0.63 mmol) prepared in example 46b was reacted with 2,4-bis-(4-methoxyphenyl)-1,3-dithia-2,4-diphosphetane 2,4-disulfide (0.32 g, 0.77 mmol) in toluene to give racemic (2'R,3R,4'S)-6-chloro-4'-(3-chlorophenyl)-2'-(3,4-difluorophenyl)-6'-thioxospiro[3H-indole-3,3'-piperidine]-2(1H)-one (Yield 0.29 g, 94%).

HRMS (ES$^+$) m/z Calcd for $C_{24}H_{16}Cl_2F_2N_2OS$+H [(M+H)$^+$]: 489.0401. Found: 489.0402.

EXAMPLE 49

Preparation of racemic (2'R,3R,4'S)-[6-chloro-4'-(3-chlorophenyl)-2'-(3,4-difluorophenyl)-2,3-dihydro-2-oxospiro[3H-indole-3,3'-piperidin]-6-ylene]hydrazine carboxylic acid ethyl ester

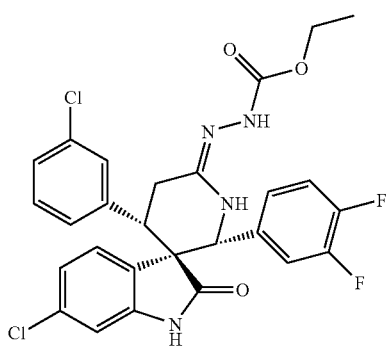

M. W. 559.40 $C_{27}H_{22}Cl_2F_2N_4O_3$

In a manner similar to the method described in example 40, racemic (2'R,3R,4'S)-6-chloro-4'-(3-chlorophenyl)-2'-(3,4-difluorophenyl)-6'-thioxospiro[3H-indole-3,3'-piperidine]-2(1H)-one (0.24 g, 0.49 mmol) prepared in example 48 was reacted with ethyl carbazate (0.1 g, 0.99 mmol), mercuric acetate (0.24 g, 0.76 mmol) and triethylamine (0.1 g, 0.99 mmol) in tetrahydrofuran (20 mL) to give racemic (2'R,3R,4'S)-[6-chloro-4'-(3-chlorophenyl)-2'-(3,4-difluorophenyl)-2,3-dihydro-2-oxospiro[3H-indole-3,3'-piperidin]-6-ylene]hydrazine carboxylic acid ethyl ester as a white solid (Yield 0.21 g, 77.8%).

HRMS (ES$^+$) m/z Calcd for $C_{27}H_{22}Cl_2F_2N_4O_3$+H [(M+H)$^+$]: 559.1110. Found: 559.1109.

EXAMPLE 50a

Preparation of intermediate 1-(1,3-benzodioxol-4-yl)-3-trimethylsilyoxy-2-aza-1,3-butadiene

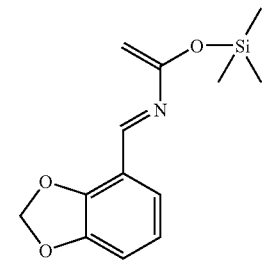

M. W. 263.37 $C_{13}H_{17}NO_3Si$

In a manner similar to the method described in example 1b, 2,3-(methylenedioxy)-benzaldehyde (1.5 g, 10 mmol) (Aldrich) was used as the starting material in place of 3-chlorobenzaldehyde to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(1, 3-benzodioxol-4-yl)-3-trimethylsilyoxy-2-aza-1,3-butadiene as a yellow oil and used for the next step without further purification.

EXAMPLE 50b

Preparation of racemic (2'R,3R,4'S)-2'-(1,3-benzodioxol-4-yl)-6-chloro-4'-(3-chlorophenyl)spiro[3H-indole-3,3'-piperidine]-2,6'(1H)-dione

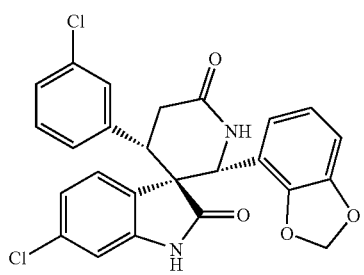

M. W. 481.34 $C_{25}H_{18}Cl_2N_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.25 g, 0.67 mmol) was reacted with 1-(1,3-benzodioxol-4-yl)-3-trimethylsilyoxy-2-aza-1,3-butadiene (2.1 g, 7.98 mmol) prepared in example 50a in toluene and then trifluoroacetic acid (10 mL) in dichloromethane to give racemic (2'R,3R,4'S)-2'-(1,3-benzodioxol-4-yl)-6-chloro-4'-(3-chlorophenyl)spiro[3H-indole-3,3'-piperidine]-2,6'(1H)-dione as an off-white solid (0.20 g, 62%).

HRMS (ES$^+$) m/z Calcd for $C_{25}H_{18}Cl_2N_2O_4$+H [(M+H)$^+$]: 481.0717. Found: 481.0717.

EXAMPLE 51

Preparation of racemic (2'R,3R,4'S)-[6-chloro-4'-(3-chlorophenyl)-2'-(5-fluoro-2-methylphenyl)-2,3-dihydro-2-oxospiro[3H-indole-3,3'-piperidin]-6-ylene]hydrazine carboxylic acid ethyl ester

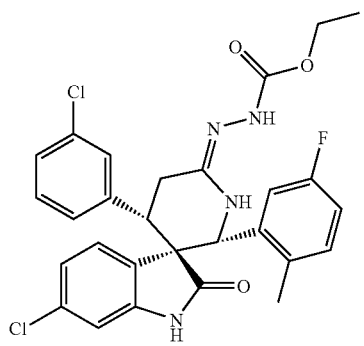

M. W. 555.44 $C_{28}H_{25}Cl_2FN_4O_3$

In a manner similar to the method described in example 40, (2'R,3R,4'S)-6-chloro-4'-(3-chlorophenyl)-2'-(5-fluoro-2-methylphenyl)-6'-thioxospiro[3H-indole-3,3'-piperidine]-2(1H)-one (0.17 g, 0.35 mmol) prepared in example 39 was reacted with ethyl carbazate (0.15 g, 1.49 mmol), mercuric acetate (0.26 g, 0.82 mmol) and triethylamine (0.17 g, 1.69 mmol) in tetrahydrofuran (20 mL) to give racemic (2'R,3R,4'S)-[6-chloro-4'-(3-chlorophenyl)-2'-(5-fluoro-2-methylphenyl)-2,3-dihydro-2-oxospiro[3H-indole-3,3'-piperidin]-6-ylene]hydrazine carboxylic acid ethyl ester as a white solid (Yield 0.14 g, 73.7%).

EXAMPLE 52a

Preparation of intermediate 2,3-difluoro-6-methyl-benzaldehyde

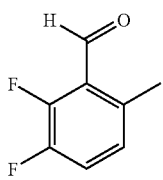

M. W. 156.13 $C_8H_6F_2O$

To a solution of 1,2-difluoro-4-methyl-benzene (5.0 g, 39 mmol) in tetrahydrofuran (200 mL) at −78° C. was added lithium diisopropyl amine (24 mL, 1.8 M in THF, 43 mmol) dropwise during a period of 15 mins. The mixture was stirred at −78° C. for another 20 min. Then N,N-dimethyl-formamide (3.6 mL, 47 mmol) was added in one portion. The mixture was stirred at −78° C. for 10 min, then quenched with acetic acid (9.4 g, 1.56 mmol) and followed by the addition of water (37.6 mL). The mixture was partitioned between ethyl acetate and water. The organic layer was separated, concentrated. The residue was purified by chromatography (EtOAc: hexanes=1:1) to give 2,3-difluoro-6-methyl-benzaldehyde as colorless oil (Yield: 3.5 g, 57.5%).

EXAMPLE 52b

Preparation of intermediate 1-(2,3-difluoro-6-methylphenyl)-3-trimethylsilyoxy-2-aza-1,3-butadiene

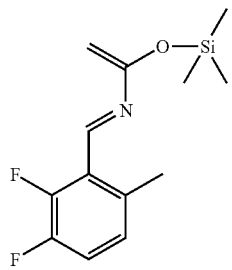

M. W. 269.37 $C_{13}H_{17}F_2NOSi$

In a manner similar to the method described in example 1b, 2,3-difluoro-6-methyl-benzaldehyde (1.56 g, 10 mmol) prepared in example 52a was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,3-difluoro-6-methylphenyl)-3-trimethylsilyoxy-2-aza-1,3-butadiene as an orange gum and used for the next step without further purification.

EXAMPLE 52c

Preparation of racemic (2'R,3R,4'S)-6-chloro-4'-(3-chlorophenyl)-2'-(2,3-difluoro-6-methylphenyl)spiro[3H-indole-3,3'-piperidine]-2,6'(1H)-dione

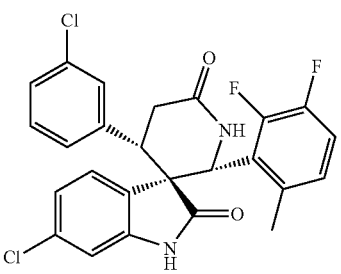

M. W. 487.34 $C_{25}H_{18}Cl_2F_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.03 mmol) was reacted with 1-(2,3-difluoro-6-methylphenyl)-3-trimethylsilyoxy-2-aza-1,3-butadiene (2.7 g, 10.0 mmol) prepared in example 52b in toluene and then trifluoroacetic acid (10 mL) in dichloromethane to give racemic (2'R,3R,4'S)-6-chloro-4'-(3-chlorophenyl)-2'-(2,3-difluoro-6-methylphenyl)spiro[3H-indole-3,3'-piperidine]-2,6'(1H)-dione (Yield: 0.41 g, 83.7%).

HRMS (ES$^+$) m/z Calcd for $C_{25}H_{18}Cl_2F_2N_2O_2$+H [(M+H)$^+$]: 487.0786 Found: 487.0780.

EXAMPLE 53a

Preparation of intermediate E/Z-6-chloro-3-(3-chloro-benzylidene)-5-fluoro-1,3-dihydro-indol-2-one

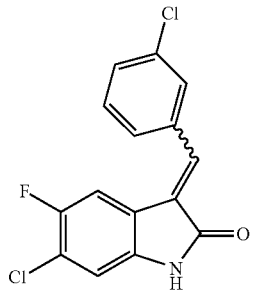

M. W. 308.14 $C_{15}H_8Cl_2FNO$

In a manner similar to the method described in example 1a, 6-chloro-5-fluoro-1,3-dihydro-indol-2-one (0.25 g, 1.35 mmol, prepared in procedure described in EP153818) was reacted with 3-chloro-benzaldehyde (0.34 g, 2.44 mmol) and pyrrolidine (0.19 g, 2.68 mmol) in methanol to give a mixture of E- and Z-6-chloro-3-(3-chloro-benzylidene)-5-fluoro-1,3-dihydro-indol-2-one as a yellow solid.

EXAMPLE 53b

Preparation of intermediate E/Z-6-chloro-3-(3-chloro-benzylidene)-5-fluoro-2-oxo-2,3-dihydro-indole-1-carboxylic acid tert-butyl ester

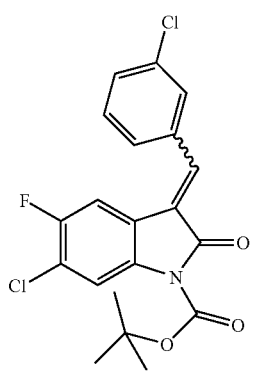

M. W. 408.26 $C_{20}H_{16}Cl_2FNO_3$

In a manner similar to the method described in example 24a, E/Z-6-chloro-3-(3-chloro-benzylidene)-5-fluoro-1,3-dihydro-indol-2-one (0.45 g, 1.46 mmol) was reacted with di-tert-butyl-dicarbonate (0.4 g, 1.83 mmol) (Aldrich), triethyl amine (0.5 g, 4.95 mmol) and 4-dimethylaminopyridine (5 mg) in dichloromethane (30 mL) to give E/Z-6-chloro-3-(3-chloro-benzylidene)-5-fluoro-2-oxo-2,3-dihydro-indole-1-carboxylic acid tert-butyl ester as a yellow solid (Yield: 0.6 g, 100%).

EXAMPLE 53c

Preparation of racemic (2'R,3R,4'S)-6-chloro-4'-(3-chlorophenyl)-5-fluoro-2'-(5-fluoro-2-methylphenyl) spiro[3H-indole-3,3'-piperidine]-2,6'(1H)-dione

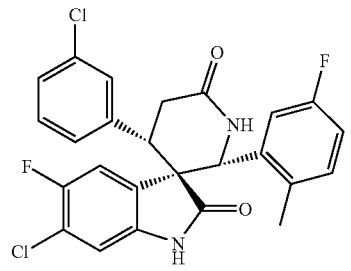

M. W. 487.34 $C_{25}H_{18}Cl_2F_2N_2O_2$

In a manner similar to the method described in example 41b, E/Z-6-chloro-3-(3-chloro-benzylidene)-5-fluoro-2-oxo-2,3-dihydro-indole-1-carboxylic acid tert-butyl ester prepared in example 53b (0.4 g, 0.98 mmol) was reacted with 1-(5-fluoro-2-methylphenyl)-3-trimethylsilyoxy-2-aza-1,3-butadiene (2.1 g, 8.37 mmol) prepared in example 36a in toluene and then trifluoroacetic acid (10 mL) in dichloromethane to give racemic (2'R,3R,4'S)-6-chloro-4'-(3-chlorophenyl)-5-fluoro-2'-(5-fluoro-2-methylphenyl)spiro[3H-indole-3,3'-piperidine]-2,6'(1H)-dione (Yield: 0.35 g, 72.9%).

HRMS (ES$^+$) m/z Calcd for $C_{25}H_{18}Cl_2F_2N_2O_2$+H [(M+H)$^+$]: 487.0786. Found: 487.0779.

EXAMPLE 54

Preparation of racemic (2'R,3R,4'S)-6-chloro-4'-(3-chlorophenyl)-2'-(2,3-difluoro-6-methylphenyl)-6'-thioxospiro[3H-indole-3,3'-piperidine]-2(1H)-one

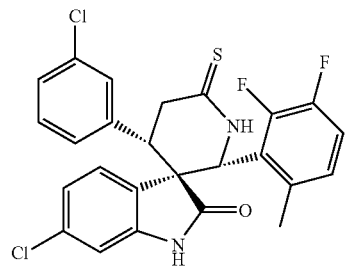

M. W. 503.40 $C_{25}H_{18}Cl_2F_2N_2OS$

In a manner similar to the method described in example 30, racemic (2'S,3R,4'S)-6-chloro-4'-(3-chlorophenyl)-2'-(2,3-difluoro-6-methylphenyl)spiro[3H-indole-3,3'-piperidine]-2,6'(1H)-dione (0.18 g, 0.37 mmol) prepared in example 52c was reacted with 2,4-bis-(4-methoxyphenyl)-1,3-dithia-2,4-diphosphetane 2,4-disulfide (0.32 g, 0.96 mmol) in toluene to give racemic (2'R,3R,4'S)-6-chloro-4'-(3-chlorophenyl)-2'-(2,3-difluoro-6-methylphenyl)-6'-thioxospiro[3H-indole-3,3'-piperidine]-2(1H)-one (Yield 0.13 g, 69.8%).

HRMS (ES$^+$) m/z Calcd for $C_{25}H_{18}Cl_2F_2N_2OS$+H [(M+H)$^+$]: 503.0558. Found: 503.0554.

EXAMPLE 55a

Preparation of intermediate E/Z-6-chloro-3-(3-chloro-benzylidene)-1-(2-trimethylsilanyl-ethoxymethyl)-1,3-dihydro-indole-2-one

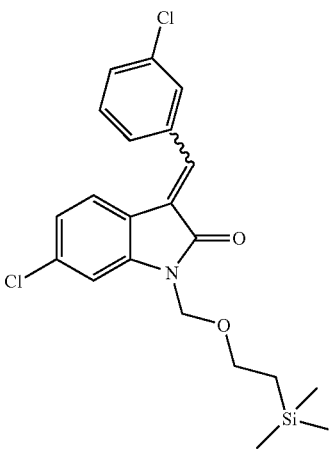

M. W. 420.41 $C_{21}H_{23}Cl_2NO_2Si$

To a solution of E/Z-6-chloro-3-(3-chloro-benzylidene)-1,3-dihydro-indol-2-one prepared in example 4a (2.3 g, 7.9 mmol) in N,N-dimethyl-formamide (20 mL) at 0° C. was added NaH (60% in mineral oil) (0.32 g, 7.9 mmol) (Aldrich), followed by the dropwise addition of 2-(trimethylsilyl)ethoxymethyl chloride (1.32 g, 7.9 mmol) in tetrahydrofuran (20 mL). The reaction mixture was stirred at 0° C. for 0.5 h, then poured into ice-water. The crude was extracted with ethyl acetate twice. The combined organic layer was dried over $Na_2SO_4$. The solvent was removed and the residue was purified by chromatography (EtOAc:hexanes=1:5) to give E/Z-6-chloro-3-(3-chloro-benzylidene)-1-(2-trimethylsilanyl-ethoxymethyl)-1,3-dihydro-indole-2-one as yellow oil (Yield 3.0 g, 90%).

EXAMPLE 55b

Preparation of intermediate racemic (2'R,3R,4'S)-6-chloro-4'-(3-chlorophenyl)-2'-(5-fluoro-2-methylphenyl)-2,3-dihydro-2,6'-dioxospiro[indole-3,3'-piperidine]-1-methoxyethyl trimethylsilane

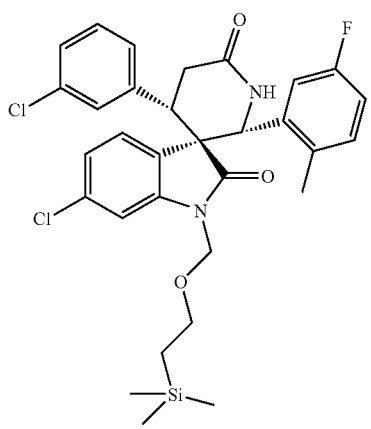

M. W. 599.61 $C_{31}H_{33}Cl_2FN_2O_3Si$

To a solution of 1-(5-fluoro-2-methylphenyl)-3-trimethylsilyoxy-2-aza-1,3-butadiene prepared in example 36a in toluene (50 mL) was added E/Z-6-chloro-3-(3-chloro-benzylidene)-1-(2-trimethylsilanyl-ethoxymethyl)-1,3-dihydroindole-2-one prepared in example 55a (3.0 g, 7.14 mmol). The reaction mixture was stirred under nitrogen in a sealed tube at 148° C. for 40 min. After the solution was cooled to room temperature, methanol (50 mL) was added, and then the mixture was concentrated. The residue was purified by chromatography (EtOAc:Hexane=2:1) to give racemic (2'R,3R,4'S)-6-chloro-4'-(3-chlorophenyl)-2'-(5-fluoro-2-methylphenyl)-2,3-dihydro-2,6'-dioxospiro[indole-3,3'-piperidine]-1-methoxyethyl trimethylsilane as an off-white solid (Yield 2.1 g, 49%).

EXAMPLE 55c

Preparation of intermediate racemic (2'R,3R,4'S)-6-chloro-4'-(3-chlorophenyl)-2'-(5-fluoro-2-methylphenyl)-2,3-dihydro-1'-[(tert-butoxycarbonyl)methyl]-2,6'-dioxospiro[indole-3,3'-piperidine]-1-methoxyethyl trimethylsilane

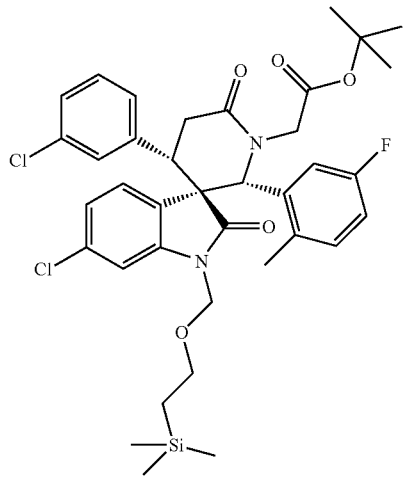

M. W. 713.76 $C_{37}H_{43}Cl_2FN_2O_5Si$

To a solution of racemic (2'R,3R,4'S)-6-chloro-4'-(3-chlorophenyl)-2'-(5-fluoro-2-methylphenyl)-2,3-dihydro-2,6'-dioxospiro[indole-3,3'-piperidine]-1-methoxyethyl trimethylsilane (1.0 g, 1.67 mmol) prepared in example 55b in N,N-dimethyl-formamide (20 mL) at room temperature was added bromo-acetic acid tert-butyl ester (0.8 g, 4.1 mmol) and cesium carbonate (3.0 g, 9.20 mmol). The reaction mixture was stirred under nitrogen for 4 h, then poured into saturated aqueous $NH_4Cl$ solution. The mixture was extracted with ethyl acetate. The organic layers were combined, dried over $Na_2SO_4$ and concentrated. The residue was purified by chromatography (EtOAc:Hexanes=1:4) to give racemic (2'R,3R,4'S)-6-chloro-4'-(3-chlorophenyl)-2'-(5-fluoro-2-methylphenyl)-2,3-dihydro-1'-[(tert-butoxycarbonyl)methyl]-2,6'-dioxospiro[indole-3,3'-piperidine]-1-methoxyethyl trimethylsilane as a white foam (Yield 0.58 g, 48.7%).

EXAMPLE 55d

Preparation of racemic (2'R,3R,4'S)-6-chloro-4'-(3-chlorophenyl)-2'-(5-fluoro-2-methyl phenyl)-1'-hydroxycarbonylmethylspiro[3H-indole-3,3'-piperidine]-2,6'(1H)-dione

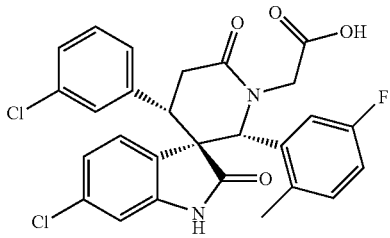

M. W. 527.38 $C_{27}H_{21}Cl_2FN_2O_4$

To a solution of racemic (2'R,3R,4'S)-6-chloro-4'-(3-chlorophenyl)-2'-(5-fluoro-2-methylphenyl)-2,3-dihydro-1'-[(tert-butoxycarbonyl)methyl]-2,6'-dioxospiro[indole-3,3'-piperidine]-1-methoxyethyl trimethylsilane (0.54 g, 0.76 mmol) prepared in example 55c in dichloromethane (10 mL) was added trifluoroacetic acid (20 mL). The reaction mixture was stirred at room temperature for 18 h. The reaction mixture was concentrated. The residue was redissolved in methanol (10 mL). To the resulting solution was added N,N'-diisopropylethylamine (1 mL, 5.53 mmol) and the crude was refluxed for 1 h. The reaction mixture was concentrated and the residue was partitioned between ethyl acetate and HCl aqueous solution (1N). The organic layer was separated, dried over $MgSO_4$ and concentrated. The residue was triturated with ethyl acetate and hexane to give racemic (2'R,3R,4'S)-6-chloro-4'-(3-chlorophenyl)-2'-(5-fluoro-2-methylphenyl)-1'-hydroxycarbonylmethylspiro[3H-indole-3,3'-piperidine]-2,6'(1H)-dione as a white solid (Yield 0.3 g, 75%).

HRMS (ES$^+$) m/z Calcd for $C_{27}H_{21}Cl_2FN_2O_4$+H [(M+H)$^+$]: 527.0935 Found: 527.0926.

EXAMPLE 56a

Preparation of intermediate racemic (2'R,3R,4'S)-6-chloro-4'-(3-chlorophenyl)-2'-(5-fluoro-2-methylphenyl)-2,3-dihydro-1'-methyl-2,6'-dioxospiro[indole-3,3'-piperidine]-1-methoxyethyl trimethylsilane

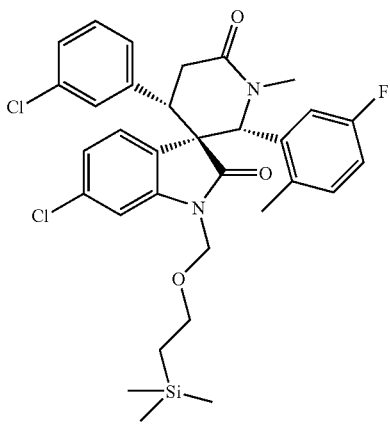

M. W. 613.64 $C_{32}H_{35}Cl_2FN_2O_3Si$

In a manner similar to the method described in example 24c, racemic (2'R,3R,4'S)-6-chloro-4'-(3-chlorophenyl)-2'-(5-fluoro-2-methylphenyl)-2,3-dihydro-2,6'-dioxospiro[indole-3,3'-piperidine]-1-methoxyethyl trimethylsilane (0.3 g, 0.5 mmol) prepared in example 55b was reacted with LiH (0.17 g, 21.4 mmol) (Aldrich) and iodomethane (4 g, 28.2 mmol) in N,N-dimethyl-formamide (40 mL) to give racemic (2'R,3R,4'S)-6-chloro-4'-(3-chlorophenyl)-2'-(5-fluoro-2-methylphenyl)-2,3-dihydro-1'-methyl-2,6'-dioxospiro[indole-3,3'-piperidine]-1-methoxyethyl trimethylsilane as a white solid (Yield: 0.16 g, 51.6%).

EXAMPLE 56b

Preparation of intermediate racemic (2'R,3R,4'S)-6-chloro-4'-(3-chlorophenyl)-2'-(5-fluoro-2-methylphenyl)-2,3-dihydro-1'-methyl-2,6'-dioxospiro[indole-3,3'-piperidine]-1-ethanol

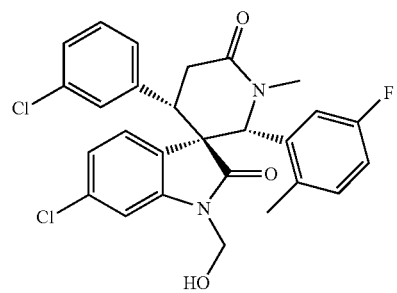

M. W. 513.40 $C_{27}H_{23}Cl_2FN_2O_3$

To a solution of racemic (2'R,3R,4'S)-6-chloro-4'-(3-chlorophenyl)-2'-(5-fluoro-2-methylphenyl)-2,3-dihydro-1'-methyl-2,6'-dioxospiro[indole-3,3'-piperidine]-1-methoxyethyl trimethylsilane (0.16 g, 0.26 mmol) prepared in example 56a in dichloromethane (10 mL) was added trifluoroacetic acid (20 mL). The reaction mixture was stirred at room temperature for 3 h. The reaction mixture was concentrated. The residue was neutralized with saturated $NaHCO_3$ aqueous solution, then extracted with ethyl acetate. The organic layer was separated, dried over $MgSO_4$ and concentrated. The residue was purified by chromatography (EtOAc:$CH_2Cl_2$=1:1) to give racemic (2'R,3R,4'S)-6-chloro-4'-(3-chlorophenyl)-2'-(5-fluoro-2-methylphenyl)-2,3-dihydro-1'-methyl-2,6'-dioxospiro[indole-3,3'-piperidine]-1-ethanol (Yield 90 mg, 67.7%).

EXAMPLE 56c

Preparation of racemic (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione

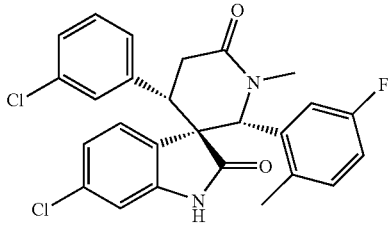

M. W. 483.37 $C_{26}H_{21}Cl_2FN_2O_2$

To a solution of racemic (2'R,3R,4'S)-6-chloro-4'-(3-chlorophenyl)-2'-(5-fluoro-2-methylphenyl)-2,3-dihydro-1'-methyl-2,6'-dioxospiro[indole-3,3'-piperidine]-1-ethanol (0.09 g, 0.175 mmol) prepared in example 56b in methanol (10 mL) was added N,N'-diisopropylethylamine (2 mL, 11.1 mmol) and the crude was refluxed for 1 h. The reaction mixture was concentrated and the residue was partitioned between ethyl acetate and water. The organic layer was separated, and concentrated. The residue was purified by chromatography (EtOAc:$CH_2Cl_2$=1:2) to give racemic (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione as a white solid (Yield 0.06 g, 70.6%).

HRMS (ES$^+$) m/z Calcd for $C_{26}H_{21}Cl_2FN_2O_2$+H [(M+H)$^+$]: 483.1037. Found: 483.1042.

EXAMPLE 56d

Preparation of chiral (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione

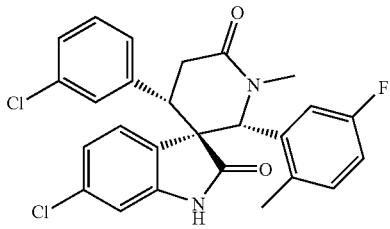

M. W. 483.37 $C_{26}H_{21}Cl_2FN_2O_2$

Separation of the two enantiomers from racemic (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione (50 mg) prepared in example 56c was conducted by chiral SFC to provide chiral (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione as a white solid (Yield: 20 mg, 40%) and chiral (2'S,3S,4'R)-6-chloro-4'-(3-chlorophenyl)-2'-(5-fluoro-2-methylphenyl)-1'-methylspiro[3H-indole-3,3'-piperidine]-2,6'(1H)-dione as a white solid (Yield: 20 mg, 40%).

EXAMPLE 57a

Preparation of racemic (2'R,3R,4'S)-6-chloro-4'-(3-chlorophenyl)-1'-fluorocarbonylmethyl-2'-(5-fluoro-2-methylphenyl)spiro[3H-indole-3,3'-piperidine]-2,6'(1H)-dione

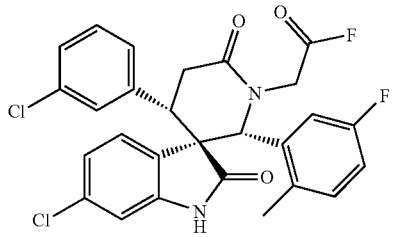

M. W. 529.37 $C_{27}H_{20}Cl_2F_2N_2O_3$

In a manner similar to the method described in example 34a, racemic (2'R,3R,4'S)-6-chloro-4'-(3-chlorophenyl)-2'-(5-fluoro-2-methylphenyl)-1'-(hydroxycarbonyl-methyl)spiro[3H-indole-3,3'-piperidine]-2,6'(1H)-dione g, 0.19 mmol) prepared in example 55d was reacted with cyanuric fluoride (51 mg, 0.38 mmol) (Alfa) and pyridine (45 mg, 0.57 mmol) in dichloromethane to give racemic (2'R,3R,4'S)-6-chloro-4'-(3-chlorophenyl)-1'-fluorocarbonylmethyl-2'-(5-fluoro-2-methylphenyl)spiro[3H-indole-3,3'-piperidine]-2,6'(1H)-dione (yield: 0.1 g, 100%).

EXAMPLE 57b

Preparation of racemic (2'R,3R,4'S)-6-chloro-4'-(3-chlorophenyl)-2'-(5-fluoro-2-methyl phenyl)-1'-[(1-methyl-piperidin-4-yl)aminocarbonyl)-methyl]spiro[3H-indole-3,3'-piperidine]-2,6'(1H)-dione

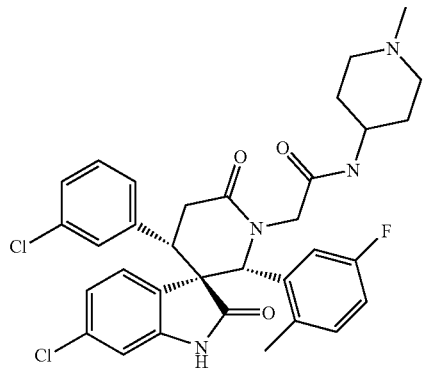

M. W. 623.56 $C_{33}H_{33}Cl_2FN_4O_3$

In a manner similar to the method described in example 34b, racemic (2'R,3R,4'S)-6-chloro-4'-(3-chlorophenyl)-1'-[(fluorocarbonyl)-methyl]-2'-(5-fluoro-2-methylphenyl)spiro[3H-indole-3,3'-piperidine]-2,6'(1H)-dione (0.1 g, 0.18 mmol) prepared in example 57a was reacted with 1-methylpiperidin-4-ylamine (0.1 g, 0.88 mmol), N-methylmorpholine (0.1 g, 0.99 mmol) and 4-dimethylaminopyridine (1 mg, 0.008 mmol) in tetrahydrofuran to give racemic (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione as an off-white solid (Yield 0.041 g, 36.7%).

HRMS (ES$^+$) m/z Calcd for $C_{33}H_{33}Cl_2FN_4O_3$+H [(M+H)$^+$]: 623.1987. Found: 623.1989.

EXAMPLE 57c

Preparation of chiral (2'R,3R,4'S)-6-chloro-4'-(3-chlorophenyl)-2'-(5-fluoro-2-methyl phenyl)-1'-[(1-methyl-piperidin-4-yl)aminocarbonyl)-methyl]spiro[3H-indole-3,3'-piperidine]-2,6'(1H)-dione

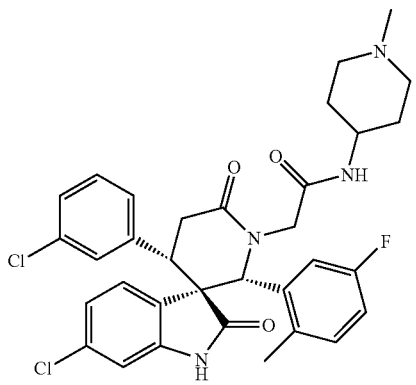

M. W. 623.56 $C_{33}H_{33}Cl_2FN_4O_3$

Separation of the two enantiomers from (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione (30 mg) prepared in example 57b was conducted by chiral SFC to provide chiral (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione as a white solid (Yield: 10 mg, 17%) and chiral (2'S,3S,4'R)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione as a white solid (Yield: 10 mg, 17%).

EXAMPLE 58

Preparation of racemic (2'R,3R,4'S)-1'-[1-tert-butoxycarbonyl-piperidin-4-yl)aminocarbonyl-methyl]-6-chloro-4'-(3-chlorophenyl)-2'-(5-fluoro-2-methylphenyl)spiro[3H-indole-3,3'-piperidine]-2,6'(1H)-dione

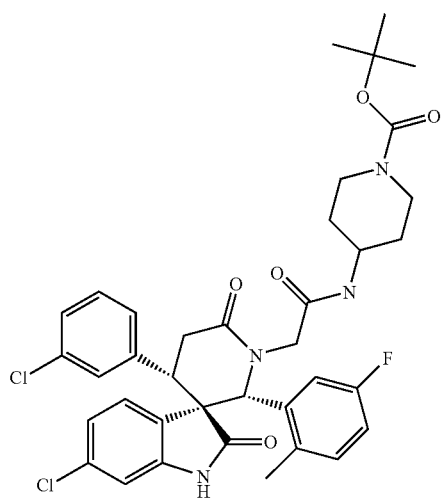

M. W. 709.65 $C_{37}H_{39}Cl_2FN_4O_5$

In a manner similar to the method described in example 34b, racemic (2'R,3R,4'S)-6-chloro-4'-(3-chlorophenyl)-1'-fluorocarbonylmethyl-2'-(5-fluoro-2-methylphenyl)spiro[3H-indole-3,3'-piperidine]-2,6'(1H)-dione (0.1 g, 0.18 mmol) prepared in example 57a was reacted with 4-amino-piperidine-1-carboxylic acid tert-butyl ester (0.1 g, 0.50 mmol), N-methylmorpholine (0.1 g, 0.99 mmol) and 4-dimethylaminopyridine (2 mg, 0.017 mmol) in tetrahydrofuran to give racemic (2'R,3R,4'S)-1'-[1-tert-butoxycarbonyl-piperidin-4-yl)aminocarbonyl-methyl]-6-chloro-4'-(3-chlorophenyl)-2'-(5-fluoro-2-methylphenyl)spiro[3H-indole-3,3'-piperidine]-2,6'(1H)-dione as a white solid (Yield 0.075 g, 58.6%).

HRMS (ES$^+$) m/z Calcd for $C_{37}H_{39}Cl_2FN_4O_5$+H [(M+H)$^+$]: 709.2355. Found: 709.2354.

EXAMPLE 59a

Preparation of racemic (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione

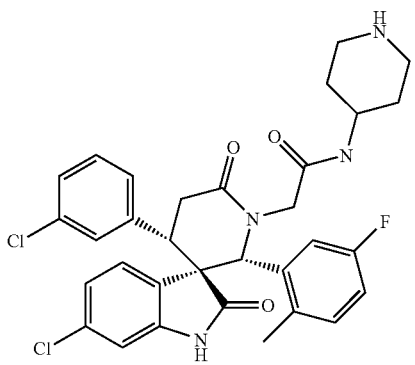

M. W. 609.53 $C_{32}H_{31}Cl_2FN_4O_3$

To a solution of racemic (2'R,3R,4'S)-1'-[1-tert-butoxycarbonyl-piperidin-4-yl)aminocarbonyl-methyl]-6-chloro-4'-(3-chlorophenyl)-2'-(5-fluoro-2-methylphenyl)spiro[3H-indole-3,3'-piperidine]-2,6'(1H)-dione (0.07 g, 0.099 mmol) prepared in 58 in dichloromethane (20 mL) was added trifluoroacetic acid (5 mL). The reaction mixture was stirred at room temperature for 1 h, then concentrated. The residue was neutralized with saturated NaHCO$_3$ solution, extracted with ethyl acetate. The organic layer was separated, dried over MgSO$_4$, concentrated to give racemic (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione as a white solid (Yield 0.06 g, 99%).

HRMS (ES$^+$) m/z Calcd for $C_{32}H_{31}Cl_2FN_4O_3$+H [(M+H)$^+$]: 609.1830 Found: 609.1820.

EXAMPLE 59b

Preparation of chiral (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione

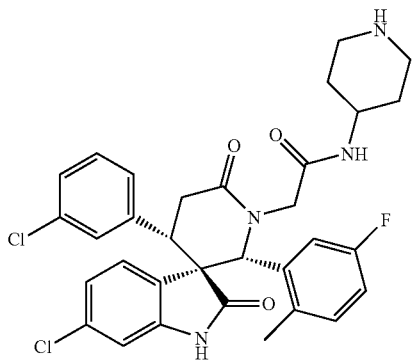

M. W. 609.53 $C_{32}H_{31}Cl_2FN_4O_3$

Separation of the two enantiomers from racemic (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione (40 mg) prepared in example 59a was conducted by chiral SFC to provide chiral (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione as a white solid (Yield: 12 mg, 30%) and chiral (2'S,3S,4'R)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione as a white solid (Yield: 12 mg, 30%).

EXAMPLE 60a

Preparation of intermediate racemic (2'R,3R,4'S)-6-chloro-4'-(3-chlorophenyl)-1'-(3-chloro-propyl)-2'-(5-fluoro-2-methylphenyl)-2,3-dihydro-2,6'-dioxospiro[indole-3,3'-piperidine]-1-methoxyethyl trimethylsilane

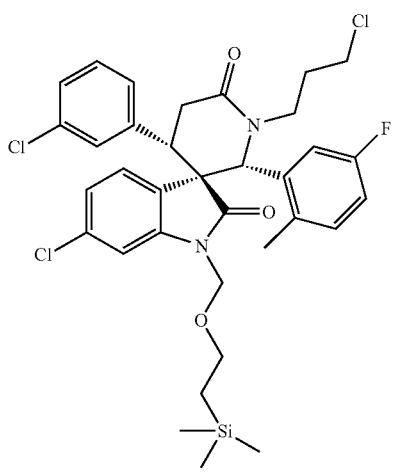

M. W. 676.14 $C_{34}H_{38}Cl_3FN_2O_5Si$

In a manner similar to the method described in example 24c, racemic (2'R,3R,4'S)-6-chloro-4'-(3-chlorophenyl)-2'-(5-fluoro-2-methylphenyl)-2,3-dihydro-2,6'-dioxospiro[indole-3,3'-piperidine]-1-methoxyethyl trimethylsilane (0.8 g, 1.33 mmol) prepared in example 55b was reacted with LiH (0.5 g, 62.5 mmol) and 1-chloro-3-iodo-propane (3.9 g, 19.1 mmol) in N,N-dimethyl-formamide (20 mL) to give racemic (2'R,3R,4'S)-6-chloro-4'-(3-chlorophenyl)-1'-(3-chloro-propyl)-2'-(5-fluoro-2-methylphenyl)-2,3-dihydro-2,6'-dioxospiro[indole-3,3'-piperidine]-1-methoxyethyl trimethylsilane as a white form (Yield: 0.43 g, 47.8%).

EXAMPLE 60b

Preparation of racemic (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione

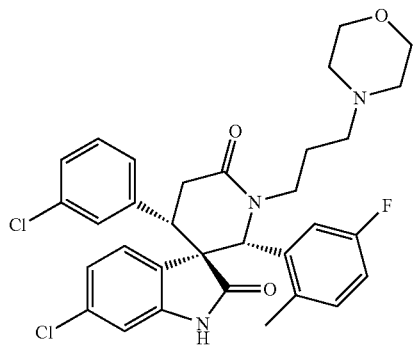

M. W. 596.53 $C_{32}H_{32}Cl_2FN_3O_3$

The mixture of racemic (2'R,3R,4'S)-6-chloro-4'-(3-chlorophenyl)-2'-(5-fluoro-2-methylphenyl)-2,3-dihydro-1'-(3-chloro-propyl)-2,6'-dioxospiro[indole-3,3'-piperidine]-1-methoxyethyl trimethylsilane (0.24 g, 0.36 mmol) prepared in example 60a and morpholine (10 mL) was heated at 120° C. for 1 h. The mixture was concentrated to dryness. The resulting residue was added dichloromethane (20 mL) and then trifluoroacetic acid (20 mL). The reaction mixture was stirred at room temperature for 4 h. The reaction mixture was concentrated and the residue was partitioned between ethyl acetate and saturated NaHCO₃ solution. The organic layer was separated and concentrated. The residue was redissolved in methanol (10 mL). To the resulting solution was added N,N'-diisopropylethylamine (2 mL, 11.0 mmol) and the crude was heated at 100° C. for 1 h. The reaction mixture was concentrated and the residue was purified by chromatography (MeOH:EtOAc=1:9) to give racemic (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione as a white solid (Yield 0.08 g, 37.9%).

HRMS (ES⁺) m/z Calcd for $C_{32}H_{32}Cl_2FN_3O_3$+H [(M+H)⁺]: 596.1878 Found: 596.1877.

EXAMPLE 60c

Preparation of chiral (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione

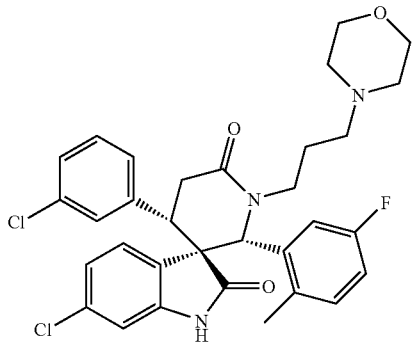

M. W. 596.53 C$_{32}$H$_{32}$Cl$_2$FN$_3$O$_3$

Separation of the two enantiomers from racemic (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione (100 mg) prepared in example 60b was conducted by chiral SFC to provide chiral (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione as a white solid (Yield: 34 mg, 34%) and chiral (2'S,3S,4'R)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione as a white solid (Yield: 35 mg, 35%).

EXAMPLE 61a

Preparation of intermediate 1-(1-isopropyl-4-methyl-1-pentenyl)-3-trimethylsilyoxy-2-aza-1,3-butadiene

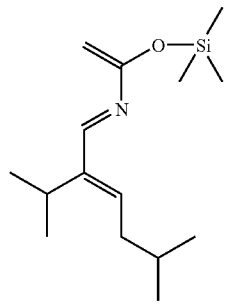

M. W. 267.49 C$_{15}$H$_{29}$NOSi

In a manner similar to the method described in example 1b, 2-isopropyl-5-methyl-2-hexenal (1.54 g, 10 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(1-isopropyl-4-methyl-1-pentenyl)-3-trimethylsilyoxy-2-aza-1,3-butadiene and used for the next step without further purification.

EXAMPLE 61b

Preparation of racemic (2'R,3R,4'S)-6-chloro-4'-(3-chlorophenyl)-2'-(1-isopropyl-4-methyl-pent-1-enyl)spiro[3H-indole-3,3'-piperidine]-2,6'(1H)-dione

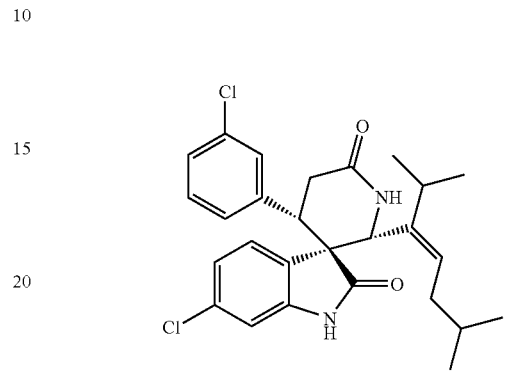

M. W. 485.46 C$_{27}$H$_{30}$Cl$_2$N$_2$O$_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.3 g, 0.77 mmol) was reacted with 1-(1-isopropyl-4-methyl-1-pentenyl)-3-trimethylsilyoxy-2-aza-1,3-butadiene (2.1 g, 8.2 mmol) prepared in example 61a in toluene and then trifluoroacetic acid (10 mL) in dichloromethane to give racemic (2'R,3R,4'S)-6-chloro-4'-(3-chlorophenyl)-2'-(1-isopropyl-4-methyl-pent-1-enyl)spiro[3H-indole-3,3'-piperidine]-2,6'(1H)-dione as an off-white solid (0.18 g, 48.7%).

HRMS (ES$^+$) m/z Calcd for C$_{27}$H$_{30}$Cl$_2$N$_2$O$_2$+H [(M+H)$^+$]: 485.1757. Found: 485.1755.

EXAMPLE 62a

Preparation of intermediate 1,2-difluoro-4-isopropoxy-benzene

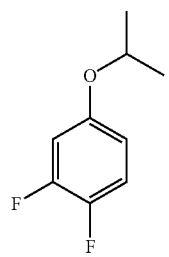

M. W. 172.18 C$_9$H$_{10}$F$_2$O

To a solution of 3,4-difluoro-phenol (5 g, 38.4 mmol) in acetone (50 mL) was added potassium carbonate (54 g, 38.4 mmol) and 2-iodo-propane. The reaction mixture was heated at refluxing for 24 h. The crude was cooled down and filtered through a short pad of celite. The filtrate was concentrated and the residue was purified by chromatography (EtOAc:Hexanes=1:9) to give 1,2-difluoro-4-isopropoxy-benzene as colorless oil (Yield 6.12 g, 92.3%).

EXAMPLE 62b

Preparation of intermediate
2,3-difluoro-6-isopropoxy-benzaldehyde

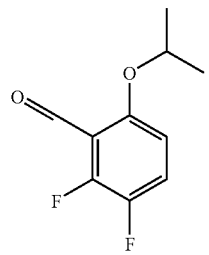

M. W. 200.19 $C_{10}H_{10}F_2O_2$

In a manner similar to the method described in example 52a, 1,2-difluoro-4-isopropoxy-benzene (5.77 g, 33.5 mmol) prepared in example 62a was reacted with lithium diisopropyl amine (20.5 mL, 1.8 M in THF, 36.9 mmol), N,N-dimethyl-formamide (3.11 mL, 40.2 mmol) and quenched with acetic acid (8.0 g, 134 mmol) in tetrahydrofuran to give 2,3-difluoro-6-isopropoxy-benzaldehyde as a white crystal (Yield: 6.02 g, 89.9%).

EXAMPLE 62c

Preparation of intermediate 1-(2,3-difluoro-6-isopropoxy-phenyl)-3-trimethylsilyoxy-2-aza-1,3-butadiene

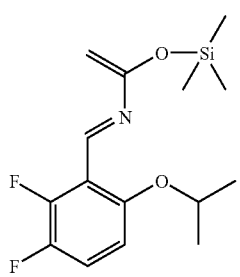

M. W. 313.42 $C_{15}H_{21}F_2NO_2Si$

In a manner similar to the method described in example 1b, 2,3-difluoro-6-isopropoxy-benzaldehyde (2.0 g, 10 mmol) prepared in example 62b was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,3-difluoro-6-isopropoxy-phenyl)-3-trimethylsilyoxy-2-aza-1,3-butadiene as yellow oil and used for the next step without further purification.

EXAMPLE 62d

Preparation of racemic (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione

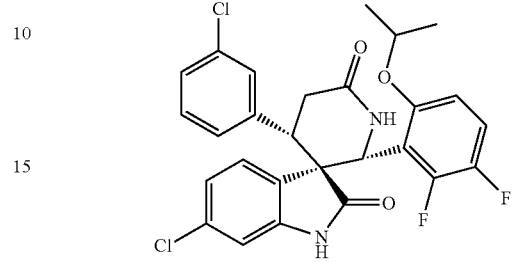

M. W. 531.39 $C_{27}H_{22}Cl_2F_2N_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(2,3-difluoro-6-isopropoxy-phenyl)-3-trimethylsilyoxy-2-aza-1,3-butadiene (2.5 g, 7.98 mmol) prepared in example 62c in toluene and then trifluoroacetic acid (10 mL) in dichloromethane to give racemic (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione as a white solid (0.41 g, 75.9%).

HRMS (ES$^+$) m/z Calcd for $C_{27}H_{22}Cl_2F_2N_2O_3$+H [(M+H)$^+$]: 531.1049. Found: 531.1049.

EXAMPLE 62e

Preparation of chiral (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione

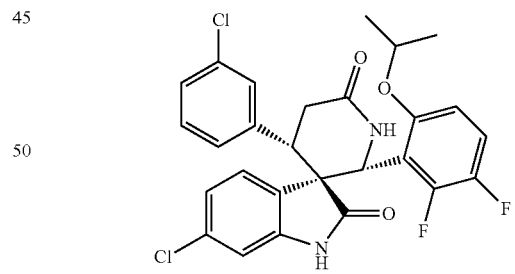

M. W. 531.39 $C_{27}H_{22}Cl_2F_2N_2O_3$

Separation of the two enantiomers from (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione prepared in example 62d was conducted by chiral SFC to provide chiral (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione as a white solid (RO5131636-000-001) and chiral (2'R,3S,4'R)-6-chloro-4'-(3-chlorophenyl)-2'-(2,3-difluoro-6-isopropoxy-phenyl)spiro[3H-indole-3,3'-piperidine]-2,6'(1H)-dione as a white solid.

EXAMPLE 63

Preparation of racemic (2'R,3R,4'S)-6-chloro-4'-(3-chlorophenyl)-2'-(5-fluoro-2-methyl phenyl)-1'-(3-pyrrolidin-1-yl-propyl)spiro[3H-indole-3,3'-piperidine]-2,6'(1H)-dione

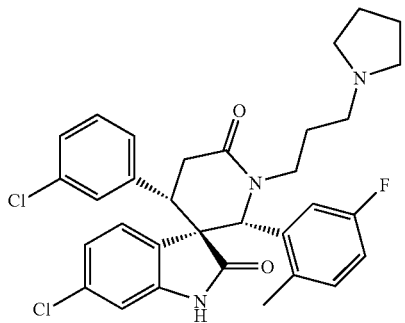

M. W. 580.54 $C_{32}H_{32}Cl_2FN_3O_2$

In a manner similar to the method described in example 60b, racemic (2'R,3R,4'S)-6-chloro-4'-(3-chlorophenyl)-1'-(3-chloro-propyl)-2'-(5-fluoro-2-methylphenyl)-2,3-dihydro-2,6'-dioxospiro[indole-3,3'-piperidine]-1-methoxyethyl trimethylsilane prepared in example 60a (91 mg, 0.134 mmol) was reacted with pyrrolidine (2 mL), trifluoroacetic acid (10 mL) and then N,N'-diisopropylethylamine (2 mL) to give racemic (2'R,3R,4'S)-6-chloro-4'-(3-chlorophenyl)-2'-(5-fluoro-2-methylphenyl)-1'-(3-pyrrolidin-1-yl-propyl)spiro[3H-indole-3,3'-piperidine]-2,6'(1H)-dione as a white solid (21 mg, 26.9%).

HRMS (ES$^+$) m/z Calcd for $C_{32}H_{32}Cl_2FN_3O_2$+H [(M+H)$^+$]: 580.1929. Found: 580.1926.

EXAMPLE 64a

Preparation of intermediate 1-(3-methoxycarboxyl-phenyl)-3-trimethylsilyoxy-2-aza-1,3-butadiene

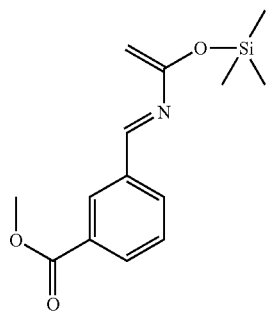

M. W. 277.40 $C_{14}H_{19}NO_3Si$

In a manner similar to the method described in example 1b, 3-formyl-benzoic acid methyl ester (1.5 g, 10 mmol) (Acros) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(3-methoxycarboxyl-phenyl)-3-trimethylsilyoxy-2-aza-1,3-butadiene as yellow gum and used for the next step without further purification.

EXAMPLE 64b

Preparation of racemic (2'R,3R,4'S)-6-chloro-4'-(3-chlorophenyl)-2'-(3-methoxycarbonyl-phenyl)spiro[3H-indole-3,3'-piperidine]-2,6'(1H)-dione

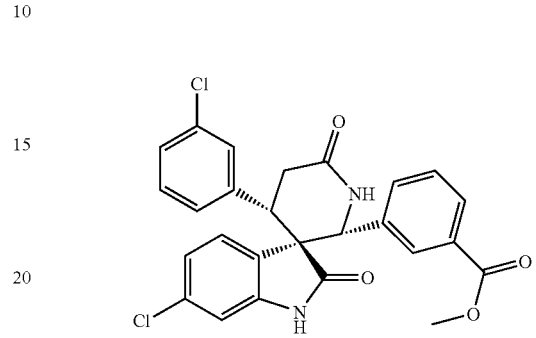

M. W. 495.37 $C_{26}H_{20}Cl_2N_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(3-methoxycarbonyl-phenyl)-3-trimethylsilyoxy-2-aza-1,3-butadiene (2.4 g, 8.65 mmol) prepared in example 64a in toluene and then trifluoroacetic acid (10 mL) in dichloromethane to give racemic (2'R,3R,4'S)-6-chloro-4'-(3-chlorophenyl)-2'-(3-methoxycarbonyl-phenyl)spiro[3H-indole-3,3'-piperidine]-2,6'(1H)-dione as a white solid (0.28 g, 56%).

HRMS (ES$^+$) m/z Calcd for $C_{26}H_{20}Cl_2N_2O_4$+H [(M+H)$^+$]: 495.0873 Found: 495.0872.

EXAMPLE 65

Preparation of racemic (2'R,3R,4'S)-1'-[3-(4-acetyl-piperazin-1-yl)-propyl]-6-chloro-4'-(3-chlorophenyl)-2'-(5-fluoro-2-methylphenyl)spiro[3H-indole-3,3'-piperidine]-2,6'(1H)-dione

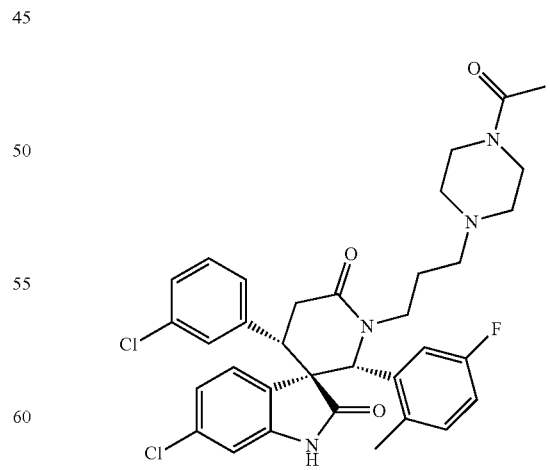

M. W. 637.59 $C_{34}H_{35}Cl_2FN_4O_3$

In a manner similar to the method described in example 60b, racemic (2'R,3R,4'S)-6-chloro-4'-(3-chlorophenyl)-1'-(3-chloro-propyl)-2'-(5-fluoro-2-methylphenyl)-2,3-dihydro-2,6'-dioxospiro[indole-3,3'-piperidine]-1-methoxyethyl trimethylsilane prepared in example 60a (88 mg, 0.134 mmol) was reacted with pyrrolidine (0.4 g, 3.1 mmol), trifluoroacetic acid (10 mL) and then N,N'-diisopropylethylamine (2 mL) to give racemic (2'R,3R,4'S)-1'-[3-(4-acetylpiperazin-1-yl)-propyl]-6-chloro-4'-(3-chlorophenyl)-2'-(5-fluoro-2-methylphenyl)spiro[3H-indole-3,3'-piperidine]-2,6'(1H)-dione as a white solid (33 mg, 38.8%).

HRMS (ES+) m/z Calcd for $C_{34}H_{35}Cl_2FN_4O_3$+H [(M+H)+]: 637.2143 Found: 637.2139.

EXAMPLE 66a

Preparation of intermediate 1-(1-ethyl-propenyl)-3-trimethylsilyoxy-2-aza-1,3-butadiene

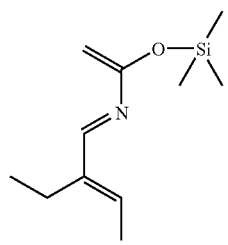

M. W. 211.38 $C_{11}H_{21}NOSi$

In a manner similar to the method described in example 1b, 2-ethyl-but-2-enal (1.54 g, 10 mmol) (TCI-US) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(1-ethyl-propenyl)-3-trimethylsilyoxy-2-aza-1,3-butadiene and used for the next step without further purification.

EXAMPLE 66b

Preparation of racemic (2'R,3R,4'S)-6-chloro-4'-(3-chlorophenyl)-2'-(1-ethyl-propenyl)spiro[3H-indole-3,3'-piperidine]-2,6'(1H)-dione

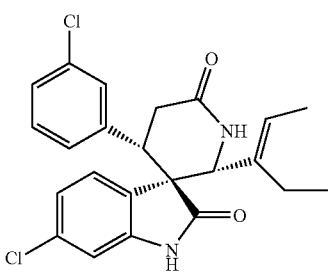

M. W. 429.35 $C_{23}H_{22}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(1-ethyl-propenyl)-3-trimethylsilyoxy-2-aza-1,3-butadiene (2.1 g, 9.93 mmol) prepared in example 66a in toluene and then trifluoroacetic acid (20 mL) in dichloromethane to give racemic (2'R,3R,4'S)-6-chloro-4'-(3-chlorophenyl)-2'-(1-ethyl-propenyl)spiro[3H-indole-3,3'-piperidine]-2,6'(1H)-dione as a white solid (0.24 g, 54.5%).

HRMS (ES+) m/z Calcd for $C_{23}H_{22}Cl_2N_2O_2$+H [(M+H)+]: 429.1131. Found: 429.1129.

EXAMPLE 66c

Preparation of chiral (2'R,3R,4'S)-6-chloro-4'-(3-chlorophenyl)-2'-(1-ethyl-propenyl)spiro[3H-indole-3,3'-piperidine]-2,6'(1H)-dione

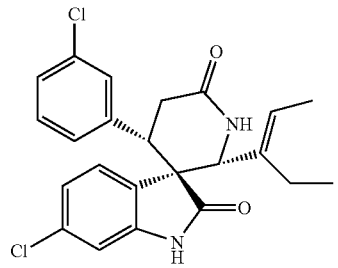

M. W. 429.35 $C_{23}H_{22}Cl_2N_2O_2$

Separation of the two enantiomers (2'R,3R,4'S)-6-chloro-4'-(3-chlorophenyl)-2'-(1-ethyl-propenyl)spiro[3H-indole-3,3'-piperidine]-2,6'(1H)-dione prepared in example 66b was conducted by chiral SFC to provide chiral (2'R,3R,4'S)-6-chloro-4'-(3-chlorophenyl)-2'-(1-ethyl-propenyl)spiro[3H-indole-3,3'-piperidine]-2,6'(1H)-dione as a white solid and chiral (2'S,3S,4'R)-6-chloro-4'-(3-chlorophenyl)-2'-(1-ethyl-propenyl)spiro[3H-indole-3,3'-piperidine]-2,6'(1H)-dione as a white solid.

EXAMPLE 67a

Preparation of racemic (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione

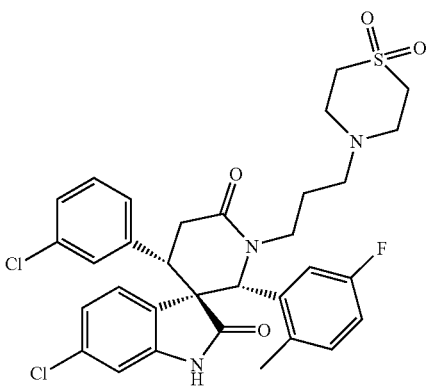

M. W. 644.60 $C_{32}H_{32}Cl_2FN_3O_4S$

In a manner similar to the method described in example 60b, racemic (2'R,3R,4'S)-6-chloro-4'-(3-chlorophenyl)-1'-(3-chloro-propyl)-2'-(5-fluoro-2-methylphenyl)-2,3-dihydro-2,6'-dioxospiro[indole-3,3'-piperidine]-1-methoxyethyl trimethylsilane prepared in example 60a (0.21 mg, 0.31 mmol) was reacted with thiomorpholin 1,1-dioxide (0.47 g, 3.48 mmol), trifluoroacetic acid (10 mL) and then N,N'-diisopropylethylamine (2 mL) to give racemic (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione as a white solid (72 mg, 36.2%).

HRMS (ES+) m/z Calcd for $C_{32}H_{32}Cl_2FN_3O_4S+H$ [(M+H)+]: 644.1548. Found: 644.1542.

EXAMPLE 67b

Preparation of chiral (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione

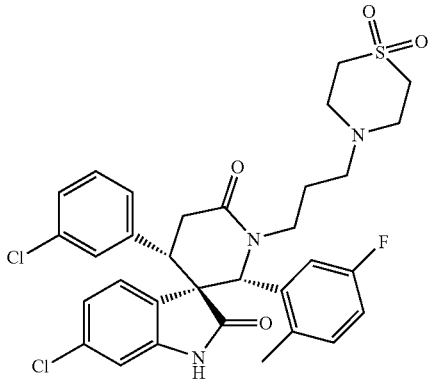

M. W. 644.60 $C_{32}H_{32}Cl_2FN_3O_4S$

Separation of the two enantiomers from racemic (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione prepared in example 67a was conducted by chiral SFC to provide chiral (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione as a white solid and chiral (2'S,3S,4'R)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione as a white solid.

EXAMPLE 68a

Preparation of intermediate 1-(2,5-dimethyl-phenyl)-3-trimethylsilyoxy-2-aza-1,3-butadiene

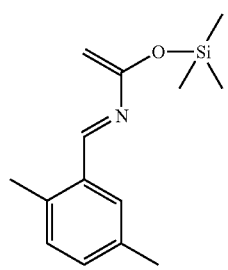

M. W. 247.42 $C_{14}H_{21}NOSi$

In a manner similar to the method described in example 1b, 2,5-dimethyl-benzaldehyde (1.34 g, 10 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,5-dimethyl-phenyl)-3-trimethylsilyoxy-2-aza-1,3-butadiene as yellow gum and used for the next step without further purification.

EXAMPLE 68b

Preparation of racemic (2'R,3R,4'S)-6-chloro-4'-(3-chlorophenyl)-2'-(2,5-dimethyl-phenyl)spiro[3H-indole-3,3'-piperidine]-2,6'(1H)-dione

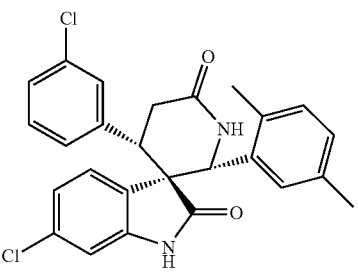

M. W. 465.38 $C_{26}H_{22}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(2,5-dimethyl-phenyl)-3-trimethylsilyoxy-2-aza-1,3-butadiene (2.3 g, 9.31 mmol) prepared in example 68a in toluene and then trifluoroacetic acid (20 mL) in dichloromethane to give racemic (2'R,3R,4'S)-6-chloro-4'-(3-chlorophenyl)-2'-(2,5-dimethyl-phenyl)spiro[3H-indole-3,3'-piperidine]-2,6'(1H)-dione as a white solid.

HRMS (ES+) m/z Calcd for $C_{26}H_{22}Cl_2N_2O_2+H$ [(M+H)+]: 465.1131 Found: 465.1128.

EXAMPLE 68c

Preparation of chiral (2'R,3R,4'S)-6-chloro-4'-(3-chlorophenyl)-2'-(2,5-dimethyl-phenyl)spiro[3H-indole-3,3'-piperidine]-2,6'(1H)-dione

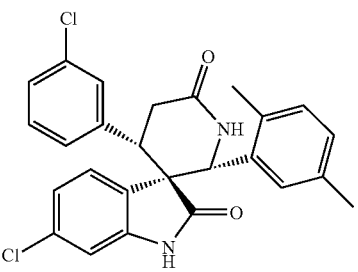

M. W. 465.38 $C_{26}H_{22}Cl_2N_2O_2$

Separation of the two enantiomers from racemic (2'R,3R,4'S)-6-chloro-4'-(3-chlorophenyl)-2'-(2,5-dimethyl-phenyl)

spiro[3H-indole-3,3'-piperidine]-2,6'(1H)-dione prepared in example 68b was conducted by chiral SFC to provide chiral (2'R,3R,4'S)-6-chloro-4'-(3-chlorophenyl)-2'-(2,5-dimethyl-phenyl)spiro[3H-indole-3,3'-piperidine]-2,6'(1H)-dione as a white solid and chiral ((2'S,3S,4'R)-6-chloro-4'-(3-chlorophenyl)-2'-(2,5-dimethyl-phenyl)spiro[3H-indole-3,3'-piperidine]-2,6'(1H)-dione as a white solid.

EXAMPLE 69a

Preparation of intermediate 1-(2,5-dimethyl-2H-pyrazole-3-yl)-3-trimethylsilyoxy-2-aza-1,3-butadiene

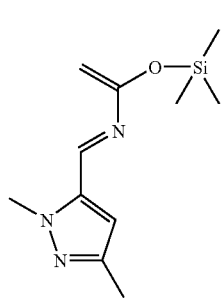

M. W. 237.38 $C_{11}H_{19}N_3OSi$

In a manner similar to the method described in example 1b, 2,5-dimethyl-2H-pyrazole-3-carbaldehyde (1.24 g, 10 mmol) (ASDI-INTER) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(2,5-dimethyl-2H-pyrazole-3-yl)-3-trimethylsilyoxy-2-aza-1,3-butadiene as yellow gum and used for the next step without further purification.

EXAMPLE 69b

Preparation of racemic (2'R,3R,4'S)-6-chloro-4'-(3-chlorophenyl)-2'-(2,5-dimethyl-2H-pyrazole-3-yl)spiro[3H-indole-3,3'-piperidine]-2,6'(1H)-dione

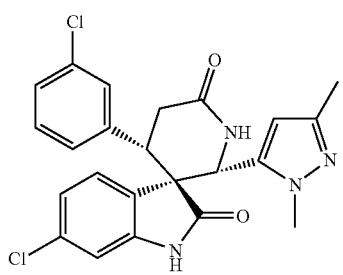

M. W. 455.35 $C_{23}H_{20}Cl_2N_4O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(2,5-dimethyl-2H-pyrazole-3-yl)-3-trimethylsilyoxy-2-aza-1,3-butadiene (2.5 g, 10.5 mmol) prepared in example 69a in toluene and then trifluoroacetic acid (15 mL) in dichloromethane to give racemic (2'R,3R,4'S)-6-chloro-4'-(3-chlorophenyl)-2'-(2,5-dimethyl-2H-pyrazole-3-yl)spiro[3H-indole-3,3'-piperidine]-2,6'(1H)-dione as a white solid (Yield 0.14 g, 30.4%).

HRMS (ES$^+$) m/z Calcd for $C_{23}H_{20}Cl_2N_4O_2$+H [(M+H)$^+$]: 455.1036 Found: 455.1035.

EXAMPLE 70a

Preparation of intermediate 1-(1-methyl-propenyl)-3-trimethylsilyoxy-2-aza-1,3-butadiene

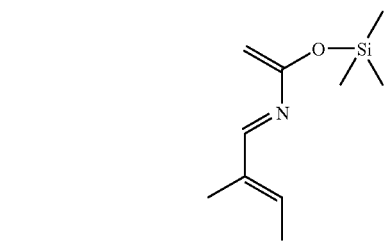

M. W. 197.36 $C_{10}H_{19}NOSi$

In a manner similar to the method described in example 1b, 2-methyl-but-2-enal (0.84 g, 10 mmol) (EASTMAN) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(1-methyl-propenyl)-3-trimethylsilyoxy-2-aza-1,3-butadiene and used for the next step without further purification.

EXAMPLE 70b

Preparation of racemic (2'R,3R,4'S)-6-chloro-4'-(3-chlorophenyl)-2'-(1-methyl-propenyl)spiro[3H-indole-3,3'-piperidine]-2,6'(1H)-dione

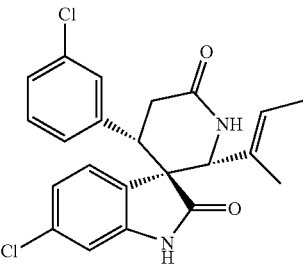

M. W. 415.32 $C_{22}H_{20}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.35 g, 0.89 mmol) was reacted with 1-(1-methyl-propenyl)-3-trimethylsilyoxy-2-aza-1,3-butadiene (2.1 g, 9.93 mmol) prepared in example 70a in toluene and then trifluoroacetic acid (20 mL) in dichloromethane to give racemic (2'R,3R,4'S)-6-chloro-4'-(3-chlorophenyl)-2'-(1-methyl-propenyl)spiro[3H-indole-3,3'-piperidine]-2,6'(1H)-dione as a white solid (0.19 g, 51.4%).

HRMS (ES$^+$) m/z Calcd for $C_{22}H_{20}Cl_2N_2O_2$+H [(M+H)$^+$]: 415.0975. Found: 415.0975.

EXAMPLE 71a

Preparation of intermediate 1-(1-methyl-but-1-enyl)-3-trimethylsilyoxy-2-aza-1,3-butadiene

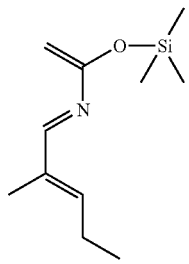

M. W. 211.38 C$_{11}$H$_{21}$NOSi

In a manner similar to the method described in example 1b, 2-methyl-pent-2-enal (2.0 g, 20 mmol) (Aldrich) was used as the starting material in place of 3-chloro-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.7 g, 26 mmol) and acetyl chloride (2.0 g, 26 mmol) to give 1-(1-methyl-but-1-enyl)-3-trimethylsilyoxy-2-aza-1,3-butadiene and used for the next step without further purification.

EXAMPLE 71b

Preparation of racemic (2'R,3R,4'S)-6-chloro-4'-(3-chlorophenyl)-2'-(1-methyl-but-1-enyl)spiro[3H-indole-3,3'-piperidine]-2,6'(1H)-dione

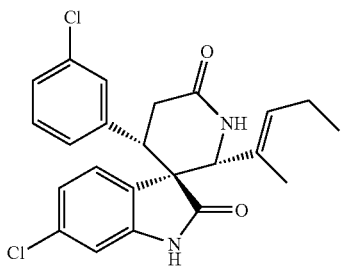

M. W. 429.35 C$_{23}$H$_{22}$Cl$_2$N$_2$O$_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(1-methyl-but-1-enyl)-3-trimethylsilyoxy-2-aza-1,3-butadiene (3.2 g, 15.2 mmol) prepared in example 71a in toluene and then trifluoroacetic acid (10 mL) in dichloromethane to give racemic (2'R,3R,4'S)-6-chloro-4'-(3-chlorophenyl)-2'-(1-methyl-but-1-enyl)spiro[3H-indole-3,3'-piperidine]-2,6' (1H)-dione as a white solid (0.24 g, 54.5%).

HRMS (ES$^+$) m/z Calcd for C$_{23}$H$_{22}$Cl$_2$N$_2$O$_2$+H [(M+H)$^+$]: 429.1131. Found: 429.1127.

EXAMPLE 72a

Preparation of racemic (2'R,3R,4'S)-6-chloro-4'-(3-chlorophenyl)-2'-(1-ethyl-propyl)spiro[3H-indole-3,3'-piperidine]-2,6'(1H)-dione

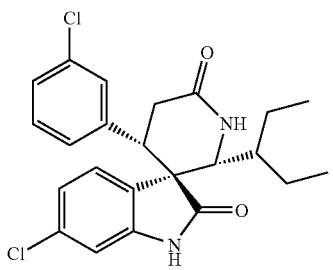

M. W. 431.37 C$_{23}$H$_{24}$Cl$_2$N$_2$O$_2$

To a solution of racemic (2'R,3R,4'S)-6-chloro-4'-(3-chlorophenyl)-2'-(1-ethyl-propenyl)spiro[3H-indole-3,3'-piperidine]-2,6'(1H)-dione (0.3 g, 0.70 mmol) prepared in example 66b in ethyl acetate (30 mL) was added platinum oxide (0.35 g, 1.54 mmol). The resulting suspension was vigorously shaken under hydrogen (50 psi) for 6 h. The mixture was filtered through a short pad of celite. The filtrate was concentrated. The residue was purified by chromatography (EtOAc:CH$_2$Cl$_2$=1:1) to give racemic (2'R,3R,4'S)-6-chloro-4'-(3-chlorophenyl)-2'-(1-ethyl-propyl)spiro[3H-indole-3,3'-piperidine]-2,6'(1H)-dione as a white solid (Yield 0.11 g, 37.7%).

HRMS (ES$^+$) m/z Calcd for C$_{23}$H$_{24}$Cl$_2$N$_2$O$_2$+H [(M+H)$^+$]: 431.1288 Found: 431.1285.

EXAMPLE 72b

Preparation of chiral (2'R,3R,4'S)-6-chloro-4'-(3-chlorophenyl)-2'-(1-ethyl-propyl)spiro[3H-indole-3,3'-piperidine]-2,6'(1H)-dione

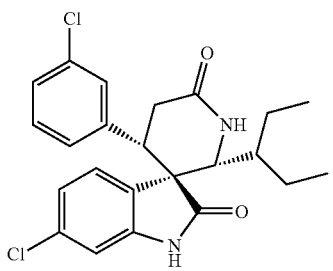

M. W. 431.37 C$_{23}$H$_{24}$Cl$_2$N$_2$O$_2$

Separation of the two enantiomers from racemic (2'R,3R,4'S)-6-chloro-4'-(3-chlorophenyl)-2'-(1-ethyl-propyl)spiro[3H-indole-3,3'-piperidine]-2,6'(1H)-dione (60 mg) was conducted by chiral SFC to provide chiral (2'R,3R,4'S)-6-chloro-4'-(3-chlorophenyl)-2'-(1-ethyl-propyl)spiro[3H-indole-3,3'-piperidine]-2,6'(1H)-dione as a white solid (Yield: 24 mg, 40%) and chiral (2'S,3S,4'R)-6-chloro-4'-(3-chlorophenyl)-2'-(1-ethyl-propyl)spiro[3H-indole-3,3'-piperidine]-2,6'(1H)-dione (Yield: 24 mg, 40%).

EXAMPLE 73a

Preparation of intermediate racemic (2'R,3R,4'S)-6-chloro-4'-(3-chlorophenyl)-2'-(2,3-difluoro-6-isopropoxy-phenyl)-2,3-dihydro-2,6'-dioxospiro[indole-3,3'-piperidine]-1-methoxyethyl trimethylsilane

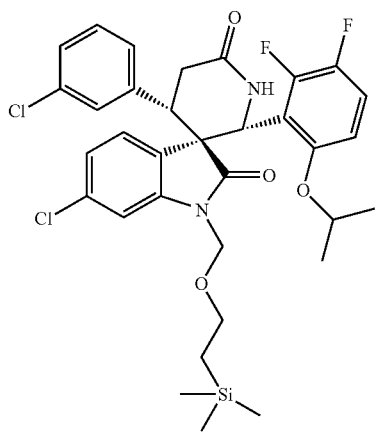

M. W. 661.65 $C_{33}H_{36}Cl_2F_2N_2O_4Si$

In a manner similar to the method described in example 55b, E/Z-6-chloro-3-(3-chloro-benzylidene)-1-(2-trimethylsilanyl-ethoxymethyl)-1,3-dihydro-indole-2-one prepared in example 55a (3.4 g, 8.10 mmol) was reacted with 1-(2,3-difluoro-6-isopropoxy-phenyl)-3-trimethylsilyoxy-2-aza-1,3-butadiene (16 g, 51.1 mmol) prepared in example 62c in toluene to give racemic (2'R,3R,4'S)-6-chloro-4'-(3-chlorophenyl)-2'-(2,3-difluoro-6-isopropoxy-phenyl)-2,3-dihydro-2,6'-dioxospiro[indole-3,3'-piperidine]-1-methoxyethyl trimethylsilane as an off-white solid.

EXAMPLE 73b

Preparation of intermediate racemic (2'R,3R,4'S)-6-chloro-4'-(3-chloro-phenyl)-1'-(3-chloro-propyl)-2'-(2,3-difluoro-6-isopropoxy-phenyl)-2,3-dihydro-2,6'-dioxospiro[indole-3,3'-piperidine]-1-methoxyethyl trimethylsilane

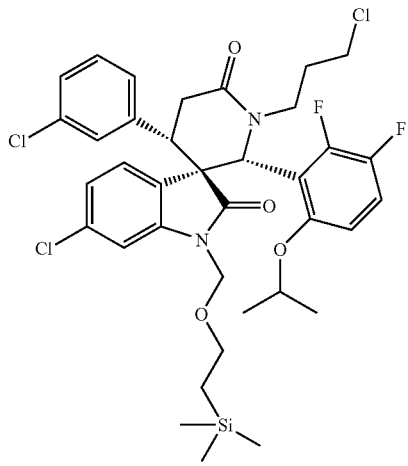

M. W. 738.18 $C_{36}H_{41}Cl_3F_2N_2O_4Si$

In a manner similar to the method described in example 24c, racemic (2'S,3R,4'S)-6-chloro-4'-(3-chlorophenyl)-2'-(2,3-difluoro-6-isopropoxy-phenyl)-2,3-dihydro-2,6'-dioxospiro[indole-3,3'-piperidine]-1-methoxyethyl trimethylsilane (1.8 g, 2.72 mmol) prepared in example 73a was reacted with LiH (1.0 g, 125 mmol) and 1-chloro-3-iodo-propane (5.0 g, 24.5 mmol) in N,N-dimethyl-formamide (40 mL) to give racemic (2'R,3R,4'S)-6-chloro-4'-(3-chloro-phenyl)-1'-(3-chloro-propyl)-2'-(2,3-difluoro-6-isopropoxy-phenyl)-2,3-dihydro-2,6'-dioxospiro[indole-3,3'-piperidine]-1-methoxyethyl trimethylsilane as a white form (Yield: 0.67 g, 33.5%).

EXAMPLE 73c

Preparation of racemic (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione

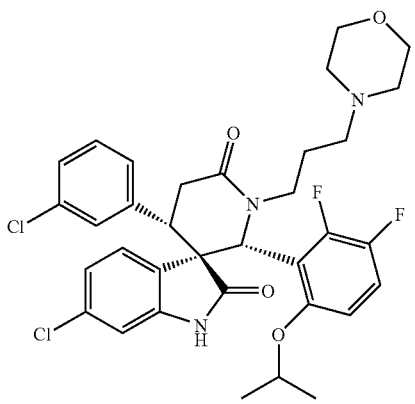

M. W. 658.58 $C_{34}H_{35}Cl_2F_2N_3O_4$

In a manner similar to the method described in example 60b, racemic (2'S,3R,4'S)-6-chloro-4'-(3-chloro-phenyl)-1'-(3-chloro-propyl)-2'-(2,3-difluoro-6-isopropoxy-phenyl)-2,3-dihydro-2,6'-dioxospiro[indole-3,3'-piperidine]-1-methoxyethyl trimethylsilane prepared in example 73b (0.3 g, 0.41 mmol) was reacted with morpholine (10 mL), trifluoroacetic acid (10 mL) and then N,N'-diisopropylethylamine (1 mL) to give racemic (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione as a white solid (0.15 g, 55.6%).

HRMS (ES$^+$) m/z Calcd for $C_{34}H_{35}Cl_2F_2N_3O_4$+H [(M+H)$^+$]: 658.2046. Found: 658.2038.

EXAMPLE 73d

Preparation of chiral (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione

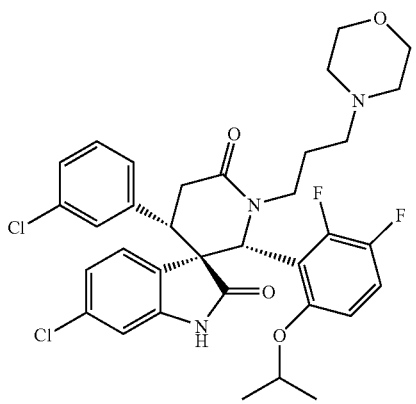

M. W. 658.58 $C_{34}H_{35}Cl_2F_2N_3O_4$

Separation of the two enantiomers from racemic (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione (120 mg) prepared in example 73c was conducted by chiral SFC to provide chiral (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione as a white solid (Yield: 55 mg, 46%) and chiral (2'R,3S,4'R)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione as a white solid (Yield: 54 mg, 45%).

EXAMPLE 74a

Preparation of intermediate 1-(1-ethylidene-pentyl)-3-trimethylsilyoxy-2-aza-1,3-butadiene

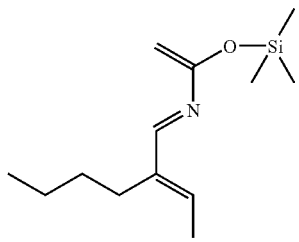

M. W. 239.44 $C_{13}H_{25}NOSi$

In a manner similar to the method described in example 1b, 2-ethylidene-hexanal (1.1 g, 8.68 mmol) (Aldrich) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (2.7 g, 13 mmol) and acetyl chloride (1.0 g, 26 mmol) to give 1-(1-ethylidene-pentyl)-3-trimethylsilyoxy-2-aza-1,3-butadiene and used for the next step without further purification.

EXAMPLE 74b

Preparation of racemic (2'R,3R,4'S)-6-chloro-4'-(3-chlorophenyl)-2'-(1-ethylidene-pentyl)spiro[3H-indole-3,3'-piperidine]-2,6'(1H)-dione

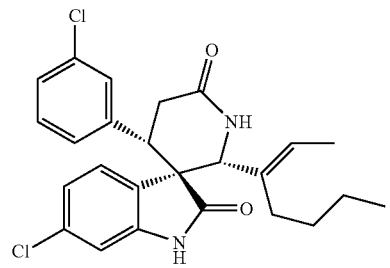

M. W. 457.40 $C_{25}H_{26}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(1-ethylidene-pentyl)-3-trimethylsilyoxy-2-aza-1,3-butadiene (2.1 g, 8.77 mmol) prepared in example 74a in toluene and then trifluoroacetic acid (15 mL) in dichloromethane to give racemic (2'R,3R,4'S)-6-chloro-4'-(3-chlorophenyl)-2'-(1-ethylidene-pentyl)spiro[3H-indole-3,3'-piperidine]-2,6'(1H)-dione as an off-white solid (0.13 g, 27.7%).

HRMS (ES$^+$) m/z Calcd for $C_{25}H_{26}Cl_2N_2O_2$+H [(M+H)$^+$]: 457.1444 Found: 457.1443.

EXAMPLE 75

Preparation of racemic (2'R,3R,4'S)-6-chloro-4'-(3-chlorophenyl)-2'-(2,3-difluoro-6-isopropoxy-phenyl)-6'-thioxospiro[3H-indole-3,3'-piperidine]-2(1H)-one

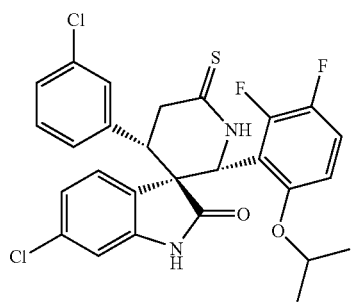

M. W. 547.46 $C_{27}H_{22}Cl_2F_2N_2O_2S$

In a manner similar to the method described in example 30, racemic (2'S,3R,4'S)-6-chloro-4'-(3-chlorophenyl)-2'-(2,3-difluoro-6-isopropoxy-phenyl)spiro[3H-indole-3,3'-piperidine]-2,6'(1H)-dione (0.45 g, 0.85 mmol) prepared in example 62d was reacted with 2,4-bis-(4-methoxyphenyl)-1,3-dithia-2,4-diphosphetane 2,4-disulfide (0.6 g, 1.8 mmol) in toluene to give racemic (2'S,3R,4'S)-6-chloro-4'-(3-chlorophenyl)-2'-(2,3-difluoro-6-isopropoxy-phenyl)-6'-thioxospiro[3H-indole-3,3'-piperidine]-2(1H)-one (Yield 0.36 g, 78.3%).

HRMS (ES$^+$) m/z Calcd for $C_{27}H_{22}Cl_2F_2N_2O_2S$+H [(M+H)$^+$]: 547.0820. Found: 547.0821.

EXAMPLE 76

Preparation of racemic (2'R,3R,4'S)-[6-chloro-4'-(3-chlorophenyl)-2'-(2,3-difluoro-6-isopropoxy-phenyl)-2,3-dihydro-2-oxospiro[3H-indole-3,3'-piperidin]-6-ylene]hydrazine carboxylic acid ethyl ester

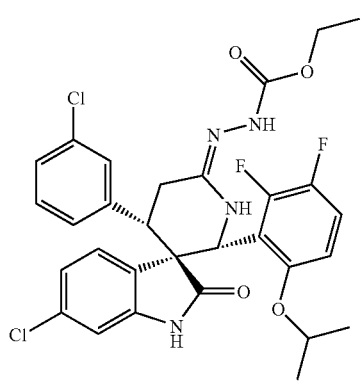

M. W. 617.48 $C_{30}H_{28}Cl_2F_2N_4O_4$

In a manner similar to the method described in example 40, racemic (2'S,3R,4'S)-6-chloro-4'-(3-chlorophenyl)-2'-(2,3-difluoro-6-isopropoxy-phenyl)-6'-thioxospiro[3H-indole-3,3'-piperidine]-2(1H)-one (0.30 g, 0.55 mmol) prepared in example 75 was reacted with ethyl carbazate (0.3 g, 2.97 mmol), mercuric acetate (0.30 g, 0.95 mmol) and triethylamine (0.1 g, 0.99 mmol) in tetrahydrofuran (40 mL) to give racemic (2'R,3R,4'S)-[6-chloro-4'-(3-chlorophenyl)-2'-(2,3-difluoro-6-isopropoxy-phenyl)-2,3-dihydro-2-oxospiro[3H-indole-3,3'-piperidin]-6-ylene]hydrazine carboxylic acid ethyl ester as a white solid (Yield 0.25 g, 73.5%).

HRMS (ES$^+$) m/z Calcd for $C_{30}H_{28}Cl_2F_2N_4O_4$+H [(M+H)$^+$]: 617.1529. Found: 617.1523.

EXAMPLE 77a

Preparation of intermediate cyclopent-1-enecarbaldehyde

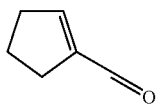

M. W. 96.13 $C_6H_8O$

To an acidic solution of sodium periodate (28.3 g, 0.13 mol) (Aldrich) in water (250 mL) was added the solution of 1,2-cyclohexanediol (12 g, 0.10 mol) (Acros) in ethyl ether (150 mL). The mixture was stirred vigorously for 0.5 h at room temperature. After addition of KOH aqueous solution (20%, 38.4 mL), the reaction mixture was stirred for an additional 1 h. The mixture was extracted with ethyl ether. The organic layers were combined and dried. The solvent was removed to give cyclopent-1-enecarbaldehyde as yellow oil (Yield: 7.2 g, 75%)

EXAMPLE 77b

Preparation of intermediate 1-(cyclopent-1-enyl)-3-trimethylsilyoxy-2-aza-1,3-butadiene

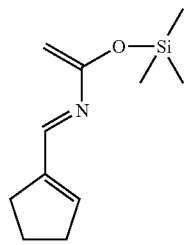

M. W. 209.37 $C_{11}H_{19}NOSi$

In a manner similar to the method described in example 1b, 2 cyclopent-1-enecarbaldehyde (1.4 g, 14.6 mmol) prepared in example 77a was used as the starting material in place of 3-chloro-benzaldehyde to react with 1,1,1,3,3,3-hexamethyl-disilazane (1.6 g, 10 mmol), n-butyllithium (2.5 M, 4 mL, 10 mmol), trimethylsilyl chloride (1.1 g, 10 mmol), triethylamine (2.7 g, 13 mmol) and acetyl chloride (1.0 g, 26 mmol) to give 1-(cyclopent-1-enyl)-3-trimethylsilyoxy-2-aza-1,3-butadiene and used for the next step without further purification.

EXAMPLE 77c

Preparation of racemic (2'R,3R,4'S)-6-chloro-4'-(3-chlorophenyl)-2'-(cyclopent-1-enyl)spiro[3H-indole-3,3'-piperidine]-2,6'(1H)-dione

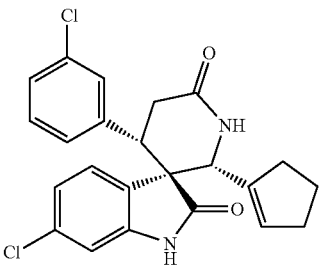

M. W. 427.33 $C_{23}H_{20}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(cyclopent-1-enyl)-3-trimethylsilyoxy-2-aza-1,3-butadiene (2.0 g, 9.55 mmol) prepared in example 77b in toluene and then trifluoroacetic acid (10 mL) in dichloromethane to give racemic (2'R,3R,4'S)-6-chloro-4'-(3-chlorophenyl)-2'-(cyclopent-1-enyl)spiro[3H-indole-3,3'-piperidine]-2,6'(1H)-dione as a white solid (0.12 g, 27.3%).

HRMS (ES$^+$) m/z Calcd for $C_{23}H_{20}Cl_2N_2O_2$+H [(M+H)$^+$]: 427.0975 Found: 427.0972.

EXAMPLE 78a

Preparation of racemic (2'R,3R,4'S)-6-chloro-4'-(3-chlorophenyl)-2'-cyclopentylspiro[3H-indole-3,3'-piperidine]-2,6'(1H)-dione

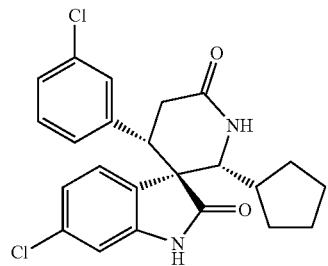

M. W. 429.35 $C_{23}H_{22}Cl_2N_2O_2$

In a manner similar to the method described in example 72, racemic (2'R,3R,4'S)-6-chloro-4'-(3-chlorophenyl)-2'-(cyclopent-1-enyl)spiro[3H-indole-3,3'-piperidine]-2,6'(1H)-dione (0.1 g, 0.23 mmol) prepared in example 77c was treated with platinum oxide in ethyl acetate under hydrogen (50 psi) to give racemic (2'R,3R,4'S)-6-chloro-4'-(3-chlorophenyl)-2'-cyclopentylspiro[3H-indole-3,3'-piperidine]-2,6'(1H)-dione as a white solid (0.031 g, 31%).

HRMS (ES$^+$) m/z Calcd for $C_{23}H_{22}Cl_2N_2O_2$+H [(M+H)$^+$]: 429.1131 Found: 429.1131.

EXAMPLE 78b

Preparation of chiral (2'R,3R,4'S)-6-chloro-4'-(3-chlorophenyl)-2'-cyclopentylspiro[3H-indole-3,3'-piperidine]-2,6'(1H)-dione

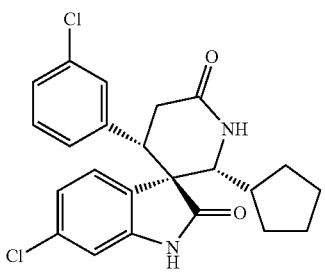

M. W. 429.35 $C_{23}H_{22}Cl_2N_2O_2$

Separation of the two enantiomers from (2'R,3R,4'S)-6-chloro-4'-(3-chlorophenyl)-2'-cyclopentylspiro[3H-indole-3,3'-piperidine]-2,6'(1H)-dione (30 mg) prepared in example 78a was conducted by chiral SFC to provide chiral (2'R,3R,4'S)-6-chloro-4'-(3-chlorophenyl)-2'-cyclopentylspiro[3H-indole-3,3'-piperidine]-2,6'(1H)-dione as a white solid (6 mg, 20%) and chiral (2'S,3S,4'R)-6-chloro-4'-(3-chlorophenyl)-2'-cyclopentylspiro[3H-indole-3,3'-piperidine]-2,6'(1H)-dione as a white solid (6 mg, 20%).

EXAMPLE 79a

Preparation of intermediate E-2-Isopropyl-but-2-en-1-ol

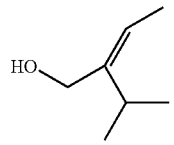

M. W. 114.19 $C_7H_{14}O$

To a solution of 2-butyn-1-ol (14 g, 0.2 mol) (Aldrich) and CuI (32 g, 0.2 mol) (Aldrich) in ether at 0° C. was added isopropylmagnesium chloride (2 M, 300 mL, 0.6 mol) solution in tetrahydrofuran dropwise. The reaction mixture was stirred at room temperature for 24 h. The reaction mixture was quenched with aqueous saturated NH$_4$Cl solution, extracted with ether twice. The organic layers were combined, washed with water, brine, dried over MgSO$_4$, filtered and concentrated. The residue was purified with chromatography (EtOAc:Hexane=1:8) to give E-2-isopropyl-but-2-en-1-ol as pale yellow oil (Yield 5.3 g, 23%).

The same transformation has been reported by Duboudin, J. G.; Jousseaume, B. in *J. Organometallic Chem.* (1979), 168(1), 1-11 and *J. Organometallic Chem.* (1975), 91(1), C1-C3.

EXAMPLE 79b

Preparation of intermediate E-2-Isopropyl-but-2-enal

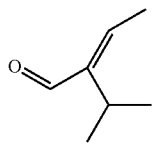

M. W. 112.17 $C_7H_{12}O$

To a solution of oxalyl chloride (6.49 g, 51 mmol) (Aldrich) in dichloromethane (50 mL) at −78° C. was added a solution of dimethyl sulfoxide (7.25 mL, 102 mmol) in dichloromethane (40 mL) dropwise. After 5 mins, the solution of E-2-isopropyl-but-2-en-1-ol (5.3 g, 46 mmol) prepared in example 79a in dichloromethane (10 mL) was added dropwise. The reaction mixture was stirred at −78° C. for 15 min. Triethylamine (22 mL, 0.19 mol) was added and the reaction mixture was slowly warmed to room temperature and stirred at room temperature for 45 mins. Water was added, and organic layer was separated. The aqueous layer was extracted with ether. The organic layers were combined, washed with 10% of HCl, saturated NaHCO$_3$, brine, dried over MgSO$_4$, and concentrated to give crude E-2-Isopropyl-but-2-enal as a yellow oil (Yield 5.3 g, 98%).

EXAMPLE 79c

Preparation of intermediate 1-(1-isopropyl-propenyl)-3-trimethylsilyoxy-2-aza-1,3-butadiene

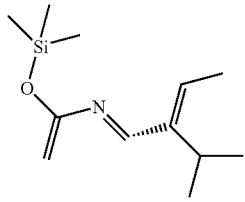

M. W. 225.41 C$_{12}$H$_{23}$NOSi

In a manner similar to the method described in example 1b, E-2-isopropyl-but-2-enal prepared in example 79b (2.2 g, 20 mmol) was used as the starting material in place of 3-chlorobenzaldehyde to react with 1,1,1,3,3,3-hexamethyldisilazane (3.2 g, 20 mmol), n-butyllithium (2.5 M, 4 mL, 20 mmol), trimethylsilyl chloride (2.2 g, 20 mmol), triethylamine (2.72 g, 26 mmol) and acetyl chloride (2 g, 26 mmol) to give 1-(1-isopropyl-propenyl)-3-trimethylsilyoxy-2-aza-1,3-butadiene and used for the next step without further purification.

EXAMPLE 79d

Preparation of racemic (2'R,3R,4'S)-6-chloro-4'-(3-chlorophenyl)-2'-(1-isopropyl-propenyl)spiro[3H-indole-3,3'-piperidine]-2,6'(1H)-dione

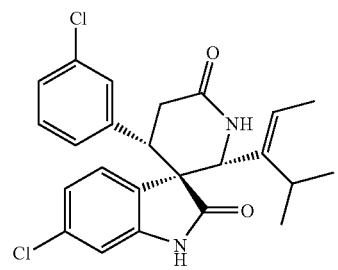

M. W. 443.38 C$_{24}$H$_{24}$Cl$_2$N$_2$O$_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.5 g, 1.3 mmol) was reacted with 1-(1-ethyl-propenyl)-3-trimethylsilyoxy-2-aza-1,3-butadiene (3.7 g, 16.4 mmol) prepared in example 79c in toluene and then trifluoroacetic acid (20 mL) in dichloromethane to give racemic (2'R,3R,4'S)-6-chloro-4'-(3-chlorophenyl)-2'-(1-isopropyl-propenyl)spiro[3H-indole-3,3'-piperidine]-2,6'(1H)-dione as a white solid (0.28 g, 50%).

HRMS (ES$^+$) m/z Calcd for C$_{24}$H$_{24}$Cl$_2$N$_2$O$_2$+H [(M+H)$^+$]: 443.1288. Found: 443.1284

EXAMPLE 79e

Preparation of chiral (2'R,3R,4'S)-6-chloro-4'-(3-chlorophenyl)-2'-(1-isopropyl-propenyl)spiro[3H-indole-3,3'-piperidine]-2,6'(1H)-dione

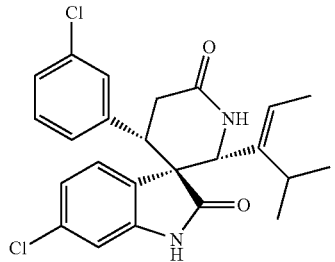

M. W. 443.38 C$_{24}$H$_{24}$Cl$_2$N$_2$O$_2$

Separation of the two enantiomers (2'R,3R,4'S)-6-chloro-4'-(3-chlorophenyl)-2'-(1-ethyl-propenyl)spiro[3H-indole-3,3'-piperidine]-2,6'(1H)-dione (40 mg) prepared in example 79d was conducted by chiral SFC to provide chiral (2'R,3R,4'S)-6-chloro-4'-(3-chlorophenyl)-2'-(1-isopropyl-propenyl) spiro[3H-indole-3,3'-piperidine]-2,6'(1H)-dione as a white solid (12 mg, 30%) and chiral (2'S,3S,4'R)-6-chloro-4'-(3-chlorophenyl)-2'-(1-isopropyl-propenyl)spiro[3H-indole-3,3'-piperidine]-2,6'(1H)-dione as a white solid (12 mg, 30%).

EXAMPLE 80a

Preparation of intermediate 1-(1-methylene-propyl)-3-trimethylsilyoxy-2-aza-1,3-butadiene

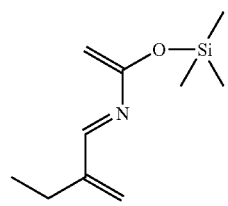

M. W. 197.36 C$_{10}$H$_{19}$NOSi

In a manner similar to the method described in example 1b, ethylacrolein (2.1 g, 22 mmol) (TCI-US) was used as the starting material in place of 3-chloro-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.9 g, 27 mmol) and acetyl chloride (2 g, 27 mmol) to give 1-(1-methylene-propyl)-3-trimethylsilyoxy-2-aza-1,3-butadiene and used for the next step without further purification.

EXAMPLE 80b

Preparation of racemic (2'R,3R,4'S)-6-chloro-4'-(3-chlorophenyl)-2'-(1-methylene-propyl)spiro[3H-indole-3,3'-piperidine]-2,6'(1H)-dione

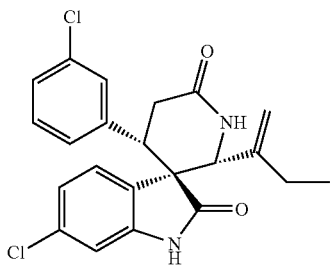

M. W. 415.32 $C_{22}H_{20}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.42 g, 1.1 mmol) was reacted with 1-(1-methylene-propyl)-3-trimethylsilyoxy-2-aza-1,3-butadiene (3.2 g, 16.2 mmol) prepared in example 80a in toluene and then trifluoroacetic acid (10 mL) in dichloromethane to give racemic (2'R,3R,4'S)-6-chloro-4'-(3-chlorophenyl)-2'-(1-methylene-propyl)spiro[3H-indole-3,3'-piperidine]-2,6'(1H)-dione as a white solid (0.31 g, 67%).

HRMS (ES+) m/z Calcd for $C_{22}H_{20}Cl_2N_2O_2$+H [(M+H)+]: 415.0975. Found: 415.0975

EXAMPLE 80c

Preparation of chiral (2'R,3R,4'S)-6-chloro-4'-(3-chlorophenyl)-2'-(1-methylene-propyl)spiro[3H-indole-3,3'-piperidine]-2,6'(1H)-dione

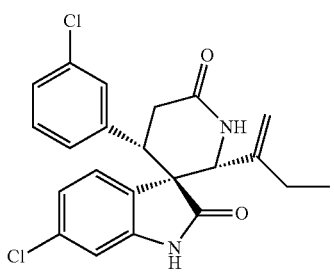

M. W. 415.32 $C_{22}H_{20}Cl_2N_2O_2$

Separation of the two enantiomers of racemic (2'R,3R,4'S)-6-chloro-4'-(3-chlorophenyl)-2'-(1-methylene-propyl)spiro[3H-indole-3,3'-piperidine]-2,6'(1H)-dione (150 mg) prepared in example 80b was conducted by chiral SFC to provide chiral (2'R,3R,4'S)-6-chloro-4'-(3-chlorophenyl)-2'-(1-methylene-propyl)spiro[3H-indole-3,3'-piperidine]-2,6'(1H)-dione as a white solid (63 mg, 42%) and chiral (2'S,3S,4'R)-6-chloro-4'-(3-chlorophenyl)-2'-(1-methylene-propyl)spiro[3H-indole-3,3'-piperidine]-2,6'(1H)-dione as a white solid (60 mg, 40%).

EXAMPLE 81a

Preparation of intermediate racemic (2'R,3R,4'S)-6-chloro-4'-(3-chlorophenyl)-2'-(1-ethyl-propenyl)-2,3-dihydro-2,6'-dioxo-spiro[indole-3,3'-piperidine]-1-methoxyethyl trimethylsilane

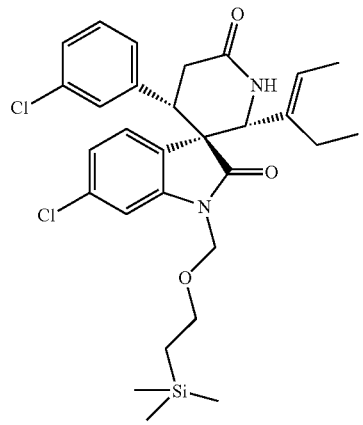

M. W. 559.61 $C_{29}H_{36}Cl_2N_2O_3Si$

In a manner similar to the method described in example 55b, E/Z-6-chloro-3-(3-chloro-benzylidene)-1-(2-trimethyl-silanyl-ethoxymethyl)-1,3-dihydro-indole-2-one (5.4 g, 12.8 mmol) prepared in example 55a was reacted with 1-(1-ethyl-propenyl)-3-trimethylsilyoxy-2-aza-1,3-butadiene (20 g, 95 mmol) prepared in example 66a in toluene (200 mL) to give racemic (2'R,3R,4'S)-6-chloro-4'-(3-chloro-phenyl)-2'-(1-ethyl-propenyl)-2,3-dihydro-2,6'-dioxospiro[indole-3,3'-piperidine]-1-methoxyethyl trimethylsilane as a white gum (Yield 6.1 g, 85%).

EXAMPLE 81b

Preparation of intermediate racemic (2'R,3R,4'S)-1'-[(tert-butoxycarbonyl)methyl]-6-chloro-4'-(3-chlorophenyl)-2'-(1-ethyl-propenyl)-2,3-dihydro-2,6'-dioxospiro[indole-3,3'-piperidine]-1-methoxyethyl trimethylsilane

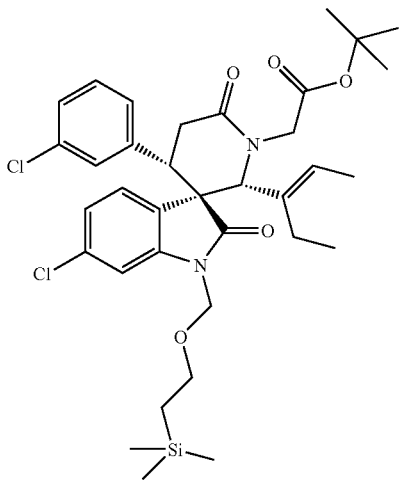

M. W. 673.76 $C_{35}H_{46}Cl_2N_2O_5Si$

In a manner similar to the method described in example 55c, racemic (2'R,3R,4'S)-6-chloro-4'-(3-chloro-phenyl)-2'-(1-ethyl-propenyl)-2,3-dihydro-2,6'-dioxospiro[indole-3,3'- piperidine]-1-methoxyethyl trimethylsilane (1.6 g, 2.8 mmol) prepared in example 81a was reacted with bromoacetic acid tert-butyl ester and cesium carbonate in N,N-dimethylformamide to give racemic (2'R,3R,4'S)-1'-[(tert-butoxycarbonyl)methyl]-6-chloro-4'-(3-chlorophenyl)-2'-(1-ethyl-propenyl)-2,3-dihydro-2,6'-dioxospiro[indole-3,3'-piperidine]-1-methoxyethyl trimethylsilane as a white foam (Yield 0.7 g, 37%).

EXAMPLE 81c

Preparation of racemic (2'R,3R,4'S)-6-chloro-4'-(3-chlorophenyl)-2'-(1-ethyl-propenyl)-1'-hydroxycarbonylmethyl-spiro[3H-indole-3,3'-piperidine]-2,6'(1H)-dione

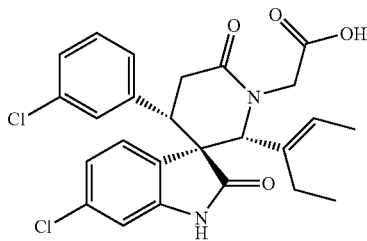

M. W. 487.39 $C_{25}H_{24}Cl_2N_2O_4$

In a manner similar to the method described in example 55d, racemic (2'R,3R,4'S)-1'-[(tert-butoxycarbonyl)methyl]-6-chloro-4'-(3-chlorophenyl)-2'-(1-ethyl-propenyl)-2,3-dihydro-2,6'-dioxospiro[indole-3,3'-piperidine]-1-methoxyethyl trimethylsilane (0.6 g, 0.89 mmol) prepared in example 81b was reacted to form racemic (2'R,3R,4'S)-6-chloro-4'-(3-chlorophenyl)-2'-(1-ethyl-propenyl)-1'-hydroxycarbonylmethyl-spiro[3H-indole-3,3'-piperidine]-2,6'(1H)-dione as a white solid (0.35 g, 80%).

HRMS (ES$^+$) m/z Calcd for $C_{25}H_{24}Cl_2N_2O_4$+H [(M+H)$^+$]: 487.1186, Found: 487.1186

EXAMPLE 82a

Preparation of intermediate racemic (2'R,3R,4'S)-6-chloro-4'-(3-chlorophenyl)-2'-(1-ethyl-propenyl)-1'-fluorocarbonylmethylspiro[3H-indole-3,3'-piperidine]-2,6'(1H)-dione

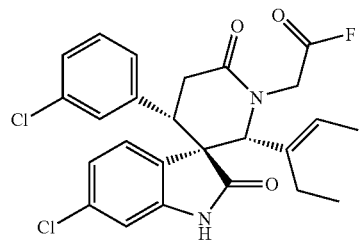

M. W. 489.38 $C_{25}H_{23}Cl_2FN_2O_3$

In a manner similar to the method described in example 34a, racemic (2'R,3R,4'S)-6-chloro-4'-(3-chlorophenyl)-2'-(1-ethyl-propenyl)-1-hydroxycarbonyl-methylspiro[3H-indole-3,3'-piperidine]-2,6'(1H)-dione (0.16 g, 0.33 mmol) prepared in example 81c was reacted with cyanuric fluoride (0.044 mL, 1.64 mmol) (Alfa) and pyridine (0.13 g, 1.64 mmol) in dichloromethane to give racemic (2'R,3R,4'S)-6-chloro-4'-(3-chlorophenyl)-2'-(1-ethyl-propenyl)-1'-fluorocarbonylmethyl-spiro[3H-indole-3,3'-piperidine]-2,6'(1H)-dione (yield: 0.12 g, 75%).

EXAMPLE 82b

Preparation of racemic (2'R,3R,4'S)-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione

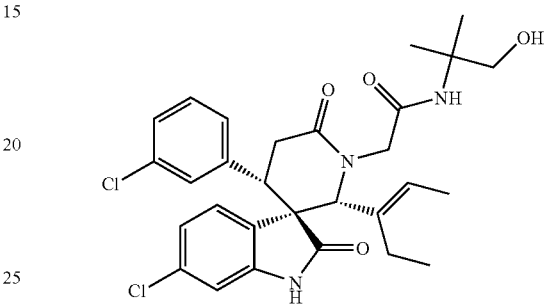

M. W. 558.51 $C_{29}H_{33}Cl_2N_3O_4$

In a manner similar to the method described in example 34b, racemic (2'R,3R,4'S)-6-chloro-4'-(3-chlorophenyl)-2'-(1-ethyl-propenyl)-1'-fluorocarbonylmethyl-spiro[3H-indole-3,3'-piperidine]-2,6'(1H)-dione (0.12 g, 0.24 mmol) prepared in example 82a was reacted with 2-amino-2-methyl-propan-1-ol (73 mg, 0.82 mmol), N-methylmorpholine (0.2 g, 1.98 mmol) and 4-dimethylaminopyridine (2 mg, 0.016 mmol) in tetrahydrofuran to give racemic (2'R,3R,4'S)-6-chloro-4'-(3-chlorophenyl)-2'-(1-ethyl-propenyl)-1'-[(2-hydroxy-1,1-dimethylethyl)aminocarbonylmethyl]spiro[3H-indole-3,3'-piperidine]-2,6'(1H)-dione as an off-white solid (Yield 92 mg, 67%).

HRMS (ES$^+$) m/z Calcd for $C_{29}H_{33}Cl_2N_3O_4$+H [(M+H)$^+$]: 558.1921. Found: 558.1921

EXAMPLE 82c

Preparation of chiral (2'R,3R,4'S)-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione

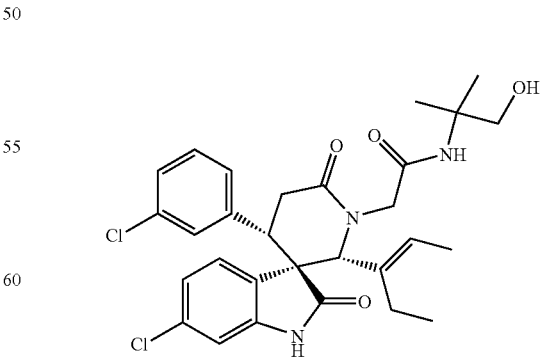

M. W. 558.51 $C_{29}H_{33}Cl_2N_3O_4$

Separation of the two enantiomers from racemic (2'R,3R,4'S)-6-chloro-4'-(3-chlorophenyl)-2'-(1-ethyl-propenyl)-1'-

[(2-hydroxy-1,1-dimethyl ethyl)aminocarbonyl-methyl]spiro[3H-indole-3,3'-piperidine]-2,6'(1H)-dione (50 mg) prepared in example 82b was conducted by chiral SFC to provide chiral (2'R,3R,4'S-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione as a white solid (Yield: 21 mg, 42%) and chiral (2'S,3S,4'R)-6-chloro-4'-(3-chlorophenyl)-2'-(1-ethyl-propenyl)-1'-[(2-hydroxy-1,1-dimethyl ethyl)aminocarbonyl-methyl]spiro[3H-indole-3,3'-piperidine]-2,6'(1H)-dione as a white solid (Yield: 19 mg, 38%).

EXAMPLE 83a

Preparation of intermediate racemic (2'R,3R,4'S)-6-chloro-4'-(3-chloro-phenyl)-1'-(3-chloro-propyl)-2'-(1-ethyl-propenyl)-2,3-dihydro-2,6'-dioxospiro[indole-3,3'-piperidine]-1-methoxyethyl trimethylsilane

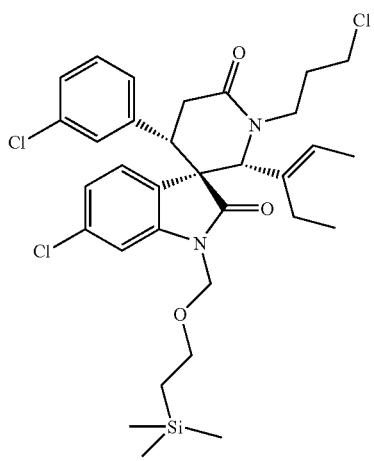

M. W. 636.14 $C_{32}H_{41}Cl_3N_2O_3Si$

In a manner similar to the method described in example 24c, racemic (2'R,3R,4'S)-6-chloro-4'-(3-chloro-phenyl)-2'-(1-ethyl-propenyl)-2,3-dihydro-2,6'-dioxospiro[indole-3,3'-piperidine]-1-methoxyethyl trimethylsilane (2.4 g, 4.3 mmol) prepared in example 81a was reacted with LiH (1 g, 125 mmol) and 1-chloro-3-iodo-propane (8 g, 39 mmol) in N,N-dimethyl-formamide (40 mL) to give racemic (2'R,3R,4'S)-6-chloro-4'-(3-chloro-phenyl)-1'-(3-chloro-propyl)-2'-(1-ethyl-propenyl)-2,3-dihydro-2,6'-dioxospiro[indole-3,3'-piperidine]-1-methoxyethyl trimethylsilane as a white form (Yield: 0.61 g, 22%).

EXAMPLE 83b

Preparation of racemic (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione

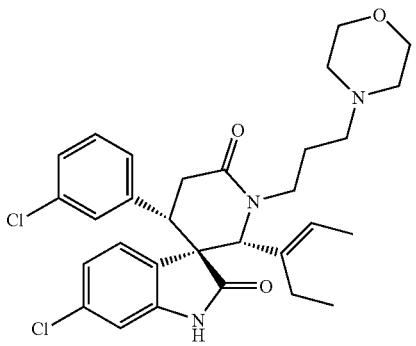

M. W. 556.54 $C_{30}H_{35}Cl_2N_3O_3$

In a manner similar to the method described in example 60b, racemic (2'R,3R,4'S)-6-chloro-4'-(3-chloro-phenyl)-1'-(3-chloro-propyl)-2'-(1-ethyl-propenyl)-2,3-dihydro-2,6'-dioxospiro[indole-3,3'-piperidine]-1-methoxyethyl trimethylsilane prepared in example 83a (0.3 g, 0.47 mmol) was reacted with morpholine (12 mL), trifluoroacetic acid (5 mL) and then N,N-diisopropylethylamine (2 mL) to give racemic (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione as a white solid (0.15 g, 57%).

HRMS (ES$^+$) m/z Calcd for $C_{30}H_{35}Cl_2N_3O_3$+H [(M+H)$^+$]: 556.2128. Found: 556.2123.

EXAMPLE 83c

Preparation of chiral (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione

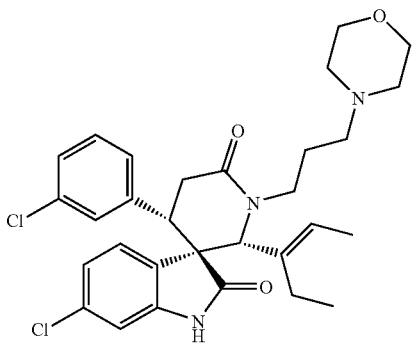

M. W. 556.54 $C_{30}H_{35}Cl_2N_3O_3$

Separation of the two enantiomers from racemic (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione (150 mg) prepared in example 83b was conducted by chiral SFC to provide chiral (2'R,3R,4'S)-6- chloro-4'-(3-chlorophenyl)-2'-(1-ethyl-propenyl)-1'-(3-morpholin-4-yl-propyl)spiro[3H-indole-3,3'-piperidine]-2,6'(1H)-dione as a white solid (Yield: 61 mg, 41%) and chiral (2'S,3S,4'R)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione as a white solid (Yield: 63 mg, 42%).

EXAMPLE 84a

Preparation of intermediate
3-Methyl-2-methylene-butan-1-ol

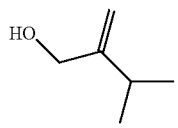

M. W. 100.16 $C_6H_{12}O$

In a manner similar to the method described in example 79a, isopropyl magnesium chloride (2M in ether, 300 mL, 0.6 mol) was reacted with propargyl alcohol (11.2 g, 0.2 mol, Aldrich) and CuI (32 g, 0.2 mol) to give 3-methyl-2-methylene-butan-1-ol as a colorless oil (Yield, 2.4 g, 12%)

EXAMPLE 84b

Preparation of intermediate
3-Methyl-2-methylene-butyraldehyde

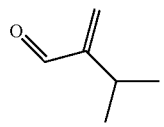

M. W. 98.15 $C_6H_{10}O$

In a manner similar to the method described in example 79b, 3-methyl-2-methylene-butan-1-ol (2.4 g, 24 mmol) prepared in example 84a was oxidized to give 3-methyl-2-methylene-butyraldehyde as a yellow oil (Yield: 1.6 g, 68%)

EXAMPLE 84c

Preparation of intermediate 1-(2-methyl-1-methylene-propyl)-3-trimethylsilyoxy-2-aza-1,3-butadiene

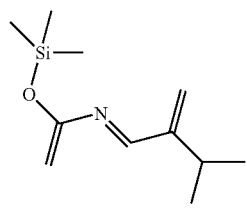

M. W. 211.38 $C_{11}H_{21}NOSi$

In a manner similar to the method described in example 1b, 3-methyl-2-methylene-butyraldehyde prepared in example 84b (1.3 g, 13 mmol) was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13 mmol) and acetyl chloride (1.02 g, 13 mmol) to give 1-(2-methyl-1-methylene-propyl)-3-trimethylsilyoxy-2-aza-1,3-butadiene and used for the next step without further purification.

EXAMPLE 84d

Preparation of racemic (2'R,3R,4'S)-6-chloro-4'-(3-chlorophenyl)-2'-(2-methyl-1-methylene-propyl)spiro[3H-indole-3,3'-piperidine]-2,6'(1H)-dione

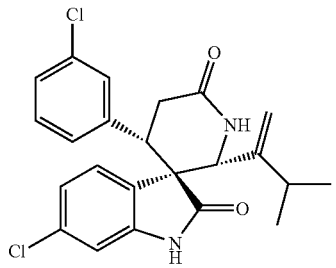

M. W. 429.35 $C_{23}H_{22}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.41 g, 1.1 mmol) was reacted with 1-(2-methyl-1-methylene-propyl)-3-trimethylsilyoxy-2-aza-1,3-butadiene (2.1 g, 10 mmol) prepared in example 84c in toluene and then trifluoroacetic acid (10 mL) in dichloromethane to give racemic (2'R,3R,4'S)-6-chloro-4'-(3-chlorophenyl)-2'-(2-methyl-1-methylene-propyl)spiro[3H-indole-3,3'-piperidine]-2,6'(1H)-dione as a off white solid (0.13 g, 28%).

HRMS (ES$^+$) m/z Calcd for $C_{23}H_{22}Cl_2N_2O_2$+H [(M+H)$^+$]: 429.1131. Found: 429.1133

EXAMPLE 85a

Preparation of intermediate
3,3-Dimethyl-2-methylene-butan-1-ol

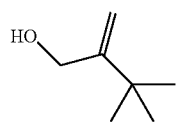

M. W. 114.19 $C_7H_{14}O$

In a manner similar to the method described in example 79a, tert-butyl magnesium chloride (2 M in ether, 300 mL, 0.6 mol) was reacted with propargyl alcohol (11.2 g, 0.2 mol, Aldrich) and CuI (32 g, 0.2 mol) to give 3,3-dimethyl-2-methylene-butan-1-ol as a pale yellow oil (Yield, 12.3 g, 54%)

EXAMPLE 85b

Preparation of intermediate
3,3-Dimethyl-2-methylene-butyraldehyde

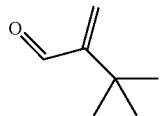

M. W. 112.17 C$_7$H$_{12}$O

In a manner similar to the method described in example 79b, 3,3-dimethyl-2-methylene-butan-1-ol (12.3 g, 0.11 mol) prepared in example 85a was oxidized to give 3,3-dimethyl-2-methylene-butyraldehyde as a yellow oil (Yield: 8.3 g, 67%)

EXAMPLE 85c

Preparation of intermediate 1-(2,2-dimethyl-1-methylene-propyl)-3-trimethylsilyoxy-2-aza-1,3-butadiene

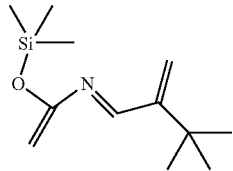

M. W. 225.41 C$_{12}$H$_{23}$NOSi

In a manner similar to the method described in example 1b, 3,3-dimethyl-2-methylene-butyraldehyde prepared in example 85b (2.2 g, 20 mmol) was used as the starting material in place of 3-chloro-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.7 g, 27 mmol) and acetyl chloride (2 g, 27 mmol) to give 1-(2,2-dimethyl-1-methylene-propyl)-3-trimethylsilyoxy-2-aza-1,3-butadiene and used for the next step without further purification.

EXAMPLE 85d

Preparation of racemic (2'R,3R,4'S)-6-chloro-4'-(3-chlorophenyl)-2'-(2,2-dimethyl-1-methylene-propyl)spiro[3H-indole-3,3'-piperidine]-2,6'(1H)-dione

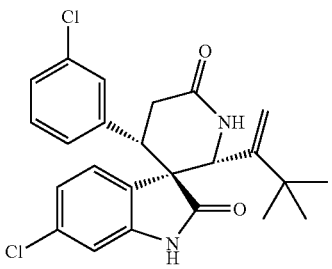

M. W. 443.38 C$_{24}$H$_{24}$Cl$_2$N$_2$O$_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.41 g, 1.1 mmol) was reacted with 1-(2,2-dimethyl-1-methylene-propyl)-3-trimethylsilyoxy-2-aza-1,3-butadiene (3.4 g, 15 mmol) prepared in example 85c in toluene and then trifluoroacetic acid (10 mL) in dichloromethane to give racemic (2'R,3R,4'S)-6-chloro-4'-(3-chlorophenyl)-2'-(2,2-dimethyl-1-methylene-propyl)spiro[3H-indole-3,3'-piperidine]-2,6'(1H)-dione as a off white solid (0.27 g, 55%).

HRMS (ES$^+$) m/z Calcd for C$_{24}$H$_{24}$Cl$_2$N$_2$O$_2$+H [(M+H)$^+$]: 443.1288. Found: 443.1288

EXAMPLE 86

Preparation of racemic (2'R,3R,4'S)-6-chloro-4'-(3-chlorophenyl)-2'-(1-ethyl-propenyl)-1'-[(2-morpholin-4-yl-ethyl)aminocarbonyl-methyl]spiro[3H-indole-3,3'-piperidine]-2,6'(1H)-dione

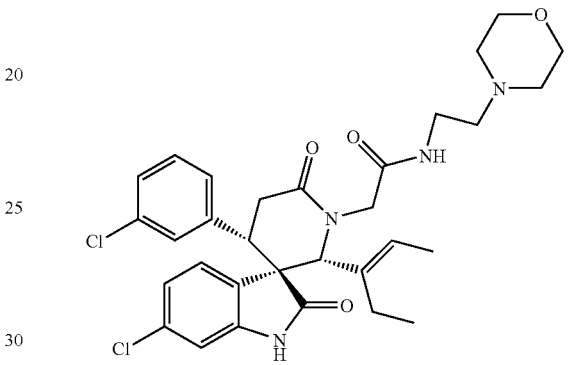

M. W. 599.56 C$_{31}$H$_{36}$Cl$_2$N$_4$O$_4$

In a manner similar to the method described in example 34b, racemic (2'R,3R,4'S)-6-chloro-4'-(3-chlorophenyl)-1'-fluorocarbonylmethyl-2'-(1-ethyl-propenyl)spiro[3H-indole-3,3'-piperidine]-2,6'(1H)-dione (0.12 g, 0.24 mmol) prepared in example 83a was reacted with 4-(2-aminoethyl)morpholine (85 mg, 0.66 mmol) (Aldrich), N-methylmorpholine (0.1 g, 0.98 mmol) and 4-dimethylaminopyridine (2 mg, 0.015 mmol) in tetrahydrofuran to give racemic (2'R,3R,4'S)-6-chloro-4'-(3-chlorophenyl)-2'-(1-ethyl-propenyl)-1'-[(2-morpholin-4-yl-ethyl)aminocarbonyl-methyl]spiro[3H-indole-3,3'-piperidine]-2,6'(1H)-dione as an off-white solid (Yield 31 mg, 22%).

HRMS (ES$^+$) m/z Calcd for C$_{31}$H$_{36}$Cl$_2$N$_4$O$_4$+H [(M+H)$^+$]: 599.2187. Found: 599.2185

EXAMPLE 87a

Preparation of intermediate 1-isopropenyl-3-trimethylsilyoxy-2-aza-1,3-butadiene

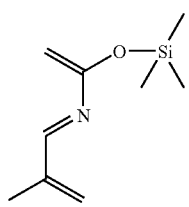

M. W. 183.33 C$_9$H$_{17}$NOSi

In a manner similar to the method described in example 1b, 2-methacrolein (2 g, 20 mmol) (Acros) was used as the starting material in place of 3-chloro-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.7 g, 27 mmol) and acetyl chloride (2.0 g, 27 mmol) to give 1-isopropenyl-3-trimethylsilyoxy-2-aza-1,3-butadiene and used for the next step without further purification.

EXAMPLE 87b

Preparation of racemic (2'R,3R,4'S)-6-chloro-4'-(3-chlorophenyl)-2'-isopropenylspiro[3H-indole-3,3'-piperidine]-2,6'(1H)-dione

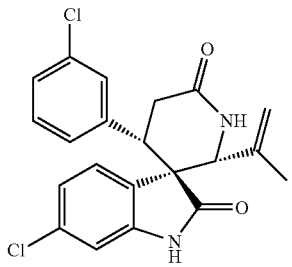

M. W. 401.30 $C_{21}H_{18}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.41 g, 1.1 mmol) was reacted with 1-isopropenyl-3-trimethylsilyoxy-2-aza-1,3-butadiene (3.4 g, 18 mmol) prepared in example 87a in toluene and then trifluoroacetic acid (20 mL) in dichloromethane to give racemic (2'R,3R,4'S)-6-chloro-4'-(3-chlorophenyl)-2'-(1-methylenepropyl)spiro[3H-indole-3,3'-piperidine]-2,6'(1H)-dione as a white solid (0.27 g, 61%).

HRMS (ES$^+$) m/z Calcd for $C_{21}H_{18}Cl_2N_2O_2$+H [(M+H)$^+$]: 401.0818. Found: 401.0818

EXAMPLE 87c

Preparation of chiral (2'R,3R,4'S)-6-chloro-4'-(3-chlorophenyl)-2'-isopropenylspiro[3H-indole-3,3'-piperidine]-2,6'(1H)-dione

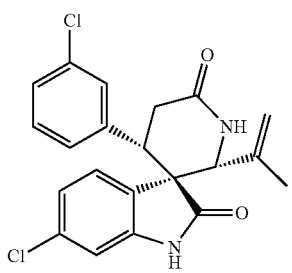

M. W. 401.30 $C_{21}H_{18}Cl_2N_2O_2$

Separation of the two enantiomers from racemic (2'R,3R,4'S)-6-chloro-4'-(3-chlorophenyl)-2'-isopropenylspiro[3H-indole-3,3'-piperidine]-2,6'(1H)-dione (80 mg) prepared in example 87b was conducted by chiral SFC to provide chiral (2'R,3R,4'S)-6-chloro-4'-(3-chlorophenyl)-2'-isopropenyl-spiro[3H-indole-3,3'-piperidine]-2,6'(1H)-dione as a white solid (28 mg, 35%) and chiral (2'S,3S,4'R)-6-chloro-4'-(3-chlorophenyl)-2'-isopropenylspiro[3H-indole-3,3'-piperidine]-2,6'(1H)-dione as a white solid (26 mg, 33%).

EXAMPLE 88a

Preparation of intermediate 2-Methylene-pentan-1-ol

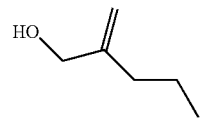

M. W. 100.16 $C_6H_{12}O$

In a manner similar to the method described in example 79a, propylmagnesium chloride (2 M in ether, 375 mL, 0.75 mol) was reacted with propargyl alcohol (14 g, 0.25 mol) and CuI (40 g, 0.25 mol) to give 2-methylene-pentan-1-ol as a colorless oil (Yield, 16.9 g, 67%)

EXAMPLE 88b

Preparation of intermediate 2-Methylene-pentanal

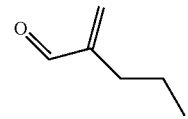

M. W. 98.15 $C_6H_{10}O$

In a manner similar to the method described in example 79b, 2-methylene-pentan-1-ol (16.5 g, 0.165 mol) prepared in example 88a was oxidized to give 2-methylene-pentanal as a yellow oil (Yield: 6.7 g, 41%)

EXAMPLE 88c

Preparation of intermediate 1-(1-methylene-butyl)-3-trimethylsilyoxy-2-aza-1,3-butadiene

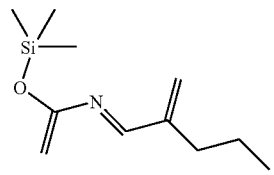

M. W. 211.38 $C_{11}H_{21}NOSi$

In a manner similar to the method described in example 1b, 2-methylene-pentanal prepared in example 88b (2.1 g, 21 mmol) was used as the starting material in place of 3-chloro-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.7 g, 27 mmol) and acetyl chloride (2 g, 27 mmol) to give 1-(1-methylene-butyl)-3-trimethylsilyoxy-2-aza-1,3-butadiene and used for the next step without further purification.

EXAMPLE 88d

Preparation of racemic (2'R,3R,4'S)-6-chloro-4'-(3-chlorophenyl)-2'-(1-methylene-butyl)spiro[3H-indole-3,3'-piperidine]-2,6'(1H)-dione

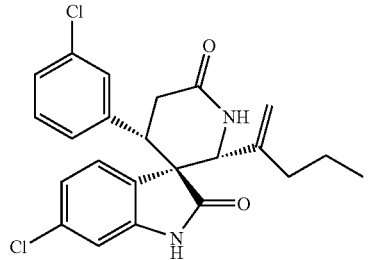

M. W. 429.35 $C_{23}H_{22}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.45 g, xx mmol) was reacted with 1-(1-methylene-butyl)-3-trimethylsilyoxy-2-aza-1,3-butadiene (0.45 g, 1.1 mmol) prepared in example 88c in toluene and then trifluoroacetic acid (10 mL) in dichloromethane to give racemic (2'R,3R,4'S)-6-chloro-4'-(3-chlorophenyl)-2'-(1-methylene-butyl)spiro[3H-indole-3,3'-piperidine]-2,6'(1H)-dione as a off white solid (0.34 g, 72%).

HRMS (ES$^+$) m/z Calcd for $C_{23}H_{22}Cl_2N_2O_2$+H [(M+H)$^+$]: 429.1131. Found: 429.1131

EXAMPLE 88e

Preparation of chiral (2'R,3R,4'S)-6-chloro-4'-(3-chlorophenyl)-2'-(1-methylene-butyl)spiro[3H-indole-3,3'-piperidine]-2,6'(1H)-dione

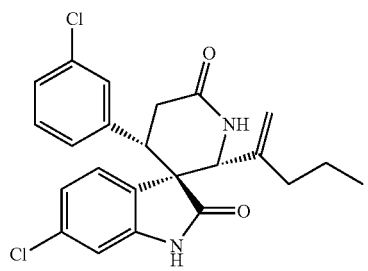

M. W. 429.35 $C_{23}H_{22}Cl_2N_2O_2$

Separation of the two enantiomers from racemic (2'R,3R,4'S)-6-chloro-4'-(3-chlorophenyl)-2'-(1-methylene-butyl) spiro[3H-indole-3,3'-piperidine]-2,6'(1H)-dione (90 mg) prepared in example 88d was conducted by chiral SFC to provide chiral (2'R,3R,4'S)-6-chloro-4'-(3-chlorophenyl)-2'-(1-methylene-butyl)spiro[3H-indole-3,3'-piperidine]-2,6'(1H)-dione as a white solid (32 mg, 36%) and chiral (2'S,3S,4'R)-6-chloro-4'-(3-chlorophenyl)-2'-(1-methylene-butyl)spiro[3H-indole-3,3'-piperidine]-2,6'(1H)-dione as a white solid (30 mg, 33%).

EXAMPLE 89a

Preparation of intermediate 4-Methyl-2-methylene-pentan-1-ol

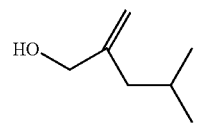

M. W. 114.19 $C_7H_{14}O$

In a manner similar to the method described in example 79a, isobutyl magnesium chloride (2 M in ether, 375 mL, 0.75 mol) was reacted with propargyl alcohol (14 g, 0.25 mol) and CuI (40 g, 0.25 mol) to give 4-methyl-2-methylene-pentan-1-ol as a colorless oil (Yield, 27 g, 95%)

EXAMPLE 89b

Preparation of intermediate 4-Methyl-2-methylene-pentanal

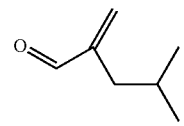

M. W. 112.17 $C_7H_{12}O$

In a manner similar to the method described in example 79b, 4-methyl-2-methylene-pentan-1-ol prepared in example 89a was oxidized to give 4-methyl-2-methylene-pentanal as a yellow oil (Yield: 21 g, 77%)

EXAMPLE 89c

Preparation of intermediate 1-(3-Methyl-1-methylene-butyl)-3-trimethylsilyoxy-2-aza-1,3-butadiene

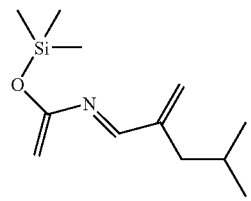

M. W. 225.41 $C_{12}H_{23}NOSi$

In a manner similar to the method described in example 1b, 4-methyl-2-methylene-pentanal prepared in example 89b (11 g, 100 mmol) was used as the starting material in place of 3-chloro-benzaldehyde to react with 1,1,1,3,3,3-hexamethyl-disilazane (16 g, 100 mmol), n-butyllithium (2.5 M, 40 mL, 100 mmol), trimethylsilyl chloride (11 g, 100 mmol), triethylamine (13.6 g, 14 mmol) and acetyl chloride (10.2 g, 14 mmol) to give 1-(3-methyl-1-methylene-butyl)-3-trimethylsilyoxy-2-aza-1,3-butadiene and used for the next step without further purification.

EXAMPLE 89d

Preparation of racemic (2'R,3R,4'S)-6-chloro-4'-(3-chlorophenyl)-2'-(3-methyl-1-methylene-butyl)spiro[3H-indole-3,3'-piperidine]-2,6'(1H)-dione

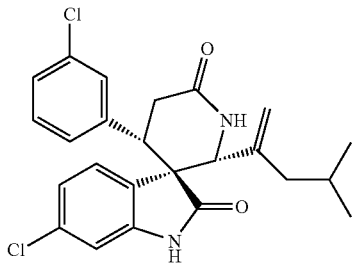

M. W. 443.38 $C_{24}H_{24}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (2 g, 5 mmol) was reacted with 1-(3-methyl-1-methylene-butyl)-3-trimethylsilyoxy-2-aza-1,3-butadiene (21 g, 93 mmol) prepared in example 89c in toluene and then trifluoroacetic acid (20 mL) in dichloromethane to give racemic (2'R,3R,4'S)-6-chloro-4'-(3-chlorophenyl)-2'-(3-methyl-1-methylene-butyl)spiro[3H-indole-3,3'-piperidine]-2,6'(1H)-dione as a white solid (1.3 g, 59%).

HRMS (ES$^+$) m/z Calcd for $C_{24}H_{24}Cl_2N_2O_2$+H [(M+H)$^+$]: 443.1288. Found: 443.1285

EXAMPLE 89e

Preparation of chiral (2'R,3R,4'S)-6-chloro-4'-(3-chlorophenyl)-2'-(3-methyl-1-methylene-butyl)spiro[3H-indole-3,3'-piperidine]-2,6'(1H)-dione

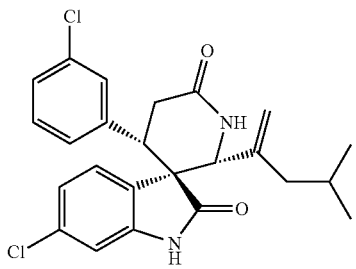

M. W. 443.38 $C_{24}H_{24}Cl_2N_2O_2$

Separation of the two enantiomers from racemic (2'R,3R,4'S)-6-chloro-4'-(3-chlorophenyl)-2'-(3-methyl-1-methylene-butyl)spiro[3H-indole-3,3'-piperidine]-2,6'(1H)-dione (300 mg) prepared in example 89d was conducted by chiral SFC to provide chiral (2'R,3R,4'S)-6-chloro-4'-(3-chlorophenyl)-2'-(3-methyl-1-methylene-butyl)spiro[3H-indole-3,3'-piperidine]-2,6'(1H)-dione as a white solid (130 mg, 43%) and chiral (2'S,3S,4'R)-6-chloro-4'-(3-chlorophenyl)-2'-(1-methylene-butyl)spiro[3H-indole-3,3'-piperidine]-2,6'(1H)-dione as a white solid (130 mg, 43%).

EXAMPLE 90

Preparation of racemic (2'R,3R,4'S)-6-chloro-4'-(3-chlorophenyl)-2'-(1-methylene-butyl)-6'-thioxospiro[3H-indole-3,3'-piperidine]-2(1H)-one

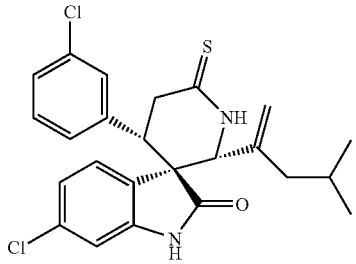

M. W. 459.44 $C_{24}H_{24}Cl_2N_2OS$

In a manner similar to the method described in example 30, racemic (2'R,3R,4'S)-6-chloro-4'-(3-chlorophenyl)-2'-(1-methylene-butyl)spiro[3H-indole-3,3'-piperidine]-2,6'(1H)-dione (1.4 g, 3.1 mmol) prepared in example 89d was reacted with 2,4-bis-(4-methoxyphenyl)-1,3-dithia-2,4-diphosphetane 2,4-disulfide (1.7 g, 4.25 mmol) in toluene to give racemic (2'R,3R,4'S)-6-chloro-4'-(3-chlorophenyl)-2'-(1-methylene-butyl)-6'-thioxospiro[3H-indole-3,3'-piperidine]-2(1H)-one as a off white solid (Yield 1.2 g, 84%).

HRMS (ES$^+$) m/z Calcd for $C_{24}H_{24}Cl_2N_2OS$+H [(M+H)$^+$]: 459.1059. Found: 459.1055.

EXAMPLE 91a

Preparation of intermediate 4-Ethoxy-1,2-difluoro-benzene

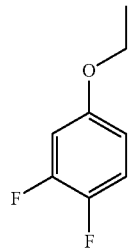

M. W. 158.15 $C_8H_8F_2O$

To a solution of 3,4-difluoro-phenol (10 g, 77 mmol) in N,N-dimethylformamide (50 mL) was added potassium carbonate (20 g, 145 mmol) and iodoethane (50 g, 320 mmol, Aldrich). The reaction mixture was heated at refluxing for 48 h. The crude was cooled to room temperature and filtered through a short pad of celite. The filtrate was concentrated and the residue was purified by chromatography (EtOAc:Hexanes=1:8) to give 4-ethoxy-1,2-difluoro-benzene as colorless oil (Yield 11 g, 90%).

EXAMPLE 91b

Preparation of intermediate
6-Ethoxy-2,3-difluoro-benzaldehyde

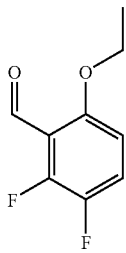

M. W. 186.16 $C_9H_8F_2O_2$

In a manner similar to the method described in example 52a, 4-ethoxy-1,2-difluoro-benzene (10 g, 63 mmol) prepared in example 91a was reacted with lithium diisopropylamine (39 mL, 1.8 M in THF, 70 mmol), N,N-dimethylformamide (5.88 mL, 76 mmol) and quenched with acetic acid (15.2 g, 253 mmol) in tetrahydrofuran to give 6-ethoxy-2,3-difluoro-benzaldehyde as a off white solid (Yield: 8.9 g, 76%).

EXAMPLE 91c

Preparation of intermediate 1-(4-ethoxy-1,2-difluoro-phenyl)-3-trimethylsilyoxy-2-aza-1,3-butadiene

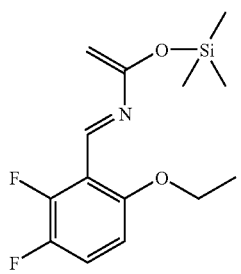

M. W. 299.40 $C_{14}H_{19}F_2NO_2Si$

In a manner similar to the method described in example 1b, 6-ethoxy-2,3-difluoro-benzaldehyde (1.9 g, 11 mmol) prepared in example 91b was used as the starting material in place of 3-chloro-benzaldehyde to react with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-(4-ethoxy-1,2-difluoro-phenyl)-3-trimethylsilyoxy-2-aza-1,3-butadiene as yellow oil and used for the next step without further purification.

EXAMPLE 91d

Preparation of racemic (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione

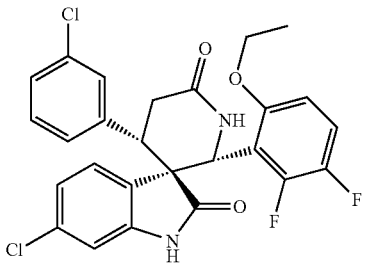

M. W. 517.36 $C_{26}H_{20}Cl_2F_2N_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.6 g, 1.5 mmol) was reacted with 1-(4-ethoxy-1,2-difluoro-phenyl)-3-trimethylsilyoxy-2-aza-1,3-butadiene (2.3 g, 7.6 mmol) prepared in example 91c in toluene and then trifluoroacetic acid (10 mL) in dichloromethane to give racemic (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione as a white solid (0.39 g, 50%).

HRMS (ES⁺) m/z Calcd for $C_{26}H_{20}Cl_2F_2N_2O_3$+H [(M+H)⁺]: 517.0892. Found: 517.0889.

EXAMPLE 91e

Preparation of chiral (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione

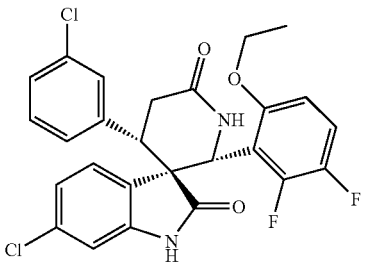

M. W. 517.36 $C_{26}H_{20}Cl_2F_2N_2O_3$

Separation of the two enantiomers from (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione (98 mg) prepared in example 91d was conducted by chiral SFC to provide chiral (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione as a white solid (36 mg, 36%) and chiral (2'R,3S,4'R)-6-chloro-4'-(3-chlorophenyl)-2'-(4-ethoxy-1,2-difluoro-phenyl)spiro[3H-indole-3,3'-piperidine]-2,6'(1H)-dione as a white solid (33 mg, 33%).

EXAMPLE 92a

Preparation of intermediate E/Z-3-Chloro-5-(6-chloro-2-oxo-1,2-dihydro-indol-3-ylidenemethyl)-benzoic acid methyl ester

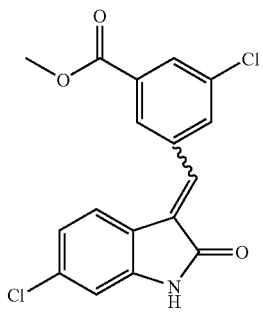

M. W. 348.19 C$_{17}$H$_{11}$Cl$_2$NO$_3$

In a manner similar to the method described in example 1a, 6-chlorooxindole (3.2 g, 18 mmol) was reacted with 3-chloro-5-formyl-benzoic acid methyl ester (3.92 g, 18 mmol) and pyrrolidine (1.3 g, 18 mmol) in methanol to give a mixture of E- and Z-3-Chloro-5-(6-chloro-2-oxo-1,2-dihydro-indol-3-ylidenemethyl)-benzoic acid methyl ester as a yellow solid (Yield: 6.1 g, 97%).

3-chloro-5-formyl-benzoic acid methyl ester was prepared using dimethyl 5-chloroisophthalate (Matrix.) as the starting material according to the procedure described by Mitchelotti et al. in U.S. Pat. No. 5,254,584

EXAMPLE 92b

Preparation of intermediate E/Z-6-Chloro-3-(3-chloro-5-methoxycarbonyl-benzylidene)-2-oxo-2,3-dihydro-indole-1-carboxylic acid tert-butyl ester

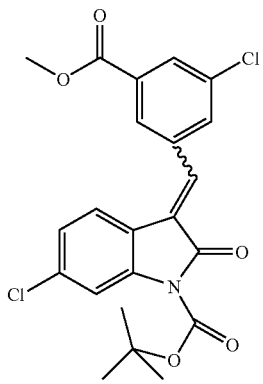

M. W. 448.31 C$_{22}$H$_{19}$Cl$_2$NO$_5$

In a manner similar to the method described in example 24a, E/Z-3-Chloro-5-(6-chloro-2-oxo-1,2-dihydro-indol-3-ylidenemethyl)-benzoic acid methyl ester (3 g, 8.6 mmol) was reacted with di-tert-butyl-dicarbonate (1.9 g, 8.6 mmol) (Aldrich), triethylamine (0.87 g, 8.6 mmol) and 4-dimethylaminopyridine (5 mg) in dichloromethane (100 mL) to give E/Z-6-Chloro-3-(3-chloro-5-methoxycarbonyl-benzylidene)-2-oxo-2,3-dihydro-indole-1-carboxylic acid tert-butyl ester as a yellow solid (Yield: 3.7 g, 96%).

EXAMPLE 92c

Preparation of racemic (2'R,3R,4'S)-6-chloro-4'-(3-chloro-5-methoxycarbonyl-phenyl)-2'-(1-methylene-propyl)spiro[3H-indole-3,3'-piperidine]-2,6'(1H)-dione

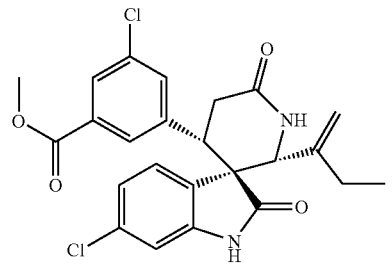

M. W. 473.36 C$_{24}$H$_{22}$Cl$_2$N$_2$O$_4$

In a manner similar to the method described in example 41b, E/Z-6-Chloro-3-(3-chloro-5-methoxycarbonyl-benzylidene)-2-oxo-2,3-dihydro-indole-1-carboxylic acid tert-butyl ester prepared in example 92b (2.4 g, 5.3 mmol) was reacted with 1-(1-methylene-propyl)-3-trimethylsilyoxy-2-aza-1,3-butadiene (13 g, 66 mmol) prepared in example 80a in toluene and then trifluoroacetic acid (20 mL) in dichloromethane to give racemic (2'R,3R,4'S)-6-chloro-4'-(3-chloro-5-methoxycarbonyl-phenyl)-2'-(1-methylene-propyl)spiro[3H-indole-3,3'-piperidine]-2,6'(1H)-dione as a white solid (1.6 g, 64%).

HRMS (ES$^+$) m/z Calcd for C$_{24}$H$_{22}$Cl$_2$N$_2$O$_4$+H [(M+H)$^+$]: 473.1030. Found: 473.1031.

EXAMPLE 93

Preparation of racemic (2'R,3R,4'S)-6-chloro-4'-(3-chloro-5-hydroxycarbonyl-phenyl)-2'-(1-methylene-propyl)spiro[3H-indole-3,3'-piperidine]-2,6'(1H)-dione

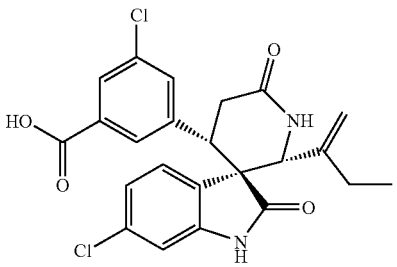

M. W. 459.33 C$_{23}$H$_{20}$Cl$_2$N$_2$O$_4$

To a solution of racemic (2'R,3R,4'S)-6-chloro-4'-(3-chloro-5-methoxycarbonyl-phenyl)-2'-(1-methylene-propyl)spiro[3H-indole-3,3'-piperidine]-2,6'(1H)-dione (1.6 g, 33 mmol) prepared in example 92c in the mixture of tetrahydrofuran (60 mL) and methanol (30 mL) was added the solution of sodium hydroxide (1N, 30 mL). After the reaction mixture was stirred at room temperature for 2 h, the crude was concentrated. The residue was neutralized to "pH"-4 with the dilute hydrochloride solution, then extracted with ethyl acetate. The organic layer was separated, dried over MgSO$_4$, concentrated to give racemic (2'R,3R,4'S)-6-chloro-4'-(3-chloro-5-hydroxycarbonyl-phenyl)-2'-(1-methylene-propyl)spiro[3H-indole-3,3'-piperidine]-2,6'(1H)-dione as a white solid (Yield 1.5 g, 99%).

HRMS (ES+) m/z Calcd for $C_{23}H_{20}Cl_2N_2O_4$+H [(M+H)+]: 459.0873. Found: 459.0873.

EXAMPLE 94a

Preparation of racemic (2'R,3R,4'S)-6-chloro-4'-(3-chloro-5-fluorocarbonyl-phenyl)-2'-(1-methylene-propyl)spiro[3H-indole-3,3'-piperidine]-2,6'(1H)-dione

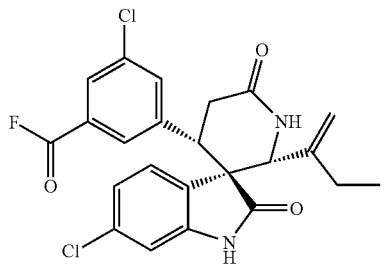

M. W. 461.32 $C_{23}H_{19}Cl_2FN_2O_3$

To the solution of racemic (2'R,3R,4'S)-6-chloro-4'-(3-chloro-5-hydroxycarbonyl-phenyl)-2'-(1-methylene-propyl)spiro[3H-indole-3,3'-piperidine]-2,6'(1H)-dione (0.2 g, 0.43 mmol) prepared in example 93 in dichloromethane (20 mL) at 0° C. was added cyanuric fluoride (48 mg, 0.35 mmol) (Alfa) and pyridine (37 mg, 0.48 mmol). After the mixture was stirred at 0° C. for 2 h, the mixture was partitioned between $H_2O$ and dichloromethane. The organic layer was separated and the aqueous layer was extracted with dichloromethane. The organic layers were combined, dried over $MgSO_4$, concentrated to give racemic (2'R,3R,4'S)-6-chloro-4'-(3-chloro-5-fluorocarbonyl-phenyl)-2'-(1-methylene-propyl)spiro[3H-indole-3,3'-piperidine]-2,6'(1H)-dione as a yellow gum and used for the next step without further purification (Yield: 0.2 g, 100%).

EXAMPLE 94b

Preparation of racemic (2'R,3R,4'S)-6-chloro-4'-[3-chloro-5-(4-methanesulfonyl-piperazine-1-carbonyl)-phenyl]-2'-(1-methylene-propyl)spiro[3H-indole-3,3'-piperidine]-2,6'(1H)-dione

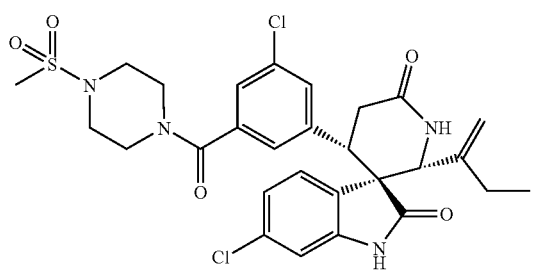

M. W. 605.55 $C_{28}H_{30}Cl_2N_4O_5S$

In a manner similar to the method described in example 34b, racemic (2'R,3R,4'S)-6-chloro-4'-(3-chloro-5-fluorocarbonyl-phenyl)-2'-(1-methylene-propyl)spiro[3H-indole-3,3'-piperidine]-2,6'(1H)-dione (0.16 g, 36 mmol) prepared in example 94a was reacted with N-methylsulfonylpiperazine (59 mg, 36 mmol), N-methylmorpholine (0.1 g, 0.99 mmol) and 4-dimethylaminopyridine (1 mg, 0.008 mmol) in tetrahydrofuran to give racemic (2'R,3R,4'S)-6-chloro-4'-[3-chloro-5-(4-methanesulfonyl-piperazine-1-carbonyl)-phenyl]-2'-(1-methylene-propyl)spiro[3H-indole-3,3'-piperidine]-2,6'(1H)-dione as an off-white solid (Yield 0.2 g, 92%).

HRMS (ES+) m/z Calcd for $C_{28}H_{30}Cl_2N_4O_5S$+H [(M+H)+]: 619.1543. Found: 619.1544.

EXAMPLE 95a

Preparation of racemic (2'R,3R,4'S)-6-chloro-4'-(3-chlorophenyl)-2'-(1-ethyl-propenyl)-1'-methylspiro[3H-indole-3,3'-piperidine]-2,6'(1H)-dione

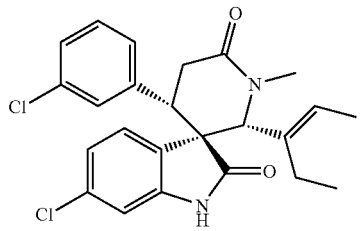

M. W. 443.38 $C_{24}H_{24}Cl_2N_2O_2$

In a manner similar to the methods described in example 56a, 56b, 56c, racemic (2'R,3R,4'S)-6-chloro-4'-(3-chlorophenyl)-2'-(1-ethyl-propenyl)-2,3-dihydro-2,6'-dioxospiro[indole-3,3'-piperidine]-1-methoxyethyl trimethylsilane (1 g, 1.8 mmol) prepared in example 81a was reacted to give racemic (2'R,3R,4'S)-6-chloro-4'-(3-chlorophenyl)-2'-(1-ethyl-propenyl)-1'-methylspiro[3H-indole-3,3'-piperidine]-2,6'(1H)-dione as a white solid (Yield, 0.50 g, 65%)

HRMS (ES+) m/z Calcd for $C_{24}H_{24}Cl_2N_2O_2$+H [(M+H)+]: 443.1288. Found: 443.1288.

EXAMPLE 95b

Preparation of chiral (2'R,3R,4'S)-6-chloro-4'-(3-chlorophenyl)-2'-(1-ethyl-propenyl)-1'-methylspiro[3H-indole-3,3'-piperidine]-2,6'(1H)-dione

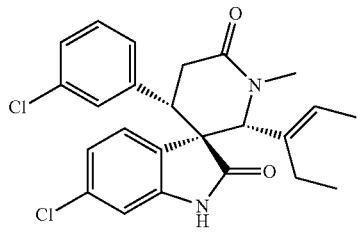

M. W. 443.38 $C_{24}H_{24}Cl_2N_2O_2$

Separation of the two enantiomers from racemic (2'R,3R,4'S)-6-chloro-4'-(3-chlorophenyl)-2'-(1-ethyl-propenyl)-1'-methylspiro[3H-indole-3,3'-piperidine]-2,6'(1H)-dione (85 mg) was conducted by chiral SFC to provide chiral (2'R,3R,4'S)-6-chloro-4'-(3-chlorophenyl)-2'-(1-ethyl-propenyl)-1'-methylspiro[3H-indole-3,3'-piperidine]-2,6'(1H)-dione as a white solid (Yield: 33 mg, 39%) and chiral (2'S,3S,4'R)-6-chloro-4'-(3-chlorophenyl)-2'-(1-ethyl-propenyl)-1'-methyl-spiro[3H-indole-3,3'-piperidine]-2,6'(1H)-dione (Yield: 26 mg, 31%).

EXAMPLE 96a

Preparation of racemic (2'R,3R,4'S)-6-chloro-4'-(3-chlorophenyl)-2'-isopropylspiro[3H-indole-3,3'-piperidine]-2,6'(1H)-dione

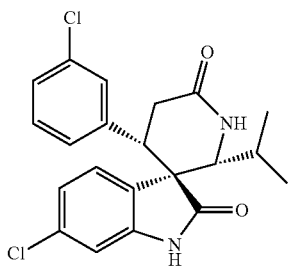

M. W. 403.31 $C_{21}H_{20}Cl_2N_2O_2$

In a manner similar to the method described in example 72a, racemic (2'R,3R,4'S)-6-chloro-4'-(3-chlorophenyl)-2'-(1-methyl ene-propyl)spiro[3H-indole-3,3'-piperidine]-2,6'(1H)-dione (0.1 g, 0.25 mmol) prepared in example 87b was hydrogenated to give racemic (2'R,3R,4'S)-6-chloro-4'-(3-chlorophenyl)-2'-isopropylspiro[3H-indole-3,3'-piperidine]-2,6'(1H)-dione as a white solid (Yield 61 mg, 60%).

HRMS (ES$^+$) m/z Calcd for $C_{21}H_{20}Cl_2N_2O_2$+H [(M+H)$^+$]: 403.0975 Found: 403.0976.

EXAMPLE 96b

Preparation of chiral (2'R,3R,4'S)-6-chloro-4'-(3-chlorophenyl)-2'-isopropylspiro[3H-indole-3,3'-piperidine]-2,6'(1H)-dione

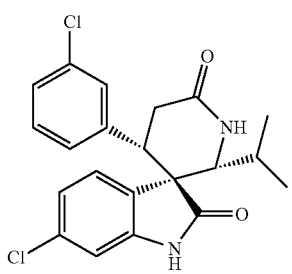

M. W. 403.31 $C_{21}H_{20}Cl_2N_2O_2$

Separation of the two enantiomers from racemic (2'R,3R,4'S)-6-chloro-4'-(3-chlorophenyl)-2'-isopropylspiro[3H-indole-3,3'-piperidine]-2,6'(1H)-dione (50 mg) was conducted by chiral SFC to provide chiral (2'R,3R,4'S)-6-chloro-4'-(3-chlorophenyl)-2'-isopropylspiro[3H-indole-3,3'-piperidine]-2,6'(1H)-dione as a white solid (Yield: 15 mg, 30%) and chiral (2'S,3S,4'R)-6-chloro-4'-(3-chlorophenyl)-2'-isopropylspiro[3H-indole-3,3'-piperidine]-2,6'(1H)-dione (Yield: 14 mg, 28%).

EXAMPLE 97a

Preparation of intermediate racemic (2'R,3R,4'S)-6-chloro-4'-(3-chlorophenyl)-2'-(1-methylene-propyl)-2,3-dihydro-2,6'-dioxo-spiro[indole-3,3'-piperidine]-1-methoxyethyl trimethylsilane

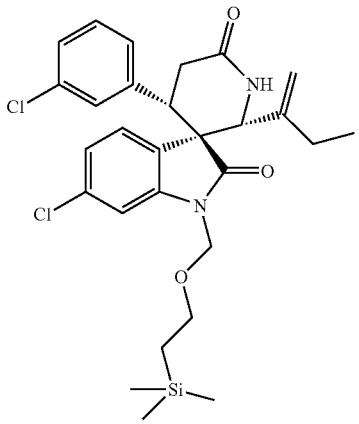

M. W. 545.59 $C_{28}H_{34}Cl_2N_2O_3Si$

In a manner similar to the method described in example 55b, E/Z-6-chloro-3-(3-chloro-benzylidene)-1-(2-trimethyl-silanyl-ethoxymethyl)-1,3-dihydro-indole-2-one (3 g, 7.1 mmol) prepared in example 55a was reacted with 1-(1-methylene-propyl)-3-trimethylsilyoxy-2-aza-1,3-butadiene (19 g, 96 mmol) prepared in example 80a in toluene (200 mL) to give racemic (2'R,3R,4'S)-6-chloro-4'-(3-chloro-phenyl)-2'-(1-methylene-propyl)-2,3-dihydro-2,6'-dioxospiro[indole-3,3'-piperidine]-1-methoxyethyl trimethylsilane as a white foam (Yield 3.5 g, 90%).

EXAMPLE 97b

Preparation of racemic (2'R,3R,4'S)-6-chloro-4'-(3-chlorophenyl)-2'-(1-methylene-propyl)-1'-methyl-spiro[3H-indole-3,3'-piperidine]-2,6'(1H)-dione

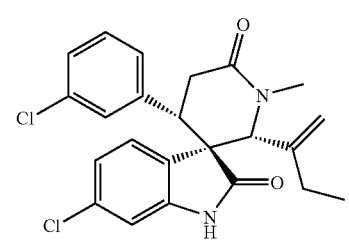

M. W. 429.35 $C_{23}H_{22}Cl_2N_2O_2$

In a manner similar to the methods described in example 56a, 56b, 56c, racemic (2'R,3R,4'S)-6-chloro-4'-(3-chlorophenyl)-2'-(1-methylene-propyl)-2,3-dihydro-2,6'-diox-ospiro[indole-3,3'-piperidine]-1-methoxyethyl trimethylsilane (0.6 g, 1.1 mmol) prepared in example 97a was reacted to form racemic (2'R,3R,4'S)-6-chloro-4'-(3-chlorophenyl)-2'-

(1-methylene-propyl)-1'-methylspiro[3H-indole-3,3'-piperidine]-2,6'(1H)-dione as a white solid (Yield, 0.16 g, 35%)

HRMS (ES$^+$) m/z Calcd for $C_{23}H_{22}Cl_2N_2O_2$+H [(M+H)$^+$]: 429.1131. Found: 429.1131.

EXAMPLE 97c

Preparation of chiral (2'R,3R,4'S)-6-chloro-4'-(3-chlorophenyl)-2'-(1-methylene-propyl)-1'-methyl-spiro[3H-indole-3,3'-piperidine]-2,6'(1H)-dione

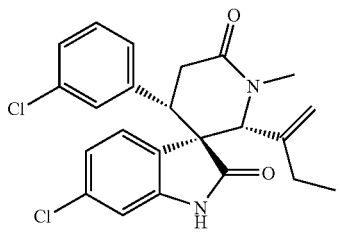

M. W. 429.35 $C_{23}H_{22}Cl_2N_2O_2$

Separation of the two enantiomers from racemic (2'R,3R,4'S)-6-chloro-4'-(3-chlorophenyl)-2'-(1-methylene-propyl)-1'-methylspiro[3H-indole-3,3'-piperidine]-2,6'(1H)-dione (160 mg) was conducted by chiral SFC to provide chiral (2'R,3R,4'S)-6-chloro-4'-(3-chlorophenyl)-2'-(1-methylene-propyl)-1'-methylspiro[3H-indole-3,3'-piperidine]-2,6'(1H)-dione as a white solid (Yield: 80 mg, 50%) and chiral (2'S,3S,4'R)-6-chloro-4'-(3-chlorophenyl)-2'-(1-methylene-propyl)-1'-methylspiro[3H-indole-3,3'-piperidine]-2,6'(1H)-dione (Yield: 80 mg, 50%).

EXAMPLE 98

Preparation of racemic (2'R,3R,4'S)-2'-sec-Butyl-6-chloro-4'-(3-chlorophenyl)spiro[3H-indole-3,3'-piperidine]-2,6'(1H)-dione

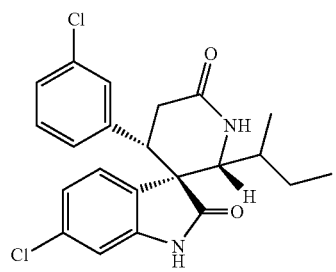

M. W. 417.34 $C_{22}H_{22}Cl_2N_2O_2$

In a manner similar to the method described in example 72a, (2'R,3R,4'S)-6-chloro-4'-(3-chlorophenyl)-2'-(1-methylene-propyl)spiro[3H-indole-3,3'-piperidine]-2,6'(1H)-dione (0.38 g, 0.91 mmol) prepared in example 80b was hydrogenated to give racemic (2'R,3R,4'S)-2'-sec-butyl-6-chloro-4'-(3-chlorophenyl)spiro[3H-indole-3,3'-piperidine]-2,6'(1H)-dione as a white solid (Yield 0.25 g, 66%).

HRMS (ES$^+$) m/z Calcd for $C_{22}H_{22}Cl_2N_2O_2$+H [(M+H)$^+$]: 417.1131 Found: 417.1134

EXAMPLE 99a

Preparation of intermediate 2-(tert-butyl-dimethyl-silanyloxymethyl)-prop-2-en-1-ol

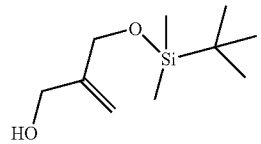

M. W. 202.37 $C_{10}H_{22}O_2Si$

To a solution of 2-methylene-propane-1,3-diol (5.3 g, 60.15 mmol) (Aldrich) in tetrahydrofuran (100 mL) was added sodium hydride (3.61 g, 90.3 mmol). After the reaction mixture was stirred at room temperature for 20 min, tert-butyldimethylchlorosilane (10.89 g, 72.2 mmol) was added. The reaction mixture was stirred at room temperature for 3 h, then poured into water and extracted with ethyl acetate. The organic layers were combined, washed with water, brine, dried over dried over MgSO$_4$, filtered and concentrated to give 2-(tert-butyl-dimethyl-silanyloxymethyl)-prop-2-en-1-ol as colorless oil (Yield 12.0 g, 99%).

EXAMPLE 99b

Preparation of intermediate 2-(tert-butyl-dimethyl-silanyloxymethyl)-propenal

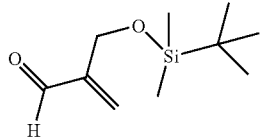

M. W. 200.36 $C_{10}H_{20}O_2Si$ 2-(Tert-butyl-dimethyl-silanyloxymethyl)-prop-2-en-1-ol (6 g, 29.7 mmol) prepared in example 99a was dissolved in dichloromethane (296 mL) containing both the molecular sieves (4 A) (Aldrich) and N-methyl morpholine oxide (5.2 g, 44.47 mmol). After stirring the mixture for 1 h, (Tetra-n-butyl ammonium perruthenate) (0.47 g, 1.48 mmol) (Aldrich) was added and the reaction mixture was stirred at room temperature for 1 h. Then another batch of (Tetra-n-butyl ammonium per-ruthenate) (0.23 g, 0.74 mmol) was added and the mixture was stirred at room temperature for another 1 h. The reaction mixture was diluted with dichloromethane. The organic layer was washed with Na$_2$S$_2$O$_3$ solution, brine and saturated copper (II) sulfate solution, then dried over dried over MgSO$_4$, filtered and concentrated. The residue was purified with chromatography to give 2-(tert-butyl-dimethyl-silanyloxymethyl)-propenal to as colorless oil (Yield 1.3 g, 22%).

EXAMPLE 99c

Preparation of intermediate 1-[1-(tert-butyl-dimethyl-silanyloxymethyl)-vinyl]-3-trimethylsilyoxy-2-aza-1,3-butadiene

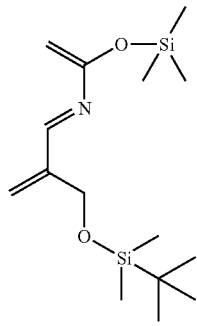

M. W. 313.59 $C_{15}H_{31}NO_2Si_2$

In a manner similar to the method described in example 1b, 2-(tert-butyl-dimethyl-silanyloxymethyl)-propenal (1.05 g, 5.25 mmol) prepared in example 99b was used as the starting material in place of 3-chloro-benzaldehyde to react with 1,1,1,3,3,3-hexamethyldisilazane (1.09 mL, 5.25 mmol), n-butyllithium (2.5 M, 2.1 mL, 5.25 mmol), trimethylsilyl chloride (0.67 mL, 5.25 mmol), triethylamine (0.95 mL, 6.8 mmol) and acetyl chloride (0.48 mL, 6.8 mmol) to give 1-[1-(tert-butyl-dimethyl-silanyloxymethyl)-vinyl]-3-trimethylsilyoxy-2-aza-1,3-butadiene as a yellow gum and used for the next step without further purification.

EXAMPLE 99d

Preparation of racemic (2'R,3R,4'S)-6-chloro-4'-(3-chlorophenyl)-2'-(1-hydroxymethyl-vinyl)-spiro[3H-indole-3,3'-piperidine]-2,6'(1H)-dione

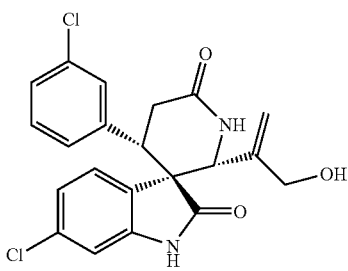

M. W. 417.34 $C_{21}H_{18}Cl_2N_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.2 g, 0.51 mmol) was reacted with 1-[1-(tert-butyl-dimethyl-silanyloxymethyl)-vinyl]-3-trimethylsilyoxy-2-aza-1,3-butadiene prepared in example 99c in toluene and then trifluoroacetic acid (20 mL) in dichloromethane to give racemic (2'R,3R,4'S)-6-chloro-4'-(3-chlorophenyl)-2'-(1-hydroxymethyl-vinyl)-spiro[3H-indole-3,3'-piperidine]-2,6'(1H)-dione as a yellow solid.

HRMS (ES$^+$) m/z Calcd for $C_{21}H_{18}Cl_2N_2O_3$+H [(M+H)$^+$]: 417.0767 Found: 417.0767.

EXAMPLE 100a

Preparation of intermediate 2-methoxymethyl-propenal

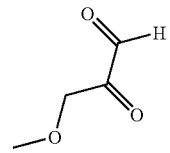

M. W. 100.12 $C_5H_8O_2$

A stirred mixture of acrolein (22.4 g, 0.4 mol) (Aldrich), methanol (62 g, 1.82 mol), triethanolamine (1.5 g, 0.01 mol) and 85% phosphoric acid (1.14 g, 0.0098 mol) in water was heated at refluxing temperature for overnight, then cooled to room temperature and filtered. The filtrate is diluted with water and then treated with a 37% formaldehyde solution (32.4 g, 0.4 mol) (Aldrich), concentrated sulfuric acid (2.32 g, 0.02 mol) and dibutylamine (5.4 g, 0.04 mol) (Aldrich). The crude mixture was heated at refluxing temperature for 4 h, cooled to room temperature and extracted with dichloromethane. The organic layers were combined, washed with brine, dried over MgSO$_4$, filtered and concentrated. The residue was purified with chromatography (hexanes) to give 2-methoxymethyl-propenal as colorless oil (Yield 2.8 g, 7.0%).

EXAMPLE 100b

Preparation of intermediate 1-(1-methoxymethyl-vinyl)-3-trimethylsilyoxy-2-aza-1,3-butadiene

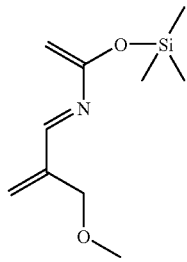

M. W. 213.75 $C_{10}H_{19}NO_2Si$

In a manner similar to the method described in example 1b, 2-methoxymethyl-propenal (1.35 mL, 10.5 mmol) prepared in example 100a was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(1-methoxymethyl-vinyl)-3-trimethylsilyoxy-2-aza-1,3-butadiene as a yellow gum and used for the next step without further purification.

EXAMPLE 100c

Preparation of racemic (2'R,3R,4'S)-6-chloro-4'-(3-chlorophenyl)-2'-(1-methoxymethyl-vinyl)spiro[3H-indole-3,3'-piperidine]-2,6'(1H)-dione

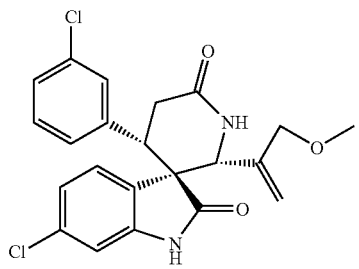

M. W. 431.32 $C_{22}H_{20}Cl_2N_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(1-methoxymethyl-vinyl)-3-trimethylsilyoxy-2-aza-1,3-butadiene prepared in example 158b in toluene and then trifluoroacetic acid (20 mL) in dichloromethane to give racemic (2'R,3R,4'S)-6-chloro-4'-(3-chlorophenyl)-2'-(1-methoxymethyl-vinyl)spiro[3H-indole-3,3'-piperidine]-2,6'(1H)-dione as a white solid (Yield: 0.12 g, 27.2%).

HRMS (ES$^+$) m/z Calcd for $C_{22}H_{20}Cl_2N_2O_3$+H [(M+H)$^+$]: 431.0924 Found: 431.0928.

EXAMPLE 101a

Preparation of intermediate 1,2-difluoro-4-(2-methoxy-ethoxy)-benzene

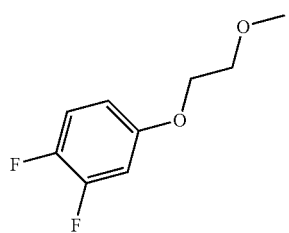

M. W. 188.18 $C_9H_{10}F_2O_2$

To a solution of 3,4-difluoro-phenol (10 g, 76.9 mmol) (Aldrich) in N,N-dimethylformamide (100 mL) was added sodium hydride (4.6 g, 115 mmol) and 1-bromo-2-methoxy-ethane (12.8 g, 92.2 mmol) (Aldrich). The reaction mixture was stirred at room temperature for 2 h, then heated at 80 ° C. for 16 h. The reaction mixture was cooled to room temperature and poured into water, extracted with ethyl acetate. The organic layers were combined, washed with water, brine, dried over dried over MgSO$_4$, filtered and concentrated. The residue was purified with chromatography (EtOAc:Hexane=1:10) to give 1,2-difluoro-4-(2-methoxy-ethoxy)-benzene as colorless oil (Yield 6.3 g, 44%).

EXAMPLE 101b

Preparation of intermediate 2,3-difluoro-6-(2-methoxy-ethoxy)-benzaldehyde

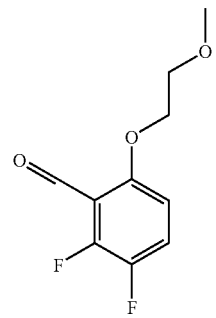

M. W. 216.19 $C_{10}H_{10}F_2O_3$

In a manner similar to the method described in example 52a, 1,2-difluoro-4-(2-methoxy-ethoxy)-benzene (6.3 g, 33.4 mmol) prepared in example 101a was reacted with lithium diisopropylamine (20.1 mL, 2.0 M in THF, 40.1 mmol), N,N-dimethyl-formamide (3.11 mL, 40.1 mmol) and quenched with acetic acid (8.1 g, 134 mmol) and water (41.2 mL) in tetrahydrofuran to give 2,3-difluoro-6-(2-methoxy-ethoxy)-benzaldehyde as yellow oil (Yield: 5.8 g, 80.6%).

EXAMPLE 101c

Preparation of intermediate 1-[2,3-difluoro-6-(2-methoxy-ethoxy)-phenyl]-3-trimethylsilyoxy-2-aza-1,3-butadiene

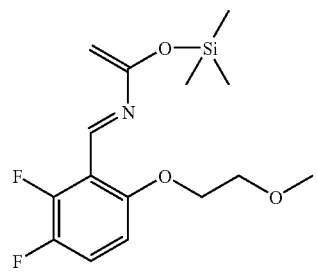

M. W. 329.42 $C_{15}H_{21}F_2NO_3Si$

In a manner similar to the method described in example 1b, 2,3-difluoro-6-(2-methoxy-ethoxy)-benzaldehyde (2.23 g, 10.5 mmol) prepared in example 101b was reacted with 1,1,1,3,3,3-hexamethyldisilazane (1.7 g, 10.5 mmol), n-butyl-lithium (2.5 M, 4.2 mL, 10.5 mmol), trimethylsilyl chloride (1.33 g, 10.5 mmol), triethylamine (1.9 mL, 13 mmol) and acetyl chloride (0.97, 13 mmol) to give 1-[2,3-difluoro-6-(2-methoxy-ethoxy)-phenyl]-3-trimethylsilyoxy-2-aza-1,3-butadiene as yellow gum and used for the next step without further purification.

EXAMPLE 101d

Preparation of racemic (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione

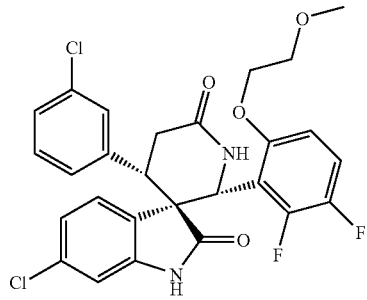

M. W. 547.39 $C_{27}H_{22}Cl_2F_2N_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-[2,3-difluoro-6-(2-methoxy-ethoxy)-phenyl]-3-trimethylsilyoxy-2-aza-1,3-butadiene prepared in example 101c in toluene and then trifluoroacetic acid (8 mL) in dichloromethane to give racemic (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione as a white solid (0.12 g, 21.4%).

HRMS (ES$^+$) m/z Calcd for $C_{27}H_{22}Cl_2F_2N_2O_4$+H [(M+H)$^+$]: 547.0998 Found: 547.0997.

EXAMPLE 101e

Preparation of chiral (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione

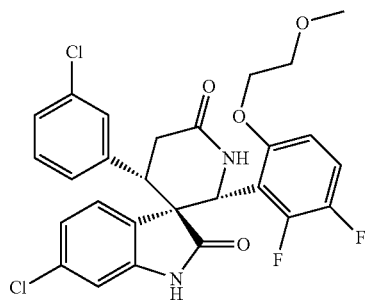

M. W. 483.37 $C_{26}H_{21}Cl_2FN_2O_2$

Separation of the two enantiomers from racemic (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione (80 mg) prepared in example 101d was conducted by chiral SFC to provide chiral (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione as a white solid (Yield: 35 mg, 43.7%) and chiral (2'R,3S,4'R)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione as a white solid (Yield: 33 mg, 41.2%).

EXAMPLE 102a

Preparation of intermediate 2,3-dimethyl-but-2-enoic acid ethyl ester

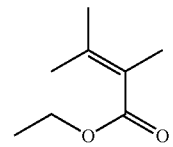

M. W. 142.20 $C_8H_{14}O_2$

Triethyl phosphonopropionate (23.8 g, 0.1 mol) (Aldrich) was added dropwise to a stirred solution of sodium hydride (2.64 g, 0.11 mol) in dimethoxyethane (100 mL) at 0° C. After stirring at room temperature for 20 mins, acetone (5.8 g, 0.1 mol) was added and the reaction mixture was refluxed for overnight. The two phase mixture was cooled, diluted with water and extracted with ether. The combined organic layers were dried over MgSO$_4$, filtered and concentrated. The residue was purified with chromatography (Hexane) to give 2,3-dimethyl-but-2-enoic acid ethyl ester as colorless oil (Yield 9.6 g, 67.7%).

EXAMPLE 102b

Preparation of intermediate 2,3-dimethyl-but-2-en-1-ol

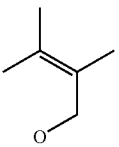

M. W. 100.16 $C_6H_{12}O$

The solution of 2,3-dimethyl-but-2-enoic acid ethyl ester (9.6 g, 67.7 mmol) in ether (100 mL) was added to a stirred solution of LAH (1M in ether, 67 mL, 67.7 mmol) dropwisely. After stirring at room temperature for 30 mins, the reaction mixture was quenched with saturate NH$_4$Cl solution, extracted with ether. The organic layers were combined, washed with water, brine, dried over MgSO$_4$ and filtered. The solvent was removed to give 2,3-dimethyl-but-2-en-1-ol as colorless oil (Yield 4.4 g, 66%).

EXAMPLE 102c

Preparation of intermediate 2,3-dimethyl-but-2-enal

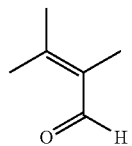

M. W. 98.15 $C_6H_{10}O$

To a solution of oxalyl chloride (6.13 g, 48.3 mmol) (Aldrich) in dichloromethane (50 mL) at −78° C. was added the solution of dimethyl sulfoxide (6.85 mL, 96.6 mmol) in dichloromethane dropwise. After 5 mins, the solution of 2,3-dimethyl-but-2-en-1-ol (4.4 g, 43.9 mmol) prepared in example 160b in dichloromethane (10 mL) was added dropwise. The reaction mixture was stirred at −78° C. for 15 mins. Triethyl amine (22 mL, 0.19 mol) was added and the reaction mixture was slowly warmed up to room temperature and stirred at room temperature for 45 mins. The water was added. The organic layers were separated, combined, washed with 10% of HCl, saturated $NaHCO_3$, brine, dried over $MgSO_4$, filtered and concentrated to give 2,3-dimethyl-but-2-enal as yellow liquid (Yield 4.0 g, 93%).

EXAMPLE 102d

Preparation of intermediate 1-(1,2-dimethyl-propenyl)-3-trimethylsilyoxy-2-aza-1,3-butadiene

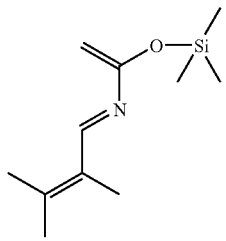

M. W. 211.38 $C_{11}H_{21}NOSi$

In a manner similar to the method described in example 1b, 2,3-dimethyl-but-2-enal (1.03 g, 10.5 mmol) prepared in example 102c was used as the starting material in place of 3-chloro-benzaldehyde to react with 1,1,1,3,3,3-hexamethyl-disilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(1,2-dimethyl-propenyl)-3-trimethylsilyoxy-2-aza-1,3-butadiene as a yellow gum and used for the next step without further purification.

EXAMPLE 102e

Preparation of racemic (2'R,3R,4'S)-6-chloro-4'-(3-chlorophenyl)-2'-(1,2-dimethyl-propenyl)spiro[3H-indole-3,3'-piperidine]-2,6'(1H)-dione

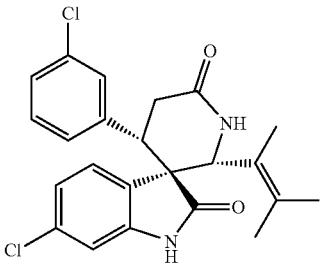

M. W. 429.35 $C_{23}H_{22}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(1,2-dimethyl-propenyl)-3-trimethylsilyoxy-2-aza-1,3-butadiene prepared in example 102d in toluene and then trifluoroacetic acid (20 mL) in dichloromethane to give racemic (2'R,3R,4'S)-6-chloro-4'-(3-chlorophenyl)-2'-(1,2-dimethyl-propenyl)spiro[3H-indole-3,3'-piperidine]-2,6'(1H)-dione as a yellow solid.

HRMS (ES$^+$) m/z Calcd for $C_{23}H_{22}Cl_2N_2O_2$+H [(M+H)$^+$]: 429.1131 Found: 429.1132.

EXAMPLE 103

Preparation of racemic (2'R,3R,4'S)-6-chloro-4'-(3-chlorophenyl)-2'-propionylspiro[3H-indole-3,3'-piperidine]-2,6'(1H)-dione

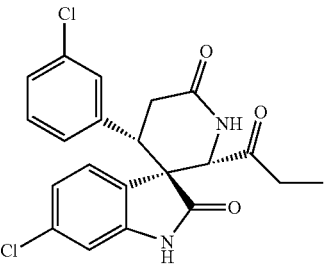

M. W. 417.30 $C_{21}H_{18}Cl_2N_2O_3$

To a solution of racemic (2'R,3R,4'S)-6-chloro-4'-(3-chlorophenyl)-2'-(1-methylene-propyl)spiro[3H-indole-3,3'-piperidine]-2,6'(1H)-dione (300 mg, 0.72 mmol) prepared in example 80b in methanol and dichloromethane (1:1, 50 mL) at −78° C. was passed a stream of ozone until the color of the solution turned blue. The reaction mixture was degassed with nitrogen, then methyl disulfide (5 mL) was added. The reaction was slowly warmed to room temperature and stirred overnight. The mixture was concentrated, and the residue was purified by chromatography (EtOAc:$CH_2Cl_2$=1:1) to give the racemic (2'R,3R,4'S)-6-chloro-4'-(3-chlorophenyl)-2'-propionylspiro[3H-indole-3,3'-piperidine]-2,6'(1H)-dione as a white solid (Yield 160 mg, 50%)

HRMS (ES$^+$) m/z Calcd for $C_{21}H_{18}Cl_2N_2O_3$+H [(M+H)$^+$]: 417.0767. Found: 417.0770.

EXAMPLE 104a

Preparation of intermediate
1,2-difluoro-4-propoxy-benzene

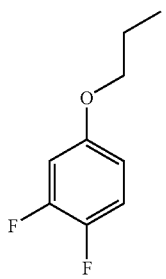

M. W. 172.18 $C_9H_{10}F_2O$

To a solution of 3,4-difluoro-phenol (20 g, 154 mmol) in N,N-dimethylformamide (70 mL) was added potassium carbonate (30 g, 217 mmol) and iodopropane (50 g, 293 mmol, Aldrich). The reaction mixture was heated at refluxing for 48 h. The crude was cooled to room temperature and filtered through a short pad of celite. The filtrate was concentrated and the residue was purified by chromatography (EtOAc:Hexanes=1:8) to give 1,2-difluoro-4-propoxy-benzene as a colorless oil (Yield 17 g, 100%).

EXAMPLE 104b

Preparation of intermediate
2,3-difluoro-6-propoxy-benzaldehyde

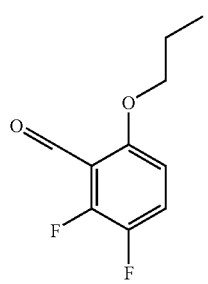

M. W. 200.19 $C_{10}H_{10}F_2O_2$

In a manner similar to the method described in example 52a, 1,2-difluoro-4-propoxy-benzene (17 g, 98.8 mmol) prepared in example 104a was reacted with lithium diisopropyl amine (59.2 mL, 2.0 M in THF, 0.118 mmol), N,N-dimethylformamide (9.17 mL, 0.118 mol) and quenched with acetic acid (23.7 g, 0.395 mol) and water (41.2 mL) in tetrahydrofuran to give 2,3-difluoro-6-propoxy-benzaldehyde as a yellow solid (Yield: 8.2 g, 42%).

EXAMPLE 104c

Preparation of intermediate 1-(2,3-difluoro-6-propoxy-phenyl)-3-trimethylsilyoxy-2-aza-1,3-butadiene

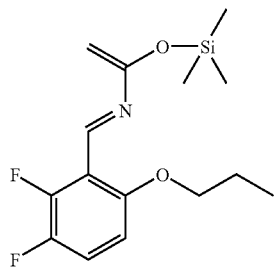

M. W. 313.42 $C_{15}H_{21}F_2NO_2Si$

In a manner similar to the method described in example 1b, 2,3-difluoro-6-propoxy-benzaldehyde (2.1 g, 10.5 mmol) prepared in example 104b was used as the starting material in place of 3-chloro-benzaldehyde to react with 1,1,1,3,3,3-hexamethyldisilazane (1.7 g, 10.5 mmol), n-butyllithium (2.5 M, 4.2 mL, 10.5 mmol), trimethylsilyl chloride (1.33 g, 10.5 mmol), triethylamine (1.9 mL, 13 mmol) and acetyl chloride (0.97, 13 mmol) to give 1-(2,3-difluoro-6-propoxy-phenyl)-3-trimethylsilyoxy-2-aza-1,3-butadiene as yellow gum and used for the next step without further purification.

EXAMPLE 104d

Preparation of racemic (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione

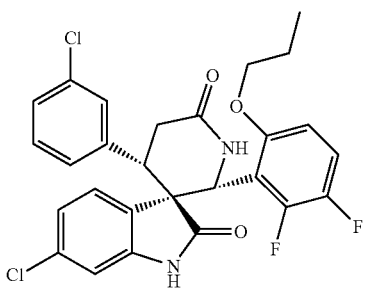

M. W. 531.39 $C_{27}H_{22}Cl_2F_2N_2O_3$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.4 g, 1.02 mmol) was reacted with 1-(2,3-difluoro-6-propoxy-phenyl)-3-trimethylsilyoxy-2-aza-1,3-butadiene prepared in example 104c in toluene and then trifluoroacetic acid (8 mL) in dichloromethane to give racemic (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione as yellow oil.

HRMS (ES$^+$) m/z Calcd for $C_{27}H_{22}Cl_2F_2N_2O_3$+H [(M+H)$^+$]: 531.1049 Found: 531.1049.

EXAMPLE 104e

Preparation of chiral (2'R,3R,4'S)-6-chloro-4'-(3-chlorophenyl)-2'-(2,3-difluoro-6-propoxy-phenyl) spiro[3H-indole-3,3'-piperidine]-2,6'(1H)-dione

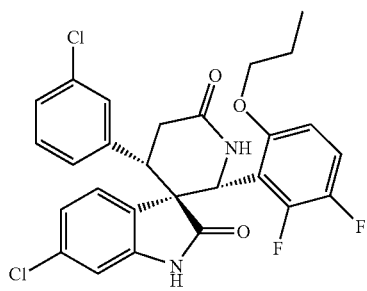

M. W. 531.39 C$_{27}$H$_{22}$Cl$_2$F$_2$N$_2$O$_3$

Separation of the two enantiomers from racemic (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione (0.67 g) prepared in example 104d was conducted by chiral SFC to provide chiral (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione as a white solid (Yield: 135 mg, 20.1%) and chiral (2'R,3S,4'R)-6-chloro-4'-(3-chlorophenyl)-2'-(2,3-difluoro-6-propoxy-phenyl)spiro[3H-indole-3,3'-piperidine]-2,6'(1H)-dione as a white solid (Yield: 150 mg, 22.3%).

EXAMPLE 105a

Preparation of intermediate 2-cyclopropyl-prop-2-en-1-ol

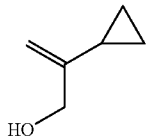

M. W. 98.15 C$_6$H$_{10}$O

To a solution of propargyl alcohol (4.2 g, 74.9 mmol) (Aldrich) and CuI (14.28 g, 74.9 mmol) (Aldrich) in ether at 0° C. was added cyclopropylmagnesium chloride (0.5 M, 0.45 L, 0.225 mol) solution in tetrahydrofuran dropwise. The reaction mixture was stirred at room temperature for 48 h. The reaction mixture was quenched with saturate NH$_4$Cl solution, extracted with ether. The organic layers were combined, washed with water, brine, dried over MgSO$_4$, filtered and concentrated. The residue was purified with chromatography (EtOAc:Hexane=1:8) to give 2-cyclopropyl-prop-2-en-1-ol as yellow oil (Yield 5.9 g, 80.9%).

EXAMPLE 105b

Preparation of intermediate 2-cyclopropyl-propenal

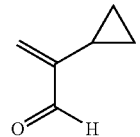

M. W. 96.13 C$_6$H$_8$O

In a manner similar to the method described in example 102c, 2-cyclopropyl-prop-2-en-1-ol (5.95 g, 60.7 mmol) prepared in example 105a was reacted with oxalyl chloride (8.48 g, 60.7 mmol), dimethyl sulfoxide (9.47 mL, 133.5 mmol) and triethylamine (30.4 mL, 218 mmol) in dichloromethane to give 2-cyclopropyl-propenal as yellow oil (Yield: 4.8 g, 34.5%).

EXAMPLE 105c

Preparation of intermediate 1-(1-cyclopropyl-vinyl)-3-trimethylsilyoxy-2-aza-1,3-butadiene

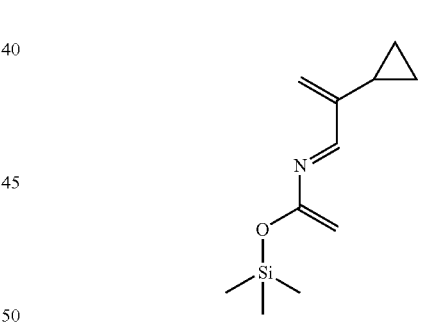

M. W. 209.37 C$_{11}$H$_{19}$NOSi

In a manner similar to the method described in example 1b, 2-cyclopropyl-propenal (1.0 g, 10.5 mmol) prepared in example 105b was used as the starting material in place of 3-chloro-benzaldehyde to react with 1,1,1,3,3,3-hexamethyl-disilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(1-cyclopropyl-vinyl)-3-trimethylsilyoxy-2-aza-1,3-butadiene as a yellow gum and used for the next step without further purification.

EXAMPLE 105d

Preparation of racemic (2'R,3R,4'S)-6-chloro-4'-(3-chlorophenyl)-2'-(1-cyclopropyl-vinyl)spiro[3H-indole-3,3'-piperidine]-2,6'(1H)-dione

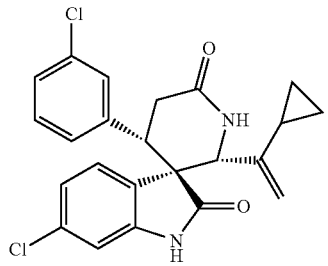

M. W. 427.33 $C_{23}H_{20}Cl_2N_2O_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.35 g, 0.90 mmol) was reacted with 1-(1-cyclopropyl-vinyl)-3-trimethylsilyoxy-2-aza-1,3-butadiene prepared in example 105c in toluene and then trifluoroacetic acid (20 mL) in dichloromethane to give racemic (2'R,3R,4'S)-6-chloro-4'-(3-chlorophenyl)-2'-(1-cyclopropyl-vinyl)spiro[3H-indole-3,3'-piperidine]-2,6'(1H)-dione as a yellow solid.

HRMS (ES$^+$) m/z Calcd for $C_{23}H_{20}Cl_2N_2O_2$+H [(M+H)$^+$]: 427.0975 Found: 427.0973.

EXAMPLE 106

Preparation of racemic (2'R,3R,4'S)-6-chloro-4'-(3-chlorophenyl)-1'-hydroxycarbonylmethyl-2'-(1-methylene-propyl)spiro[3H-indole-3,3'-piperidine]-2,6'(1H)-dione

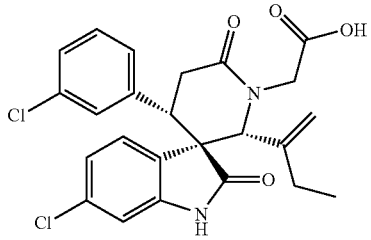

M. W. 473.36 $C_{24}H_{22}Cl_2N_2O_4$

In a manner similar to the methods described in example 81b, 81c, racemic (2'R,3R,4'S)-6-chloro-4'-(3-chloro-phenyl)-2'-(1-methylene-propyl)-2,3-dihydro-2,6'-dioxospiro[indole-3,3'-piperidine]-1-methoxyethyl trimethylsilane (7 g, 12.8 mmol) prepared in example 97a was reacted to form racemic (2'R,3R,4'S)-6-chloro-4'-(3-chlorophenyl)-1'-hydroxycarbonylmethyl-2'-(1-methylene-propyl)spiro[3H-indole-3,3'-piperidine]-2,6'(1H)-dione as a white solid (3.6 g, 59%).

HRMS (ES$^+$) m/z Calcd for $C_{24}H_{22}Cl_2N_2O_4$+H [(M+H)$^+$]: 473.1030 Found: 473.1032.

EXAMPLE 107a

Preparation of intermediate racemic (2'R,3R,4'S)-6-chloro-4'-(3-chlorophenyl)-1'-fluorocarbonylmethyl-2'-(1-methylene-propyl)spiro[3H-indole-3,3'-piperidine]-2,6'(1H)-dione

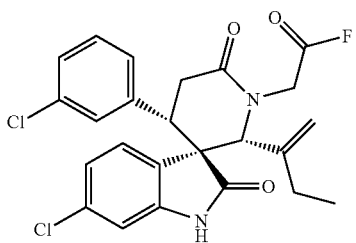

M. W. 475.35 $C_{24}H_{21}Cl_2FN_2O_3$

In a manner similar to the method described in example 82a, racemic (2'R,3R,4'S)-6-chloro-4'-(3-chlorophenyl)-1'-hydroxycarbonylmethyl-2'-(1-methylene-propyl)spiro[3H-indole-3,3'-piperidine]-2,6'(1H)-dione (1.2 g, 2.5 mmol) prepared in example 166 was reacted to form racemic (2'R,3R,4'S)-6-chloro-4'-(3-chlorophenyl)-1'-fluorocarbonylmethyl-2'-(1-methylene-propyl)spiro[3H-indole-3,3'-piperidine]-2,6'(1H)-dione (yield: 1.1 g, 92%).

EXAMPLE 107b

Preparation of racemic (2'R,3R,4'S)-6-chloro-4'-(3-chlorophenyl)-2'-(1-methylene-propyl)-1'-[(1-methanesulfonyl-piperidin-4-yl)aminocarbonyl-methyl]spiro[3H-indole-3,3'-piperidine]-2,6'(1H)-dione

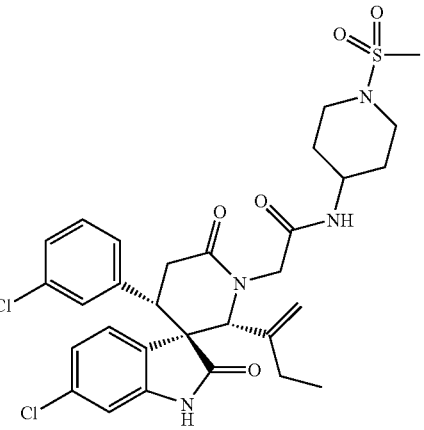

M. W. 633.60 $C_{30}H_{34}Cl_2N_4O_5S$

In a manner similar to the method described in example 34b, racemic (2'R,3R,4'S)-6-chloro-4'-(3-chlorophenyl)-1'-fluorocarbonylmethyl-2'-(1-methylene-propyl)spiro[3H-indole-3,3'-piperidine]-2,6'(1H)-dione (0.1 g, 0.21 mmol) prepared in example 107a was reacted with 1-methanesulfonyl-piperidin-4-ylamine trifluoroacetic acid salt (0.2 g, 0.34 mmol), N-methylmorpholine (0.2 g, 2 mmol) and 4-dimethylaminopyridine (1 mg) in tetrahydrofuran to give racemic (2'R,3R,4'S)-6-chloro-4'-(3-chlorophenyl)-2'-(1-methylene-propyl)-1'-[(1-methanesulfonyl-piperidin-4-yl)aminocarbonyl-methyl]spiro[3H-indole-3,3'-piperidine]-2,6'(1H)-dione as an off-white solid (Yield 58 mg, 44%).

HRMS (ES+) m/z Calcd for $C_{30}H_{34}Cl_2N_4O_5S+H$ [(M+H)+]: 633.1700. Found: 633.1701.

EXAMPLE 108a

Preparation of racemic (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione

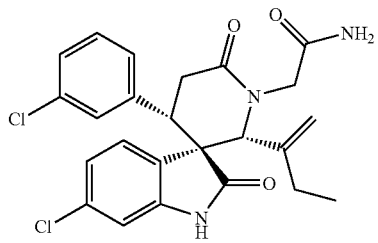

M. W. 472.38 $C_{24}H_{23}Cl_2N_3O_3$

Racemic (2'R,3R,4'S)-6-chloro-4'-(3-chlorophenyl)-1'-fluorocarbonylmethyl-2'-(1-methylene-propyl)spiro[3H-indole-3,3'-piperidine]-2,6'(1H)-dione (0.1 g, 0.21 mmol) prepared in example 107a was stirred in a methanolic ammonia solution (7N, 10 mL) at room temperature for 18 h. The reaction mixture was concentrated, and the residue was purified by chromatography (EtOAc:MeOH=10:1) to give racemic (2'R,3R,4'S)-6-chloro-4'-(3-chlorophenyl)-2'-(1-methylene-propyl)-1'-[aminocarbonyl-methyl]spiro[3H-indole-3,3'-piperidine]-2,6'(1H)-dione as a yellow solid (Yield 41 mg, 40%).

HRMS (ES+) m/z Calcd for $C_{24}H_{23}Cl_2N_3O_3+Na$ [(M+Na)+]: 494.1008 Found: 494.1008

EXAMPLE 108b

Preparation of chiral (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione

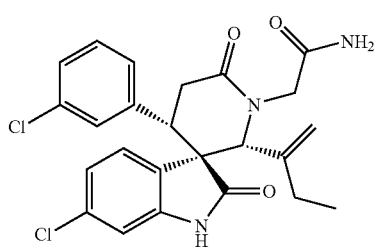

M. W. 472.38 $C_{24}H_{23}Cl_2N_3O_3$

Separation of the two enantiomers from racemic (2'R,3R,4'S)-6-chloro-4'-(3-chlorophenyl)-2'-(1-methylene-propyl)-1'-[aminocarbonyl-methyl]spiro[3H-indole-3,3'-piperidine]-2,6'(1H)-dione (32 mg) was conducted by chiral SFC to provide chiral (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione as a white solid (Yield: 9 mg, 28%) and chiral (2'S,3S,4'R)-6-chloro-4'-(3-chlorophenyl)-2'-(1-methylene-propyl)-1'-(aminocarbonyl-methyl)spiro[3H-indole-3,3'-piperidine]-2,6'(1H)-dione (Yield: 9 mg, 28%).

EXAMPLE 109a

Preparation of intermediate 2-ethyl-3-methyl-but-2-enoic acid ethyl ester

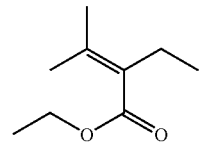

M. W. 156.23 $C_9H_{16}O_2$

In a manner similar to the method described in example 102a, triethyl 2-phosphonobutyrate (25.2 g, 0.1 mol) was reacted with NaH (2.64 g, 0.11 mol), and then acetone (5.8 g, 0.1 mol) in dimethoxyethane to give 2-ethyl-3-methyl-but-2-enoic acid ethyl ester as colorless oil (Yield: 11.4 g, 73%).

EXAMPLE 109b

Preparation of intermediate 2-ethyl-3-methyl-but-2-en-1-ol

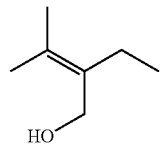

M. W. 114.19 $C_7H_{14}O$

In a manner similar to the method described in example 102b, 2-ethyl-3-methyl-but-2-enoic acid ethyl ester (11.4 g, 73 mmol) prepared in example 109a was reacted with LAH (1M in ether, 73 mL, 73 mmol) in diethyl ether to give 2-ethyl-3-methyl-but-2-en-1-ol as colorless oil (Yield: 7.62 g, 91.5%).

EXAMPLE 109c

Preparation of intermediate 2-ethyl-3-methyl-but-2-enal

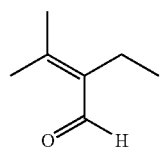

M. W. 112.17 $C_7H_{12}O$

In a manner similar to the method described in example 102c, 2-ethyl-3-methyl-but-2-en-1-ol (7.62 g, 66.8 mmol) prepared in example 109b was reacted with oxalyl chloride (9.3 g, 73.5 mmol), dimethyl sulfoxide (10.44 mL, 146.9 mmol) and triethylamine (33.4 mL, 240 mmol) in dichloromethane to give 2-ethyl-3-methyl-but-2-enal as yellow oil (Yield: 7.5 g, 99%).

EXAMPLE 109d

Preparation of intermediate 1-(1-ethyl-2-methyl-propenyl)-3-trimethylsilyoxy-2-aza-1,3-butadiene

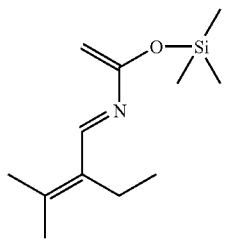

M. W. 225.41 C$_{12}$H$_{23}$NOSi

In a manner similar to the method described in example 1b, 2-ethyl-3-methyl-but-2-enal (1.18 g, 10.5 mmol) prepared in example 109c was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(1-ethyl-2-methyl-propenyl)-3-trimethylsilyoxy-2-aza-1,3-butadiene as a yellow gum and used for the next step without further purification.

EXAMPLE 109e

Preparation of racemic (2'R,3R,4'S)-6-chloro-4'-(3-chlorophenyl)-2'-(1-ethyl-2-methyl-propenyl)spiro[3H-indole-3,3'-piperidine]-2,6'(1H)-dione

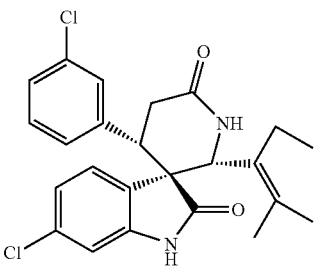

M. W. 443.38 C$_{24}$H$_{24}$Cl$_2$N$_2$O$_2$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.35 g, 0.89 mmol) was reacted with 1-(1-ethyl-2-methyl-propenyl)-3-trimethylsilyoxy-2-aza-1,3-butadiene prepared in example 109d in toluene and then trifluoroacetic acid (20 mL) in dichloromethane to give racemic (2'R,3R,4'S)-6-chloro-4'-(3-chlorophenyl)-2'-(1-ethyl-2-methyl-propenyl)spiro[3H-indole-3,3'-piperidine]-2,6'(1H)-dione as a yellow solid.

HRMS (ES$^+$) m/z Calcd for C$_{24}$H$_{24}$Cl$_2$N$_2$O$_2$+H [(M+H)$^+$]: 443.1288 Found: 443.1287.

EXAMPLE 110a

Preparation of racemic (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6' (1H)-dione

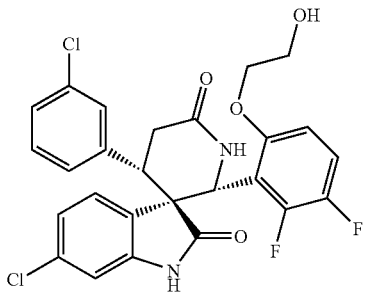

M. W. 533.36 C$_{26}$H$_{20}$Cl$_2$F$_2$N$_2$O$_4$

To a suspension of racemic (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione (0.12 g, 0.22 mmol) prepared in example 101d in dichloromethane (5 mL) at −78° C. was added boron tribromide (1M, 2.19 ml, 2.19 mmol) dropwise. The reaction was gradually warmed up to room temperature and stirred at room temperature for 2 h. Then the crude was diluted with dichloromethane. The organic layer was washed with water, brine, dried over MgSO$_4$, filtered and concentrated. The residue was purified with chromatography (EtOAc) to give racemic (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione as white solid (Yield: 46 mg, 39.3%).

HRMS (ES$^+$) m/z Calcd for C$_{26}$H$_{20}$Cl$_2$F$_2$N$_2$O$_4$+H [(M+H)$^+$]: 533.0841. Found: 533.0842.

EXAMPLE 110b

Preparation of chiral (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6' (1H)-dione

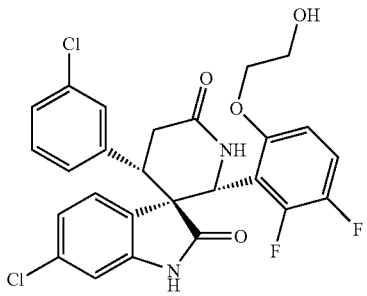

M. W. 533.36 C$_{26}$H$_{20}$Cl$_2$F$_2$N$_2$O$_4$

Separation of the two enantiomers from racemic (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6' (1H)-dione (70 mg) was conducted by chiral SFC to provide chiral (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione as a white solid (Yield: 30 mg, 42.8%) and chiral (2'R,3S,4'R)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione as a white solid (Yield: 20 mg, 28.5%).

EXAMPLE 111

Preparation of racemic (2'R,3R,4'S)-6-chloro-4'-(3-chlorophenyl)-2'-(2,3-difluoro-6-hydroxy-phenyl)spiro[3H-indole-3,3'-piperidine]-2,6'(1H)-dione

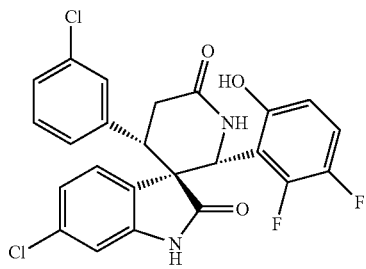

M. W. 489.31 $C_{24}H_{16}Cl_2F_2N_2O_4$

In preparation of racemic (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione in example 110a, racemic (2'R,3R,4'S)-6-chloro-4'-(3-chlorophenyl)-2'-(2,3-difluoro-6-hydroxy-phenyl)spiro[3H-indole-3,3'-piperidine]-2,6'(1H)-dione was obtained as a side product.

HRMS (ES$^+$) m/z Calcd for $C_{24}H_{16}Cl_2F_2N_2O_4$+H [(M+H)$^+$]: 489.0579. Found: 489.0580.

EXAMPLE 112

Preparation of racemic (2'R,3R,4'S)-6-chloro-4'-(3-chlorophenyl)-2'-(1-ethyl-1-hydroxy-propyl)spiro[3H-indole-3,3'-piperidine]-2,6'(1H)-dione

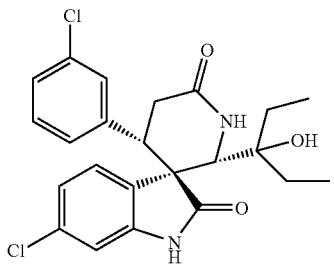

M. W. 447.37 $C_{23}H_{24}Cl_2N_2O_3$

To a solution of racemic (2'R,3R,4'S)-6-chloro-4'-(3-chlorophenyl)-2'-propionylspiro[3H-indole-3,3'-piperidine]-2,6'(1H)-dione (100 mg, 0.24 mmol) prepared in example 103 in tetrahydrofuran (3 mL) at −78° C. was added a tetrahydrofuran solution of ethylmagnesium chloride (2M, 6 mL, 12 mmol). The reaction mixture was stirred at −78° C. for 0.5 h, then slowly warmed to room temperature and stirred for 2 h. The mixture was poured into saturated aqueous NH$_4$Cl solution, and the mixture was extracted with ethyl acetate. The organic layer was separated, dried over MgSO$_4$, concentrated. The residue was purified by chromatography (EtOAc:MeOH=10:1) to give racemic (2'R,3R,4'S)-6-chloro-4'-(3-chlorophenyl)-2'-(1-ethyl-1-hydroxy-propyl)spiro[3H-indole-3,3'-piperidine]-2,6'(1H)-dione as a white solid (Yield 100 mg, 93%)

HRMS (ES$^+$) m/z Calcd for $C_{23}H_{24}Cl_2N_2O_3$+H [(M+H)$^+$]: 447.1237. Found: 447.1237.

EXAMPLE 113a

Preparation of intermediate racemic (2'R,3R,4'S)-6-chloro-4'-(3-chlorophenyl)-2'-(1-ethyl-3-methyl-oxiranyl)-2,3-dihydro-2,6'-dioxo-spiro[indole-3,3'-piperidine]-1-methoxyethyl trimethylsilane

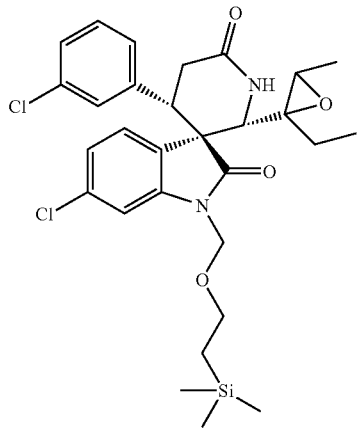

M. W. 575.61 $C_{29}H_{36}Cl_2N_2O_4Si$

To a solution of racemic (2'R,3R,4'S)-6-chloro-4'-(3-chloro-phenyl)-2'-(1-ethyl-propenyl)-2,3-dihydro-2,6'-dioxospiro[indole-3,3'-piperidine]-1-methoxyethyl trimethylsilane (1.2 g, 2.1 mmol) prepared in example 81a in dichloromethane (50 mL) was added m-chloroperoxybenzoic acid (77%, 8.9 g,) and NaHCO$_3$ (2 g). The reaction mixture was stirred at room temperature for 18 h, the poured into an aqueous solution of Na$_2$SO$_3$, then extracted with ethyl acetate. The organic layer was separated, dried over Na$_2$SO$_4$, concentrated. The residue was purified by chromatography (EtOAc:hexanes=1:1) to give racemic (2'R,3R,4'S)-6-chloro-4'-(3-chlorophenyl)-2'-(1-ethyl-3-methyl-oxiranyl)-2,3-dihydro-2,6'-dioxospiro[indole-3,3'-piperidine]-1-methoxyethyl trimethylsilane as a white foam (Yield, 1.0 g, 82%).

EXAMPLE 113b

Preparation of racemic (2'R,3R,4'S)-6-chloro-4'-(3-chlorophenyl)-2'-(1-ethyl-3-methyl-oxiranyl)spiro[3H-indole-3,3'-piperidine]-2,6'(1H)-dione

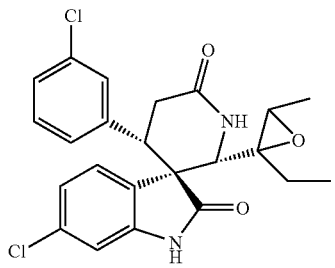

M. W. 445.35 $C_{23}H_{22}Cl_2N_2O_3$

In a manner similar to the methods described in example 56b and 56c, racemic (2'R,3R,4'S)-6-chloro-4'-(3-chlorophenyl)-2'-(1-ethyl-3-methyl-oxiranyl)-2,3-dihydro-2,6'-dioxospiro[indole-3,3'-piperidine]-1-methoxyethyl trimethylsilane (0.19 g, 0.33 mmol) prepared in example 113a was reacted to give racemic (2'R,3R,4'S)-6-chloro-4'-(3-chlorophenyl)-2'-(1-ethyl-3-methyl-oxiranyl)spiro[3H-indole-3,3'-piperidine]-2,6'(1H)-dione as a white solid (Yield, 0.42 g, 29%)

HRMS (ES$^+$) m/z Calcd for $C_{23}H_{22}Cl_2N_2O_3$+H [(M+H)$^+$]: 445.1080. Found: 445.1081.

EXAMPLE 114a

Preparation of intermediate 2-fluoro-3-methyl-but-2-enoic acid ethyl ester

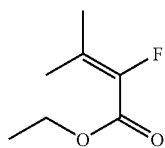

M. W. 146.16 $C_7H_{11}FO_2$

Triethyl 2-fluoro-2-phosphonoacetate (20 g, 82.6 mmol) (Aldrich) was added dropwise to a stirred solution of sodium hydride (3.6 g, 90.8 mmol) in dimethoxyethane (100 mL) at 0° C. After stirring at room temperature for 20 min, acetone (4.78 g, 82.6 mmol) was added and the reaction mixture was refluxed for overnight. The two phase mixture was cooled, diluted with water and extracted with ether. The combined organic layers were dried over MgSO$_4$, filtered and concentrated. The residue was purified with chromatography (Hexanes) to give 2-fluoro-3-methyl-but-2-enoic acid ethyl ester as colorless oil (Yield: 9.0 g, 61.6%).

EXAMPLE 114b

Preparation of intermediate 2-fluoro-3-methyl-but-2-en-1-ol

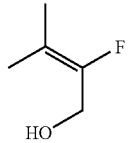

M. W. 104.14 $C_5H_9FO$

The solution of 2-fluoro-3-methyl-but-2-enoic acid ethyl ester (9.0 g, 61.6 mmol) in ether (100 mL) was added to a stirred solution of LAH (1M in ether, 61.6 mL, 67.7 mmol) dropwise. After stirring at room temperature for 30 mins, the reaction mixture was quenched with saturate NH$_4$Cl solution, extracted with ether. The organic layers were combined, washed with water, brine, dried over MgSO$_4$ and filtered. The solvent was removed to give 2-fluoro-3-methyl-but-2-en-1-ol as colorless oil (Yield: 5.21 g, 81.3%).

EXAMPLE 114c

Preparation of intermediate 2-fluoro-3-methyl-but-2-enal

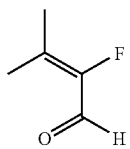

M. W. 102.11 $C_5H_7FO$

To a solution of oxalyl chloride (6.98 g, 50 mmol) (Aldrich) in dichloromethane (50 mL) at −78° C. was added the solution of dimethyl sulfoxide (7.80 mL, 110 mmol) in dichloromethane dropwise. After 5 mins, the solution of 2-fluoro-3-methyl-but-2-en-1-ol (5.21 g, 50 mmol) prepared in example 114b in dichloromethane (10 mL) was added dropwise. The reaction mixture was stirred at −78° C. for 15 min. Triethylamine (25 mL, 0.18 mol) was added and the reaction mixture was slowly warmed up to room temperature and stirred at room temperature for 45 min. The water was added. The organic layers were separated, combined, washed with 10% of HCl, saturated NaHCO$_3$, brine, dried over MgSO$_4$, filtered and concentrated to give 2-fluoro-3-methyl-but-2-enal as yellow liquid (Yield: 4.02 g, 82.4%).

EXAMPLE 114d

Preparation of intermediate 1-(1-fluoro-2-methyl-propenyl)-3-trimethylsilyoxy-2-aza-1,3-butadiene

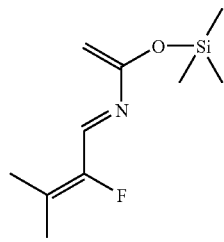

M. W. 215.35 $C_{10}H_{18}FNOSi$

In a manner similar to the method described in example 1b, 2-fluoro-3-methyl-but-2-enal (2.14 g, 21 mmol) prepared in example 114c was used as the starting material in place of 3-chloro-benzaldehyde to react with 1,1,1,3,3,3-hexamethyl-disilazane (4.36 mL, 21 mmol), n-butyllithium (2.5 M, 8.4 mL, 21 mmol), trimethylsilyl chloride (2.66 mL, 21 mmol), triethylamine (3.8 mL, 27.2 mmol) and acetyl chloride (1.94 mL, 27.2 mmol) to give 1-(1-fluoro-2-methyl-propenyl)-3-trimethylsilyoxy-2-aza-1,3-butadiene as a yellow gum and used for the next step without further purification.

EXAMPLE 114e

Preparation of racemic (2'R,3R,4'S)-6-chloro-4'-(3-chlorophenyl)-2'-(1-fluoro-2-methyl-propenyl)spiro[3H-indole-3,3'-piperidine]-2,6'(1H)-dione

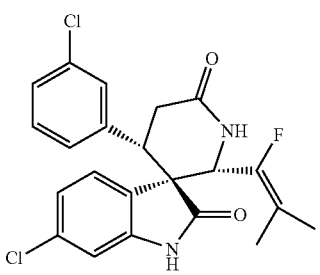

M. W. 433.31 $C_{22}H_{19}Cl_2FN_2O_2$

In a manner similar to the method described in example 41b, E/Z-6-chloro-3-(3-chloro-benzylidene)-2-oxo-2,3-di-hydro-indole-1-carboxylic acid tert-butyl ester prepared in example 24a (1.0 g, 2.56 mmol) was reacted with 1-(1-fluoro-2-methyl-propenyl)-3-trimethylsilyoxy-2-aza-1,3-butadiene prepared in example 114e in toluene and then trifluoroacetic acid (20 mL) in dichloromethane to give racemic (2'R,3R,4'S)-6-chloro-4'-(3-chlorophenyl)-2'-(1-fluoro-2-methyl-propenyl)spiro[3H-indole-3,3'-piperidine]-2,6'(1H)-dione as a yellow solid.

HRMS (ES$^+$) m/z Calcd for $C_{22}H_{19}Cl_2FN_2O_2$+H [(M+H)$^+$]: 433.0881 Found: 433.0879.

EXAMPLE 115

Preparation of racemic (2'R,3R,4'S)-6-chloro-4'-(3-chlorophenyl)-2'-isobutyrylspiro[3H-indole-3,3'-piperidine]-2,6'(1H)-dione

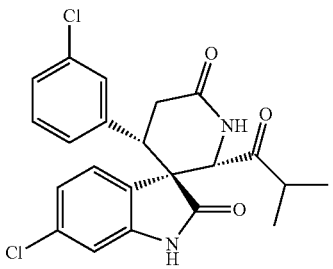

M. W. 431.32 $C_{22}H_{20}Cl_2N_2O_3$

In a manner similar to the methods described in example 103, racemic (2'R,3R,4'S)-6-chloro-4'-(3-chlorophenyl)-2'-(2-methyl-1-methylene-propyl)spiro[3H-indole-3,3'-piperidine]-2,6'(1H)-dione (0.2 g, 0.47 mmol) prepared in example 139d was reacted to form racemic (2'R,3R,4'S)-6-chloro-4'-(3-chlorophenyl)-2'-isobutyrylspiro[3H-indole-3,3'-piperidine]-2,6'(1H)-dione as a white solid (Yield, 0.13 g, 66%).

HRMS (ES$^+$) m/z Calcd for $C_{22}H_{20}Cl_2N_2O_3$+H [(M+H)$^+$]: 431.0924. Found: 431.0925.

EXAMPLE 116a

Preparation of intermediate racemic (2'R,3R,4'S)-6-chloro-4'-(3-chlorophenyl)-2'-isopropenyl-2,3-dihydro-2,6'-dioxospiro[indole-3,3'-piperidine]-1-methoxyethyl trimethylsilane

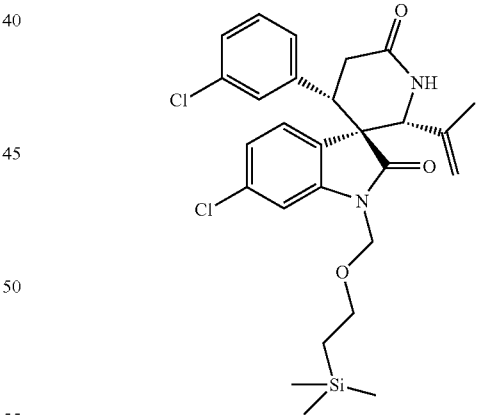

M. W. 531.56 $C_{27}H_{32}Cl_2N_2O_3Si$

In a manner similar to the method described in example 55b, E/Z-6-chloro-3-(3-chlorobenzylidene)-1-(2-trimethyl-silanyl-ethoxymethyl)-1,3-dihydro-indole-2-one (8 g, 20 mmol) prepared in example 55a was reacted with 1-isopropenyl-3-trimethylsilyoxy-2-aza-1,3-butadiene (21 g, 99 mmol) prepared in example 87a in toluene (200 mL) to give racemic (2'R,3R,4'S)-6-chloro-4'-(3-chlorophenyl)-2'-isopropenyl-2,3-dihydro-2,6'-dioxospiro[indole-3,3'-piperidine]-1-methoxyethyl trimethylsilane as a white gum (3.5 g, 33%)

EXAMPLE 116b

Preparation of intermediate racemic (2'R,3R,4'S)-6-chloro-4'-(3-chlorophenyl)-2'-isopropenyl-2,3-dihydro-1'-[(tert-butoxycarbonyl)methyl]-2,6'-dioxospiro[indole-3,3'-piperidine]-1-methoxyethyl trimethylsilane

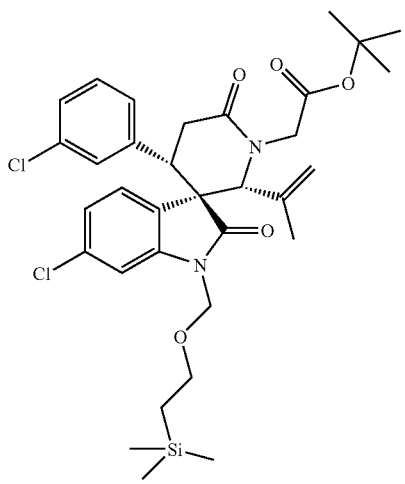

M. W. 645.71 C$_{33}$H$_{42}$Cl$_2$N$_2$O$_5$Si

In a manner similar to the method described in example 55c, racemic (2'R,3R,4'S)-6-chloro-4'-(3-chlorophenyl)-2'-isopropenyl-2,3-dihydro-2,6'-dioxospiro[indole-3,3'-piperidine]-1-methoxyethyl trimethylsilane (3 g, 5.64 mmol) prepared in example 116a was reacted with bromo-acetic acid tert-butyl ester and cesium carbonate in N,N-dimethyl-formamide to give racemic (2'R,3R,4'S)-6-chloro-4'-(3-chlorophenyl)-2'-isopropenyl-2,3-dihydro-1'-[(tert-butoxycarbonyl)methyl]-2,6'-dioxospiro[indole-3,3'-piperidine]-1-methoxyethyl trimethylsilane as a white foam (Yield: 2.98 g, 79%).

EXAMPLE 116c

Preparation of racemic (2'R,3R,4'S)-6-chloro-4'-(3-chlorophenyl)-2'-isopropenyl-1'-hydroxycarbonylmethylspiro[3H-indole-3,3'-piperidine]-2,6'(1H)-dione

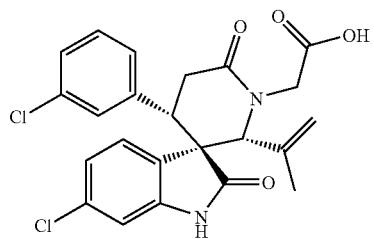

M. W. 459.33 C$_{23}$H$_{22}$Cl$_2$N$_2$O$_4$

In a manner similar to the method described in example 55d, racemic (2'R,3R,4'S)-6-chloro-4'-(3-chlorophenyl)-2'-isopropenyl-2,3-dihydro-1'-[(tert-butoxycarbonyl)methyl]-2,6'-dioxospiro[indole-3,3'-piperidine]-1-methoxyethyl trimethylsilane (2.88 g, 4.46 mmol) prepared in example 116b was reacted with trifluoroacetic acid, then ethyl-diisopropylamine to give racemic (2'R,3R,4'S)-6-chloro-4'-(3-chlorophenyl)-2'-isopropenyl-1'-hydroxycarbonylmethylspiro[3H-indole-3,3'-piperidine]-2,6'(1H)-dione as yellow oil (Yield 1.7 g, 85.8%).

EXAMPLE 116d

Preparation of intermediate racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione

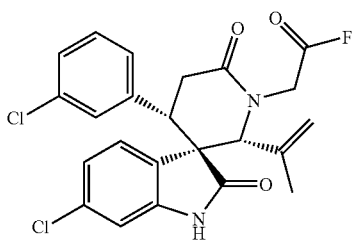

M. W. 461.32 C$_{23}$H$_{19}$Cl$_2$FN$_2$O$_3$

In a manner similar to the method described in example 34a, racemic (2'R,3R,4'S)-6-chloro-4'-(3-chlorophenyl)-2'-isopropenyl-1'-[hydroxycarbonyl-methyl]spiro[3H-indole-3,3'-piperidine]-2,6'(1H)-dione (0.42 g, 0.91 mmol) prepared in example 116c was reacted with cyanuric fluoride (0.31 mL, 2.01 mmol) (Alfa) and pyridine (0.14 g, 1.82 mmol) in dichloromethane to give racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (Yield: 0.38 g, 90%).

EXAMPLE 116e

Preparation of racemic (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione

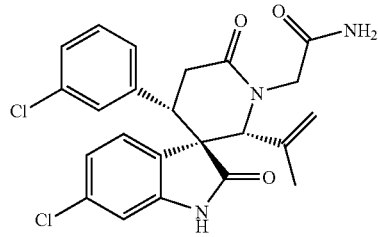

M. W. 458.35 C$_{23}$H$_{21}$Cl$_2$N$_3$O$_3$

To a solution of ammonia (2 M, 10 mL) in methanol was added racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (0.18 g, 0.39 mmol) prepared in example 116d. The reaction mixture was stirred at room temperature for overnight. The solvent was removed and the residue was partitioned between ethyl acetate and water. The organic layer was separated, combined and concentrated. The residue was purified with chromatography (MeOH:EtOAc=5:95) to give racemic (2'R,3R,4'S)-1'-(aminocarbonyl-methyl)-6-chloro-4'-(3-chlorophenyl)-2'-isopropenyl-spiro[3H-indole-3,3'-piperidine]-2,6'(1H)-dione as a white solid (Yield: 70 mg, 38.9%).

HRMS (ES$^+$) m/z Calcd for $C_{23}H_{21}Cl_2N_3O_3$+H [(M+H)$^+$]: 458.1033. Found: 458.1033.

EXAMPLE 117

Preparation of racemic (2'R,3R,4'S)-6-chloro-4'-(3-chlorophenyl)-1'-(cyclopropylaminocarbonyl-methyl)-2'-isopropenylspiro[3H-indole-3,3'-piperidine]-2,6'(1H)-dione

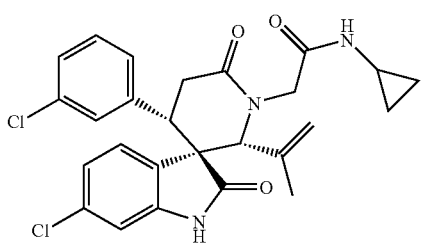

M. W. 498.41 $C_{26}H_{25}Cl_2N_3O_3$

In a manner similar to the method described in example 34b, racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (0.2 g, 0.433 mmol) prepared in example 116d was reacted with 2-amino-2-methyl-propan-1-ol (49 mg, 0.86 mmol), N-methylmorpholine (90 mg, 0.86 mmol) and 4-dimethylaminopyridine (5 mg) in tetrahydrofuran to give racemic (2'R,3R,4'S)-6-chloro-4'-(3-chlorophenyl)-1'-(cyclopropylaminocarbonyl-methyl)-2'-isopropenyl-spiro[3H-indole-3,3'-piperidine]-2,6'(1H)-dione as an off-white solid (Yield: 80 mg, 38%).

HRMS (ES$^+$) m/z Calcd for $C_{26}H_{25}Cl_2N_3O_3$+H [(M+H)$^+$]: 498.1346 Found: 498.1345.

EXAMPLE 118

Preparation of racemic (2'R,3R,4'S)-6-chloro-4'-(3-chlorophenyl)-2'-isopropenyl-1'-[(1-methyl-piperidin-4-yl)aminocarbonyl-methyl]spiro[3H-indole-3,3' piperidine]-2,6'(1H)-dione

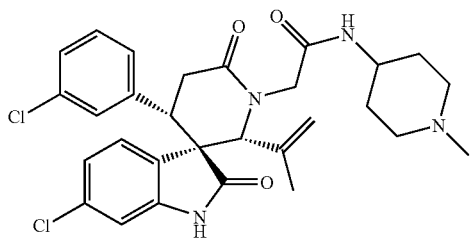

M. W. 555.51 $C_{29}H_{32}Cl_2N_4O_3$

In a manner similar to the method described in example 34b, racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (0.2 g, 0.433 mmol) prepared in example 116d was reacted with 1-methyl-piperidin-4-ylamine (0.134 mg, 0.95 mmol), N-methylmorpholine (99 mg, 0.95 mmol) and 4-dimethylaminopyridine (5 mg) in tetrahydrofuran to give racemic (2'R,3R,4'S)-6-chloro-4'-(3-chlorophenyl)-2'-isopropenyl-1'-[(1-methyl-piperidin-4-yl) aminocarbonyl-methyl]spiro[3H-indole-3,3' piperidine]-2,6' (1H)-dione as an off-white solid (Yield: 75 mg, 31.2%).

HRMS (ES$^+$) m/z Calcd for $C_{29}H_{32}Cl_2N_4O_3$+H [(M+H)$^+$]: 555.1924 Found: 555.1925.

EXAMPLE 119

Preparation of racemic (2'R,3R,4'S)-6-chloro-4'-(3-chlorophenyl)-2'-isopropenyl-1'-[(1-methylsulfonyl-piperidin-4-yl)aminocarbonyl-methyl]spiro[3H-indole-3,3' piperidine]-2,6'(1H)-dione

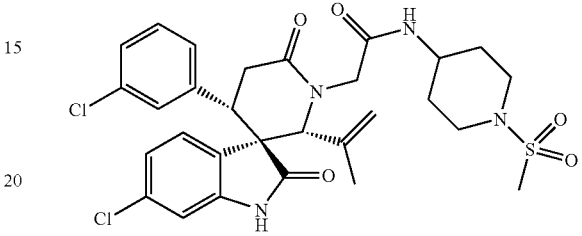

M. W. 619.57 $C_{29}H_{32}Cl_2N_4O_5S$

In a manner similar to the method described in example 34b, racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (0.2 g, 0.433 mmol) prepared in example 116d was reacted with 1-methylsulfonyl-piperidin-4-yl-amine (0.15 g, 0.86 mmol), N-methylmorpholine (90 mg, 0.86 mmol) and 4-dimethylaminopyridine (5 mg) in tetrahydrofuran to give racemic (2'R,3R,4'S)-6-chloro-4'-(3-chlorophenyl)-2'-isopropenyl-1'-[(1-methylsulfonyl-piperidin-4-yl)aminocarbonyl-methyl]spiro[3H-indole-3,3' piperidine]-2,6'(1H)-dione as an off-white solid (Yield: 92 mg, 38.3%).

HRMS (ES$^+$) m/z Calcd for $C_{29}H_{32}Cl_2N_4O_5S$+H [(M+H)$^+$]: 619.1543 Found: 619.1541.

EXAMPLE 120

Preparation of racemic (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione

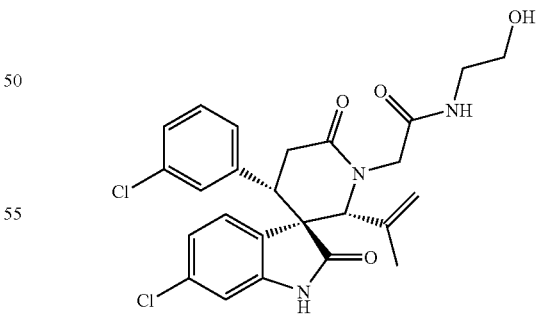

M. W. 502.40 $C_{25}H_{25}Cl_2N_3O_4$

In a manner similar to the method described in example 34b, racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (0.2 g, 0.433 mmol) prepared in example 116d was reacted with 2-amino-ethanol (61 mg, 0.86 mmol), N-methylmorpholine (90 mg, 0.86 mmol) and 4-dimethylaminopyridine (5 mg) in tetrahydrofuran to give racemic (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione as an off-white solid (Yield: 80 mg, 36.8%).

HRMS (ES$^+$) m/z Calcd for $C_{25}H_{25}Cl_2N_3O_4$+H [(M+H)$^+$]: 502.1295 Found: 502.1296.

EXAMPLE 121

Preparation of racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione

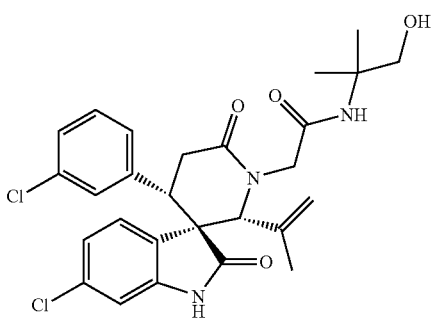

M. W. 530.46 $C_{27}H_{29}Cl_2N_3O_4$

In a manner similar to the method described in example 34b, racemic (2'R,3R,4'S)-6-chloro-4'-(3-chlorophenyl)-1'-fluorocarbonylmethyl-2'-isopropenylspiro[3H-indole-3,3'-piperidine]-2,6'(1H)-dione (0.18 g, 0.39 mmol) prepared in example 116d was reacted with 2-amino-2-methyl-propan-1-ol (69 mg, 0.78 mmol), N-methylmorpholine (81 mg, 0.78 mmol) and 4-dimethylaminopyridine (5 mg) in tetrahydrofuran to give racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione as an off-white solid (Yield: 74 mg, 35.9%).

HRMS (ES$^+$) m/z Calcd for $C_{27}H_{29}Cl_2N_3O_4$+H [(M+H)$^+$]: 502.1295 Found: 502.1296.

EXAMPLE 122a

Preparation of intermediate Z-(6-Chloro-2-oxo-1,2-dihydro-indol-3-ylidene)-(3-chloro-phenyl)-acetonitrile

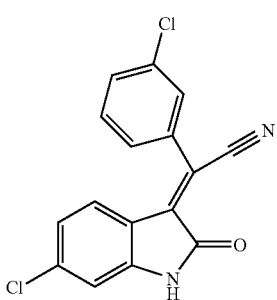

M. W. 315.16 $C_{16}H_8Cl_2N_2O$

To the mixture of 3-chlorobenzyl cyanide (1.8 g, 12 mmol) (Aldrich) and 6-chloroisotin (1.81 g, 10 mmol) (TCI-US) in ethanol (40 mL) was added DBU (1.9 g, 12.5 mmol) (Aldrich). The reaction mixture was heated at 100° C. for 1 h. TCL analysis indicated the formation of mixture of E- and Z-isomers of the desired product and almost complete consumption of starting materials. The mixture was cooled to room temperature, concentrated to a small volume, then diluted with ethyl ether, washed with dilute HCl aqueous solution. The organic layer was separated, dried over $Na_2SO_4$, concentrated, and purified by chromatography (EtOAc:hexanes=1:2) to give the desire Z-(6-Chloro-2-oxo-1,2-dihydro-indol-3-ylidene)-(3-chloro-phenyl)-acetonitrile as an orange solid (0.9 g, 29%). The other isomer E-(6-Chloro-2-oxo-1,2-dihydro-indol-3-ylidene)-(3-chloro-phenyl)-acetonitrile was also obtained as an orange solid (0.9 g, 29%).

EXAMPLE 122b

Preparation of intermediate Z-6-Chloro-3-[(3-chloro-phenyl)-cyano-methylene]-2-oxo-2,3-dihydro-indole-1-carboxylic acid tert-butyl ester

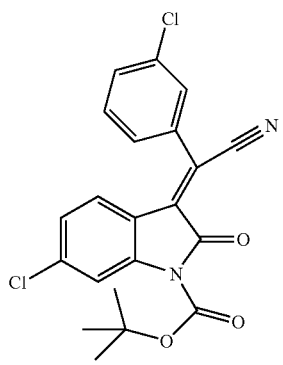

M. W. 415.28 $C_{21}H_{16}Cl_2N_2O_3$

In a manner similar to the method described in example 24a, Z-(6-Chloro-2-oxo-1,2-dihydro-indol-3-ylidene)-(3-chloro-phenyl)-acetonitrile (0.4 g, 1.3 mmol) was reacted with di-tert-butyl-dicarbonate (1.9 g, 8.6 mmol) (Aldrich), triethylamine (0.87 g, 8.6 mmol) and 4-dimethylaminopyridine (5 mg) in dichloromethane (100 mL) to give Z-6-Chloro-3-[(3-chloro-phenyl)-cyano-methylene]-2-oxo-2,3-dihydro-indole-1-carboxylic acid tert-butyl ester as a yellow solid (Yield: 0.3 g, 56%).

EXAMPLE 122c

Preparation of racemic (2'R,3S,4'R)-6-chloro-4'-(3-chloro-phenyl)-4'-cyano-2'-(1-methylene-propyl)spiro[3H-indole-3,3'-piperidine]-2,6'(1H)-dione

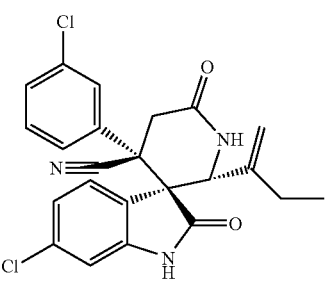

M. W. 440.33 $C_{23}H_{19}Cl_2N_3O_2$

In a manner similar to the method described in example 41b, Z-6-Chloro-3-[(3-chloro-phenyl)-cyano-methylene]-2-oxo-2,3-dihydro-indole-1-carboxylic acid tert-butyl ester prepared in example 122b (0.3 g, 0.72 mmol) was reacted with 1-(1-methylene-propyl)-3-trimethylsilyoxy-2-aza-1,3-butadiene (2 g, 10 mmol) prepared in example 80a in toluene and then trifluoroacetic acid (10 mL) in dichloromethane to give racemic (2'R,3S,4'R)-6-chloro-4'-(3-chloro-phenyl)-4'- cyano-2'-(1-methylene-propyl)spiro[3H-indole-3,3'-piperidine]-2,6'(1H)-dione as a off white solid (0.1 g, 31%).

HRMS (ES⁺) m/z Calcd for $C_{23}H_{19}Cl_2N_3O_2$+H [(M+H)⁺]: 440.0927. Found: 440.0927.

EXAMPLE 123a

Preparation of intermediate racemic (2'R,3R,4'S)-6-chloro-4'-(3-chloro-phenyl)-1'-(3-chloro-propyl)-2'-isopropenyl-2,3-dihydro-2,6'-dioxospiro[indole-3,3'-piperidine]-1-methoxyethyl trimethylsilane

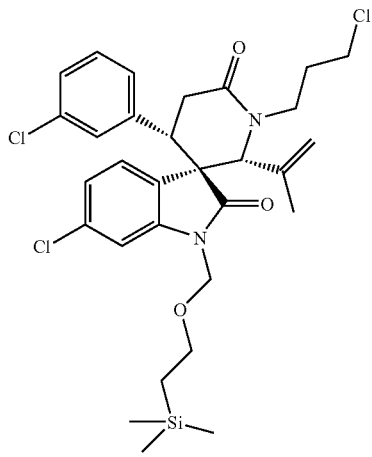

M. W. 608.09 $C_{30}H_{37}Cl_3N_2O_3Si$

In a manner similar to the method described in example 24c, racemic (2'R,3R,4'S)-6-chloro-4'-(3-chloro-phenyl)-2'-isopropenyl-2,3-dihydro-2,6'-dioxospiro[indole-3,3'-piperidine]-1-methoxyethyl trimethylsilane (1.57 g, 2.95 mmol) prepared in example 116a was reacted with LiH (2.3 g, 29.5 mmol) and 1-chloro-3-iodo-propane (6.04 g, 29.5 mmol) in N,N-dimethyl-formamide (100 mL) to give racemic (2'R,3R,4'S)-6-chloro-4'-(3-chloro-phenyl)-1'-(3-chloro-propyl)-2'-isopropenyl-2,3-dihydro-2,6'-dioxospiro[indole-3,3'-piperidine]-1-methoxyethyl trimethylsilane as a white form (Yield: 0.6 g, 33.5%).

EXAMPLE 123b

Preparation of racemic (2'R,3R,4'S)-1'-[3-(4-acetylamino-piperidin-1-yl)-propyl]-6-chloro-4'-(3-chlorophenyl)-2'-isopropenylspiro[3H-indole-3,3' piperidine]-2,6'(1H)-dione

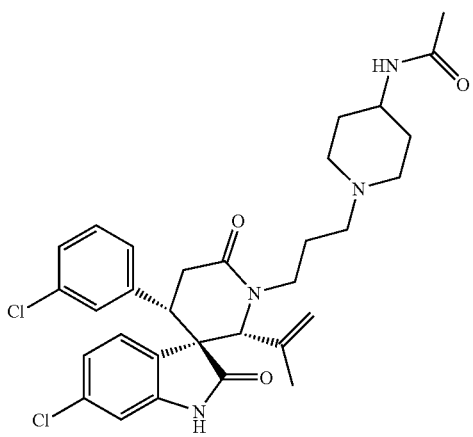

M. W. 583.56 $C_{31}H_{36}Cl_2N_4O_3$

In a manner similar to the method described in example 60b, (2'R,3R,4'S)-6-chloro-4'-(3-chloro-phenyl)-1'-(3-chloro-propyl)-2'-isopropenyl-2,3-dihydro-2,6'-dioxospiro[indole-3,3'-piperidine]-1-methoxyethyl trimethylsilane prepared in example 123a (0.12 g, 0.20 mmol) was reacted with N-piperidin-4-yl-acetamide (0.56 g, 4 mmol), trifluoroacetic acid (2 mL) and then N,N'-diisopropylethylamine (2 mL) to give racemic (2'R,3R,4'S)-1'-[3-(4-acetylamino-piperidin-1-yl)-propyl]-6-chloro-4'-(3-chlorophenyl)-2'-isopropenyl-spiro[3H-indole-3,3' piperidine]-2,6'(1H)-dione as a brown solid (Yield: 47 mg, 40.8%).

HRMS (ES⁺) m/z Calcd for $C_{31}H_{36}Cl_2N_4O_3$+H [(M+H)⁺]: 583.2237 Found: 583.2239.

EXAMPLE 124a

Preparation of intermediate E/Z-6-chloro-3-(3-chloro-benzylidene)-1,3-dihydro-indol-2-one

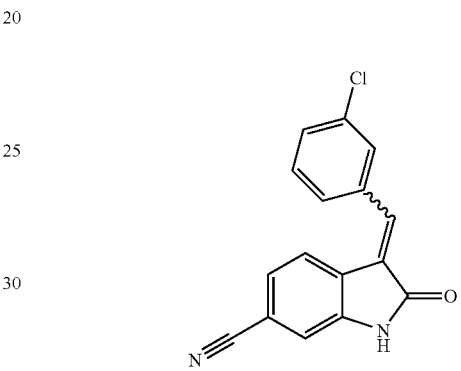

M. W. 280.72 $C_{16}H_9ClN_2O$

In a manner similar to the method described in example 1a, 6-cyanooxindole (1 g, 6.44 mmol) (Combi-blocks) was reacted with 3-chloro-benzaldehyde (0.73 mL, 6.44 mmol) (Aldrich) and piperidine (0.635 mL, 6.44 mmol) in methanol to give a mixture of E- and Z-6-cyano-3-(3-chloro-benzylidene)-1,3-dihydro-indol-2-one as a brown solid (Yield: 1.34 g, 74.4%).

EXAMPLE 124b

Preparation of intermediate E/Z-6-cyano-3-(3-chloro-benzylidene)-2-oxo-2,3-dihydro-indole-1-carboxylic acid tert-butyl ester

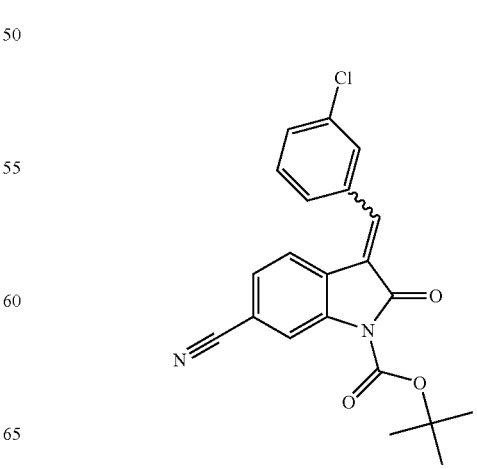

M. W. 380.83 $C_{21}H_{17}ClN_2O_3$

In a manner similar to the method described in example 24a, E/Z-6-chloro-3-(3-chloro-benzylidene)-1,3-dihydro-indol-2-one (1.34 g, 4.77 mmol) was reacted with di-tert-butyl-dicarbonate (1.91 g, 8.73 mmol) (Aldrich), triethylamine (3.29 mL, 23.6 mmol) and 4-dimethylaminopyridine (25 mg) in dichloromethane (100 mL) to give E/Z-6-cyano-3-(3-chloro-benzylidene)-2-oxo-2,3-dihydro-indole-1-carboxylic acid tert-butyl ester as a yellow solid (Yield: 1.7 g, 93.4%).

EXAMPLE 124c

Preparation of racemic (2'R,3R,4'S)-4'-(3-chloro-phenyl)-6'-cyano-2'-(1-methylene-propyl)spiro[3H-indole-3,3'-piperidine]-2,6'(1H)-dione

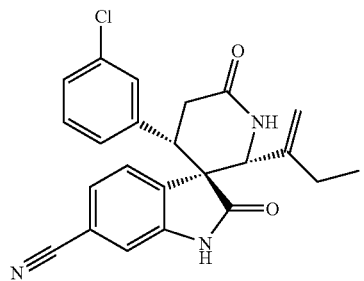

M. W. 405.89 $C_{23}H_{20}ClN_3O_2$

In a manner similar to the method described in example 41b, E/Z-6-cyano-3-(3-chloro-benzylidene)-2-oxo-2,3-dihydro-indole-1-carboxylic acid tert-butyl ester prepared in example 124b (0.4 g, 1.05 mmol) was reacted with 1-(1-methylene-propyl)-3-trimethylsilyoxy-2-aza-1,3-butadiene prepared in example 80a in toluene and then trifluoroacetic acid (20 mL) in dichloromethane to give racemic (2'R,3R,4'S)-4'-(3-chloro-phenyl)-6'-cyano-2'-(1-methylene-propyl)spiro[3H-indole-3,3'-piperidine]-2,6'(1H)-dione as a yellow solid (Yield: 90 mg, 21.1%).

HRMS (ES$^+$) m/z Calcd for $C_{23}H_{20}ClN_3O_2$+H [(M+H)$^+$]: 406.1317 Found: 406.1316.

EXAMPLE 125

Preparation of racemic (2'R,3R,4'S)-4'-(3-chloro-phenyl)-6'-cyano-2'-(5-fluoro-2-methyl-phenyl)spiro[3H-indole-3,3'-piperidine]-2,6'(1H)-dione

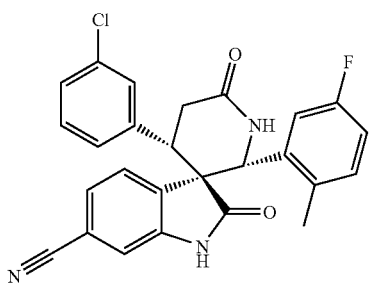

M. W. 459.91 $C_{26}H_{19}ClFN_3O_2$

In a manner similar to the method described in example 41b, E/Z-6-cyano-3-(3-chloro-benzylidene)-2-oxo-2,3-dihydro-indole-1-carboxylic acid tert-butyl ester prepared in example 124b (0.4 g, 1.05 mmol) was reacted with 1-(5-fluoro-2-methyl-phenyl)-3-trimethylsilyoxy-2-aza-1,3-butadiene prepared in example 36a in toluene and then trifluoroacetic acid (20 mL) in dichloromethane to give racemic (2'R,3R,4'S)-4'-(3-chloro-phenyl)-6'-cyano-2'-(5-fluoro-2-methyl-phenyl)spiro[3H-indole-3,3'-piperidine]-2,6'(1H)-dione as a yellow solid (Yield: 0.12 g, 16.9%).

HRMS (ES$^+$) m/z Calcd for $C_{26}H_{19}ClFN_3O_2$+H [(M+H)$^+$]: 460.1223. Found: 460.1223.

EXAMPLE 126

Preparation of racemic (2'R,3R,4'S)-1'-[3-(4-acetyl-piperazin-1-yl)-propyl]-6-chloro-4'-(3-chlorophenyl)-2'-isopropenylspiro[3H-indole-3,3'-piperidine]-2,6'(1H)-dione

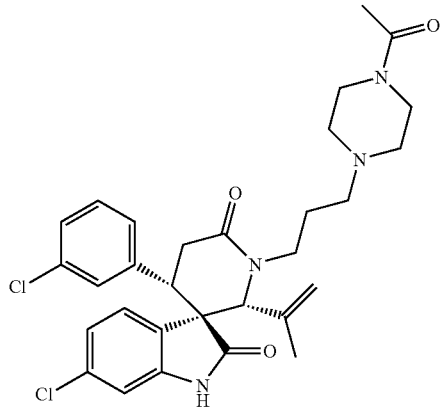

M. W. 569.54 $C_{30}H_{34}Cl_2N_4O_3$

In a manner similar to the method described in example 60b, (2'R,3R,4'S)-6-chloro-4'-(3-chloro-phenyl)-1'-(3-chloro-propyl)-2'-isopropenyl-2,3-dihydro-2,6'-dioxospiro[indole-3,3'-piperidine]-1-methoxyethyl trimethylsilane prepared in example 123a (0.2 g, 0.20 mmol) was reacted with 1-piperazin-1-yl-ethanone (0.51 g, 4 mmol), trifluoroacetic acid (2 mL) and then N,N'-diisopropylethylamine (2 mL) to give racemic (2'R,3R,4'S)-1'-[3-(4-acetyl-piperazin-1-yl)-propyl]-6-chloro-4'-(3-chlorophenyl)-2'-isopropenylspiro[3H-indole-3,3' piperidine]-2,6'(1H)-dione as a yellow solid (Yield: 95 mg, 50.8%).

HRMS (ES$^+$) m/z Calcd for $C_{30}H_{34}Cl_2N_4O_3$+H [(M+H)$^+$]: 569.2081 Found: 569.2079.

EXAMPLE 127

Preparation of racemic (2'R,3R,4'S)-6-chloro-4'-(3-chlorophenyl)-2'-isopropenyl-1'-(3-piperidin-1-yl-propyl)spiro[3H-indole-3,3' piperidine]-2,6'(1H)-dione

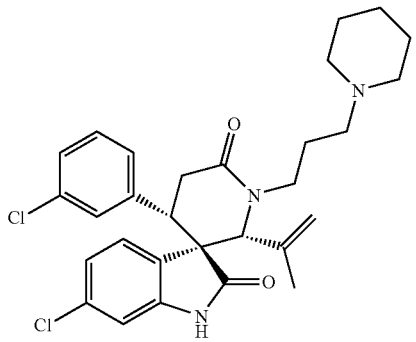

M. W. 526.51 $C_{29}H_{33}Cl_2N_3O_2$

In a manner similar to the method described in example 60b, (2'R,3R,4'S)-6-chloro-4'-(3-chloro-phenyl)-1'-(3-chloro-propyl)-2'-isopropenyl-2,3-dihydro-2,6'-dioxospiro[indole-3,3'-piperidine]-1-methoxyethyl trimethylsilane prepared in example 123a (0.12 g, 0.20 mmol) was reacted with piperidine (2 mL), trifluoroacetic acid (1 mL) and then N,N'-diisopropylethylamine (1.5 mL) to give racemic (2'R,3R,4'S)-6-chloro-4'-(3-chlorophenyl)-2'-isopropenyl-1'-(3-piperidin-1-yl-propyl)spiro[3H-indole-3,3' piperidine]-2,6'(1H)-dione as a yellow solid (Yield: 40 mg, 23.1%).

HRMS (ES$^+$) m/z Calcd for $C_{29}H_{33}Cl_2N_3O_2$+H [(M+H)$^+$]: 526.2023 Found: 526.2020.

EXAMPLE 128a

Preparation of intermediate Acetic acid 2-(2-formyl-4-methyl-phenoxy)-ethyl ester

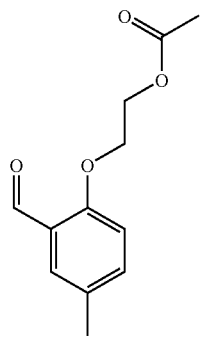

M. W. 222.24 $C_{12}H_{14}O_4$

To a solution of 2-hydroxy-5-methyl-benzaldehyde (2.4 g, 18 mmol) (Aldrich) in N,N-dimethylformamide (30 mL) was added cesium carbonate (6 g, 18 mmol), potassium iodide (3 g, 18 mmol) and 2-bromoethyl acetate (7 g, 42 mmol), Aldrich). The reaction mixture was heated at 100° C. for 3 h. The mixture was cooled to room temperature and diluted with ethyl ether, washed with water, brine, separated, and concentrated. The residue was purified by chromatography (EtOAc: Hexanes=1:6) to give acetic acid 2-(2-formyl-4-methyl-phenoxy)-ethyl ester as a yellow oil (Yield 4 g, 100%).

EXAMPLE 128b

Preparation of intermediate 1-[2-(2-Acetoxy-ethoxy)-5-methyl-phenyl]-3-trimethylsilyoxy-2-aza-1,3-butadiene

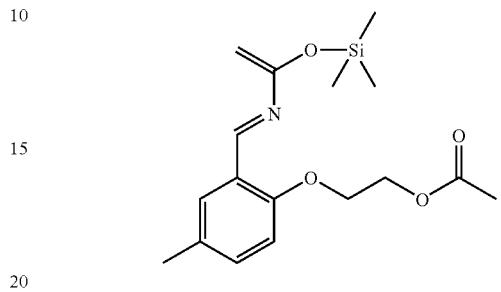

M. W. 335.48 $C_{17}H_{25}NO_4Si$

In a manner similar to the method described in example 1b, acetic acid 2-(2-formyl-4-methyl-phenoxy)-ethyl ester (2.5 g, 11 mmol) prepared in example 128a was reacted with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-[2-(2-acetoxy-ethoxy)-5-methyl-phenyl]-3-trimethylsilyoxy-2-aza-1,3-butadiene as yellow oil and used for the next step without further purification.

EXAMPLE 128c

Preparation of racemic (2'R,3R,4'S)-2'-[2-(2-acetoxy-ethoxy)-5-methyl-phenyl]-6-chloro-4'-(3-chlorophenyl)spiro[3H-indole-3,3'-piperidine]-2,6'(1H)-dione

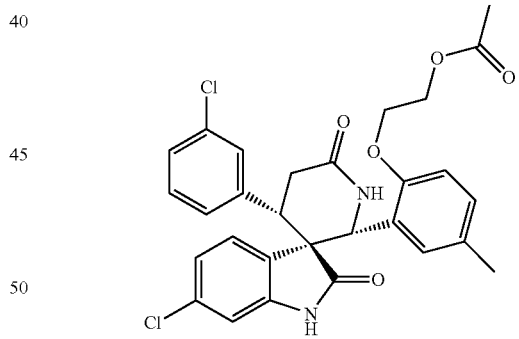

M. W. 553.45 $C_{29}H_{26}Cl_2N_2O_5$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.5 g, 1.28 mmol) was reacted with 1-[2-(2-acetoxy-ethoxy)-5-methyl-phenyl]-3-trimethylsilyoxy-2-aza-1,3-butadiene (2 g, 6 mmol) prepared in example 128b in toluene and then trifluoroacetic acid (10 mL) in dichloromethane to give racemic (2'R,3R,4'S)-2'-[2-(2-acetoxy-ethoxy)-5-methyl-phenyl]-6-chloro-4'-(3-chlorophenyl)spiro[3H-indole-3,3'-piperidine]-2,6'(1H)-dione as a white solid (0.2 g, 28%).

HRMS (ES$^+$) m/z Calcd for $C_{29}H_{26}Cl_2N_2O_5$+H [(M+H)$^+$]: 553.1292. Found: 553.1291.

EXAMPLE 129

Preparation of racemic (2'R,3R,4'S)-6-chloro-4'-(3-chlorophenyl)-2'-[6-(2-hydroxy-ethoxy)-3-methyl-phenyl]spiro[3H-indole-3,3'-piperidine]-2,6'(1H)-dione

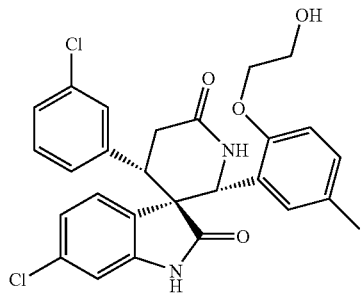

M. W. 511.41 $C_{27}H_{24}Cl_2N_2O_4$

To a solution of racemic (2'R,3R,4'S)-2'-[2-(2-acetoxy-ethoxy)-5-methyl-phenyl]-6-chloro-4'-(3-chlorophenyl)spiro[3H-indole-3,3'-piperidine]-2,6'(1H)-dione (0.16 g, 0.29 mmol) prepared in example 128c in tetrahydrofuran (30 mL) and methanol (10 mL) was added sodium hydroxide aqueous solution (1N, 10 mL). the reaction mixture was stirred at room temperature for 3 h, then neutralized to "pH" 7 by aqueous HCl. The mixture was then extracted with ethyl acetate. The organic layer was separated, concentrated, and purified by chromatography (EtOAc:MeOH=19:1) to give racemic (2'R,3R,4'S)-6-chloro-4'-(3-chlorophenyl)-2'-[2-(2-hydroxy-ethoxy)-5-methyl-phenyl]spiro[3H-indole-3,3'-piperidine]-2,6'(1H)-dione as a white solid (70 mg, 47%)

HRMS (ES$^+$) m/z Calcd for $C_{27}H_{24}Cl_2N_2O_4$+H [(M+H)$^+$]: 511.1186. Found: 511.1185.

EXAMPLE 130a

Preparation of intermediate 5-bromo-2-[2-(tert-butyl-dimethyl-silanyloxy)-ethoxy]-benzaldehyde

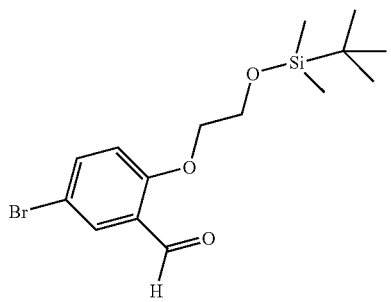

M. W. 359.34 $C_{15}H_{23}BrO_2Si$

To a solution of 5-bromo-2-hydroxy-benzaldehyde (14 g, 69.6 mmol) (Aldrich) in N,N-dimethylformamide (300 mL) was added $K_2CO_3$ (29 g, 208.9 mmol) and (2-bromo-ethoxy)-tert-butyl-dimethyl-silane (20 g, 83.5 mmol) (Aldrich). The reaction mixture was stirred at 60° C. for 16 h. The reaction mixture was cooled to room temperature and poured into water, extracted with ethyl acetate. The organic layers were combined, washed with water, brine, dried over $MgSO_4$, filtered and concentrated to give 5-bromo-2-[2-(tert-butyl-dimethyl-silanyloxy)-ethoxy]-benzaldehyde as brown oil (Yield: 25 g, 100%).

EXAMPLE 130b

Preparation of intermediate 2-[2-(tert-butyl-dimethyl-silanyloxy)-ethoxy]-5-cyclopropyl-benzaldehyde

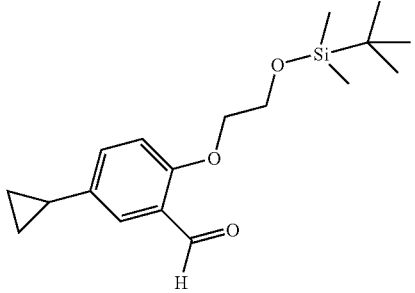

M. W. 320.51 $C_{18}H_{28}O_3Si$

To a solution of 5-bromo-2-[2-(tert-butyl-dimethyl-silanyloxy)-ethoxy]-benzaldehyde (5 g, 13.9 mmol) prepared in example 130a in toluene (75 mL) and water (7.5 mL) was added cyclopropylboronic acid (1.7 g, 19.8 mmol) (Aldrich) and potassium phosphate (14.6 g, 68.9 mmol). After the reaction mixture was degassed for 5 min, dichloro-bis-(tricyclohexyl-phosphine) (1.03 g, 1.39 mmol) (Strem) was added and the reaction mixture was heated at 100° C. under nitrogen for 4 h. The reaction mixture was cooled to room temperature and diluted with water, extracted with ethyl acetate. The organic layers were combined, washed with water, brine, dried over $MgSO_4$, filtered and concentrated. The residue was purified with chromatography to give 2-[2-(tert-butyl-dimethyl-silanyloxy)-ethoxy]-5-cyclopropyl-benzaldehyde as yellow oil (Yield: 3.2 g, 76.2%).

EXAMPLE 130c

Preparation of intermediate 1-{2-[2-(tert-butyl-dimethyl-silanyloxy)-ethoxy]-5-cyclopropyl-phenyl}-3-trimethylsilyoxy-2-aza-1,3-butadiene

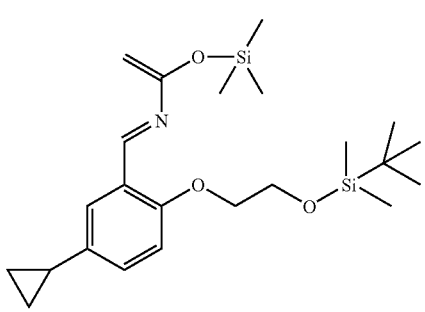

M. W. 433.74 $C_{23}H_{39}NO_3Si_2$

In a manner similar to the method described in example 1b, 2-[2-(tert-butyl-dimethyl-silanyloxy)-ethoxy]-5-cyclopropyl-benzaldehyde (3.36 g, 10.5 mmol) prepared in example 130b was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-{2-[2-(tert-butyl-dimethyl-silanyloxy)-ethoxy]-5-cyclopropyl-phenyl}-3-trimethylsilyoxy-2-aza-1,3-butadiene as a yellow gum and used for the next step without further purification.

EXAMPLE 130d

Preparation of racemic (2'R,3R,4'S)-6-chloro-4'-(3-chlorophenyl)-2'-[5-cyclopropyl-2-(2-hydroxy-ethoxy)-phenyl]spiro[3H-indole-3,3'-piperidine]-2,6'(1H)-dione

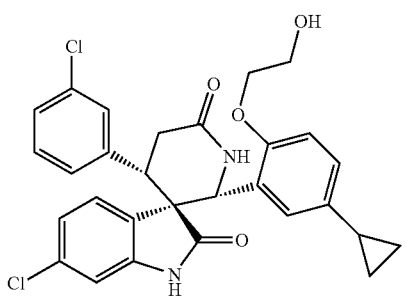

M. W. 537.45 $C_{29}H_{26}Cl_2N_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.5 g, 1.28 mmol) was reacted with 1-{2-[2-(tert-butyl-dimethyl-silanyloxy)-ethoxy]-5-cyclopropyl-phenyl}-3-trimethylsilyoxy-2-aza-1,3-butadiene prepared in example 130c in toluene and then trifluoroacetic acid (20 mL) in dichloromethane to give racemic (2'R,3R,4'S)-6-chloro-4'-(3-chlorophenyl)-2'-[5-cyclopropyl-2-(2-hydroxy-ethoxy)-phenyl]spiro[3H-indole-3,3'-piperidine]-2,6'(1H)-dione as a white solid (0.14 g, 20.3%).

HRMS (ES$^+$) m/z Calcd for $C_{29}H_{26}Cl_2N_2O_4$+H [(M+H)$^+$]: 537.1343 Found: 537.1343.

EXAMPLE 131a

Preparation of intermediate 2-[2-(tert-Butyl-dimethyl-silanyloxy)-ethoxy]-5-chloro-benzaldehyde

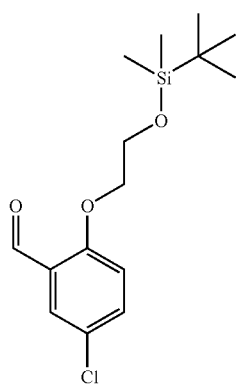

M. W. 314.89 $C_{15}H_{23}ClO_3Si$

To a solution of 5-chlorosalicylaldehyde (5 g, 32 mmol) (Aldrich) in N,N-dimethylformamide (40 mL) was added potassium carbonate (20 g, 145 mmol), and (2-bromo-ethoxy)-tert-butyl-dimethyl-silane (10 g, 42 mmol, Aldrich). The reaction mixture was heated at 60° C. for 18 h. The crude was cooled to room temperature, diluted with ethyl acetate, washed with water, brine. The organic layer was separated, concentrated, and the residue was purified by chromatography (EtOAc:Hexanes=1:8, then 1:4) to give 2-[2-(tert-butyl-dimethyl-silanyloxy)-ethoxy]-5-chloro-benzaldehyde as a white solid (Yield 10 g, 99%).

EXAMPLE 131b

Preparation of intermediate 1-[2-(tert-butyl-dimethyl-silanyloxy)-ethoxy]-5-chloro-phenyl]-3-trimethylsilyoxy-2-aza-1,3-butadiene

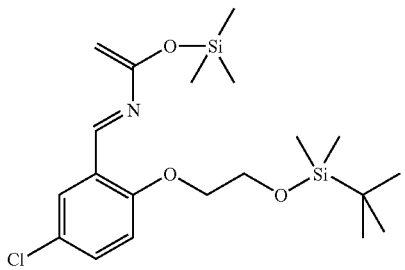

M. W. 428.12 $C_{20}H_{34}ClNO_3Si_2$

In a manner similar to the method described in example 1b, 2-[2-(tert-butyl-dimethyl-silanyloxy)-ethoxy]-5-chloro-benzaldehyde (5.2 g, 17 mmol) prepared in example 131a was reacted with 1,1,1,3,3,3-hexamethyldisilazane (2.4 g, 15 mmol), n-butyllithium (2.5 M, 6 mL, 15 mmol), trimethylsilyl chloride (1.6 g, 15 mmol), triethylamine (1.6 g, 20 mmol) and acetyl chloride (1.5 g, 20 mmol) to give 1-[2-(tert-butyl-dimethyl-silanyloxy)-ethoxy]-5-chloro-phenyl]-3-trimethylsilyoxy-2-aza-1,3-butadiene as yellow oil and used for the next step without further purification.

EXAMPLE 131c

Preparation of racemic (2'R,3R,4'S)-6-chloro-2'-[5-chloro-2-(2-hydroxy-ethoxy)-phenyl]-4'-(3-chlorophenyl)spiro[3H-indole-3,3'-piperidine]-2,6'(1H)-dione

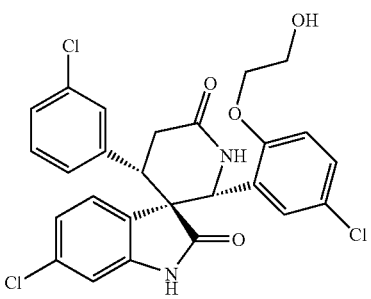

M. W. 531.83 $C_{26}H_{21}Cl_3N_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.6 g, 1.5 mmol) was reacted with 1-[2-(tert-butyl-dimethyl-silanyloxy)-ethoxy]-5-chloro-phenyl]-3-trimethylsilyoxy-2-aza-1,3-butadiene (5.2 g, 12 mmol) prepared in example 131b in toluene and then trifluoroacetic acid (10 mL) in dichloromethane to give racemic (2'R,3R,4'S)-6-chloro-2'-[5-chloro-2-(2-hydroxy-ethoxy)-phenyl]-4'-(3-chlorophenyl)spiro[3H-indole-3,3'-piperidine]-2,6'(1H)-dione as a white solid (0.25 g, 31%).

HRMS (ES$^+$) m/z Calcd for $C_{26}H_{21}Cl_3N_2O_4$+H [(M+H)$^+$]: 531.0640. Found: 531.0640.

EXAMPLE 132a

Preparation of intermediate tert-Butyl-[2-(4-chloro-3-fluoro-phenoxy)-ethoxy]-dimethyl-silane

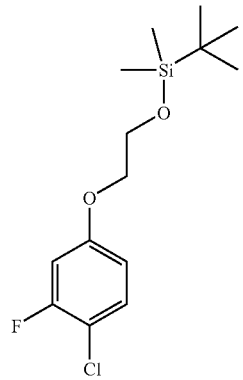

M. W. 304.87 $C_{14}H_{22}ClFO_2Si$

To a solution of 4-chloro-3-fluoro-phenol (10 g, 68 mmol) in N,N-dimethylformamide (50 mL) was added potassium carbonate (19 g, 136 mmol), potassium iodide (11 g, 68 mmol), and (2-bromo-ethoxy)-tert-butyl-dimethyl-silane (18 g, 75 mmol, Aldrich). The reaction mixture was heated at 100° C. for 24 h. The crude was cooled, diluted with ethyl ether, washed with water, NaHCO$_3$ solution, and brine. The organic layer was separated, dried over Na$_2$SO$_4$, and concentrated. The filtrate was concentrated and the residue was purified by chromatography (EtOAc:Hexanes=1:20) to give tert-butyl-[2-(4-chloro-3-fluoro-phenoxy)-ethoxy]-dimethyl-silane as colorless oil (Yield 14 g, 69%).

EXAMPLE 132b

Preparation of intermediate 6-[2-(tert-Butyl-dimethyl-silanyloxy)-ethoxy]-3-chloro-2-fluoro-benzaldehyde

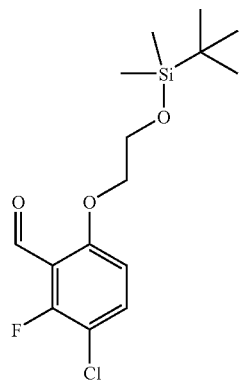

M. W. 332.88 $C_{15}H_{22}ClFO_2Si$

In a manner similar to the method described in example 52a, tert-butyl-[2-(4-chloro-3-fluoro-phenoxy)-ethoxy]-dimethyl-silane (14.3 g, 47 mmol) prepared in example 132a was reacted with lithium diisopropylamine (34 mL, 1.8 M in THF, 61 mmol), N,N-dimethyl-formamide (4.7 mL, 61 mmol) and quenched with acetic acid (14 g, 234 mmol) in tetrahydrofuran to give 6-[2-(tert-butyl-dimethyl-silanyloxy)-ethoxy]-3-chloro-2-fluoro-benzaldehyde as a white solid (Yield: 6.4 g, 41%).

EXAMPLE 132c

Preparation of intermediate 1-[2-(tert-butyl-dimethyl-silanyloxy)-ethoxy-3-chloro-2-fluoro-phenyl]-3-trimethylsilyoxy-2-aza-1,3-butadiene

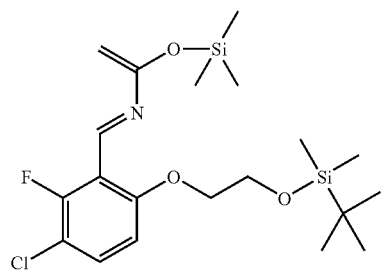

M. W. 446.11 $C_{20}H_{33}Cl_fFNO_3Si_2$

In a manner similar to the method described in example 1b, 6-[2-(tert-butyl-dimethyl-silanyloxy)-ethoxy]-3-chloro-2-fluoro-benzaldehyde (3.3 g, 10 mmol) prepared in example 132b was reacted with 1,1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.4 g, 13 mmol) and acetyl chloride (1.0 g, 13 mmol) to give 1-[2-(tert-butyl-dimethyl-silanyloxy)-ethoxy-3-chloro-2-fluoro-phenyl]-3-trimethylsilyoxy-2-aza-1,3-butadiene as an orange oil and used for the next step without further purification.

EXAMPLE 132d

Preparation of racemic (2'R,3R,4'S)-6-chloro-2'-[3-chloro-2-fluoro-6-(2-hydroxy-ethoxy)-phenyl]-4'-(3-chlorophenyl)spiro[3H-indole-3,3'-piperidine]-2,6'(1H)-dione

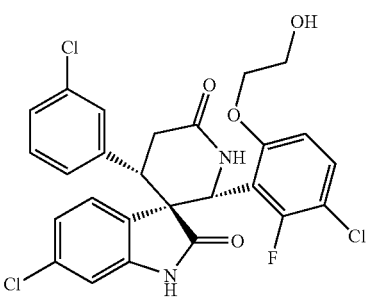

M. W. 549.82 $C_{26}H_{20}Cl_3FN_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.5 g, 1.28 mmol) was reacted with 1-[2-(tert-butyl-dimethyl-silanyloxy)-ethoxy-phenyl]-3-trimethylsilyoxy-2-aza-1,3-butadiene (3 g, 6.7 mmol) prepared in example 132c in toluene and then trifluoroacetic acid (10 mL) in dichloromethane to give racemic (2'R,3R,4'S)-6-chloro-2'-[3-chloro-2-fluoro-6-(2-hydroxy-ethoxy)-phenyl]-4'-(3-chlorophenyl)spiro[3H-indole-3,3'-piperidine]-2,6'(1H)-dione as a white solid (0.28 g, 40%).

HRMS (ES$^+$) m/z Calcd for $C_{26}H_{20}Cl_3FN_2O_4$+H [(M+H)$^+$]: 549.0546 Found: 549.0545.

EXAMPLE 133a

Preparation of intermediate E/Z-6-Chloro-3-(3,5-difluoro-benzylidene)-1-(2-trimethylsilanyl-ethoxymethyl)-1,3-dihydro-indol-2-one

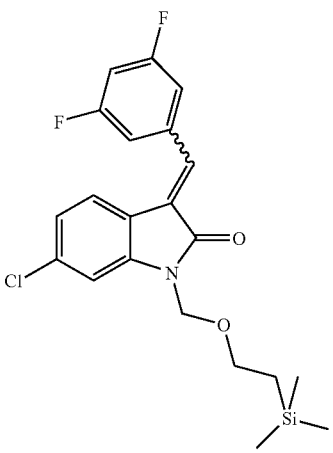

M. W. 421.95 $C_{21}H_{22}ClF_2NO_2Si$

In a manner similar to the methods described in example 4a, 55a, 3,5-difluoro-benzaldehyde (0.89 g, 6.27 mmol) in place of 3-chlorobenzaldehyde was reacted in two steps to give E/Z-6-Chloro-3-(3,5-difluoro-benzylidene)-1-(2-trimethylsilanyl-ethoxymethyl)-1,3-dihydro-indol-2-one as a yellow oil (1.25 g, 50% for two steps).

EXAMPLE 133b

Preparation of racemic (2'R,3R,4'S)-6-chloro-4'-(3,5-difluoro-phenyl)-2'-(1-methylene-propyl)spiro[3H-indole-3,3'-piperidine]-2,6'(1H)-dione

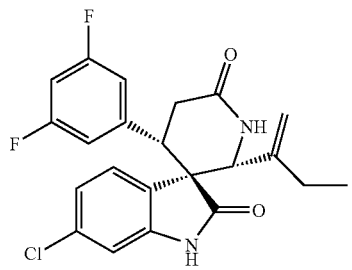

M. W. 416.86 $C_{22}H_{19}ClF_2N_2O_2$

In a manner similar to the method described in example 97a, 55d, E/Z-6-Chloro-3-(3,5-difluoro-benzylidene)-1-(2-trimethylsilanyl-ethoxymethyl)-1,3-dihydro-indol-2-one (0.21 g, 0.5 mmol) prepared in example 133a was reacted with 1-(1-methylene-propyl)-3-trimethylsilyoxy-2-aza-1,3-butadiene (1 g, 5.25 mmol) prepared in example 80a in toluene, then treated with trifluoroacetic acid (5 ml) in dichloromethane, followed by treatment with diisopropylethylamine (1 mL) in methanol to give racemic (2'R,3R,4'S)-6-chloro-4'-(3-chlorophenyl)-2'-(1-methylene-propyl)spiro[3H-indole-3,3'-piperidine]-2,6'(1H)-dione as a white solid (35 mg, 18% for two steps).

HRMS (ES$^+$) m/z Calcd for $C_{22}H_{19}ClN_2O_2F_2$+H[(M+H)]: 417.1176; Found: 417.1177

EXAMPLE 134a

Preparation of intermediate E/Z-3-(6-Chloro-2-oxo-1,2-dihydro-indol-3-ylidenemethyl)-benzonitrile

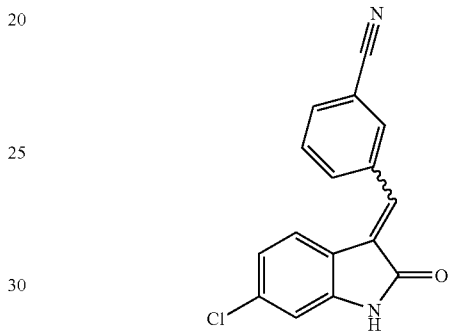

M. W. 280.72 $C_{16}H_9ClN_2O$

In a manner similar to the method described in example 1a, 3-formyl-benzonitrile was used in place of 3-chlorobenzaldehyde to form E/Z-3-(6-Chloro-2-oxo-1,2-dihydro-indol-3-ylidenemethyl)-benzonitrile as a yellow solid.

EXAMPLE 134b

Preparation of racemic (2'R,3R,4'S)-6-chloro-4'-(3-cyano-phenyl)-2'-(1-methylene-propyl)spiro[3H-indole-3,3'-piperidine]-2,6'(1H)-dione

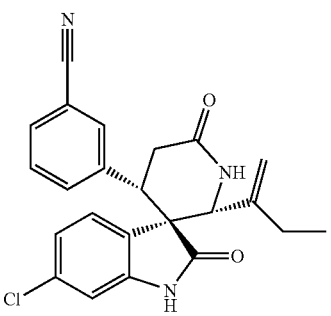

M. W. 405.89 $C_{23}H_{20}ClN_3O_2$

E/Z-3-(6-Chloro-2-oxo-1,2-dihydro-indol-3-ylidenemethyl)-benzonitrile (280 mg, 1 mmol) prepared in example 134a was heated with 1-(1-methylene-propyl)-3-trimethylsilyoxy-2-aza-1,3-butadiene freshly prepared in example 80a (2.06 g, 10.5 mmol) in toluene (20 mL) in a sealed tube at 135° C. for 1 h, then cooled to room temperature. Methanol (80 mL) was added, and the mixture was filtered through a short pad of celite. The filtrate was concentrated, the residue was purified by chromatography (EtOAc) to give racemic (2'R,3R,4'S)-6-chloro-4'-(3-cyano-phenyl)-2'-(1-methylene-propyl)spiro[3H-indole-3,3'-piperidine]-2,6'(1H)-dione as a solid (180 mg, 35%).

HRMS (ES+) m/z Calcd for $C_{23}H_{20}ClN_3O_2$+H [(M+H)]: 406.1317; Found: 406.1315

EXAMPLE 135

Preparation of racemic (2'R,3R,4'S)-4'-(3-Bromo-phenyl)-6-chloro-2'-(1-methylene-propyl)spiro[3H-indole-3,3'-piperidine]-2,6'(1H)-dione

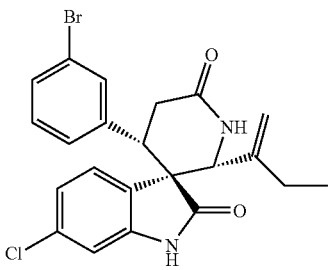

M. W. 459.77 $C_{22}H_{20}BrClN_2O_2$

In a manner similar to the methods described in example 134a, 134b, 3-bromo-benzaldehyde was used in place of 3-formyl-benzonitrile in two steps to give racemic (2'R,3R,4'S)-4'-(3-bromo-phenyl)-6-chloro-2'-(1-methyl ene-propyl)spiro[3H-indole-3,3'-piperidine]-2,6'(1H)-dione as a solid (142 mg).

HRMS (ES+) m/z Calcd for $C_{22}H_{20}BrClN_2O_2$+H [(M+H)]: 459.0470; Found: 459.0469

EXAMPLE 136

Preparation of racemic (2'R,3R,4'S)-6-chloro-4'-(3-methoxy-phenyl)-2'-(1-methylene-propyl)spiro[3H-indole-3,3'-piperidine]-2,6'(1H)-dione

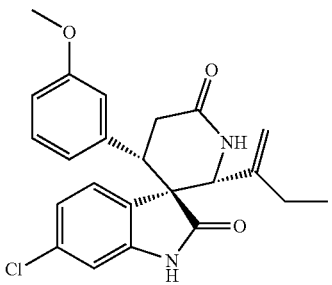

M. W. 410.90 $C_{23}H_{23}ClN_2O_3$

In a manner similar to the methods described in example 134a, 134b, 3-methoxy-benzaldehyde was used in place of 3-formyl-benzonitrile to give racemic (2'R,3R,4'S)-6-chloro-4'-(3-methoxy-phenyl)-2'-(1-methylene-propyl)spiro[3H-indole-3,3'-piperidine]-2,6'(1H)-dione as a solid (20 mg).

HRMS (ES+) m/z Calcd for $C_{23}H_{23}ClN_2O_3$+H[(M+H)]: 433.1289; Found: 433.1288

EXAMPLE 137

Preparation of racemic (2'R,3R,4'S)-6-chloro-4'-(5-fluoro-2-methyl-phenyl)-2'-(1-methylene-propyl) spiro[3H-indole-3,3'-piperidine]-2,6'(1H)-dione

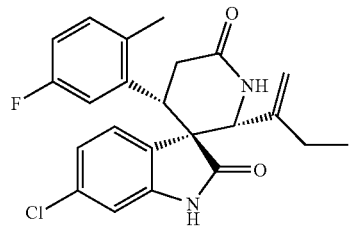

M. W. 412.90 $C_{23}H_{22}ClFN_2O_2$

In a manner similar to the methods described in example 134a, 134b, 5-fluoro-2-methyl-benzaldehyde was used in place of 3-formyl-benzonitrile to give racemic (2'R,3R,4'S)-6-chloro-4'-(5-fluoro-2-methyl-phenyl)-2'-(1-methylene-propyl)spiro[3H-indole-3,3'-piperidine]-2,6'(1H)-dione as a white solid (Yield 100 mg, 15%).

HRMS (ES+) m/z Calcd for $C_{23}H_{22}ClFN_2O_2$+Na [(M+Na)]: 435.1246; Found: 435.1243

EXAMPLE 138

Preparation of racemic (2'R,3R,4'S)-6-chloro-4'-(3-fluoro-phenyl)-2'-(1-methylene-propyl)spiro[3H-indole-3,3'-piperidine]-2,6'(1H)-dione

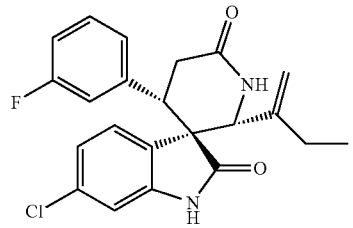

M. W. 398.87 $C_{22}H_{20}ClFN_2O_2$

In a manner similar to the methods described in example 134a, 134b, 3-fluoro-benzaldehyde was used in place of 3-formyl-benzonitrile to give racemic (2'R,3R,4'S)-6-chloro-4'-(3-fluoro-phenyl)-2'-(1-methylene-propyl)spiro[3H-indole-3,3'-piperidine]-2,6'(1H)-dione as a white solid (Yield 100 mg, 17%).

HRMS (ES+) m/z Calcd for $C_{22}H_{20}ClFN_2O_2$+H [(M+H)]: 399.1270; Found: 399.1267

EXAMPLE 139

Preparation of racemic (2'R,3R,4'S)-6-chloro-2'-(1-methylene-propyl)-4'-m-tolylspiro[3H-indole-3,3'-piperidine]-2,6'(1H)-dione

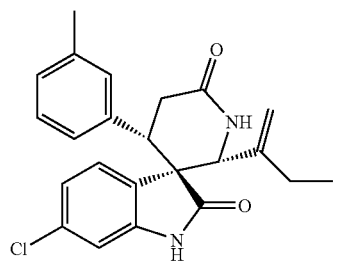

M. W. 394.90 $C_{23}H_{23}ClFN_2O_2$

In a manner similar to the methods described in example 134a, 134b, 3-methyl-benzaldehyde was used in place of 3-formyl-benzonitrile to give racemic (2'R,3R,4'S)-6-chloro-2'-(1-methylene-propyl)-4'-m-tolylspiro[3H-indole-3,3'-piperidine]-2,6'(1H)-dione as a white solid (Yield 130 mg, 33%).

HRMS (ES$^+$) m/z Calcd for $C_{23}H_{23}ClFN_2O_2$+H [(M+H)]: 395.1521; Found: 395.1521

EXAMPLE 140

Preparation of racemic (2'R,3R,4'S)-6-chloro-2'-(1-methylene-propyl)-4'-o-tolylspiro[3H-indole-3,3'-piperidine]-2,6'(1H)-dione

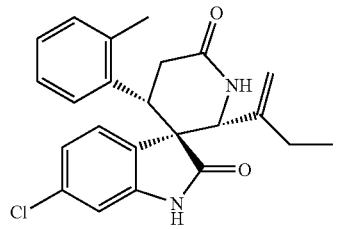

M. W. 394.90 $C_{23}H_{23}ClFN_2O_2$

In a manner similar to the methods described in example 134a, 134b, 2-methyl-benzaldehyde was used in place of 3-formyl-benzonitrile to give racemic (2'R,3R,4'S)-6-chloro-2'-(1-methylene-propyl)-4'-o-tolylspiro[3H-indole-3,3'-piperidine]-2,6'(1H)-dione as a white solid (Yield 55 mg, 14%).

HRMS (ES$^+$) m/z Calcd for $C_{23}H_{23}ClFN_2O_2$+H[(M+H)]: 395.1521; Found: 395.1521

EXAMPLE 141

Preparation of racemic (2'R,3R,4'R)-6-chloro-2'-(1-methylene-propyl)-4'-thiophen-3-ylspiro[3H-indole-3,3'-piperidine]-2,6'(1H)-dione

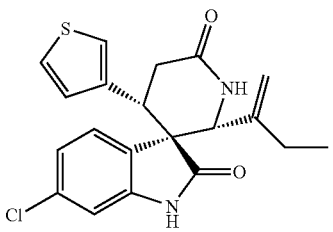

M. W. 386.90 $C_{20}H_{19}ClN_2O_2S$

In a manner similar to the methods described in example 134a, 134b, thiophene-3-carbaldehyde was used in place of 3-formyl-benzonitrile to give racemic (2'R,3R,4'S)-6-chloro-2'-(1-methylene-propyl)-4'-thiophen-3-ylspiro[3H-indole-3,3'-piperidine]-2,6'(1H)-dione as a white solid (Yield 74 mg, 19%).

HRMS (ES$^+$) m/z Calcd for $C_{20}H_{19}ClN_2O_2S$+H[(M+H)]: 387.0929; Found: 387.0929

EXAMPLE 142

Preparation of racemic (2'R,3R,4'S)-6-chloro-4'-(3,5-dichloro-phenyl)-2'-(1-methylene-propyl)spiro[3H-indole-3,3'-piperidine]-2,6'(1H)-dione

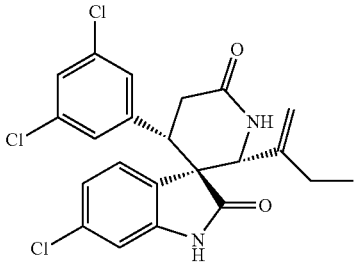

M. W. 449.77 $C_{22}H_{19}Cl_3N_2O_2$

In a manner similar to the methods described in example 134a, 134b, 3,5-dichloro-benzaldehyde was used in place of 3-formyl-benzonitrile to give racemic (2'R,3R,4'S)-6-chloro-4'-(3,5-dichloro-phenyl)-2'-(1-methylene-propyl)spiro[3H-indole-3,3'-piperidine]-2,6'(1H)-dione as a white solid (Yield 50 mg, 11%).

HRMS (ES$^+$) m/z Calcd for $C_{22}H_{19}Cl_3N_2O_2$+H [(M+H)]: 449.0585; Found: 449.0585

EXAMPLE 143

Preparation of racemic (2'R,3R,4'S)-6-chloro-4'-(5-chloro-2-trifluoromethyl-phenyl)-2'-(1-methylene-propyl)spiro[3H-indole-3,3'-piperidine]-2,6'(1H)-dione

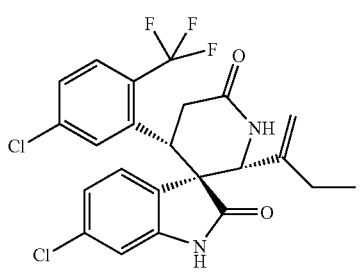

M. W. 483.32 $C_{23}H_{19}Cl_2F_3N_2O_2$

In a manner similar to the methods described in example 134a, 134b, 5-chloro-2-trifluoromethyl-benzaldehyde was used in place of 3-formyl-benzonitrile to give racemic (2'R, 3R,4'S)-6-chloro-4'-(5-chloro-2-trifluoromethyl-phenyl)-2'-(1-methylene-propyl)spiro[3H-indole-3,3'-piperidine]-2,6'(1H)-dione as a white solid (Yield 50 mg, 10%).

HRMS (ES$^+$) m/z Calcd for $C_{23}H_{19}Cl_2F_3N_2O_2$+H[(M+H)]: 483.0849; Found: 483.0848

EXAMPLE 144

Preparation of racemic (2'R,3R,4'S)-4'-(3-Bromo-phenyl)-6-chloro-2'-isopropenylspiro[3H-indole-3,3'-piperidine]-2,6'(1H)-dione

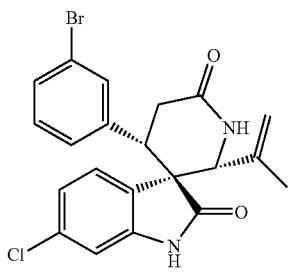

M. W. 445.75 $C_{21}H_{18}BrClN_2O_2$

In a manner similar to the method described in example 197, 1-isopropenyl-3-trimethylsilyoxy-2-aza-1,3-butadiene freshly prepared in example 142a was used in place of 1-(1-methylene-propyl)-3-trimethylsilyoxy-2-aza-1,3-butadiene prepared in example 135a to give racemic (2'R,3R,4'S)-4'-(3-bromo-phenyl)-6-chloro-2'-isopropenylspiro[3H-indole-3, 3'-piperidine]-2,6'(1H)-dione as a white solid (Yield 21 mg).

HRMS (ES$^+$) m/z Calcd for $C_{21}H_{18}BrClN_2O_2$+H [(M+H)]: 445.0313; Found: 445.0313

EXAMPLE 145a

Preparation of intermediate E/Z-6-chloro-3-(5-fluoro-2-methyl-benzylidene)-1,3-dihydro-indol-2-one

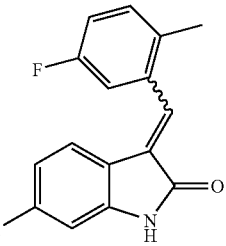

M. W. 287.72 $C_{16}H_{11}ClFNO$

To the mixture of 6-chlorooxindole (3.6 g, 21.6 mmol) and 5-Fluoro-2-methyl-benzaldehyde (3.0 g, 21.6 mmol) in methanol (25 mL) was added pyrrolidine (1.53 g, 21.6 mmol) dropwise. The mixture was then heated at 70° C. for 3 h. After cooled to 4° C., the mixture was filtered and resulting precipitate was collected, dried to give E/Z-6-chloro-3-(3-chloro-benzylidene)-1,3-dihydro-indol-2-one as a bright yellow solid (Yield 5.3 g, 85%).

EXAMPLE 145b

Preparation of intermediate E/Z-6-chloro-3-(5-fluoro-2-methyl-benzylidene)-2-oxo-2,3-dihydro-indole-1-carboxylic acid ethyl ester

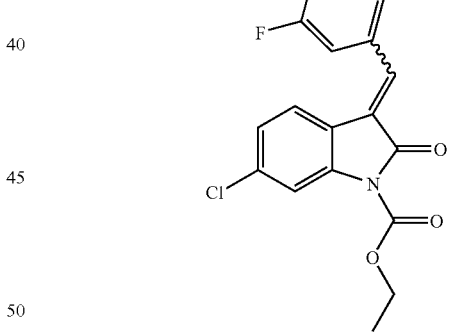

M. W. 359.79 $C_{19}H_{15}ClFNO_3$

To a solution of E/Z-6-chloro-3-(5-fluoro-2-methyl-benzylidene)-1,3-dihydro-indol-2-one prepared in example 145a (0.20 g, 0.71 mmol) in dichloromethane (3 mL) at 0° C. was added ethyl chloroformate (0.10 mL, 1.1 mmol), followed by the addition of triethylamine (0.14 g, 1.4 mmol). The reaction mixture was stirred at 0° C. for 30 minutes. The mixture was then poured into aqueous HCl solution (1 N). The organic layer was separated and the aqueous layer was extracted with ethyl acetate. The organic layers were combined and dried over Na$_2$SO$_4$, and concentrated to give E/Z-6-chloro-3-(5-fluoro-2-methyl-benzylidene)-2-oxo-2,3-dihydro-indole-1-carboxylic acid ethyl ester as a yellow solid. The crude product was purified by chromatography to obtain 75 mg yellow solid (Yield 1.7 g, 30%).

EXAMPLE 145c

Preparation of intermediate racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-carboxylic acid ethyl ester

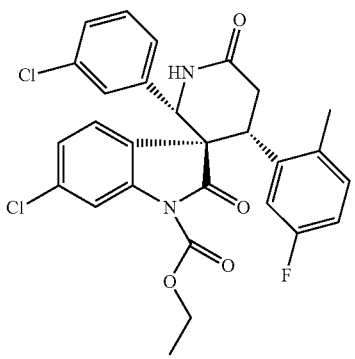

M. W. 541.41 C$_{28}$H$_{23}$Cl$_2$FN$_2$O$_4$

To a toluene (15 ml) solution of 1-(3-chlorophenyl)-3-trimethylsilyoxy-2-aza-1,3-butadiene prepared in example 1b in toluene (30 ml) was added E/Z-6-chloro-3-(5-fluoro-2-methyl-benzylidene)-2-oxo-2,3-dihydro-indole-1-carboxylic acid ethyl ester (0.16 g, 0.45 mmol) prepared in example 145b. The reaction tube was sealed and heated by microwave irradiation at 135° C. for 35 min. After the solution was cooled to room temperature, methanol (25 mL) was added, and then the mixture was concentrated. The residue was purified by chromatography (EtOAc:CH$_2$Cl$_2$=1:3) to give racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-carboxylic acid ethyl ester as a yellow oil (Yield 200 mg, 82%).

EXAMPLE 145d

Preparation of racemic (2'S,3S,4'R)-6-chloro-2'-(3-chlorophenyl)-4'-(5-fluoro-2-methyl-phenyl)-spiro[3H-indole-3,3'-piperidine]-2,6'(1H)-dione

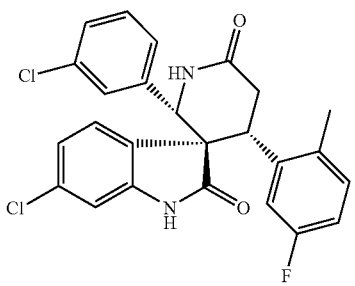

M. W. 469.35 C$_{25}$H$_{19}$Cl$_2$FN$_2$O$_2$

To a solution of racemic (2'S,3S,4'R)-6-chloro-2'-(3-chlorophenyl)-4'-(5-fluoro-2-methyl-phenyl)-2,3-dihydro-2,6'-dioxo-spiro[indole-3,3'-piperidine]-1-carboxylic acid ethyl ester prepared in example 145c (0.20 g, 0.31 mmol) in methanol (12 mL) was added NaOH (22 mg, 0.56 mmol). The mixture was stirred at room temperature for 0.5 h. The solvent was removed and the residue was partitioned between ethyl acetate and aqueous HCl solution (1 N). The aqueous layer was extracted with ethyl acetate. The organic layers were combined and then concentrated. The residue was purified with Prep-HPLC to give racemic (2'S,3S,4'R)-6-chloro-2'-(3-chlorophenyl)-4'-(5-fluoro-2-methyl-phenyl)-spiro[3H-indole-3,3'-piperidine]-2,6'(1H)-dione (9 mg).

MS m/z (M+H)$^+$: 469

EXAMPLE 146a

Preparation of intermediate E/Z-6-chloro-3-(5-fluoro-2-methyl-benzylidene)-1-(2-trimethylsilanyl-ethoxymethyl)-1,3-dihydro-indole-2-one

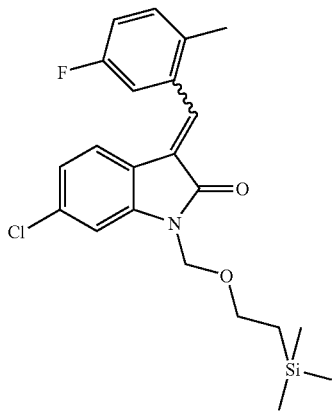

M. W. 417.99 C$_{22}$H$_{25}$ClFNO$_2$Si

To a solution E/Z-6-chloro-3-(3-chloro-benzylidene)-1,3-dihydro-indol-2-one prepared in example 145a (5.0 g, 17.4 mmol) in N,N-dimethyl-formamide (40 mL) at 0° C. was added NaH (60% in mineral oil) (0.70 g, 17.4 mmol), followed by the dropwise addition of 2-(trimethylsilyl)ethoxymethyl chloride (2.9 g, 17.4 mmol) in tetrahydrofuran (40 mL). The reaction mixture was stirred at 0° C. for 0.5 h, then poured into ice-water. The crude was extracted with ethyl acetate twice. The combined organic layer was dried over Na$_2$SO$_4$. The solvent was removed and the residue was purified by chromatography (hexanes) to give E/Z-6-chloro-3-(5-fluoro-2-methyl-benzylidene)-1-(2-trimethylsilanyl-ethoxymethyl)-1,3-dihydro-indole-2-one as yellow oil (Yield 5.7 g, 78%).

EXAMPLE 146b

Preparation of intermediate racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane

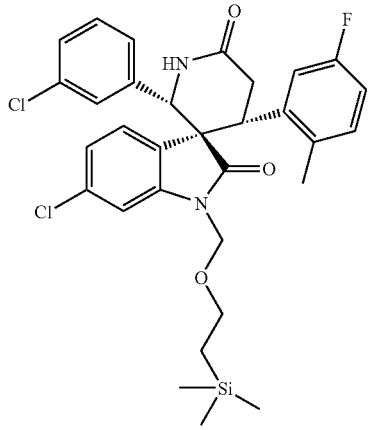

M. W. 599.61 $C_{31}H_{33}Cl_2FN_2O_3Si$

To a toluene (12 ml) solution of 1-(3-chlorophenyl)-3-trimethylsilyloxy-2-aza-1,3-butadiene prepared in example 1b in toluene (50 mL) was added E/Z-6-chloro-3-(5-fluoro-2-methyl-benzylidene)-1-(2-trimethylsilanyl-ethoxymethyl)-1,3-dihydro-indole-2-one (0.30 g, 0.72 mmol) prepared in example 146a. The reaction tube was then placed into the cavity of a focused monomode microwave reactor and the contents of the flask were irradiated for 35 min at 135° C. After the solution was cooled to room temperature, methanol (25 mL) was added. The reaction solutions were concentrated. The residue was purified by chromatography (EtOAc:$CH_2Cl_2$=1:3) to give racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane as a yellow solid (0.45 g)

EXAMPLE 146c

Preparation of intermediate racemic (2'S,3S,4'R)-6-chloro-2'-(3-chlorophenyl)-4'-(5-fluoro-2-methyl-phenyl)-2,3-dihydro-1'-[(tert-butoxycarbonyl)methyl]-2,6'-dioxospiro[indole-3,3'-piperidine]-1-methoxyethyl trimethylsilane

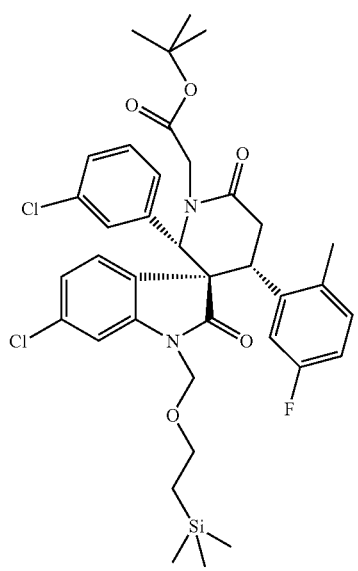

M. W. 713.76 $C_{37}H_{43}Cl_2FN_2O_5Si$

To a solution of racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane (2.5 g, 4.18 mmol) prepared in example 146b in N,N-dimethyl-formamide (20 mL) at room temperature was added bromo-acetic acid tert-butyl ester (2.0 g, 10.4 mmol) and cesium carbonate (7.5 g, 23.0 mmol). The reaction mixture was stirred under nitrogen for 4 h, then was poured into saturated aqueous $NH_4Cl$ solution. The mixture was extracted with ethyl acetate. The organic layers were combined, dried over $Na_2SO_4$ and concentrated. The residue was purified by chromatography (EtOAc:Hexanes=1:4) to give racemic (2'S,3S,4'R)-6-chloro-2'-(3-chlorophenyl)-4'-(5-fluoro-2-methyl-phenyl)-2,3-dihydro-1'-[(tert-butoxycarbonyl)methyl]-2,6'-dioxospiro[indole-3,3'-piperidine]-1-methoxyethyl trimethylsilane as a yellow solid (Yield 0.85 g).

EXAMPLE 146d

Preparation of racemic (2'S,3S,4'R)-6-chloro-2'-(3-chlorophenyl)-4'-(5-fluoro-2-methyl-phenyl)-1'-hydroxycarbonylmethyl-spiro[3H-indole-3,3'-piperidine]-2,6'(1H)-dione

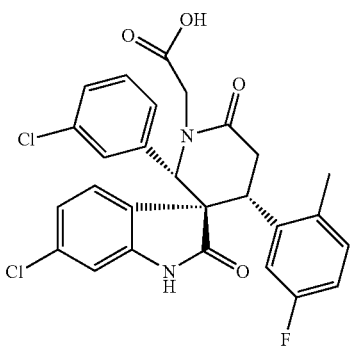

M. W. 527.38 $C_{27}H_{21}Cl_2FN_2O_4$

To a solution of racemic (2'S,3S,4'R)-6-chloro-2'-(3-chlorophenyl)-4'-(5-fluoro-2-methyl-phenyl)-2,3-dihydro-1'-[(tert-butoxycarbonyl)methyl]-2,6'-dioxospiro[indole-3,3'-piperidine]-1-methoxyethyl trimethylsilane (0.85 g, 1.19 mmol) prepared in example 146d in dichloromethane (10 mL) was added trifluoroacetic acid (20 mL). The reaction mixture was stirred at room temperature for 18 h. The reaction mixture was concentrated. The residue was redissolved in methanol (10 mL). To the resulting solution was added N,N'-diisopropylethylamine (1.57 mL, 8.70 mmol) and the crude was refluxed for 1 h. The reaction mixture was concentrated and the residue was partitioned between ethyl acetate and HCl aqueous solution (1N). The organic layer was separated, dried over $MgSO_4$ and concentrated. The residue was triturated with ethyl acetate and hexane to give racemic (2'S,3S,4'R)-6-chloro-2'-(3-chlorophenyl)-4'-(5-fluoro-2-methyl-phenyl)-1'-hydroxycarbonylmethyl-spiro[3H-indole-3,3'-piperidine]-2,6'(1H)-dione as a yellow solid (Yield 440 mg, 70%).

MS m/z (M+H)$^+$: 527

EXAMPLE 147

Preparation of racemic (2'S,3S,4'R)-6-chloro-2'-(3-chlorophenyl)-4'-(5-fluoro-2-methyl-phenyl)-1'-(methylamino-carbonyl-methyl)spiro[3H-indole-3,3'-piperidine]-2,6'(1H)-dione

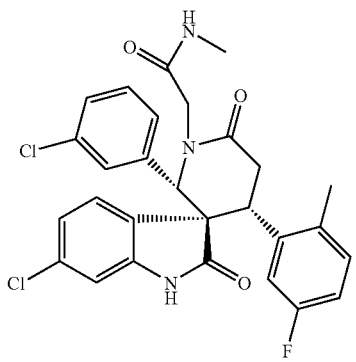

M. W. 540.43 $C_{28}H_{24}Cl_2FN_3O_3$

The mixture of racemic (2'S,3S,4'R)-6-chloro-2'-(3-chlorophenyl)-4'-(5-fluoro-2-methyl-phenyl)-1'-hydroxycarbonylmethyl-spiro[3H-indole-3,3'-piperidine]-2,6'(1H)-dione (70 mg, 0.13 mmol) prepared in example 146d, Methylamine hydrochloride (11 mg, 0.16 mmol), EDC.HCl (31 mg, 0.16 mmol), HOBt (22 mg, 0.16 mmol) and DIPEA (69 mg, 0.533 mmol) in DMF (2 mL) was stirred at room temperature for overnight. The crude was then purified with Prep-HPLC to give racemic (2'S,3S,4'R)-6-chloro-2'-(3-chlorophenyl)-4'-(5-fluoro-2-methyl-phenyl)-1'-(methylamino-carbonyl-methyl)spiro[3H-indole-3,3'-piperidine]-2,6'(1H)-dione (29 mg as a white solid.

MS m/z [M+H]$^+$: 540.

EXAMPLE 148

Preparation of racemic (2'S,3S,4'R)-6-chloro-2'-(3-chlorophenyl)-1'-(dimethylamino-carbonyl-methyl)-4'-(5-fluoro-2-methyl-phenyl)-spiro[3H-indole-3,3'-piperidine]-2,6'(1H)-dione

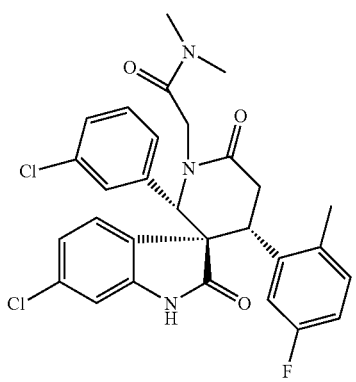

M. W. 554.45 $C_{29}H_{26}Cl_2FN_3O_3$

In a similar manner to the method described in example 147, racemic (2'S,3S,4'R)-6-chloro-2'-(3-chlorophenyl)-1'-(dimethylamino-carbonyl-methyl)-4'-(5-fluoro-2-methyl-phenyl)-spiro[3H-indole-3,3'-piperidine]-2,6'(1H)-dione was prepared.

MS m/z (M+H)$^+$: 554

EXAMPLE 149

Preparation of racemic (2'S,3S,4'R)-1'-[(4-aminocarbonyl-piperidin-1-yl)carbonyl-methyl]-6-chloro-2'-(3-chlorophenyl)-4'-(5-fluoro-2-methyl-phenyl)spiro[3H-indole-3,3'-piperidine]-2,6'(1H)-dione

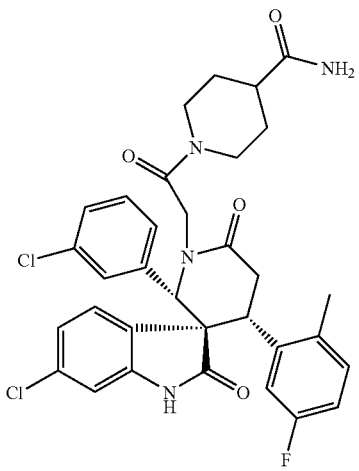

M. W. 637.54 $C_{33}H_{31}Cl_2FN_4O_4$

In a similar manner described in example 147, racemic (2'S,3S,4'R)-1'-[(4-aminocarbonyl-piperidin-1-yl)carbonyl-methyl]-6-chloro-2'-(3-chlorophenyl)-4'-(5-fluoro-2-methyl-phenyl)spiro[3H-indole-3,3'-piperidine]-2,6'(1H)-dione was prepared.

MS m/z (M+H)$^+$: 637

EXAMPLE 150

Preparation of racemic (2'S,3S,4'R)-1'-[(3-aminocarbonyl-piperidin-1-yl)carbonyl-methyl]-6-chloro-2'-(3-chlorophenyl)-4'-(5-fluoro-2-methyl-phenyl)-spiro[3H-indole-3,3'-piperidine]-2,6'(1H)-dione

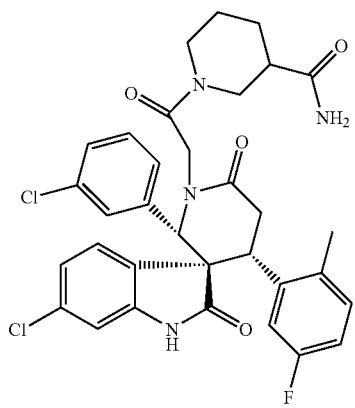

M. W. 637.54 $C_{33}H_{31}Cl_2FN_4O_4$

In a similar manner described in example 147, racemic (2'S,3S,4'R)-1'-[(3-aminocarbonyl-piperidin-1-yl)carbonyl-methyl]-6-chloro-2'-(3-chlorophenyl)-4'-(5-fluoro-2-methyl-phenyl)-spiro[3H-indole-3,3'-piperidine]-2,6'(1H)-dione was prepared.

MS m/z (M+H)$^+$: 637

EXAMPLE 151

Preparation of racemic (2'S,3S,4'R)-1'-(aminocarbonyl-methyl)-6-chloro-2'-(3-chlorophenyl)-4'-(5-fluoro-2-methyl-phenyl)spiro[3H-indole-3,3'-piperidine]-2,6'(1H)-dione

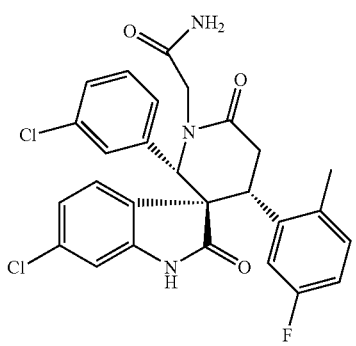

M. W. 526.40 $C_{27}H_{22}Cl_2FN_3O_3$

In a manner similar to the method described in example 146d and 146e racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane (50 mg g, 0.08 mmol) was reacted with 2-bromoacetamide (35 mg, 0.25 mmol) and cesium carbonate (163 mg, 0.50 mmol) in DMF (2 ml). The resulting residue was dissolved in a mixture solution of trifluoroacetic acid (5 mL) and dichloromethane (5 mL). The reaction mixture was stirred at room temperature for 18 h. The reaction mixture was concentrated. The residue was redissolved in methanol (10 mL). To the resulting solution was added N,N'-diisopropylethylamine and the crude was refluxed for 1 h. The reaction mixture was concentrated and the residue was partitioned between ethyl acetate and HCl aqueous solution (1N). The organic layer was separated, dried over MgSO$_4$ and concentrated. The residue was triturated purified by Prep-HPLC to give racemic (2'S,3S,4'R)-1'-(aminocarbonyl-methyl)-6-chloro-2'-(3-chlorophenyl)-4'-(5-fluoro-2-methyl-phenyl)spiro[3H-indole-3,3'-piperidine]-2,6'(1H)-dione as a white solid (8 mg).

MS m/z (M+H)$^+$: 526

EXAMPLE 152a

Preparation of intermediate racemic (2'S,3S,4'R)-6-chloro-1'-(3-chloro-propyl)-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane

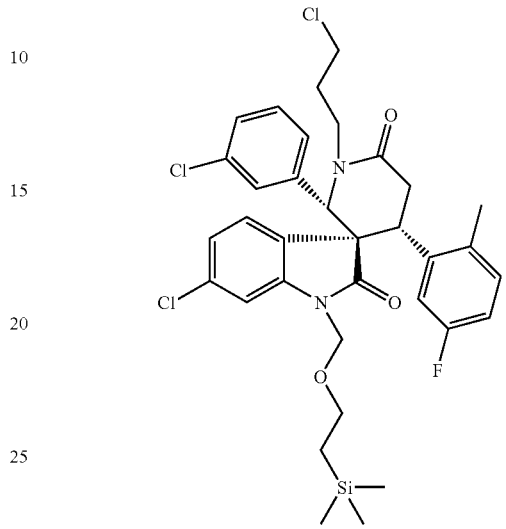

M. W. 676.14 $C_{34}H_{38}Cl_3FN_2O_5Si$

Racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane (0.40 g, 0.67 mmol) prepared in example 146a was reacted with LiH (0.13 g, 16.70 mmol) and 1-chloro-3-bromo-propane (0.63 g, 4.01 mmol) in N,N-dimethyl-formamide (3 mL), a catalytic amount of KI. After the solution was stirred overnight, the solution was poured into water. The water layer was extracted with ethyl acetate and the combined organic layers were dried, concentrated to obtain the crude product. The crude product was purified by chromatography to give racemic (2'S,3S,4'R)-6-chloro-1'-(3-chloro-propyl)-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane as a yellow solid (Yield: 0.11 g, 24%).

EXAMPLE 152b

Preparation of racemic (2'S,3S,4'R)-6-chloro-2'-(3-chlorophenyl)-1'-(dimethylamino-propyl)-4'-(5-fluoro-2-methyl-phenyl)-spiro[3H-indole-3,3'-piperidine]-2,6'(1H)-dione

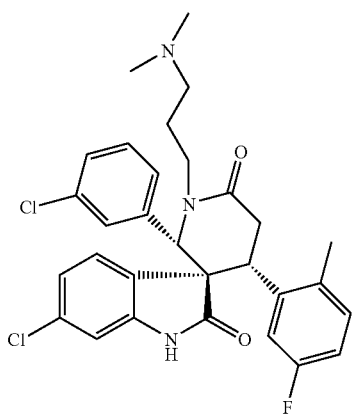

M. W. 554.50 C₃₀H₃₀Cl₂FN₃O₂

To a solution of racemic (2'S,3S,4'R)-6-chloro-1'-(3-chloro-propyl)-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane (0.11 g, 0.16 mmol) prepared in example 152a in N,N-dimethyl-formamide (3 mL) at room temperature was added dimethylamine hydrochloride (0.53 g, 6.53 mmol) and cesium carbonate (2.66 g, 8.16 mmol), and a catalytic amount of KI. The reaction mixture was stirred overnight, then the solution was poured into saturated aqueous NH₄Cl solution. The mixture was extracted with ethyl acetate. The organic layers were combined, dried over Na₂SO₄ and concentrated to obtain 110 mg yellow solid. To the yellow solid was added dichloromethane (10 mL) and trifluoracetic acid (10 mL). The reaction mixture was stirred at room temperature for 4 h. The reaction mixture was concentrated and the residue was partitioned between ethyl acetate and saturated NaHCO₃ solution. The organic layer was separated and concentrated. The residue was redissolved in methanol (10 mL). To the resulting solution was added N,N'-diisopropylethylamine (2 mL) and the crude was heated at 100° C. for 1 h. The reaction mixture was concentrated and the residue was purified by Prep-HPLC to give of racemic (2'S,3S,4'R)-6-chloro-2'-(3-chlorophenyl)-1'-(dimethylamino-propyl)-4'-(5-fluoro-2-methyl-phenyl)-spiro[3H-indole-3,3'-piperidine]-2,6'(1H)-dione as a white solid (10 mg).

MS m/z (M+H)⁺: 554

EXAMPLE 153a

Preparation of intermediate racemic (2'S,3S,4'R)-1'-[(tert-butoxycarbonylamino)ethyl]-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane

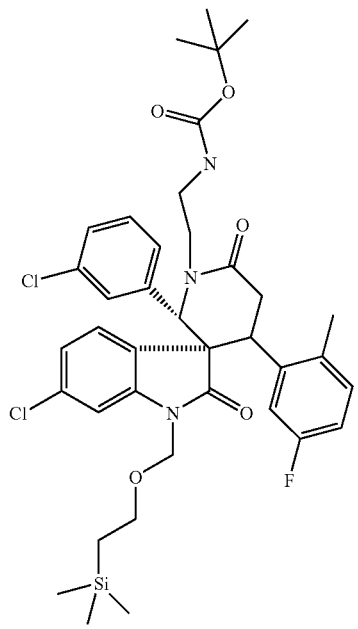

M. W. 742.80 C₃₈H₄₆Cl₂FN₃O₅Si

In a manner similar to the method described in example 152a, racemic (2'S,3S,4'R)-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane (0.45 g, 0.75 mmol) was reacted with LiH (0.15 g, 18.8 mmol) and (2-bromo-ethyl)-carbamic acid tert-butyl ester (1.0 g, 4.52 mmol) in N,N-dimethyl-formamide (3 mL), a catalytic amount of KI to give racemic (2'S,3S,4'R)-1'-[(tert-butoxycarbonylamino)ethyl]-6-chloro-2'-(3-chlorophenyl)-4'-(5-fluoro-2-methyl-phenyl)-2,3-dihydro-2,6'-dioxospiro[indole-3,3'-piperidine]-1-methoxyethyl trimethylsilane as a yellow solid (80 mg).

EXAMPLE 153b

Preparation of racemic (2'S,3S,4'R)-6-chloro-4'-(3-chlorophenyl)-2'-(5-fluoro-2-methylphenyl)-1'-[(1-methanesulfonyl-piperidine-4-yl)carbonylamino-ethyl]spiro[3H-indole-3,3'-piperidine]-2,6'(1H)-dione

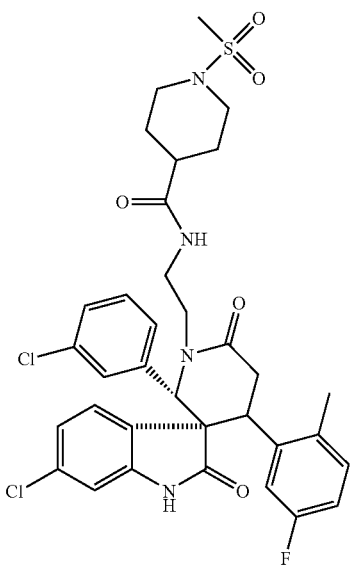

M. W. 701.6 C₃₄H₃₅Cl₂FN₄O₅S

Racemic (2'S,3S,4'R)-6-chloro-2'-(3-chlorophenyl)-4'-(5-fluoro-2-methyl-phenyl)-2,3-dihydro-1'-[(tert-butoxycarbamoy)ethyl]-2,6'-dioxospiro[indole-3,3'-piperidine]-1-methoxyethyl trimethylsilane prepared in example 153a (80 mg) was added dichloromethane (5 mL) and then trifluoroacetic acid (5 mL). The reaction mixture was stirred at room temperature for 4 h. The reaction mixture was concentrated and the residue was partitioned between ethyl acetate and saturated NaHCO₃ solution. The organic layer was separated and concentrated. The residue was redissolved in methanol (5 mL). To the resulting solution was added N,N'-diisopropylethylamine (2 mL) and the crude was heated at 100° C. for 1 h. The reaction mixture was concentrated. The mixture of the residue, 1-methanesulfonyl-piperidine-4-carboxylic acid (60 mg, 0.29 mmol), EDC.HCl (56 mg, 0.29 mmol), HOBt (39 mg, 0.29 mmol) and DIPEA (101 mg, 0.78 mmol) in DMF (2 mL) was stirred at room temperature for overnight. The crude was then purified with Prep-HPLC to give racemic (2'S,3S,4'R)-6-chloro-4'-(3-chlorophenyl)-2'-(5-fluoro-2-methylphenyl)-1'-[(1-methanesulfonyl-piperidine-4-yl)carbonylamino-ethyl]spiro[3H-indole-3,3'-piperidine]-2,6'(1H)-dione as a yellow solid (14 mg).

MS m/z (M+H)⁺: 701

EXAMPLE 154a

Preparation of intermediate E/Z-6-chloro-3-(4-chloro-thiophen-2-ylmethylene)-1,3-dihydro-indol-2-one

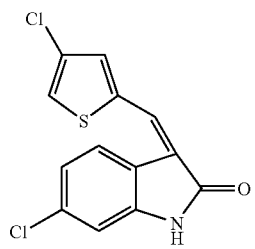

M. W. 296.18 $C_{13}H_7Cl_2NOS$

In a manner similar to the method described in example 1a, 6-chlorooxindole (1.2 g, 7.2 mmol) was reacted with 4-chloro-thiophene-2-carbaldehyde (1.05 g, 7.2 mmol) and pyrrolidine (0.7 g, 9.9 mmol) to give E/Z-6-chloro-3-(4-chloro-thiophen-2-ylmethylene)-1,3-dihydro-indol-2-one as a yellow solid (Yield 1.3 g, 62%)

EXAMPLE 154b

Preparation of racemic (2'R,3R,4'R)-6-chloro-4'-[2-(4-chloro-2-thiophenyl)]-2'-(5-fluoro-2-methylphenyl)-spiro[3H-indole-3,3'-piperidine]-2,6'(1H)-dione

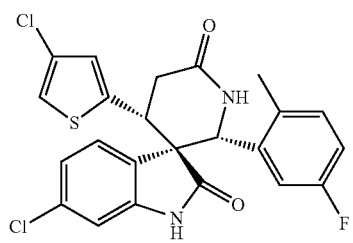

M. W. 475.37 $C_{23}H_{17}Cl_2FN_2O_2S$

In a manner similar to the method described in example 1c, E/Z-6-chloro-3-(4-chloro-thiophen-2-ylmethylene)-1,3-dihydro-indol-2-one (0.2 g, 0.68 mmol) prepared in example 154a was reacted with 1-(5-fluoro-2-methyl-phenyl)-3-trimethylsilyoxy-2-aza-1,3-butadiene prepared in example 36a to give racemic (2'R,3R,4'R)-6-chloro-4'-[2-(4-chloro-2-thiophenyl)]-2'-(5-fluoro-2-methylphenyl)-spiro[3H-indole-3,3'-piperidine]-2,6'(1H)-dione as an white solid (7 mg).

MS m/z (M+H)$^+$: 475

EXAMPLE 155a

Preparation of intermediate E/Z-6-chloro-3-(5-chloro-thiophen-2-ylmethylene)-1,3-dihydro-indol-2-one

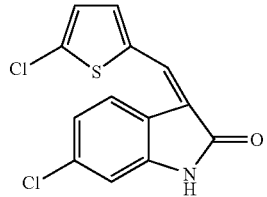

M. W. 296.18 $C_{13}H_7Cl_2NOS$

In a manner similar to the method described in example 1a, 6-chlorooxindole (1.2 g, 7.2 mmol) was reacted with 5-chloro-thiophene-2-carbaldehyde (1.05 g, 7.2 mmol) and pyrrolidine (0.7 g, 9.9 mmol) to give E/Z-6-chloro-3-(5-chloro-thiophen-2-ylmethylene)-1,3-dihydro-indol-2-one as a yellow solid (Yield 1.5 g, 71%)

EXAMPLE 155b

Preparation of racemic (2'R,3R,4'R)-6-chloro-4'-[2-(5-chloro-2-thiophenyl)]-2'-(5-fluoro-2-methylphenyl)-spiro[3H-indole-3,3'-piperidine]-2,6'(1H)-dione

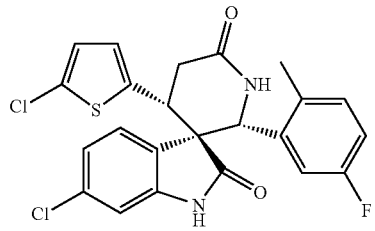

M. W. 475.37 $C_{23}H_{17}Cl_2FN_2O_2S$

In a manner similar to the method described in example 1c, E/Z-6-chloro-3-(5-chloro-thiophen-2-ylmethylene)-1,3-dihydro-indol-2-one (0.2 g, 0.68 mmol) prepared in example 155a was reacted with 1-(5-fluoro-2-methyl-phenyl)-3-trimethylsilyoxy-2-aza-1,3-butadiene prepared in example 6b to give racemic (2'R,3R,4'R)-6-chloro-4'-[2-(5-chloro-2-thiophenyl)]-2'-(5-fluoro-2-methylphenyl)-spiro[3H-indole-3,3'-piperidine]-2,6'(1H)-dione as an white solid (6 mg).

MS m/z (M+H)$^+$: 475

EXAMPLE 156

Preparation of racemic (2'R,3R,4'S)-6-chloro-4'-(2,2-dimethylpropyl)-2'-(5-fluoro-2-methylphenyl)-spiro[3H-indole-3,3'-piperidine]-2,6'(1H)-dione

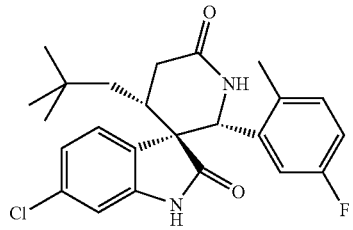

M. W. 428.94 C$_{24}$H$_{26}$ClFN$_2$O$_2$

In a manner similar to the method described in example 1c, E/Z-6-Chloro-3-(3,3-dimethyl-butylidene)-1,3-dihydro-indol-2-one (0.2 g, 0.80 mmol) prepared in example 1a was reacted with 1-(5-fluoro-2-methyl-phenyl)-3-trimethylsilyoxy-2-aza-1,3-butadiene prepared in example 36a to give racemic (2'R,3R,4'S)-6-chloro-4'-(2,2-dimethylpropyl)-2'-(5-fluoro-2-methyl phenyl)-spiro[3H-indole-3,3'-piperidine]-2,6'(1H)-dione as an white solid (7 mg).

MS m/z (M+H)$^+$: 429

EXAMPLE 157a

Preparation of intermediate E/Z-6-bromo-3-(3-chloro-benzylidene)-1,3-dihydro-indol-2-one

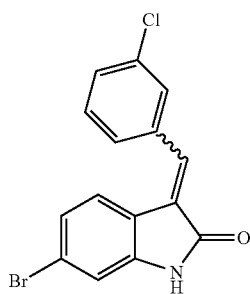

M. W. 334.60 C$_{15}$H$_9$BrClNO

To the mixture of 6-bromooxindole (16.2 g, 92 mmol) (Combi-block) and 3-chloro-benzaldehyde (12.9 g, 92 mmol) in methanol (109 mL) was added pyrrolidine (6.55 g, 92 mmol) dropwise. The mixture was then heated at 65° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 16.2 g, 63%).

EXAMPLE 157b

Preparation of racemic (2'R,3R,4'S)-6-bromo-4'-(3-chlorophenyl)-2'-(2-methylphenyl)spiro[3H-indole-3,3'-piperidine]-2,6'(1H)-dione

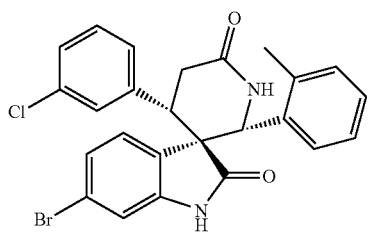

M. W. 495.81 C$_{25}$H$_{20}$BrClN$_2$O$_2$

To a solution of 1-(2-methylphenyl)-3-trimethylsilyoxy-2-aza-1,3-butadiene prepared in example 17a in toluene (20 mL) was added E/Z-6-bromo-3-(3-chloro-benzylidene)-2-oxo-2,3-dihydro-indole prepared in example 157a (0.3 g, 0.83 mmol). The reaction mixture was stirred and heated under microwave irradiation in a sealed tube at 135° C. for 0.5 h. After the solution was cooled to room temperature, methanol (50 mL) was added, and then the mixture was concentrated. The residue was purified by chromatography (EtOAc:CH$_2$Cl$_2$=1:3) to give racemic (2'R,3R,4'S)-6-bromo-4'-(3-chlorophenyl)-2'-(2-methylphenyl)spiro[3H-indole-3,3'-piperidine]-2,6'(1H)-dione as a white solid. (Yield 0.22 g, 53%).

MS m/z [(M+H)$^+$]: 495

EXAMPLE 158a

Preparation of racemic (2'R,3R,4'S)-6-bromo-4'-(3-chlorophenyl)-2'-(5-fluoro-2-methylphenyl)spiro[3H-indole-3,3'-piperidine]-2,6'(1H)-dione

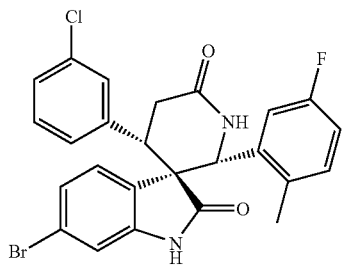

M. W. 513.80 C$_{25}$H$_{19}$BrClFN$_2$O$_2$

In a manner similar to the method described in example 157b, E/Z-6-bromo-3-(3-chloro-benzylidene)-2-oxo-2,3-dihydro-indole (0.4 g, 1.10 mmol) prepared in example 157a was reacted with 1-(5-fluoro-2-methylphenyl)-3-trimethylsilyoxy-2-aza-1,3-butadiene prepared in example 36a in toluene to give racemic (2'R,3R,4'S)-6-bromo-4'-(3-chlorophenyl)-2'-(5-fluoro-2-methylphenyl)spiro[3H-indole-3,3'-piperidine]-2,6'(1H)-dione as a white solid (Yield 0.3 g, 54%).

MS m/z [(M+H)$^+$]: 513

EXAMPLE 158b

Preparation of chiral (2'R,3R,4'S)-6-chloro-4'-(3-chlorophenyl)-2'-(5-fluoro-2-methylphenyl)spiro[3H-indole-3,3'-piperidine]-2,6'(1H)-dione

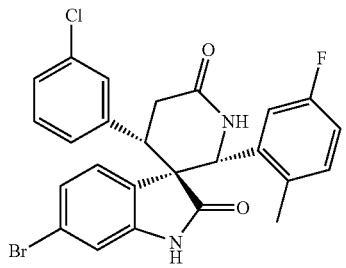

M. W. 513.80 C$_{25}$H$_{19}$BrClFN$_2$O$_2$

Separation of the two enantiomers from racemic (2'R,3R,4'S)-6-bromo-4'-(3-chlorophenyl)-2'-(5-fluoro-2-methylphenyl)spiro[3H-indole-3,3'-piperidine]-2,6'(1H)-dione (35 mg) prepared in example 158a was conducted by chiral column chromatography to provide chiral (2'R,3R,4'S)-6-bromo-4'-(3-chlorophenyl)-2'-(5-fluoro-2-methylphenyl)spiro[3H-indole-3,3'-piperidine]-2,6'(1H)-dione as a white solid (Yield: 11 mg, 31%) and chiral (2'S,3S,4'R)-6-bromo-4'-(3-chlorophenyl)-2'-(5-fluoro-2-methylphenyl)spiro[3H-indole-3,3'-piperidine]-2,6'(1H)-dione as a white solid (Yield: 11 mg, 31%).

MS m/z [(M+H)⁺]: 513

EXAMPLE 159a

Preparation of intermediate 1-(2,5-dichlorophenyl)-3-trimethylsilyoxy-2-aza-1,3-butadiene

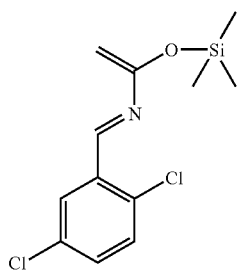

M. W. 288.25 $C_{12}H_{15}Cl_2NOSi$

In a manner similar to the method described in example 1b, 2,5-dichloro-benzaldehyde (1.75 g, 10 mmol) was used as the starting material in place of 3-chlorobenzaldehyde to react with Lithium bis(trimethylsilyl)amide (1M solution in THF, 10 mL, 10 mmol), trimethylsilyl chloride (1.1 g, 10 mmol), triethylamine (1.4 g, 13 mmol) and acetyl chloride (1.0 g, 13 mmol) to give 1-(2,5-dichlorophenyl)-3-trimethylsilyoxy-2-aza-1,3-butadiene as a yellow gum and used for the next step without further purification.

EXAMPLE 159b

Preparation of racemic (2'R,3R,4'S)-6-bromo-4'-(3-chlorophenyl)-2'-(2,5-dichlorophenyl)spiro[3H-indole-3,3'-piperidine]-2,6'(1H)-dione

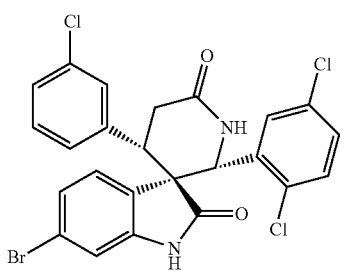

M. W. 550.67 $C_{24}H_{16}BrCl_3N_2O_2$

In a manner similar to the method described in example 157b, E/Z-6-bromo-3-(3-chloro-benzylidene)-2-oxo-2,3-dihydro-indole (0.4 g, 1.10 mmol) prepared in example 157a was reacted with 1-(2,5-dichlorophenyl)-3-trimethylsilyoxy-2-aza-1,3-butadiene prepared in example 159a, in toluene to give racemic (2'R,3R,4'S)-6-bromo-4'-(3-chlorophenyl)-2,3-dihydro-2'-(2,5-dichlorophenyl)-2,6'-dioxospiro[indole-3,3'-piperidine as a white solid. (Yield 0.4 g, 67%).

MS m/z [(M+H)⁺]: 549

EXAMPLE 160a

Preparation of intermediate 1-(5-chloro-2-methyl phenyl)-3-trimethylsilyoxy-2-aza-1,3-butadiene

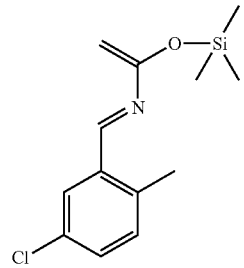

M. W. 267.83 $C_{13}H_{18}ClNOSi$

In a manner similar to the method described in example 1b, 5-chloro-2-methyl-benzaldehyde (1.54 g, 10 mmol) was used as the starting material in place of 2-methylbenzaldehyde to react with react with Lithium bis(trimethylsilyl)amide (1M solution in THF, 10 mL, 10 mmol), trimethylsilyl chloride (1.1 g, 10 mmol), triethylamine (1.4 g, 13 mmol) and acetyl chloride (1.0 g, 13 mmol) to give 1-(5-fluoro-2-methylphenyl)-3-trimethylsilyoxy-2-aza-1,3-butadiene as a yellow gum and used for the next step without further purification.

EXAMPLE 160b

Preparation of racemic (2'R,3R,4'S)-6-bromo-4'-(3-chlorophenyl)-2'-(5-chloro-2-methylphenyl)spiro[3H-indole-3,3'-piperidine]-2,6'(1H)-dione

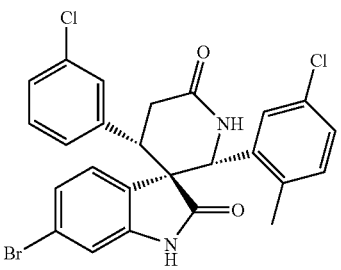

M. W. 530.25 $C_{25}H_{19}BrCl_2N_2O_2$

In a manner similar to the method described in example 157b, E/Z-6-bromo-3-(3-chloro-benzylidene)-2-oxo-2,3-dihydro-indole (0.4 g, 1.10 mmol) prepared in example 157a was reacted with 1-(5-chloro-2-methylphenyl)-3-trimethylsilyoxy-2-aza-1,3-butadiene prepared in example 160a, in toluene to give racemic (2'R,3R,4'S)-6-bromo-4'-(3-chlorophenyl)-2,3-dihydro-2'-(5-chloro-2-methylphenyl)-2,6'-dioxospiro[indole-3,3'-piperidine] as a white solid. (Yield 0.3 g, 51%).

MS m/z [(M+H)⁺]: 529

EXAMPLE 161a

Preparation of intermediate E/Z-6-Bromo-3-(3-chloro-benzylidene)-1-(2-trimethylsilanyl-ethoxymethyl)-1,3-dihydro-indole-2-one

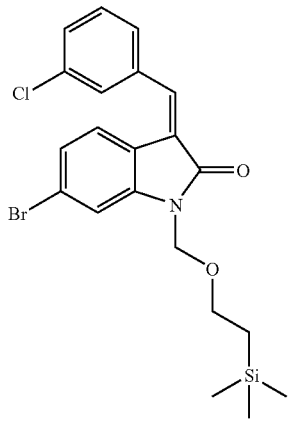

M. W. 464.87

$C_{21}H_{23}BrClNO_2Si$

To a solution of E/Z 6-Bromo-3-(3-chloro-benzylidene)-1,3-dihydro-indol-2-one (5.3 g, 16 mmol) prepared in example 157a in N,N-dimethyl-formamide (50 mL) at 0° C. was added NaH (60% in mineral oil) (0.64 g, 16 mmol), followed by the dropwise addition of 2-(trimethylsilyl)ethoxymethyl chloride (2.65 g, 16 mmol) in tetrahydrofuran (40 mL). The reaction mixture was stirred at 0° C. for 0.5 h, then poured into ice-water. The crude was extracted with ethyl acetate twice. The combined organic layer was dried over $Na_2SO_4$. The solvent was removed and the residue was purified by chromatography (hexanes) to give E/Z-6-Bromo-3-(3-chloro-benzylidene)-1-(2-trimethylsilanyl-ethoxymethyl)-1,3-dihydro-indole-2-one as a yellow oil (Yield 4.5 g, 60%).

EXAMPLE 161b

Preparation of intermediate racemic (2'R,3R,4'S)-6-bromo-4'-(3-chlorophenyl)-2'-(1-methylene-propyl)-2,3-dihydro-2,6'-dioxospiro[indole-3,3'-piperidine]-1-methoxyethyl trimethylsilane

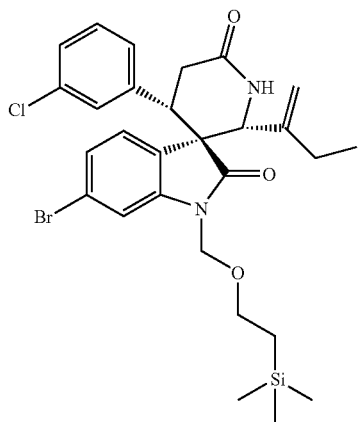

M. W. 590.04 $C_{28}H_{34}BrClN_2O_3Si$

To a solution of 1-(1-ethyl-ethenyl)-3-trimethylsilyoxy-2-aza-1,3-butadiene (42 mmol) prepared in example 80a in toluene (50 mL) was added E/Z-6-Bromo-3-(3-chloro-benzylidene)-1-(2-trimethylsilanyl-ethoxymethyl)-1,3-dihydro-indole-2-one (2 g, 4.3 mmol) prepared in example 161a. The reaction mixture was stirred under nitrogen in a sealed tube at 135° C. for 1 h. After cooling to room temperature, methanol (100 mL) was added, and then the mixture was concentrated. The residue was purified by chromatography (EtOAc:Hexane=2:1) gave racemic (2'R,3R,4'S)-6-bromo-4'-(3-chlorophenyl)-2'-(1-methylene-propyl)-2,3-dihydro-2,6'-dioxospiro[indole-3,3'-piperidine]-1-methoxyethyl trimethylsilane as a solid (Yield 350 mg).

EXAMPLE 161c

Preparation of racemic (2'R,3R,4'S)-6-bromo-4'-(3-chlorophenyl)-2'-(1-methylene-propyl)-spiro[3H-indole-3,3'-piperidine]-2,6'(1H)-dione

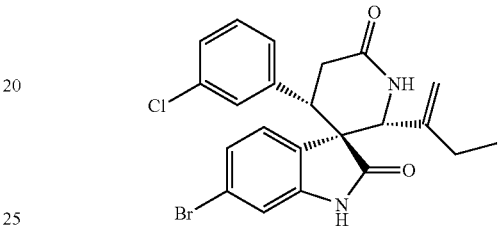

M. W. 459.77 $C_{22}H_{20}BrClN_2O_2$

To a solution of racemic (2'R,3R,4'S)-6-bromo-4'-(3-chlorophenyl)-2'-(1-methylene-propyl)-2,3-dihydro-2,6'-dioxospiro[indole-3,3'-piperidine]-1-methoxyethyl trimethylsilane (50 mg, 0.08 mmol) prepared in example 161b in dichloromethane (5 mL) was added trifluoroacetic acid (5 mL). The reaction mixture was stirred at room temperature for 0.5 h. After removing the solvent, the residue was dissolved in methanol (2 mL). To the resulting solution was added N,N'-diisopropylethylamine (1 mL). The reaction tube was then heated at 135 °C. for 20 min. The reaction mixture was concentrated and the residue was purified by Prep-HPLC to obtain racemic (2'R,3R,4'S)-6-bromo-4'-(3-chlorophenyl)-2'-(1-methylene-propyl)-spiro[3H-indole-3,3'-piperidine]-2,6'(1H)-dione as solid (30 mg).

EXAMPLE 161d

Preparation of chiral (2'R,3R,4'S)-6-bromo-4'-(3-chlorophenyl)-2'-(1-methylene-propyl)-spiro[3H-indole-3,3'-piperidine]-2,6'(1H)-dione

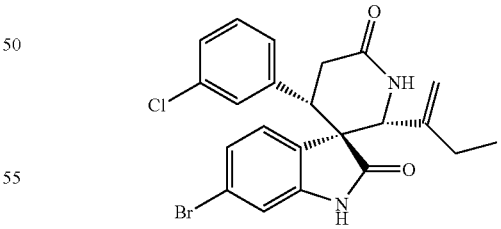

M. W. 459.77

$C_{22}H_{20}BrClN_2O_2$

Racemic (2'R,3R,4'S)-6-bromo-4'-(3-chlorophenyl)-2'-(1-methylene-propyl)-spiro[3H-indole-3,3'-piperidine]-2,6'(1H)-dione (30 mg) was separated by chiral column chromatography to give chiral (2'R,3R,4'S)-6-bromo-4'-(3-chlorophenyl)-2'-(1-methylene-propyl)-spiro[3H-indole-3, 3'-piperidine]-2,6'(1H)-dione (7 mg white solid) and chiral (2'S,3S,4'R)-6-bromo-4'-(3-chlorophenyl)-2'-(1-methylene-propyl)-spiro[3H-indole-3,3'-piperidine]-2,6'(1H)-dione as a white solid (7 mg).

MS m/z [(M+H)+]: 459

EXAMPLE 162a

Preparation of intermediate racemic (2'R,3R,4'S)-6-bromo-4'-(3-chlorophenyl)-2'-(1-ethyl-cyclopropyl)-2,3-dihydro-2,6'-dioxospiro[indole-3,3'-piperidine]-1-methoxyethyl trimethylsilane

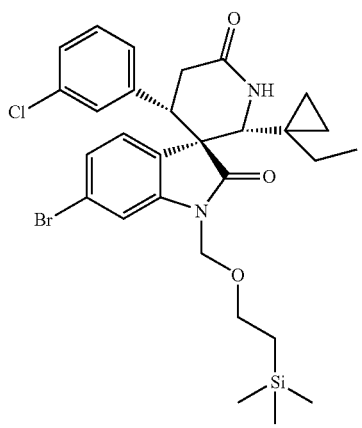

M. W. 604.06 $C_{29}H_{36}BrClN_2O_3Si$ $CH_2I_2$ (1.2 g, 4.6 mmol) was dissolved in dry toluene (5 mL) at 0° C. After stirred for 10 min under Argon, $Et_2Zn$ (1 M in THF, 3.3 mL, 3.67 mmol) was added. After stirred for 15 min, a solution of racemic (2'R,3R,4'S)-6-bromo-4'-(3-chlorophenyl)-2'-(1-methylene-propyl)-2,3-dihydro-2,6'-dioxospiro[indole-3,3'-piperidine]-1-methoxyethyl trimethylsilane (270 mg, 0.46 mmol) prepared in example 161b in dry toluene (10 mL) was added. After stirred at room temperature for 3 h, the reaction was quenched with saturated $NH_4Cl$ (20 mL). The aqueous layer was extracted with EtOAc. The combined organic layer was dried over $Na_2SO_4$, concentrated, the residue, was used for next step without further purification.

EXAMPLE 162b

Preparation of chiral (2'R,3R,4'S)-6-bromo-4'-(3-chlorophenyl)-2'-(1-ethyl-cyclopropyl)spiro[3H-indole-3,3'-piperidine]-2,6'(1H)-dione

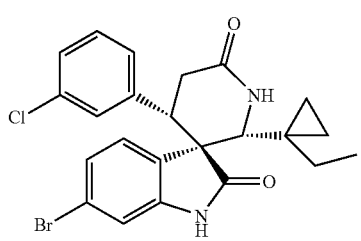

M. W. 473.80 $C_{23}H_{22}BrClN_2O_2$

To a solution of racemic (2'R,3R,4'S)-6-bromo-4'-(3-chlorophenyl)-2'-(1-ethyl-cyclopropyl)-2,3-dihydro-2,6'-dioxospiro[indole-3,3'-piperidine]-1-methoxyethyl trimethylsilane (48 mg, 0.079 mmol) prepared in example 162a in dichloromethane (5 mL) was added trifluoroacetic acid (5 mL). The mixture was stirred at room temperature for 5 h. Then the solvent was removed in vacuo. The residue was dissolved in methanol (2 mL). To the resulting solution was added N,N'-diisopropylethylamine (1 mL). The mixture was heated at 135 ° C. for 20 min. The reaction mixture was concentrated and the residue was purified by Prep-HPLC to obtain racemic (2'R,3R,4'S)-6-bromo-4'-(3-chlorophenyl)-2'-(1-ethyl-cyclopropyl)-spiro[3H-indole-3,3'-piperidine]-2,6'(1H)-dione. The racemic compound was separated by chiral column chromatography to obtain chiral (2R,3R,4'S)-6-bromo-4'-(3-chlorophenyl)-2'-(1-ethyl-cyclopropyl)-spiro[3H-indole-3,3'-piperidine]-2,6'(1H)-dione (4.5 mg) and chiral (2S,3S,4'R)-6-bromo-4'-(3-chlorophenyl)-2'-(1-ethyl-cyclopropyl)-spiro[3H-indole-3,3'-piperidine]-2,6'(1H)-dione (4.5 mg).

MS m/z [(M+H)+]: 473

EXAMPLE 163a

Preparation of intermediate racemic (2'R,3R,4'S)-6-bromo-4'-(3-chlorophenyl)-2'-(1-ethyl-cyclopropyl)-2,3-dihydro-2,6'-dioxospiro[indole-3,3'-piperidine]-1-carboxylic acid tert-butyl ester

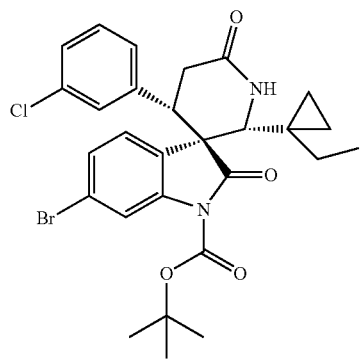

M. W. 573.92 $C_{28}H_{30}BrClN_2O_4$

Racemic (2'R,3R,4'S)-6-bromo-4'-(3-chlorophenyl)-2'-(1-ethyl-cyclopropyl)-spiro[3H-indole-3,3'-piperidine]-2,6'(1H)-dione (220 mg, 0.47 mmol) prepared in example 162b, $(Boc)_2O$ (121.9 mg, 0.56 mmol) and DMAP (73.9 mg, 0.61 mmol) were mixed in tetrahydrofuran (10 mL). After stirred for 0.5 h, the solution was concentrated and the residue was dissolved in EtOAc. The organic layer was washed with 0.5N HCl aqueous solution for several times. Then the organic layer was dried and concentrated to obtain yellow solid (240 mg).

EXAMPLE 163b

Preparation of intermediate racemic (2'R,3R,4'S)-4'-(3-chlorophenyl)-6-cyclopropyl-2'-(1-ethyl-cyclopropyl)-2,3-dihydro-2,6'-dioxospiro[indole-3,3'-piperidine]-1-carboxylic acid tert-butyl ester

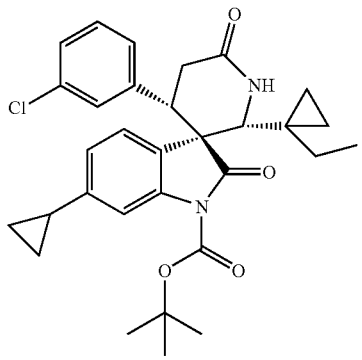

M. W. 535.09 $C_{31}H_{35}ClN_2O_4$

Under Argon atmosphere, racemic (2'R,3R,4'S)-6-bromo-4'-(3-chlorophenyl)-2'-(1-ethyl-cyclopropyl)-2,3-dihydro-2,6'-dioxospiro[indole-3,3'-piperidine]-1-carboxylic acid tert-butyl ester (28 mg, 0.049 mmol), cyclopropylboronic acid (4.5 mg, 0.0524 mmol), Pd(PPh$_3$)$_4$ (5 mg), K$_3$PO$_4$ (50 mg) and a few drops of water were mixed in toluene (3 mL). The mixture was heated under microwave irradiation at 130° C. for 20 min. Then the solution was poured into water and the aqueous layer was extracted with EtOAc. The organic layer was dried and concentrated. The residue was purified by Prep-TLC to obtain racemic (2'R,3R,4'S)-6-cyclopropyl-4'-(3-chlorophenyl)-2'-(1-ethyl-cyclopropyl)-2,3-dihydro-2,6'-dioxospiro[indole-3,3'-piperidine]-1-carboxylic acid tert-butyl ester (10 mg).

EXAMPLE 163c

Preparation of racemic (2'R,3R,4'S)-6-cyclopropyl-4'-(3-chlorophenyl)-2'-(1-ethyl-cyclopropyl)-spiro[3H-indole-3,3'-piperidine]-2,6'(1H)-dione

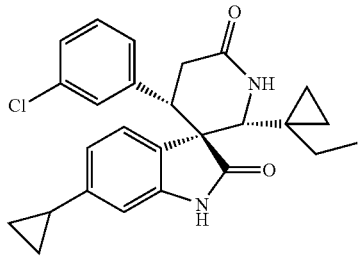

M. W. 434.97 $C_{26}H_{27}ClN_2O_2$

Racemic (2'R,3R,4'S)-6-cyclopropyl-4'-(3-chlorophenyl)-2'-(1-ethyl-cyclopropyl)-2,3-dihydro-2,6'-dioxospiro[indole-3,3'-piperidine]-1-carboxylic acid tert-butyl ester (10 mg, 0.019 mmol) was dissolved in a methanolic solution of HCl (6 M, 10 mL). After 10 min, the solution was concentrated to obtain racemic (2'R,3R,4'S)-6-cyclopropyl-4'-(3-chlorophenyl)-2'-(1-ethyl-cyclopropyl)-spiro[3H-indole-3,3'-piperidine]-2,6'(1H)-dione as a white solid. (Yield, 5.9 mg, 72%)

MS m/z [(M+H)$^+$]: 435

EXAMPLE 164a

Preparation of intermediate racemic (2'R,3R,4'S)-6-chloro-4'-(3-chlorophenyl)-2'-(5-fluoro-2-methyl-phenyl)-2,3-dihydro-2,6'-dioxo-spiro[indole-3,3'-piperidine]-1-carboxylic acid tert-butyl ester

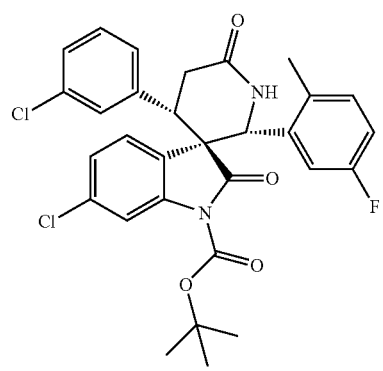

M. W. 569.47 $C_{30}H_{27}Cl_2FN_2O_4$

To a mixture of racemic (2'R,3R,4'S)-6-chloro-4'-(3-chlorophenyl)-2'-(5-fluoro-2-methyl-phenyl)-spiro[3H-indole-3,3'-piperidine]-2,6'(1H)-dione (300 mg, 0.64 mmol) prepared in example 36c in dichloromethane (30 mL) was added 4-dimethylaminopyridine (94 mg, 0.77 mmol) and di-tert-butyl-dicarbonate (153 mg, 0.71 mmol). The mixture was stirred at room temperature for 30 min, and then purified by column chromatography to give racemic (2'R,3R,4'S)-6-chloro-4'-(3-chlorophenyl)-2'-(5-fluoro-2-methyl-phenyl)-2,3-dihydro-2,6'-dioxo-spiro[indole-3,3'-piperidine]-1-carboxylic acid tert-butyl ester as solid (350 mg, 96%).

EXAMPLE 164b

Preparation of intermediate racemic (2'R,3R,4'S)-(2-bromomethyl-5-fluoro-phenyl)-6-chloro-4'-(3-chlorophenyl)-2'-2,3-dihydro-2,6'-dioxo-spiro[indole-3,3'-piperidine]-1-carboxylic acid tert-butyl ester

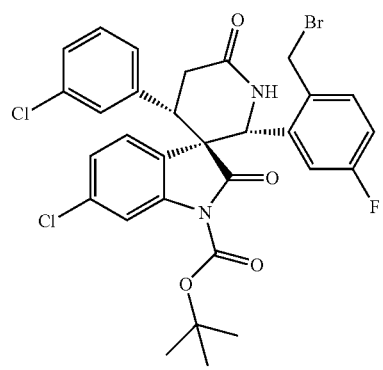

M. W. 648.36 $C_{30}H_{26}BrCl_2FN_2O_4$

To a solution of racemic (2'R,3R,4'S)-6-chloro-4'-(3-chlorophenyl)-2'-(5-fluoro-2-methyl-phenyl)-2,3-dihydro-2,6'-dioxo-spiro[indole-3,3'-piperidine]-1-carboxylic acid tert-butyl ester (900 mg, 1.58 mmol) in carbon tetrachloride (20 mL) was added benzoyl peroxide (380 mg, 1.58 mmol) and NBS (280 mg, 1.58 mmol). The mixture was heated under microwave irradiation at 100° C. for 30 min, then purified by column chromatography to give racemic (2'R,3R,4'S)-(2-bromomethyl-5-fluoro-phenyl)-6-chloro-4'-(3-chlorophenyl)-2'-2,3-dihydro-2,6'-dioxo-spiro[indole-3,3'-piperidine]-1-carboxylic acid tert-butyl ester as solid (170 mg, 16%). The starting material racemic (2'R,3R,4'S)-6-chloro-4'-(3-chlorophenyl)-2'-(5-fluoro-2-methyl-phenyl)-2,3-dihydro-2,6'-dioxo-spiro[indole-3,3'-piperidine]-1-carboxylic acid tert-butyl ester (550 mg, 0.96 mmol) was recovered.

EXAMPLE 164c

Preparation of racemic (2'R,3R,4'S)-2'-[2-(4-aminocarbonyl-piperidin-1-yl)methyl-5-fluoro-phenyl)-6-chloro-4'-(3-chlorophenyl)-spiro[3H-indole-3,3'-piperidine]-2,6'(1H)-dione

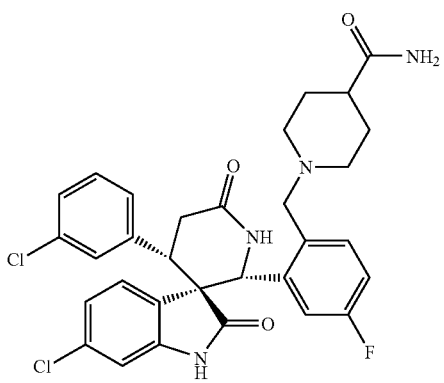

M. W. 595.51 $C_{31}H_{29}Cl_2FN_4O_3$

To a solution of racemic (2'R,3R,4'S)-(2-bromomethyl-5-fluoro-phenyl)-6-chloro-4'-(3-chlorophenyl)-2'-2,3-dihydro-2,6'-dioxo-spiro[indole-3,3'-piperidine]-1-carboxylic acid tert-butyl ester (30 mg, 0.046 mmol) prepared inexample 164b in acetonitrile (5 mL) was added K₂CO₃ (13 mg, 0.094 mmol) and piperidine-4-carboxylic acid amide (12 mg, 0.094 mmol). The mixture was refluxed for 2 h, then concentrated. The residue was purified by prep-HPLC to give racemic (2'R,3R,4'S) 2'-[2-(4-aminocarbonyl-piperidin-1-yl)methyl-5-fluoro-phenyl)-6-chloro-4'-(3-chlorophenyl)-spiro[3H-indole-3,3'-piperidine]-2,6'(1H)-dione as solid (2.6 mg,).

MS m/z [(M+H)⁺]: 595

EXAMPLE 165

Preparation of racemic (2'R,3R,4'S)-6-chloro-4'-(3-chlorophenyl)-2'-[5-fluoro-2-(4-methanesulfonyl-piperazin-1-yl)methyl-phenyl]-spiro[3H-indole-3,3'-piperidine]-2,6'(1H)-dione

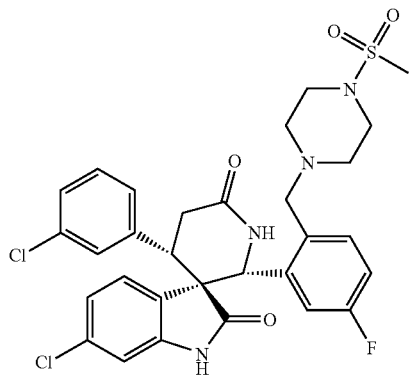

M. W. 631.56 $C_{30}H_{29}Cl_2FN_4O_4S$

To a solution of racemic (2'R,3R,4'S)-2'-(2-bromomethyl-5-fluoro-phenyl)-6-chloro-4'-(3-chlorophenyl)-2,3-dihydro-2,6'-dioxo-spiro[indole-3,3'-piperidine]-1-carboxylic acid tert-butyl ester (30 mg, 0.046 mmol) prepared in example 164b in acetonitrile (5 mL) was added K₂CO₃ (13 mg, 0.094 mmol) and 1-methanesulfonyl-piperazine (15 mg, 0.094 mmol). The mixture was refluxed for 2 h, concentrated. The residue was dissolved in trifluoroacetic acid and stirred at room temperature for 30 min, then concentrated and purified by prep-HPLC to give (2'R,3R,4'S)-6-chloro-4'-(3-chlorophenyl)-2'-[5-fluoro-2-(4-methanesulfonyl-piperazin-1-yl)methyl-phenyl]-spiro[3H-indole-3,3'-piperidine]-2,6'(1H)-dione as solid (5 mg, 17%).

EXAMPLE 166

Preparation of racemic (2'R,3R,4'S)-6-chloro-4'-(3-chlorophenyl)-2'-{5-fluoro-2-[(1-methanesulfonyl-piperidin-4-yl)carbonylamino-methyl]-phenyl}-spiro[3H-indole-3,3'-piperidine]-2,6'(1H)-dione

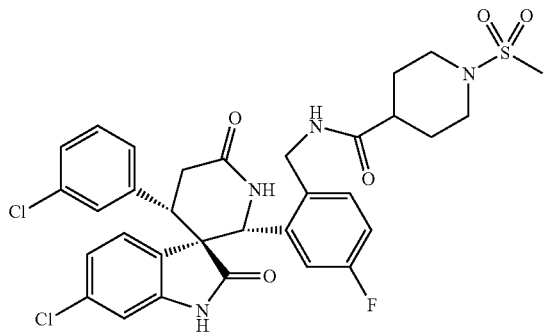

M. W. 673.6 $C_{32}H_{31}Cl_2FN_4O_5S$

To aqueous ammonia solution (17%, 2 mL, ~20 mmol) was added a solution of racemic (2'R,3R,4'S)-(2-bromomethyl-5-fluoro-phenyl)-6-chloro-4'-(3-chlorophenyl)-2'-2,3-dihydro-2,6'-dioxo-spiro[indole-3,3'-piperidine]-1-carboxylic acid tert-butyl ester (40 mg, 0.06 mmol) prepared in example 164b in N,N-dimethylformamide (2 mL). The mixture was stirred at room temperature for 2 h, followed by addition of EtOAc (20 mL). The organic phase was separated and washed by water, dried over $Na_2SO_4$. The solvent was removed in vacuo, and the residue was dissolved in dichloromethane. Then 1-methanesulfonyl-piperidine-4-carboxylic acid (20 mg) dimethylaminepiperidine (25 mg) and EDCI (40 mg) were added to the solution. The mixture was stirred at room temperature for 2 h, then diluted with dichloromethane, washed by aqueous HCl solution (1N, 10 mL), water (10 mL), dried over $Na_2SO_4$. The organic layer was separated, concentrated and the residue was purified by preparative HPLC to give the titled compound as solid (12 mg).

MS m/z [(M+H)$^+$]: 673

EXAMPLE 167a

Preparation of intermediate 6-fluoro-1,3-dihydro-indol-2-one

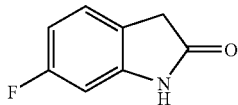

M. W. 151.14 $C_8H_6FNO$

To a mixture of NaH (60%, 7 g, 0.16 mol) in dimethyl sulfoxide (150 mL) was added dropwise dimethyl malonate (20 mL, 0.16 mol). The mixture was heated to 100° C. for 10 min then cooled to room temperature, followed by the addition of 2,5-difluoronitrobenzene (14 g, 0.08 mol). After stirred at 90° C. for 2 h, the mixture was cooled and poured into 5% aq.HCl with ice cooling. EtOAc (50 mL) was added and the organic phase was separated, washed by water and dried with $Na_2SO_4$. The solvent was removed in vacuo to give 2-(4-fluoro-2-nitro-phenyl)-malonic acid dimethyl ester (19.4 g). 2-(4-fluoro-2-nitro-phenyl)-malonic acid dimethyl ester (6 g, 22 mmol) was dissolved in glacial acetic acid (30 mL), the aqueous HCl (6N, 30 mL) was added and the reaction mixture were heated ar refluxing for 4 h, Iron power (5 g, 88 mmol) was added portionwise to the mixture and the refluxing was allowed to continue for another 2 h. The solvent was removed in vacuo and the remaining residue was extracted by EtOAc. The organic phase washed with aqueous HCl (1N), brine and dried over $Na_2SO_4$. concentrated to give the titled compound as a yellow solid (3 g, 89%).

MS m/z (M+H)$^+$: 152

EXAMPLE 167b

Preparation of intermediate E/Z-6-fluoro-3-(3-chloro-benzylidene)-1,3-dihydro-indol-2-one

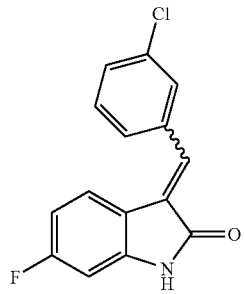

M. W. 273.70 $C_{15}H_9ClFNO$

To the mixture of 6-fluorooxindole (13.9 g, 92 mmol) and 3-chloro-benzaldehyde (12.9 g, 92 mmol) in methanol (109 mL) was added pyrrolidine (6.55 g, 92 mmol) dropwise. The mixture was then heated at 65° C. for 3 h. After cooled to 4° C., the mixture was filtered and resulting precipitate was collected, dried to give a mixture of E/Z-6-fluoro-3-(3-chloro-benzylidene)-1,3-dihydro-indol-2-one as a bright yellow solid (Yield 17.5 g, 64%).

MS m/z (M+H)$^+$: 274

EXAMPLE 167c

Preparation of chiral (2'R,3R,4'S)-4'-(3-chlorophenyl)-6-fluoro-2'-(5-fluoro-2-methylphenyl)spiro[3H-indole-3,3'-piperidine]-2,6'(1H)-dione

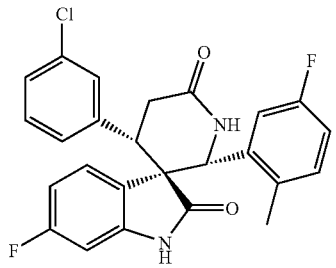

M. W. 452.89 $C_{25}H_{19}ClF_2N_2O_2$

In a manner similar to the method described in example 1c, E/Z-6-fluoro-3-(3-chloro-benzylidene)-2-oxo-2,3-dihydro-indole (0.4 g, 1.10 mmol) prepared in example 167b was reacted with 1-(5-fluoro-2-methylphenyl)-3-trimethylsilyoxy-2-aza-1,3-butadiene prepared in example 36a, in toluene to give racemic (2'R,3R,4'S)-4'-(3-chlorophenyl)-6-fluoro-2'-(5-fluoro-2-methylphenyl)spiro[3H-indole-3,3'-piperidine]-2,6'(1H)-dione as a white solid (Yield 0.1 g). The racemic (2'R,3R,4'S)-4'-(3-chlorophenyl)-6-fluoro-2'-(5-fluoro-2-methylphenyl)spiro[3H-indole-3,3'-piperidine]-2,6'(1H)-dione was separated by chiral column chromatography to give the titled compounds as a white solid.

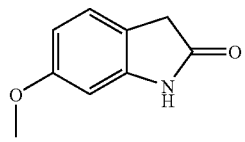

MS m/z (M+H)$^+$: 453

EXAMPLE 168a

Preparation of intermediate 6-methoxy-1,3-dihydro-indol-2-one

M. W. 163.18 $C_9H_9NO_2$

In a manner similar to the method described in example 167a, 1-chloro-4-methoxy-2-nitro-benzene (19 g, 0.1 mol) was reacted with dimethyl malonate (16 g, 0.2 mol), NaH and iron power to give 6-methoxy-1,3-dihydro-indol-2-one (3 g, 18%).

MS m/z (M+H)$^+$: 164

EXAMPLE 168b

Preparation of intermediate E/Z-6-methoxy-3-(3-chloro-benzylidene)-1,3-dihydro-indol-2-one

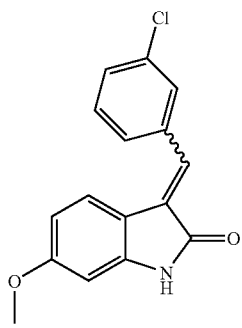

M. W. 285.73 $C_{16}H_{12}ClNO_2$

To the mixture of 6-methoxyoxindole (1.60 g, 10 mmol) and 3-chloro-benzaldehyde (1.4 g, 10 mmol) in methanol (10 mL) was added pyrrolidine (0.82 mL, 10 mmol) dropwise. The mixture was then heated at 65° C. for 3 h. After cooled to 4° C., the mixture was filtered and resulting precipitate was collected, dried to give a mixture of E/Z-6-methoxy-3-(3-chloro-benzylidene)-1,3-dihydro-indol-2-one as a bright yellow solid (Yield 1.7 g, 60%).

MS m/z (M+H)$^+$: 286

EXAMPLE 168c

Preparation of racemic (2'R,3R,4'S)-4'-(3-chlorophenyl)-2'-(5-fluoro-2-methylphenyl)-6-methoxy spiro[3H-indole-3,3'-piperidine]-2,6'(1H)-dione

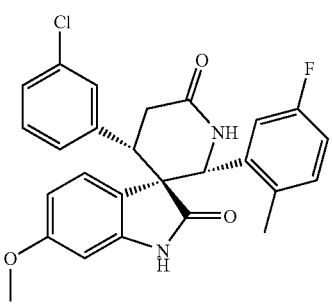

M. W. 464.93 $C_{26}H_{22}ClFN_2O_3$

In a manner similar to the method described in example 1c, E/Z-6-methoxy-3-(3-chloro-benzylidene)-2-oxo-2,3-dihydro-indole (0.4 g, 1.10 mmol) prepared in example 168b was reacted with 1-(5-fluoro-2-methylphenyl)-3-trimethylsilyoxy-2-aza-1,3-butadiene prepared in example 36a, in toluene to give racemic (2'R,3R,4'S)-4'-(3-chlorophenyl)-2'-(5-fluoro-2-methylphenyl)-6-methoxy spiro[3H-indole-3,3'-piperidine]-2,6'(1H)-dione as a white solid (Yield 0.05 g, 10%).

MS m/z (M+H)$^+$: 465

EXAMPLE 169a

Preparation of intermediate E/Z-3-(3-chloro-benzylidene)-1,3-dihydro-indol-2-one

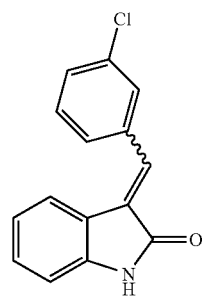

M. W. 255.71 $C_{15}H_{10}ClNO$

To the mixture of oxindole (2.66 g, 20 mmol) and 3-chloro-benzaldehyde (2.81 g, 20 mmol) in methanol (20 mL) was added pyrrolidine (1.65 mL, 20 mmol) dropwise. The mixture was then heated at 65° C. for 3 h. After cooled to 4° C., the mixture was filtered and resulting precipitate was collected, dried to give a mixture of E/Z-3-(3-chloro-benzylidene)-1,3-dihydro-indol-2-one as a bright yellow solid (Yield 4 g, 78%).

MS m/z (M+H)$^+$: 256

EXAMPLE 169b

Preparation of racemic (2'R,3R,4'S)-4'-(3-chlorophenyl)-2'-(5-fluoro-2-methylphenyl)spiro[3H-indole-3,3'-piperidine]-2,6'(1H)-dione

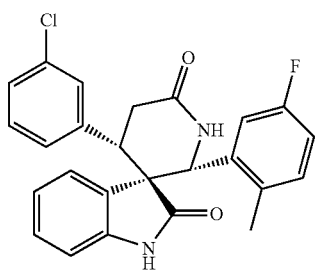

M. W. 434.90 $C_{25}H_{20}ClFN_2O_2$

In a manner similar to the method described in example 1c, E/Z-3-(3-chloro-benzylidene)-2-oxo-2,3-dihydro-indole (0.4 g, 1.10 mmol) prepared in example 169a was reacted with 1-(5-fluoro-2-methylphenyl)-3-trimethylsilyoxy-2-aza-1,3-butadiene prepared in example 36a, in toluene to give racemic (2'R,3R,4'S)-4'-(3-chlorophenyl)-2'-(5-fluoro-2- methylphenyl)spiro[3H-indole-3,3'-piperidine]-2,6'(1H)-dione as a white solid (Yield 0.08 g, 15%).

MS m/z (M+H)+: 435

EXAMPLE 170a

Preparation of intermediate
5-fluoro-1,3-dihydro-indol-2-one

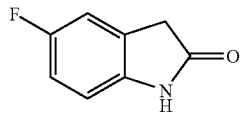

M. W. 151.14 C8H6FNO

To the solution of 3-fluorophenylacetic acid (1.23 g, 8 mmol) in concentrated H2SO4 (2.0 mL, 40 mmol) at 0° C. was added HNO3 (0.374 mL, 8 mmol) slowly. The resulting reaction mixture was stirred under argon for 2 h at 0° C., and poured into ice-water. The white solid was precipitated, and the aqueous phase was extracted with ethyl acetate. The organic phase was washed with brine, dried with Na2SO4, and concentrated. The crude (5-fluoro-2-nitro-phenyl)-acetic acid was dissolved in acetic acid. To the solution was added iron power (1.79 g, 32 mmol). The reaction mixture was stirred and heated at reflux for 2 h. Then the mixture was concentrated in vacuo. The residue was extracted with ethyl acetate, and The organic layer was separated, washed by aqueous HCl (1N), brine, dried over Na2SO4, concentrated in vacuo to give the desired product (1 g, 82%).

MS m/z (M+H)+: 152

EXAMPLE 170b

Preparation of intermediate E/Z-5-fluoro-3-(3-chloro-benzylidene)-1,3-dihydro-indol-2-one

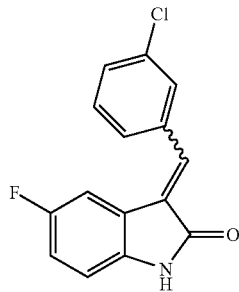

M. W. 273.70 C15H9ClFNO

To the mixture of 5-fluorooxindole (3.00 g, 20 mmol) and 3-chloro-benzaldehyde (2.8 g, 20 mmol) in methanol (20 mL) was added pyrrolidine (1.72 mL, 10 mmol) dropwise. The mixture was then heated at 65° C. for 3 h. After cooled to 4° C., the mixture was filtered and resulting precipitate was collected, dried to give a mixture of E/Z-5-fluoro-3-(3-chloro-benzylidene)-1,3-dihydro-indol-2-one as a bright yellow solid (Yield 1.7 g, 30%).

MS m/z (M+H)+: 274

EXAMPLE 170c

Preparation of racemic (2'R,3R,4'S)-4'-(3-chlorophenyl)-5-fluoro-2'-(5-fluoro-2-methylphenyl)spiro[3H-indole-3,3'-piperidine]-2,6'(1H)-dione

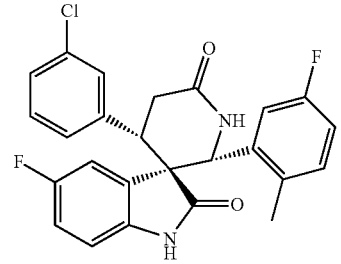

M. W. 452.89 C25H19ClF2N2O2

In a manner similar to the method described in example 1c, E/Z-5-fluoro-3-(3-chloro-benzylidene)-2-oxo-2,3-dihydro-indole (0.4 g, 1.10 mmol) prepared in example 170b was reacted with 1-(5-fluoro-2-methylphenyl)-3-trimethylsilyoxy-2-aza-1,3-butadiene prepared in example 36a, in toluene to give racemic (2'R,3R,4'S)-4'-(3-chlorophenyl)-5-fluoro-2'-(5-fluoro-2-methylphenyl)spiro[3H-indole-3,3'-piperidine]-2,6'(1H)-dione as a white solid (Yield 2 g, 41%).

MS m/z (M+H)+: 453

EXAMPLE 171a

Preparation of intermediate racemic (2'R,3R,4'S)-6-chloro-4'-(3-chlorophenyl)-2'-isopropenyl-2,6'-dioxospiro[indole-3,3'-piperidine]-1-carboxylic acid tert-butyl ester

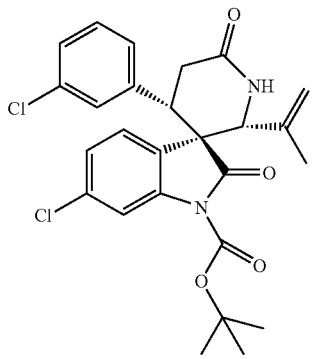

M. W. 501.41 C26H26Cl2N2O2

To a solution of racemic (2'R,3R,4'S)-6-chloro-4'-(3-chlorophenyl)-2'-(1-methylene-propyl)spiro[3H-indole-3,3'-piperidine]-2,6'(1H)-dione (0.4 g, 1 mmol) prepared in example 87c in dichloromethane (10 mL) at 0° C. was added di-tert-butyl-dicarbonate (0.47 g, 2 mmol), followed by the addition of 4-dimethylaminopyridine (0.29 g, 2.4 mmol). The reaction mixture was stirred at room temperature for 1 h, then poured into ice-water. The organic layer was separated, washed by aqueous HCl (0.5 N), dried over Na2SO4, concentrated to give racemic (2'R,3R,4'S)-6-chloro-4'-(3-chlorophenyl)-2'-isopropenyl-2,6'-dioxospiro[indole-3,3'-piperidine]-1-carboxylic acid tert-butyl ester as a white solid. (Yield 0.47 g, 95%).

MS m/z (M+H)+: 501

EXAMPLE 171b

Preparation of chiral (2'R,3R,4'S)-6-chloro-4'-(3-chloro-phenyl)-2'-(1-methyl-cyclopropyl)spiro[3H-indole-3,3'-piperidine]-2,6'(1H)-dione

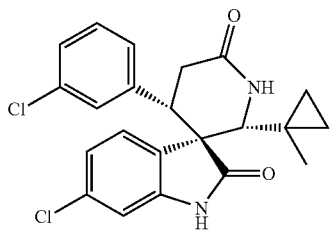

M. W. 415.32 $C_{22}H_{20}Cl_2N_2O_2$

To a solution of $CH_2I_2$ (1.2 g, 4.6 mmol) in anhydrous toluene (5 mL) under Argon at 0° C. was added a toluene solution of $Et_2Zn$ (1.1M, 3.3 ml, 3.67 mmol). The mixture was stirred for 15 min, then a toluene solution (10 mL) of racemic (2'R,3R,4'S)-6-chloro-4'-(3-chlorophenyl)-2'-isopropenyl-2,6'-dioxospiro[indole-3,3'-piperidine]-1-carboxylic acid tert-butyl ester (230 mg, 0.46 mmol) prepared in example 171a was added. The reaction mixture was stirred at room temperature for 3 h, then quenched with aqueous saturated $NH_4Cl$ (20 mL). The organic layer was separated, and the aqueous layer was extracted with ethyl acetate. The organic layers were combined, dried over $Na_2SO_4$ and concentrated to give racemic (2'R,3R,4'S)-6-chloro-4'-(3-chlorophenyl)-2'-(1-methyl-cyclopropyl)spiro[3H-indole-3,3'-piperidine]-2,6'(1H)-dione as a white solid (162 mg). Then racemic (2'R,3R,4'S)-6-chloro-4'-(3-chloro-phenyl)-2'-(1-methyl-cyclopropyl)spiro[3H-indole-3,3'-piperidine]-2,6'(1H)-dione by chiral SFC to give chiral (2'R,3R,4'S)-6-chloro-4'-(3-chloro-phenyl)-2'-(1-methyl-cyclopropyl)spiro[3H-indole-3,3'-piperidine]-2,6'(1H)-dione as a white solid (50 mg).

HRMS (ES⁺) m/z Calcd for $C_{22}H_{20}Cl_2N_2O_2$+H [(M+H)⁺]: 415.0975 Found: 415.0975.

EXAMPLE 172a

Preparation of intermediate E/Z-6-Bromo-3-(3-chloro-benzylidene)-2-oxo-2,3-dihydro-indole-1-carboxylic acid tert-butyl ester

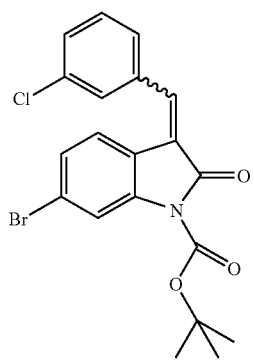

M. W. 434.72 $C_{20}H_{17}BrClNO_3$

In a manner similar to the method described in example 24a, E/Z-6-bromo-3-(3-chloro-benzylidene)-1,3-dihydro-indol-2-one (2.4 g, 7.2 mmol) prepared in example 157a was reacted with di-tert-butyl-dicarbonate (1.86 g, 10 mmol) and 4-dimethylaminopyridine (1.46 g, 12 mmol) to give E/Z-6-bromo-3-(3-chloro-benzylidene)-2-oxo-2,3-dihydro-indole-1-carboxylic acid tert-butyl ester as a yellow solid (Yield 1.5 g, 48%).

MS m/z (M+H)⁺: 434

EXAMPLE 172b

Preparation of racemic (2'R,3R,4'S)-6-bromo-4'-(3-chlorophenyl)-2'-isopropenylspiro[3H-indole-3,3'-piperidine]-2,6'(1H)-dione

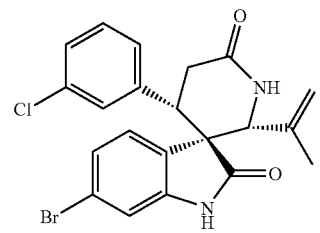

M. W. 445.75 $C_{21}H_{18}BrClN_2O_2$

In a manner similar to the method described in example 41b, E/Z-6-bromo-3-(3-chloro-benzylidene)-2-oxo-2,3-dihydro-indole-1-carboxylic acid tert-butyl ester (5 g, 12.8 mmol) prepared in example 172a was reacted with 1-isopropenyl-3-trimethylsilyoxy-2-aza-1,3-butadiene prepared in example 87b in toluene, then treated with trifluoroacetic acid to give racemic (2'R,3R,4'S)-6-bromo-4'-(3-chlorophenyl)-2'-isopropenylspiro[3H-indole-3,3'-piperidine]-2,6'(1H)-dione as a yellow solid (Yield 2.2 g, 40%).

MS m/z (M+H)⁺: 445

EXAMPLE 173a

Preparation of racemic (2'R,3R,4'S)-6-bromo-4'-(3-chlorophenyl)-2'-isopropenyl-2,6'-dioxospiro[indole-3,3'-piperidine]-1-carboxyl acid tert-butyl ester

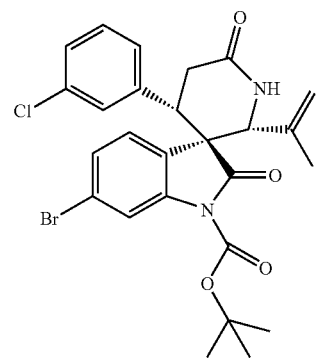

M. W. 545.87 $C_{26}H_{26}BrClN_2O_4$

In a manner similar to the method described in example 171a, racemic (2'R,3R,4'S)-6-bromo-4'-(3-chlorophenyl)-2'-isopropenylspiro[3H-indole-3,3'-piperidine]-2,6'(1H)-dione (0.45 g, 1 mmol) prepared in example 172b was reacted with ditert-butyl-dicarbonate (0.24 g, 1 mmol) and 4-dimethylaminopyridine (0.15 g, 1.2 mmol) to give racemic (2'R,3R,4'S)-6-bromo-4'-(3-chlorophenyl)-2'-isopropenyl-2,6'-dioxospiro[indole-3,3'-piperidine]-1-carboxyl acid tert-butyl ester as a white solid (Yield 0.49 g, 90%).

MS m/z (M+H)+: 545

EXAMPLE 173b

Preparation of chiral (2'R,3R,4'S)-6-bromo-4'-(3-chloro-phenyl)-2'-(1-methyl-cyclopropyl)spiro[3H-indole-3,3'-piperidine]-2,6'(1H)-dione

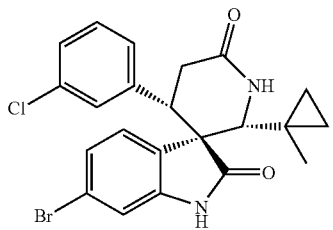

M. W. 459.77 $C_{22}H_{20}BrClN_2O_2$

In a manner similar to the method described in example 171b, racemic (2'R,3R,4'S)-6-bromo-4'-(3-chlorophenyl)-2'-isopropenyl-2,6'-dioxospiro[indole-3,3'-piperidine]-1-carboxyl acid tert-butyl ester (250 mg, 0.46 mmol) prepared in example 173a was reacted with $CH_2I_2$ (1.2 g, 4.6 mmol) and $Et_2Zn$ (3.3 ml, 3.67 mmol) to give racemic (2'R,3R,4'S)-6-bromo-4'-(3-chloro-phenyl)-2'-(1-methyl-cyclopropyl)spiro[3H-indole-3,3'-piperidine]-2,6'(1H)-dione as a white solid (Yield 183 mg, 87%). The racemic (2'R,3R,4'S)-6-bromo-4'-(3-chloro-phenyl)-2'-(1-methyl-cyclopropyl)spiro[3H-indole-3,3'-piperidine]-2,6'(1H)-dione was separated by chiral column chromatography to give chiral (2'R,3R,4'S)-6-bromo-4'-(3-chloro-phenyl)-2'-(1-methyl-cyclopropyl)spiro[3H-indole-3,3'-piperidine]-2,6'(1H)-dione as white solid (15 mg).

MS m/z (M+H)+: 459

EXAMPLE 174

Preparation of racemic (2'R,3R,4'S)-4'-(3-chlorophenyl)-6-ethynyl-2'-isopropenylspiro[3H-indole-3,3'-piperidine]-2,6'(1H)-dione

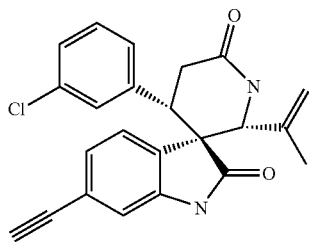

M. W. 390.87 $C_{23}H_{17}ClN_2O_2$

A mixture of racemic (2'R,3R,4'S)-6-bromo-4'-(3-chlorophenyl)-2'-isopropenyl-2,6'-dioxospiro[indole-3,3'-piperidine]-1-carboxylic acid tert-butyl ester-1,3-dihydro-indole-2-one (54 mg, 0.1 mmol) prepared in example 173a, $Pd(PPh_3)_4$ (20 mg, 0.02 mmol), $K_3PO_4$ (110 mg, 0.5 mmol), dimethyl trimethylsilylethynylborate (1 mL, 0.5 M, 0.5 mmol) in toluene (3 mL) was heated under microwave irradiation at 130° C. for 1 hour. The solvent was removed in vacuo. To the residue was added methanol (3 mL) and aqueous NaOH (2 N, 3 mL). The mixture was stirred at room temperature for 2 h. The solvent was removed in vacuo, the residue was diluted with ethyl acetate (20 mL), washed with brine, saturated $NH_4Cl$, brine, then organic layer was separated, and concentrated. The residue was purified by preparative HPLC to give racemic (2'R,3R,4'S)-4'-(3-chlorophenyl)-6-ethynyl-2'-isopropenylspiro[3H-indole-3,3'-piperidine]-2,6'(1H)-dione (2 mg).

Dimethyl trimethylsilylethynylborate solution was prepared according to literature procedure in Lutzen, L. et al Synthesis, 2006, No 3, 519-527

EXAMPLE 175

Preparation of chiral (2'R,3R,4'S)-6-chloro-4'-(chlorophenyl)-2'-(5-fluoro-2-methylphenyl)-1'-[(1-methylsulphonyl-4-piperidinyl)aminocarbonyl-methyl]spiro[3H-indole-3,3'-piperidine]-2,6'(1H)-dione

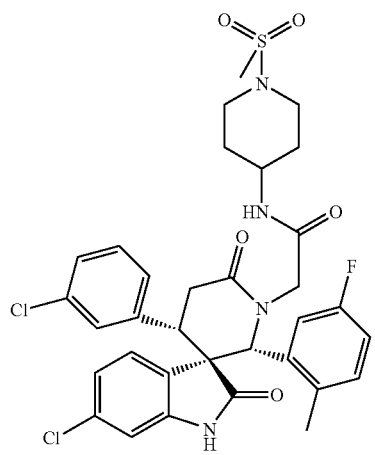

M. W. 687.62 $C_{33}H_{33}Cl_2FN_4O_5S$

The 1-methanesulfonyl-piperidin-4-ylamine trifluoroacetic acid salt (111 mg, 0.38 mmol) was stirred with N-methyl morpholine (208 uL, 1.9 mmol) and DMAP (3 mg) in DMF (2 ml) for 5 min to obtain a clear solution. A solution of racemic (2'R,3R,4'S)-6-chloro-4'-(3-chlorophenyl)-1'-[(fluorocarbonyl)-methyl]-2'-(5-fluoro-2-methylphenyl)spiro[3H-indole-3,3'-piperidine]-2,6'(1H)-dione (0.1 g, 0.18 mmol) prepared in example 57a in DMF (1 mL) was added and the mixture was heated in a microwave oven for 15 min at 100° C. The mixture was poured into water and was extracted with EtOAc (4×). The organic layer was washed with water, brine, dried and concentrated to give a yellow residue which was purified by a 12 g silica gel column eluted with 0-5% MeOH in methylene chloride. A white powder (74.3 mg, 60% yield) was obtained as desired racemic mixture. This was separated into two optically pure enantiomeric compounds (24 mg each) by chiral SFC using 30% methanol.

MS m/z (M+H)+: 687

EXAMPLE 176a

Preparation of intermediate 4-[2-(1,1-Dioxo-isothiazolidin-2-yl)-ethyl]-piperazine-1-carboxylic acid tert-butyl ester

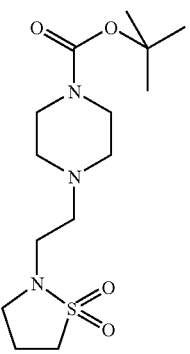

M. W. 333.45 $C_{14}H_{27}N_3O_4S$

To a stirred solution of 1-Boc-4-(2-aminoethyl)-piperazine (1.26 g, 6.8 mmol) and triethylamine (1 mL) in THF (10 ML), 3-chloro-propylsulfonyl chloride (Aldrich, 0.68 mL, 6.94 mmol) was added slowly at room temperature. The mixture was stirred for 30 minutes at and the reaction was quenched with water. The new mixture was extracted with ethyl acetate and the extracts were combined and dried ($Na_2SO_4$). The solution was concentrated and the residue was dissolved in THF (20 mL) and $Cs_2CO_3$ (500 mg), NaI (80 mg) were added and the mixture was stirred at reflux overnight. The mixture was cooled to room temperature and poured into water. The new mixture was extracted with ethyl acetate (3×15 mL) and the extracts were combined and dried ($Na_2SO_4$). Removal of the solvent on a rotary evaporator gave a solid. 2.01 g.

MS m/z (M+H)$^+$: 334

EXAMPLE 176b

Preparation of intermediate 1-[2-(1,1-dioxo-isothiazolidin-2-yl)-ethyl]-piperazine di-trifluoroacetic acid

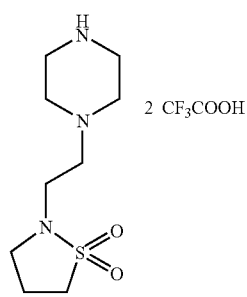

M. W. 233.33 $C_9H_{19}N_3O_2S$

4-[2-(1,1-dioxo-isothiazolidin-2-yl)-ethyl]-piperazine-1-carboxylic acid tert-butyl ester (2.01 g) was treated with 30% TFA/$CH_2Cl_2$ (10 mL) and the mixture was stirred at room temperature for 30 min. The solvent was removed under reduced pressure to give a solid. 2.46 g.

MS m/z (M+H)$^+$: 234

EXAMPLE 176c

Preparation of chiral (2'R,3R,4'S)-6-chloro-4'-(3-chlorophenyl)-2'-(5-fluoro-2-methyl phenyl)-1'-{[4-(1,1-dioxido-2-isothiazolidinyl)ethyl]piperazinyl-carbonyl-methyl}spiro[3H-indole-3,3'-piperidine]-2,6'(1H)-dione

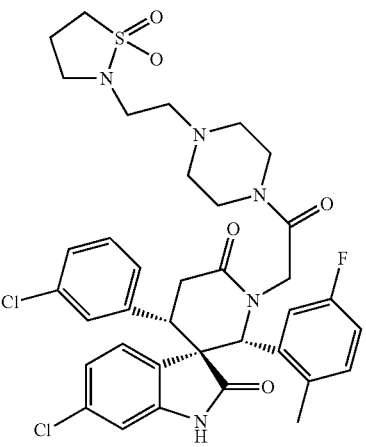

M. W. 742.70 $C_{36}H_{38}Cl_2FN_5O_5S$

In a manner similar to the method described in example 175, racemic (2'R,3R,4'S)-6-chloro-4'-(3-chlorophenyl)-1'-[(fluorocarbonyl)-methyl]-2'-(5-fluoro-2-methylphenyl) spiro[3H-indole-3,3'-piperidine]-2,6'(1H)-dione (0.1 g, 0.18 mmol) prepared in example 57a was reacted with 1-[2-(1,1-dioxo-isothiazolidin-2-yl)-ethyl]-piperazine di-trifluoroacetic acid prepared in example 176b and chiral SFC separation to give chiral (2'R,3R,4'S)-6-chloro-4'-(3-chlorophenyl)-2'-(5-fluoro-2-methyl phenyl)-1'-{[4-(1,1-dioxido-2-isothiazolidinyl)ethyl]piperazinyl-carbonyl-methyl}spiro[3H-indole-3,3'-piperidine]-2,6'91H)-dione.

MS m/z (M+H)$^+$: 742

EXAMPLE 177

Preparation of chiral (2'R,3R,4'S)-6-chloro-4'-(3-chlorophenyl)-2'-(5-fluoro-2-methylphenyl)-1'-{[3-(methylsulphonyl)propyl]piperazinyl-carbonyl-methyl}spiro[3H-indole-3,3'-piperidine]-2,6'(1H)-dione

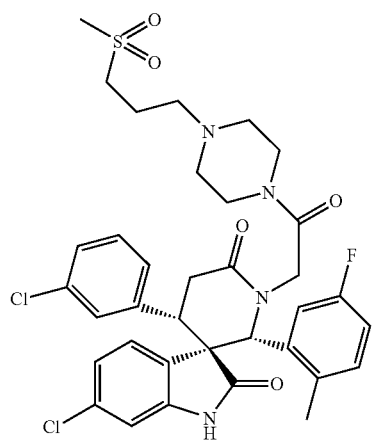

M. W. 715.68 C$_{35}$H$_{37}$Cl$_2$FN$_4$O$_5$S

In a manner similar to the method described in example 176, racemic (2'R,3R,4'S)-6-chloro-4'-(3-chlorophenyl)-1'-[(fluorocarbonyl)-methyl]-2'-(5-fluoro-2-methylphenyl)spiro[3H-indole-3,3'-piperidine]-2,6'(1H)-dione (0.1 g, 0.18 mmol) prepared in example 57a was reacted with 1-[(3-methylsulfonyl)propyl]piperazine dihydrochloride (US23289) and chiral separation to give chiral (2'R,3R,4'S)-6-chloro-4'-(3-chlorophenyl)-2'-(5-fluoro-2-methylphenyl)-1'-{[3-(methylsulphonyl)propyl]piperazinyl-carbonyl-methyl}spiro[3H-indole-3,3'-piperidine]-2,6'(1H)-dione.

MS m/z (M+H)$^+$: 715

EXAMPLE 178a

Preparation of intermediate 1-(2-Bromo-2-fluorophenyl)-3-trimethylsilyoxy-2-aza-1,3-butadiene

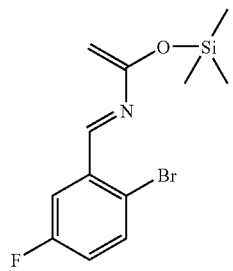

M. W. 316.25 C$_{12}$H$_{15}$BrFNOSi

In a manner similar to the method described in example 1b, 2-bromo-2-fluoro-benzaldehyde (8.1 g, 40 mmol) (Alfa) was used as the starting material in place of 3-chloro-benzaldehyde to react with 1,1,1,3,3,3-hexamethyldisilazane (6.4 g, 40 mmol), n-butyllithium (2.5 M, 16 mL, 40 mmol), trimethylsilyl chloride (4.4 g, 40 mmol), triethylamine (5.6 g, 52 mmol) and acetyl chloride (4.1 g, 52 mmol) to give 1-(2-bromo-2-fluorophenyl)-3-trimethylsilyoxy-2-aza-1,3-butadiene as a yellow gum and used for the next step without further purification.

EXAMPLE 178b

Preparation of racemic (2'R,3R,4'S)-2'-(2-bromo-5-fluorophenyl) 6-chloro-4'-(3-chlorophenyl)spiro[3H-indole-3,3'-piperidine]-2,6'(1H)-dione

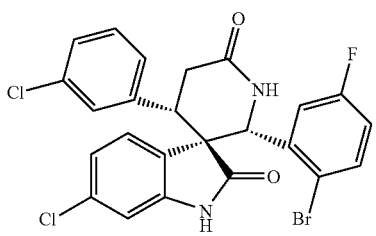

M. W. 534.22 C$_{24}$H$_{16}$BrCl$_2$FN$_2$O$_2$

To a stirred solution of E/Z-6-chloro-3-(3-chloro-benzylidene)-1-(2-trimethylsilanyl-ethoxymethyl)-1,3-dihydro-indole-2-one (3.76 g, 8.13 mmol) prepared in example 55a in toluene (40 mL), 1-(2-bromo-2-fluorophenyl)-3-trimethylsilyoxy-2-aza-1,3-butadiene (10.25 g, 32 mmol) prepared in example 178a was added and the mixture was stirred at reflux for 2.5 h. The reaction mixture was cooled to room temperature and methanol (20 mL) was added. The new mixture was stirred for 1 hr at room temperature and then passed through a short silica gel pad. The column was rinsed with 30% (EtOAc/Hexanes). The solvent was removed and the residue was purified by chromatography on an ISCO machine (0-44% EtOAc/Hexanes, 30 min.) to give a pale yellow solid. 4.22 g.

This solid (1.5 g, 2.12 mmol) was treated with TFA/CH$_2$Cl$_2$ (30%) and the mixture was stirred at room temperature overnight. The solvent was removed and the residue was dissolved in methanol (20 mL). DIPEA (Aldrich, 2 mL) was then added and the mixture was stirred at reflux for 2 h. The solvent was removed and the residue was purified by chromatography on an ISCO machine (25-48% EtOAc/Hexanes, 30 min.) to give an off-white solid. 520 mg.

MS m/z (M+H)$^+$: 534

EXAMPLE 179

Preparation of racemic (2'R,3R,4'S)-2'-6-chloro-4'-(3-chlorophenyl)-(2-ethynyl-5-fluorophenyl)spiro[3H-indole-3,3'-piperidine]-2,6'(1H)-dione

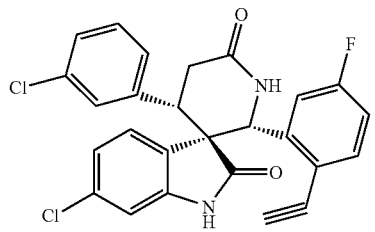

M. W. 479.34 C$_{26}$H$_{17}$Cl$_2$FN$_2$O$_2$

To a stirred solution of racemic (2'R,3R,4'S)-2'-(2-bromo-5-fluorophenyl) 6-chloro-4'-(3-chlorophenyl)spiro[3H-indole-3,3'-piperidine]-2,6'(1H)-dione (120 mg, 0.23 mmol) prepared in example 178b in DMF (2 mL), trimethylsilanyl-acetylene (Aldrich, 88 mg, 0.92 mmol), PdCl$_2$(PPh$_3$)$_2$ (Aldrich, 10 mg) and Et$_3$N (Aldrich, 0.35 mL) were added and the mixture was purged with nitrogen and then heated at 100° C. for 2 h. The solvent was removed under reduced pressure and the residue was dissolved in methanol (5 mL). To the stirred solution, KF (210 mg) was added and the new mixture was stirred at room temperature overnight. The solvent was removed and the residue was purified by chromatography on an ISCO machine (30-40 EtOAc/Hexanes, 30 min.) to give a pale yellow solid. 32 mg.

MS m/z (M+H)$^+$: 479

EXAMPLE 180

Preparation of racemic (2'R,3R,4'S)-2'-6-chloro-4'-(3-chlorophenyl)-{5-fluoro-2-[3-(methanesulfonyl-methyl-amino)-prop-1-ynyl-phenyl]spiro[3H-indole-3,3'-piperidine]-2,6'(1H)-dione

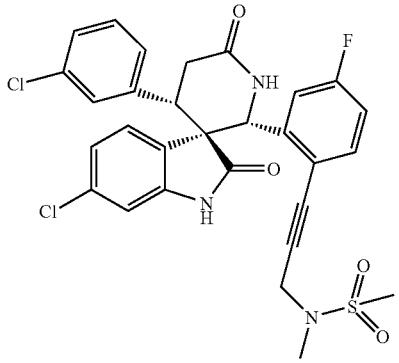

M. W. 600.50 $C_{29}H_{24}Cl_2FN_3O_4S$

To a stirred solution of racemic (2'R,3R,4'S)-2'-(2-bromo-5-fluorophenyl) 6-chloro-4'-(3-chlorophenyl)spiro[3H-indole-3,3'-piperidine]-2,6'(1H)-dione (63 mg, 0.12 mmol) prepared in example 178b in DMF (2 mL), N-methyl-N-prop-2-ynyl-methanesulfonamide (prepared by treatment of the amine chloride with triethylamine, methanesulfonyl chloride, 70 mg, 0.48 mmol), $PdCl_2(PPh_3)_2$ (20 mg) and $Et_3N$ (0.5 mL) were added and the mixture was purged with nitrogen and then heated at 100° C. for 4 h. The solvent was removed under reduced pressure and the residue was purified by chromatography on an ISCO machine (50% EtOAc/hexanes, 30 min.) to give a white solid. 20 mg.

MS m/z (M+H)$^+$: 479

EXAMPLE 181a

Preparation of intermediate 1-[5-bromo-2-(tert-butyl-dimethyl-silanyloxy)-ethoxy]-phenyl]-3-trimethylsi-lyoxy-2-aza-1,3-butadiene

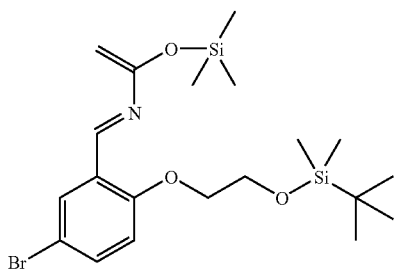

M. W. 472.57 $C_{20}H_{34}BrNO_3Si_2$

In a manner similar to the method described in example 1b, 5-bromo-2-[2-(tert-butyl-dimethyl-silanyloxy)-ethoxy]-benzaldehyde (17.25 g, 48 mmol) prepared in example 130a was reacted with 1,1,1,3,3,3-hexamethyldisilazane (8.28 g, 48 mmol), n-butyllithium (2.5 M, 19.2 mL, 48 mmol), trimethylsilyl chloride (6.07 mL, 48 mmol), triethylamine (8.7 mL, 62.5 mmol) and acetyl chloride (4.53 mL, 62 mmol) to give 1-[2-(tert-butyl-dimethyl-silanyloxy)-ethoxy]-5-chloro-phenyl]-3-trimethylsilyoxy-2-aza-1,3-butadiene as yellow oil and used for the next step without further purification.

EXAMPLE 181b

Preparation of racemic (2'R,3R,4'S)-2'-[5-bromo-2-(2-hydroxyethoxy)-phenyl]-6-chloro-4'-(3-chlorophenyl)spiro[3H-indole-3,3'-piperidine]-2,6'(1H)-dione

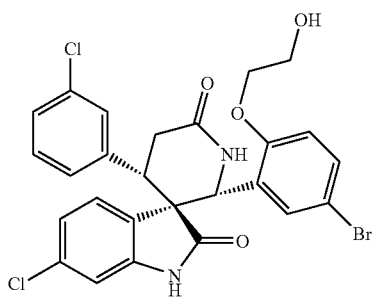

M. W. 576.28 $C_{26}H_{21}BrCl_2N_2O_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (2.5 g, 6.4 mmol) was reacted with 1-[5-bromo-2-(tert-butyl-dimethyl-silanyloxy)-ethoxy]-phenyl]-3-trimethylsilyoxy-2-aza-1,3-butadiene prepared in example 181a in toluene and then trifluoroacetic acid in dichloromethane to give racemic (2'R,3R,4'S)-2'-[5-bromo-2-(2-hydroxyethoxy)-phenyl]-6-chloro-4'-(3-chlorophenyl)spiro[3H-indole-3,3'-piperidine]-2,6'(1H)-dione as a solid (1.52 g, 41%).

MS m/z (M+H)$^+$: 576

EXAMPLE 182a

Preparation of racemic (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione

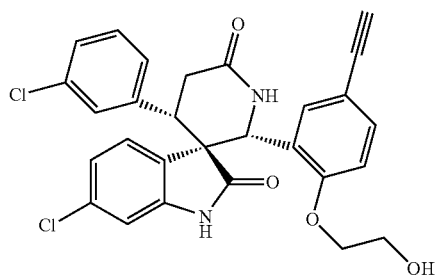

M. W. 521.40 $C_{28}H_{22}Cl_2N_2O_4$

To a solution of racemic (2'R,3R,4'S)-2'-[5-bromo-2-(2-hydroxy-ethoxy)-phenyl]-6-chloro-4'-(3-chlorophenyl)spiro[3H-indole-3,3'-piperidine]-2,6'(1H)-dione (60 mg, 0.11 mmol) prepared in example 181b in DMF (2 mL), $Et_3N$ (0.3 mL), $PdCl_2(Ph_3P)_2$ (Aldrich, 15 mg) were added and the mixture was purged with nitrogen and sealed. The vessel was heated on a microwave reactor for 25 min. and the mixture was poured into water. The mixture was extracted with EtOAc. The extracts were combined and dried with sodium sulfate and dried to give a brown oil, which was purified by chromatography on an ISCO machine (30-100% EtOAc/

Hexanes) to give a foam. 45 mg. The foam was then dissolved in methanol (4 mL) and KF (Aldrich, 53 mg) was added. The mixture was stirred at room temperature overnight. The solvent was removed and the residue was partioned between EtOAc/water. The organic layer was dried and concentrated and the residue was purified by chromatography on ISCO machine (30-100% EtOAc/Hexane) to give an off-white solid. 25 mg.

MS m/z (M+H)$^+$: 521

EXAMPLE 182b

Preparation of chiral (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione

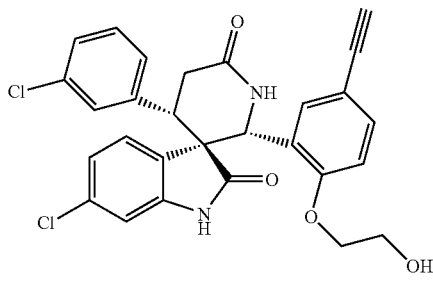

M. W. 521.40 $C_{28}H_{22}Cl_2N_2O_4$

Separation of the two enantiomers from racemic (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione (65 mg) was conducted by chiral SFC to provide chiral (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione as a white solid (Yield: 26.3 mg, 40%) (RO5195715-000) and chiral (2'S,3S,4'R)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione as a white solid (Yield: 25 mg, 38%).

EXAMPLE 183a

Preparation of intermediate [2-(4-bromo-3-fluoro-phenoxy)-ethoxy]-tert-butyl-dimethyl-silane

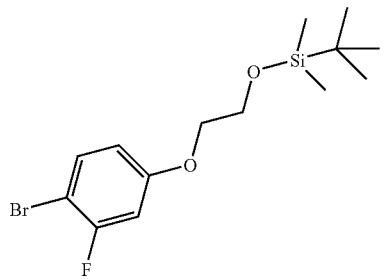

M. W. 349.32 $C_{14}H_{22}BrFO_2Si$

In a manner similar to the method described in example 132a, 4-bromo-3-fluoro-phenol (12 g, 62.3 mmol) was reacted with $K_2CO_3$ (26 g, 188 mmol) and (2-bromo-ethoxy)-tert-butyl-dimethyl-silane (18.0 g, 75.3 mmol) to give [2-(4-bromo-3-fluoro-phenoxy)-ethoxy]-tert-butyl-dimethyl-silane as yellow oil (17.2 g, 77%).

EXAMPLE 183b

Preparation of intermediate 3-bromo-6-[2-(tert-butyl-dimethyl-silanyloxy)-ethoxy]-2-fluoro-benzaldehyde

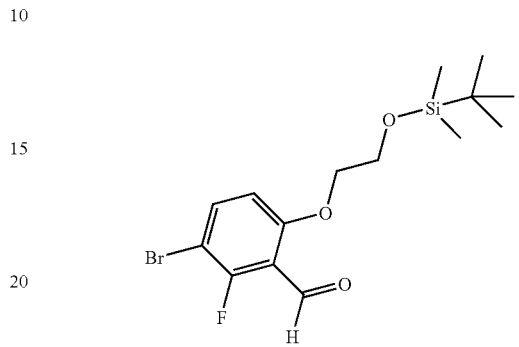

M. W. 377.33 $C_{15}H_{22}BrFO_3Si$

In a manner similar to the method described in example 52a, 1 [2-(4-bromo-3-fluoro-phenoxy)-ethoxy]-tert-butyl-dimethyl-silane (17.2 g, 49.3 mmol) prepared in example 183a was reacted with lithium diisopropyl amide (32.8 mL, 2.0 M in THF, 59.1 mmol), N,N-dimethyl-formamide (4.57 mL, 59.1 mmol) and quenched with acetic acid (12.1 g, 197.2 mmol) and water (61.8 mL) in tetrahydrofuran to give 3-bromo-6-[2-(tert-butyl-dimethyl-silanyloxy)-ethoxy]-2-fluoro-benzaldehyde as white solid (Yield: 12 g, 67%).

EXAMPLE 183c

Preparation of intermediate 1-{3-bromo-6-[2-(tert-butyl-dimethyl-silanyloxy)-ethoxy]-2-fluoro-phenyl}-3-trimethylsilyoxy-2-aza-1,3-butadiene

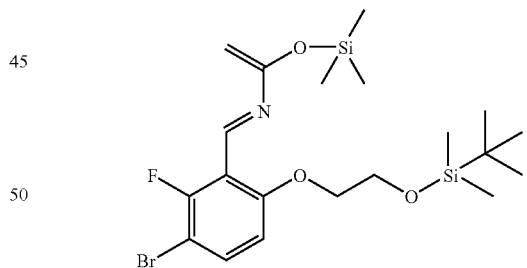

M. W. 490.57 $C_{20}H_{33}BrFNO_3Si_2$

In a manner similar to the method described in example 1b, 3-bromo-6-[2-(tert-butyl-dimethyl-silanyloxy)-ethoxy]-2-fluoro-benzaldehyde (3.96 g, 10.5 mmol) prepared in example 183b was used as the starting material in place of 3-chloro-benzaldehyde to react with 1,1,1,3,3,3-hexamethyl-disilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13 mmol) and acetyl chloride (0.97 mL, 13 mmol) to give 1-{3-bromo-6-[2-(tert-butyl-dimethyl-silanyloxy)-ethoxy]-2-fluoro-phenyl}-3-trimethylsilyoxy-2-aza-1,3-butadiene as yellow gum and used for the next step without further purification.

EXAMPLE 183d

Preparation of racemic (2'R,3R,4'S)-2'-[3-bromo-2-fluoro-6-(2-hydroxy-ethoxy)-phenyl]-6-chloro-4'-(3-chlorophenyl)spiro[3H-indole-3,3'-piperidine]-2,6'(1H)-dione

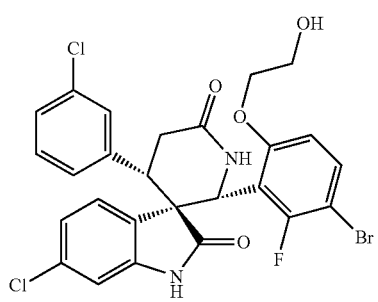

M. W. 594.27 $C_{26}H_{20}BrCl_2FN_2O_4$

To a solution of 1-{3-bromo-2-fluoro-6-[2-(tert-butyl-dimethyl-silanyloxy)-ethoxy]-phenyl}-3-trimethylsilyoxy-2-aza-1,3-butadiene prepared in example 183c in toluene (30 mL) was added E/Z-6-chloro-3-(3-chlorobenzylidene)-2-oxo-2,3-dihydro-indole-1-carboxylic acid tert-butyl ester prepared in example 24a (0.5 g, 1.28 mmol). The reaction mixture was stirred under nitrogen in a sealed tube at 140° C. for 45 min. After the solution was cooled to room temperature, methanol (10 mL) was added. The reaction mixture was filtered through a short pad of celite gel and washed with ethyl acetate. The filtrate was concentrated. The residue was dissolved in dichloromethane (20 mL) and trifluoroactic acid (15 mL) was added. After the reaction mixture was stirred at room temperature for 1 h, the mixture was concentrated. The residue was partitioned between saturated NaHCO₃ solution and ethyl acetate. The aqueous layer was extracted with ethyl acetate. The combined organic layer was dried over $Na_2SO_4$ and concentrated. The residue was dissolved in tetrahydrofuran (10 mL) and tetrabutylammonium fluoride solution (1M in THF, 10 mL) was added. The reaction mixture was stirred at room temperature for 10 min, then poured into water and extracted with ethyl acetate. The combined organic layer was dried over MgSO₄ and concentrated. The residue was purified by chromatography to give racemic (2'R,3R,4'S)-2'-[3-bromo-2-fluoro-6-(2-hydroxy-ethoxy)-phenyl]-6-chloro-4'-(3-chlorophenyl)spiro[3H-indole-3,3'-piperidine]-2,6'(1H)-dione as a yellow solid (Yield 0.4 g, 65.6%).

HRMS (ES⁺) m/z Calcd for $C_{26}H_{20}BrCl_2FN_2O_4$+H [(M+H)⁺]: 593.0041. Found: 593.0039.

EXAMPLE 184a

Preparation of intermediate racemic (2'R,3R,4'S)-6-chloro-4'-(3-chlorophenyl)-2'-[2-fluoro-6-(2-hydroxy-ethoxy)-3-trimethylsilanylethynyl-phenyl]spiro[3H-indole-3,3'-piperidine]-2,6'(1H)-dione

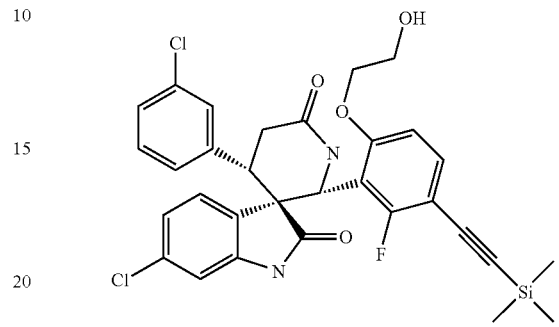

M. W. 611.58 $C_{31}H_{29}Cl_2FN_2O_4Si$

To a solution of racemic (2'R,3R,4'S)-2'-[3-bromo-2-fluoro-6-(2-hydroxy-ethoxy)-phenyl]-6-chloro-4'-(3-chlorophenyl)spiro[3H-indole-3,3'-piperidine]-2,6'(1H)-dione (0.12 g, 0.202 mmol) prepared in example 183d in N,N-dimethyl formamide (1 mL) was added ethynyl-trimethyl-silane (0.28 mL, 2.0 mmol) (Aldrich) and triethylamine (0.127 g, 2.0 mmol). After the reaction mixture was degassed for 5 min, dichloro-bis-(triphenyl-phosphine) (14 mg, 0.02 mmol) (Strem) was added and the reaction mixture was heated at 100° C. under nitrogen for overnight. The reaction mixture was cooled to room temperature and diluted with water, extracted with ethyl acetate. The organic layers were combined, washed with water, brine, dried over MgSO₄, filtered and concentrated. The residue was purified with chromatography to give racemic (2'R,3R,4'S)-6-chloro-4'-(3-chlorophenyl)-2'-[2-fluoro-6-(2-hydroxy-ethoxy)-3-trimethylsilanylethynyl-phenyl]spiro[3H-indole-3,3'-piperidine]-2,6'(1H)-dione as brown solid (Yield: 50 mg, 40.6%).

EXAMPLE 184b

Preparation of racemic (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione

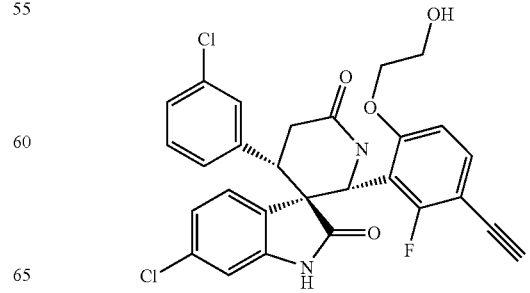

M. W. 539.39 C$_{28}$H$_{21}$Cl$_2$FN$_2$O$_4$

To a solution of racemic (2'R,3R,4'S)-6-chloro-4'-(3-chlorophenyl)-2'-[2-fluoro-6-(2-hydroxy-ethoxy)-3-trimethylsilanylethynyl-phenyl]spiro[3H-indole-3,3'-piperidine]-2,6'(1H)-dione (50 mg, 0.08 mmol) prepared in example 184a in methanol (2 mL) was added KF (9.5 mg, 0.16 mmol) (Aldrich). The reaction mixture was stirred at room temperature for overnight. The solvent was removed and the residue was diluted with water and extracted with ethyl acetate. The organic layers were combined, washed with water, brine, dried over MgSO$_4$, filtered and concentrated. The residue was purified with chromatography to give racemic (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione as brown solid.

HRMS (ES$^+$) m/z Calcd for C$_{28}$H$_{21}$Cl$_2$FN$_2$O$_4$+H [(M+H)$^+$]: 539.0935. Found: 539.0935.

EXAMPLE 185a

Preparation of intermediate 2-[2-(tert-Butyl-dimethyl-silanyloxy)-ethoxy]-5-ethyl-benzaldehyde

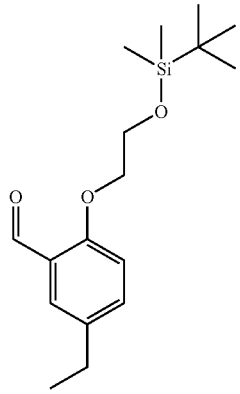

M. W. 308.50 C$_{17}$H$_{28}$O$_3$Si

In a manner similar to the method described in example 130a, 5-ethyl-2-hydroxy-benzaldehyde (4.75 g, 31.7 mmol) was reacted with K$_2$CO$_3$ (13.1 g, 95.1 mmol) and (2-bromoethoxy)-tert-butyl-dimethyl-silane (9.09 g, 38.0 mmol) to give 2-[2-(tert-Butyl-dimethyl-silanyloxy)-ethoxy]-5-ethyl-benzaldehyde as dark brown oil (9.0 g, 92.7%).

EXAMPLE 185b

Preparation of intermediate 1-{2-[2-(tert-butyl-dimethyl-silanyloxy)-ethoxy]-5-ethyl-phenyl}-3-trimethylsilyoxy-2-aza-1,3-butadiene

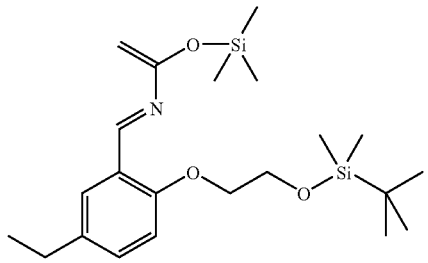

M. W. 421.73 C$_{22}$H$_{39}$NO$_3$Si$_2$

In a manner similar to the method described in example 1b, 2-[2-(tert-Butyl-dimethyl-silanyloxy)-ethoxy]-5-ethyl-benzaldehyde (3.24 g, 10.5 mmol) prepared in example 185a was used as the starting material in place of 3-chloro-benzaldehyde to react with 1,1,1,3,3,3-hexamethyldisilazane (2.18 mL, 10.5 mmol), n-butyllithium (2.5 M, 4 mL, 10.5 mmol), trimethylsilyl chloride (1.1 g, 10 mmol), triethylamine (1.4 g, 13 mmol) and acetyl chloride (1.0 g, 13 mmol) to give 1-{2-[2-(tert-butyl-dimethylsilanyloxy)-ethoxy]-5-ethyl-phenyl}-3-trimethylsilyoxy-2-aza-1,3-butadiene as yellow gum and used for the next step without further purification.

EXAMPLE 185c

Preparation of racemic (2'R,3R,4'S)-6-chloro-4'-(3-chlorophenyl)-2'-[5-ethyl-2-(2-hydroxy-ethoxy)-phenyl]spiro[3H-indole-3,3'-piperidine]-2,6'(1H)-dione

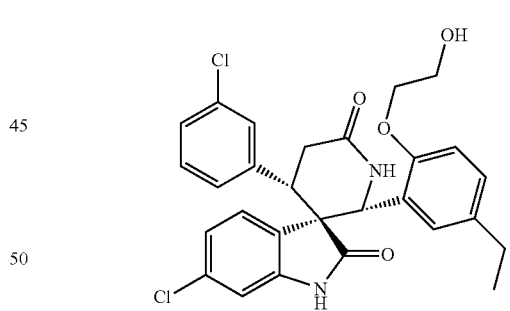

M. W. 525.44 C$_{28}$H$_{26}$Cl$_2$N$_2$O$_4$

In a manner similar to the method described in example 41b, E/Z-6-chloro-3-(3-chloro-benzylidene)-2-oxo-2,3-dihydro-indole-1-carboxylic acid tert-butyl ester prepared in example 24a (0.5 g, 1.28 mmol) was reacted with 1-{2-[2-(tert-butyl-dimethyl-silanyloxy)-ethoxy]-5-ethyl-phenyl}-3-trimethylsilyoxy-2-aza-1,3-butadiene prepared in example 185b in toluene and then trifluoroacetic acid (20 mL) in dichloromethane to give racemic (2'R,3R,4'S)-6-chloro-4'-(3-chlorophenyl)-2'-[5-ethyl-2-(2-hydroxy-ethoxy)-phenyl]spiro[3H-indole-3,3'-piperidine]-2,6'(1H)-dione as a white solid (0.20 g, 29.8%).

HRMS (ES$^+$) m/z Calcd for C$_{28}$H$_{26}$Cl$_2$N$_2$O$_4$+H [(M+H)$^+$]: 525.1343 Found: 525.1343.

EXAMPLE 186

Preparation of Chiral (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione

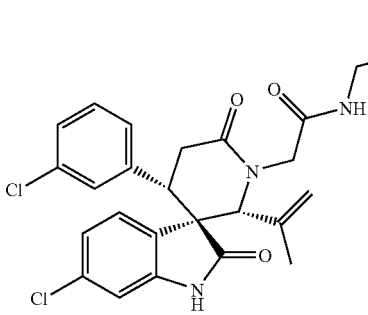

M. W. 502.40 $C_{25}H_{25}Cl_2N_3O_4$

Separation of the two enantiomers from racemic (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione (Example 120, 50 mg) was conducted by chiral SFC to provide chiral (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione as a white solid (24 mg, 48%) and chiral (2'S,3S,4'R)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione as a white solid (16 mg, 32%).

EXAMPLE 187

Preparation of Chiral (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione

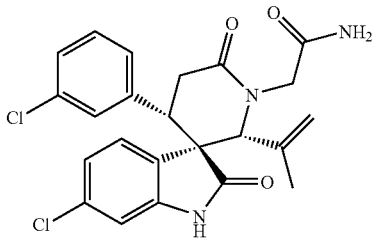

M. W. 458.35 $C_{23}H_{21}Cl_2N_3O_3$

Separation of the two enantiomers from racemic (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione (Example 116e, 37 mg) was conducted by chiral SFC to provide chiral (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione as a white solid (11 mg, 30%) and chiral (2'S,3S,4'R)-1'-(aminocarbonyl-methyl)-6-chloro-4'-(3-chlorophenyl)-2'-isopropenylspiro[3H-indole-3,3'-piperidine]-2,6'(1H)-dione as a white solid (9 mg, 24%).

EXAMPLE 188

Preparation of Chiral (2'R,3R,4'S)-6-chloro-4'-(3-chlorophenyl)-1'-(cyclopropylaminocarbonyl-methyl)-2'-isopropenylspiro[3H-indole-3,3'-piperidine]-2,6'(1H)-dione

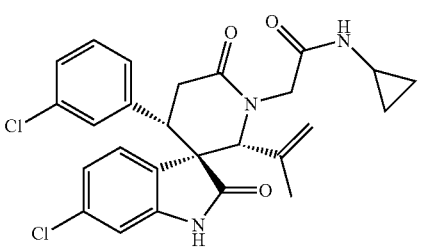

M. W. 498.41 $C_{26}H_{25}Cl_2N_3O_3$

Separation of the two enantiomers from racemic (2'R,3R,4'S)-6-chloro-4'-(3-chlorophenyl)-1'-(cyclopropylaminocarbonyl-methyl)-2'-isopropenylspiro[3H-indole-3,3'-piperidine]-2,6'(1H)-dione (Example 117, 50 mg) was conducted by chiral SFC to provide chiral (2'R,3R,4'S)-6-chloro-4'-(3-chlorophenyl)-1'-(cyclopropylaminocarbonyl-methyl)-2'-isopropenylspiro[3H-indole-3,3'-piperidine]-2,6'(1H)-dione as a white solid (12 mg, 24%) and chiral (2'S,3S,4'R)-6-chloro-4'-(3-chlorophenyl)-1'-(cyclopropylaminocarbonyl-methyl)-2'-isopropenylspiro[3H-indole-3,3'-piperidine]-2,6'(1H)-dione as a white solid (14 mg, 28%).

EXAMPLE 189

Preparation of racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione

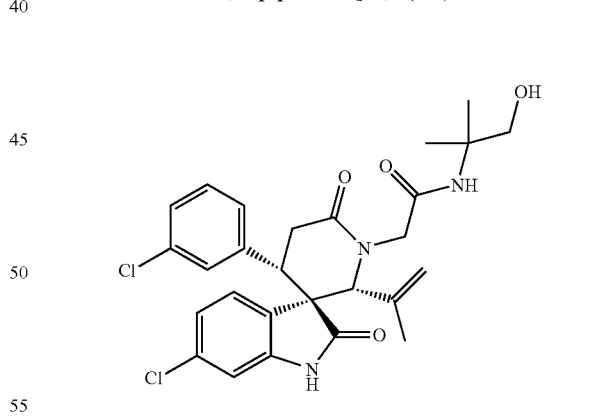

M. W. 530.46 $C_{27}H_{29}Cl_2N_3O_4$

Separation of the two enantiomers from racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione (Example 121, 60 mg) was conducted by chiral SFC to provide chiral (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione as a white solid (14 mg, 23%) and chiral (2'S,3S,4'R)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione as a white solid (18 mg, 30%).

EXAMPLE 190a

Preparation of intermediate 2-[2-(tert-Butyl-dimethyl-silanyloxy)-ethoxy]-5-iodo-benzaldehyde

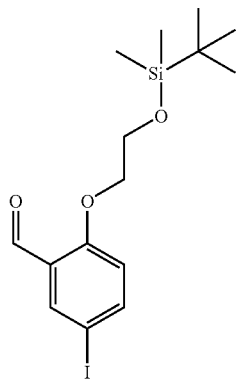

M. W. 406.34 $C_{15}H_{23}IO_3Si$

To a solution of 5-iodosalicylaldehyde (6.68 g, 26.9 mmol) (Aldrich) in N,N-dimethylformamide (150 mL) was added anhydrous $K_2CO_3$ (11.17 g, 80.7 mmol), and (2-bromoethoxy)-tert-butyl-dimethyl-silane (7.74 g, 32.3 mmol, Aldrich). The reaction mixture was heated at 65° C. for 18 h. The crude was cooled to room temperature, diluted with ethyl acetate, washed with water, brine. The organic layer was separated, dried over $MgSO_4$, concentrated to give 2-[2-(tert-butyl-dimethyl-silanyloxy)-ethoxy]-5-iodo-benzaldehyde as a yellow oil (Yield 10 g, 100%).

EXAMPLE 190b

Preparation of intermediate 1-[2-(tert-butyl-dimethyl-silanyloxy)-ethoxy]-5-iodo-phenyl]-3-trimethylsilyoxy-2-aza-1,3-butadiene

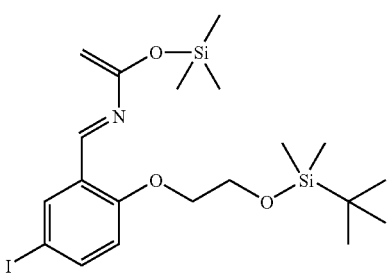

M. W. 519.58 $C_{20}H_{34}INO_3Si_2$

To 1,1,1,3,3,3-hexamethyldisilazane (4.36 mL, 21 mmol) (Aldrich) under nitrogen at room temperature was added n-butyllithium (2.5 M, 8.4 mL, 21 mmol) (Aldrich). The reaction mixture was stirred at room temperature for 10 minutes. Then dry tetrahydrofuran (60 mL) was added, followed by the addition of 2-[2-(tert-butyl-dimethyl-silanyloxy)-ethoxy]-5-iodo-benzaldehyde (8.53 g, 21 mmol) prepared in Example 190c. After the mixture was stirred at room temperature for 0.5 h, trimethylsilyl chloride (2.66 mL, 21 mmol) (Aldrich) was added dropwise. Then the temperature of the mixture was lowered to 0° C. on a cooling ice bath. To this mixture was added triethylamine (3.8 mL, 27.2 mmol) in one portion, followed by the dropwise addition of a solution of acetyl chloride (1.94 mL, 27.2 mmol) in diethyl ether (100 mL). The cooling bath was removed, and the mixture was stirred at room temperature for 1 h. The mixture was quickly filtered on celite under nitrogen, and filtrate was concentrated under reduced pressure to give crude 1-[2-(tert-butyl-dimethyl-silanyloxy)-ethoxy]-5-iodo-phenyl]-3-trimethylsilyoxy-2-aza-1,3-butadiene as a yellow oil and used for the next step without further purification.

EXAMPLE 190c

Preparation of racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione

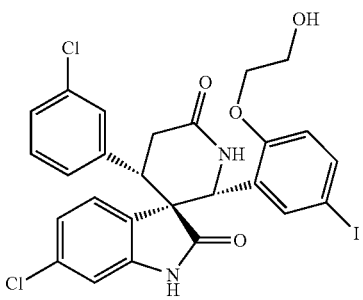

M. W. 623.28 $C_{26}H_{21}Cl_2IN_2O_4$

To a solution of 1-[2-(tert-butyl-dimethyl-silanyloxy)-ethoxy]-5-iodo-phenyl]-3-trimethylsilyoxy-2-aza-1,3-butadiene prepared in example 190b (21 mmol) in toluene (30 mL) was added E/Z-6-chloro-3-(3-chlorobenzylidene)-2-oxo-2,3-dihydro-indole-1-carboxylic acid tert-butyl ester prepared in Example 24a (1.2 g, 3.1 mmol). The reaction mixture was stirred under nitrogen in a sealed tube at 140° C. for 45 min. After the solution was cooled to room temperature, the reaction mixture was concentrated. The residue was dissolved in dichloromethane (20 mL) and trifluoroactic acid (20 mL) was added. After the reaction mixture was stirred at room temperature for 4 h, the mixture was concentrated. The residue was partitioned between saturated $NaHCO_3$ solution and ethyl acetate. The aqueous layer was extracted with ethyl acetate. The combined organic layer was dried over $Na_2SO_4$ and concentrated. The residue was purified by chromatography ($EtOAc:CH_2Cl_2=1:3$) to give racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione as a light yellow solid (Yield 0.46 g, 25%).

HRMS (ES$^+$) m/z Calcd for $C_{26}H_{21}Cl_2IN_2O_4$+H [(M+H)$^+$]: 622.9996. Found: 622.9995.

EXAMPLE 191

Preparation of racemic (2'R,3R,4'S)-6-chloro-4'-(3-chlorophenyl)-2'-[5-cyano-2-(2-hydroxy-ethoxy)-phenyl]spiro[3H-indole-3,3'-piperidine]-2,6'(1H)-dione

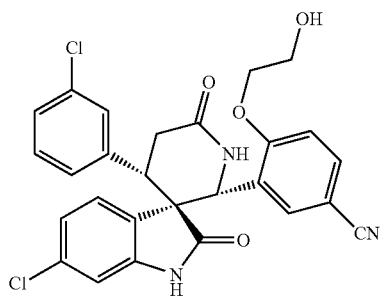

M. W. 521.09 $C_{27}H_{21}Cl_2N_2O_4$

To a mixture of racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione (0.1 g, 0.16 mmol) prepared in Example 190c in triethylamine (0.8 mL) was added trimethylsilyl cyanide (23.8 mg, 0.24 mmol) (Aldrich), Tetrakis(triphenylphosphine)palladium (3.7 mg, Aldrich) sequentially. The reaction mixture was refluxed under nitrogen for 2 h. After cooled to room temperature, the reaction mixture was partitioned between saturated water and ethyl acetate. The aqueous layer was extracted with ethyl acetate. The combined organic layer was dried over $Na_2SO_4$ and concentrated. The residue was purified by chromatography (EtOAc) to give racemic (2'R,3R,4'S)-6-chloro-4'-(3-chlorophenyl)-2'-[5-cyano-2-(2-hydroxy-ethoxy)-phenyl]spiro[3H-indole-3,3'-piperidine]-2,6'(1H)-dione as a white solid (Yield 38 mg, 46%).

HRMS (ES$^+$) m/z Calcd for $C_{27}H_{21}Cl_2N_2O_4$+H [(M+H)$^+$]: 522.0982. Found: 522.0984.

EXAMPLE 192a

Preparation of intermediate 1-(3-iodophenyl)-3-trimethylsilyoxy-2-aza-1,3-butadiene

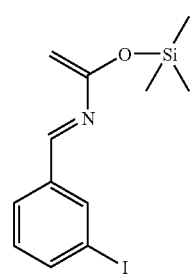

M. W. 345.25 $C_{12}H_{16}INOSi$

In a manner similar to the method described in example 190b, 3-iodo-benzaldehyde (0.9 g, 3.88 mmol) (Aldrich) was used as the starting material in place of 2-[2-(tert-butyl-dimethyl-silanyloxy)-ethoxy]-5-iodo-benzaldehyde to react with 1,1,3,3,3-hexamethyldisilazane (0.62 g, 3.88 mmol), n-butyllithium (2.5 M, 1.6 mL, 3.88 mmol), trimethylsilyl chloride (0.42 g, 3.88 mmol), triethylamine (0.53 g, 5.28 mmol) and acetyl chloride (0.41 g, 5.28 mmol) to give 1-(3-iodophenyl)-3-trimethylsilyoxy-2-aza-1,3-butadiene as a yellow gum and used for the next step without further purification.

EXAMPLE 192b

Preparation of racemic (2'R,3R,4'S)-6-chloro-4'-(3-chlorophenyl)-2'-(3-iodophenyl)spiro[3H-indole-3,3'-piperidine]-2,6'(1H)-dione

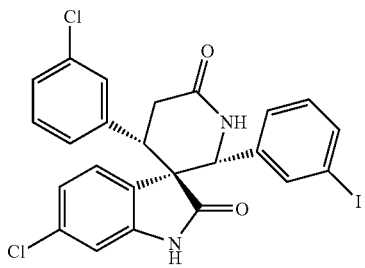

M. W. 563.23 $C_{24}H_{17}Cl_2IN_2O_2$

To a solution of 1-(3-iodophenyl)-3-trimethylsilyoxy-2-aza-1,3-butadiene prepared in example 192a (1.2 g, 3.5 mmol) in toluene (40 mL) was added E/Z-6-chloro-3-(3-chlorobenzylidene)-2-oxo-2,3-dihydro-indole-1-carboxylic acid tert-butyl ester prepared in Example 24a (0.5 g, 1.28 mmol). The reaction mixture was stirred under nitrogen in a sealed tube at 140° C. for 1 h. After the solution was cooled to room temperature and concentrated. The residue was dissolved in dichloromethane (20 mL) and trifluoroactic acid (10 mL) was added. After the reaction mixture was stirred at room temperature for 0.5 h, the mixture was concentrated. The residue was partitioned between saturated $NaHCO_3$ solution and ethyl acetate. The aqueous layer was extracted with ethyl acetate. The combined organic layer was dried over $Na_2SO_4$ and concentrated. The residue was purified by chromatography (EtOAc:$CH_2Cl_2$=1:3 then 1:2) to give racemic (2'R,3R,4'S)-6-chloro-4'-(3-chlorophenyl)-2'-(3-iodophenyl)spiro[3H-indole-3,3'-piperidine]-2,6'(1H)-dione as a white solid (Yield 0.56 g, 77%).

HRMS (ES$^+$) m/z Calcd for $C_{24}H_{17}Cl_2IN_2O_2$+H [(M+H)$^+$]: 562.9785. Found: 562.9786.

EXAMPLE 193

Preparation of racemic (2'R,3R,4'S)-6-chloro-4'-(3-chlorophenyl)-2'-(3-ethynyl-phenyl)spiro[3H-indole-3,3'-piperidine]-2,6'(1H)-dione

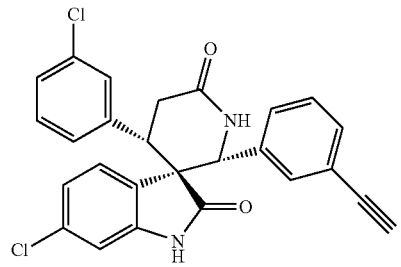

M. W. 461.35 $C_{26}H_{18}Cl_2N_2O_2$

A solution of racemic (2'R,3R,4'S)-6-chloro-4'-(3-chlorophenyl)-2'-(3-iodophenyl)spiro[3H-indole-3,3'-piperidine]-2,6'(1H)-dione (0.56 g, 1 mmol) prepared in example 192b in anhydrous tetrahydrofuran (30 mL) was added trimethylsilyl acetylene (0.1 g, 2.0 mmol) (Aldrich), CuI (0.38 g, 2.0 mmol) (Aldrich) and triethylamine (0.2 g, 2.0 mmol) was degassed under nitrogen for 5 min, then dichlorobis(triphenylphosphine)palladium(0) (140 mg, 0.2 mmol) (Strem) was added and the reaction mixture was heated at 100° C. under nitrogen for 3 h. The reaction mixture was cooled to room temperature and filtered through a short pad of silica gel, the silica gel was washed with ethyl acetate. The filtrate was concentrated. To the residue was added methanol (10 mL) and aqueous NaOH solution (1 N, 2 mL). The mixture was stirred at room temperature for 2 h, then partitioned between ethyl acetate and water. The organic layer was separated, and the aqueous layer was extracted with ethyl acetate. The organic layers were combined, dried over $MgSO_4$ and concentrated. The residue was purified with chromatography (EtOAc:hexanes=2:1) to give racemic (2'R,3R,4'S)-6-chloro-4'-(3-chlorophenyl)-2'-(3-ethynyl-phenyl)spiro[3H-indole-3,3'-piperidine]-2,6'(1H)-dione as a white solid (Yield: 0.24 g, 52%).

HRMS (ES$^+$) m/z Calcd for $C_{26}H_{18}Cl_2N_2O_2$+H [(M+H)$^+$]: 461.0818. Found: 461.0818.

EXAMPLE 194a

Preparation of intermediate 1-(2-fluoro-5-iodophenyl)-3-trimethylsilyoxy-2-aza-1,3-butadiene

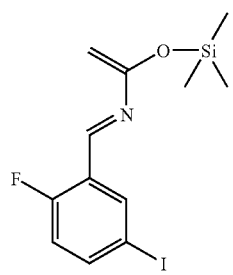

M. W. 363.25 $C_{12}H_{15}FINOSi$

In a manner similar to the method described in example 190b, 2-fluoro-5-iodobenzaldehyde (2.62 g, 10.5 mmol) (Aldrich) was used as the starting material in place of 2-[2-(tert-butyl-dimethyl-silanyloxy)-ethoxy]-5-iodo-benzaldehyde to react with 1,1,3,3,3-hexamethyldisilazane (2.14 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give crude 1-(2-fluoro-5-iodophenyl)-3-trimethylsilyoxy-2-aza-1,3-butadiene as a yellow gum and used for the next step without further purification.

EXAMPLE 194b

Preparation of racemic (2'R,3R,4'S)-6-chloro-4'-(3-chlorophenyl)-2'-(2-fluoro-5-iodophenyl)spiro[3H-indole-3,3'-piperidine]-2,6'(1H)-dione

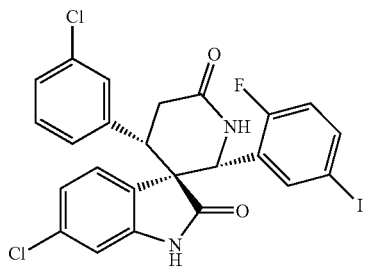

M. W. 581.22 $C_{24}H_{16}Cl_2FIN_2O_2$

In a manner similar to the method described in example 192b, E/Z-6-chloro-3-(3-chloro-benzylidene)-2-oxo-2,3-dihydro-indole-1-carboxylic acid tert-butyl ester prepared in example 24a (1 g, 2.56 mmol) was reacted with crude 1-(2-fluoro-5-iodophenyl)-3-trimethylsilyoxy-2-aza-1,3-butadiene prepared in example 194a (10.5 mmol) in toluene and then trifluoroacetic acid in dichloromethane to give racemic (2'R,3R,4'S)-6-chloro-4'-(3-chlorophenyl)-2'-(2-fluoro-5-iodophenyl)spiro[3H-indole-3,3'-piperidine]-2,6'(1H)-dione as a white solid (Yield 0.61 g, 41%)

HRMS (ES$^+$) m/z Calcd for $C_{24}H_{16}Cl_2FIN_2O_2$+H [(M+H)$^+$]: 580.9691. Found: 580.9691.

EXAMPLE 195

Preparation of racemic (2'R,3R,4'S)-6-chloro-4'-(3-chlorophenyl)-2'-(5-ethynyl-2-fluoro-phenyl)spiro[3H-indole-3,3'-piperidine]-2,6'(1H)-dione

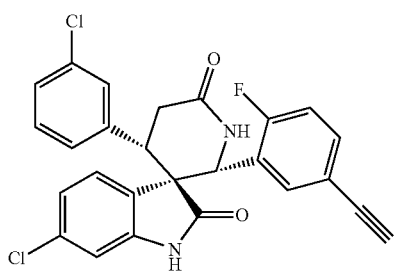

M. W. 479.34 $C_{26}H_{17}Cl_2FN_2O_2$

In a manner similar to the method described in example 193, racemic (2'S,3R,4'S)-6-chloro-4'-(3-chlorophenyl)-2'-(2-fluoro-5-iodophenyl)spiro[3H-indole-3,3'-piperidine]-2,6'(1H)-dione prepared in example 194b (0.45 g, 0.77 mmol) was reacted with trimethylsilyl acetylene (1.1 mL, 7.7 mmol), CuI (10 mg), triethylamine (3.22 mL, 23 mmol), and dichlorobis(triphenylphosphine)palladium (54 mg, 0.077 mmol) in anhydrous N,N-dimethylformamide, and then treated with aqueous NaOH in methanol to give racemic (2'R,3R,4'S)-6-chloro-4'-(3-chlorophenyl)-2'-(5-ethynyl-2-fluoro-phenyl)spiro[3H-indole-3,3'-piperidine]-2,6'(1H)-dione as a light brown solid (Yield 57 mg)

HRMS (ES$^+$) m/z Calcd for $C_{26}H_{17}Cl_2FN_2O_2$+H [(M+H)$^+$]: 479.0724. Found: 479.0725.

EXAMPLE 196a

Preparation of intermediate 2-[2-(tert-Butyl-dimethyl-silanyloxy)-ethoxy]-5-iodo-3-methoxy-benzaldehyde

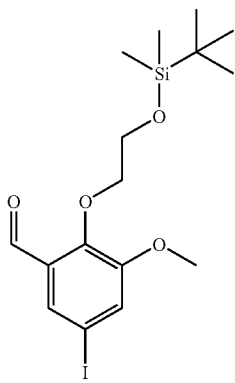

M. W. 406.34 $C_{15}H_{23}IO_3Si$

To a solution of 5-iodovanillin (10 g, 35.9 mmol) (Aldrich) in N,N-dimethylformamide (150 mL) was added anhydrous $K_2CO_3$ (14.9 g, 108 mmol), and (2-bromo-ethoxy)-tert-butyl-dimethyl-silane (10.3 g, 43 mmol, Aldrich). The reaction mixture was heated at 60° C. for 18 h. The crude was cooled to room temperature, diluted with ethyl acetate, washed with water, brine. The organic layer was separated, dried over $MgSO_4$, concentrated, and purified by chromatography to give 2-[2-(tert-butyl-dimethyl-silanyloxy)-ethoxy]-5-iodo-3-methoxy-benzaldehyde as a yellow oil (Yield 15 g, 96%).

EXAMPLE 196b

Preparation of intermediate 1-[2-(tert-butyl-dimethyl-silanyloxy)-ethoxy]-5-iodo-3-methoxy-phenyl]-3-trimethylsilyoxy-2-aza-1,3-butadiene

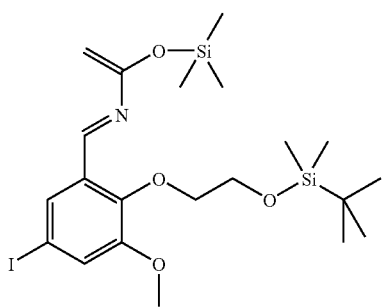

M. W. 549.60 $C_{21}H_{36}INO_4Si_2$

In a manner similar to the method described in example 190b, 2-[2-(tert-butyl-dimethyl-silanyloxy)-ethoxy]-5-iodo-3-methoxy-benzaldehyde (4.58 g, 11 mmol) was used as the starting material in place of 2-[2-(tert-butyl-dimethyl-silanyloxy)-ethoxy]-5-iodo-benzaldehyde to react with 1,1,3,3,3-hexamethyldisilazane (2.18 mL, 11 mmol), n-butyllithium (2.5 M, 4.2 mL, 11 mmol), trimethylsilyl chloride (1.33 mL, 10.5 mmol), triethylamine (1.9 mL, 13.6 mmol) and acetyl chloride (0.97 mL, 13.6 mmol) to give crude 1-[2-(tert-butyl-dimethyl-silanyloxy)-ethoxy]-5-iodo-3-methoxy-phenyl]-3-trimethylsilyoxy-2-aza-1,3-butadiene as a yellow gum and used for the next step without further purification.

EXAMPLE 196c

Preparation of racemic (2'R,3R,4'S)-6-chloro-4'-(3-chlorophenyl)-2'-[2-(2-hydroxy-ethoxy)-5-iodo-3-methoxy-phenyl]spiro[3H-indole-3,3'-piperidine]-2,6'(1H)-dione

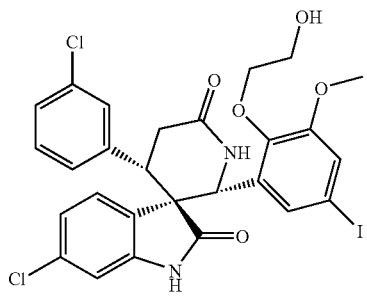

M. W. 653.31 $C_{27}H_{23}Cl_2IN_2O_5$

In a manner similar to the method described in example 190c, E/Z-6-chloro-3-(3-chloro-benzylidene)-2-oxo-2,3-dihydro-indole-1-carboxylic acid tert-butyl ester prepared in example 24a (1 g, 2.56 mmol) was reacted with 1-[2-(tert-butyldimethyl-silanyloxy)-ethoxy]-5-iodo-3-methoxy-phenyl]-3-trimethylsilyoxy-2-aza-1,3-butadiene prepared in example 196b (11 mmol) in toluene and then trifluoroacetic acid in dichloromethane to give racemic (2'R,3R,4'S)-6-chloro-4'-(3-chlorophenyl)-2'-[2-(2-hydroxy-ethoxy)-5-iodo-3-methoxy-phenyl]spiro[3H-indole-3,3'-piperidine]-2,6'(1H)-dione as a white solid (Yield 0.62 g, 42%).

HRMS (ES$^+$) m/z Calcd for $C_{27}H_{23}Cl_2IN_2O+H$ [(M+H)$^+$]: 653.0102. Found: 653.0102.

EXAMPLE 197

Preparation of racemic (2'R,3R,4'S)-6-chloro-4'-(3-chlorophenyl)-2'-[5-ethynyl-2-(2-hydroxy-ethoxy)-3-methoxy-phenyl]spiro[3H-indole-3,3'-piperidine]-2,6'(1H)-dione

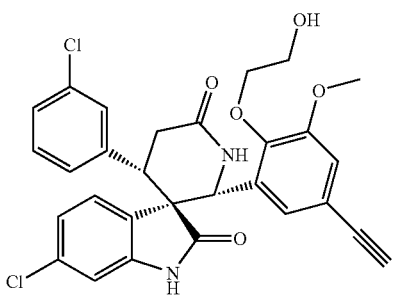

M. W. 551.43 $C_{29}H_{24}Cl_2N_2O_5$

In a manner similar to the method described in example 193, racemic (2'R,3R,4'S)-6-chloro-4'-(3-chlorophenyl)-2'-[2-(2-hydroxy-ethoxy)-5-iodo-3-methoxy-phenyl]spiro[3H-indole-3,3'-piperidine]-2,6'(1H)-dione prepared in example 196c (0.3 g, 0.46 mmol) was reacted with trimethylsilyl acetylene (0.65 mL, 4.6 mmol), CuI (10 mg), triethylamine (1.9 mL, 13.8 mmol), and dichlorobis(triphenylphosphine)palladium (32 mg, 0.046 mmol) in anhydrous N,N-dimethylformamide, and then treated with aqueous NaOH in methanol to give racemic (2'R,3R,4'S)-6-chloro-4'-(3-chlorophenyl)-2'-[5-ethynyl-2-(2-hydroxy-ethoxy)-3-methoxy-phenyl]spiro[3H-indole-3,3'-piperidine]-2,6'(1H)-dione as a light brown solid (Yield 28 mg).

HRMS (ES$^+$) m/z Calcd for $C_{29}H_{24}Cl_2N_2O_5$+H [(M+H)$^+$]: 551.1135. Found: 551.1136.

EXAMPLE 198a

Preparation of intermediate
5-Iodo-2-methyl-benzaldehyde

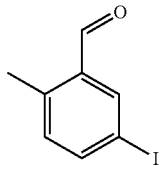

M. W. 246.05 $C_8H_7IO$

To a solution of 5-iodo-2-methyl benzoic acid (24 g, 91 mmol) (AKSCI) in anhydrous tetrahydrofuran (100 mL) at 0° C. was added borane tetrahydrofuran (1 M, 250 mL, 250 mmol) dropwise. The reaction mixture was then stirred at room temperature for 2 h. The mixture was concentrated and residue was partitioned between ethyl acetate and water. Organic layer was separated, washed with brine, dried over MgSO$_4$, and concentrated to give an off-white solid. The solid was dissolved into dichloromethane (300 mL), and activated MnO$_2$ (20 g) was added. The mixture was then heated at reflux for 4 h, cooled to room temperature, and filtered through a short pad of celite. The filtrated was concentrated and purified by chromatography (EtOAc:hexanes=1;8) to give 5-Iodo-2-methyl-benzaldehyde as an off-white solid (Yield 5.5 g, 25%).

EXAMPLE 198b

Preparation of intermediate 1-(5-iodo-2-methylphenyl)-3-trimethylsilyoxy-2-aza-1,3-butadiene

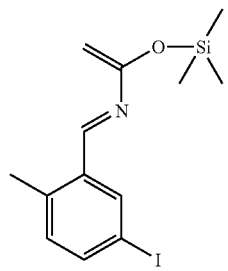

M. W. 359.28 $C_{13}H_{18}INOSi$

In a manner similar to the method described in example 190b, 5-iodo-2-methylbenzaldehyde prepared in example 198a (5.4 g, 22 mmol) was used as the starting material in place of 2-[2-(tert-butyl-dimethyl-silanyloxy)-ethoxy]-5-iodo-benzaldehyde to react with 1,1,3,3,3-hexamethyldisilazane (3.53 g, 22 mmol), n-butyllithium (2.5 M, 8.8 mL, 22 mmol), trimethylsilyl chloride (2.22 g, 22 mmol), triethylamine (3 mL, 30 mmol) and acetyl chloride (2.34 g, 30 mmol) to give crude 1-(5-iodo-2-methylphenyl)-3-trimethylsilyoxy-2-aza-1,3-butadiene as a yellow gum and used for the next step without further purification.

EXAMPLE 198c

Preparation of racemic (2'R,3R,4'S)-6-chloro-4'-(3-chlorophenyl)-2'-(5-iodo-2-methylphenyl)spiro[3H-indole-3,3'-piperidine]-2,6'(1H)-dione

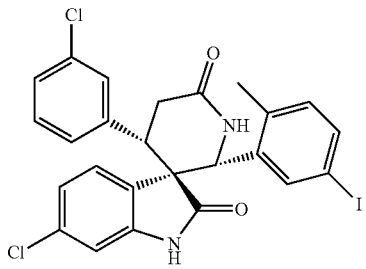

M. W. 577.25 $C_{25}H_{19}Cl_2IN_2O_2$

In a manner similar to the method described in example 192b, E/Z-6-chloro-3-(3-chloro-benzylidene)-2-oxo-2,3-dihydro-indole-1-carboxylic acid tert-butyl ester prepared in example 24a (2.2 g, 5.6 mmol) was reacted with 1-(5-Iodo-2-methylphenyl)-3-trimethylsilyloxy-2-aza-1,3-butadiene prepared in example 198b (6.8 g, 19 mmol) in toluene and then trifluoroacetic acid in dichloromethane to give racemic (2'R,3R,4'S)-6-chloro-4'-(3-chlorophenyl)-2'-(5-iodo-2-methylphenyl)spiro[3H-indole-3,3'-piperidine]-2,6'(1H)-dione as a white solid (Yield 2.5 g, 77%)

HRMS (ES$^+$) m/z Calcd for $C_{25}H_{19}Cl_2IN_2O_2$+H [(M+H)$^+$]: 576.9941. Found: 576.9942.

EXAMPLE 199

Preparation of racemic (2'R,3R,4'S)-6-chloro-4'-(3-chlorophenyl)-2'-(5-ethynyl-2-methylphenyl)spiro[3H-indole-3,3'-piperidine]-2,6'(1H)-dione

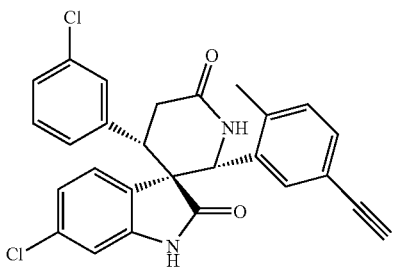

M. W. 475.38 $C_{27}H_{20}Cl_2N_2O_2$

In a manner similar to the method described in example 193, racemic (2'R,3R,4'S)-6-chloro-4'-(3-chlorophenyl)-2'-(5-iodo-2-methylphenyl)spiro[3H-indole-3,3'-piperidine]-2,6'(1H)-dione prepared in example 198c (0.27 g, 0.47 mmol) was reacted with trimethylsilyl acetylene (92 mg, 0.94 mmol), CuI (0.18 g, 0.94 mmol), triethylamine (95 mg, 0.94 mmol), and dichlorobis(triphenylphosphine)palladium (66 mg, 0.094 mmol) in anhydrous tetrahydrofuran, and then treated with aqueous NaOH in methanol to give racemic (2'R,3R,4'S)-6-chloro-4'-(3-chlorophenyl)-2'-(5-ethynyl-2-methylphenyl)spiro[3H-indole-3,3'-piperidine]-2,6'(1H)-dione as a white solid (Yield 0.12 g, 54%)

HRMS (ES$^+$) m/z Calcd for $C_{27}H_{20}Cl_2N_2O_2$+H [(M+H)$^+$]: 475.0975. Found: 475.0977.

EXAMPLE 200

Preparation of Chiral (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione

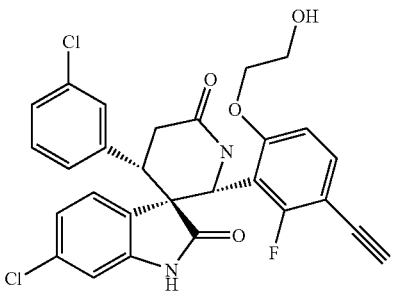

M. W. 539.39 $C_{28}H_{21}Cl_2FN_2O_4$

Separation of the two enantiomers from racemic (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione (Example 184b, 70 mg) was conducted by chiral SFC to provide chiral (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione as a white solid (32 mg, 47%) and chiral (2'R,3S,4'R)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione as a white solid (31 mg, 44%).

EXAMPLE 201a

Preparation of intermediate 5-Iodo-2-nitro-benzaldehyde

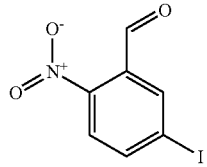

M. W. 277.02 $C_7H_4INO_3$

To a solution of 5-iodo-2-nitrobenzoic acid (37 g, 126 mmol) (APIN) in anhydrous tetrahydrofuran (200 mL) at 0° C. was added borane tetrahydrofuran (1 M, 360 mL, 360 mmol) dropwise. The reaction mixture was then stirred at room temperature for 24 h. The mixture was concentrated and residue was partitioned between ethyl acetate and water. Organic layer was separated, washed with brine, dried over MgSO$_4$, concentrated, and triturated. The precipitate 5-Iodo-2-nitro-phenyl)-methanol was collected as a yellow solid (20 g, 57%). The solid (5.5 g) was dissolved into dichloromethane (100 mL), and activated MnO$_2$ (15 g) was added. The mixture was then heated at reflux for 4 h, cooled to room temperature, and filtered through a short pad of celite. The filtrated was concentrated to give 5-Iodo-2-nitro-benzaldehyde as a yellow solid (Yield 4.2 g, 76%).

EXAMPLE 201b

Preparation of intermediate 1-(5-iodo-2-nitrophenyl)-3-trimethylsilyoxy-2-aza-1,3-butadiene

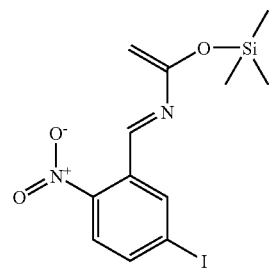

M. W. 390.26 $C_{12}H_{15}IN_2OSi$

In a manner similar to the method described in example 190b, 5-iodo-2-nitrobenzaldehyde prepared in Example 201a (4.2 g, 15 mmol) was used as the starting material in place of 2-[2-(tert-butyl-dimethyl-silanyloxy)-ethoxy]-5-iodo-benzaldehyde to react with 1,1,3,3,3-hexamethyldisilazane (2.4 g, 15 mmol), n-butyllithium (2.5 M, 6 mL, 15 mmol), trimethylsilyl chloride (1.6 g, 15 mmol), triethylamine (2.1 g, 20 mmol) and acetyl chloride (1.5 g, 20 mmol) to give crude 1-(5-Iodo-2-nitrophenyl)-3-trimethylsilyoxy-2-aza-1,3-butadiene as a yellow gum and used for the next step without further purification.

EXAMPLE 201c

Preparation of racemic (2'R,3R,4'S)-6-chloro-4'-(3-chlorophenyl)-2'-(5-iodo-2-nitrophenyl)spiro[3H-indole-3,3'-piperidine]-2,6'(1H)-dione

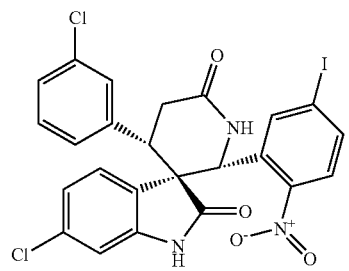

M. W. 608.22 $C_{24}H_{16}Cl_2IN_3O_4$

In a manner similar to the method described in example 192b, E/Z-6-chloro-3-(3-chloro-benzylidene)-2-oxo-2,3-dihydro-indole-1-carboxylic acid tert-butyl ester prepared in example 24a (2 g, 5 mmol) was reacted with 1-(5-iodo-2-nitrophenyl)-3-trimethylsilyoxy-2-aza-1,3-butadiene prepared in example 201b (15 mmol) in toluene and then trifluoroacetic acid in dichloromethane to give racemic (2'R,3R,4'S)-6-chloro-4'-(3-chlorophenyl)-2'-(5-iodo-2-nitrophenyl)spiro[3H-indole-3,3'-piperidine]-2,6'(1H)-dione as a yellow solid (Yield 1.8 g, 59%)

HRMS (ES$^+$) m/z Calcd for $C_{24}H_{16}Cl_2IN_3O_4$+H [(M+H)$^+$]: 607.9636. Found: 607.9638.

EXAMPLE 202

Preparation of racemic (2'R,3R,4'S)-6-chloro-4'-(3-chlorophenyl)-2'-(5-ethynyl-2-nitrophenyl)spiro[3H-indole-3,3'-piperidine]-2,6'(1H)-dione

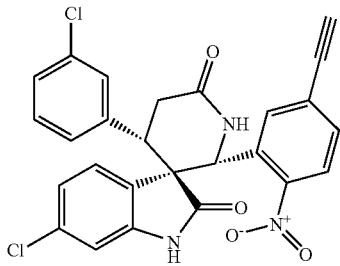

M. W. 506.35 $C_{26}H_{17}Cl_2N_3O_4$

In a manner similar to the method described in example 193, racemic (2'R,3R,4'S)-6-chloro-4'-(3-chlorophenyl)-2'-(5-iodo-2-nitrophenyl)spiro[3H-indole-3,3'-piperidine]-2,6'(1H)-dione prepared in example 201c (0.36 g, 0.59 mmol) was reacted with trimethylsilyl acetylene (120 mg, 1.18 mmol), CuI (0.23 g, 1.18 mmol), triethylamine (120 mg, 1.18 mmol), and dichlorobis(triphenylphosphine)palladium(0) (83 mg, 0.118 mmol) in anhydrous tetrahydrofuran, and then treated with aqueous NaOH in methanol to give racemic (2'R,3R,4'S)-6-chloro-4'-(3-chlorophenyl)-2'-(5-ethynyl-2-nitrophenyl)spiro[3H-indole-3,3'-piperidine]-2,6'(1H)-dione as a white solid (Yield 0.25 g, 84%)

HRMS (ES$^+$) m/z Calcd for $C_{26}H_{17}Cl_2N_3O_4$+H [(M+H)$^+$]: 506.0669. Found: 506.0671.

EXAMPLE 203

Preparation of racemic (2'R,3R,4'S)-2'-(2-amino-5-iodophenyl)-6-chloro-4'-(3-chlorophenyl)spiro[3H-indole-3,3'-piperidine]-2,6'(1H)-dione

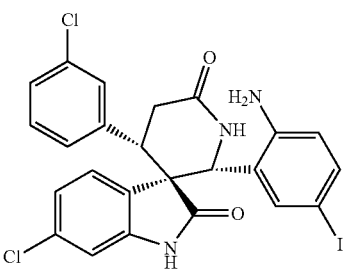

M. W. 578.24 $C_{24}H_{18}Cl_2IN_3O_2$

To a suspension of racemic (2'R,3R,4'S)-6-chloro-4'-(3-chlorophenyl)-2'-(5-iodo-2-nitrophenyl)spiro[3H-indole-3,3'-piperidine]-2,6'(1H)-dione prepared in Example 201c (0.7 g, 1.15 mmol) in methanol (50 ml) was added aqueous NH$_4$Cl solution (0.61 g, 11.5 mmol, 20 mL), followed by addition of Zn powder (0.75 g, 11.5 mmol). The reaction mixture was stirred at room temperature for 1 h, then filtered throught a short pad of celite. The filtrate was concentrated, extracted with ethyl acetate and dichloromethane. The organic layers were combined, dried over MgSO$_4$, and concentrated. The residue was purified by chromatography (EtOAc, then EtOAc:MeOH=19;1) to give racemic (2'R,3R,4'S)-2'-(2-amino-5-iodophenyl)-6-chloro-4'-(3-chlorophenyl)spiro[3H-indole-3,3'-piperidine]-2,6'(1H)-dione as a white solid (Yield 0.41 g, 61%)

HRMS (ES$^+$) m/z Calcd for $C_{24}H_{18}Cl_2IN_3O_2$+H [(M+H)$^+$]: 577.9894. Found: 577.9894.

EXAMPLE 204

Preparation of racemic (2'R,3R,4'S)-2'-(2-amino-5-ethynylphenyl)-6-chloro-4'-(3-chlorophenyl)spiro[3H-indole-3,3'-piperidine]-2,6'(1H)-dione

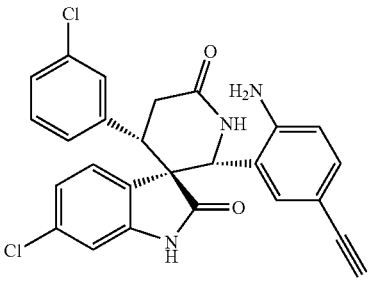

M. W. 476.37 $C_{26}H_{19}Cl_2N_3O_2$

In a manner similar to the method described in example 193, racemic (2'R,3R,4'S)-2'-(2-amino-5-iodophenyl)-6-chloro-4'-(3-chlorophenyl)spiro[3H-indole-3,3'-piperidine]-2,6'(1H)-dione prepared in example 203 (0.2 g, 0.35 mmol) was reacted with trimethylsilyl acetylene (68 mg, 0.69 mmol), CuI (0.13 g, 0.69 mmol), triethylamine (70 mg, 0.69 mmol), and dichlorobis(triphenylphosphine)palladium (49 mg, 0.069 mmol) in anhydrous tetrahydrofuran, and then treated with aqueous NaOH in methanol to give racemic (2'R,3R,4'S)-2'-(2-amino-5-ethynylphenyl)-6-chloro-4'-(3-chlorophenyl)spiro[3H-indole-3,3'-piperidine]-2,6'(1H)-dione as a white solid (Yield 0.25 g, 84%)

HRMS (ES$^+$) m/z Calcd for $C_{26}H_{19}Cl_2N_3O_2$+H [(M+H)$^+$]: 476.0927. Found: 476.0929.

EXAMPLE 205a

Preparation of intermediate 1-(3-bromo-4-fluorophenyl)-3-trimethylsilyoxy-2-aza-1,3-butadiene

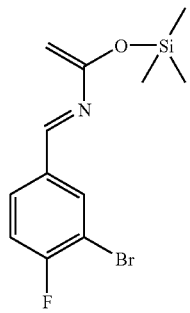

M. W. 316.25 C$_{12}$H$_{15}$BrFNOSi

In a manner similar to the method described in example 190b, 3-bromo-4-fluorobenzaldehyde (4.6 g, 21 mmol) (Lancaster) was used as the starting material in place of 2-[2-(tert-butyl-dimethyl-silanyloxy)-ethoxy]-5-iodo-benzaldehyde to react with 1,1,3,3,3-hexamethyldisilazane (4.36 mL, 21 mmol), n-butyllithium (2.5 M, 8.4 mL, 21 mmol), trimethylsilyl chloride (2.66 mL, 21 mmol), triethylamine (3.8 mL, 27.2 mmol) and acetyl chloride (1.94 mL, 27.2 mmol) to give crude 1-(3-bromo-4-fluorophenyl)-3-trimethylsilyoxy-2-aza-1,3-butadiene as a yellow gum and used for the next step without further purification.

EXAMPLE 205b

Preparation of racemic (2'R,3R,4'S)-2'-(3-bromo-4-fluoro-phenyl)-6-chloro-4'-(3-chlorophenyl)spiro[3H-indole-3,3'-piperidine]-2,6'(1H)-dione

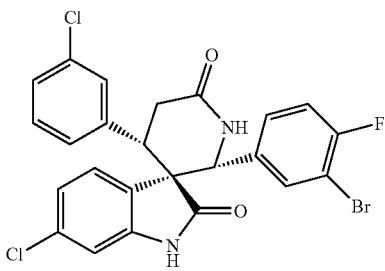

M. W. 534.22 C$_{24}$H$_{16}$BrCl$_2$FN$_2$O$_2$

In a manner similar to the method described in example 192b, E/Z-6-chloro-3-(3-chloro-benzylidene)-2-oxo-2,3-dihydro-indole-1-carboxylic acid tert-butyl ester prepared in example 24a (2 g, 5.6 mmol) was reacted with crude 1-(3-bromo-4-fluoro-phenyl)-3-trimethylsilyoxy-2-aza-1,3-butadiene prepared in example 20a (10.5 mmol) in toluene and then trifluoroacetic acid in dichloromethane to give racemic (2'R,3R,4'S)-2'-(3-bromo-4-fluoro-phenyl)-6-chloro-4'-(3-chlorophenyl)spiro[3H-indole-3,3'-piperidine]-2,6'(1H)-dione as a white solid (Yield 2 g, 67%)

HRMS (ES$^+$) m/z Calcd for C$_{24}$H$_{16}$BrCl$_2$FN$_2$O$_2$+H [(M+H)$^+$]: 532.9829. Found: 532.9832.

EXAMPLE 206

Preparation of racemic (2'R,3R,4'S)-6-chloro-4'-(3-chlorophenyl)-2'-(3-ethynyl-4-fluoro-phenyl)spiro[3H-indole-3,3'-piperidine]-2,6'(1H)-dione

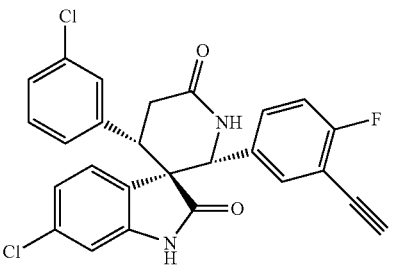

M. W. 479.34 C$_{26}$H$_{17}$Cl$_2$FN$_2$O$_2$

In a manner similar to the method described in example 193, racemic (2'R,3R,4'S)-2'-(3-bromo-2-fluoro-phenyl)-6-chloro-4'-(3-chlorophenyl)spiro[3H-indole-3,3'-piperidine]-2,6'(1H)-dione prepared in example 205b (0.3 g, 0.56 mmol) was reacted with trimethylsilyl acetylene (0.8 mL, 5.6 mmol), CuI (10 mg), triethylamine (2.34 mL, 16.8 mmol), and dichlorobis(triphenylphosphine)palladium(0) (39 mg, 0.056 mmol) in anhydrous N,N-dimethylformamide, and then treated with aqueous NaOH in methanol to give racemic (2'R,3R,4'S)-6-chloro-4'-(3-chlorophenyl)-2'-(3-ethynyl-4-fluoro-phenyl)spiro[3H-indole-3,3'-piperidine]-2,6'(1H)-dione as a grey solid (Yield 56 mg)

HRMS (ES$^+$) m/z Calcd for C$_{26}$H$_{17}$Cl$_2$FN$_2$O$_2$+H [(M+H)$^+$]: 479.0724. Found: 479.0724.

EXAMPLE 207a

Preparation of intermediate 1-(1-benzofuran-5-yl)-3-trimethylsilyoxy-2-aza-1,3-butadiene

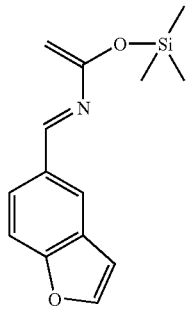

M. W. 259.38 C$_{14}$H$_{17}$NO$_2$Si

In a manner similar to the method described in example 190b, 1-benzofuran-5-carbaldehyde (1.2 g, 10 mmol) (Maybr-INT) was used as the starting material in place of 2-[2-(tert-butyl-dimethyl-silanyloxy)-ethoxy]-5-iodo-benzaldehyde to react with 1,1,3,3,3-hexamethyldisilazane (1.6 g, 10 mmol), n-butyllithium (2.5 M, 4 mL, 10 mmol), trimethylsilyl chloride (1.1 g, 10 mmol), triethylamine (1.36 g, 13.6 mmol) and acetyl chloride (1 g, 13.6 mmol) to give crude 1-(1-benzofuran-5-yl)-3-trimethylsilyoxy-2-aza-1,3-butadiene as a yellow gum and used for the next step without further purification.

EXAMPLE 207b

Preparation of racemic (2'R,3R,4'S)-2'-(1-benzofuran-5-yl)-6-chloro-4'-(3-chlorophenyl)spiro[3H-indole-3,3'-piperidine]-2,6'(1H)-dione

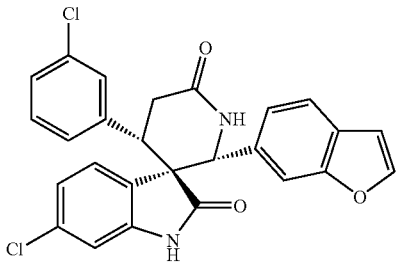

M. W. 477.35 $C_{26}H_{18}Cl_2N_2O_3$

In a manner similar to the method described in example 192b, E/Z-6-chloro-3-(3-chloro-benzylidene)-2-oxo-2,3-dihydro-indole-1-carboxylic acid tert-butyl ester prepared in example 5b (0.4 g, 1.4 mmol) was reacted with crude 1-(1-benzofuran-5-yl)-3-trimethylsilyoxy-2-aza-1,3-butadiene prepared in example 207a (10 mmol) in toluene and then trifluoroacetic acid in dichloromethane to give racemic (2'R,3R,4'S)-2'-(1-benzofuran-5-yl)-6-chloro-4'-(3-chlorophenyl)spiro[3H-indole-3,3'-piperidine]-2,6'(1H)-dione as a white solid (Yield 0.3 g, 45%)

HRMS (ES$^+$) m/z Calcd for $C_{26}H_{18}Cl_2N_2O_3$+H [(M+H)$^+$]: 477.0767. Found: 477.0767.

EXAMPLE 208a

Preparation of intermediate 5-chloro-2-Iodo-benzaldehyde

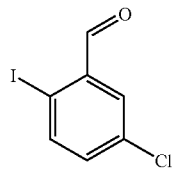

M. W. 266.47 $C_7H_4ClIO$

To a solution of 5-chloro-2-iodo benzoic acid (4.92 g, 17 mmol) (TRANS) in anhydrous tetrahydrofuran (100 mL) at 0° C. was added borane tetrahydrofuran (1 M, 34 mL, 34 mmol) dropwise. The reaction mixture was then stirred at room temperature for 18 h. The mixture was concentrated and residue was partitioned between ethyl acetate and water. Organic layer was separated, washed with brine, dried over MgSO$_4$, and concentrated to give a colorless oil. The oil was dissolved into 1,2-dichloroethane (50 mL), and activated MnO$_2$ (15 g) was added. The mixture was then heated at reflux for 2 h, cooled to room temperature, and filtered through a short pad of celite. The filtrated was concentrated and purified by chromatography (EtOAc:hexanes=1;8) to give 5-chloro-2-Iodo-benzaldehyde as a white solid (Yield 5.5 g, 25%).

EXAMPLE 208b

Preparation of intermediate 1-(5-chloro-2-iodophenyl)-3-trimethylsilyoxy-2-aza-1,3-butadiene

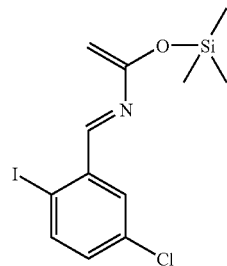

M. W. 379.70 $C_{12}H_{15}ClINOSi$

In a manner similar to the method described in example 190b, 5-chloro-2-iodobenzaldehyde prepared in example 208a (3.97 g, 15 mmol) was used as the starting material in place of 2-[2-(tert-butyl-dimethyl-silanyloxy)-ethoxy]-5-iodo-benzaldehyde to react with 1,1,3,3,3-hexamethyldisilazane (2.4 g, 15 mmol), n-butyllithium (2.5 M, 6 mL, 15 mmol), trimethylsilyl chloride (1.6 g, 15 mmol), triethylamine (2 g, 20 mmol) and acetyl chloride (1.5 g, 20 mmol) to give crude 1-(5-chloro-2-iodophenyl)-3-trimethylsilyoxy-2-aza-1,3-butadiene as a yellow gum and used for the next step without further purification.

EXAMPLE 208c

Preparation of racemic (2'R,3R,4'S)-6-chloro-4'-(3-chlorophenyl)-2'-(5-chloro-2-iodophenyl)spiro[3H-indole-3,3'-piperidine]-2,6'(1H)-dione

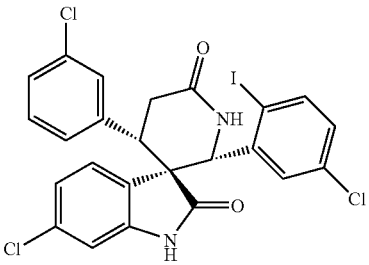

M. W. 597.67 $C_{24}H_{16}Cl_3IN_2O_2$

In a manner similar to the method described in example 192b, E/Z-6-chloro-3-(3-chloro-benzylidene)-2-oxo-2,3-dihydro-indole-1-carboxylic acid tert-butyl ester prepared in example 24a (2 g, 5.6 mmol) was reacted with crude 1-(5-chloro-2-iodophenyl)-3-trimethylsilyoxy-2-aza-1,3-butadiene prepared in example 208b (5.6 g, 15 mmol) in toluene and then trifluoroacetic acid in dichloromethane to give racemic (2'R,3R,4'S)-6-chloro-4'-(3-chlorophenyl)-2'-(5-chloro-2-iodophenyl)spiro[3H-indole-3,3'-piperidine]-2,6'(1H)-dione as a yellow solid (Yield 2.1 g, 63%)

HRMS (ES$^+$) m/z Calcd for $C_{24}H_{16}Cl_3IN_2O_2$+H [(M+H)$^+$]: 596.9395. Found: 596.9393.

EXAMPLE 209a

Preparation of racemic (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione

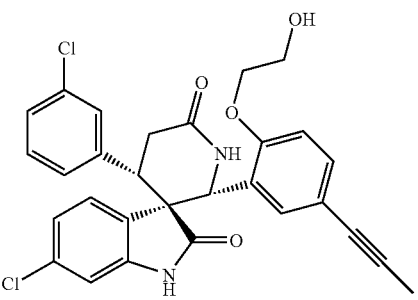

M. W. 535.43 $C_{29}H_{24}Cl_2N_2O_4$

To a suspension of racemic (2'R,3R,4'S)-6-chloro-4'-(3-chlorophenyl)-2'-[5-iodo-2-(2-hydroxy-ethoxy)-phenyl] spiro[3H-indole-3,3'-piperidine]-2,6'(1H)-dione (0.2 g, 0.32 mmol) prepared in Example 190c in dioxane (10 mL) was added CuI (5 mg, 0.026 mmol) (Aldrich). The mixture was degassed under nitrogen for 5 min, then tris(dibenzylideneacetone)dipalladium(0) (23 mg, 0.026 mmol, Strem), tri-phenylphosphine (6.7 mg, 0.026 mmol), and tributyl(1-propynyl)tin (1.1 g, 3.2 mmol, Aldrich) were added sequentially.

The reaction mixture was heated at 80° C. under nitrogen for 1 h. After cooled to room temperature, the reaction mixture was filtered through a short pad of celite. The filtrate was partitioned between saturated water and ethyl acetate. The aqueous layer was extracted with ethyl acetate. The combined organic layer was dried over $Na_2SO_4$ and concentrated. The residue was purified by chromatography to give racemic (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione as a yellow solid (Yield 0.17 g, 99%).

HRMS (ES$^+$) m/z Calcd for $C_{29}H_{24}Cl_2N_2O_4$+H [(M+H)$^+$]: 535.1186. Found: 535.1187.

EXAMPLE 209b

Preparation of chiral (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione

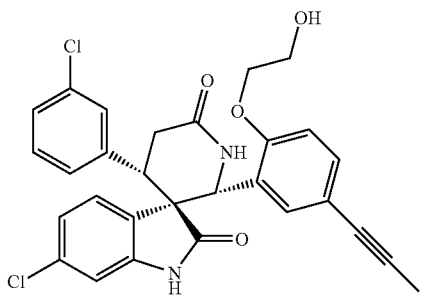

M. W. 535.43 $C_{29}H_{24}Cl_2N_2O_4$

Separation of the two enantiomers from racemic (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione prepared in Example 209a (200 mg) was conducted by chiral SFC to provide chiral (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione as a yellow solid (50 mg, 25%) and chiral (2'S,3S,4'R)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione as a yellow solid (49 mg, 25%).

EXAMPLE 210

Preparation of racemic (2'R,3R,4'S)-6-chloro-4'-(3-chlorophenyl)-2'-[5-(3,3-dimethyl-1-butynyl)-2-(2-hydroxy-ethoxy)-phenyl]spiro[3H-indole-3,3'-piperidine]-2,6'(1H)-dione

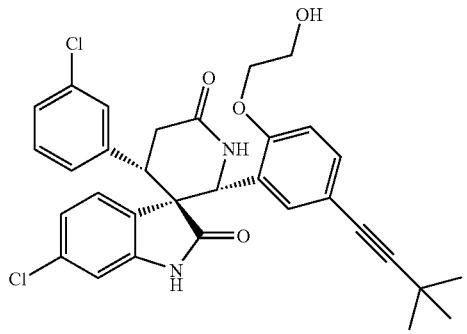

M. W. 577.51 $C_{32}H_{30}Cl_2N_2O_4$

A solution of racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione (0.15 g, 0.24 mmol) prepared in Example 190c in anhydrous N,N-dimethylformamide (10 mL) was added CuI (3 mg), 3,3-dimethyl-1-butyne (19.7 mg, 2.4 mmol) (Aldrich), and triethylamine (1 mL, 7.2 mmol). The mixture was degassed under nitrogen for 5 min, then dichlorobis(triphenylphosphine)palladium (8.4 mg, 0.012 mmol) (Strem) was added and the reaction mixture was heated at 80° C. under nitrogen for 0.5 h. The reaction mixture was cooled to room temperature and partitioned between ethyl acetate and water. The organic layer was separated, and the aqueous layer was extracted with ethyl acetate. The organic layers were combined, dried over $MgSO_4$ and concentrated. The residue was purified with chromatography to give racemic (2'R,3R,4'S)-6-chloro-4'-(3-chlorophenyl)-2'-[5-(3,3-dimethyl-1-butynyl)-2-(2-hydroxy-ethoxy)-phenyl]spiro[3H-indole-3,3'-piperidine]-2,6'(1H)-dione as a white solid (Yield: 41 mg, 30%).

HRMS (ES$^+$) m/z Calcd for $C_{32}H_{30}Cl_2N_2O_4$+H [(M+H)$^+$]: 577.1656. Found: 577.1655.

EXAMPLE 211

Preparation of racemic (2'R,3R,4'S)-6-chloro-4'-(3-chlorophenyl)-2'-[5-(3-cyclopropyl-1-butynyl)-2-(2-hydroxy-ethoxy)-phenyl]spiro[3H-indole-3,3'-piperidine]-2,6'(1H)-dione

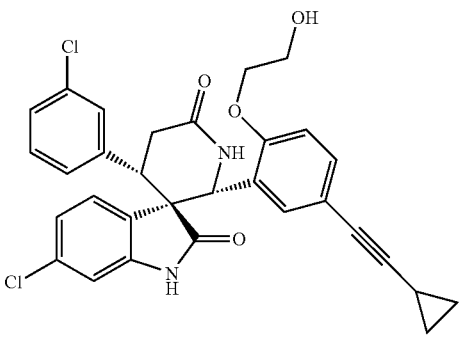

M. W. 561.47 $C_{31}H_{26}Cl_2N_2O_4$

In a manner similar to the method described in example 209, ethynylcyclopropane (0.16 g, 2.4 mmol) was used in place of 3,3-dimethyl-1-butyne to react with racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione (0.15 g, 0.24 mmol) prepared in Example 190c, CuI (3 mg), triethylamine (1 mL, 7.2 mmol), and dichlorobis(triphenylphosphine)palladium(0) (8.4 mg, 0.012 mmol) in anhydrous N,N-dimethylformamide to give racemic (2'R,3R,4'S)-6-chloro-4'-(3-chlorophenyl)-2'-[5-(3-cyclopropyl-1-butynyl)-2-(2-hydroxy-ethoxy)-phenyl]spiro[3H-indole-3,3'-piperidine]-2,6'(1H)-dione as a white solid (Yield 84 mg, 62%)

HRMS (ES$^+$) m/z Calcd for $C_{31}H_{26}Cl_2N_2O_4$+H [(M+H)$^+$]: 561.1343. Found: 561.1344.

EXAMPLE 212

Preparation of racemic (2'R,3R,4'S)-6-chloro-4'-(3-chlorophenyl)-2'-[5-(3-methyl-1-butynyl)-2-(2-hydroxy-ethoxy)-phenyl]spiro[3H-indole-3,3'-piperidine]-2,6'(1H)-dione

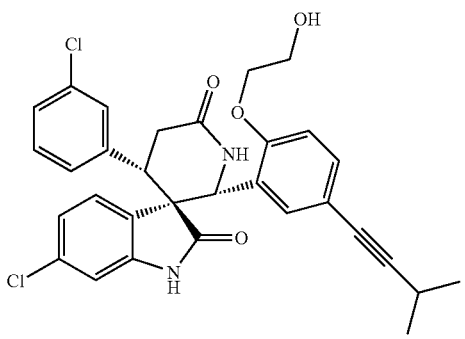

M. W. 563.49 $C_{31}H_{28}Cl_2N_2O_4$

In a manner similar to the method described in example 209a, 3-methyl-1-butyne (0.22 g, 3.2 mmol) was used in place of 3,3-dimethyl-1-butyne to react with racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione (0.2 g, 0.32 mmol) prepared in Example 190c, CuI (3 mg), triethylamine (0.97 g, 9.6 mmol), and dichlorobis(triphenylphosphine)palladium (11.2 mg, 0.016 mmol) in anhydrous N,N-dimethylformamide to give racemic (2'R,3R,4'S)-6-chloro-4'-(3-chlorophenyl)-2'-[5-(3-methyl-1-butynyl)-2-(2-hydroxy-ethoxy)-phenyl]spiro[3H-indole-3,3'-piperidine]-2,6'(1H)-dione as a off white solid (Yield 50 mg, 28%)

HRMS (ES$^+$) m/z Calcd for $C_{31}H_{28}Cl_2N_2O_4$+H [(M+H)$^+$]: 563.1499. Found: 561.1501.

EXAMPLE 213

Preparation of racemic (2'R,3R,4'S)-6-chloro-4'-(3-chlorophenyl)-2'-[2-(2-hydroxy-ethoxy)-5-vinyl-phenyl]spiro[3H-indole-3,3'-piperidine]-2,6'(1H)-dione

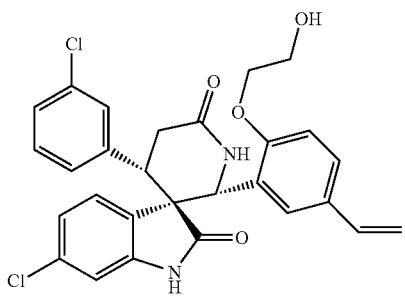

M. W. 523.41 $C_{28}H_{24}Cl_2N_2O_4$

To a suspension of racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione (0.1 g, 0.16 mmol) prepared in Example 190c in dioxane (10 mL) was added CuI (5 mg, 0.026 mmol) (Aldrich). The mixture was degassed under nitrogen for 5 min, then tris(dibenzylideneacetone)dipalladium(0) (11.7 mg, 0.013 mmol, Strem), triphenylphosphine (3.35 mg, 0.013 mmol), and tributyl(vinyl)tin (46 uL, 1.0 mmol, Aldrich) were added sequentially. The reaction mixture was heated at 60° C. under nitrogen for 2 h. After cooled to room temperature, the reaction mixture was partitioned between saturated water and ethyl acetate. The aqueous layer was extracted with ethyl acetate. The combined organic layer was dried over $Na_2SO_4$ and concentrated. The residue was purified by chromatography to give racemic (2'R,3R,4'S)-6-chloro-4'-(3-chlorophenyl)-2'-[2-(2-hydroxy-ethoxy)-5-vinyl-phenyl]spiro[3H-indole-3,3'-piperidine]-2,6'(1H)-dione as a yellow solid (Yield 80 mg, 96%).

HRMS (ES$^+$) m/z Calcd for $C_{28}H_{24}Cl_2N_2O_4$+H [(M+H)$^+$]: 523.1186. Found: 523.1187.

EXAMPLE 214a

Preparation of intermediate 4-iodo-2-tert-butyl-dimethylsilanyloxy-benzaldehyde

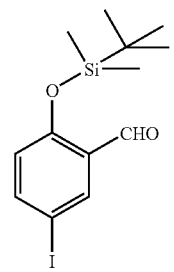

M. W. 362.29 $C_{13}H_{19}IO_2Si$

To a stirred solution of 5-iodo-2hydroxy-benzaldehyde (Aldrich, 15.5 g, 62.5 mmol) in methylene chloride (100 mL) were added imidazole (Aldrich, 4.28 g, 63 mmol) and tert-butyl-dimethyl-chloro-silane (Aldrich, 9.45 g, 63 mmol). The mixture was stirred at room temperature for 5.5 hrs and then poured into 1 N sodium hydroxide solution (150 mL). The organic layer was separated and the aqueous layer was extracted with methylene chloride (2×50 mL). The combined extracts were washed with water, brine and dried over magnesium sulfate. Removal of the solvent gave an oil, which was chromatographed (hexane as eluent) to give a colorless oil. 16.6 g.

EXAMPLE 214b

Preparation of intermediate 1-[5-bromo-2-(tert-butyl-dimethylsilanyloxy)-phenyl]-3-trimethylsilanyloxy-2-aza-1,3-butadiene

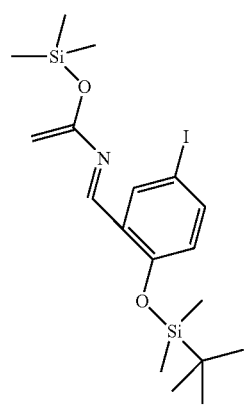

M. W. 475.52 C$_{18}$H$_{30}$INO$_2$Si$_2$

To a stirred solution of 1,1,1,3,3,3-hexamethyldisilazane (6.4 g, 40 mmol) at 0° C., n-BuLi (2.5 M, 16 mL) was added slowly and the mixture was stirred for 15 min. Then THF (80 mL) was added followed by 4-iodo-2-tert-butyl-dimethylsilanyloxy-benzaldehyde (14.48 g, 40 mmol). The mixture was stirred at rt for 30 min. Then, trimethylsilanyl chloride (40 mmol), acetyl chloride (40 mmol) and trimethylamine (40 mmol) were added and the mixture was stirred at rt for 1 hr. The mixture was quickly passed through a short pad of silica gel and the pad was washed with 30 EtOAc/Hexanes to make sure the azadiene has completely passed through. The filtrate was concentrated at rt and directly used for the next step.

EXAMPLE 214c

Preparation of intermediate racemic (2'R,3R,4'S)-2'-[2-(tert-butyl-dimethylsilanyloxy)-5-iodo-phenyl]-6-chloro-4'-(3-chlorophenyl)-2,6'-dioxo-spiro[3H-indole-3,3'-piperidine]-1-carboxylic acid tert-butyl ester

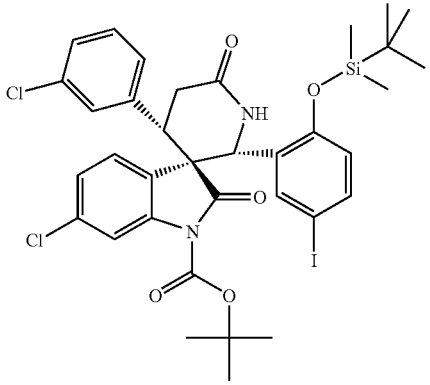

M. W. 793.61 C$_{35}$H$_{39}$Cl$_2$IN$_2$O$_5$Si

E/Z-6-chloro-3-(3-chloro-benzylidene)-2-oxo-2,3-dihydro-indole-1-carboxylic acid tert-butyl ester prepared in Example 24a (3.85 g, 13 mmol) and 1-[5-bromo-2-(tert-butyl-dimethylsilanyloxy)-phenyl]-3-trimethylsilanyloxy-2-aza-1,3-butadiene (40 mmol) were combined into toluene (110 mL). The mixture was stirred at 110° C. for 2 hrs. The solvent was removed and the residue was chromatographed (15%-35% EtOAc/Hexanes) to give a foam. 4.65 g. MS (H$^+$), 693.

EXAMPLE 214d

Preparation of racemic (2'R,3R,4'S)-6-chloro-4'-(3-chlorophenyl)-2'-[2-hydroxy-5-iodo-phenyl]spiro[3H-indole-3,3'-piperidine]-2,6'-dione

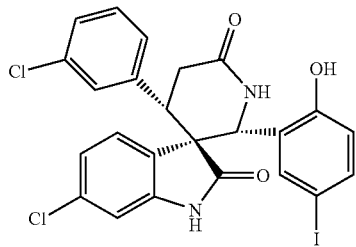

M. W. 579.23 C$_{24}$H$_{17}$Cl$_2$IN$_2$O$_3$

Racemic (2'R,3R,4'S)-2'-[2-(tert-butyl-dimethylsilanyloxy)-5-iodo-phenyl]-6-chloro-4'-(3-chlorophenyl)-2,6'-dioxo-spiro[3H-indole-3,3'-piperidine]-1-carboxylic acid tert-butyl ester (200 mg, 0.25 mmol) was dissolved in 30% TFA/CH$_2$Cl$_2$ (5 mL) and the solution was stirred at rt for 2 h. The solvent was removed and the residue was partioned between water and methylene chloride. The organic layer was separated and dried with sodium sulfate and concentrated. The residue was chromatographed to give a white solid which was directly used for next step. MS (H$^+$), 579.

EXAMPLE 214e

Preparation of intermediate racemic (2'R,3R,4'S)-6-chloro-4'-(3-chlorophenyl)-2'-[2-hydroxy-5-(2-trimethylsilanyl-ethynyl)-phenyl]spiro[3H-indole-3,3'-piperidine]-2,6'-dione

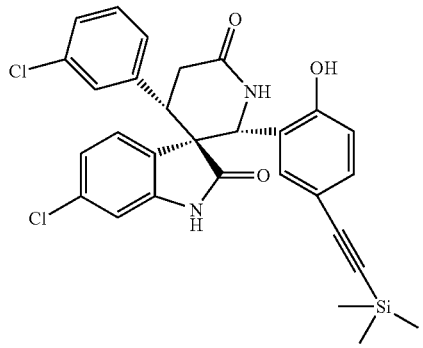

M. W. 549.53 C$_{29}$H$_{26}$Cl$_2$N$_2$O$_3$Si

To a stirred solution of racemic (2'R,3R,4'S)-6-chloro-4'-(3-chlorophenyl)-2'-[2-hydroxy-5-iodo-phenyl]spiro[3H-indole-3,3'-piperidine]-2,6'-dione (100 mg) in DMF (2 mL) were added PdCl$_2$(PPh$_3$)$_2$ (18 mg), CuI (4 mg), trimethylsilyl acetylene (Aldrich, 0.40 mL) and Et$_3$N (Aldrich, 0.62 mL) and the mixture was purged with nitrogen and then heated at 83° C. for 3 hrs. The solvent was removed and the crude was directly used for next step. MS (H$^+$), 549.

EXAMPLE 214f

Preparation of racemic (2'R,3R,4'S)-6-chloro-4'-(3-chlorophenyl)-2'-[5-ethynyl-2-hydroxy-phenyl]spiro[3H-indole-3,3'-piperidine]-2,6'-dione

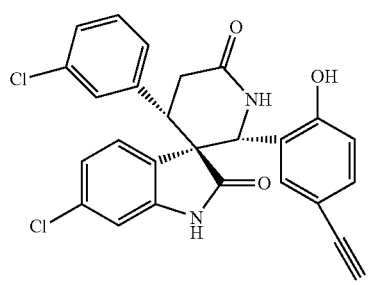

M. W. 477.35 C$_{26}$H$_{18}$Cl$_2$N$_2$O$_3$

Racemic (2'R,3R,4'S)-6-chloro-4'-(3-chlorophenyl)-2'-[2-hydroxy-5-(2-trimethylsilanyl-ethynyl)-phenyl]spiro[3H-indole-3,3'-piperidine]-2,6'-dione was dissolved in methanol (10 mL). To the stirred solution, KF (Aldrich, 270 mg) was added and the mixture was stirred at rt overnight. The solvent was removed under reduced and the residue was treated with 6 mL of 5% MeOH in methylene chloride. The solid was filtered out and the filtrate was concentrated to about 2 mL and loaded on to an ISCO column. Chromatography (eluent with 5% MeOH in methylene chloride) gave a white solid. 30 mg. MS (H$^+$), 477.

EXAMPLE 214g

Preparation of chiral (2'R,3R,4'S)-6-chloro-4'-(3-chlorophenyl)-2'-[5-ethynyl-2-hydroxy-phenyl]spiro[3H-indole-3,3'-piperidine]-2,6'-dione

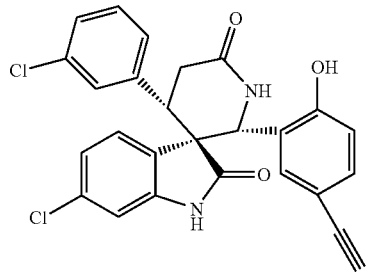

M. W. 477.35 $C_{26}H_{18}Cl_2N_2O_3$

Separation of the two enantiomers from racemic (2'R,3R,4'S)-6-chloro-4'-(3-chlorophenyl)-2'-[5-ethynyl-2-hydroxyphenyl]spiro[3H-indole-3,3'-piperidine]-2,6'-dione (50 mg) was conducted by chiral SFC to provide chiral (2'R,3R,4'S)-6-chloro-4'-(3-chlorophenyl)-2'-[5-ethynyl-2-hydroxy-phenyl]spiro[3H-indole-3,3'-piperidine]-2,6'-dione as a white solid (8 mg, 16%) and chiral (2'S,3S,4'R)-6-chloro-4'-(3-chlorophenyl)-2'-[5-ethynyl-2-hydroxy-phenyl]spiro[3H-indole-3,3'-piperidine]-2,6'-dione as a white solid (6 mg, 12%).

EXAMPLE 215a

Preparation of intermediate racemic (2'R,3R,4'S)-2'-[2-(2-allyloxy)-5-iodo-phenyl]-6-chloro-4'-(3-chlorophenyl)-2,6'-dioxo-spiro[3H-indole-3,3'-piperidine]-1-carboxylic acid tert-butyl ester

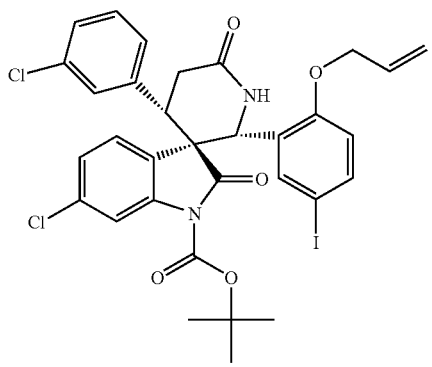

M. W. 719.41 $C_{32}H_{29}Cl_2IN_2O_5$

To a stirred solution of racemic (2'R,3R,4'S)-2'-[2-(tert-butyl-dimethylsilanyloxy)-5-iodo-phenyl]-6-chloro-4'-(3-chlorophenyl)-2,6'-dioxo-spiro[3H-indole-3,3'-piperidine]-1-carboxylic acid tert-butyl ester (500 mg, 0.63 mmol) in THF (3 mL) was added Tetrabutylammonium fluoride (Aldrich, 0.56 mL, 1 M in THF) at room temperature and the mixture was stirred for 20 min. To the resulting mixture, sodium bicarbonate (300 mg) and allyl iodide (0.075 mL, 0.82 mmol) were added and the mixture was stirred at 40° C. for overnight. The solvent was removed and the residue was chromatographed (5% MeOH/CH$_2$Cl$_2$) to give a yellow foam, 340 mg. MS (H$^+$), 719.

EXAMPLE 215b

Preparation of racemic (2'R,3R,4'S)-2'-[2-(2-allyloxy)-5-iodo-phenyl)]-6-chloro-4'-(3-chlorophenyl)spiro[3H-indole-3,3'-piperidine]-2,6'-dione

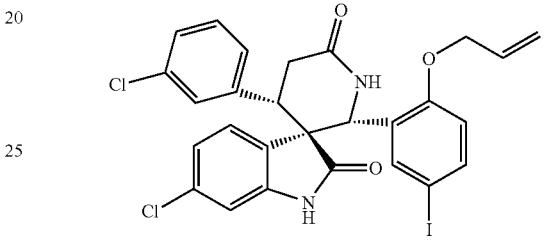

M. W. 619.29 $C_{27}H_{21}Cl_2IN_2O_3$

Racemic (2'R,3R,4'S)-2'-[2-(2-allyloxy)-5-iodo-phenyl]-6-chloro-4'-(3-chlorophenyl)-2,6'-dioxo-spiro[3H-indole-3,3'-piperidine]-1-carboxylic acid tert-butyl ester (335 mg) was dissolved in 30% TFA/CH$_2$Cl$_2$ (5 mL) and the solution was stirred at rt for 30 min. The solvent was removed under reduced pressure and the residue was treated with aqueous saturated NaHCO$_3$ solution, extracted with ethyl acetate. The organic layer was separated, washed with brine, dried over MgSO$_4$ and concentrated to give an off white foam. 225 mg. MS (H$^+$), 619

EXAMPLE 215c

Preparation of racemic (2'R,3R,4'S)-6-chloro-4'-(3-chlorophenyl)-2'-[2-(2,3-dihydroxy-propoxy)-5-iodo-phenyl]spiro[3H-indole-3,3'-piperidine]-2,6'-dione

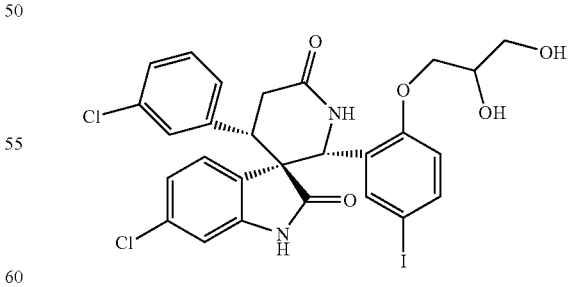

M. W. 653.31 $C_{27}H_{23}Cl_2IN_2O_5$

To a stirred solution of racemic (2'R,3R,4'S)-2'-[2-(2-allyloxy)-5-iodo-phenyl)]-6-chloro-4'-(3-chlorophenyl)spiro[3H-indole-3,3'-piperidine]-2,6'-dione (120 mg, 0.194 mmol) in CH$_2$Cl$_2$ (3 ml) was added acetone (2 ml) and water (2 ml), followed by a solution of OsO$_4$ (50 mg, 0.194 mmol)

in water. N-methyl morpholine oxide (24 uL, 0.214 mmol) was added and the reaction was stirred at r.t. for 20 minutes, and then quenched by a solution of $Na_2SO_3$. The reaction was diluted with $CH_2Cl_2$ and water. Organic layer was separated, the aqueous layer was extracted $CH_2Cl_2$. The combined organic solution was concentrated and purified by flash chromatography eluting with EtOAc to 5% MeOH in EtOAc. Yield 68 mg (54%) white foam. MS ($H^+$), 653

EXAMPLE 215d

Preparation of intermediate racemic (2'R,3R,4'S)-6-chloro-4'-(3-chlorophenyl)-2'-[2-(2,3-dihydroxy-propoxy)-5-(2-trimethylsilanyl-ethynyl)-phenyl]spiro[3H-indole-3,3'-piperidine]-2,6'-dione

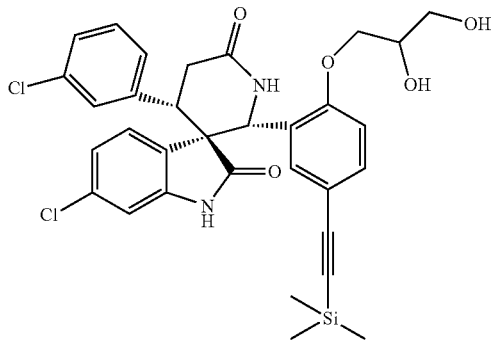

M. W. 623.61 $C_{32}H_{32}Cl_2N_2O_5Si$

To a stirred solution of racemic (2'R,3R,4'S)-6-chloro-4'-(3-chlorophenyl)-2'-[2-(2,3-dihydroxy-propoxy)-5-iodo-phenyl]spiro[3H-indole-3,3'-piperidine]-2,6'-dione (120 mg, 0.183 mmol) in DMF (2 mL) were added $PdCl_2(PPh_3)_2$ (15 mg), CuI (2 mg), trimethylsilyl acetylene (Aldrich, 2 mL) and $Et_3N$ (Aldrich, 2 mL) and the mixture was purged with nitrogen and then heated at 75° C. for 3 hrs. The mixture was partitioned between ethyl acetate and water. The organic layer was separated, washed with water, brine, dried, and concentrated. The residue was purified by chromatography (0-4% MeOH in EtOAc). Yield 8 mg. MS ($H^+$), 623

EXAMPLE 215e

Preparation of racemic (2'R,3R,4'S)-6-chloro-4'-(3-chlorophenyl)-2'-[5-ethynyl-2-(2,3-dihydroxy-propoxy)-phenyl]-spiro[3H-indole-3,3'-piperidine]-2,6'-dione

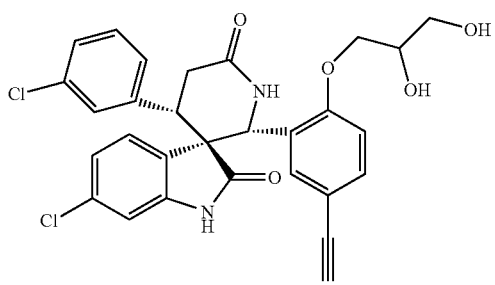

M. W. 551.43 $C_{29}H_{24}Cl_2N_2O_5$

To a stirred solution of racemic (2'R,3R,4'S)-6-chloro-4'-(3-chlorophenyl)-2'-[2-(2,3-dihydroxy-propoxy)-5-(2-trim-ethylsilanyl-ethynyl)-phenyl]spiro[3H-indole-3,3'-piperidine]-2,6'-dione (7.8 mg, 0.013 mmol) in MeOH (3 ml) was added 2N NaOH (1 mL) dropwise. The reaction mixture was stirred at room temperature for 30 min and then extracted with ethyl acetate several times. The combined organic extract was dried over $MgSO_4$ and concentrated to give the title compound as a white solid (6.2 mg). MS ($H^+$), 551

EXAMPLE 216

Preparation of racemic (2'R,3R,4'S)-2'-[5-bromo-2-methylsulfanyl-phenyl]-6-chloro-4'-(3-chlorophenyl)spiro[3H-indole-3,3'-piperidine]-2,6'-dione

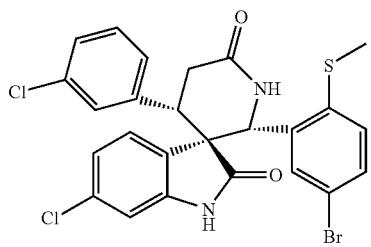

M. W. 562.32 $C_{25}H_{19}BrCl_2N_2O_2S$

In a manner similar to the method described in examples 214b, 214c, 214d, the title compound was prepared in 3 steps starting from 5-bromo-2-methylsulfanyl-benzaldehyde (Aldrich). MS ($H^+$), 561.

EXAMPLE 217

Preparation of racemic (2'R,3R,4'S)-2'-[5-bromo-2-methylsulfonyl-phenyl]-6-chloro-4'-(3-chlorophenyl)spiro[3H-indole-3,3'-piperidine]-2,6'-dione

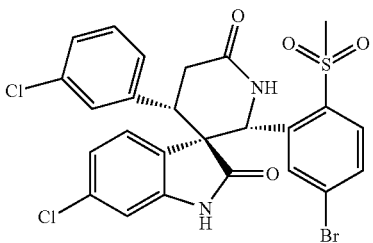

M. W. 594.32 $C_{25}H_{19}BrCl_2N_2O_4S$

To a solution of racemic (2'R,3R,4'S)-2'-[5-bromo-2-methylsulfanyl-phenyl]-6-chloro-4'-(3-chlorophenyl)spiro[3H-indole-3,3'-piperidine]-2,6'-dione (360 mg, 0.64 mmol) in dichloromethane (5 ml) at 0° C. was added MCPBA (442 mg, 2.56 mmol, Aldrich). The reaction mixture was stirred at 0° C. for 0.5 h, then at room temperature for 1.5 h. The reaction was quenched by addition of aqueous $Na_2SO_3$ solution. The mixture was extracted with ethyl acetate several times. The combined organic extract was washed with water, brine, dried over $MgSO_4$ and concentrated to give the title compound as an off white solid (360 mg). MS (M+$H^+$), 595

EXAMPLE 218a

Preparation of intermediate racemic (2'R,3R,4'S)-6-chloro-4'-(3-chlorophenyl)-2'-[2-methylsulfonyl-5-(2-trimethylsilanyl-ethynyl)-phenyl]spiro[3H-indole-3,3'-piperidine]-2,6'-dione

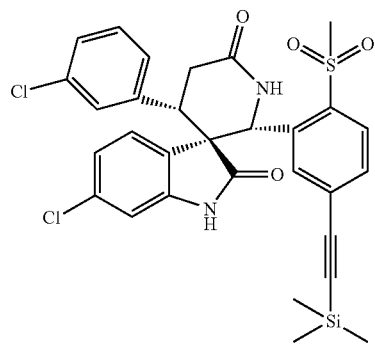

M. W. 611.62 $C_{30}H_{28}Cl_2N_2O_4SSi$

In a manner similar to the method described in example 214e, racemic (2'S,3R,4'S)-2'-[5-bromo-2-methylsulfonyl-phenyl]-6-chloro-4'-(3-chlorophenyl)spiro[3H-indole-3,3'-piperidine]-2,6'-dione reacted with PdCl$_2$(PPh$_3$)$_2$, CuI, trimethylsilyl acetylene and Et$_3$N (Aldrich, 0.62 mL) in DMF to give the title compound.

EXAMPLE 218b

Preparation of racemic (2'R,3R,4'S)-6-chloro-4'-(3-chlorophenyl)-2'-[5-ethynyl-2-methylsulfonyl-phenyl]spiro[3H-indole-3,3'-piperidine]-2,6'-dione

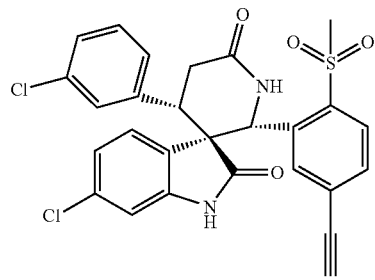

M. W. 539.44 $C_{27}H_{20}Cl_2N_2O_4S$

In a manner similar to the method described in example 214f, racemic (2'S,3R,4'S)-6-chloro-4'-(3-chlorophenyl)-2'-[2-methylsulfonyl-5-(2-trimethylsilanyl-ethynyl)-phenyl]spiro[3H-indole-3,3'-piperidine]-2,6'-dione reacted with KF in methanol to give the title compound. MS (M+H$^+$) 539

EXAMPLE 219

Preparation of racemic (2'R,3R,4'S)-2'-[5-bromo-2-methoxy-phenyl]-6-chloro-4'-(3-chlorophenyl)spiro[3H-indole-3,3'-piperidine]-2,6'-dione

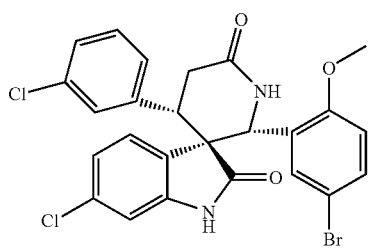

M. W. 524.25 $C_{25}H_{19}BrCl_2N_2O_3$

In a manner similar to the method described in examples 214b, 214c, 214d, the title compound was prepared in 3 steps starting from 5-bromo-2-methoxy-benzaldehyde (Aldrich). MS (H$^+$), 545.

EXAMPLE 220a

Preparation of intermediate racemic (2'R,3R,4'S)-6-chloro-4'-(3-chlorophenyl)-2'-[2-methoxy-5-(2-trimethylsilanyl-ethynyl)-phenyl]spiro[3H-indole-3,3'-piperidine]-2,6'-dione

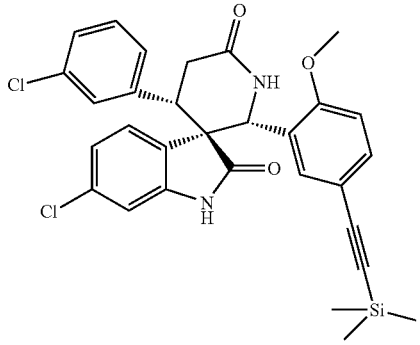

M. W. 563.56 $C_{30}H_{28}Cl_2N_2O_3Si$

In a manner similar to the method described in example 214e, racemic (2'R,3'R,4'S)-2'-[5-bromo-2-methoxy-phenyl]-6-chloro-4'-(3-chlorophenyl)spiro[3H-indole-3,3'-piperidine]-2,6'-dione reacted with PdCl$_2$(PPh$_3$)$_2$, CuI, trimethylsilyl acetylene and Et$_3$N (Aldrich, 0.62 mL) in DMF to give the title compound. MS (H$^+$),

EXAMPLE 220b

Preparation of racemic (2'R,3R,4'S)-6-chloro-4'-(3-chlorophenyl)-2'-[5-ethynyl-2-methoxy-phenyl]-spiro[3H-indole-3,3'-piperidine]-2,6'-dione

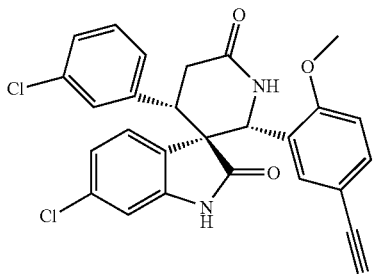

M. W. 491.38 $C_{27}H_{20}Cl_2N_2O_3$

To a stirred solution of racemic (2'R,3R,4'S)-6-chloro-4'-(3-chlorophenyl)-2'-[2-methoxy-5-(2-trimethylsilanyl-ethynyl)-phenyl]spiro[3H-indole-3,3'-piperidine]-2,6'-dione (50 mg, 0.088 mmol) in MeOH (2 ml) was added 2N NaOH dropwise. The reaction was stirred for 30 min and extracted with EtOAc. The combined organic extract was dried and concentrated and was purified by flash chromatography, eluting with $CH_2Cl_2$, then EtOAc. Recrystallization gave the title compound as a white solid (13 mg, 13% yield). MS ($H^+$), 491

EXAMPLE 221

Preparation of chiral (2'R,3R,4'S)-6-chloro-4'-(3-chlorophenyl)-2'-[2-(2-hydroxy-ethoxy)-5-(3-trifluoroprop-1-ynyl)-phenyl]spiro[3H-indole-3,3'-piperidine]-2,6'-dione

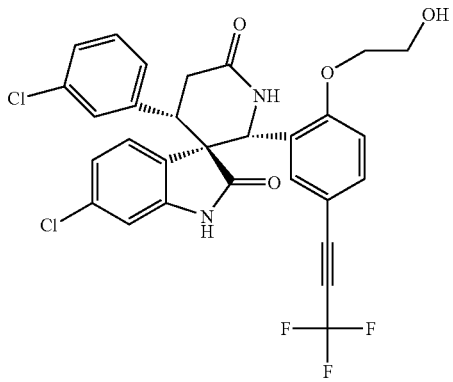

M. W. 589.40 $C_{29}H_{21}Cl_2F_3N_2O_4$

To a stirred solution of THF (10 mL) at −78° C., 3,3,3-trifluoropropyne (Aldrich) was bubbled in until 1.34 g (14 mmol) was condensed. To the stirred solution, n-BuLi (Aldrich, 2.5 M in hexanes, 5.5 mL, 14 mmol) was added slowly and the mixture was stirred for 1 hr. $Bu_3SnCl$ (Aldrich, 3.25 g, 10 mmol) was added and the reaction was gradually warmed to rt in 1 hr. The solvent was removed and the crude was directly used for next step.

Racemic (2'R,3R,4'S)-6-chloro-4'-(3-chlorophenyl)-2'-[2-(2-hydroxy-ethoxy)-5-iodo-phenyl]-spiro[3H-indole-3,3'-piperidine]-2,6'-dione (120 mg, 0.19 mmol), triphenylphosphine (Aldrich, 33 mg) and tris(dibenzylideneacetone)dipalladium (Strem, 17 mg) were combined into 1,4-dioxane (4 mL) and the mixture was stirred at 86° C. for 3 h. The solvent was removed and the residue was dissolved in 2 mL of 5% methanol/methylene chloride and chromatographed on an ISCO machine to give an off-white solid. 37 mg. The product was then resolved on a SFC machine at 2 mL/min., 30% methanol, 100 bar and 30° C. to give chiral (2'R,3R,4'S)-6-chloro-4'-(3-chlorophenyl)-2'-[2-(2-hydroxy-ethoxy)-5-(3-trifluoroprop-1-ynyl)-phenyl]spiro[3H-indole-3,3'-piperidine]-2,6'-dione. MW ($H^+$), 589.

EXAMPLE 222a

Preparation of intermediate racemic (2'R,3R,4'S)-6-chloro-4'-(3-chlorophenyl)-2'-[2-(2-hydroxy-ethoxy)-5-(2-trimethylsilanyl-ethynyl)-phenyl]-spiro[3H-indole-3,3'-piperidine]-2,6'-dione

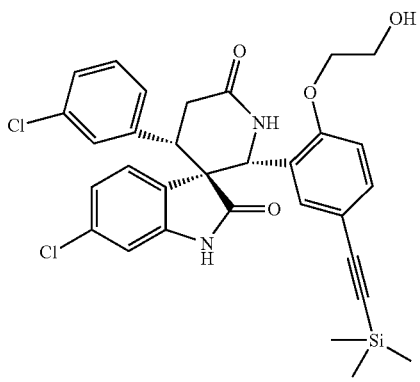

M. W. 593.59 $C_{31}H_{30}Cl_2N_2O_4Si$

To a solution of racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione (6.05 g, 9.71 mmol) prepared in example 190c in DMF (80 mL) were added trimethylsilylacetylene (10 mL), CuI (40 mg), $Et_3N$ (50 mL), $PdCl_2(Ph_3P)_2$ (Aldrich, 205 mg, 0.29 mmol) were added. The mixture was purged with nitrogen and heated at 76° C. for 1.5 h, then cooled to room temperature. The mixture was poured into water, extracted with EtOAc several times. The extracts were combined and dried with sodium sulfate and dried to give a foam. The foam was purified by chromatography to give the title compound as a light yellow solid. Yield 3.28 g, 57%.

EXAMPLE 222b

Preparation of intermediate racemic (2'R,3R,4'S)-6-chloro-4'-(3-chlorophenyl)-2'-[5-(2-trimethylsilanyl-ethynyl)-2-(2-methanesulfonoxy)-ethoxy-phenyl]-spiro[3H-indole-3,3'-piperidine]-2,6'-dione

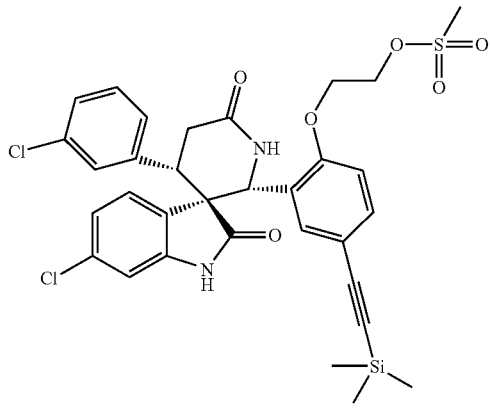

M. W. 671.68 $C_{32}H_{32}Cl_2N_2O_6SSi$

To a stirred solution of racemic (2'R,3R,4'S)-6-chloro-4'-(3-chlorophenyl)-2'-[2-(2-hydroxy-ethoxy)-5-(2-trimethyl-silanyl-ethynyl)-phenyl]-spiro[3H-indole-3,3'-piperidine]-2,6'-dione (1.68 g) in methylene chloride (20 mL) at 0° C., methanesulfonyl chloride (0.24 ml, 3.12 mmol) and triethylamine (0.44 mL, 3.12 mmol) were added successively and the mixture was stirred at room temperature for 15 min. The mixture was poured into water and the new mixture was extracted with methylene chloride (2×20 mL). The extracts were dried over sodium sulfate and concentrated to give a solid. 1.70 g. MS (H$^+$), 671.

EXAMPLE 222c

Preparation of racemic (2'R,3R,4'S)-6-chloro-4'-(3-chlorophenyl)-2'-{5-ethynyl-2-[2-(1-piperidinyl)-ethoxy]-phenyl}spiro[3H-indole-3,3'-piperidine]-2,6'-dione

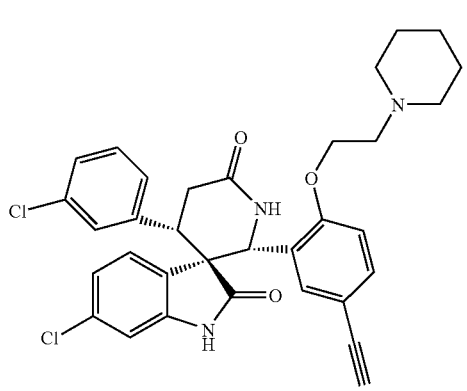

M. W. 588.54 $C_{33}H_{31}Cl_2N_3O_3$

Racemic (2'R,3R,4'S)-6-chloro-4'-(3-chlorophenyl)-2'-[5-(2-trimethylsilanyl-ethynyl)-2-(2-methanesulfonoxy)-ethoxy-phenyl]-spiro[3H-indole-3,3'-piperidine]-2,6'-dione (100 mg, 0.15 mmol) was dissolved in DMF (3 mL). To the stirred solution, piperidine (Aldrich, 240 mg) was added and the mixture was stirred at 80° C. overnight. The reaction was cooled to rt and tetrabutyl ammonium fluoride (0.15 mL, 1 M in THF) was added and the mixture was stirred for 30 min. The solvent was removed and the residue was chromatographed (ISCO machine, 4% MeOH/CH$_2$Cl$_2$) to give a white solid. 34 mg. MS (H$^+$), 588.

EXAMPLE 223

Preparation of racemic (2'R,3R,4'S)-2'-[2-(2-azido-ethoxy)-5-ethynyl-phenyl]-6-chloro-4'-(3-chlorophenyl)spiro[3H-indole-3,3'-piperidine]-2,6'-dione

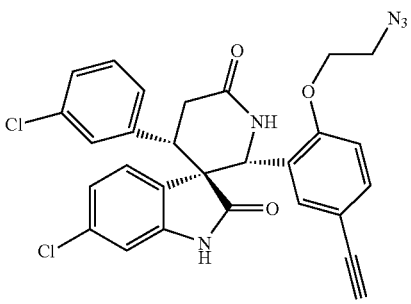

M. W. 546.42 $C_{28}H_{21}Cl_2N_5O_3$

In a manner similar to the method described in example 222c, The title compound was prepared starting from racemic (2'R,3R,4'S)-6-chloro-4'-(3-chlorophenyl)-2'-[5-(2-trimethylsilanyl-ethynyl)-2-(2-methanesulfonoxy)-ethoxy-phenyl]-spiro[3H-indole-3,3'-piperidine]-2,6'-dione using sodium azide as the reagent in place of piperidine. MS (H$^+$), 546.

EXAMPLE 224

Preparation of racemic (2'R,3R,4'S)-2'-[2-(2-amino-ethyl)-5-ethynyl-phenyl]-6-chloro-4'-(3-chlorophenyl)spiro[3H-indole-3,3'-piperidine]-2,6'-dione

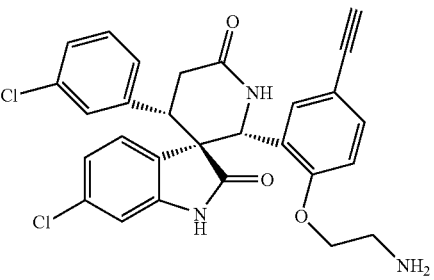

M. W. 520.42 $C_{28}H_{21}Cl_2N_5O_3$

To a solution of racemic (2'R,3R,4'S)-2'-[2-(2-azido-ethoxy)-5-ethynyl-phenyl]-6-chloro-4'-(3-chlorophenyl) spiro[3H-indole-3,3'-piperidine]-2,6'-dione (40 mg, 0.064 mmol) in THF (2 ml) was add a 1M solution of trimethyl phosphine in THF (77 uL, 0.77 mmol) and water (14 uL, 0.077 mmol). The reaction was stirred at room temperature for 4 h, after which more reagents (50 uL PMe$_3$ and 5 uL water) was added. The mixture was stirred overnight and concentrated on rotary evaporator.

The residue was dissolved in MeOH (2 mL) and 2N NaOH (1 mL) was added dropwise. After 2 h the reaction was concentrated and residue was dissolved in acetonitrile and water and the mixture was freeze dried to give a powder. To the powder was added absolute EtOH. The liquid was removed and concentrated and was purified on HPLC. The title compound was obtained as a white powder (20 mg, 60% yield, two steps) after freeze drying. MS (H+), 520

EXAMPLE 225a

Preparation of intermediate racemic (2'R,3R,4'S)-1'-(aminocarbonyl-methyl)-6-bromo-4'-(3-chlorophenyl)-2'-(1-methylene-propyl)-2,3-dihydro-2,6'-dioxospiro[indole-3,3'-piperidine]-1-methoxyethyl trimethylsilane

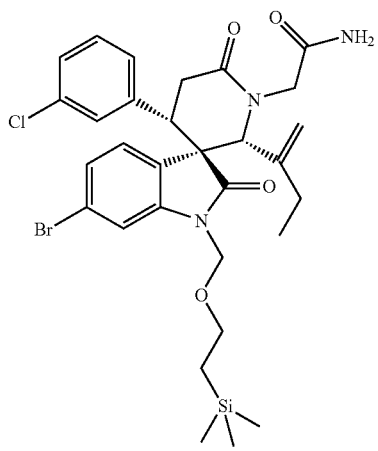

M. W. 647.09 $C_{30}H_{37}BrClN_3O_4Si$

Racemic (2'R,3R,4'S)-6-bromo-4'-(3-chlorophenyl)-2'-(1-methylene-propyl)-2,3-dihydro-2,6'-dioxospiro[indole-3,3'-piperidine]-1-methoxyethyl trimethylsilane (2 g, 3.4 mmol) prepared in Example 161b, 2-bromo-acetamide (1.4 g, 10.2 mmol) and cesium carbonate (6.6 g, 20.4 mmol) were mixed in DMF (10 mL). The mixture was stirred overnight. Then the solution was concentrated and the residue was purified by Prep-TLC to give product (800 mg).

EXAMPLE 225b

Preparation of racemic (2'R,3R,4'S)-1'-(aminocarbonyl-methyl)-6-bromo-4'-(3-chlorophenyl)-2'-(1-methylene-propyl)spiro[3H-indole-3,3'-piperidine]-2,6' (1H)-dione

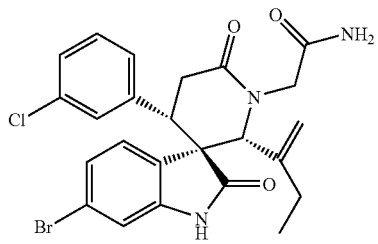

M. W. 516.83 $C_{24}H_{23}BrClN_3O_3$

Racemic (2'R,3R,4'S)-1'-(aminocarbonyl-methyl)-6-bromo-4'-(3-chlorophenyl)-2'-(1-methylene-propyl)-2,3-dihydro-2,6'-dioxo-spiro[indole-3,3'-piperidine]-1-methoxy-ethyl trimethylsilane (350 mg) was dissolved in a solution of trifluoroacetic acid (5 mL) and dichloromethane (5 mL). The reaction mixture was stirred at room temperature for 0.5 h. The reaction mixture was concentrated. The residue was redissolved in a mixture of methanol (3 ml) and DIPEA. The reaction tube was then placed into the cavity of a focused monomode microwave reactor and the contents of the flask were irradiated for 30 min at 120° C. The reaction mixture was concentrated and the residue was concentrated and the residue was purified by Prep-HPLC to obtain 70 mg product.

EXAMPLE 225c

Preparation of chiral (2'R,3R,4'S)-1'-(aminocarbonyl-methyl)-6-bromo-4'-(3-chlorophenyl)-2'-(1-methylene-propyl)-spiro[3H-indole-3,3'-piperidine]-2,6' (1H)-dione

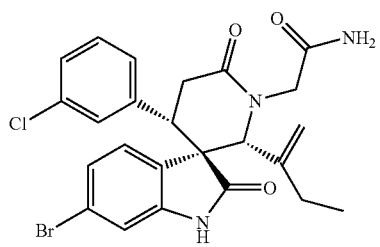

M. W. 516.83 $C_{24}H_{23}BrClN_3O_3$

Separation of the two enantiomers from racemic (2'R,3R,4'S)-1'-(aminocarbonyl-methyl)-6-bromo-4'-(3-chlorophenyl)-2'-(1-methylene-propyl)-spiro[3H-indole-3,3'-piperidine]-2,6'(1H)-dione (60 mg) was conducted by chiral HPLC to provide chiral (2'R,3R,4'S)-1'-(aminocarbonyl-methyl)-6-bromo-4'-(3-chlorophenyl)-2'-(1-methylene-propyl)spiro [3H-indole-3,3'-piperidine]-2,6'(1H)-dione as a white solid (29 mg) and chiral (2'S,3S,4'R)-1'-(aminocarbonyl-methyl)-6-bromo-4'-(3-chlorophenyl)-2'-(1-methylene-propyl)-spiro [3H-indole-3,3'-piperidine]-2,6'(1H)-dione as a white solid (24 mg).

m/z (M+H)+: 516

EXAMPLE 226a

Preparation of intermediate racemic (2'R,3R,4'S)-1'-(tert-butoxycarbonyl)-6-chloro-4'-(3-chlorophenyl)-2'-isopropenyl-2,6'-dioxospiro[indole-3,3'-piperidine]-1-carboxylic acid tert-butyl ester

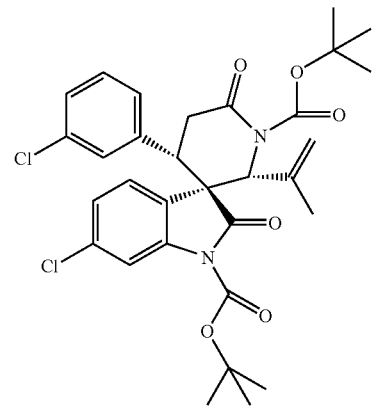

M. W. 601.53 $C_{31}H_{34}Cl_2N_2O_6$

To a solution of racemic (2'R,3R,4'S)-6-chloro-4'-(3-chlorophenyl)-2'-isopropenylspiro[3H-indole-3,3'-piperidine]-2,6'(1H)-dione (0.5 g, 1.25 mmol) prepared in Example 87c in dichloromethane (10 mL) at 0° C. was added ditert-butyl-dicarbonate (1.64 g, 7.5 mmol), followed by the addition of 4-dimethylaminopyridine (0.29 g, 2.4 mmol). The reaction mixture was stirred at r.t. overnight, the organic layer was washed by 0.5N HCl, dried over $Na_2SO_4$. The solvent was removed to give title compound as a solid (0.7 g).

m/z $(M+H)^+$: 601

EXAMPLE 226b

Preparation of intermediate trimethylsilyl fluorosulfonyldifluoroacetate

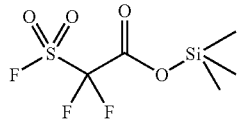

M. W. 250.27 $C_5H_9F_3O_4SSi$

Under argon protection and at 0° C., trimethylsilyl chloride (11.5 g, 106 mmol) was added dropwise slowly into 2-(fluorosulphonyl)difluoroacetic acid (5 g, 28 mmol). Then the mixture was stirred over weekend at r.t. Then the solvent was removed to give 5.3 g crude product as a liquid.

EXAMPLE 226c

Preparation of racemic (2'R,3R,4'S)-6-chloro-4'-(3-chloro-phenyl)-2'-((R)-2,2-difluoro-1-methyl-cyclopropyl)spiro[3H-indole-3,3'-piperidine]-2,6'(1H)-dione

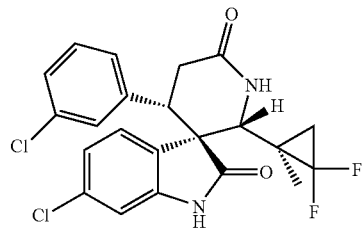

M. W. 451.30 $C_{22}H_{18}Cl_2F_2N_2O_2$

Racemic (2'R,3R,4'S)-1'-(tert-butoxycarbonyl)-6-chloro-4'-(3-chlorophenyl)-2'-isopropenyl-2,6'-dioxospiro[indole-3,3'-piperidine]-1-carboxylic acid tert-butyl ester (100 mg, 1.6 mmol) prepared in Example 226a, catalytic amount of KF and a large amount of trimethylsilyl fluorosulfonyldifluoroacetate was dissolved in toluene (1 mL). Then the reaction tube was placed into the cavity of a focused monomode microwave reactor and the contents of the flask were irradiated at 115° C. for 30 min. The solution was concentrated and the residue was purified by Prep-TLC ($CH_2Cl_2$:$CH_3OH$=30:1) to obtain title compound (2.6 mg) of Example 226d and (4.1 mg) of the title compound.

m/z $(M+H)^+$: 451.

EXAMPLE 226d

Preparation of racemic (2'R,3R,4'S)-6-chloro-4'-(3-chloro-phenyl)-2'-((S)-2,2-difluoro-1-methyl-cyclopropyl)spiro[3H-indole-3,3'-piperidine]-2,6'(1H)-dione

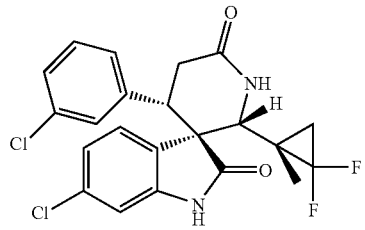

M. W. 451.30 $C_{22}H_{18}Cl_2F_2N_2O_2$

The title compound was obtained as the other product in Example 226c.

m/z $(M+H)^+$: 451.

EXAMPLE 227a

Preparation of intermediate 5-chloro-2-isopropoxy-benzaldehyde

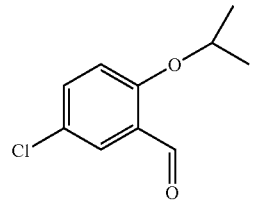

M. W. 198.65 $C_{10}H_{11}ClO_2$

5-Chloro-2-hydroxy-benzaldehyde (3 g, 19.16 mmol), 2-Iodo-propane (4.88 g, 28.74 mmol) and $K_2CO_3$ (4 g, 28.74 mmol) was mixed in anhydrous DMF. The reaction tube was placed into the cavity of a focused monomode microwave reactor and the contents of the flask were irradiated for 30 min at 100° C. Then the solution was filtered and the filtration was concentrated to obtain the crude product (3 g). The crude product was used into next step reaction without further purification.

EXAMPLE 227b

Preparation of intermediate E/Z-6-chloro-3-(5-chloro-2-isopropoxy-benzylidene)-1,3-dihydro-indol-2-one

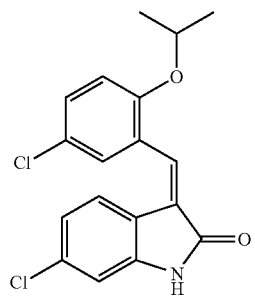

M. W. 348.23 C$_{18}$H$_{15}$Cl$_2$NO$_2$

5-Chloro-2-isopropoxy-benzaldehyde (3 g, 15.1 mmol) and 6-chlorooxindole (2 g, 12.6 mmol) were mixed in anhydrous methanol (30 mL) at room temperature. Then pyrrolidine (1.07 g, 15.1 mmol) was added slowly. The reaction mixture was heated at 70° C. for 3 h. Then the mixture was cooled to room temperature and filtered. The precipitate was dried and collected to give E/Z-6-chloro-3-(5-chloro-2-isopropoxy-benzylidene)-1,3-dihydro-indol-2-one as a yellow solid (3.4 g).

EXAMPLE 227c

Preparation of intermediate E/Z-6-chloro-3-(5-chloro-2-isopropoxy-benzylidene)-2-oxo-2,3-dihydro-indole-1-carboxylic acid tert-butyl ester

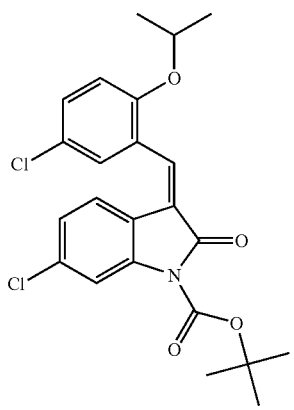

M. W. 448.35 C$_{23}$H$_{23}$Cl$_2$NO$_4$

To a solution E/Z-6-chloro-3-(5-chloro-2-isopropoxy-benzylidene)-1,3-dihydro-indol-2-one (3.4 g, 9.8 mmol) in dichloromethane (50 mL) at r.t was added ditert-butyl-dicarbonate (2.56 g, 11.7 mmol), followed by the addition of 4-dimethylaminopyridine (0.12 g, 1 mmol). The reaction mixture was stirred at r.t. for 0.5 h, then the mixture was washed with 0.5N HCl aqueous solution. The organic layer was separated, dried and concentrated to give E/Z-6-chloro-3-(5-chloro-2-isopropoxy-benzylidene)-2-oxo-2,3-dihydro-indole-1-carboxylic acid tert-butyl ester as a yellow oil. (4.2 g).

EXAMPLE 227d

Preparation of racemic (2'R,3R,4'S)-6-chloro-4'-(5-chloro-2-isopropoxy-phenyl)-2'-isopropenylspiro[3H-indole-3,3'-piperidine]-2,6'(1H)-dione

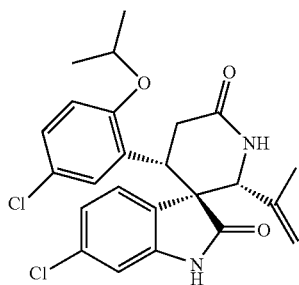

M. W. 459.38 C$_{24}$H$_{24}$Cl$_2$N$_2$O$_3$

In a manner similar to the method described in Example 41b, E/Z-6-Chloro-3-(5-chloro-2-isopropoxy-benzylidene)-2-oxo-2,3-dihydro-indole-1-carboxylic acid tert-butyl ester (2 g, 4.47 mmol) was reacted with 1-(1-methyl-ethenyl)-3-trimethylsilyoxy-2-aza-1,3-butadiene (22.37 mmol) in toluene to give title compound as a white solid (1.3 g).

m/z (M+H)$^+$: 459

EXAMPLE 228a

Preparation of intermediate acetic acid 2-(4-chloro-2-formyl-phenoxy)-ethyl ester

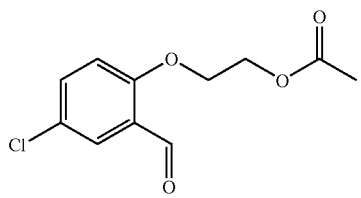

M. W. 242.66 C$_{11}$H$_{11}$ClO$_4$

5-Chloro-2-hydroxy-benzaldehyde (2 g, 12.8 mmol), acetic acid 2-bromo-ethyl ester (2.57 g, 15.4 mmol), K$_2$CO$_3$ (5.3 g, 38.5 mmol) and KI (0.26 g, 1.54 mmol) were mixed in DMF (20 mL). Then the reaction tube was placed into the cavity of a focused monomode microwave reactor and the contents of the flask were irradiated at 130° C. for 30 min. The mixture was filtered and the filtrate was concentrated. The residue was dissolved in CH$_2$Cl$_2$ and the organic layer was washed with water for several times. Then the organic layer was dried over anhydrous Na$_2$SO$_4$ and concentrated to obtain a yellow solid. (2.7 g)

EXAMPLE 228b

Preparation of intermediate E/Z-6-Chloro-3-[5-chloro-2-(2-hydroxy-ethoxy)-benzylidene]-1,3-dihydro-indol-2-one

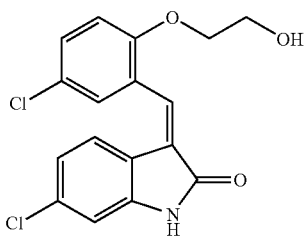

M. W. 350.20 C$_{17}$H$_{13}$Cl$_2$NO$_3$

Acetic acid 2-(4-chloro-2-formyl-phenoxy)-ethyl ester (1.5 g, 9.3 mmol) and 6-chlorooxindole (2.7 g, 11.2 mmol) were mixed in anhydrous methanol (20 mL) at room temperature. Then Pyrrolidine (0.8 g, 11.2 mmol) was added slowly. The reaction mixture was heated at 70° C. for 3 h, then cooled to r.t and the precipitation was collected by filtration to obtain title compound as a yellow solid (1.4 g).

EXAMPLE 228c

Preparation of intermediate E/Z-3-[2-(2-tert-Butoxy-carbonyloxy-ethoxy)-5-chloro-benzylidene]-6-chloro-2-oxo-2,3-dihydro-indole-1-carboxylic acid tert-butyl ester

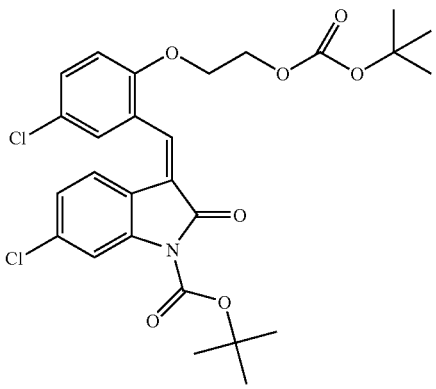

M. W. 550.44 $C_{27}H_{29}Cl_2NO_7$

To a solution of E/Z-6-Chloro-3-[5-chloro-2-(2-hydroxy-ethoxy)-benzylidene]-1,3-dihydro-indol-2-one (1.4 g, 4.01 mmol) in dichloromethane (10 mL) at r.t was added ditert-butyl-dicarbonate (1.9 g, 8.8 mmol), followed by the addition of 4-dimethylaminopyridine (0.049 g, 0.4 mmol). The reaction mixture was stirred at r.t. for 2 h and then washed by 0.1N HCl. The organic layer was separated, dried, and concentrated to give title compound as a yellow oil (1 g)

EXAMPLE 228d

Preparation of racemic (2'S,3S,4'R)-6-chloro-4'-[5-chloro-2-(2-hydroxyethoxy)-phenyl]-2'-[5-fluoro-2-methyl-phenyl]spiro[3H-indole-3,3'-piperidine]-2,6'(1H)-dione

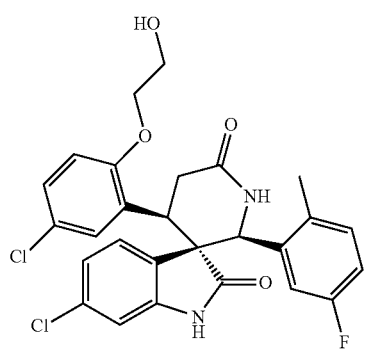

M. W. 529.40 $C_{27}H_{23}Cl_2FN_2O_4$

To a toluene solution (10 mL) of 1-(5-fluoro-2-methyl-phenyl)-3-trimethylsilyoxy-2-aza-1,3-butadiene (10.93 mmol) was added E/Z-3-[2-(2-tert-Butoxycarbonyloxy-ethoxy)-5-chloro-benzylidene]-6-chloro-2-oxo-2,3-dihydro-indole-1-carboxylic acid tert-butyl ester (1 g, 1.82 mmol). Then the reaction tube was placed into the cavity of a focused monomode microwave reactor and the contents of the flask were irradiated at 130° C. for 40 min. After the solution was cooled to room temperature, methanol was added, and then the mixture was concentrated. Then a mixture of trifluoroacetic acid and dichloromethane was added. The reaction mixture was stirred at room temperature for 10 min. The solution was concentrated and the residue was purified by Prep-HPLC to give title compound as a white solid (11 mg). m/z (M+H)$^+$: 529

EXAMPLE 228e

Preparation of chiral (2'S,3S,4'R)-6-chloro-4'-[5-chloro-2-(2-hydroxyethoxy)-phenyl]-2'-[5-fluoro-2-methylphenyl]spiro[3H-indole-3,3'-piperidine]-2,6'(1H)-dione

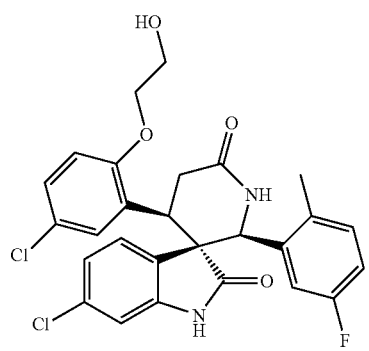

M.W 529.40 $C_{27}H_{23}Cl_2FN_2O_4$

Separation of the two enantiomers from racemic (2'S,3S,4'R)-6-chloro-4'-[5-chloro-2-(2-hydroxyethoxy)-phenyl]-2'-[5-fluoro-2-methylphenyl]spiro[3H-indole-3,3'-piperidine]-2,6'(1H)-dione was conducted by chiral HPLC to provide chiral (2'S,3S,4'R)-6-chloro-4'-[5-chloro-2-(2-hydroxy-ethoxy)-phenyl]-2'-[5-fluoro-2-methylphenyl]spiro[3H-indole-3,3'-piperidine]-2,6'(1H)-dione as a white solid (4 mg) and chiral (2'R,3R,4'S)-6-chloro-4'-[5-chloro-2-(2-hydroxy-ethoxy)-phenyl]-2'-[5-fluoro-2-methylphenyl]spiro[3H-indole-3,3'-piperidine]-2,6'(1H)-dione as a white solid (3 mg). m/z (M+H)$^+$: 529

EXAMPLE 229a

Preparation of intermediate 2-(4-Chloro-2-formyl-phenoxy)-2-methyl-propionic acid ethyl ester

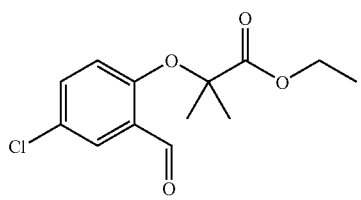

M. W. 270.72 $C_{13}H_{15}ClO_4$

5-Chloro-2-hydroxy-benzaldehyde (7 g, 45 mmol), 2-bromo-2-methyl-propionic acid ethyl ester (11.4 g, 58 mmol), $K_2CO_3$ (18.6 g, 135 mmol) and KI (0.97 g, 5.8 mmol)

were mixed in DMF (20 mL). Then the reaction mixture was heated at 110° C. for 3 h. The mixture was filtered and the filtrate was concentrated. The residue was dissolved in ethyl acetate and washed with 1N NaOH. Then the organic layer was separated, dried over $Na_2SO_4$ and concentrated to give title compound (7 g)

EXAMPLE 229b

Preparation of intermediate E/Z-2-[4-Chloro-2-(6-chloro-2-oxo-1,2-dihydro-indol-3-ylidenemethyl)-phenoxy]-2-methyl-propionic acid ethyl ester

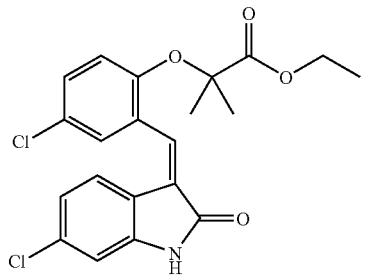

M. W. 420.30 $C_{21}H_{19}Cl_2NO_4$

In a manner similar to the method described in Example 227b, 2-(4-chloro-2-formyl-phenoxy)-2-methyl-propionic acid ethyl ester (7 g, 26 mmol) was reacted with 6-chlorooxindole (3.6 g, 22 mmol) and pyrrolidine (1.85 g, 26 mmol) in methanol to give E/Z 2-[4-chloro-2-(6-chloro-2-oxo-1,2-dihydro-indol-3-ylidenemethyl)-phenoxy]-2-methyl-propionic acid ethyl ester as a yellow solid (7.2 g).

EXAMPLE 229c

Preparation of intermediate E/Z 6-Chloro-3-[5-chloro-2-(1-ethoxycarbonyl-1-methyl-ethoxy)-benzylidene]-2-oxo-2,3-dihydro-indole-1-carboxylic acid tert-butyl ester

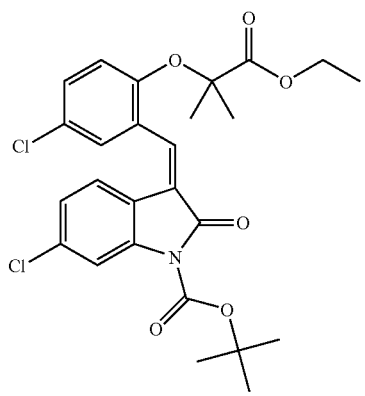

M.W 520.41 $C_{26}H_{27}Cl_2NO_6$

In a manner similar to the method described in Example 227c, E/Z 2-[4-chloro-2-(6-chloro-2-oxo-1,2-dihydro-indol-3-ylidenemethyl)-phenoxy]-2-methyl-propionic acid ethyl ester (7.2 g, 17.2 mmol) was reacted with ditert-butyl-dicarbonate (4.5 g, 20.6 mmol) and DMAP (0.2 g, 1.72 mmol) in dichloromethane to give title compound as a yellow solid (8 g).

EXAMPLE 229d

Preparation of racemic (2'S,3S,4'R)-6-chloro-4'-[5-chloro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione

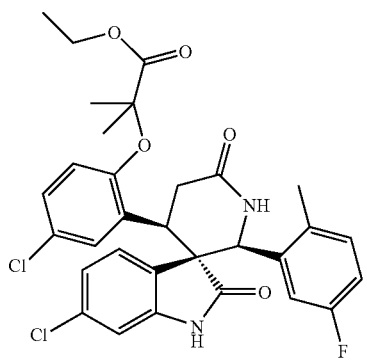

M.W 599.49 $C_{31}H_{29}Cl_2FN_2O_5$

In a manner similar to the method described in Example 228d, E/Z 6-chloro-3-[5-chloro-2-(1-ethoxycarbonyl-1-methyl-ethoxy)-benzylidene]-2-oxo-2,3-dihydro-indole-1-carboxylic acid tert-butyl ester (8 g, 15.44 mmol) was reacted with 1-(5-fluoro-2-methyl-phenyl)-3-trimethylsilyoxy-2-aza-1,3-butadiene (77 mmol) in toluene and then trifluoroacetic acid in dichloromethane to give title compound as a white solid (2.7 g).

m/z (M+H)$^+$: 599

EXAMPLE 229e

Preparation of chiral (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione

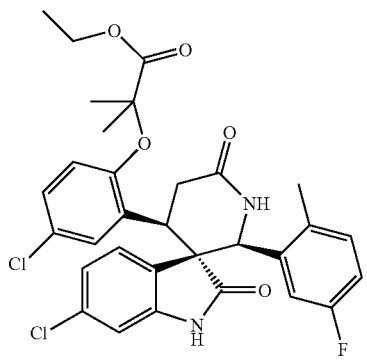

M. W. 599.49 $C_{31}H_{29}Cl_2FN_2O_5$

Separation of the two enantiomers from racemic (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione (40 mg) was conducted by chiral HPLC to provide chiral (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione as a white solid (14 mg) and chiral (2'R,3R,4'S)-6-chloro-4'-[5-chloro-2-(1-ethoxycarbonyl-1-methylethoxy)-phenyl]-2'-(5-fluoro-2-methyl phenyl)spiro[3H-indole-3,3'-piperidine]-2,6'(1H)-dione as a white solid (14 mg).

m/z (M+H)$^+$: 599

EXAMPLE 230a

Preparation of racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione

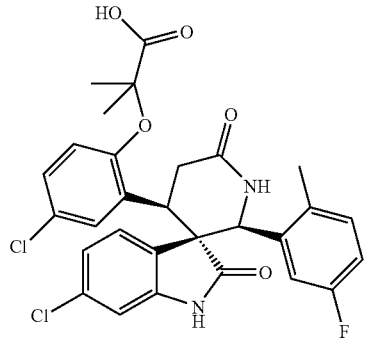

M.W 571.44 C$_{29}$H$_{25}$Cl$_2$FN$_2$O$_5$

Racemic (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione (2.7 g, 4.5 mmol) was dissolved in THF (20 mL). Then aqueous solution (10 mL) of KOH (0.5 g) was added. The mixture was refluxed for 1 h. After cooled to room temperature, the solution was concentrated and then the residue was acidified to "pH" 2-3 by addition of concentrated aqueous HCl solution. The white solid was collected by filtration to give title compound (1.6 g).

m/z (M+H)$^+$: 571

EXAMPLE 230b

Preparation of chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione

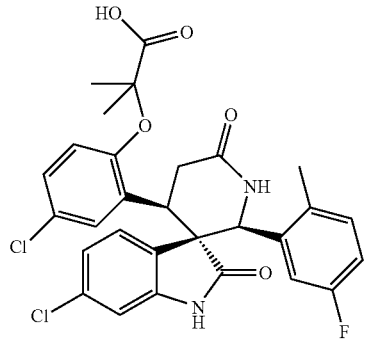

M.W 571.44 C$_{29}$H$_{25}$Cl$_2$FN$_2$O$_5$

Separation of the two enantiomers from racemic (2'S,3S,4'R)-6-chloro-4'-[5-chloro-2-(1-hydroxycarbonyl-1-methyl-ethoxy)-phenyl]-2'-(5-fluoro-2-methylphenyl)spiro[3H-indole-3,3'-piperidine]-2,6'(1H)-dione was conducted by chiral HPLC to provide chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione as a white solid (8 mg) and chiral (2'R,3R,4'S)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione as a white solid (8 mg).

m/z (M+H)$^+$: 571

EXAMPLE 231

Preparation of racemic (2'S,3S,4'R)-6-chloro-4'-[5-chloro-2-(2-hydroxy-1,1-dimethyl-ethoxy)-phenyl]-2'-[5-fluoro-2-methylphenyl]spiro[3H-indole-3,3'-piperidine]-2,6'(1H)-dione

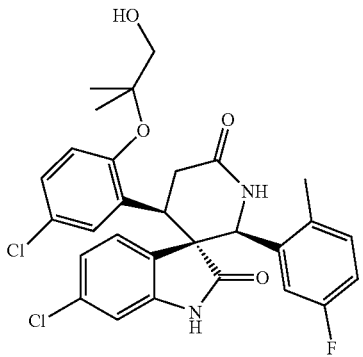

M.W 557.45 C$_{29}$H$_{27}$Cl$_2$FN$_2$O$_4$

With cooling of an ice bath, LiAlH$_4$ (19 mg, 0.5 mmol) was suspended in THF, then a solution of racemic (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione (100 mg, 0.167 mmol) in THF was added. The reaction mixture was stirred at 0° C. for 10 min, the water (1 mL) was added to the mixture. The mixture was filtered and the filtrate was concentrated. The residue was purified by Prep-HPLC to give title compound as white solid (9 mg).

m/z (M+H)$^+$: 557

EXAMPLE 232a

Preparation of intermediate 5-bromo-2-(2,2,2-trifluoro-ethoxy)-benzaldehyde

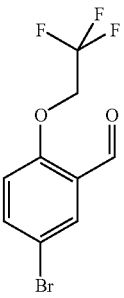

M.W 283.05 C$_9$H$_6$BrF$_3$O$_2$

5-Bromo-2-hydroxy-benzaldehyde (1.5 g, 7.5 mmol), 1,1,1-trifluoro-2-iodo-ethane (1.57 g, 7.5 mmol) and K$_2$CO$_3$ (2.07 g, 15 mmol) was mixed in anhydrous DMF (20 mL). The reaction tube was placed into the cavity of a focused monomode microwave reactor and the contents of the flask were irradiated at 180° C. for 50 min. Then the solution was filtered and the filtrate was concentrated to obtain the crude product (3 g). The crude product was purified by chromatography to give a yellow oil (1.5 g).

EXAMPLE 232b

Preparation of intermediate 1-[5-bromo-2-(2,2,2-trifluoro-ethoxy)-phenyl]-3-trimethylsilyoxy-2-aza-1,3-butadiene

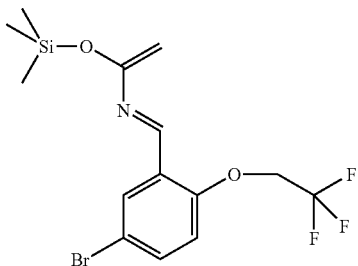

M. W. 396.28 $C_{14}H_{17}BrF_3NO_2Si$

To anhydrous tetrahydrofuran (15 mL) was added 1M THF solution of LiHMDS (5.3 mmol, 5.3 mL) under Ar at room temperature, followed by the addition of 5-bromo-2-(2,2,2-trifluoro-ethoxy)-benzaldehyde (1.5 g, 5.3 mmol). After the mixture was stirred at room temperature for 0.5 h, trimethylsilyl chloride (0.67 mL, 5.3 mmol) was added dropwise. Then the temperature of the mixture was lowered to 0° C. on a cooling ice bath. To this mixture was added triethylamine (1 mL, 6.8 mmol) in one portion, followed by the dropwise addition of a solution of acetyl chloride (0.5 mL, 6.8 mmol) in diethyl ether (50 mL). The cooling bath was removed, and the mixture was stirred at room temperature overnight. The mixture was quickly filtered on celite under nitrogen, and filtrate was concentrated under reduced pressure to give crude 1-[5-bromo-2-(2,2,2-trifluoro-ethoxy)-phenyl]-3-trimethylsilyoxy-2-aza-1,3-butadiene as a yellow gum and used for the next step without further purification.

EXAMPLE 232c

Preparation of racemic (2'R,3R,4'S)-2'-[5-bromo-2-(2,2,2-trifluoro-ethoxy)phenyl]-6-chloro-4'-(3-chlorophenylspiro[3H-indole-3,3'-piperidine]-2,6'(1H)-dione

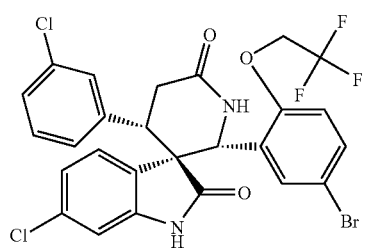

M.W 614.25 $C_{26}H_{18}BrCl_2F_3N_2O_3$

In a manner similar to the method described in Example 41b, E/Z 6-Chloro-3-(3-chloro-benzylidene)-2-oxo-2,3-dihydro-indole-1-carboxylic acid tert-butyl ester (200 mg, 0.5 mmol) prepared in Example 24a was reacted with 1-[5-bromo-2-(2,2,2-trifluoro-ethoxy)-phenyl]-3-trimethylsilyoxy-2-aza-1,3-butadiene (2.57 mmol) in toluene and then trifluoroacetic acid in dichloromethane to give title compound as a white solid (13 mg).

m/z (M+H)+: 613

EXAMPLE 233

Preparation of racemic (2'R,3R,4'S)-6-chloro-4'-[5-chloro-2-(2-hydroxyethoxy)-phenyl]-2'-isopropenyl-spiro[3H-indole-3,3'-piperidine]-2,6'(1H)-dione

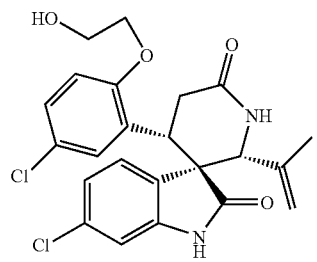

M.W 461.35 $C_{23}H_{22}Cl_2N_2O_4$

In a manner similar to the method described in Example 41b, E/Z-3-[2-(2-tert-butoxycarbonyloxy-ethoxy)-5-chloro-benzylidene]-6-chloro-2-oxo-2,3-dihydro-indole-1-carboxylic acid tert-butyl ester (350 mg, 0.637 mmol) was reacted with 1-isopropenyl-3-trimethylsilyoxy-2-aza-1,3-butadiene (3.82 mmol) in toluene and then trifluoroacetic acid in dichloromethane to give title compound as a white solid (10 mg).

m/z (M+H)+: 461

EXAMPLE 234a

Preparation of intermediate (4-chloro-2-formyl-phenoxy)-acetic acid methyl ester

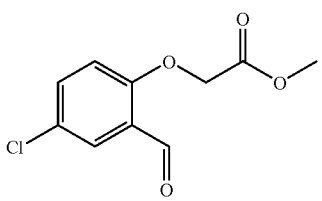

M. W. 228.63 $C_{10}H_9ClO_4$

5-Chloro-2-hydroxy-benzaldehyde (30 g, 192 mmol), bromo-acetic acid methyl ester (29.4 g, 192 mmol), $K_2CO_3$ (53 g, 384 mmol) and KI (9.6 g, 57 mmol) were mixed in acetone (100 mL). Then the mixture was heated at 80° C. for 30 min. The mixture was filtered and the filterate was concentrated. The residue was dissolve in ethyl acetate and washed with base aqueous solution (1N NaOH). The organic layer was separated, dried and concentrated to give (4-chloro-2-formyl-phenoxy)-acetic acid methyl ester yellow solid. (44 g)

EXAMPLE 234b

Preparation of intermediate E/Z-[4-Chloro-2-(6-chloro-2-oxo-1,2-dihydro-indol-3-ylidenemethyl)-phenoxy]-acetic acid methyl ester

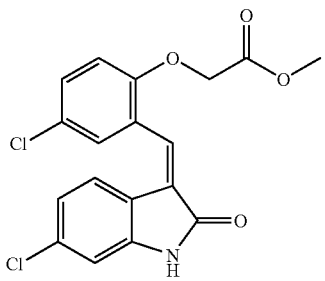

M. W. 378.21 C$_{18}$H$_{13}$Cl$_2$NO$_4$

In a manner similar to the method described in Example 227b, (4-chloro-2-formyl-phenoxy)-acetic acid methyl ester (34 g, 149 mmol) was reacted with 6-chlorooxindole (20.7 g, 124 mmol) and pyrrolidine (10.58 g, 149 mmol) in methanol to give title compound as a yellow solid (35 g).

EXAMPLE 234c

Preparation of intermediate E/Z-6-chloro-3-(5-chloro-2-methoxycarbonyl methoxy-benzylidene)-2-oxo-2,3-dihydro-indole-1-carboxylic acid tert-butyl ester

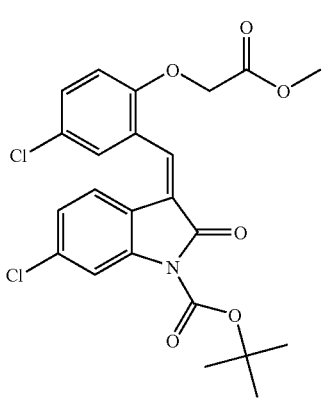

M. W. 478.33 C$_{23}$H$_{21}$Cl$_2$NO$_6$

In a manner similar to the method described in Example 227c, E/Z-[4-Chloro-2-(6-chloro-2-oxo-1,2-dihydro-indol-3-ylidenemethyl)-phenoxy]-acetic acid methyl ester (35 g, 92.8 mmol) was reacted with ditert-butyl-dicarbonate (22.3 g, 102 mmol) and DMAP (2.3 g, 18.6 mmol) in CH$_2$Cl$_2$ to give title compound as yellow oil (30 g).

EXAMPLE 234d

Preparation of racemic (2'R,3R,4'S)-6-chloro-4'-(5-chloro-2-methoxycarbonylmethoxy-phenyl)-2'-isopropenylspiro[3H-indole-3,3'-piperidine]-2,6'(1H)-dione

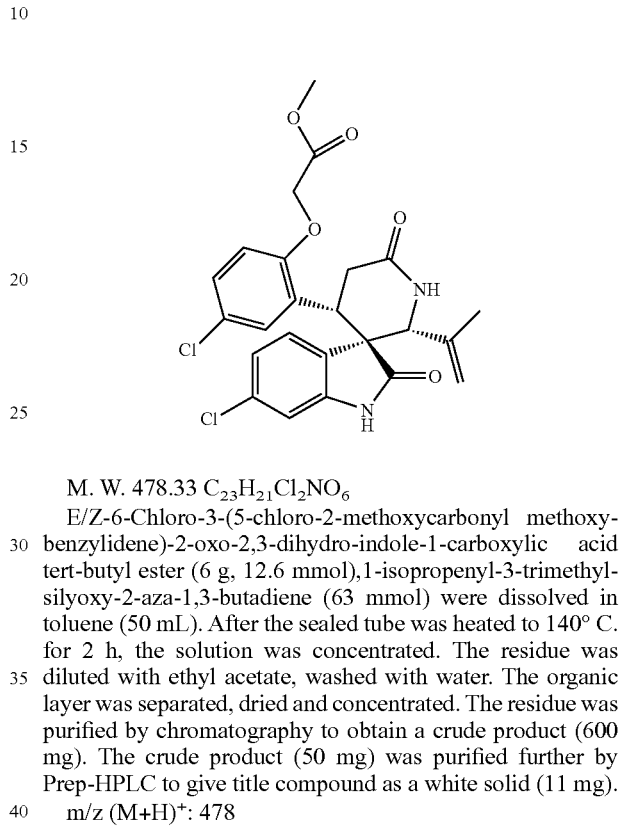

M. W. 478.33 C$_{23}$H$_{21}$Cl$_2$NO$_6$

E/Z-6-Chloro-3-(5-chloro-2-methoxycarbonyl methoxy-benzylidene)-2-oxo-2,3-dihydro-indole-1-carboxylic acid tert-butyl ester (6 g, 12.6 mmol),1-isopropenyl-3-trimethyl-silyoxy-2-aza-1,3-butadiene (63 mmol) were dissolved in toluene (50 mL). After the sealed tube was heated to 140° C. for 2 h, the solution was concentrated. The residue was diluted with ethyl acetate, washed with water. The organic layer was separated, dried and concentrated. The residue was purified by chromatography to obtain a crude product (600 mg). The crude product (50 mg) was purified further by Prep-HPLC to give title compound as a white solid (11 mg).
m/z (M+H)$^+$: 478

EXAMPLE 235

Preparation of racemic (2'R,3R,4'S)-6-chloro-4'-(5-chloro-2-hydroxycarbonylmethoxy-phenyl)-2'-isopropenylspiro[3H-indole-3,3'-piperidine]-2,6'(1H)-dione

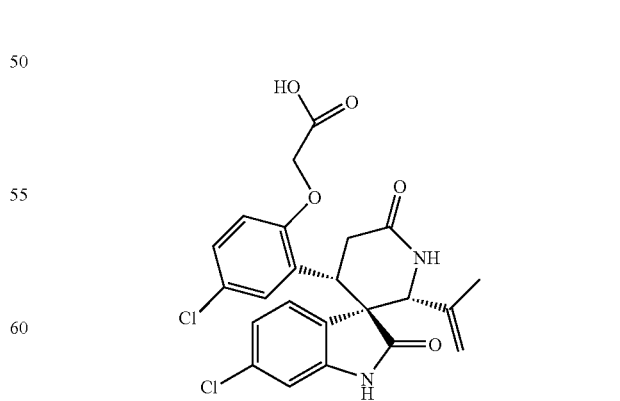

M. W. 475.33 C$_{23}$H$_{20}$Cl$_2$N$_2$O$_5$

Racemic (2'R,3R,4'S)-6-chloro-4'-(5-chloro-2-methoxy-carbonylmethoxy-phenyl)-2'-isopropenylspiro[3H-indole-3, 3'-piperidine]-2,6'(1H)-dione (80 mg, 0.164 mmol) was dissolved in THF (10 mL). Then aqueous solution (1 mL) of NaOH (20 mg) was added. The mixture was refluxed for 1 h. After cooled to room temperature, the solution was concentrated and acidified to "pH" 2-3. The mixture was extracted with ethyl acetate. The organic layer was separated, dried and concentrated. The crude product (50 mg) was purified by Prep-HPLC to give the title compound as a white solid (14 mg).

m/z (M+H)$^+$: 475

EXAMPLE 236a

Preparation of intermediate 1-(2,5-difluoro-phenyl)-3-trimethylsilyoxy-2-aza-1,3-butadiene

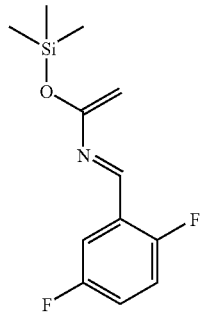

M. W. 255.34 C$_{12}$H$_{15}$F$_2$NOSi

To dry tetrahydrofuran (100 mL) was added 1M THF solution of LiHMDS (105 mmol, 105 mL) under nitrogen at room temperature, followed by the addition of 2,5-difluorobenzaldehyde (14.9 g, 105 mmol). After the mixture was stirred at room temperature for 1 h, trimethylsilyl chloride (13.3 mL, 105 mmol) was added dropwise. Then the temperature of the mixture was lowered to 0° C. on a cooling ice bath. To this mixture was added triethylamine (19 mL, 136 mmol) in one portion, followed by the dropwise addition of a solution of acetyl chloride (3.88 mL, 54.4 mmol) in diethyl ether (300 ml). The cooling bath was removed, and the mixture was stirred at room temperature overnight. The mixture was quickly filtered on celite under nitrogen, and filtrate was concentrated under reduced pressure to give 1-(2,5-difluorophenyl)-3-trimethylsilyoxy-2-aza-1,3-butadiene as a yellow gum and used for the next step without further purification.

EXAMPLE 236b

Preparation of racemic (2'R,3S,4'R)-6-chloro-4'-[5-chloro-2-(1-ethoxycarbonyl-1-methyl-ethoxy)-phenyl]-2'-(2,5-difluoro phenyl)spiro[3H-indole-3,3'-piperidine]-2,6'(1H)-dione

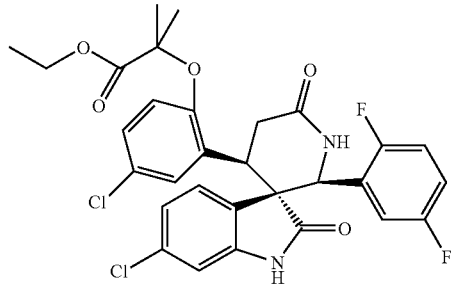

M. W. 603.45 C$_{30}$H$_{26}$Cl$_2$F$_2$N$_2$O$_5$

Under argon protection, E/Z 6-Chloro-3-[5-chloro-2-(1-ethoxycarbonyl-1-methyl-ethoxy)-benzylidene]-2-oxo-2,3-dihydro-indole-1-carboxylic acid tert-butyl ester prepared in Example 229c (8 g, 15.4 mmol) and 1-(2,5-difluoro-phenyl)-3-trimethylsilyoxy-2-aza-1,3-butadiene (30.8 mmol) were dissolved in toluene. The solution was heated at 80° C. for 5 h. Then the solution was concentrated and the residue was purified by chromatography (CH$_2$Cl$_2$:CH$_3$OH=50:1) to obtain 1.7 g crude product. The crude product (50 mg) was purified again by Prep-HPLC to obtain give title compound as a white solid (12 mg).

m/z (M+H)$^+$: 603

EXAMPLE 237

Preparation of racemic (2'R,3S,4'R)-6-chloro-4'-[5-chloro-2-(1-hydroxycarbonyl-1-methyl-ethoxy)-phenyl]-2'-(2,5-difluoro phenyl)spiro[3H-indole-3,3'-piperidine]-2,6'(1H)-dione

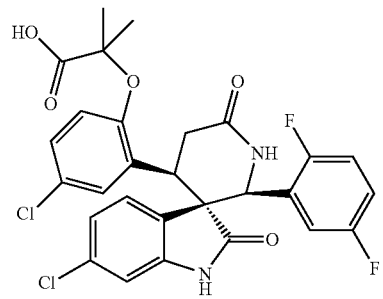

M. W. 575.40 C$_{28}$H$_{22}$Cl$_2$F$_2$N$_2$O$_5$ racemic (2'R,3S,4'R)-6-chloro-4'-[5-chloro-2-(1-ethoxycarbonyl-1-methyl-ethoxy)-phenyl]-2'-(2,5-difluoro phenyl)spiro[3H-indole-3,3'-piperidine]-2,6'(1H)-dione (400 mg, 0.66 mmol) was dissolved in THF (10 mL). Then aqueous solution (1 mL) of NaOH (111 mg, 1.99 mmol) was added. The mixture was refluxed for 1 h. The solution was cooled to room temperature, concentrated and acidified to "pH" 2-3. The precipitate was collected by filtration to give title compound as a white solid (300 mg).

m/z (M+H)$^+$: 575

EXAMPLE 238

Preparation of racemic (2'R,3S,4'R)-6-chloro-4'-[5-chloro-2-(2-hydroxy-1,1-dimethyl-ethoxy)-phenyl]-2'-(2,5-difluorophenyl)spiro[3H-indole-3,3'-piperidine]-2,6'(1H)-dione

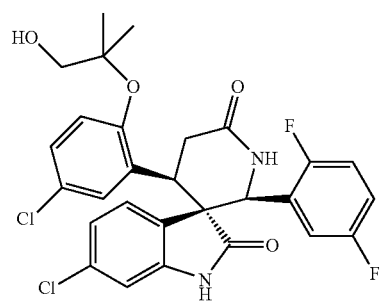

M. W. 561.42 C$_{28}$H$_{24}$Cl$_2$F$_2$N$_2$O$_4$

In a manner similar to the method described in Example 231, racemic (2'R,3S,4'R)-6-chloro-4'-[5-chloro-2-(1-ethoxycarbonyl-1-methyl-ethoxy)-phenyl]-2'-(2,5-difluoro phenyl)spiro[3H-indole-3,3'-piperidine]-2,6'(1H)-dione (200 mg, 0.33 mmol) was reacted with LiAlH$_4$ (63 mg, 1.66 mmol) in THF and the crude product was purified by Prep-HPLC to give title compound as a white solid (6 mg).

EXAMPLE 239a

Preparation of intermediate 2,2-dimethyl-3-(toluene-4-sulfonyloxy)-propionic acid methyl ester

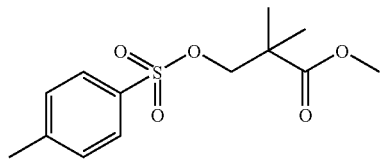

M. W. 286.35 C$_{13}$H$_{18}$O$_5$S

A mixture of 3-hydroxy-2,2-dimethyl-propionic acid methyl ester (13.2 g, 100 mmol), 4-methyl-benzenesulfonyl chloride (18.1 g, 90 mmol), 4-dimethylamino pyridine (15.9 g, 130 mmol) in dichloromethane was stirred at room temperature for 1 h. Then the mixture was washed by aqueous HCl solution (1 N), brine and dried over Na$_2$SO$_4$. The solvent was removed in vacuum to give title compound (23 g).

EXAMPLE 239b

Preparation of intermediate 3-(4-bromo-2-formyl-phenoxy)-2,2-dimethyl-propionic acid methyl ester

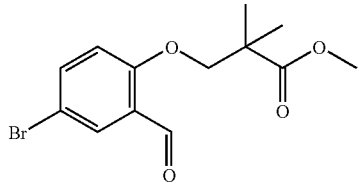

M. W. 315.17 C$_{13}$H$_{15}$BrO$_4$

5-Bromo-2-hydroxy-benzaldehyde (4 g, 2 mmol), 2,2-dimethyl-3-(toluene-4-sulfonyloxy)-propionic acid methyl ester (5.46 g, 24 mmol), K$_2$CO$_3$ (5.5 g, 40 mmol) and KI (0.1 g) were mixed in DMF (20 mL). Then the mixture was irradiated under microwave at 150° C. for 1 h. The mixture was filtered and the filtrate was concentrated. The residue was dissolved in ethyl acetate and washed with 1N NaOH. Then the organic layer was separated, dried over Na$_2$SO$_4$ and concentrated to give title compound 5.7 g.

EXAMPLE 239c

Preparation of intermediate E/Z-3-[4-bromo-2-(6-chloro-2-oxo-1,2-dihydro-indol-3-ylidenemethyl)-phenoxy]-2,2-dimethyl-propionic acid methyl ester

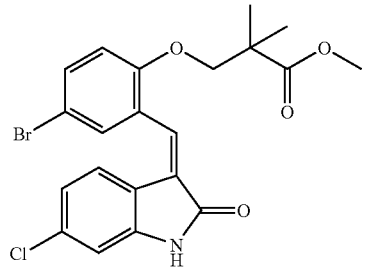

M. W. 464.75 C$_{21}$H$_{19}$BrClNO$_4$

In a manner similar to the method described in Example 227b, 3-(4-bromo-2-formyl-phenoxy)-2,2-dimethyl-propionic acid methyl ester (3.4 g, 10.8 mmol) was reacted with 6-chlorooxindole (1.8 g, 10.8 mmol) and pyrrolidine (0.84 g, 11.8 mmol) in methanol to give E/Z-3-[4-Bromo-2-(6-chloro-2-oxo-1,2-dihydro-indol-3-ylidenemethyl)-phenoxy]-2,2-dimethyl-propionic acid methyl ester as a yellow solid (2.7 g).

EXAMPLE 239d

Preparation of intermediate E/Z-3-[1-[5-Bromo-2-(2-methoxycarbonyl-2-methyl-propoxy)-phenyl]-methylidene]-6-chloro-2-oxo-2,3-dihydro-indole-1-carboxylic acid tert-butyl ester

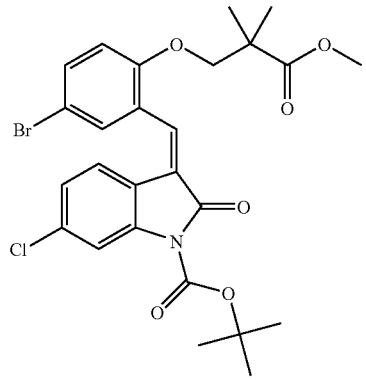

M. W. 564.87 C$_{26}$H$_{27}$BrClNO$_6$

In a manner similar to the method described in Example 227c, E/Z-3-[4-Bromo-2-(6-chloro-2-oxo-1,2-dihydro-indol-3-ylidenemethyl)-phenoxy]-2,2-dimethyl-propionic acid methyl ester (2.7 g, 5.81 mmol) was reacted with ditert-butyl-dicarbonate (1.5 g, 6.98 mmol) and DMAP (0.07 g, 0.58 mmol) in CH$_2$Cl$_2$ to give title compound as a yellow oil (2.7 g).

EXAMPLE 239e

Preparation of racemic (2'R,3S,4'R)-4'-[5-bromo-2-(2-methoxycarbonyl-2-methyl-propoxy)-phenyl]-6-chloro 2'-(2,5-dichlorophenyl)spiro[3H-indole-3,3'-piperidine]-2,6'(1H)-dione

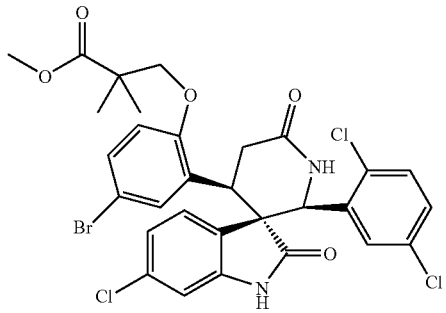

M. W. 680.82 $C_{30}H_{26}BrCl_3N_2O_5$

In a manner similar to the method described in Example 228d, E/Z-3-[1-[5-bromo-2-(2-methoxycarbonyl-2-methyl-propoxy)-phenyl]-methylidene]-6-chloro-2-oxo-2,3-dihydro-indole-1-carboxylic acid tert-butyl ester (1.3 g, 2.3 mmol) was reacted with 1-(2,5-dichloro-phenyl)-3-trimethylsilyoxy-2-aza-1,3-butadiene prepared in Example 159a (6.9 mmol) in toluene and then trifluoroacetic acid in dichloromethane to give title compound as white solid (14 mg).

m/z (M+H)$^+$: 679

EXAMPLE 240

Preparation of racemic (2'R,3S,4'R)-4'-[5-bromo-2-(3-hydroxy-2,2-dimethyl-propoxy)-phenyl]-6-chloro-2'-(2,5-dichlorophenyl)spiro[3H-indole-3,3'-piperidine]-2,6'(1H)-dione

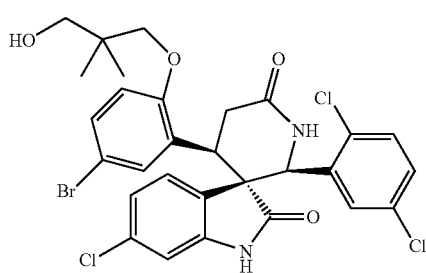

M. W. 652.80 $C_{29}H_{26}BrCl_3N_2O_4$

In a manner similar to the method described in Example 231, racemic (2'R,3S,4'R)-6-chloro-4'-[5-chloro-2-(2-methoxycarbonyl-2-methyl-propoxy)-phenyl]-2'-(2,5-dichlorophenyl)spiro[3H-indole-3,3'-piperidine]-2,6'(1H)-dione (220 mg, 0.32 mmol) was reacted with LiAlH$_4$ (61 mg, 1.62 mmol) in THF and the crude product was purified by Prep-HPLC to give title compound as a white solid (13 mg).

m/z (M+H)$^+$: 651

EXAMPLE 241

Preparation of racemic (2'S,3S,4'R)-4'-[5-bromo-2-(2-methoxycarbonyl-2-methyl-propoxy)-phenyl]-6-chloro-2'-(5-fluoro-2-methyl phenyl)spiro[3H-indole-3,3'-piperidine]-2,6'(1H)-dione

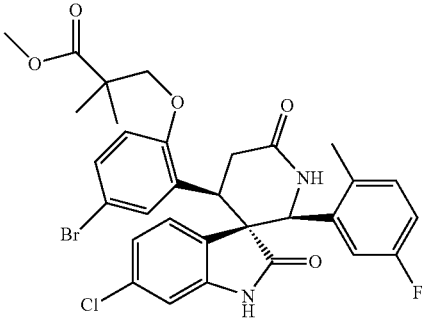

M. W. 643.94 $C_{31}H_{29}BrClFN_2O_5$

In a manner similar to the method described in Example 228d, E/Z-3-[5-bromo-2-(2-methoxycarbonyl-2-methyl-propoxy)-benzylidene]-6-chloro-2-oxo-2,3-dihydro-indole-1-carboxylic acid tert-butyl ester (1.4 g, 2.48 mmol) was reacted with 1-(5-fluoro-2-methyl-phenyl)-3-trimethylsilyoxy-2-aza-1,3-butadiene (7.44 mmol) in toluene and then trifluoroacetic acid in dichloromethane to give title compound as a white solid (260 mg).

m/z (M+H)$^+$: 643

EXAMPLE 242

Preparation of racemic (2'S,3S,4'R)-4'-[5-bromo-2-(3-hydroxy-2,2-dimethyl-propoxy)phenyl]-6-chloro-2'-(5-fluoro-2-methyl phenyl)spiro[3H-indole-3,3'-piperidine]-2,6'(1H)-dione

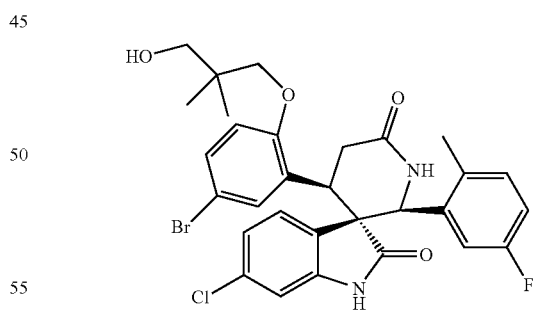

M. W. 615.93 $C_{30}H_{29}BrClFN_2O_4$

In a manner similar to the method described in Example 231, racemic (2'S,3S,4'R)-4'-[5-bromo-2-(2-methoxycarbonyl-2-methyl-propoxy)-phenyl]-6-chloro-2'-(5-fluoro-2-methyl phenyl)spiro[3H-indole-3,3'-piperidine]-2,6'(1H)-dione (120 mg, 0.187 mmol) was reacted with LiAlH$_4$ (35 mg, 0.934 mmol) in THF and the crude product was purified by Prep-HPLC to give title compound as a white solid (13 mg).

m/z (M+H)$^+$: 615

EXAMPLE 243a

Preparation of intermediate E/Z-2-[4-bromo-2-(6-chloro-2-oxo-1,2-dihydro-indol-3-ylidenemethyl)-phenoxy]-2-methyl-propionic acid ethyl ester

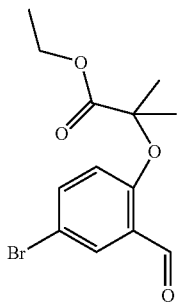

M. W. 315.17 $C_{13}H_{15}BrO_4$

5-Bromo-2-hydroxy-benzaldehyde (20 g, 100 mmol), 2-bromo-2-methyl-propionic acid ethyl ester (29 g, 150 mmol), $K_2CO_3$ (27.6 g, 200 mmol) and KI (3.2 g, 19 mmol) were mixed in DMF (100 mL). Then the reaction mixture was heated at 110° C. for 3 h. The mixture was filtered and the filtrate was concentrated. The residue was dissolved in ethyl acetate and washed with 1N NaOH. Then the organic layer was separated, dried over $Na_2SO_4$ and concentrated to give title compound (21 g)

EXAMPLE 243b

Preparation of intermediate E/Z-2-[4-bromo-2-(6-chloro-2-oxo-1,2-dihydro-indol-3-ylidenemethyl)-phenoxy]-2-methyl-propionic acid ethyl ester

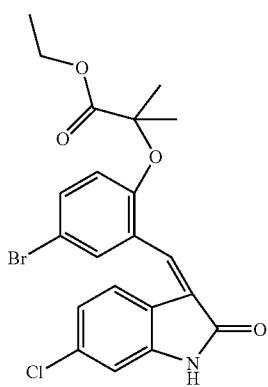

M. W. 464.75 $C_{21}H_{19}BrClNO_4$

To the mixture of 6-chlorooxindole (10.6 g, 63 mmol) and 2-(4-bromo-2-formyl-phenoxy)-2-methyl-propionic acid ethyl ester (20 g, 63 mmol) in methanol (150 mL) was added pyrrolidine (4.5 g, 6 3 mmol) dropwise. The mixture was then heated at 70° C. for 1 h. After cooled to 4° C., the mixture was filtered and the precipitate was collected, dried to give a mixture of E/Z-2-[4-bromo-2-(6-chloro-2-oxo-1,2-dihydro-indol-3-ylidenemethyl)-phenoxy]-2-methyl-propionic acid ethyl ester (18.5 g, 63%).

EXAMPLE 243c

Preparation of intermediate E/Z 3-[5-bromo-2-(1-ethoxycarbonyl-1-methyl-ethoxy)-benzylidene]-6-chloro-2-oxo-2,3-dihydro-indole-1-carboxylic acid tert-butyl ester

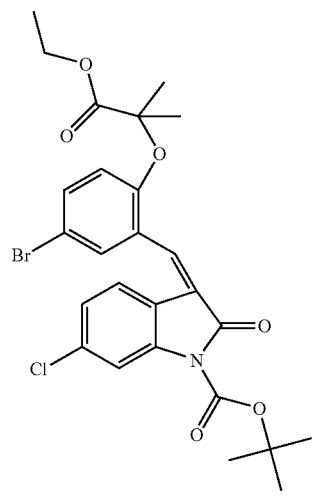

M. W. 564.87 $C_{26}H_{27}BrClNO_6$

To a solution of E/Z-2-[4-bromo-2-(6-chloro-2-oxo-1,2-dihydro-indol-3-ylidenemethyl)-phenoxy]-2-methyl-propionic acid ethyl ester (5 g, 11 mmol) in dichloromethane (50 mL) at r.t was added di-tert-butyl-dicarbonate (2.4 g, 11 mmol), followed by the addition of 4-dimethylaminopyridine (1 g, 8.2 mmol). The reaction mixture was stirred at r.t. for 2 h, washed with aqueous HCl solution (0.5M) and water. The organic layer was separated, dried over $Na_2SO_4$, concentrated to give E/Z 3-[5-bromo-2-(1-ethoxycarbonyl-1-methyl-ethoxy)-benzylidene]-6-chloro-2-oxo-2,3-dihydro-indole-1-carboxylic acid tert-butyl ester as a yellow oil (5.5 g, 88%).

EXAMPLE 243d

Preparation of racemic (2'R,3S,4'R)-4'-[5-bromo-2-(2-ethoxycarbonyl-2-methyl-ethoxy)-phenyl]-6-chloro-2'-(2,5-dichloro phenyl)spiro[3H-indole-3,3'-piperidine]-2,6'(1H)-dione

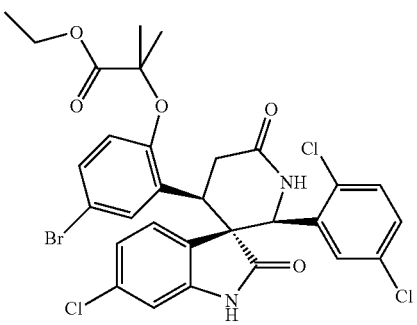

M. W. 680.82 $C_{30}H_{26}BrCl_3N_2O_5$

In a manner similar to the method described in Example 228d, E/Z-2-[4-bromo-2-(6-chloro-2-oxo-1,2-dihydro-indol-3-ylidenemethyl)-phenoxy]-2-methyl-propionic acid ethyl ester (2.2 g, 3.9 mmol) was reacted with 1-(2,5-dichloro-phenyl)-3-trimethylsilyoxy-2-aza-1,3-butadiene (7.8 mmol) in toluene and then trifluoroacetic acid in dichloromethane to give title compound as a white solid (240 mg). m/z (M+H)$^+$: 679

EXAMPLE 244

Preparation of racemic (2'R,3S,4'R)-4'-[5-bromo-2-(2-hydroxycarbonyl-2-methyl-ethoxy)-phenyl]-6-chloro-2'-(2,5-dichloro phenyl)spiro[3H-indole-3,3'-piperidine]-2,6'(1H)-dione

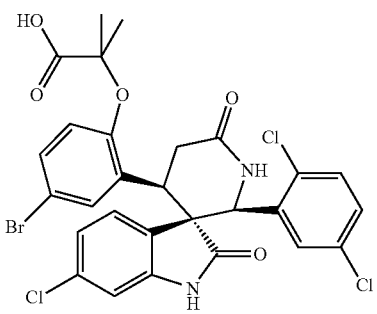

M. W. 652.76 $C_{28}H_{22}BrCl_3N_2O_5$

Racemic (2'R,3S,4'R)-4'-[5-bromo-2-(2-ethoxycarbonyl-2-methyl-ethoxy)-phenyl]-6-chloro-2'-(2,5-dichloro phenyl)spiro[3H-indole-3,3'-piperidine]-2,6'(1H)-dione (150 mg, 0.22 mmol) was dissolved in THF (5 mL). Then aqueous solution (1 mL) of KOH (50 mg, 0.88 mmol) was added. The mixed solution was refluxed for 1 h. The mixture was cooled, concentrated and acidified to "pH" 2-3. The solution was concentrated and the residue was purified by Prep-HPLC to obtain a white solid (13 mg).

m/z (M+H)$^+$: 651

EXAMPLE 245a

Preparation of intermediate 1-[5-bromo-2-(2-methoxycarbonyl-2-methyl-propoxy)phenyl]-3-trimethylsilyoxy-2-aza-1,3-butadiene

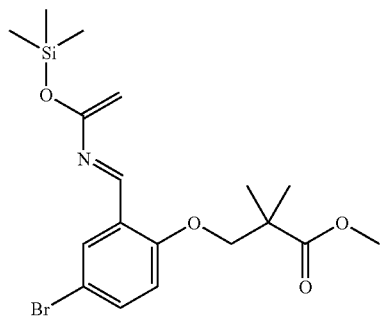

M. W. 428.40 $C_{18}H_{26}BrNO_4Si$

To anhydrous tetrahydrofuran (40 mL) was added 1M THF solution of LiHMDS (25.9 mmol, 25.9 mL) under nitrogen at room temperature, followed by the addition of 3-(4-bromo-2-formyl-phenoxy)-2,2-dimethyl-propionic acid methyl ester (8 g, 25.9 mmol). The mixture was stirred at room temperature for 1 h, then trimethylsilyl chloride (3.3 mL, 25.9 mmol) was added dropwise. The temperature of the mixture was lowered to 0° C. on a cooling ice bath. To this mixture was added triethylamine (4.6 mL, 33.2 mmol) in one portion, followed by the dropwise addition of a solution of acetyl chloride (2.35 mL, 33.2 mmol) in diethyl ether (100 ml). The cooling bath was removed, and the mixture was stirred at room temperature overnight. The mixture was quickly filtered on celite under nitrogen, and filtrate was concentrated under reduced pressure to give title compound as a yellow gum and used for the next step without further purification.

EXAMPLE 245b

Preparation of intermediate E/Z-6-Chloro-3-(2,5-dichloro-benzylidene)-1,3-dihydro-indol-2-one

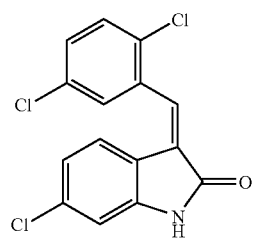

M. W. 324.60 $C_{15}H_8Cl_3NO$

In a manner similar to the method described in Example 227b, 2,5-dichloro-benzaldehyde (5 g, 28.57 mmol) was reacted with 6-chlorooxindole (4.77 g, 28.57 mmol) and pyrrolidine (2.43 g, 34.3 mmol) in methanol to give title compound as yellow solid (10 g).

EXAMPLE 245c

Preparation of intermediate E/Z-6-chloro-3-(2,5-dichloro-benzylidene)-2-oxo-2,3-dihydro-indole-1-carboxylic acid tert-butyl ester

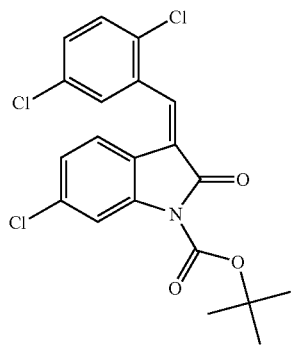

M. W. 424.71 $C_{20}H_{16}Cl_3NO_3$

In a manner similar to the method described in Example 227c, E/Z-6-Chloro-3-(2,5-dichloro-benzylidene)-1,3-dihydro-indol-2-one (10 g, 30.9 mmol) was reacted with ditert-butyl-dicarbonate (8.1 g, 37.1 mmol) and DMAP (0.38 g, 3.09 mmol) in $CH_2Cl_2$ to give title compound as a yellow oil (7.5 g).

EXAMPLE 245d

Preparation of racemic (2'R,3R,4'S)-2'-[5-bromo-2-(2-methoxycarbonyl-2-methyl-propoxy)-phenyl]-6-chloro-4'-(2,5-dichlorophenyl)spiro[3H-indole-3,3'-piperidine]-2,6'(1H)-dione

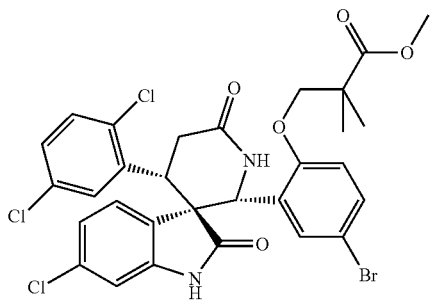

M. W. 680.82 $C_{30}H_{26}BrCl_3N_2O_5$

In a manner similar to the method described in Example 41b, E/Z-6-chloro-3-(2,5-dichloro-benzylidene)-2-oxo-2,3-dihydro-indole-1-carboxylic acid tert-butyl ester (1.8 g, 4.3 mmol) was reacted with 1-[5-bromo-2-(2-methoxycarbonyl-2-methyl-propoxy)phenyl]-3-trimethylsilyoxy-2-aza-1,3-butadiene (13 mmol) in toluene and then trifluoroacetic acid in dichloromethane to give title compound as a white solid (220 mg).

m/z (M+H)$^+$: 679

EXAMPLE 246

Preparation of racemic (2'R,3R,4'S)-2'-[5-bromo-2-(2,2-dimethyl-3-hydroxy propoxy)-phenyl]-6-chloro-4'-(2,5-dichlorophenyl)spiro[3H-indole-3,3'-piperidine]-2,6'(1H)-dione

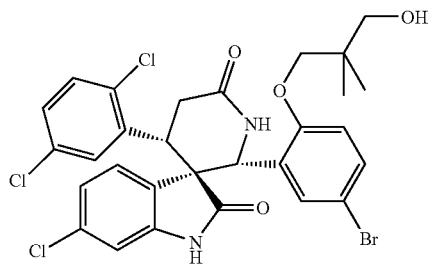

M. W. 652.80 $C_{29}H_{26}BrCl_3N_2O_4$

In a manner similar to the method described in Example 231, racemic (2'R,3R,4'S)-2'-[5-bromo-2-(2-methoxycarbonyl-2-methyl-propoxy)-phenyl]-6-chloro-4'-(2,5-dichlorophenyl)spiro[3H-indole-3,3'-piperidine]-2,6'(1H)-dione (120 mg, 0.177 mmol) was reacted with LiAlH$_4$ (34 mg, 0.885 mmol) in THF to give title compound as a white solid (21 mg).

m/z (M+H)$^+$: 651

EXAMPLE 247a

Preparation of intermediate (2-bromo-ethyl)-carbamic acid tert-butyl ester

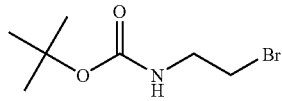

M. W. 224.10 $C_7H_{14}BrNO_2$

Di-tert-butyl-dicarbonate (17.8 g, 0.081 mol) and DIPEA (11.6 g, 0.090 mol) were dissolved in ethanol (200 mL) at room temperature. Then 2-aminoethylbromide hydrobromide (20 g, 0.098 mmol) was added. The reaction mixture was stirred at room temperature for 3 h, then concentrated. The residue was dissolved in ethyl acetate and washed with water for three times. The organic layer was separated, dried over Na$_2$SO$_4$ and concentrated to give (2-bromo-ethyl)-carbamic acid tert-butyl ester as light yellow oil. (15 g)

EXAMPLE 247b

Preparation of intermediate [2-(4-chloro-2-formyl-phenoxy)-ethyl]-carbamic acid tert-butyl ester

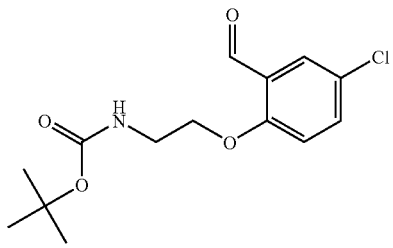

M. W. 299.76 $C_{14}H_{18}ClNO_4$

In a manner similar to the method described in Example 227a, (2-bromo-ethyl)-carbamic acid tert-butyl ester (10 g, 44.8 mmol) was reacted with 5-chloro-2-hydroxy-benzaldehyde (7 g, 44.8 mmol), K$_2$CO$_3$ (18.6 g, 134 mmol) and KI (1.48 g, 8.96 mmol) to give title compound as oil (9.56 g)

EXAMPLE 247c

Preparation of intermediate E/Z-{2-[4-Chloro-2-(6-chloro-2-oxo-1,2-dihydro-indol-3-ylidenemethyl)-phenoxy]-ethyl}-carbamic acid tert-butyl ester

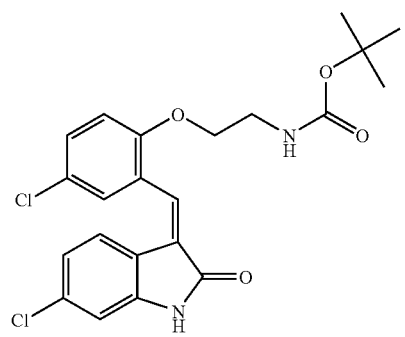

M. W. 449.34 $C_{22}H_{22}Cl_2N_2O_4$

In a manner similar to the method described in Example 227b, [2-(4-chloro-2-formyl-phenoxy)-ethyl]-carbamic acid tert-butyl ester (8 g, 27 mmol) was reacted with 6-Chlorooxindole (4.5 g, 27 mmol) and pyrrolidine (2.1 g, 30 mmol) in methanol to give title compound as a yellow solid (16 g).

EXAMPLE 247d

Preparation of intermediate E/Z-3-[2-(2-tert-butoxycarbonylamino-ethoxy)-5-chloro-benzylidene]-6-chloro-2-oxo-2,3-dihydro-indole-1-carboxylic acid tert-butyl ester

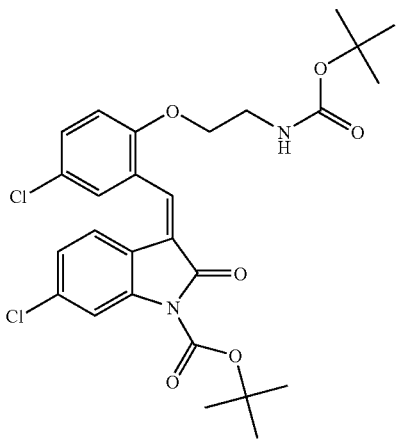

M. W. 549.46 $C_{27}H_{30}Cl_2N_2O_6$

In a manner similar to the method described in Example 227c, E/Z-{2-[4-chloro-2-(6-chloro-2-oxo-1,2-dihydro-indol-3-ylidenemethyl)-phenoxy]-ethyl}-carbamic acid tert-butyl ester (12 g, 30.27 mmol) was reacted with di-tert-butyl-dicarbonate (5.8 g, 27 mmol) and DMAP (0.66 g, 5.4 mmol) in $CH_2Cl_2$ to give E/Z-3-[2-(2-tert-Butoxycarbonylamino-ethoxy)-5-chloro-benzylidene]-6-chloro-2-oxo-2,3-dihydro-indole-1-carboxylic acid tert-butyl ester (12.4 g)

EXAMPLE 247e

Preparation of racemic (2'R,3R,4'S) 4'-[2-(2-aminoethoxy)-5-chloro-phenyl]-6-chloro-2'-(5-fluoro-2-methyl-phenyl)spiro[3H-indole-3,3'-piperidine]-2,6'(1H)-dione

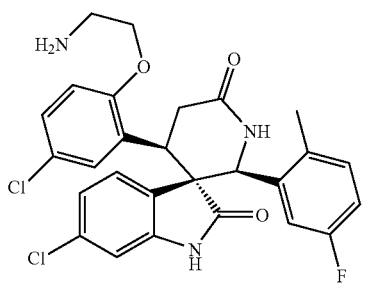

M. W. 528.42 $C_{27}H_{24}Cl_2FN_3O_3$

In a manner similar to the method described in Example 228d, E/Z-3-[2-(2-tert-butoxycarbonylamino-ethoxy)-5-chloro-benzylidene]-6-chloro-2-oxo-2,3-dihydro-indole-1-carboxylic acid tert-butyl ester (4 g, 7.3 mmol) was reacted with 1-(5-fluoro-2-methyl-phenyl)-3-trimethylsilyoxy-2-aza-1,3-butadiene (29 mmol) in toluene and then trifluoroacetic acid in dichloromethane to give title compound as a white solid (130 mg).

m/z (M+H)$^+$: 528

EXAMPLE 248

Preparation of racemic (2'R,3R,4'S)-4'-(3-chlorophenyl)-6-cyclopropyl-2'-isopropenylspiro[3H-indole-3,3'-piperidine]-2,6'(1H)-dione

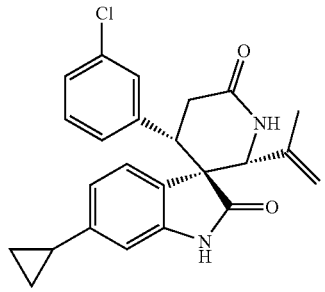

M. W. 406.92 $C_{24}H_{23}ClN_2O_2$

Under nitrogen atmosphere, to a solution of racemic (2'R,3R,4'S)-6-bromo-4'-(3-chlorophenyl)-2'-isopropenyl-2,6'-dioxospiro[indole-3,3'-piperidine]-1-carboxyl acid tert-butyl ester (0.050 g) prepared in Example 172b in toluene (5 mL) was added water (0.1 mL), cyclopropyl boronic acid (0.020 g, 0.23 mmol), $K_3PO_4$ (0.098 g, 0.46 mmol), and $Pd(PPh_3)_4$ (0.018 g, 0.016 mmol). The mixture was irradiated at 130° C. by microwave for 0.5 h. Then cooled to room temperature and filtered through a short pad of silica gel, the silica gel was washed with ethyl acetate. The filtrate was concentrated. To the residue was added trifluoroacetic acid (5 mL). The solution was stirred at room temperature for 0.5 h, then partitioned between ethyl acetate and water. The organic layer was separated, and the aqueous layer was extracted with ethyl acetate. The combined organic layer was washed with $NaHCO_3$ aqueous solution, dried over $MgSO_4$ and concentrated. The residue was purified with Prep.LC to give title compound as a white solid (Yield: 8 mg).

m/z (M+H)$^+$: 407

EXAMPLE 249a

Preparation of intermediate 3-chloro-2H-pyridine-1-carboxylic acid phenyl ester

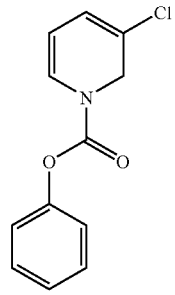

M. W. 235.67 $C_{12}H_{10}ClNO_2$

To a solution of 3-chloro-pyridine (6.0 g, 53 mmol) in methanol (50 mL) was added $NaBH_4$ (2.6 g, 69 mmol) at −78°

C., following addition of phenyl chloroformate (8.3 g, 53 mmol) at same temperature. The mixture was stirred at r.t. for 0.5 h. Then water (200 mL) was added slowly into the solution. The precipitate was collected by filtration to give crude product (Yield: 8.2 g, 67%).

m/z (M+H)$^+$: 236

EXAMPLE 249b

Preparation of intermediate 3-chloro-5-formyl-2H-pyridine-1-carboxylic acid phenyl ester

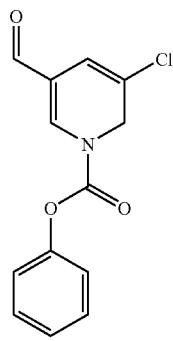

M. W. 263.68 C$_{13}$H$_{10}$ClNO$_3$

Phosphorus oxychloride (5.4 g, 57.9 mmol) was added slowly to a stirred solution of DMF (8.9 mL, 116 mmol) in dichloromethane (10 mL) at 0° C. After addition, the solution was stirred at same temperature for 25 min., then transferred a solution of 3-chloro-2H-pyridine-1-carboxylic acid phenyl ester (5.67 g, 26.3 mmol) in anhydrous dichloromethane (50 mL) at 0° C. The ice bath was removed and stirring was continued at r.t. for 2 h, then the mixture was refluxed for 40 min. After the mixture was cooled to 0° C., an aqueous solution of KOAc (15 g, 153 mmol) in water (50 mL) was added slowly. The mixture was refluxed for 20 min., organic layer was separated, and aqueous layer was extracted with dichloromethane (50 mL). The organic layers were combined, washed with saturated NaHCO$_3$, water and brine then dried over MgSO$_4$, concentrated to give the crude product (Yield: 6.7 g).

m/z (M+H)$^+$: 264

EXAMPLE 249c

Preparation of intermediate 5-chloro-pyridine-3-carbaldehyde

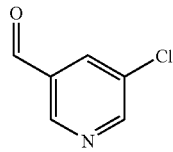

M. W. 141.56 C$_6$H$_4$ClNO

The mixture of 3-chloro-5-formyl-2H-pyridine-1-carboxylic acid phenyl ester (2.3 g, 8.8 mmol), sublimed sulfur (0.29 g, 9 mmol) and naphthalene (6 g) was refluxed under an argon atmosphere for 2 h. After the reaction was complete, the mixture was cooled to r.t., dissolved in ethyl ether (30 mL), and extracted with aqueous 10% HCl. The combined acid extracts were washed with ethyl ether (20 mL) and cooled to 0° C. Dichloromethane (30 mL) was added and "pH" of the mixture was adjusted to be basic with 25% aqueous NaOH, and the mixture was extracted with dichloromethane (20 mL). The combined organic phase was washed with brine, dried over K$_2$CO$_3$, filtered, and concentrated to give a brown solid. (0.8 g, 76%).

m/z (M+H)$^+$: 142

EXAMPLE 249d

Preparation of intermediate 6-chloro-3-(5-chloro-pyridine-3-ylmethylene)-1,3-dihydro-indol-2-one

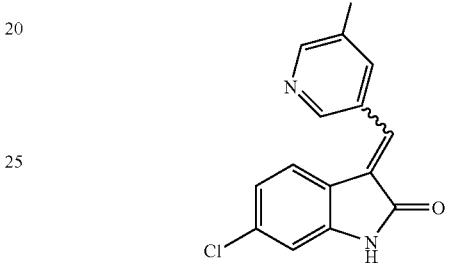

M. W. 291.14 C$_{14}$H$_8$ClN2O

To the mixture of 6-chlorooxindole (0.93 g, 5.6 mmol) and 5-chloro-pyridine-3-carbaldehyde (0.8 g, 5.6 mmol) in methanol (10 mL) was added pyrrolidine (0.6 g, 5.6 mmol) dropwise. The mixture was then heated at 70° C. for 3 h and cooled to room temperature. The precipitate was collected, dried to give a mixture of E/Z-6-chloro-3-(5-chloro-pyridine-3-ylmethylene)-1,3-dihydro-indol-2-one as a bright yellow solid (Yield 1.0 g, 63%).

m/z (M+H)$^+$: 291

EXAMPLE 249e

Preparation of intermediate E/Z-6-chloro-3-(5-chloro-pyridine-3-ylmethylene)-2-oxo-2,3-dihydro-indole-1-carboxylic acid tert-butyl ester

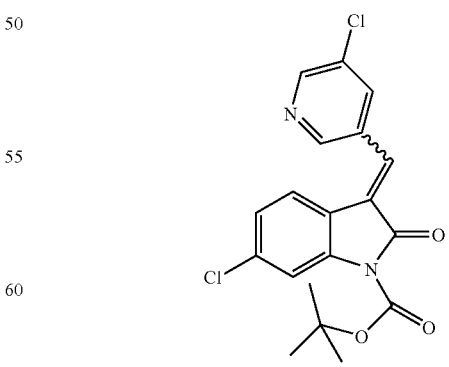

M. W. 391.26 C$_{19}$H$_{16}$Cl$_2$N$_2$O$_3$

To a solution of E/Z-6-chloro-3-(5-chloro-pyridine-3-ylmethylene)-1,3-dihydro-indol-2-one (1 g, 3.4 mmol) in dichloromethane (50 mL) was added di-tert-butyl-dicarbonate (1.5 g, 6.9 mmol) at room temperature, followed by the addition of 4-dimethylaminopyridine (1 g, 8.2 mmol). The reaction mixture was stirred at same temperature for 1 h. The mixture was then concentrated and the residue was purified by chromatography to give E/Z-6-chloro-3-(3-chloro-benzylidene)-2-oxo-2,3-dihydro-indole-1-carboxylic acid tert-butyl ester (Yield: 1.3 g, 96%).

m/z (M+H)$^+$: 391

EXAMPLE 249f

Preparation of chiral (2'R,3R,4'S)-6-chloro-4'-(5-chloro-3-pyridinyl)-2'-isopropenylspiro[3H-indole-3, 3'-piperidine]-2,6'(1H)-dione

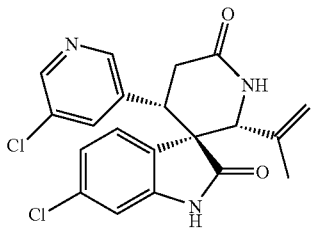

M. W. 402.28 C$_{20}$H$_{17}$Cl$_2$N$_3$O$_2$

In a manner similar to the method described in Example 41b, E/Z-6-chloro-3-(5-chloro-pyridine-3-ylmethylene)-2-oxo-2,3-dihydro-indole-1-carboxylic acid tert-butyl ester (0.4 g, 1 mmol) was reacted with 1-isopropenyl-3-trimethylsilyoxy-2-aza-1,3-butadiene (10.5 mmol) in toluene and then trifluoroacetic acid in dichloromethane to give racemic (2'R, 3R,4'S)-6-chloro-4'-(5-chloro-3-pyridinyl)-2'-isopropenyl-spiro[3H-indole-3,3'-piperidine]-2,6'(1H)-dione as a white solid (Yield: 31 mg). Separation of the two enantiomers from racemic compound (21 mg) was conducted by chiral HPLC to provide chiral (2'R,3R,4'S)-6-chloro-4'-(5-chloro-3-pyridinyl)-2'-isopropenylspiro[3H-indole-3,3'-piperidine]-2,6'(1H)-dione (6 mg) and chiral (2'S,3S,4'R)-6-chloro-4'-(5-chloro-3-pyridinyl)-2'-isopropenylspiro[3H-indole-3,3'-piperidine]-2,6'(1H)-dione as a white solid (8 mg).

m/z (M+H)$^+$: 402

EXAMPLE 250a

Preparation of intermediate E/Z-6-chloro-3-(5-chloro-2-nitro-benzylidene)-1,3-dihydro-indol-2-one

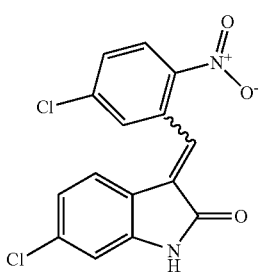

M. W. 335.15 C$_{15}$H$_8$Cl$_2$N$_2$O$_3$

To the mixture of 6-Chlorooxindole (3.3 g, 20 mmol) and 5-chloro-2-nitro-benzaldehyde (3.75 g, 20 mmol) in metha-nol (30 mL) was added pyrrolidine (1.63 mL, 20 mmol) dropwise. The mixture was then heated at 70° C. for 3 h and cooled to room temperature. The precipitate was collected, dried to give a mixture of E/Z-6-chloro-3-(5-chloro-2-nitro-benzylidene)-1,3-dihydro-indol-2-one as a bright yellow solid (Yield 6 g, 91%).

m/z (M+H)$^+$: 335

EXAMPLE 250b

Preparation of intermediate E/Z-6-chloro-3-(5-chloro-2-nitro-benzylidene-2-oxo-2,3-dihydro-indole-1-carboxylic acid tert-butyl ester

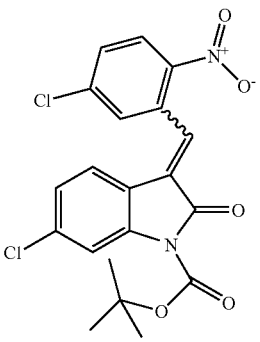

M. W. 435.27 C$_{20}$H$_{16}$Cl$_2$N$_2$O$_5$

To a solution of E/Z-6-chloro-3-(5-chloro-2-nitro-benzylidene)-1,3-dihydro-indol-2-one (6.68 g, 20 mmol) in dichloromethane (50 mL) at room temperature was added di-tert-butyl-dicarbonate (5.2 g, 24 mmol), followed by the addition of 4-dimethylaminopyridine (0.24 g, 2 mmol). The reaction mixture was stirred at room temperature for 1 h. The mixture was then concentrated and the residue was purified by chromatography to give E/Z-6-chloro-3-(5-chloro-2-nitro-benzylidene-2-oxo-2,3-dihydro-indole-1-carboxylic acid tert-butyl ester (Yield 2.7 g).

m/z (M+H)$^+$: 435

EXAMPLE 250c

Preparation of racemic (2'R,3R,4'S)-6-chloro-4'-(5-chloro-2-nitro-phenyl)-2'-isopropenylspiro[3H-indole-3,3'-piperidine]-2,6'(1H)-dione

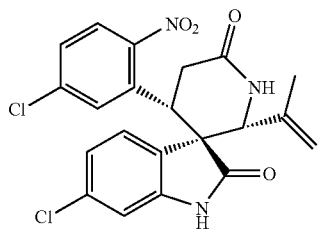

M. W. 446.29 C$_{21}$H$_{17}$Cl$_2$N$_3$O$_4$

In a manner similar to the method described in Example 41b, E/Z-6-chloro-3-(5-chloro-2-nitro-benzylidene-2-oxo-2, 3-dihydro-indole-1-carboxylic acid tert-butyl ester (2.7 g, 6.2 mmol) was reacted with 1-isopropenyl-3-trimethylsilyoxy-2- aza-1,3-butadiene (31 mmol) in toluene and then trifluoroacetic acid in dichloromethane to give the title compound as a solid (Yield: 0.44 g).

m/z (M+H)$^+$: 446

EXAMPLE 251

Preparation of racemic (2'R,3R,4'S)-4'-(2-amino-5-chloro-phenyl)-6-chloro-2'-isopropenylspiro[3H-indole-3,3'-piperidine]-2,6'(1H)-dione

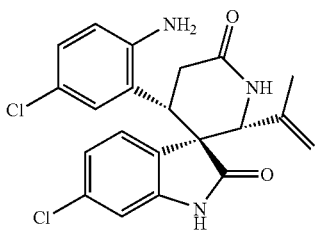

M. W. 416.31 $C_{21}H_{19}Cl_2N_3O_2$

The reaction mixture of racemic (2'R,3R,4'S)-6-chloro-4'-(5-chloro-2-nitro-phenyl)-2'-isopropenylspiro[3H-indole-3,3'-piperidine]-2,6'(1H)-dione (290 mg, 0.65 mmol), Raney Ni (39 mg) and NH$_2$NH$_2$.H$_2$O (320 mg) in methanol was stirred at 80° C. for 0.5 h. The mixture was cooled to 4° C., and concentrated. To the residue were added ethyl acetate (10 mL) and water (10 mL). The organic layer was separated, washed with brine, dried over MgSO$_4$ and concentrated. The residue was purified by column chromatography to give the title compound as a solid (Yield: 260 mg).

m/z (M+H)$^+$: 416

EXAMPLE 252

Preparation of racemic (2'R,3R,4'S)-4'-(2-acetylamino-5-chloro-phenyl)-6-chloro-2'-isopropenyl-spiro[3H-indole-3,3'-piperidine]-2,6'(1H)-dione

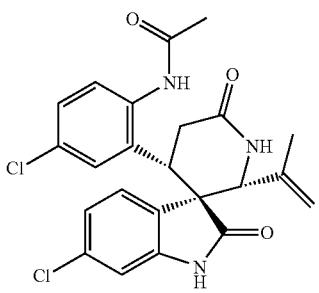

M. W. 458.35 $C_{23}H_{21}Cl_2N_3O_3$

To a mixture of racemic (2'R,3R,4'S)-4'-(2-amino-5-chloro-phenyl)-6-chloro-2'-isopropenylspiro[3H-indole-3,3'-piperidine]-2,6'(1H)-dione (40 mg, 0.1 mmol), acetic acid (9 mg, 0.15 mmol), EDCI.HCl (29 mg, 0.15 mmol), and HOBt (20 mg, 0.15 mmol) in acetonitrile (5 mL) was added DIPEA (0.052 mL, 0.3 mmol) at r.t. The reaction mixture was stirred for 4 h. The mixture was concentrated and partitioned between ethyl acetate and water. The organic layer was separated, and the aqueous layer was extracted with ethyl acetate. The organic layers were dried over MgSO$_4$ and concentrated.

The residue was purified with Prep HPLC to give the title compound as a white solid (Yield: 9 mg).

m/z (M+H)$^+$: 458

EXAMPLE 253

Preparation of racemic (2'R,3R,4'S)-6-chloro-4'-(5-chloro-2-methanesulfonylamino-phenyl)-2'-isopropenylspiro[3H-indole-3,3'-piperidine]-2,6'(1H)-dione

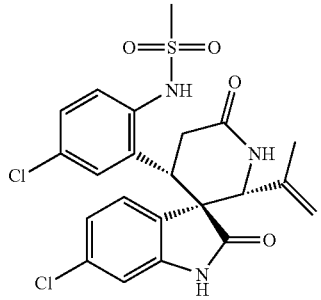

M. W. 494.40 $C_{22}H_{21}Cl_2N_3O_4S$

To a mixture of racemic (2'R,3R,4'S)-4'-(2-amino-5-chloro-phenyl)-6-chloro-2'-isopropenylspiro[3H-indole-3,3'-piperidine]-2,6'(1H)-dione (40 mg, 0.1 mmol), methanesulfonyl chloride (0.0092 mL, 0.15 mmol), in acetonitrile (5 mL) was added pyridine (23 mg, 0.3 mmol) at r.t. The reaction mixture was stirred for 4 h. The mixture was concentrated and partitioned between ethyl acetate and water. The organic layer was separated, and the aqueous layer was extracted with ethyl acetate. The combined organic layers were dried over MgSO$_4$ and concentrated. The residue was purified with Prep. HPLC to give the title compound as a white solid (Yield: 8 mg).

m/z (M+H)$^+$: 494

EXAMPLE 254a

Preparation of intermediate E/Z-6-chloro-3-(5-chloro-2-iodo-benzylidene)-1,3-dihydro-indol-2-one

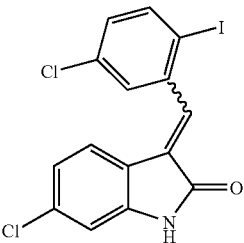

M. W. 416.05 C15H8Cl2INO

To the mixture of 6-chlorooxindole (3.3 g, 20 mmol) and 5-chloro-2-iodo-benzaldehyde prepared in Example 208a (5 g, 20 mmol) in methanol (30 mL) was added pyrrolidine (1.63 mL, 20 mmol) dropwise. The mixture was then heated at 70° C. for 3 h and cooled to room temperature. Then the precipitate was collected by filtration to give a mixture of E/Z-6-chloro-3-(5-chloro-2-iodo-benzylidene)-1,3-dihydro-indol-2-one as a bright yellow solid (Yield 5.3 g).

m/z (M+H)$^+$: 416

EXAMPLE 254b

Preparation of intermediate E/Z-6-chloro-3-(5-chloro-2-iodo-benzylidene-2-oxo-2,3-dihydro-indole-1-carboxylic acid tert-butyl ester

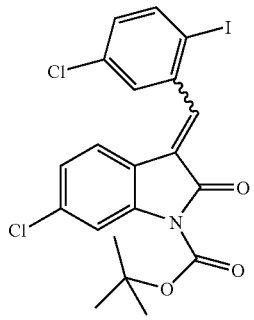

M. W. 516.17 C20H16Cl2INO3

To a solution of E/Z-6-chloro-3-(5-chloro-2-iodo-benzylidene)-1,3-dihydro-indol-2-one (5.3 g, 12.8 mmol) in dichloromethane (50 mL) at room temperature was added di-tert-butyl-dicarbonate (3.4 g, 15.3 mmol), followed by the addition of 4-dimethylaminopyridine (0.16 g, 1.3 mmol). The reaction mixture was stirred at room temperature for 1 h. The mixture was then concentrated and the residue was purified by chromatography to give E/Z-6-chloro-3-(5-chloro-2-iodo-benzylidene-2-oxo-2,3-dihydro-indole-1-carboxylic acid tert-butyl ester (Yield 5.5 g).

m/z (M+H)+: 516

EXAMPLE 254c

Preparation of racemic (2'R,3R,4'S)-6-chloro-4'-(5-chloro-2-iodophenyl)-2'-(5-fluoro-2-methylphenyl)spiro[3H-indole-3,3'-piperidine]-2,6'(1H)-dione

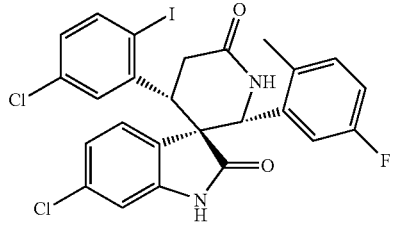

M. W. 595.24 $C_{25}H_{18}Cl_2FIN_2O_2$

In a manner similar to the method described in Example 41b, E/Z-6-chloro-3-(5-chloro-2-iodo-benzylidene)-2-oxo-2,3-dihydro-indole-1-carboxylic acid tert-butyl ester (2 g, 4 mmol) was reacted with 1-(5-fluoro-2-methylphenyl)-3-trimethylsilyoxy-2-aza-1,3-butadiene (10 mmol) in toluene and then trifluoroacetic acid in dichloromethane to give title compound as a white solid (Yield: 0.8 g).

m/z (M+H)+: 595

EXAMPLE 255a

Preparation of intermediate 5-chloro-2-(3-hydroxy-2,2-dimethyl-propoxy)-benzaldehyde

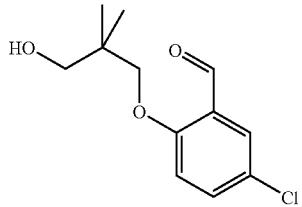

M. W. 242.70 $C_{12}H_{15}ClO_3$

5-Chloro-benzaldehyde (3.1 g, 20 mmol), 3-bromo-2,2-dimethyl-propan-1-ol (3 mL, 24 mmol), $K_2CO_3$ (5.5 g, 40 mmol) and KI (0.5 g) were mixed in DMF (20 mL). Then mixture was irradiated under microwave at 200° C. for 1 h. The mixture was filtered and the filtrate was concentrated. The residue was dissolved in ethyl acetate and washed with 1N NaOH. Then the organic layer was separated, dried over anhydrous $Na_2SO_4$ and concentrated to give title compound as yellow solid (Yield: 1.6 g).

m/z (M+H)+: 243

EXAMPLE 255b

Preparation of intermediate E/Z-6-Chloro-3-[5-chloro-2-(3-hydroxy-2,2-dimethyl-propoxy)-benzylidene]-1,3-dihydro-indol-2-one

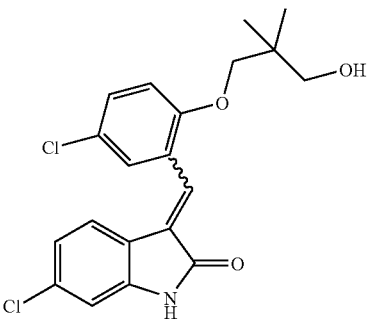

M. W. 392.29 $C_{20}H_{19}Cl_2NO_3$

5-Chloro-2-(3-hydroxy-2,2-dimethyl-propoxy)-benzaldehyde (2.4 g, 10 mmol) and 6-chloro-1,3-dihydro-indol-2-one (1.7 g, 10 mmol) were mixed in anhydrous methanol (20 mL). Then pyrrolidine (0.8 g, 11.2 mmol) was added slowly at r.t. The mixture was heated to 70° C. for 3 h and cooled to room temperature. Then the precipitate was collected by filtration to give title compound as yellow solid (Yield: 3.8 g).

m/z (M+H)+: 392

EXAMPLE 255c

Preparation of intermediate E/Z-3-[2-(3-tert-butoxy-carbonyloxy-2,2-dimethyl-propoxy)-5-chloro-benzylidene]-6-chloro-2-oxo-2,3-dihydro-indole-1-carboxylic acid tert-butyl ester

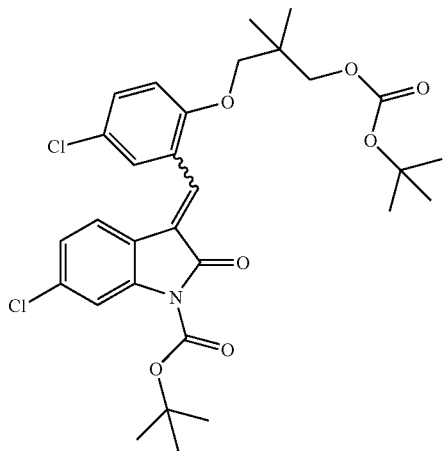

M. W. 592.52 $C_{30}H_{35}Cl_2NO_7$

To a solution of E/Z-6-chloro-3-[5-chloro-2-(3-hydroxy-2,2-dimethyl-propoxy)-benzylidene]-1,3-dihydro-indol-2-one (4 g, 10 mmol) in dichloromethane (10 mL) was added di-tert-butyl-dicarbonate (5.6 g, 25 mmol) at r.t., followed by the addition of 4-dimethylaminopyridine (0.1 g, 1 mmol). The reaction mixture was stirred for 2 h and washed with 0.1N hydrochloride, then the solvent was removed to give title compound (Yield: 5 g).

m/z (M+H)$^+$: 592

EXAMPLE 255d

Preparation of racemic (2'S,3S,4'R)-6-chloro-4'-[5-chloro-2-(3-hydroxy-2,2-dimethyl-propoxy)-phenyl]-2'-(5-fluoro-2-methyl phenyl)-spiro[3H-indole-3,3'-piperidine]-2,6'(1H)-dione

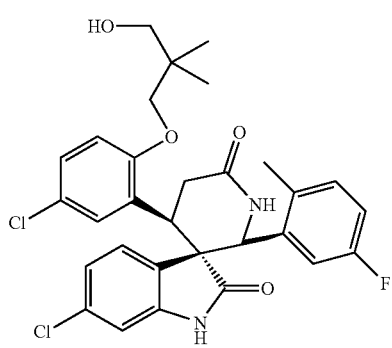

M. W. 571.48 $C_{30}H_{29}Cl_2FN_2O_4$

In a manner similar to the method described in Example 228d, E/Z-3-[2-(3-tert-butoxycarbonyloxy-2,2-dimethyl-propoxy)-5-chloro-benzylidene]-6-chloro-2-oxo-2,3-dihydro-indole-1-carboxylic acid tert-butyl ester (60 mg, 0.1 mmol) was reacted with 1-(5-fluoro-2-methylphenyl)-3-trimethylsilyoxy-2-aza-1,3-butadiene (1 mmol) in toluene and then trifluoroacetic acid in dichloromethane to give title compound as a white solid (Yield: 10 mg).

m/z (M+H)$^+$: 571

EXAMPLE 256a

Preparation of intermediate 5-Chloro-2-(2,2,2-trifluoro-ethoxy)-benzaldehyde

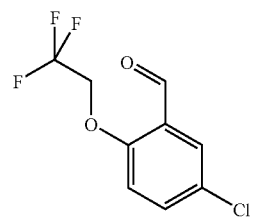

M. W. 238.60 $C_9H_6ClF_3O_2$

5-Chloro-2-hydroxy-benzaldehyde (3.1 g, 2 mmol), 1,1,1-trifluoro-2-iodo-ethane (2.4 mL, 24 mmol), K$_2$CO$_3$ (5.5 g, 40 mmol) and KI (0.1 g) were mixed in DMF (20 mL). Then the mixture was irradiated under microwave at 180° C. for 1 h. The mixture was filtered and the filtrate was concentrated. The residue was dissolved in ethyl acetate and washed with 1N NaOH. Then the organic layer was separated, dried over anhydrous Na$_2$SO$_4$ and concentrated to give title compound as a yellow solid (Yield: 4 g).

m/z (M+H)$^+$: 239

EXAMPLE 256b

Preparation of intermediate E/Z 6-Chloro-3-[5-chloro-2-(2,2,2-trifluoro-ethoxy)-benzylidene]-1,3-dihydro-indol-2-one

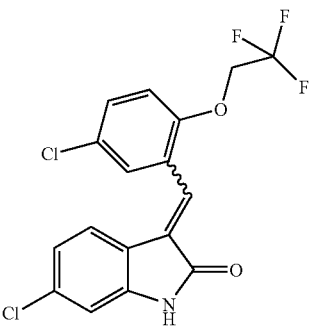

M. W. 388.18 $C_{17}H_{10}Cl_2F_3NO_2$

5-Chloro-2-(2,2,2-trifluoro-ethoxy)-benzaldehyde (4 g, 16 mmol) and 6-chlorooxindole (2.8 g, 16 mmol) were mixed in anhydrous methanol (20 mL). Then pyrrolidine (1.32 mL, 16 mmol) was added slowly at r.t. The mixture was heated to 70° C. for 3 h and cooled to room temperature. The precipitate was collected by filtration to give title compound as a yellow solid (Yield: 4.45 g, 72%).

m/z (M+H)$^+$: 338

EXAMPLE 256c

Preparation of intermediate E/Z-6-chloro-3-[5-chloro-2-(2,2,2-trifluoro-ethoxy)-benzylidene]-2-oxo-2,3-dihydro-indole-1-carboxylic acid tert-butyl ester

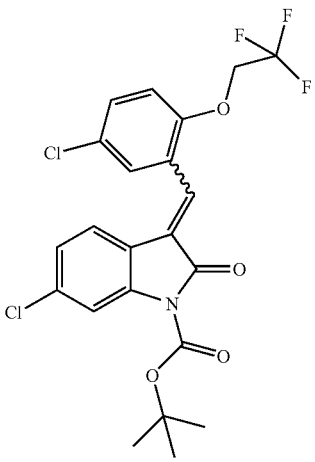

M. W. 488.29 $C_{22}H_{18}Cl_2F_3NO_4$

To a solution of E/Z-6-chloro-3-[5-chloro-2-(2,2,2-trifluoro-ethoxy)-benzylidene]-1,3-dihydro-indol-2-one (4.45 g, 11.5 mmol) in dichloromethane (10 mL) at r.t was added di-tert-butyl-dicarbonate (3.7 g, 17.2 mmol), followed by the addition of 4-dimethylaminopyridine (0.14 g, 1.7 mmol). The reaction mixture was stirred for 2 h and washed with 0.1N hydrochloride, then the solvent was removed to give title compound (Yield: 5 g, 89%).

m/z (M+H)$^+$: 488

EXAMPLE 256d

Preparation of racemic (2'S,3S,4'R)-6-chloro-4'-(5-chloro-2-(2,2,2-trifluoro-ethoxy)hydroxy-phenyl)-2'-(5-fluoro-2-methylphenyl)spiro[3H-indole-3,3'-piperidine]-2,6'(1H)-dione

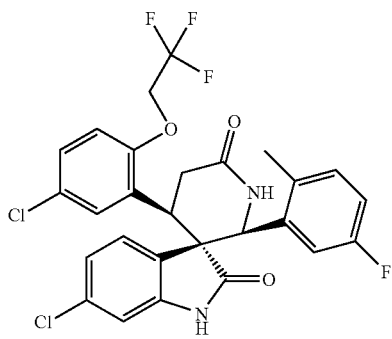

M. W. 567.37 $C_{27}H_{20}Cl_2F_4N_2O_3$

In a manner similar to the method described in Example 228d, E/Z-6-Chloro-3-[5-chloro-2-(2,2,2-trifluoro-ethoxy)-benzylidene]-2-oxo-2,3-dihydro-indole-1-carboxylic acid tert-butyl ester (1 g, 2 mmol) was reacted with 1-(5-Fluoro-2-methylphenyl)-3-trimethylsilyoxy-2-aza-1,3-butadiene (20 mmol) in toluene and then trifluoroacetic acid in dichloromethane to give title compound as a white solid (Yield: 50 mg).

m/z (M+H)$^+$: 567

EXAMPLE 257a

Preparation of intermediate 3-(4-chloro-2-formyl-phenoxy)-2,2-dimethyl-propionic acid methyl ester

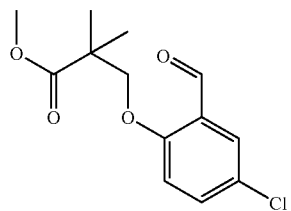

M. W. 270.72 $C_{13}H_{15}ClO_4$

5-Chloro-2-hydroxy-benzaldehyde (3.1 g, 2 mmol), 2,2-dimethyl-3-(toluene-4-sulfonyloxy)-propionic acid methyl ester (5.46 g, 24 mmol), $K_2CO_3$ (5.5 g, 40 mmol) and KI (0.1 g) were mixed in DMF (20 mL). Then the mixture was irradiated under microwave at 150° C. for 1 h. The mixture was filtered and the filtrate was concentrated. The residue was dissolved in ethyl acetate and washed with 1N NaOH. Then the organic layer was separated, dried over $Na_2SO_4$ and concentrated to give title compound (Yield: 5 g, 92.5%).

m/z (M+H)$^+$: 271

EXAMPLE 257b

Preparation of intermediate E/Z-3-[4-chloro-2-(6-chloro-2-oxo-1,2-dihydro-indol-3-ylidenemethyl)-phenoxy]-2,2-dimethyl-propionic acid methyl ester

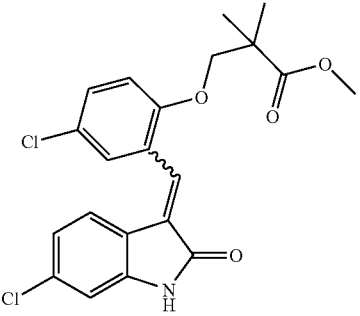

M. W. 420.30 $C_{21}H_{19}Cl_2NO_4$ 3-(4-Chloro-2-formyl-phenoxy)-2,2-dimethyl-propionic acid methyl ester (6.7 g, 25 mmol) and 6-Chlorooxindole (4.35 g, 25 mmol) were mixed in anhydrous methanol (20 mL). Then pyrrolidine (2 mL, 25 mmol) was added slowly at r.t. The mixture was heated at 70° C. for 3 h and cooled to room temperature. The precipitate was collected by filtration to give title compound as a yellow solid (Yield: 7 g, 67%).

m/z (M+H)$^+$: 420

EXAMPLE 257c

Preparation of intermediate E/Z-6-chloro-3-[5-chloro-2-(2-methoxycarbonyl-2-methyl-propoxy)-benzylidene]-2-oxo-2,3-dihydro-indole-1-carboxylic acid tert-butyl ester

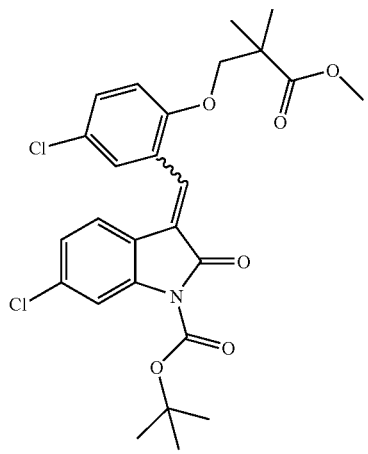

M. W. 520.41 C$_{26}$H$_{27}$Cl$_2$NO$_6$

To a solution of E/Z-3-[4-chloro-2-(6-chloro-2-oxo-1,2-dihydro-indol-3-ylidenemethyl)-phenoxy]-2,2-dimethyl-propionic acid methyl ester (7 g, 16.7 mmol) in dichloromethane (20 mL) at r.t. was added di-tert-butyl-dicarbonate (5.4 g, 25 mmol), followed by the addition of 4-dimethylaminopyridine (0.2 g, 1.7 mmol). The reaction mixture was stirred for 2 h and washed with 0.1N hydrochloride, then the solvent was removed to give title compound (Yield: 8 g).

m/z (M+H)$^+$: 420

EXAMPLE 257d

Preparation of racemic (2'S,3S,4'R)-6-chloro-4'-[5-chloro-2-(2-methoxycarbonyl-2-methyl-propoxy)-phenyl]-2'-(5-fluoro-2-methylphenyl)spiro[3H-indole-3,3'-piperidine]-2,6'(1H)-dione

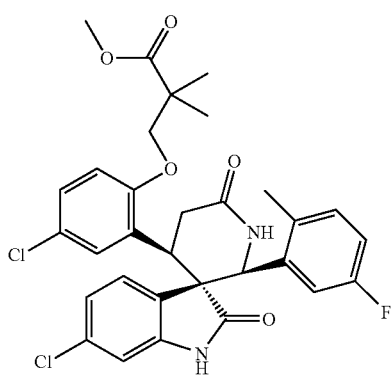

M. W. 599.49 C$_{31}$H$_{29}$Cl$_2$FN$_2$O$_5$

In a manner similar to the method described in Example 228d, E/Z-6-chloro-3-[5-chloro-2-(2-methoxycarbonyl-2-methyl-propoxy)-benzylidene]-2-oxo-2,3-dihydro-indole-1-carboxylic acid tert-butyl esteras ester (4.5 g, 9 mmol) was reacted with 1-(5-fluoro-2-methylphenyl)-3-trimethylsilyloxy-2-aza-1,3-butadiene (63 mmol) in toluene and then trifluoroacetic acid in dichloromethane to give title compound as a white solid (Yield: 300 mg, 5.5%).

m/z (M+H)$^+$: 599

EXAMPLE 258a

Preparation of racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione

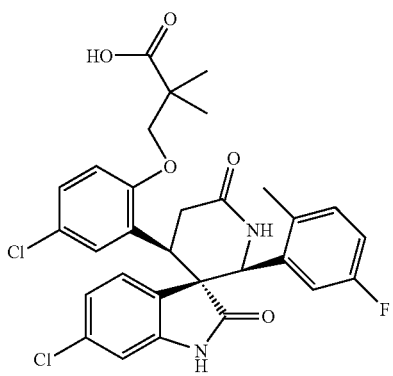

M. W. 585.46 C$_{30}$H$_{27}$Cl$_2$FN$_2$O$_5$

A mixture of racemic (2'S,3S,4'R)-6-chloro-4'-[5-chloro-2-(2-methoxycarbonyl-2-methyl-propoxy)-phenyl]-2'-(5-fluoro-2-methylphenyl)spiro[3H-indole-3,3'-piperidine]-2,6'(1H)-dione (300 mg), NaOH (80 mg), H$_2$O (10 mL) and methanol (10 mL) was heated at 80° C. for 2 h. Then the mixture was concentrated. The remaining aqueous solution was acidified to "pH" 2 by concentrated aqueous HCl. The white precipitate was collected by filtration to give title compound (Yield: 250 mg).

m/z (M+H)$^+$: 585

EXAMPLE 258b

Preparation of chiral (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione

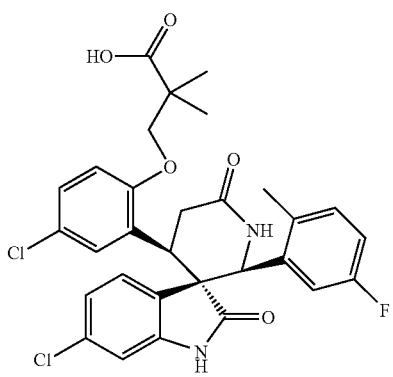

M. W. 585.46 $C_{30}H_{27}Cl_2FN_2O_5$

Separation of the two enantiomers from racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione (RO5219363-000), (20 mg) was conducted by chiral HPLC to provide chiral (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione as a white solid (6.5 mg) and chiral (2'R,3R,4'S)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione as a white solid (6.5 mg).

m/z (M+H)$^+$: 585

EXAMPLE 259a

Preparation of intermediate 5-chloro-2-(3-hydroxy-propoxy)-benzaldehyde

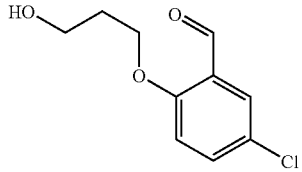

M. W. 214.65 $C_{10}H_{11}ClO_3$

5-Chloro-2-hydroxy-benzaldehyde (3.1 g, 20 mmol), 3-bromo-propan-1-ol (4.1 mL, 24 mmol), K$_2$CO$_3$ (5.5 g, 4 mmol) and KI (0.5 g) were mixed in DMF (20 mL). Then the mixture was irradiated under microwave at 200° C. for 1 h. The mixture was filtered and the filtrate was concentrated. The residue was dissolved in ethyl acetate and washed with 1N NaOH. Then the organic layer was separated, dried over Na$_2$SO$_4$ and concentrated to give title compound (Yield: 1.7 g, 59%).

m/z (M+H)$^+$: 215

EXAMPLE 259b

Preparation of intermediate of E/Z-6-chloro-3-[5-chloro-2-(3-hydroxy-propoxy)-benzylidene]-1,3-dihydro-indol-2-one

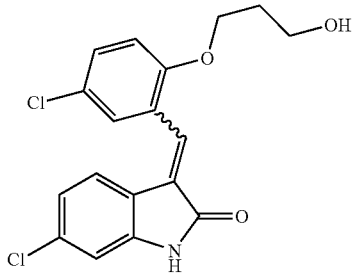

M. W. 364.23 $C_{18}H_{15}Cl_2NO_3$

5-Chloro-2-(3-hydroxy-1-propoxy)-benzaldehyde (8 g, 37 mmol) and 6-chlorooxindole (6.2 g, 37 mmol) were mixed in anhydrous methanol (20 mL). Then pyrrolidine (3 mL, 37 mmol) was added slowly at r.t. The mixture was heated to 70° C. for 3 h and cooled to room temperature. The precipitate was collected by filtration to give title compound as a yellow solid (Yield: 11.8 g).

m/z (M+H)$^+$: 364

EXAMPLE 259c

Preparation of intermediate E/Z-3-[2-(3-tert-butoxy-carbonyloxy-propoxy)-5-chloro-benzylidene]-6-chloro-2-oxo-2,3-dihydro-indole-1-carboxylic acid tert-butyl ester

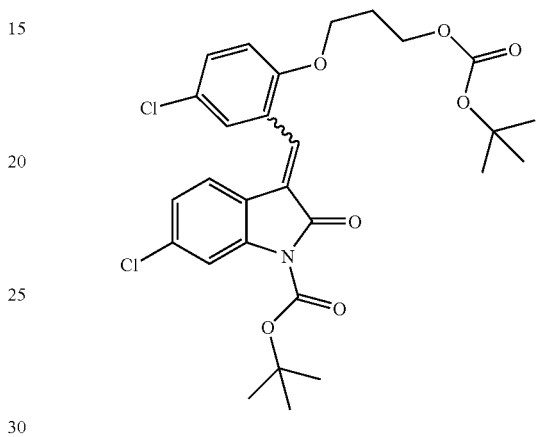

M. W. 564.47 $C_{28}H_{31}Cl_2NO_7$

To a solution of E/Z-6-chloro-3-[5-chloro-2-(3-hydroxy-propoxy)-benzylidene]-1,3-dihydro-indol-2-one (11.8 g, 31.6 mmol) in dichloromethane (100 mL) at r.t was added di-tert-butyl-dicarbonate (15 g, 69 mmol), followed by the addition of 4-dimethylaminopyridine (0.4 g, 3 mmol). The reaction mixture was stirred for 2 h and washed with 0.1N hydrochloride, then the solvent was removed to give title compound. (Yield: 12 g)

m/z (M+H)$^+$: 564

EXAMPLE 259d

Preparation of racemic (2'R,3R,4'S)-6-chloro-4'-[5-chloro-2-(3-hydroxypropoxyl)-phenyl]-2'-[5-fluoro-2-methylphenyl]spiro[3H-indole-3,3'-piperidine]-2,6'(1H)-dione

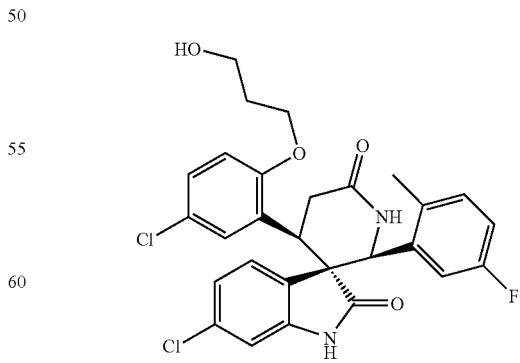

M. W. 543.43 $C_{28}H_{25}Cl_2FN_2O_4$

In a manner similar to the method described in Example 228d, E/Z-3-[2-(3-tert-butoxycarbonyloxy-propoxy)-5- chloro-benzylidene]-6-chloro-2-oxo-2,3-dihydro-indole-1-carboxylic acid tert-butyl ester (4 g, 7.1 mmol) was reacted with 1-(5-fluoro-2-methylphenyl)-3-trimethylsilyoxy-2-aza-1,3-butadiene (35 mmol) in toluene and then trifluoroacetic acid in dichloromethane to give title compound as a white solid (Yield: 6 mg).

m/z (M+H)+: 543

EXAMPLE 260

Preparation of racemic (2'R,3S,4'R)-6-chloro-4'-[5-chloro-2-(2-methoxycarbonyl-methoxy)-phenyl]-2'-(2,5-difluorophenyl)spiro[3H-indole-3,3'-piperidine]-2,6'(1H)-dione

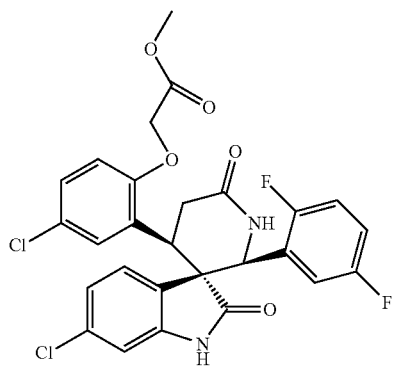

M. W. 561.37 $C_{27}H_{20}Cl_2F_2N_2O_5$

In a manner similar to the method described in Example 228d, E/Z-6-chloro-3-(5-chloro-2-methoxycarbonylmethyoxy-benzylidene)-2-oxo-2,3-dihydro-indole-1-carboxylic acid tert-butyl ester (9.5 g, 20 mmol) was reacted with 1-(2,5-difluoro-phenyl)-3-trimethylsilyoxy-2-aza-1,3-butadiene (60 mmol) in toluene and then trifluoroacetic acid in dichloromethane to give title compound as a white solid (Yield: 1.5 g).

m/z (M+)+: 561

EXAMPLE 261

Preparation of racemic (2'R,3S,4'R)-6-chloro-4'-[5-chloro-2-(2-hydroxycarbonyl-methoxy)-phenyl]-2'-(2,5-difluorophenyl)spiro[3H-indole-3,3'-piperidine]-2,6'(1H)-dione

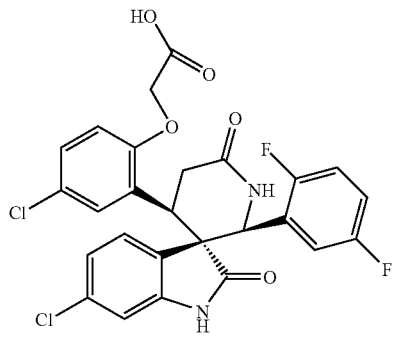

M. W. 547.35 $C_{26}H_{18}Cl_2F_2N_2O_5$

A mixture of racemic (2'R,3S,4'R)-6-chloro-4'-[5-chloro-2-(2-methoxycarbonyl-methoxy)-phenyl]-2'-(2,5-difluorophenyl)spiro[3H-indole-3,3'-piperidine]-2,6'(1H)-dione (600 mg), NaOH (120 mg), H$_2$O (5 mL) and methanol (5 mL) was heated at 80° C. for 2 h. Then the mixture was concentrated to half of its volume. The remaining aqueous solution was acidified to "pH" 2 by concentrated aqueous HCl (1.5 mL). The white precipitate was collected by filtration to give title (Yield: 500 mg).

m/z (M+H)+: 547

EXAMPLE 262a

Preparation of intermediate 5-chloro-2-methyl-benzaldehyde

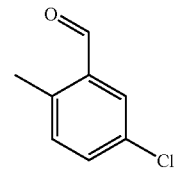

M. W. 154.60 $C_8H_7ClO$

A mixture of paraformaldehyde (11.5 g, 0.38 mol) and hydroxylamine hydrochloride (26.3 g, 0.38 mol) in water (170 mL) was heated until a clear solution was obtained. Then there was added hydrated sodium acetate (51 g, 0.38 mol), and the mixture was boiled gently under reflux for 15 min to give a 10% solution of formaldoxime.

In a separate flask, a mixture of 2-chloro-4-methylaniline (35.5 g, 0.25 mol) and water (50 mL) was stirred at room temperature, and aqueous concentrated HCl (57 mL) was added slowly. The mixture was cooled to room temperature, ice (100 g) was added, and the temperature of the mixture was maintained at −5° C. to +5° C. by an ice-salt bath. To the stirred mixture was added a solution of sodium nitrite (17.5 g, 0.25 mol) in water (25 mL). After the addition, the stirring was continued for 15 min. The stirred solution of the diazonium salt was neutralized by the addition of a solution of hydrated sodium acetate in water (35 mL).

To the aqueous 10% formaldoxime was added hydrated cupric sulfate (6.5 g, 0.026 mol), sodium sulfite (1.0 g, 0.0079 mol), and a solution of hydrated sodium acetate (160 g) in water (180 mL). The temperature of the solution was maintained at 10-15° C. by a cold-water bath and stirring vigorously. The neutral diazonium salt solution was slowly introduced below the surface of the formaldoxime. After the addition was complete, the stirring was continued for additional 1 h and then the mixture was treated with concentrated aqueous HCl (230 mL). The reaction mixture was gently heated at reflux for 2 h. The mixture was cooled to room temperature, extracted with ethyl ether (3×150 mL), and the ethereal extracts were washed with brine. The organic layer was separated, dried over Na$_2$SO$_4$ and concentrated to obtain a yellow solid (Yield: 21 g, 6%).

m/z (M+H)+: 155

EXAMPLE 262b

Preparation of intermediate E/Z-6-Chloro-3-(5-chloro-2-methyl-benzylidene)-1,3-dihydro-indol-2-one

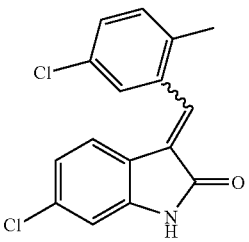

M. W. 304.18 $C_{16}H_{11}Cl_2NO$

5-Chloro-2-methyl-benzaldehyde (4 g, 16 mmol) and 6-chlorooxindole (2.5 g, 16 mmol) were mixed in anhydrous methanol (20 mL). Then pyrrolidine (1.32 mL, 16 mmol) was added slowly at r.t. The mixture was heated to 70° C. for 3 h and cooled to room temperature. The precipitate was collected by filtration to give title compound as yellow solid (Yield: 4.5 g).

m/z (M+H)$^+$: 304

EXAMPLE 262c

Preparation of intermediate E/Z-6-chloro-3-(5-chloro-2-methyl-benzylidene)-2-oxo-2,3-dihydro-indole-1-carboxylic acid tert-butyl ester

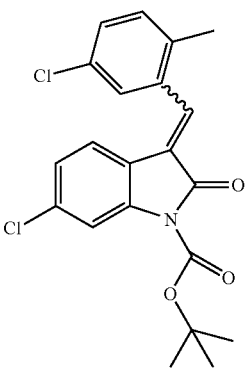

M. W. 404.30 $C_{21}H_{19}Cl_2NO_3$

To a solution of E/Z-6-chloro-3-(5-chloro-2-methyl-benzylidene)-1,3-dihydro-indol-2-one (4.7 g, 15.5 mmol) in dichloromethane (10 mL) at r.t was added di-tert-butyl-dicarbonate (5.0 g, 15.5 mmol), followed by the addition of 4-dimethylaminopyridine (0.2 g, 1.6 mmol). The reaction mixture was stirred for 2 h and washed with 0.1N hydrochloride, then the solvent was removed to give title compound. (Yield: 5 g).

m/z (M+H)$^+$: 404

EXAMPLE 262d

Preparation of racemic (2'R,3R,4'S)-2'-[5-bromo-2-(2-methoxycarbonyl-2-methyl-propoxy)-phenyl]-6-chloro-4'-(5-chloro-2-methyl-phenyl)spiro[3H-indole-3,3'-piperidine]-2,6'(1H)-dione

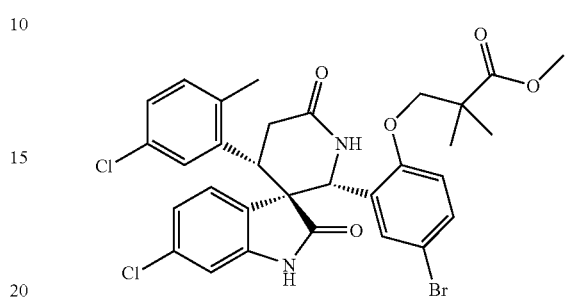

M. W. 660.40 $C_{31}H_{29}BrCl_2N_2O_5$

In a manner similar to the method described in Example 41b, E/Z-6-chloro-3-[5-chloro-2-methyl-benzylidene]-2-oxo-2,3-dihydro-indole-1-carboxylic acid tert-butyl ester (2.4 g, 6 mmol) was reacted with 1-[5-bromo-2-(2-methoxycarbonyl-2-methyl-propoxy)phenyl]-3-trimethylsilyoxy-2-aza-1,3-butadiene (13 mmol) in toluene and then trifluoroacetic acid in dichloromethane to give title compound as a white solid (Yield: 180 mg).

m/z (M+H)$^+$: 659

EXAMPLE 263

Preparation of racemic (2'R,3R,4'S)-2'-[5-bromo-2-(2-hydroxycarbonyl-2-methyl-propoxy)-phenyl]-6-chloro-4'-(5-chloro-2-methyl-phenyl)spiro[3H-indole-3,3'-piperidine]-2,6'(1H)-dione

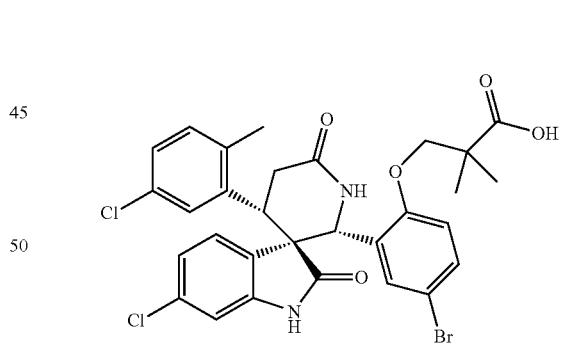

M. W. 646.37 $C_{30}H_{27}BrCl_2N_2O_5$

A mixture of (2'R,3R,4'S)-2'-[5-bromo-2-(2-methoxycarbonyl-2-methyl-propoxy)-phenyl]-6-chloro-4'-(5-chloro-2-methyl-phenyl)spiro[3H-indole-3,3'-piperidine]-2,6'(1H)-dione (50 mg), NaOH (40 mg), H$_2$O (5 mL) and THF (2 mL) was heated at 80° C. for 2 h. Then the mixture was concentrated. The remaining aqueous solution was acidified to "pH" 2 by concentrated aqueous HCl (1.5 mL). The white precipitate was collected by filtration to give the title compound as a white solid (Yield: 20 mg).

m/z (M+H)$^+$: 645

EXAMPLE 264

Preparation of racemic (2'S,3S,4'R)-4'-[5-bromo-2-(1-ethoxycarbonyl-1-methyl-ethoxy)-phenyl]-6-chloro-2'-(5-chloro-2-methyl-phenyl)spiro[3H-indole-3,3'-piperidine]-2,6'(1H)-dione

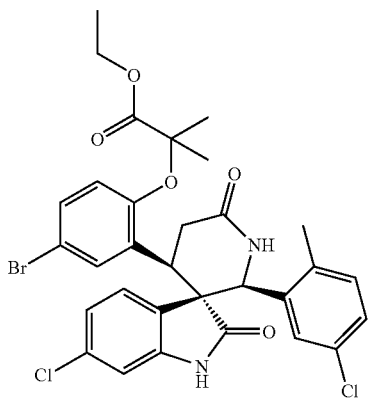

M. W. 660.40 $C_{31}H_{29}BrCl_2N_2O_5$

In a manner similar to the method described in Example 228d, 3-[5-bromo-2-(1-ethoxycarbonyl-1-methyl-ethoxy)-benzylidene]-6-chloro-2-oxo-2,3-dihydro-indole-1-carboxylic acid tert-butyl ester (3.9 g, 8 mmol) was reacted with 1-(5-chloro-2-methylphenyl)-3-trimethylsilyoxy-2-aza-1,3-butadiene prepared in Example 160a (21 mmol) in toluene and then trifluoroacetic acid in dichloromethane to give the title compound as a white solid (Yield: 600 mg).

m/z (M+H)⁺: 659

EXAMPLE 265

Preparation of racemic (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione

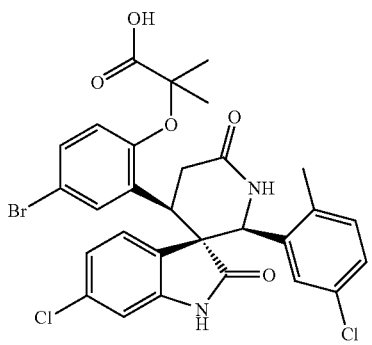

M. W. 632.34 $C_{29}H_{25}BrCl_2N_2O_5$

A mixture of racemic (2'S,3S,4'R)-4'-[5-bromo-2-(1-ethoxycarbonyl-1-methyl-ethoxy)-phenyl]-6-chloro-2'-(5-chloro-2-methyl-phenyl)spiro[3H-indole-3,3'-piperidine]-2,6'(1H)-dione (200 mg), NaOH (80 mg), H₂O (5 mL) and THF (2 mL) was heated at 80° C. for 2 h. Then the mixture was concentrated. The remaining aqueous solution was acidified to "pH" 2 by concentrated aqueous HCl solution (1.5 mL). The white precipitate was collected by filtration to give the title compound as a white solid (Yield: 100 mg).

m/z (M+H)⁺: 631

EXAMPLE 266

Preparation of racemic (2'R,3R,4'S)-2'-[5-bromo-2-(3-hydroxy-2,2-dimethyl-propoxy)-phenyl]-6-chloro-4'-(5-chloro-2-methyl-phenyl)spiro[3H-indole-3,3'-piperidine]-2,6'(1H)-dione

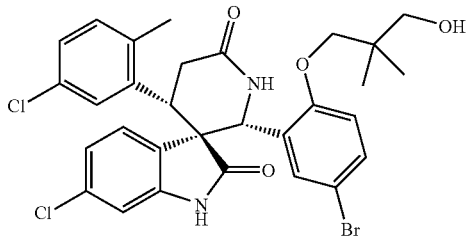

M. W. 632.39 $C_{30}H_{29}BrCl_2N_2O_4$

LiAlH₄ (11.4 mg, 0.3 mmol) was suspended in THF in ice bath, then a solution of racemic (2'R,3R,4'S)-2'-[5-bromo-2-(2-methoxycarbonyl-2-methyl-propoxy)-phenyl]-6-chloro-4'-(5-chloro-2-methyl-phenyl)spiro[3H-indole-3,3'-piperidine]-2,6'(1H)-dione prepared in Example 262d (63 mg, 0.1 mmol) in THF (2 mL) was added slowly. The reaction mixture was stirred at room temperature for 10 min, water (1 mL) was added and the resulting mixture was filtered. The filtration was concentrated and the residue was purified by Prep-HPLC to give the title compound as a white solid (Yield: 31 mg).

m/z (M+H)⁺: 631

EXAMPLE 267a

Preparation of intermediate racemic (2'R,3R,4'S)-6-bromo-4'-(3-chlorophenyl)-2'-isopropenyl-2,3-dihydro-2,6'-dioxospiro[indole-3,3'-piperidine]-1-methoxyethyl trimethylsilane

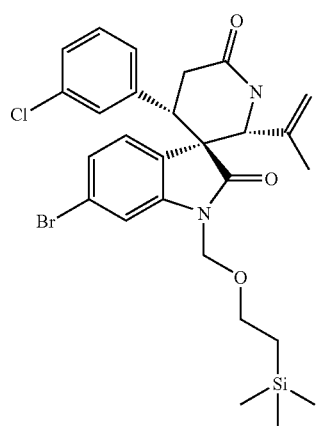

To a solution of 1-isopropenyl-3-trimethylsilyoxy-2-aza-1,3-butadiene (13 mmol) prepared in Example 87a in toluene was added E/Z-6-bromo-3-(3-chloro-benzylidene)-1-(2-trimethylsilanyl-ethoxymethyl)-1,3-dihydro-indole-2-one prepared in Example 161a (1.0 g, 2.16 mmol). The reaction mixture was refluxed under Argon for overnight. The mixture was cooled to room temperature, methanol (30 mL) was added, and then the mixture was concentrated. The residue was purified by chromatography (CH₂Cl₂:CH₃OH=50:1) to give crude product (0.42 g).

EXAMPLE 267b

Preparation of intermediate racemic (2'R,3R,4'S)-6-bromo-4'-(3-chlorophenyl)-1'-(2-hydroxyethyl)-2'-isopropenyl-2,3-dihydro-2,6'-dioxospiro[indole-3,3'-piperidine]-1-methoxyethyl trimethylsilane

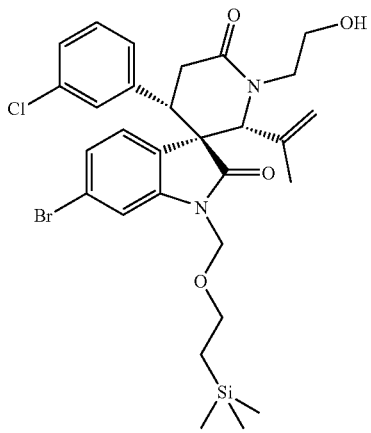

M. W. 620.06 $C_{29}H_{36}BrClN_2O_4Si$

To a mixture of racemic (2'R,3R,4'S)-6-bromo-4'-(3-chlorophenyl)-2'-isopropenyl-2,3-dihydro-2,6'-dioxospiro[indole-3,3'-piperidine]-1-methoxyethyl trimethylsilane (150 mg, 0.26 mmol) and acetic acid 2-bromo-ethyl ester (867 mg, 5.22 mmol) was added LiH (63 mg, 7.9 mmol). The mixture was stirred at room temperature for 20 h, then diluted with ethyl acetate (10 mL), quenched with water (10 mL). The organic layer was separated, washed with water for 5 times, dried over $Na_2SO_4$, and concentrated. The residue was purified by column chromatography to give product (57 mg).

EXAMPLE 267c

Preparation of intermediate chiral (2'R,3R,4'S)-6-bromo-4'-(3-chlorophenyl)-1'-(2-hydroxyethyl)-2'-isopropenyl-2,3-dihydro-2,6'-dioxospiro[indole-3,3'-piperidine]-1-methoxyethyl trimethylsilane

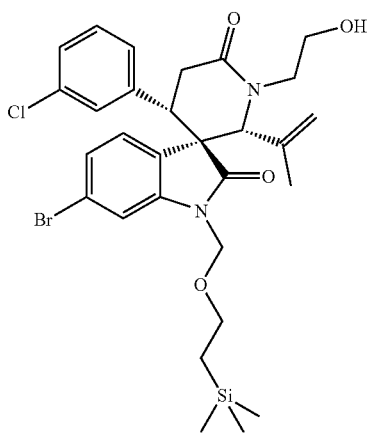

M. W. 620.06 $C_{29}H_{36}BrClN_2O_4Si$

Separation of the two enantiomers from racemic (2'R,3R,4'S)-6-bromo-4'-(3-chlorophenyl)-1'-(2-hydroxyethyl)-2'-isopropenyl-2,3-dihydro-2,6'-dioxospiro[indole-3,3'-piperidine]-1-methoxyethyl trimethylsilane (57 mg) was conducted by chiral Prep-HPLC to provide chiral (2'R,3R,4'S)-6-bromo-4'-(3-chlorophenyl)-1'-(2-hydroxyethyl)-2'-isopropenyl-2,3-dihydro-2,6'-dioxospiro[indole-3,3'-piperidine]-1-methoxyethyl trimethylsilane (27 mg) and chiral (2'S,3S,4'R)-6-bromo-4'-(3-chlorophenyl)-1'-(2-hydroxyethyl)-2'-isopropenyl-2,3-dihydro-2,6'-dioxospiro[indole-3,3'-piperidine]-1-methoxyethyl trimethylsilane (20 mg).

EXAMPLE 267d

Preparation of chiral (2'R,3R,4'S)-6-bromo-4'-(3-chlorophenyl)-1'-(2-hydroxy ethyl-2'-isopropenyl-spiro[3H-indole-3,3'-piperidine]-2,6'(1H)-dione

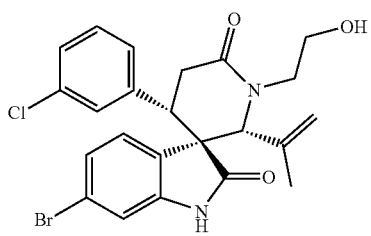

M. W. 489.80 $C_{23}H_{22}BrClN_2O_3$

The chiral (2'R,3R,4'S)-6-bromo-4'-(3-chlorophenyl)-1'-(2-hydroxyethyl)-2'-isopropenyl-2,3-dihydro-2,6'-dioxospiro[indole-3,3'-piperidine]-1-methoxyethyl trimethylsilane (27 mg) was dissolved in a solution of trifluoroacetic acid (2 mL) in dichloromethane (5 mL). The reaction mixture was stirred at room temperature for 0.5 h, then concentrated. The residue was dissolved in a solution of methanol (3 mL) and N,N'-Diisopropylethylamine (1 mL). The reaction tube was then placed into the cavity of a focused monomode microwave reactor and the contents of the flask were irradiated at 120° C. for 30 min. The reaction mixture was concentrated and the residue was purified by Prep-HPLC to give title compound (20 mg, 93%). m/z (M+H)$^+$: 489

EXAMPLE 268a

Preparation of intermediate racemic (2'R,3R,4'S)-1'-(aminocarbonyl-methyl)-6-bromo-4'-(3-chlorophenyl)-2'-isopropenyl-2,3-dihydro-2,6'-dioxospiro[indole-3,3'-piperidine]-1-methoxyethyl trimethylsilane

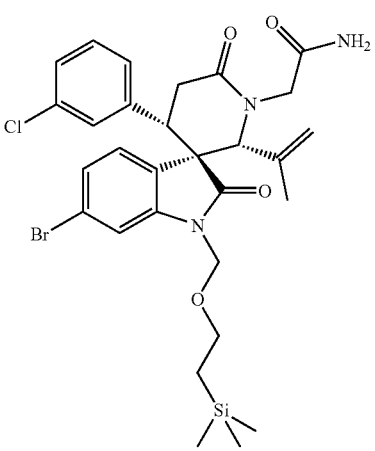

To a mixture of racemic (2'R,3R,4'S)-6-bromo-4'-(3-chlorophenyl)-2'-isopropenyl-2,3-dihydro-2,6'-dioxospiro[indole-3,3'-piperidine]-1-methoxyethyl trimethylsilane (100 mg, 0.17 mmol) and 2-bromo-acetamide (72 mg, 0.52 mmol) in DMF (1 mL) was added $Cs_2CO_3$ (332 mg, 1.01 mmol). The mixture was stirred at room temperature for overnight. Then additional 2-bromo-acetamide (72 mg, 0.52 mmol) and $Cs_2CO_3$ (332 mg, 1.01 mmol) were added to the reaction mixture. The resulting mixture was heated at 50° C. for 2 h, then poured into ethyl acetate (20 mL). The organic layer was washed with water 3 times, dried over $Na_2SO_4$, purified by column chromatography to give title compound 60 mg.

EXAMPLE 268b

Preparation of intermediate chiral (2'R,3R,4'S)-1'-(aminocarbonyl-methyl)-6-bromo-4'-(3-chlorophenyl)-2'-isopropenyl-2,3-dihydro-2,6'-dioxospiro[indole-3,3'-piperidine]-1-methoxyethyl trimethylsilane

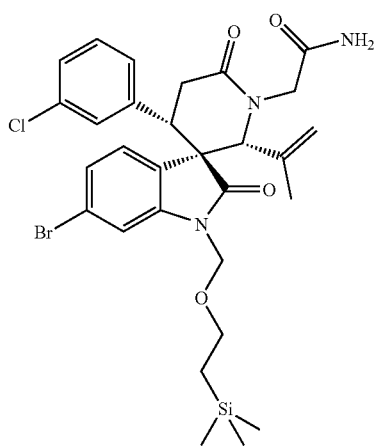

M. W. 633.06 $C_{29}H_{35}BrClN_3O_4Si$

Separation of the two enantiomers from racemic (2'R,3R,4'S)-1'-(aminocarbonyl-methyl)-6-bromo-4'-(3-chlorophenyl)-2'-isopropenyl-2,3-dihydro-2,6'-dioxospiro[indole-3,3'-piperidine]-1-methoxyethyl trimethylsilane (60 mg) was conducted by chiral Prep-HPLC to provide chiral (2'R,3R,4'S)-1'-(aminocarbonyl-methyl)-6-bromo-4'-(3-chlorophenyl)-2'-isopropenyl-2,3-dihydro-2,6'-dioxospiro[indole-3,3'-piperidine]-1-methoxyethyl trimethylsilane (27 mg, 90%) and chiral (2'S,3S,4'R)-1'-(aminocarbonyl-methyl)-6-bromo-4'-(3-chlorophenyl)-2'-isopropenyl-2,3-dihydro-2,6'-dioxospiro[indole-3,3'-piperidine]-1-methoxyethyl trimethylsilane (27 mg, 90%).

EXAMPLE 268c

Preparation of chiral (2'R,3R,4'S)-1'-(aminocarbonyl-methyl)-6-bromo-4'-(3-chlorophenyl)-2'-isopropenylspiro[3H-indole-3,3'-piperidine]-2,6'(1H)-dione

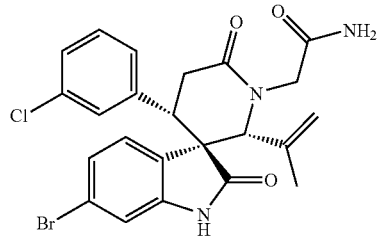

M. W. 502.80 $C_{23}H_{21}BrClN_3O_3$

The chiral (2'R,3R,4'S)-1'-(aminocarbonyl-methyl)-6-bromo-4'-(3-chlorophenyl)-2'-isopropenyl-2,3-dihydro-2,6'-dioxospiro[indole-3,3'-piperidine]-1-methoxyethyl trimethylsilane (27 mg, 0.043 mmol) was dissolved in a solution of trifluoroacetic acid (2 mL) in dichloromethane (5 mL). The reaction mixture was stirred at room temperature for 0.5 h, then concentrated. The residue was dissolved in a solution of methanol (3 mL) and N,N'-diisopropylethylamine (1 mL). The reaction tube was then placed into the cavity of a focused monomode microwave reactor and the contents of the flask were irradiated at 120° C. for 30 min. The reaction mixture was concentrated and the residue was purified by Prep-HPLC to give title compound (20 mg, 93%) m/z $(M+H)^+$: 502

EXAMPLE 269a

Preparation of intermediate racemic (2'R,3R,4'S)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane

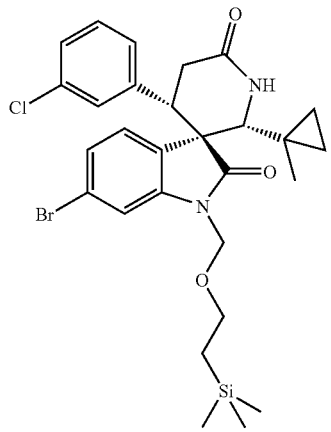

M. W. 590.04 $C_{28}H_{34}BrClN_2O_3Si$

A solution of diiodomethane (3.7 g, 0.013 mmol) in toluene (10 mL) was cooled in ice-salt bath. Then diethylzinc (1.1M in toluene, 10 mL, 11 mmol) was added dropwise into the above solution slowly. After the addition, the mixture was stirred for 10 min. To the resulting mixture was added a solution of racemic (2'R,3R,4'S)-6-bromo-4'-(3-chlorophenyl)-2'-isopropenyl-2,3-dihydro-2,6'-dioxospiro[indole-3,3'-piperidine]-1-methoxyethyl trimethylsilane prepared in Example 267a (800 mg, 1.4 mmol) in toluene (10 mL). The mixture was then allowed to warm to room temperature and stirred for 3 h, quenched with aqueous NH$_4$Cl. The organic layer was separated, washed with water, dried over Na$_2$SO4, purified by column chromatography to give title compound (800 mg).

EXAMPLE 269b

Preparation of intermediate racemic (2'R,3R,4'S)-1'-(aminocarbonyl-methyl)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane

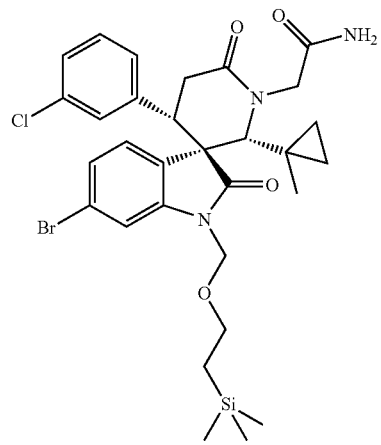

M. W. 647.09 C$_{30}$H$_{37}$BrClN$_3$O$_4$Si

To a mixture of racemic (2'R,3R,4'S)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane (800 mg, 1.36 mmol) and 2-bromo-acetamide (938 mg, 6.8 mmol) in DMF (1 mL) was added Cs$_2$CO$_3$ (4.4 g, 13.4 mmol). The mixture was stirred at 50° C. for 1.5 h, then purified by column chromatography to give title compound (60 mg, 6.8%).

EXAMPLE 269c

Preparation of intermediate chiral (2'R,3R,4'S)-1'-(aminocarbonyl-methyl)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane

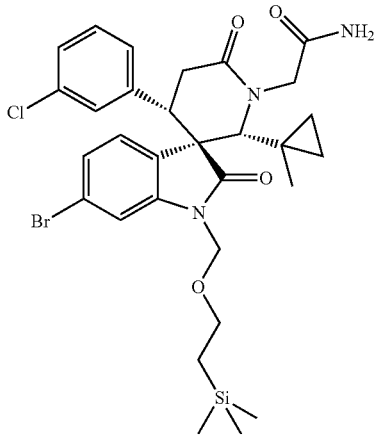

M. W. 647.09 C$_{30}$H$_{37}$BrClN$_3$O$_4$Si

Separation of the two enantiomers from racemic (2'R,3R,4'S)-1'-(aminocarbonyl-methyl)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane (60 mg) was conducted by chiral Prep-HPLC to provide chiral (2'R,3R,4'S)-1'-(aminocarbonyl-methyl)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane (25 mg) and chiral (2'S,3S,4'R)-1'-(aminocarbonyl-methyl)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane (25 mg).

EXAMPLE 269d

Preparation of chiral (2'R,3R,4'S)-1'-(aminocarbonyl-methyl)-6-bromo-4'-(3-chlorophenyl)-2'-(1-methyl cyclopropyl)-spiro[3H-indole-3,3'-piperidine]-2,6'(1H)-dione

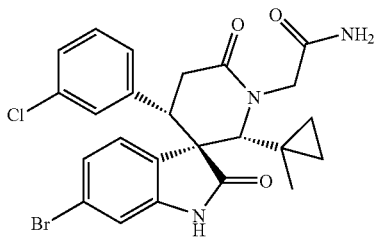

M. W. 516.83 C$_{24}$H$_{23}$BrClN$_3$O$_3$

The chiral (2'R,3R,4'S)-1'-(aminocarbonyl-methyl)-6-bromo-4'-(3-chlorophenyl)-2'-(1-methyl cyclopropyl)-2,3- dihydro-2,6'-dioxospiro[indole-3,3'-piperidine]-1-methoxyethyl trimethylsilane (25 mg, 0.039 mmol) was dissolved in a solution of trifluoroacetic acid (2 mL) in dichloromethane (5 mL). The reaction mixture was stirred at room temperature for 0.5 h, then concentrated. The residue was dissolved in a solution of methanol (3 mL) and N,N'-diisopropylethylamine (1 mL). The reaction tube was then placed into the cavity of a focused monomode microwave reactor and the contents of the flask were irradiated at 120° C. for 30 min. The reaction mixture was concentrated and the residue was purified by Prep-HPLC to give title compound (10 mg, 50%) m/z (M+H)$^+$: 516

EXAMPLE 270a

Preparation of intermediate racemic (2'R,3R,4'S)-1'-allyl-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane

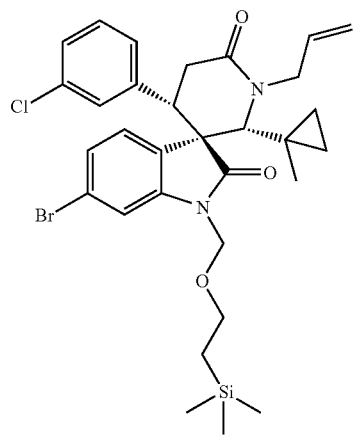

M. W. 630.10 C$_{31}$H$_{38}$BrClN$_2$O$_3$Si

To a solution of racemic (2'R,3R,4'S)-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane (200 mg, 0.34 mmol) and allyl bromide (1.2 g, 10 mmol) in DMF (15 mL) was added Cs$_2$CO$_3$ (4 g, 12.1 mmol). The mixture was stirred at room temperature for 2 h, then poured into water (100 mL), extracted with ethyl acetate for 3 times. The organic layer was washed with water, dried over Na$_2$SO$_4$, concentrated to give crude product as a light yellow solid (210 mg).

EXAMPLE 271b

Preparation of intermediate racemic (2'R,3R,4'S)-6-bromo-4'-(3-chlorophenyl)-1'-(2,3-dihydroxy-propyl)-2'-(1-methyl cyclopropyl)-2,3-dihydro-2,6'-dioxospiro[indole-3,3'-piperidine]-1-methoxyethyl trimethylsilane

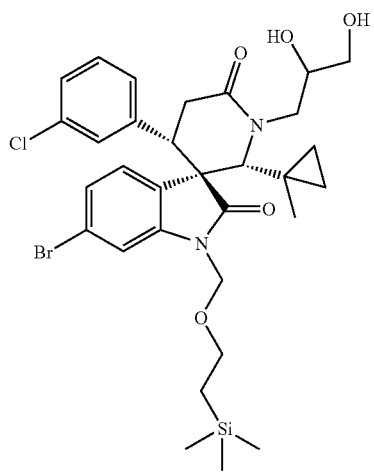

M. W. 664.12 C$_{31}$H$_{40}$BrClN$_2$O$_5$Si

To a mixture of racemic (2'R,3R,4'S)-1'-allyl-6-bromo-4'-(3-chlorophenyl)-2'-(1-methyl cyclopropyl)-2,3-dihydro-2,6'-dioxospiro[indole-3,3'-piperidine]-1-methoxyethyl trimethylsilane (100 mg, 0.16 mmol), N-methylmorpholine N-oxide (30 mg, 0.22 mmol) and 3 drops of water in acetone (3 mL) was added OsO$_4$ (10 mg, 0.04 mmol). The mixture was stirred at room temperature for 1 h, then purified by Prep-HPLC to give the title compound as a white solid (40 mg, 37%).

EXAMPLE 271c

Preparation of racemic (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione

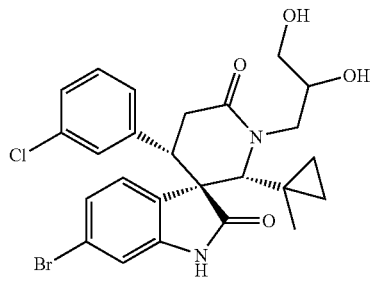

M. W. 533.85 C$_{25}$H$_{26}$BrClN$_2$O$_4$

The compound racemic (2'R,3R,4'S)-6-bromo-4'-(3-chlorophenyl)-1'-(2,3-dihydroxy-propyl)-2'-(1-methyl cyclopropyl)-2,3-dihydro-2,6'-dioxospiro[indole-3,3'-piperidine]-1-methoxyethyl trimethylsilane (40 mg, 0.06 mmol) was dissolved in trifluoroacetic acid (3 mL). The solution was stirred at room temperature for 1 h, then concentrated. The residue was dissolved in a solution of methanol (3 mL) and N,N'-diisopropylethylamine (1 mL). The reaction tube was then placed into the cavity of a focused monomode microwave reactor and the contents of the flask were irradiated at 120° C. for 30 min. The reaction mixture was concentrated and the residue was purified by Prep-HPLC to give title compound (20 mg, 63%) m/z (M+H)+: 533

EXAMPLE 271d

Preparation of chiral (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione

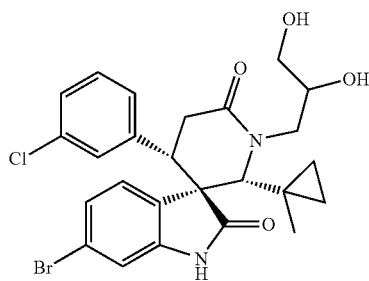

M. W. 533.85 C$_{25}$H$_{26}$BrClN$_2$O$_4$

Separation of the two enantiomers from racemic (2'R,3R, 4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione (14 mg) was conducted by chiral Prep-HPLC to provide chiral (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione as a white solid (5.1 mg, 73%) and chiral (2'S,3S,4'R)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione (5.1 mg, 73%). m/z (M+H)+: 533

EXAMPLE 272a

Preparation of intermediate 2-bromo-propenal

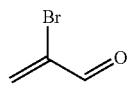

M. W. 134.96 C$_3$H$_3$BrO

A dichloromethane solution of propenal (0.6 M, 1.13 L, 0.68 mol) was cooled in ice-bath. To this solution was added aqueous HBr (2 M, 750 mL, 1.5 mol) and OXONE® (450 g, 0.72 mol) slowly. After the addition, the mixture was stirred at room temperature for 1.5 h. Then triethylamine (250 mL) was added slowly. The resulting mixture was stirred at room temperature for additional 1.5 h. The organic layer was separated and washed with aqueous HCl (0.8 N) (3×) and water (2×), then concentrated in vacuo. The residue was distilled to give product 2-bromo-propenal as oil (15 g, 16%).

EXAMPLE 272b

Preparation of intermediate 1-(1-bromo-vinyl)-3-trimethylsilyoxy-2-aza-1,3-butadiene

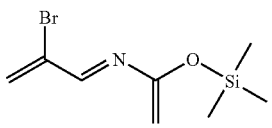

M. W. 248.20 C$_8$H$_{14}$BrNOSi

In a manner similar to the method described in Example 87a, 2-bromo-propenal (5 g, 37 mmol) was used as the starting material in place of 2-methacrolein to react with LiHMDS (1M solution in THF, 37 mL, 37 mmol), trimethylsilyl chloride (4.65 mL, 37 mmol), triethylamine (6.8 mL, 48 mmol) and acetyl chloride (3.43 mL, 48 mmol) to give 1-(1-bromo-vinyl)-3-trimethylsilyoxy-2-aza-1,3-butadiene and used for the next step without further purification.

EXAMPLE 272c

Preparation of racemic (2'R,3R,4'S)-2'-(1-bromo-vinyl)-6-chloro-4'-(3-chlorophenyl)spiro[3H-indole-3,3'-piperidine]-2,6'(1H)-dione

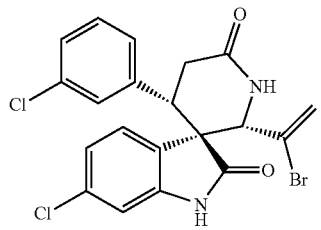

M. W. 466.16 C$_{20}$H$_{15}$BrCl$_2$N$_2$O$_2$

To a toluene solution of 1-(1-bromo-vinyl)-3-trimethylsilyoxy-2-aza-1,3-butadiene in toluene (1 M, 37 mL, 37 mmol) was added E/Z-6-chloro-3-(3-chloro-benzylidene)-2-oxo-2,3-dihydro-indole-1-carboxylic acid tert-butyl ester prepared in Example 24a (2.8 g, 7.2 mmol). The reaction mixture was refluxed overnight under argon protection and purified by Prep-HPLC to give product as a white solid (120 mg, 7%).

m/z (M+H)+: 465

EXAMPLE 273a

Preparation of intermediate racemic (2'R,3R,4'S)-2'-(1-bromo-vinyl)-6-chloro-4'-(3-chlorophenyl)-2,3-dihydro-2,6'-dioxospiro[indole-3,3'-piperidine]-1-carboxylic acid tert-butyl ester

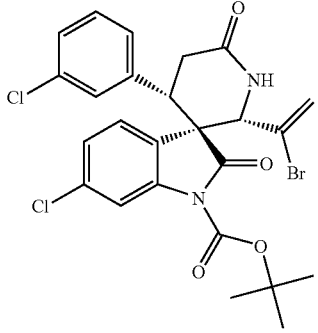

M. W. 566.28 $C_{25}H_{23}BrCl_2N_2O_4$

To a mixture of racemic (2'R,3R,4'S)-2'-(1-bromo-vinyl)-6-chloro-4'-(3-chlorophenyl)spiro[3H-indole-3,3'-piperidine]-2,6'(1H)-dione (120 mg, 0.26 mmol) and 4-dimethylaminopyridine (32 mg, 0.26 mmol) in dichloromethane (10 mL) was added Di-t-butyldicarbonate (74 mg, 0.34 mmol). The mixture was stirred at room temperature for 2 h, then washed with aqueous HCl (0.5 M) and water. The organic layer was separated, dried over $Na_2SO_4$, concentrated to give the title compound (130 mg, 88%).

EXAMPLE 273b

Preparation of intermediate chiral (2'R,3R,4'S)-2'-(1-bromo-vinyl)-6-chloro-4'-(3-chlorophenyl)-2,3-dihydro-2,6'-dioxospiro[indole-3,3'-piperidine]-1-carboxylic acid tert-butyl ester

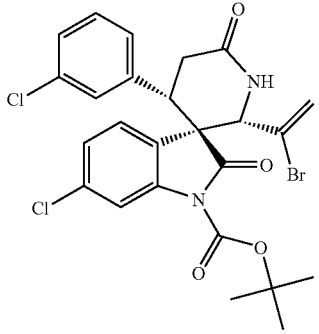

M. W. 566.28 $C_{25}H_{23}BrCl_2N_2O_4$

Separation of the two enantiomers from racemic (2'R,3R,4'S)-2'-(1-bromo-vinyl)-6-chloro-4'-(3-chlorophenyl)-2,3-dihydro-2,6'-dioxospiro[indole-3,3'-piperidine]-1-carboxylic acid tert-butyl ester (20 mg) was conducted by chiral Prep-HPLC to provide chiral (2'R,3R,4'S)-2'-(1-bromo-vinyl)-6-chloro-4'-(3-chlorophenyl)-2,3-dihydro-2,6'-dioxospiro[indole-3,3'-piperidine]-1-carboxylic acid tert-butyl ester as a white solid (9 mg, 90%) and chiral (2'R,3S,4'R)-2'-(1-bromo-vinyl)-6-chloro-4'-(3-chlorophenyl)-2,3-dihydro-2,6'-dioxospiro[indole-3,3'-piperidine]-1-carboxylic acid tert-butyl ester (9 mg, 90%).

EXAMPLE 273c

Preparation of chiral (2'R,3R,4'S)-2'-(1-bromo-vinyl)-6-chloro-4'-(3-chlorophenyl)spiro[3H-indole-3,3'-piperidine]-2,6'(1H)-dione

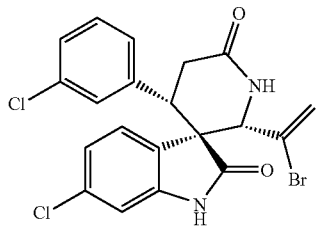

M. W. 466.16 $C_{20}H_{15}BrCl_2N_2O_2$

A solution of chiral (2'R,3R,4'S)-2'-(1-bromo-vinyl)-6-chloro-4'-(3-chlorophenyl)-2,3-dihydro-2,6'-dioxospiro[indole-3,3'-piperidine]-1-carboxylic acid tert-butyl ester (9 mg, 0.016 mmol) in trifluoroacetic acid (1 mL) was stirred at room temperature for 10 min, then concentrated in vacuo. The residue was purified by Prep-HPLC to give title compound (5.7 mg, 76%). m/z (M+H)$^+$: 465

EXAMPLE 274a

Preparation of intermediate 2-(4-chloro-phenyl)-4,4-dimethyl-oxazolidine

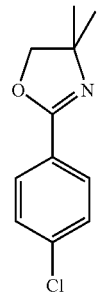

To a solution of 2-amino-2-methyl-propan-1-ol (59 g, 0.66 mol) in dichloromethane (120 mL) at 0° C. was added dropwise a solution of 4-chloro-benzoyl chloride (53 g, 0.3 mol) in dichloromethane (75 mL). The resulting mixture was stirred at r.t. for 2.5 h, then filtered and the filtrate was concentrated. Then $SOCl_2$ (120 g, 1 mol) was added dropwise. The mixture was stirred at room temperature for overnight, then diluted with ethyl ether (150 mL). The resulting mixture was cooled in an ice bath, neutralized with aqueous NaOH (20%). The organic layer was separated, and aqueous layer was extracted with ethyl ether for 3 times. The organic lays were combined and washed with water twice, dried over anhydrous $Na_2SO_4$ and concentrated. The residue was distilled in vacuo to give the title product (25 g) as oil.

EXAMPLE 274b

Preparation of intermediate 5-chloro-2-(4,4-dimethyl-4,5-dihydro-oxazol-2-yl)-benzaldehyde

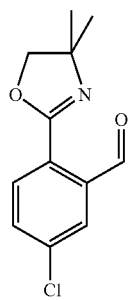

To a cold solution of 2-(4-chloro-phenyl)-4,4-dimethyl-oxazolidine (17.2 g, 82 mmol) in ethyl ether (100 mL) and hexane (100 mL) at −30° C. was added n-BuLi (1.6 M in hexane, 67 mL, 107 mmol). The mixture was allowed to warm to room temperature and stirred for 3 h, then cooled to −20° C. To the mixture was added DMF (12.6 mL), and the reaction mixture was allowed to warm to room temperature and stirred overnight. The mixture was poured into water (200 mL), extracted with ethyl ether for 3 times. The organic layers were combined, washed with water, dried over anhydrous $Na_2SO_4$, concentrated in vacuo to give the title product (13 g).

EXAMPLE 274c

Preparation of intermediate 5-chloro-3-hydroxy-3H-isobenzofuran-1-one

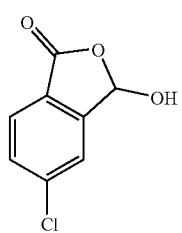

The mixture of 5-chloro-2-(4,4-dimethyl-4,5-dihydro-oxazol-2-yl)-benzaldehyde (10 g, 42 mmol) in aqueous HCl solution (4 M, 300 mL) was refluxed for 4 h, then cooled to room temperature, extracted with ethyl ether twice. The organic layers were combined, washed with water, dried over anhydrous $Na_2SO_4$, and concentrated in vacuo to give the title product as light yellow solid (3.8 g).

EXAMPLE 274d

Preparation of intermediate 4-chloro-2-formyl-benzoic acid methyl ester

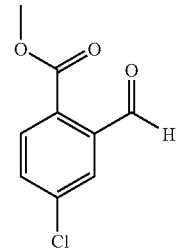

A solution of 5-chloro-3-hydroxy-3H-isobenzofuran-1-one (10 g, 54 mmol) and iodomethane (80 g, 560 mmol) in dichloromethane (200 mL) was heated at reflux, then the heating bath was removed. To the above solution was added triethylamine (60 g) at a rate that maintained a brisk reflux. After the addition was completed, the mixture was allowed to cool to room temperature and stirred for 72 h. The mixture was purified by column chromatography to give the title product (1.5 g).

EXAMPLE 274e

Preparation of intermediate E/Z 4-Chloro-2-(6-chloro-2-oxo-1,2-dihydro-indol-3-ylidenemethyl)-benzoic acid methyl ester

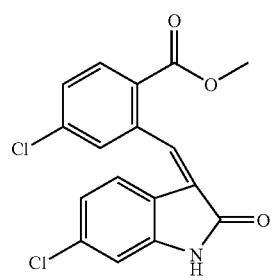

M. W. 348.19 $C_{17}H_{11}Cl_2NO_3$

To the mixture of 6-chlorooxindole (1.2 g, 7 mmol) and 4-chloro-2-formyl-benzoic acid methyl ester (1.4 g, 7 mmol) in methanol (10 mL) was added pyrrolidine (490 mg, 7 mmol) dropwise. The mixture was then heated at 70° C. for 3 h. After cooled to 4° C., the mixture was filtered and the precipitate was collected, dried to give a mixture of E/Z-6-chloro-3-(5-chloro-2-hydroxy-benzylidene)-1,3-dihydro-indol-2-one as a bright yellow solid (500 mg).

EXAMPLE 274f

Preparation of intermediate E/Z 6-Chloro-3-(5-chloro-2-methoxycarbonyl-benzylidene)-2-oxo-2,3-dihydro-indole-1-carboxylic acid tert-butyl ester

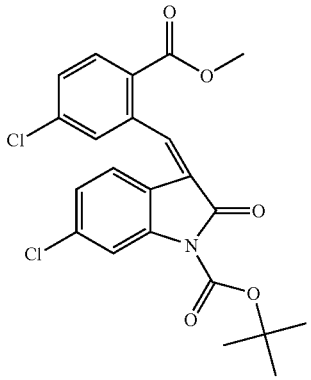

M. W. 448.31 $C_{22}H_{19}Cl_2NO_5$

To a solution of E/Z 4-Chloro-2-(6-chloro-2-oxo-1,2-dihydro-indol-3-ylidenemethyl)-benzoic acid methyl ester (500 mg, 1.4 mmol) in dichloromethane (10 mL) at r.t was added di-tert-butyl-dicarbonate (470 mg, 2.1 mmol), followed by the addition of 4-dimethylaminopyridine (100 mg, 0.82 mmol). The reaction mixture was stirred at r.t. for 2 h, then purified by column chromatography to give E/Z 6-Chloro-3-(5-chloro-2-methoxycarbonyl-benzylidene)-2-oxo-2,3-dihydro-indole-1-carboxylic acid tert-butyl ester as a yellow oil (450 mg)

EXAMPLE 274g

Preparation of racemic (2'R,3R,4'S)-6-chloro-4'-(5-chloro-2-methoxycarbonyl-phenyl)-2'-isopropenyl-spiro[3H-indole-3,3'-piperidine]-2,6'(1H)-dione

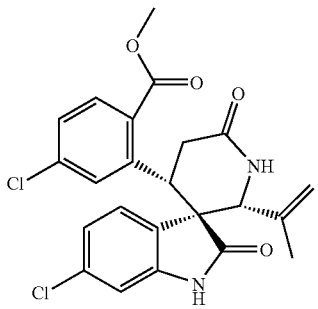

M. W. 459.33 $C_{23}H_{20}Cl_2N_2O_4$

In a manner similar to the method described in Example 41b, E/Z 6-Chloro-3-(5-chloro-2-methoxycarbonyl-benzylidene)-2-oxo-2,3-dihydro-indole-1-carboxylic acid tert-butyl ester (450 mg, 1 mmol) was reacted with 1-isopropenyl-3-trimethylsilyoxy-2-aza-1,3-butadiene prepared in Example 87a, (1M solution in toluene, 4 mL, 4 mmol) and then trifluoroacetic acid in dichloromethane to give the title compound (60 mg). m/z (M+H)+: 459

EXAMPLE 275

Preparation of racemic (2'R,3R,4'S)-6-chloro-4'-(5-chloro-2-hydroxycarbonyl-phenyl)-2'-isopropenyl-spiro[3H-indole-3,3'-piperidine]-2,6'(1H)-dione

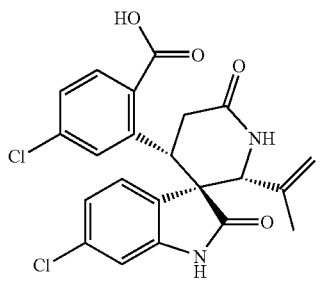

M. W. 445.31 $C_{22}H_{18}Cl_2N_2O_4$

To a mixture of racemic (2'R,3R,4'S)-6-chloro-4'-(5-chloro-2-methoxycarbonyl-phenyl)-2'-isopropenylspiro [3H-indole-3,3'-piperidine]-2,6'(1H)-dione (60 mg, 0.13 mmol) in methanol (3.5 mL) was added a solution of NaOH (26 mg, 0.6 mmol) in water (1.5 mL). The mixture was heated at 70° C. for 3 h, concentrated to remove most of methanol, cooled to room temperature, and acidified to "pH" 2 with aqueous HCl solution. The precipitate was collected and dried to give title compound as a white solid (33 mg). m/z (M+H)+: 445

EXAMPLE 276a

Preparation of racemic (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione

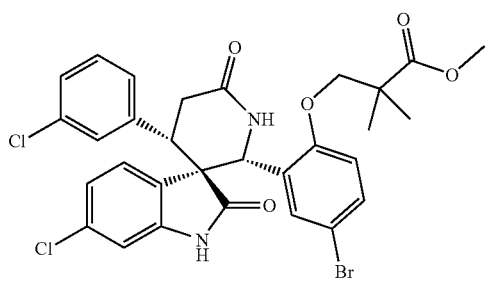

M. W. 646.37 $C_{30}H_{27}BrCl_2N_2O_5$

In a manner similar to the method described in Example 41b, E/Z-6-chloro-3-(3-chloro-benzylidene)-2-oxo-2,3-dihydro-indole-1-carboxylic acid tert-butyl ester prepared in Example 24a (1.5 g, 3.8 mmol) was reacted with 1-[5-bromo-2-(2-methoxycarbonyl-2-methyl-propoxy)-phenyl]-3-trimethylsilyoxy-2-aza-1,3-butadiene prepared in Example 245a (1 M solution in toluene, 12 mL, 12 mmol) and then trifluoroacetic acid in dichloromethane to give the title compound (300 mg).

EXAMPLE 276b

Preparation of chiral (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione

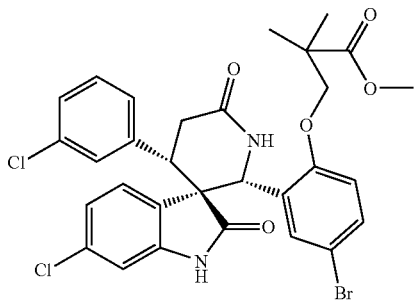

M. W. 646.37 $C_{30}H_{27}BrCl_2N_2O_5$

Separation of the two enantiomers from racemic (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione (20 mg) was conducted by chiral Prep-HPLC to provide chiral (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione as a white solid (5 mg, 50%) and (2'S,3S,4'R)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione as a white solid (6 mg, 60%) (RO5223164-000). m/z (M+H)$^+$: 645

EXAMPLE 277a

Preparation of racemic (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione

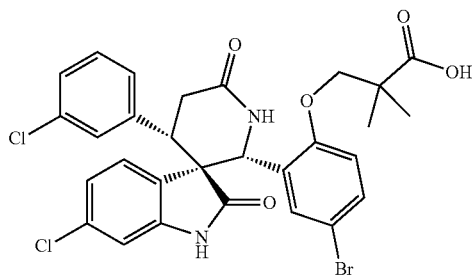

M. W. 632.34 $C_{29}H_{25}BrCl_2N_2O_5$

To a mixture of racemic (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione (106 mg, 0.16 mmol) in methanol (6 mL) was added a solution of NaOH (30 mg, 0.75 mmol) in water (3 mL). The mixture was heated at 60° C. for 5 h, evaporated to remove most of methanol, cooled to room temperature, and acidified to "pH" 2 with aqueous HCl solution. The precipitate was collected and dried to give title product as a white solid (70 mg). m/z (M+H)$^+$: 631

EXAMPLE 277b

Preparation of chiral (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione

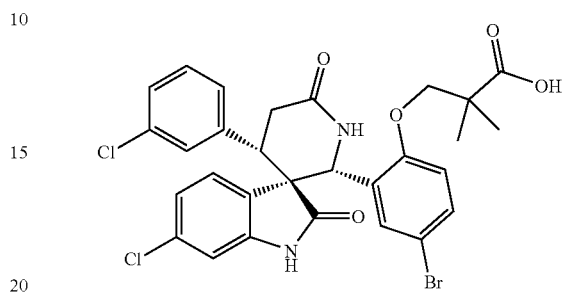

M. W. 632.34 $C_{29}H_{25}BrCl_2N_2O_5$

Separation of the two enantiomers from racemic (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione (10 mg) was conducted by chiral Prep-HPLC to provide chiral (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione as a white solid (3.1 mg, 62%) and (2'S,3S,4'R)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione as a white solid (2.9 mg, 58%). m/z (M+H)$^+$: 631

EXAMPLE 278a

Preparation of racemic (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione

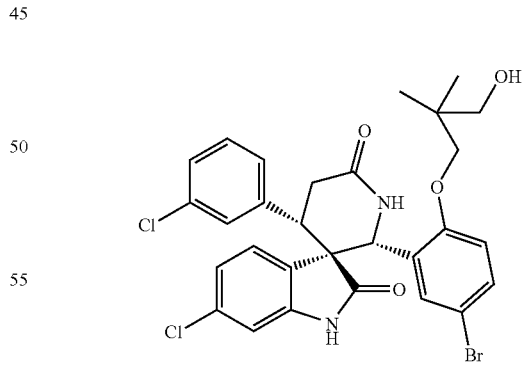

M. W. 618.36 $C_{29}H_{27}BrCl_2N_2O_4$

To a mixture of LiAlH$_4$ (10 mg, 0.26 mmol) in diethyl ether (2 mL) was added racemic (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione prepared in Example 276b (40 mg, 0.062 mmol). The mixture was stirred at room temperature for 10 min, quenched with methanol, purified by Prep-HPLC to give title compound (16 mg, 42%). m/z (M+H)+: 617

EXAMPLE 278b

Preparation of chiral (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione

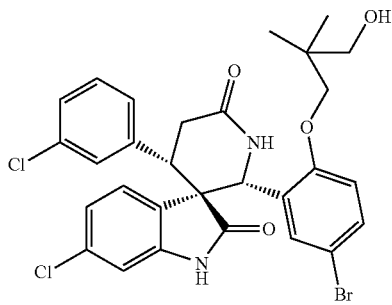

M. W. 618.36 $C_{29}H_{27}BrCl_2N_2O_4$

Separation of the two enantiomers from racemic (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione (20 mg) was conducted by chiral Prep-HPLC to provide chiral racemic (2'R,3R,4'S)-2'-[5-bromo-2-(3-hydroxy-2,2-dimethylpropoxy)-phenyl]-6-chloro-4'-(3-chlorophenyl)spiro[3H-indole-3,3'-piperidine]-2,6'(1H)-dione as a white solid (6 mg, 60%) and racemic (2'S,3S,4'R)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione as a white solid (6 mg, 60%).

EXAMPLE 279a

Preparation of intermediate 1-[5-bromo-2-(1-ethoxycarbonyl-1-methyl-ethoxy)phenyl]-3-trimethylsilyoxy-2-aza-1,3-butadiene

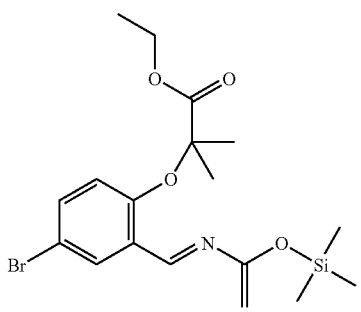

M. W. 428.4 $C_{18}H_{26}BrNO_4Si$

In a manner similar to the method described in Example 1b, 2-(4-bromo-2-formyl-phenoxy)-2-methyl-propionic acid ethyl ester (g, 19 mmol) was used as the starting material in place of 3-chlorobenzaldehyde to react with LiHMDS (1M solution in THF, 19 mL, 19 mmol), trimethylsilyl chloride (2.4 mL, 19 mmol), triethylamine (3.44 mL, 24.6 mmol) and acetyl chloride (1.75 mL, 24.6 mmol) to give title compound and used for the next step without further purification.

EXAMPLE 279b

Preparation of racemic (2'R,3R,4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione

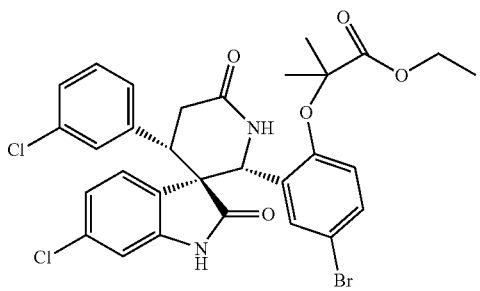

M. W. 646.37 $C_{30}H_{27}BrCl_2N_2O_5$

In a manner similar to the method described in Example 41b, E/Z-6-chloro-3-(3-chloro-benzylidene)-2-oxo-2,3-dihydro-indole-1-carboxylic acid tert-butyl ester prepared in Example 24a (1.5 g, 3.8 mmol).) was reacted with 1-[5-bromo-2-(2-ethoxycarbonyl-2-methyl-ethoxy)-phenyl]-3-trimethylsilyoxy-2-aza-1,3-butadiene (1M solution in toluene, 12 mL, 12 mmol) and then trifluoroacetic acid in dichloromethane to give the title compound (800 mg).

EXAMPLE 279c

Preparation of racemic (2'R,3R,4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione

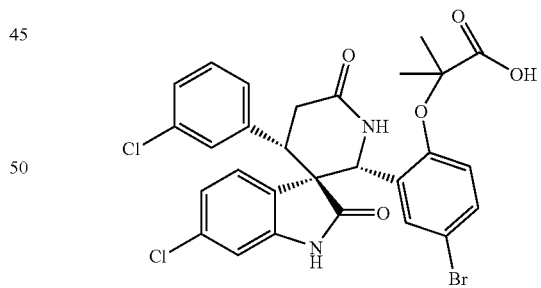

M. W. 618.32 $C_{28}H_{23}BrCl_2N_2O_5$

To a mixture of racemic (2'R,3R,4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione (700 mg, 1.08 mmol) in methanol (20 mL) was added a solution of NaOH (120 mg, 3 mmol) in water (10 mL). The mixture was heated at 60° C. for 1.5 h, evaporated to remove most of methanol, cooled to room temperature, and acidified to "pH" 2 with aqueous HCl solution. The precipitate was collected and dried to give product as a white solid (610 mg). m/z (M+H)+: 617

EXAMPLE 280

Preparation of racemic (2'R,3R,4'S)-6-chloro-4'-(3-chlorophenyl)-2'-[5-bromo-2-(2-hydroxy-1,1-dimethyl-ethoxy)phenyl]spiro[3H-indole-3,3'-piperidine]-2,6'(1H)-dione

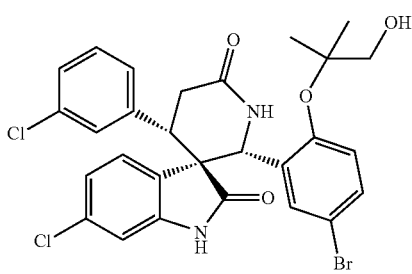

M. W. 604.33 $C_{28}H_{25}BrCl_2N_2O_4$

To a mixture of LiAlH$_4$ (2.5 mg, 0.066 mmol) in diethyl ether (1 mL) was added racemic (2'R,3R,4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione (10 mg, 0.016 mmol). The mixture was stirred at room temperature for 10 min, quenched with MeOH, purified by Prep-HPLC to give product (3.7 mg, 38%). (M+H)$^+$: 603

EXAMPLE 281

Preparation of racemic (2'S,3S,4'R)-4'-[5-bromo-2-(1-ethoxycarbonyl-1-methyl-ethoxy)-phenyl]-6-chloro-2'-(5-fluoro-2-methyl-phenyl)spiro[3H-indole-3,3'-piperidine]-2,6'(1H)-dione

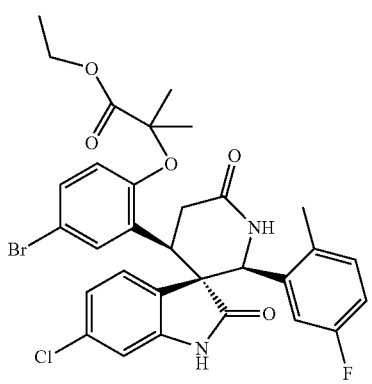

M. W. 643.94 $C_{31}H_{29}BrClFN2O_5$

In a manner similar to the method described in Example 228d, E/Z-3-[5-bromo-2-(1-ethoxycarbonyl-1-methyl-ethoxy)-benzylidene]-6-chloro-2-oxo-2,3-dihydro-indole-1-carboxylic acid tert-butyl ester prepared in Example 243c (1.5 g, 2.6 mmol).) was reacted with 1-(5-fluoro-2-methyl-phenyl)-3-trimethylsilyoxy-2-aza-1,3-butadiene (2 M solution in toluene, 5 mL, 10 mmol) and then trifluoroacetic acid in dichloromethane to give the title compound (700 mg). m/z (M+H)$^+$: 643

EXAMPLE 282

Preparation of racemic (2'S,3S,4'R)-4'-[5-bromo-2-(1-hydroxycarbonyl-1-methyl-ethoxy)-phenyl]-6-chloro-2'-(5-fluoro-2-methyl-phenyl)spiro[3H-indole-3,3'-piperidine]-2,6'(1H)-dione

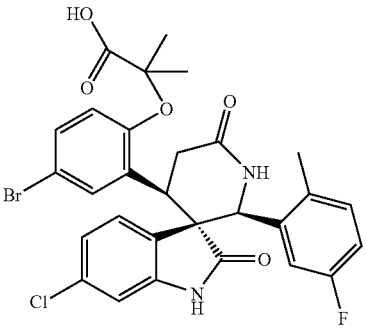

M. W. 615.89 $C_{29}H_{25}BrClFN_2O_5$

To a mixture of racemic (2'S,3S,4'R)-4'-[5-bromo-2-(1-ethoxycarbonyl-1-methyl-ethoxy)-phenyl]-6-chloro-2'-(5-fluoro-2-methyl-phenyl)spiro[3H-indole-3,3'-piperidine]-2,6'(1H)-dione (120 mg, 0.19 mmol) in methanol (4 mL) was added a solution of NaOH (24 mg, 0.6 mmol) in water (2 mL). The mixture was heated at 70° C. for 3 h, evaporated to remove most of methanol, cooled to room temperature, and acidified to "pH" 1 with aqueous HCl solution. The precipitate was collected and dried to give product as a white solid (75 mg). m/z (M+H)$^+$: 615

EXAMPLE 283

Preparation of racemic (2'R,3S,4'R)-4'-[5-bromo-2-(1-ethoxycarbonyl-1-methyl-ethoxy)-phenyl]-6-chloro-2'-(2,5-difluorophenyl)spiro[3H-indole-3,3'-piperidine]-2,6'(1H)-dione

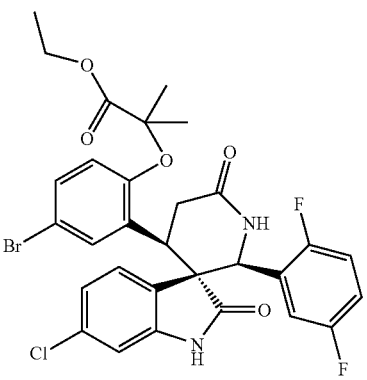

M. W. 647.91 C30H26BrClF2N2O5

In a manner similar to the method described in Example 228d, product E/Z 3-[5-bromo-2-(1-ethoxycarbonyl-1-methyl-ethoxy)-benzylidene]-6-chloro-2-oxo-2,3-dihydro-indole-1-carboxylic acid tert-butyl ester (1.5 g, 2.6 mmol).) was reacted with 1-(2,5-difluorophenyl)-3-trimethylsilyoxy-2-aza-1,3-butadiene (2 M solution in toluene, 5 mL, 10 mmol)

EXAMPLE 284

Preparation of racemic (2'R,3S,4'R)-4'-[5-bromo-2-(1-hydroxycarbonyl-1-methyl-ethoxy)-phenyl]-6-chloro-2'-(2,5-difluorophenyl)spiro[3H-indole-3,3'-piperidine]-2,6'(1H)-dione

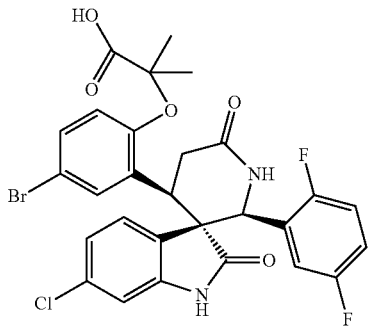

M. W. 619.85 $C_{28}H_{22}BrClF_2N_2O_5$

To a mixture of racemic (2'R,3S,4'R)-4'-[5-bromo-2-(1-ethoxycarbonyl-1-methyl-ethoxy)-phenyl]-6-chloro-2'-(2,5-difluorophenyl)spiro[3H-indole-3,3'-piperidine]-2,6'(1H)-dione (120 mg, 0.19 mmol) in methanol (4 mL) was added a solution of NaOH (24 mg, 0.6 mmol) in water (2 mL). The mixture was heated at 70° C. for 3 h, evaporated to remove most of methanol, cooled to room temperature, and acidified to "pH" 1 with aqueous HCl solution. The precipitate was collected and dried to give product as a white solid (80 mg). m/z (M+H)⁺: 619

EXAMPLE 285a

Preparation of intermediate 1-(4-Chloro-2-formyl-phenoxy)-cyclobutanecarboxylic acid methyl ester

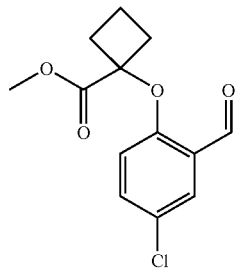

M. W. 268.70 $C_{13}H_{13}ClO_4$

To a mixture of 5-chloro-2-hydroxy-benzaldehyde (10 g, 64 mmol) and $K_2CO_3$ (13 g, 94 mmol) in DMF (100 mL) was added 1-bromo-cyclobutanecarboxylic acid methyl ester (15 g, 77 mmol, prepared according to *Bulletin of the Chemical Society of Japan*, 36, 145-7; 1963). The mixture was heated at 140° C. for 1.5 h. Then additional 1-Bromo-cyclobutanecarboxylic acid methyl ester (0.5 g, 2.6 mmol) was added and the mixture was heated at 140° C. for additional 10 min. The mixture was cooled to room temperature and poured into water (200 mL). The mixture was extracted with ethyl acetate twice. The organic layers were combined, washed with water (4×), dried over $Na_2SO_4$, concentrated to afford crude product 1-(4-chloro-2-formyl-phenoxy)-cyclobutanecarboxylic acid methyl ester as a dark oil (18 g).

EXAMPLE 285b

Preparation of intermediate E/Z-1-[4-Chloro-2-(6-chloro-2-oxo-1,2-dihydro-indol-3-ylidenemethyl)-phenoxy]-cyclobutanecarboxylic acid methyl ester

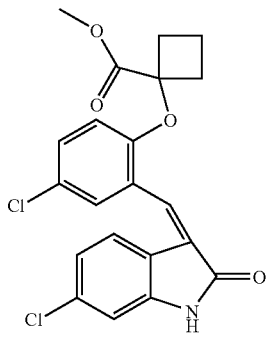

M. W. 418.28 $C_{21}H_{17}Cl_2NO_4$

To the mixture of 6-chlorooxindole (10 g, 60 mmol) and 1-(4-chloro-2-formyl-phenoxy)-cyclobutanecarboxylic acid methyl ester (18 g, 64 mmol) in methanol (100 mL) was added pyrrolidine (4.5 g, 63 mmol) dropwise. The mixture was then heated at 70° C. for 1 h. After cooled to room temperature, the mixture was filtered and the precipitate was collected, dried to give a mixture of E/Z 1-[4-Chloro-2-(6-chloro-2-oxo-1,2-dihydro-indol-3-ylidenemethyl)-phenoxy]-cyclobutanecarboxylic acid methyl ester (6 g, 24%).

EXAMPLE 285c

Preparation of intermediate E/Z-6-Chloro-3-[5-chloro-2-(1-methoxycarbonyl-cyclobutoxy)-benzylidene]-2-oxo-2,3-dihydro-indole-1-carboxylic acid tert-butyl ester

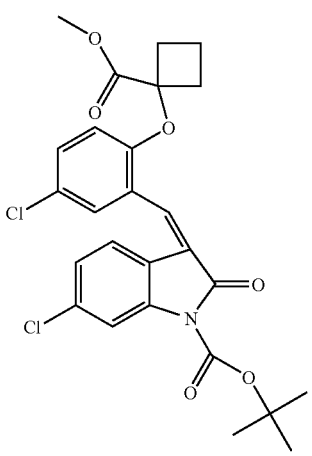

M. W. 518.40 $C_{26}H_{25}Cl_2NO_6$

To a solution of E/Z-1-[4-chloro-2-(6-chloro-2-oxo-1,2-dihydro-indol-3-ylidenemethyl)-phenoxy]-cyclobutanecarboxylic acid methyl ester (6 g, 14 mmol) in dichloromethane (50 mL) at r.t was added di-tert-butyl-dicarbonate (4.7 g, 21 mmol), followed by the addition of 4-dimethylaminopyridine (1 g, 8.2 mmol). The reaction mixture was stirred at r.t. for 2 h, washed with aqueous HCl solution (0.5 M) and water, dried over Na$_2$SO$_4$, concentrated to give E/Z 6-Chloro-3-[5-chloro-2-(1-methoxycarbonyl-cyclobutoxy)-benzylidene]-2-oxo-2,3-dihydro-indole-1-carboxylic acid tert-butyl ester as a yellow oil (5 g, 69%)

EXAMPLE 285d

Preparation of racemic (2'S,3S,4'R)-6-chloro-4'-[5-chloro-2-(1-methoxycarbonyl-cyclobutoxy)-phenyl]-2'-(5-fluoro-2-methyl-phenyl)spiro[3H-indole-3,3'-piperidine]-2,6'(1H)-dione

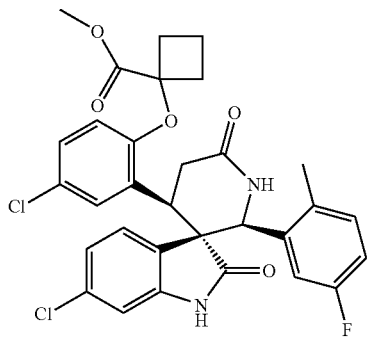

M. W. 597.48 C$_{31}$H$_{27}$Cl$_2$FN$_2$O$_5$

In a manner similar to the method described in Example 228d, E/Z-6-chloro-3-[5-chloro-2-(1-methoxycarbonyl-cyclobutoxy)-benzylidene]-2-oxo-2,3-dihydro-indole-1-carboxylic acid tert-butyl ester (1.5 g, 2.9 mmol).) was reacted with 1-(5-fluoro-2-methyl-phenyl)-3-trimethylsilyoxy-2-aza-1,3-butadiene (2 M solution in toluene, 5 mL, 10 mmol) and then trifluoroacetic acid in dichloromethane to give the title compound (340 mg). m/z (M+H)$^+$: 597

EXAMPLE 286

Preparation of racemic (2'S,3S,4'R)-6-chloro-4'-[5-chloro-2-(1-hydroxycarbonyl-cyclobutoxy)-phenyl]-2'-(5-fluoro-2-methyl-phenyl)spiro[3H-indole-3,3'-piperidine]-2,6'(1H)-dione

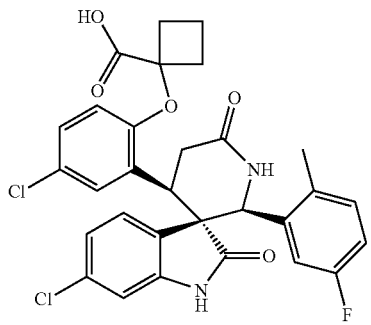

M. W. 583.45 C$_{30}$H$_{25}$Cl$_2$FN$_2$O$_5$

To a mixture of racemic (2'S,3S,4'R)-6-chloro-4'-[5-chloro-2-(1-methoxycarbonyl-cyclobutoxy)-phenyl]-2'-(5-fluoro-2-methyl-phenyl)spiro[3H-indole-3,3'-piperidine]-2,6'(1H)-dione (200 mg, 0.33 mmol) in methanol (4 mL) was added a solution of NaOH (40 mg, 1 mmol) in water (2 mL). The mixture was heated at 70° C. for 2 h, evaporated to remove most of methanol, cooled to room temperature, and acidified to "pH" 1 with aqueous HCl solution. The precipitate was collected and dried to give product as a white solid (175 mg). m/z (M+H)$^+$: 583

EXAMPLE 287

Preparation of racemic (2'R,3R,4'S)-6-chloro-4'-[5-chloro-2-(1-hydroxymethyl-cyclobutoxy)-phenyl]-2'-(5-fluoro-2-methyl phenyl)spiro[3H-indole-3,3'-piperidine]-2,6'(1H)-dione

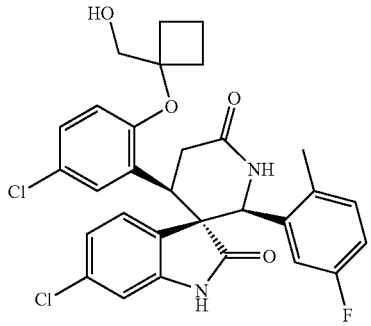

M. W. 569.47 C$_{30}$H$_{27}$Cl$_2$FN$_2$O$_4$

To a mixture of LiAlH$_4$ (15 mg, 0.4 mmol) in THF (2 mL) was added racemic (2'S,3S,4'R)-6-chloro-4'-[5-chloro-2-(1-methoxycarbonyl-cyclobutoxy)-phenyl]-2'-(5-fluoro-2-methyl-phenyl)spiro[3H-indole-3,3'-piperidine]-2,6'(1H)-dione (RO5247453-000) (60 mg, 0.1 mmol). The mixture was stirred in a ice bath for 1.5 h, quenched with MeOH, purified by Prep-HPLC to give title compound (14 mg, 24%). m/z (M+H)$^+$: 569

EXAMPLE 288a

Preparation of intermediate 2-(tert-butyl-dimethyl-silanyloxy)-5-chloro-benzaldehyde

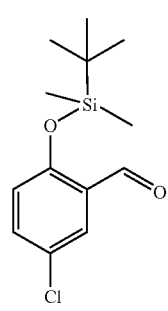

M. W. 270.83 C$_{13}$H$_{19}$ClO$_2$Si

To a solution of 5-chloro-2-hydroxy-benzaldehyde (9.3 g) in DMF (45 mL) was added DIPEA (20 mL) and tert-butyl-chloro-dimethyl-silane (19 g). The mixture was stirred at room temperature for 1.5 h. Then the mixture was poured into ice water (200 mL), extracted with ether (2×100 mL). The combined organic layers were washed with brine, dried over $Na_2SO_4$. The solvent was removed to give the title compound which was used directly for next step.

EXAMPLE 288b

Preparation of intermediate E/Z-6-chloro-3-(5-chloro-2-hydroxy-benzylidene)-1,3-dihydro-indol-2-one

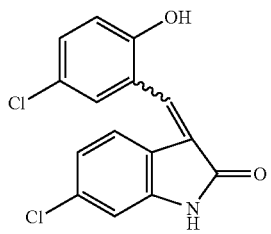

M. W. 306.15 $C_{15}H_9Cl_2NO_2$

To the mixture of 6-chlorooxindole (3.34 g) and 2-(tert-butyl-dimethylsilanyloxy)-5-chloro-benzaldehyde (7.1 g) in methanol (40 mL) was added pyrrolidine (2 g) dropwise. The mixture was then heated at 70° C. for 3 h. After cooled to 4° C., the mixture was filtered and resulting precipitate was collected, dried to give a mixture of E/Z-6-chloro-3-(5-chloro-2-hydroxy-benzylidene)-1,3-dihydro-indol-2-one as a bright yellow solid.

EXAMPLE 288c

Preparation of intermediate E/Z 3-(2-tert-butoxycarbonyloxy-5-chloro-benzylidene)-6-chloro-2-oxo-2,3-dihydro-indole-1-carboxylic acid tert-butyl ester

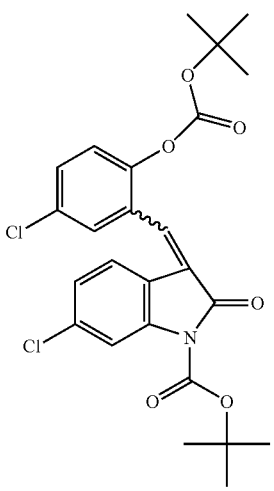

M. W. 506.39 $C_{25}H_{25}Cl_2NO_6$

To a solution of E/Z-6-chloro-3-(5-chloro-2-hydroxy-benzylidene)-1,3-dihydro-indol-2-one prepared above (3.05 g, 10 mmol) in dichloromethane (30 mL) at room temperature was added Di-tert-butyl-dicarbonate (5.2 g, 24 mmol), followed by the addition of 4-dimethylaminopyridine (0.5 g, 4.1 mmol). The reaction mixture was stirred at room temperature for 1 h. The mixture was then concentrated and the residue was purified by chromatography to give title compound as brown oil (4.8 g).

MS$^+$: 506

EXAMPLE 288d

Preparation of racemic (2'R,3R,4'S)-6-chloro-4'-(5-chloro-2-hydroxy-phenyl)-2'-isopropenylspiro[3H-indole-3,3'-piperidine]-2,6'(1H)-dione

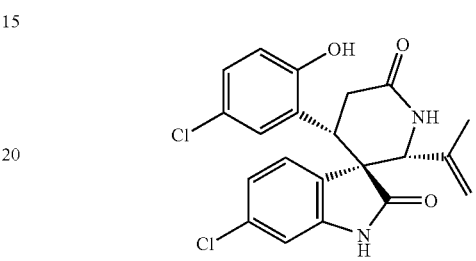

M. W. 417.30 $C_{21}H_{18}Cl_2N_2O_3$

In a manner similar to the method described in Example 41b, E/Z-3-(2-tert-butoxycarbonyloxy-5-chloro-benzylidene)-6-chloro-2-oxo-2,3-dihydro-indole-1-carboxylic acid tert-butyl (1.52 g, 3 mmol) was reacted with 1-isopropenyl-3-trimethylsilyoxy-2-aza-1,3-butadiene (2.2 g, 12 mmol) in toluene and then trifluoroacetic acid in dichloromethane to give racemic (2'R,3R,4'S)-6-chloro-4'-(5-chloro-2-hydroxy-phenyl)-2'-(1-methylene-propyl)spiro[3H-indole-3,3'-piperidine]-2,6'(1H)-dione as a solid (0.18 g).

m/z (M+H)$^+$: 417

EXAMPLE 289

Preparation of racemic (2'R,3R,4'S)-6-chloro-4'-[5-chloro-2-(2-methoxycarbonyl-2-methyl-propoxy)-phenyl]-2'-isopropenylspiro[3H-indole-3,3'-piperidine]-2,6'(1H)-dione

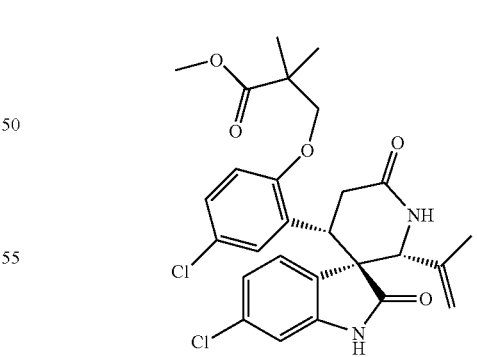

M. W. 531.44 $C_{27}H_{28}Cl_2N_2O_5$

In a manner similar to the method described in Example 41b, E/Z-6-Chloro-3-[5-chloro-2-(2-methoxycarbonyl-2-methyl-propoxy)-benzylidene]-2-oxo-2,3-dihydro-indole-1-carboxylic acid tert-butyl ester prepared in Example 229c (0.41 g, 0.8 mmol) was reacted with 1-isopropenyl-3-trimethylsilyoxy-2-aza-1,3-butadiene (3.5 mmol) in toluene and

EXAMPLE 290

Preparation of racemic (2'R,3R,4'S)-6-chloro-4'-[5-chloro-2-(2-hydroxycarbonyl-2-methyl-propoxy)-phenyl]-2'-isopropenylspiro[3H-indole-3,3'-piperidine]-2,6'(1H)-dione

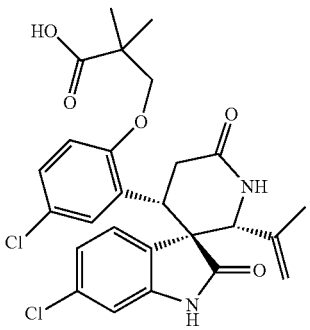

M. W. 517.41 C$_{26}$H$_{26}$Cl$_2$N$_2$O$_5$

A mixture of racemic (2'R,3R,4'S)-6-chloro-4'-[5-chloro-2-(2-methoxycarbonyl-2-methyl-propoxy)-phenyl]-2'-isopropenylspiro[3H-indole-3,3'-piperidine]-2,6'(1H)-dione (20 mg), NaOH (80 mg), H$_2$O (5 mL) and MeOH (1 mL) was heated at 80° C. for 2 h. Then the mixture was concentrated. The remaining aqueous solution was acidified by concentrated aqueous HCl solution (1.5 mL). The white precipitate was collected by filtration to give title compound (15 mg).

m/z (M+H)$^+$: 517

EXAMPLE 291

Preparation of racemic (2'R,3R,4'S)-2'-[5-bromo-2-(2-methoxycarbonyl-2-methyl-propoxy)-phenyl]-6-chloro-4'-[5-chloro-2-(methoxycarbonyl-methoxy)-phenyl]spiro[3H-indole-3,3'-piperidine]-2,6'(1H)-dione

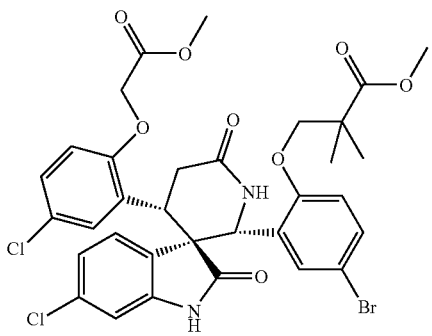

M. W. 734.43 C$_{33}$H$_{31}$BrCl$_2$N$_2$O$_8$

In a manner similar to the method described in Example 41b, E/Z-6-chloro-3-(5-chloro-2-methoxycarbonylmethoxy-benzylidene)-2-oxo-2,3-dihydro-indole-1-carboxylic acid tert-butyl ester prepared in Example 234c (0.24 g, 0.5 mmol) was reacted with 1-[5-bromo-2-(2-methoxycarbonyl-2-methyl-propoxy)phenyl]-3-trimethylsilyoxy-2-aza-1,3-butadiene prepared in Example 245a (4 mmol) in toluene and then trifluoroacetic acid in dichloromethane to give title compound as a white solid (0.03 g).

m/z (M+H)$^+$: 733

EXAMPLE 292

Preparation of racemic (2'R,3R,4'S)-6-chloro-4'-[5-chloro-2-hydroxyethoxy)-phenyl]-2'-[5-bromo-2-(3-hydroxy-2,2-dimethyl-propoxy)-phenyl]spiro[3H-indole-3,3'-piperidine]-2,6'(1H)-dione

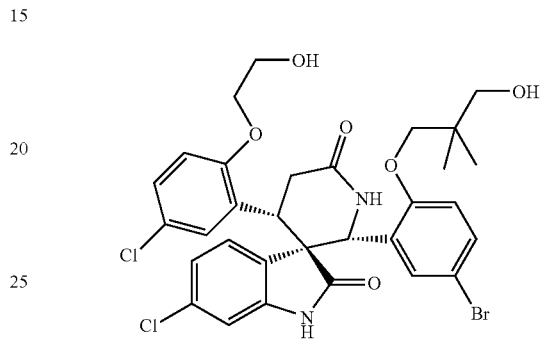

M. W. 678.41 C$_{31}$H$_{31}$BrCl$_2$N$_2$O$_6$

To a cooled solution of racemic (2'R,3R,4'S)-2'-[5-bromo-2-(2-methoxycarbonyl-2-methyl-propoxy)-phenyl]-6-chloro-4'-[5-chloro-2-(methoxycarbonyl-methoxy)-phenyl]spiro[3H-indole-3,3'-piperidine]-2,6'(1H)-dione (22 mg) in THF (3 mL) was added LiAlH$_4$ (3.7 mg). The mixture was stirred at 0° C. for 30 min, followed by addition of ethyl acetate (2 mL). Then the mixture was filtrated and the filtrate was concentrated. The residue was purified by preparative HPLC to give title compound as a white solid (6.7 mg).

m/z (M+H)$^+$: 677

EXAMPLE 293

Preparation of racemic (2'S,3S,4'R)-6-chloro-4'-[5-chloro-2-(methoxycarbonyl-methoxy)-phenyl]-2-(5-fluoro-2-methyl-phenyl)spiro[3H-indole-3,3'-piperidine]-2,6'(1H)-dione

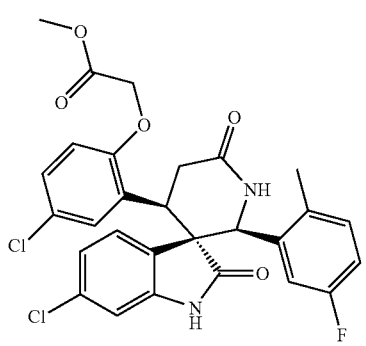

M. W. 557.41 C$_{28}$H$_{23}$Cl$_2$FN$_2$O$_5$

In a manner similar to the method described in Example 228d, E/Z-6-chloro-3-(5-chloro-2-methoxycarbonyl-methoxy-benzylidene)-2-oxo-2,3-dihydro-indole-1-carboxylic acid tert-butyl ester prepared in Example 234c (0.95 g, 2 mmol) was reacted with 1-(5-fluoro-2-methylphenyl)-3-trimethylsilyoxy-2-aza-1,3-butadiene (10 mmol) in toluene and then trifluoroacetic acid in dichloromethane to give title compound as a white solid (0.06 g).

EXAMPLE 294

Preparation of racemic (2'S,3S,4'R)-6-chloro-4'-[5-chloro-2-(hydroxycarbonyl-methoxy)-phenyl]-2-(5-fluoro-2-methyl-phenyl)spiro[3H-indole-3,3'-piperidine]-2,6'(1H)-dione

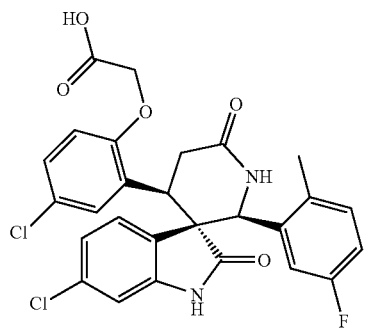

M. W. 543.38 $C_{27}H_{21}Cl_2FN_2O_5$

A mixture of racemic (2'S,3S,4'R)-6-chloro-4'-[5-chloro-2-(methoxycarbonyl-methoxy)-phenyl]-2-(5-fluoro-2-methyl-phenyl)spiro[3H-indole-3,3'-piperidine]-2,6'(1H)-dione (12 mg), NaOH (20 mg), $H_2O$ (5 mL) and methanol (1 mL) was heated at 80° C. for 2 h. Then the mixture was concentrated. The remaining aqueous solution was acidified by concentrated aqueous HCl solution (1.5 mL). The white precipitate was collected by filtration to give title compound (5 mg) m/z (M+H)$^+$: 543

EXAMPLE 295a

Preparation of intermediate E/Z-3-[5-bromo-2-(2,2,2-trifluoro-ethoxy)-benzylidene]-6-chloro-1,3-dihydro-indol-2-one

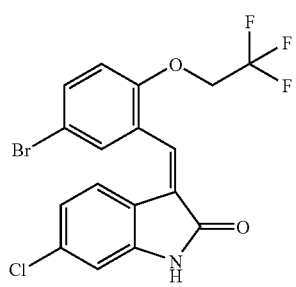

M.W 432.63 $C_{17}H_{10}BrClF_3NO_2$

5-Bromo-2-(2,2,2-trifluoro-ethoxy)-benzaldehyde prepared in Example 232a (11 g, 39 mmol) and 6-chlorooxindole (5.4 g, 32 mmol) were mixed in anhydrous methanol (50 mL) at room temperature. Then pyrrolidine (2.7 g, 39 mmol) was added dropwise. The mixture was then heated at 70° C. for 3 h. After cooled to 4° C., the mixture was filtered and resulting precipitate was collected, dried to give E/Z-3-[5-Bromo-2-(2,2,2-trifluoro-ethoxy)-benzylidene]-6-chloro-1,3-dihydro-indol-2-one as yellow solid (9.6 g).

EXAMPLE 295b

Preparation of intermediate E/Z-3-[5-bromo-2-(2,2,2-trifluoro-ethoxy)-benzylidene]-6-chloro-2-oxo-2,3-dihydro-indole-1-carboxylic acid tert-butyl ester

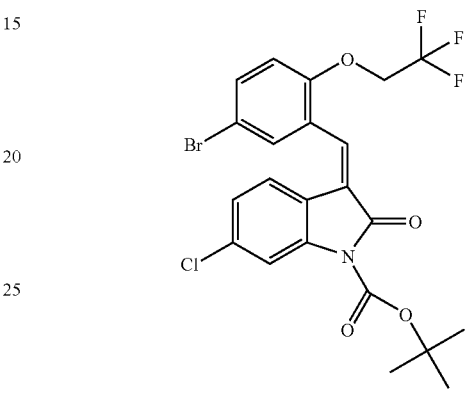

M. W. 532.75 $C_{22}H_{18}BrClF_3NO_4$

To a solution of E/Z-3-[5-bromo-2-(2,2,2-trifluoro-ethoxy)-benzylidene]-6-chloro-1,3-dihydro-indol-2-one (9.6 g, 22 mmol) in dichloromethane (100 mL) at r.t was added di-tert-butyl-dicarbonate (5.8 g, 27 mmol), followed by the addition of 4-dimethylaminopyridine (0.27 g, 2 mmol). The reaction mixture was stirred at r.t. for 0.5 h, then washed with 0.5N HCl aqueous solution, dried and concentrated to give E/Z-3-[5-Bromo-2-(2,2,2-trifluoro-ethoxy)-benzylidene]-6-chloro-2-oxo-2,3-dihydro-indole-1-carboxylic acid tert-butyl ester as a yellow oil. (11 g)

EXAMPLE 295c

Preparation of racemic (2'S,3S,4'R)-4'-[5-bromo-2-(2,2,2-trifluoro-ethoxy)-phenyl]-6-chloro-2'-(5-fluoro-2-methylphenyl)spiro[3H-indole-3,3'-piperidine]-2,6'(1H)-dione

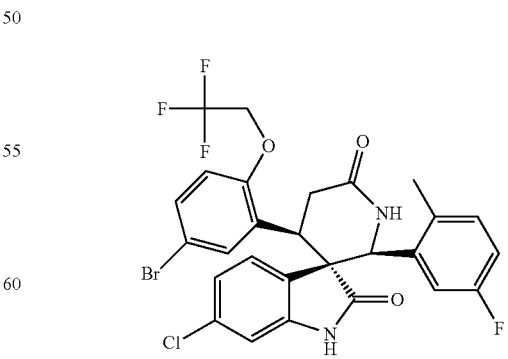

M. W. 611.82 $C_{27}H_{20}BrClF_4N_2O_3$

In a manner similar to the method described in Example 228d, E/Z-3-[5-bromo-2-(2,2,2-trifluoro-ethoxy)-benzylidene]-6-chloro-2-oxo-2,3-dihydro-indole-1-carboxylic acid tert-butyl ester (1.06 g, 2 mmol) was reacted with 1-(5-fluoro-2-methylphenyl)-3-trimethylsilyoxy-2-aza-1,3-butadiene (10 mmol) in toluene and then trifluoroacetic acid in dichloromethane to give title compound as a white solid (0.06 g).

m/z MS$^{-+}$: 609

EXAMPLE 296

Preparation of racemic (2'R,3S,4'R)-4'-[5-bromo-2-(2,2,2-trifluoro-ethoxy)-phenyl]-6-chloro-2'-(2,5-dichlorophenyl)spiro[3H-indole-3,3'-piperidine]-2,6'(1H)-dione

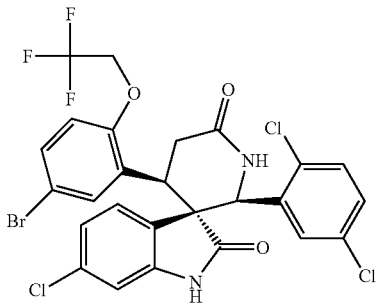

M. W. 648.70 C$_{26}$H$_{17}$BrCl$_3$F$_3$N$_2$O$_3$

In a manner similar to the method described in Example 228d, E/Z-3-[5-bromo-2-(2,2,2-trifluoro-ethoxy)-benzylidene]-6-chloro-2-oxo-2,3-dihydro-indole-1-carboxylic acid tert-butyl ester (0.53 g, 1 mmol) was reacted with 1-(2,5-dichlorophenyl)-3-trimethylsilyoxy-2-aza-1,3-butadiene prepared in Example 159a (6 mmol) in toluene and then trifluoroacetic acid in dichloromethane to give title compound as a white solid (0.06 g).

m/z MS$^{-+}$: 645

EXAMPLE 297a

Preparation of intermediate 1-(5-chloro-2-fluorophenyl)-3-trimethylsilyoxy-2-aza-1,3-butadiene

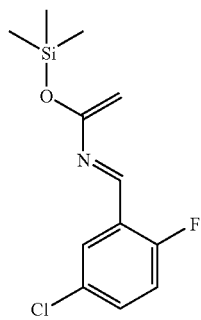

M. W. 271.80 C$_{12}$H$_{15}$ClFNOSi

In a manner similar to the method described in Example 1b, 2-fluoro-5-chloro benzaldehyde (3 g, 19 mmol) was used as the starting material in place of 3-chlorobenzaldehyde to react with LiHMDS (1M solution in THF, 19 mL, 19 mmol), trimethylsilyl chloride (2.4 mL, 19 mmol), triethylamine (3.44 mL, 24.6 mmol) and acetyl chloride (1.75 mL, 24.6 mmol) to give title compound and used for the next step without further purification.

EXAMPLE 297b

Preparation of racemic (2'R,3S,4'R)-6-chloro-4'-[5-chloro-2-(1-ethoxycarbonyl-1-methyl-ethoxy)-phenyl]-2'-(5-chloro-2-fluoro-phenyl)spiro[3H-indole-3,3'-piperidine]-2,6'(1H)-dione

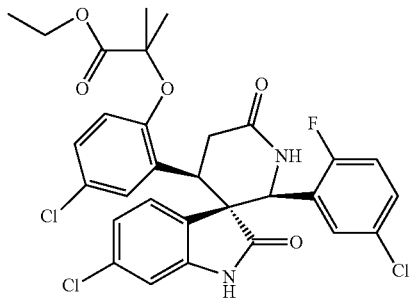

M. W. 619.91 C30H26Cl3FN2O5

In a manner similar to the method described in Example 228d, E/Z-6-chloro-3-[5-chloro-2-(1-ethoxycarbonyl-1-methyl-ethoxy)-benzylidene]-2-oxo-2,3-dihydro-indole-1-carboxylic acid tert-butyl ester prepared in Example 229c (1.04 g, 2 mmol) was reacted with 1-(2-fluoro-5-chlorophenyl)-3-trimethylsilyoxy-2-aza-1,3-butadiene (10 mmol) in toluene and then trifluoroacetic acid in dichloromethane to give title compound as a white solid (0.48 g).

m/z (M+H)$^+$: 619

EXAMPLE 298

Preparation of racemic (2'R,3S,4'R)-6-chloro-4'-[5-chloro-2-(1-hydroxycarbonyl-1-methyl-ethoxy)-phenyl]-2'-(5-chloro-2-fluoro-phenyl)spiro[3H-indole-3,3'-piperidine]-2,6'(1H)-dione

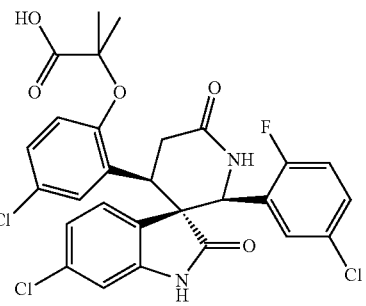

M. W. 591.86 C28H22Cl3FN2O5

A mixture of racemic (2'R,3S,4'R)-6-chloro-4'-[5-chloro-2-(1-ethoxycarbonyl-1-methyl-ethoxy)-phenyl]-2'-(5-chloro-2-fluoro-phenyl)spiro[3H-indole-3,3'-piperidine]-2,6'(1H)-dione (185 mg), NaOH (120 mg), H$_2$O (15 mL) and methanol (5 mL) was heated at 80° C. for 2 h. Then the mixture was concentrated. The remaining aqueous solution was acidified to "pH" 1 by concentrated aqueous HCl solution. The white precipitate was collected by filtration to give title compound as a white solid (150 mg).

m/z (M+H)+: 591

EXAMPLE 299

Preparation of chiral (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione

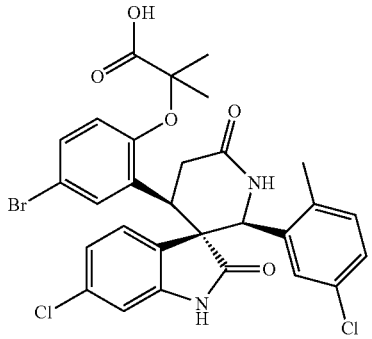

M. W. 632.34 $C_{29}H_{25}BrCl_2N_2O_5$

Separation of the two enantiomers from racemic (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione (20 mg) was conducted by chiral HPLC to provide chiral (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione as a white solid (8 mg) and chiral (2'R,3R,4'S)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione as a white solid (8 mg).

EXAMPLE 300a

Preparation of intermediate 1-(2-chloro-5-fluoro-phenyl)-3-trimethylsilyoxy-2-aza-1,3-butadiene

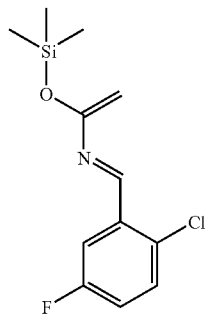

M. W. 271.80 $C_{12}H_{15}ClFNOSi$

In a manner similar to the method described in Example 1b, 2-chloro-5-fluoro benzaldehyde (3 g, 19 mmol) was used as the starting material in place of 3-chlorobenzaldehyde to react with LiHMDS (1M solution in THF, 19 mL, 19 mmol), trimethylsilyl chloride (2.4 mL, 19 mmol), triethylamine (3.44 mL, 24.6 mmol) and acetyl chloride (1.75 mL, 24.6 mmol) to give title compound and used for the next step without further purification.

EXAMPLE 300b

Preparation of racemic (2'R,3S,4'R)-6-chloro-4'-[5-chloro-2-(1-ethoxycarbonyl-1-methyl-ethoxy)-phenyl]-2'-(2-chloro-5-fluoro-phenyl)spiro[3H-indole-3,3'-piperidine]-2,6'(1H)-dione

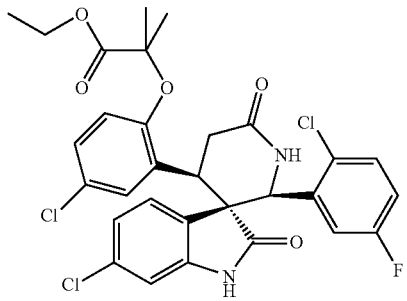

M. W. 619.91 C30H26Cl3FN2O5

In a manner similar to the method described in Example 228d, E/Z-6-chloro-3-[5-chloro-2-(1-ethoxycarbonyl-1-methyl-ethoxy)-benzylidene]-2-oxo-2,3-dihydro-indole-1-carboxylic acid tert-butyl ester prepared in Example 229c (3 g, 5.8 mmol) was reacted with 1-(2-chloro-5-fluorophenyl)-3-trimethylsilyoxy-2-aza-1,3-butadiene (23 mmol) in toluene and then trifluoroacetic acid in dichloromethane to give title compound as a white solid (0.4 g).

m/z (M+H)+: 619

EXAMPLE 301a

Preparation of intermediate 2-(4-fluoro-2-formyl-phenoxy)-2-methyl-propionic acid ethyl ester

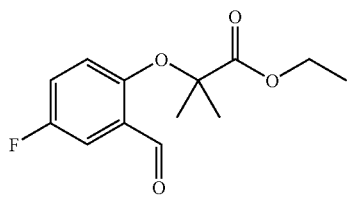

M. W. 25426 $C_{13}H_{15}FO_4$

5-Fluoro-2-hydroxy-benzaldehyde (14 g, 100 mmol), 2-bromo-2-methyl-propionic acid ethyl ester (19.5 g, 100 mmol), $K_2CO_3$ (27 g, 196 mmol) and KI (0.97 g, 5.8 mmol) were mixed in DMF (150 mL). Then the reaction mixture was heated at 110° C. for 3 h. The mixture was filtered and the filtrate was concentrated. The residue was dissolved in ethyl acetate and washed with aqueous 1N NaOH. Then the organic layer was separated, dried over $Na_2SO_4$ and concentrated to give title compound (9 g).

EXAMPLE 301b

Preparation of intermediate E/Z-2-[4-fluoro-2-(6-chloro-2-oxo-1,2-dihydro-indol-3-ylidenemethyl)-phenoxy]-2-methyl-propionic acid ethyl ester

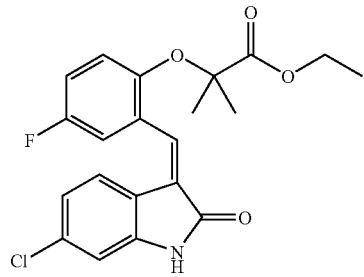

M. W. 403.84 $C_{21}H_{19}ClFNO_4$

In a manner similar to the method described in Example 227b, 2-(4-fluoro-2-formyl-phenoxy)-2-methyl-propionic acid ethyl ester (8 g, 31.5 mmol) was reacted with 6-chlorooxindole (5.3 g, 33 mmol) and pyrrolidine (2.6 mL) in methanol to give E/Z 2-[4-chloro-2-(6-fluoro-2-oxo-1,2-dihydro-indol-3-ylidenemethyl)-phenoxy]-2-methyl-propionic acid ethyl ester as a yellow solid (10 g).

EXAMPLE 301c

Preparation of intermediate E/Z-6-Chloro-3-[5-fluoro-2-(1-ethoxycarbonyl-1-methyl-ethoxy)-benzylidene]-2-oxo-2,3-dihydro-indole-1-carboxylic acid tert-butyl ester

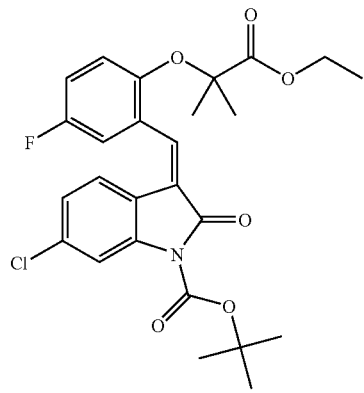

M.W 520.41 $C_{26}H_{27}Cl_2NO_6$

In a manner similar to the method described in Example 227c, E/Z-2-[4-fluoro-2-(6-chloro-2-oxo-1,2-dihydro-indol-3-ylidenemethyl)-phenoxy]-2-methyl-propionic acid ethyl ester (5 g, 12 mmol) was reacted with di-tert-butyl-dicarbonate (3.1 g, 14 mmol) and DMAP (0.2 g, 1.72 mmol) in dichloromethane to give title compound as a yellow oil (6.5 g).

EXAMPLE 301d

Preparation of racemic (2'R,3S,4'R)-6-chloro-4'-[5-fluoro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione

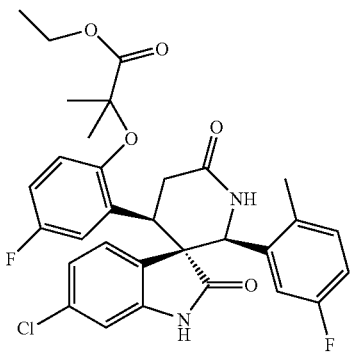

M.W 583.04 $C_{31}H_{29}ClF_2N_2O_5$

In a manner similar to the method described in Example 228d, E/Z-6-chloro-3-[5-fluoro-2-(1-ethoxycarbonyl-1-methyl-ethoxy)-benzylidene]-2-oxo-2,3-dihydro-indole-1-carboxylic acid tert-butyl ester (5 g, 9.6 mmol) was reacted with 1-(5-fluoro-2-methyl-phenyl)-3-trimethylsilyoxy-2-aza-1,3-butadiene (40 mmol) in toluene and then trifluoroacetic acid in dichloromethane to give title compound as a white solid (0.8 g).

m/z (M+H)⁺: 583

EXAMPLE 302

Preparation of racemic (2'R,3S,4'R)-6-chloro-4'-[5-fluoro-2-(1-hydroxycarbonyl-1-methyl-ethyl)-phenyl]-2'-(5-fluoro-2-methyl-phenyl)spiro[3H-indole-3,3'-piperidine]-2,6'(1H)-dione

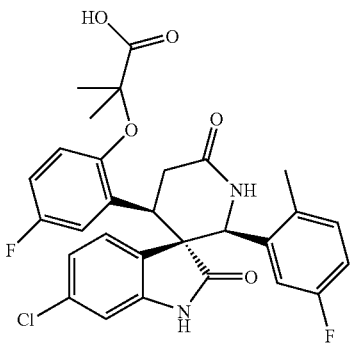

M.W 554.98 $C_{29}H_{25}Cl_2FN_2O_5$

Racemic (2'S,3S,4'R)-6-chloro-4'-[5-fluoro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione (300 mg, 0.52 mmol) was dissolved in THF (10 mL). Then aqueous solution (1 mL) of NaOH (0.2 g) was added. The mixture was refluxed for 1 h. After cooled to room temperature, the solution was concentrated and then the residue was acidified to "pH" 2-3 by addition of concentrated aqueous HCl solution. The white solid was collected by filtration to give title compound (0.26 g).

m/z (M+H)$^+$: 555

EXAMPLE 303a

Preparation of intermediate 2-(4-Chloro-2-formyl-phenoxy)-2-methyl-propionic acid tert-butyl ester

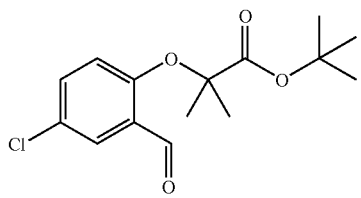

M. W. 298.77 $C_{15}H_{19}ClO_4$

5-Chloro-2-hydroxy-benzaldehyde (15.6 g, 100 mmol), 2-bromo-2-methyl-propionic acid tert-butyl ester (33.4 g, 150 mmol), $K_2CO_3$ (27.6 g, 200 mmol) and KI (3 g, 19 mmol) were mixed in DMF (100 mL). Then the reaction mixture was heated at 110° C. for 3 h. The mixture was filtered and the filtrate was concentrated. The residue was dissolved in ethyl acetate and washed with 1N NaOH. Then the organic layer was separated, dried over $Na_2SO_4$ and concentrated to give title compound (16 g)

EXAMPLE 303b

Preparation of intermediate E/Z-2-[4-Chloro-2-(6-chloro-2-oxo-1,2-dihydro-indol-3-ylidenemethyl)-phenoxy]-2-methyl-propionic acid tert-butyl ester

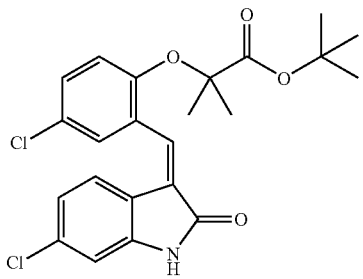

M. W. 448.35 $C_{23}H_{23}Cl_2NO_4$

In a manner similar to the method described in Example 227b, 2-(4-chloro-2-formyl-phenoxy)-2-methyl-propionic acid tert-butyl ester (9 g, 30 mmol) was reacted with 6-chlorooxindole (5.1 g, 30 mmol) and pyrrolidine (2.49 g, 35 mmol) in methanol to give E/Z 2-[4-chloro-2-(6-chloro-2-oxo-1,2-dihydro-indol-3-ylidenemethyl)-phenoxy]-2-methyl-propionic acid tert-butyl ester as a yellow oil (6.2 g).

EXAMPLE 303c

Preparation of intermediate E/Z-6-Chloro-3-[5-chloro-2-(1-tert-butoxycarbonyl-1-methyl-ethoxy)-benzylidene]-2-oxo-2,3-dihydro-indole-1-carboxylic acid tert-butyl ester

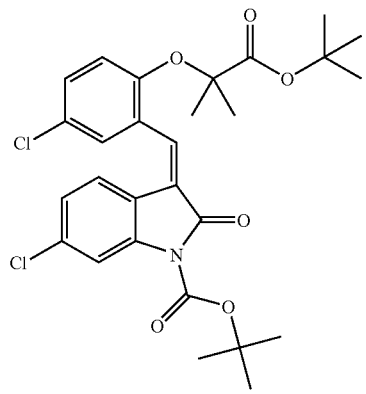

M.W 548.47 $C_{28}H_{31}Cl_2NO_6$

In a manner similar to the method described in Example 227c, E/Z 2-[4-chloro-2-(6-chloro-2-oxo-1,2-dihydro-indol-3-ylidenemethyl)-phenoxy]-2-methyl-propionic acid tert-butyl ester (5.49 g, 10 mmol) was reacted with di-tert-butyl-dicarbonate (2.5 g, 11.5 mmol) and DMAP (0.12 g, 1 mmol) in dichloromethane to give title compound as a yellow solid (3.8 g).

EXAMPLE 303d

Preparation of racemic (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione

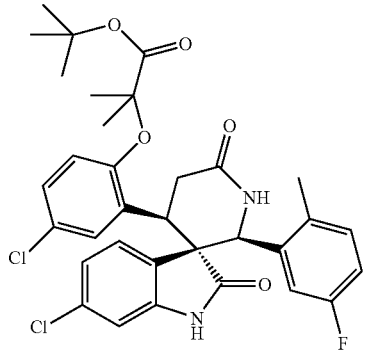

M.W 627.55 $C_{33}H_{33}Cl_2FN_2O_5$

In a manner similar to the method described in Example 228d, E/Z 6-chloro-3-[5-chloro-2-(1-tert-butoxycarbonyl-1-methyl-ethoxy)-benzylidene]-2-oxo-2,3-dihydro-indole-1-carboxylic acid tert-butyl ester (3 g, 5.47 mmol) was reacted with 1-(5-fluoro-2-methyl-phenyl)-3-trimethylsilyoxy-2-aza-1,3-butadiene (22 mmol) in toluene and then trifluoro-acetic acid in dichloromethane to give title compound as a white solid (0.7 g).

m/z (M+H)$^+$: 627

EXAMPLE 303e

Preparation of chiral (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione

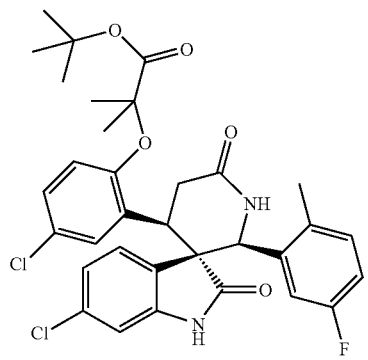

M.W 627.55 C$_{33}$H$_{33}$Cl$_2$FN$_2$O$_5$

Separation of the two enantiomers from racemic (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione (700 mg) was conducted by chiral HPLC to provide chiral (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione as a white solid (200 mg).

m/z (M+H)$^+$: 627

EXAMPLE 304a

Preparation of intermediate E/Z-6-chloro-3-(3-chloro-2-fluoro-benzylidene)-2-oxo-2,3-dihydro-indole-1-carboxylic acid tert-butyl ester

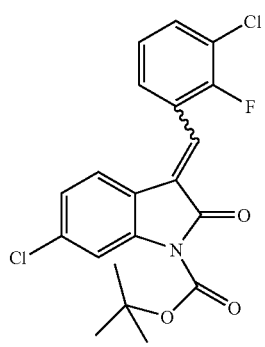

M. W. 408.26 C$_{20}$H$_{16}$Cl$_2$FNO$_3$

In a manner similar to the method describeds in Example 4a and Example 24a, 3-chloro-2-fluorobenzaldehyde (3.1 g, 20 mmol) was reacted with 6-chlorooxindole (3.3 g, 20 mmol) and pyrrolidine in methanol, then di-tert-butyl-dicarbonate (6.5 g, 30 mmol) (Aldrich), triethylamine and 4-dimethylaminopyridine in dichloromethane to give E/Z-6-chloro-3-(3-chloro-2-fluoro-benzylidene)-2-oxo-2,3-dihydro-indole-1-carboxylic acid tert-butyl ester as a yellow solid (Yield: 6.1 g, 75%).

EXAMPLE 304b

Preparation of racemic (2'R,3R,4'R)-6-chloro-4'-(3-chloro-2-fluoro-phenyl)-2'-(5-fluoro-2-methyl-phenyl)spiro[3H-indole-3,3'-piperidine]-2,6'(1H)-dione

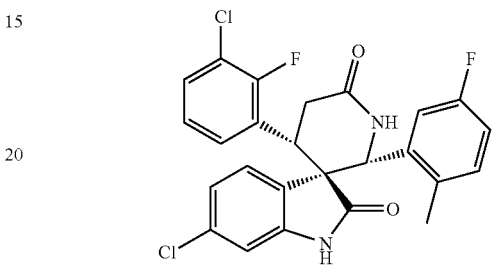

M. W. 487.33 C$_{25}$H$_{18}$Cl$_2$F$_2$N$_2$O$_2$

In a manner similar to the method described in example 41b, E/Z-6-chloro-3-(3-chloro-2-fluoro-benzylidene)-2-oxo-2,3-dihydro-indole-1-carboxylic acid tert-butyl ester (0.41 g, 1 mmol) was reacted with 1-(5-fluoro-2-methyl-phenyl)-3-trimethylsilyoxy-2-aza-1,3-butadiene (2.2 g, 8.7 mmol) prepared in example 36a in toluene and then trifluoroacetic acid in dichloromethane to give racemic (2'R,3R,4'R)-6-chloro-4'-(3-chloro-2-fluoro-phenyl)-2'-(5-fluoro-2-methyl-phenyl)spiro[3H-indole-3,3'-piperidine]-2,6'(1H)-dione (Yield 0.24 g, 49%).

HRMS (ES$^+$) m/z Calcd for C$_{25}$H$_{18}$Cl$_2$F$_2$N$_2$O$_2$+H [(M+H)$^+$]: 487.0786. Found: 487.0782

EXAMPLE 305

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$'s showing the biological activity of this invention exhibit activities less than about 10 μM.

Representative values are, for example:

| Example | $IC_{50}$ (μM, 0.02% BSA) |
|---|---|
| 5d | 2.4315 |
| 14b | 0.4403 |
| 20 | 1.8111 |
| 26b | 0.4899 |
| 31 | 0.3721 |

What is claimed is:

1. A compound of the formula

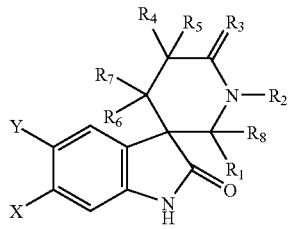

I wherein
X is selected from the group consisting of hydrogen, halogen, cyano, nitro, ethynyl, cyclopropyl, methyl, ethyl, isopropyl, methoxy and vinyl,
Y is hydrogen or fluorine,
$R_4$ and $R_5$ are hydrogen or lower alkyl,
one of $R_1$ and $R_8$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen,
one of $R_6$ and $R_7$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, cyano or lower alkyl,
$R_2$ is selected from the group consisting of hydrogen, lower alkyl and substituted lower alkyl,
$R_3$ is selected from the group consisting of oxygen, sulfur and NNH(C=O)$OR_9$,
$R_9$ is lower alkyl or substituted lower alkyl,
and the pharmaceutically acceptable salts carboxylic acid and esters thereof.

2. A compound of the formula

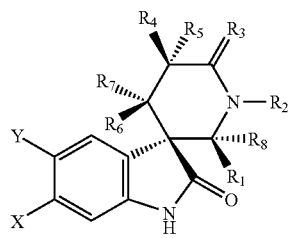

II wherein
X is hydrogen, halogen, cyano, nitro, ethynyl, cyclopropyl, methyl, ethyl, isopropyl, methoxy, and vinyl,
Y is hydrogen or fluorine,
$R_1$ is hydrogen,
$R_2$ is hydrogen, lower alkyl or substituted lower alkyl,
$R_4$ and $R_5$ are hydrogen or lower alkyl,
$R_6$ is hydrogen, cyano, or lower alkyl,
$R_3$ is O, S or NNH(C=O)$OR_9$,
$R_7$/$R_8$ is independently selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl,
$R_9$ is lower alkyl or substituted lower alkyl,
and the pharmaceutically acceptable salts carboxylic acid and esters thereof.

3. The compound of claim 2 wherein
X is chlorine or bromine,
Y is hydrogen,
$R_1$ is hydrogen,
$R_4$ and $R_5$ are both hydrogen,
$R_6$ is hydrogen,
$R_3$ is O,
$R_7$ is a substituted phenyl or substituted heteroaryl with the substituted phenyl or substituted heteroaryl selected from group consisting of

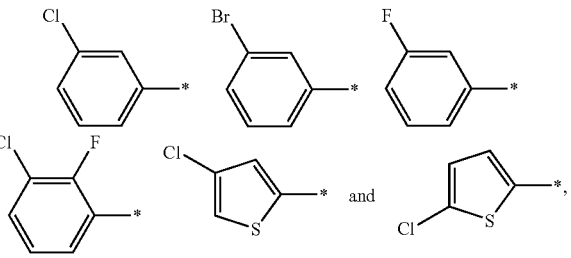

$R_8$ is independently selected from the group consisting of lower alkyl, substituted lower alkyl, lower alkenyl, substituted lower alkenyl, aryl, substituted aryl, heteroaryl, substituted heteroaryl, cycloalkyl, substituted cycloalkyl, cycloalkenyl and substituted cycloalkenyl and
$R_2$ is hydrogen, lower alkyl or substituted lower alkyl,
with the proviso that when $R_2$ is lower alkyl or substituted lower alkyl, $R_8$ is selected from lower alkenyl, substituted lower alkenyl, aryl, substituted aryl, heteroaryl, substituted heteroaryl, cycloalkyl, substituted cycloalkyl, cycloalkenyl or substituted cycloalkenyl.

4. The compound of claim 3 wherein
X is Cl or Br,
Y is hydrogen,
R$_1$ is hydrogen,
R$_4$ and R$_5$ are both hydrogen,
R$_6$ is hydrogen,
R$_3$ is O,
R$_7$ is a substituted phenyl or substituted heteroaryl with the substituted phenyl or substituted heteroaryl selected from group consisting of

[structures: 3-chlorophenyl, 3-bromophenyl, 3-fluorophenyl, 2-fluoro-3-chlorophenyl, 4-chlorothiophene, 5-chlorothiophene]

and

R$_8$ is selected from the group consisting of

[structures showing substituted vinyl, substituted alkyl, substituted phenyl, and substituted cyclopropyl groups with R$_1'$, R$_2'$, R$_3'$, R$_4'$, R$_5'$, R$_6'$, R$_7'$, R$_8'$, R$_9'$, R$_{10}'$, R$_{11}'$, R$_{12}'$]

wherein
R$_1'$ is hydrogen, methyl, ethyl, propyl, isopropyl, CF$_3$, F, CHF$_2$, or CH$_2$F,
R$_2'$ is hydrogen, methyl, ethyl, propyl, isopropyl, CF$_3$, F, CHF$_2$, or CH$_2$F,
R$_3'$ is hydrogen, F, CF$_3$, CH$_2$F, methyl, ethyl, propyl, isopropyl, cyclopropyl, tert-butyl or sec-butyl,
R$_4'$ is hydrogen, F, Cl, Br, I, methyl, ethyl, cyclopropyl, cyano, methoxy, or ethynyl,
R$_5'$ is hydrogen, F or methyl,
R$_6'$ is selected from the group consisting of hydrogen, halogen, hydroxy, cyano lower alkyl, substituted lower alkyl, lower alkoxy, substituted lower alkoxy, lower alkynyl, substituted lower alkynyl
R$_7'$ is hydrogen, F or methyl,
R$_8'$ is hydrogen, F, methyl, ethyl, propyl, isopropyl, tert-butyl or sec-butyl,
R$_9'$ is hydrogen, hydroxyl, or F,
R$_{10}'$ is hydrogen or F,
R$_{11}'$ is hydrogen or methyl,
R$_{12}'$ is hydrogen or methyl,
R$_2$ is hydrogen, lower alkyl or substituted lower alkyl
with the proviso that when R$_2$ is lower alkyl or substituted lower alkyl, R$_8$ is selected from the group consisting of

[structures: substituted vinyl, substituted phenyl, substituted cyclopropyl]

5. A compound of the formula

III

[structure of spiro-oxindole compound with substituents R$_1$, R$_2$, R$_3$, R$_4$, R$_5$, R$_6$, R$_7$, R$_8$, X, Y]

wherein
X is selected from the group consisting of hydrogen, halogen, cyano, nitro, ethynyl, cyclopropyl, methyl, ethyl, isopropyl, methoxy, and vinyl,
Y is hydrogen or fluorine,
R$_1$ is hydrogen,
R$_2$ is hydrogen, lower alkyl or substituted lower alkyl,
R$_4$ and R$_5$ are hydrogen or lower alkyl,
R$_6$ is hydrogen, cyano or lower alkyl,
R$_3$ is O, S or NNH(C=O)OR$_9$,
R$_7$/R$_8$ is independently selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl and
R$_9$ is lower alkyl or substituted lower alkyl,
and the pharmaceutically acceptable salts carboxylic acid and esters thereof.

6. The compound of claim 5 wherein
X is Cl or Br,
Y is hydrogen,
R$_1$ is hydrogen,
R$_2$ is hydrogen, lower alkyl or substituted lower alkyl,
R$_4$ and R$_5$ are both hydrogen,
R$_6$ is hydrogen,
R$_3$ is O,
R$_8$ is a substituted phenyl with the substituted phenyl selected from group consisting of

[structures: 3-chlorophenyl, 3-bromophenyl, 3-fluorophenyl] and

R$_7$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl.

7. A compound of claim 1 selected from the group consisting of
Racemic (2'S,3S,4'S)-6-chloro-2'-(3-chlorophenyl)-4'-(2,2-dimethylpropyl)spiro[3H-indole-3,3'-piperidine]-2,6'(1H)-dione,
Racemic (2'S/R,3S,4'R)-4'-(tert-butyl)-6-chloro-2'-(3-chlorophenyl)spiro[3H-indole-3,3'-piperidine]-2,6'(1H)-dione,
(2'S,3S,4'R)-6-chloro-2'-(3-chlorophenyl)-4'-isopropylspiro[3H-indole-3,3'-piperidine]-2,6'(1H)-dione,
racemic (2'R,3R,4'S)-6-chloro-2',4'-bis(3-chlorophenyl)spiro[3H-indole-3,3'-piperidine]-2,6'(1H)-dione,
chiral (2'R,3R,4'S)-6-chloro-2',4'-bis(3-chlorophenyl)spiro[3H-indole-3,3'-piperidine]-2,6'(1H)-dione,
racemic (2'S,3S,4'R)-6-chloro-2'-(3-chlorophenyl)-4'-cyclopentylspiro[3H-indole-3,3'-piperidine]-2,6'(1H)-dione,
racemic (2'S,3S,4'R)-6-chloro-2'-(3-chlorophenyl)-4'-cyclohexylspiro[3H-indole-3,3'-piperidine]-2,6'(1H)-dione,
racemic (2'S,3S,4'R)-6-chloro-2'-(4-chlorophenyl)-4'-cyclohexylspiro[3H-indole-3,3'-piperidine]-2,6'(1H)-dione,
racemic (2'R,3R,4'S)-6-chloro-2'-(4-chlorophenyl)-4'-(3-chlorophenyl)spiro[3H-indole-3,3'-piperidine]-2,6'(1H)-dione and
racemic (2'S,3S,4'R)-6-chloro-2'-(3-chlorophenyl)-4'-(4-chlorophenyl)spiro[3H-indole-3,3'-piperidine]-2,6'(1H)-dione.

8. A compound of claim 1 selected from the group consisting of
racemic (2'R,3R,4'S)-6-chloro-4'-(3-chlorophenyl)-2'-(3-methylphenyl)spiro[3H-indole-3,3'-piperidine]-2,6'(1H)-dione,
racemic (2'R,3R,4'S)-6-chloro-4'-(3-chlorophenyl)-2'-(3-fluorophenyl)spiro[3H-indole-3,3'-piperidine]-2,6'(1H)-dione,
racemic (2'S,3S,4'R)-6-chloro-2'-(3-chlorophenyl)-4'-phenylspiro[3H-indole-3,3'-piperidine]-2,6'(1H)-dione,
racemic (2'S,3S,4'R,5'R)-6-chloro-2'-(3-chlorophenyl)-5'-methyl-4'-phenylspiro[3H-indole-3,3'-piperidine]-2,6'(1H)-dione,
racemic (2'R,3R,4'S)-6-chloro-4'-(3-chlorophenyl)-2'-phenylspiro[3H-indole-3,3'-piperidine]-2,6'(1H)-dione,
chiral (2'R,3R,4'S)-6-chloro-4'-(3-chlorophenyl)-2'-phenylspiro[3H-indole-3,3'-piperidine]-2,6'(1H)-dione,
racemic (2'R,3R,4'S)-6-chloro-4'-(3-chlorophenyl)-2'-(3-methoxyphenyl)spiro[3H-indole-3,3'-piperidine]-2,6'(1H)-dione,
racemic (2'R,3R,4'S)-6-chloro-2'-(2-chlorophenyl)-4'-(3-chlorophenyl)spiro[3H-indole-3,3'-piperidine]-2,6'(1H)-dione,
chiral (2'R,3R,4'S)-6-chloro-2'-(2-chlorophenyl)-4'-(3-chlorophenyl)spiro[3H-indole-3,3'-piperidine]-2,6'(1H)-dione and
racemic (2'R,3R,4'S)-6-chloro-4'-(3-chlorophenyl)-2'-(2-methylphenyl)spiro[3H-indole-3,3'-piperidine]-2,6'(1H)-dione.

9. A compound of claim 1 selected from the group consisting of
chiral (2'R,3R,4'S)-6-chloro-4'-(3-chlorophenyl)-2'-(2-methylphenyl)spiro[3H-indole-3,3'-piperidine]-2,6'(1H)-dione,
racemic (2'R,3R,4'S)-6-chloro-4'-(3-chlorophenyl)-2'-(2-ethylphenyl)spiro[3H-indole-3,3'-piperidine]-2,6'(1H)-dione,
chiral (2'R,3R,4'S)-6-chloro-4'-(3-chlorophenyl)-2'-(2-ethylphenyl)spiro[3H-indole-3,3'-piperidine]-2,6'(1H)-dione,
racemic (2'R,3R,4'S,5'S)-6-chloro-4'-(3-chlorophenyl)-5'-methyl-2'-(2-methylphenyl)spiro[3H-indole-3,3'-piperidine]-2,6'(1H)-dione,
racemic (2'R,3R,4'S,5'S)-6-chloro-2',4'-bis(3-chlorophenyl)-5'-methylspiro[3H-indole-3,3'-piperidine]-2,6'(1H)-dione,
racemic (2'R,3R,4'S)-6-chloro-4'-(3-chlorophenyl)-2'-(2-isopropylphenyl)spiro[3H-indole-3,3'-piperidine]-2,6'(1H)-dione,
chiral (2'R,3R,4'S)-6-chloro-4'-(3-chlorophenyl)-2'-(2-isopropylphenyl)spiro[3H-indole-3,3'-piperidine]-2,6'(1H)-dione,
racemic (2'R,3R,4'S)-2'-(2-bromophenyl)-6-chloro-4'-(3-chlorophenyl)spiro[3H-indole-3,3'-piperidine]-2,6'(1H)-dione,
chiral (2'R,3R,4'S)-2'-(2-bromophenyl)-6-chloro-4'-(3-chlorophenyl)spiro[3H-indole-3,3'-piperidine]-2,6'(1H)-dione and
racemic (2'R,3R,4'S)-6-chloro-4'-(3-chlorophenyl)-2'-(3-cyanophenyl)spiro[3H-indole-3,3'-piperidine]-2,6'(1H)-dione.

10. A compound of claim 1 selected from the group consisting of
racemic (2'R,3R,4'S)-6-chloro-4'-(3-chlorophenyl)-1'-methyl-2'-(2-methylphenyl)spiro[3H-indole-3,3'-piperidine]-2,6'(1H)-dione,
chiral (2'R,3R,4'S)-6-chloro-4'-(3-chlorophenyl)-1'-methyl-2'-(2-methylphenyl)spiro[3H-indole-3,3'-piperidine]-2,6'(1H)-dione,
racemic (2'R,3R,4'S)-6-chloro-4'-(3-chlorophenyl)-2'-(3-fluoro-2-methyl-phenyl)spiro[3H-indole-3,3'-piperidine]-2,6'(1H)-dione,
chiral (2'R,3R,4'S)-6-chloro-4'-(3-chlorophenyl)-2'-(3-fluoro-2-methyl-phenyl)spiro[3H-indole-3,3'-piperidine]-2,6'(1H)-dione,
racemic (2'R,3R,4'S)-6-chloro-4'-(3-chlorophenyl)-1'-ethyl-2'-(2-methylphenyl)spiro[3H-indole-3,3'-piperidine]-2,6'(1H)-dione,
chiral (2'R,3R,4'S)-6-chloro-4'-(3-chlorophenyl)-1'-ethyl-2'-(2-methylphenyl)spiro[3H-indole-3,3'-piperidine]-2,6'(1H)-dione,
racemic (2'R,3R,4'S)-6-chloro-4'-(3-chlorophenyl)-2'-(2,6-dimethylphenyl)spiro[3H-indole-3,3'-piperidine]-2,6'(1H)-dione,
racemic (2'R,3R,4'S)-6-chloro-4'-(3-chlorophenyl)-2'-(2,3-dimethylphenyl)spiro[3H-indole-3,3'-piperidine]-2,6'(1H)-dione,
racemic (2'R,3R,4'S)-6-chloro-4'-(3-chlorophenyl)-1'-[(methoxycarbonyl)methyl]-2'-(2-methylphenyl)spiro[3H-indole-3,3'-piperidine]-2,6'(1H)-dione and
racemic (2'S,3R,4'R)-6-chloro-2'-(3-chlorophenyl)-4'-isopropyl-6'-thioxospiro[3H-indole-3,3'-piperidine]-2(1H)-one.

11. A compound of claim 1 selected from the group consisting of
racemic (2'R,3R,4'S)-6-chloro-4'-(3-chlorophenyl)-1'-[(hydroxycarbonyl)-methyl]-2'-(2-methylphenyl)spiro[3H-indole-3,3'-piperidine]-2,6'(1H)-dione,
racemic (2'R,3R,4'S)-6-chloro-4'-(3-chlorophenyl)-2'-[2-(trifluoromethyl)-phenyl]spiro[3H-indole-3,3'-piperidine]-2,6'(1H)-dione, racemic (2'R,3R,4'S)-6-chloro-4'-(3-chlorophenyl)-6'-thioxo-2'-[2-(trifluoromethyl)-phenyl]spiro[3H-indole-3,3'-piperidine]-2(1H)-one, racemic (2'R,3R,4'S)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione, chiral (2'R,3R,4'S)-6-chloro-4'-(3-chlorophenyl)-2'-(2-methylphenyl)-1'-[2-(4-morpholinyl)-carbonyl-methyl]spiro[3H-indole-3,3'-piperidine]-2,6'(1H)-dione, racemic (2'R,3R,4'S)-6-chloro-4'-(3-chlorophenyl)-2'-[5-fluoro-2-(trifluoromethyl)-phenyl]spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-1'-[(cyclopropylamino)-carbonyl-methyl]-2'-(2-methylphenyl)spiro[3H-indole-3,3'-piperidine]-2,6'(1H)-dione and racemic (2'R,3R,4'S)-6-chloro-[[2-[6-chloro-4'-(3-chlorophenyl)-2,3-dihydro-2'-(2-methylphenyl)-2,6-dioxospiro[3H-indole-3,3'-piperidin]-1-yl]-1-oxoethyl]-amino]-piperidine carboxylic acid tert-butyl ester.

12. A compound of claim 1 selected from the group consisting of racemic (2'R,3R,4'S)-6-chloro-4'-(3-chlorophenyl)-2'-(5-fluoro-2-methylphenyl)-6'-thioxospiro[3H-indole-3,3'-piperidine]-2(1H)-one, racemic (2'R,3R,4'S)-[6-chloro-4'-(3-chlorophenyl)-2,3-dihydro-2'-[2-(trifluoromethyl)phenyl)]-2-oxospiro[3H-indole-3,3'-piperidin]-6-ylene]-hydrazine carboxylic acid ethyl ester, racemic (2'R,3R,4'S)-6-chloro-4'-(3-chlorophenyl)-2'-(2,4-difluorophenyl)spiro[3H-indole-3,3'-piperidine]-2,6'(1H)-dione, racemic (2'R,3R,4'S)-6-chloro-4'-(3-chlorophenyl)-2'-(5-fluoro-2-methoxyphenyl)spiro[3H-indole-3,3'-piperidine]-2,6'(1H)-dione, racemic (2'R,3R,4'S)-6-chloro-4'-(3-chlorophenyl)-2'-(1-naphthalenyl)spiro[3H-indole-3,3'-piperidine]-2,6'(1H)-dione, racemic (2'R,3R,4'S)-6-chloro-4'-(3-chlorophenyl)-2'-(3-pyridinyl)spiro[3H-indole-3,3'-piperidine]-2,6'(1H)-dione, racemic (2'R,3R,4'S)-6-chloro-4'-(3-chlorophenyl)-2'-(2,3-difluoro-6-methoxyphenyl)spiro[3H-indole-3,3'-piperidine]-2,6'(1H)-dione, racemic (2'R,3R,4'S)-6-chloro-4'-(3-chlorophenyl)-2'-(3,4-difluorophenyl)spiro[3H-indole-3,3'-piperidine]-2,6'(1H)-dione, racemic (2'R,3R,4'S)-6-chloro-4'-(3-chlorophenyl)-2'-(1-cyclohexenyl)spiro[3H-indole-3,3'-piperidine]-2,6'(1H)-dione and racemic (2'R,3R,4'S)-6-chloro-4'-(3-chlorophenyl)-2'-(3,4-difluorophenyl)-6'-thioxospiro[3H-indole-3,3'-piperidine]-2(1H)-one.

13. A compound of claim 1 selected from the group consisting of racemic (2'R,3R,4'S)-[6-chloro-4'-(3-chlorophenyl)-2'-(3,4-difluorophenyl)-2,3-dihydro-2-oxospiro[3H-indole-3,3'-piperidin]-6-ylene]hydrazine carboxylic acid ethyl ester, racemic (2'R,3R,4'S)-2'-(1,3-benzodioxol-4-yl)-6-chloro-4'-(3-chlorophenyl)spiro[3H-indole-3,3'-piperidine]-2,6'(1H)-dione, racemic (2'R,3R,4'S)-[6-chloro-4'-(3-chlorophenyl)-2'-(5-fluoro-2-methylphenyl)-2,3-dihydro-2-oxospiro[3H-indole-3,3'-piperidin]-6-ylene]hydrazine carboxylic acid ethyl ester, racemic (2'R,3R,4'S)-6-chloro-4'-(3-chlorophenyl)-2'-(2,3-difluoro-6-methylphenyl)spiro[3H-indole-3,3'-piperidine]-2,6'(1H)-dione, racemic (2'R,3R,4'S)-6-chloro-4'-(3-chlorophenyl)-5-fluoro-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-2'-(2,3-difluoro-6-methylphenyl)-6'-thioxospiro[3H-indole-3,3'-piperidine]-2(1H)-one, racemic (2'R,3R,4'S)-6-chloro-4'-(3-chlorophenyl)-2'-(5-fluoro-2-methylphenyl)-1'-hydroxycarbonylmethyl-spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-methylspiro[3H-indole-3,3'-piperidine]-2,6'(1H)-dione and racemic (2'R,3R,4'S)-6-chloro-4'-(3-chlorophenyl)-1'-fluorocarbonylmethyl-2'-(5-fluoro-2-methylphenyl)spiro[3H-indole-3,3'-piperidine]-2,6'(1H)-dione.

14. A compound of claim 1 selected from the group consisting of racemic (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-[(1-methyl-piperidin-4-yl)aminocarbonyl)-methyl]spiro[3H-indole-3,3'-piperidine]-2,6'(1H)-dione, racemic (2'R,3R,4'S)-1'-[1-tert-butoxycarbonyl-piperidin-4-yl)aminocarbonyl-methyl]-6-chloro-4'-(3-chlorophenyl)-2'-(5-fluoro-2-methylphenyl)spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-[(piperidin-4-yl)aminocarbonyl-methyl]spiro[3H-indole-3,3'-piperidine]-2,6'(1H)-dione, racemic (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-(3-morpholin-4-yl-propyl)spiro[3H-indole-3,3'-piperidine]-2,6'(1H)-dione, racemic (2'R,3R,4'S)-6-chloro-4'-(3-chlorophenyl)-2'-(1-isopropyl-4-methyl-pent-1-enyl)spiro[3H-indole-3,3'-piperidine]-2,6'(1H)-dione, racemic (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione and chiral (2'R,3R,4'S)-6-chloro-4'-(3-chlorophenyl)-2'-(2,3-difluoro-6-isopropoxy-phenyl)spiro[3H-indole-3,3'-piperidine]-2,6'(1H)-dione.

15. A compound of claim 1 selected from the group consisting of

- racemic (2'R,3R,4'S)-6-chloro-4'-(3-chlorophenyl)-2'-(5-fluoro-2-methylphenyl)-1'-(3-pyrrolidin-1-yl-propyl)spiro[3H-indole-3,3'-piperidine]-2,6'(1H)-dione,
- racemic (2'R,3R,4'S)-6-chloro-4'-(3-chlorophenyl)-2'-(3-methoxycarbonyl-phenyl)spiro[3H-indole-3,3'-piperidine]-2,6'(1H)-dione,
- racemic (2'R,3R,4'S)-1'-[3-(4-acetyl-piperazin-1-yl)-propyl]-6-chloro-4'-(3-chlorophenyl)-2'-(5-fluoro-2-methylphenyl)spiro[3H-indole-3,3'-piperidine]-2,6'(1H)-dione,
- racemic (2'R,3R,4'S)-6-chloro-4'-(3-chlorophenyl)-2'-(1-ethyl-propenyl)spiro[3H-indole-3,3'-piperidine]-2,6'(1H)-dione,
- chiral (2'R,3R,4'S)-6-chloro-4'-(3-chlorophenyl)-2'-(1-ethyl-propenyl)spiro[3H-indole-3,3'-piperidine]-2,6'(1H)-dione,
- racemic (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione,
- chiral (2'R,3R,4'S)-6-chloro-4'-(3-chlorophenyl)-1'-[3-(1,1-dioxo-thiomorpholin-4-yl)-propyl]-2'-(5-fluoro-2-methylphenyl)-spiro[3H-indole-3,3'-piperidine]-2,6'(1H)-dione,
- racemic (2'R,3R,4'S)-6-chloro-4'-(3-chlorophenyl)-2'-(2,5-dimethyl-phenyl)spiro[3H-indole-3,3'-piperidine]-2,6'(1H)-dione,
- chiral (2'R,3R,4'S)-6-chloro-4'-(3-chlorophenyl)-2'-(2,5-dimethyl-phenyl)spiro[3H-indole-3,3'-piperidine]-2,6'(1H)-dione and
- racemic (2'R,3R,4'S)-6-chloro-4'-(3-chlorophenyl)-2'-(2,5-dimethyl-2H-pyrazole-3-yl)spiro[3H-indole-3,3'-piperidine]-2,6'(1H)-dione.

16. A compound of claim 1 selected from the group consisting of

- racemic (2'R,3R,4'S)-6-chloro-4'-(3-chlorophenyl)-2'-(1-methyl-propenyl)spiro[3H-indole-3,3'-piperidine]-2,6'(1H)-dione,
- racemic (2'R,3R,4'S)-6-chloro-4'-(3-chlorophenyl)-2'-(1-methyl-but-1-enyl)spiro[3H-indole-3,3'-piperidine]-2,6'(1H)-dione,
- racemic (2'R,3R,4'S)-6-chloro-4'-(3-chlorophenyl)-2'-(1-ethyl-propyl)spiro[3H-indole-3,3'-piperidine]-2,6'(1H)-dione,
- chiral (2'R,3R,4'S)-6-chloro-4'-(3-chlorophenyl)-2'-(1-ethyl-propyl)spiro[3H-indole-3,3'-piperidine]-2,6'(1H)-dione,
- racemic (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione,
- chiral (2'R,3R,4'S)-6-chloro-4'-(3-chlorophenyl)-2'-(2,3-difluoro-6-isopropoxy-phenyl)-1'-(3-morpholin-4-yl-propyl)spiro[3H-indole-3,3'-piperidine]-2,6'(1H)-dione,
- racemic (2'R,3R,4'S)-6-chloro-4'-(3-chlorophenyl)-2'-(1-ethylidene-pentyl)spiro[3H-indole-3,3'-piperidine]-2,6'(1H)-dione,
- racemic (2'R,3R,4'S)-6-chloro-4'-(3-chlorophenyl)-2'-(2,3-difluoro-6-isopropoxy-phenyl)-6'-thioxospiro[3H-indole-3,3'-piperidine]-2(1H)-one,
- racemic (2'R,3R,4'S)-[6-chloro-4'-(3-chlorophenyl)-2'-(2,3-difluoro-6-isopropoxy-phenyl)-2,3-dihydro-2-oxospiro[3H-indole-3,3'-piperidin]-6-ylene]hydrazine carboxylic acid ethyl ester and
- racemic (2'R,3R,4'S)-6-chloro-4'-(3-chlorophenyl)-2'-(cyclopent-1-enyl)spiro[3H-indole-3,3'-piperidine]-2,6'(1H)-dione.

17. A compound of claim 1 selected from the group consisting of

- racemic (2'R,3R,4'S)-6-chloro-4'-(3-chlorophenyl)-2'-cyclopentylspiro[3H-indole-3,3'-piperidine]-2,6'(1H)-dione,
- chiral (2'R,3R,4'S)-6-chloro-4'-(3-chlorophenyl)-2'-cyclopentylspiro[3H-indole-3,3'-piperidine]-2,6'(1H)-dione,
- racemic (2'R,3R,4'S)-6-chloro-4'-(3-chlorophenyl)-2'-(1-isopropyl-propenyl)spiro[3H-indole-3,3'-piperidine]-2,6'(1H)-dione,
- chiral (2'R,3R,4'S)-6-chloro-4'-(3-chlorophenyl)-2'-(1-isopropyl-propenyl)spiro[3H-indole-3,3'-piperidine]-2,6'(1H)-dione,
- racemic (2'R,3R,4'S)-6-chloro-4'-(3-chlorophenyl)-2'-(1-methylene-propyl)spiro[3H-indole-3,3'-piperidine]-2,6'(1H)-dione,
- chiral (2'R,3R,4'S)-6-chloro-4'-(3-chlorophenyl)-2'-(1-methylene-propyl)spiro[3H-indole-3,3'-piperidine]-2,6'(1H)-dione,
- racemic (2'R,3R,4'S)-6-chloro-4'-(3-chlorophenyl)-2'-(1-ethyl-propenyl)-1'-hydroxycarbonylmethyl-spiro[3H-indole-3,3'-piperidine]-2,6'(1H)-dione,
- racemic (2'R,3R,4'S)-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione,
- chiral (2'R,3R,4'S)-6-chloro-4'-(3-chlorophenyl)-2'-(1-ethyl-propenyl)-1'-[(2-hydroxy-1,1-dimethylethyl)aminocarbonyl-methyl]spiro[3H-indole-3,3'-piperidine]-2,6'(1H)-dione and
- racemic (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione.

18. A compound of claim 1 selected from the group consisting of

- chiral (2'R,3R,4'S)-6-chloro-4'-(3-chlorophenyl)-2'-(1-ethyl-propenyl)-1'-(3-morpholin-4-yl-propyl)spiro[3H-indole-3,3'-piperidine]-2,6'(1H)-dione,
- racemic (2'R,3R,4'S)-6-chloro-4'-(3-chlorophenyl)-2'-(2-methyl-1-methylene-propyl)spiro[3H-indole-3,3'-piperidine]-2,6'(1H)-dione,
- racemic (2'R,3R,4'S)-6-chloro-4'-(3-chlorophenyl)-2'-(2,2-dimethyl-1-methylene-propyl)spiro[3H-indole-3,3'-piperidine]-2,6'(1H)-dione,
- racemic (2'R,3R,4'S)-6-chloro-4'-(3-chlorophenyl)-2'-(1-ethyl-propenyl)-1'-[(2-morpholin-4-yl-ethyl)aminocarbonyl-methyl]spiro[3H-indole-3,3'-piperidine]-2,6'(1H)-dione,
- racemic (2'R,3R,4'S)-6-chloro-4'-(3-chlorophenyl)-2'-isopropenylspiro[3H-indole-3,3'-piperidine]-2,6'(1H)-dione,
- chiral (2'R,3R,4'S)-6-chloro-4'-(3-chlorophenyl)-2'-isopropenylspiro[3H-indole-3,3'-piperidine]-2,6'(1H)-dione,
- racemic (2'R,3R,4'S)-6-chloro-4'-(3-chlorophenyl)-2'-(1-methylene-butyl)spiro[3H-indole-3,3'-piperidine]-2,6'(1H)-dione,
- chiral (2'R,3R,4'S)-6-chloro-4'-(3-chlorophenyl)-2'-(1-methylene-butyl)spiro[3H-indole-3,3'-piperidine]-2,6'(1H)-dione,
- racemic (2'R,3R,4'S)-6-chloro-4'-(3-chlorophenyl)-2'-(3-methyl-1-methylene-butyl)spiro[3H-indole-3,3'-piperidine]-2,6'(1H)-dione and chiral (2'R,3R,4'S)-6-chloro-4'-(3-chlorophenyl)-2'-(3-methyl-1-methylene-butyl)spiro[3H-indole-3,3'-piperidine]-2,6'(1H)-dione.

19. A compound of claim 1 selected from the group consisting of
racemic (2'R,3R,4'S)-6-chloro-4'-(3-chlorophenyl)-2'-(1-methylene-butyl)-6'-thioxospiro[3H-indole-3,3'-piperidine]-2(1H)-one,
racemic (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione,
chiral (2'R,3R,4'S)-6-chloro-4'-(3-chlorophenyl)-2'-(4-ethoxy-1,2-difluoro-phenyl)spiro[3H-indole-3,3'-piperidine]-2,6'(1H)-dione,
racemic (2'R,3R,4'S)-6-chloro-4'-(3-chloro-5-methoxycarbonyl-phenyl)-2'-(1-methylene-propyl)spiro[3H-indole-3,3'-piperidine]-2,6'(1H)-dione,
racemic (2'R,3R,4'S)-6-chloro-4'-(3-chloro-5-hydroxycarbonyl-phenyl)-2'-(1-methylene-propyl)spiro[3H-indole-3,3'-piperidine]-2,6'(1H)-dione,
racemic (2'R,3R,4'S)-6-chloro-4'-(3-chloro-5-fluorocarbonyl-phenyl)-2'-(1-methylene-propyl)spiro[3H-indole-3,3'-piperidine]-2,6'(1H)-dione,
racemic (2'R,3R,4'S)-6-chloro-4'-[3-chloro-5-(4-methanesulfonyl-piperazine-1-carbonyl)-phenyl]-2'-(1-methylene-propyl)spiro[3H-indole-3,3'-piperidine]-2,6'(1H)-dione,
racemic (2'R,3R,4'S)-6-chloro-4'-(3-chlorophenyl)-2'-(1-ethyl-propenyl)-1'-methylspiro[3H-indole-3,3'-piperidine]-2,6'(1H)-dione,
chiral (2'R,3R,4'S)-6-chloro-4'-(3-chlorophenyl)-2'-(1-ethyl-propenyl)-1'-methylspiro[3H-indole-3,3'-piperidine]-2,6'(1H)-dione,
racemic (2'R,3R,4'S)-6-chloro-4'-(3-chlorophenyl)-2'-isopropylspiro[3H-indole-3,3'-piperidine]-2,6'(1H)-dione and
chiral (2'R,3R,4'S)-6-chloro-4'-(3-chlorophenyl)-2'-isopropylspiro[3H-indole-3,3'-piperidine]-2,6'(1H)-dione.

20. A compound of claim 1 selected from the group consisting of
racemic (2'R,3R,4'S)-6-chloro-4'-(3-chlorophenyl)-2'-(1-methylene-propyl)-1'-methylspiro[3H-indole-3,3'-piperidine]-2,6'(1H)-dione,
chiral (2'R,3R,4'S)-6-chloro-4'-(3-chlorophenyl)-2'-(1-methylene-propyl)-1'-methylspiro[3H-indole-3,3'-piperidine]-2,6'(1H)-dione,
racemic (2'R,3R,4'S)-2'-sec-Butyl-6-chloro-4'-(3-chlorophenyl)spiro[3H-indole-3,3'-piperidine]-2,6'(1H)-dione,
racemic (2'R,3R,4'S)-6-chloro-4'-(3-chlorophenyl)-2'-(1-hydroxymethyl-vinyl)-spiro[3H-indole-3,3'-piperidine]-2,6'(1H)-dione,
racemic (2'R,3R,4'S)-6-chloro-4'-(3-chlorophenyl)-2'-(1-methoxymethyl-vinyl)spiro[3H-indole-3,3'-piperidine]-2,6'(1H)-dione,
racemic (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione,
chiral (2'R,3R,4'S)-6-chloro-4'-(3-chlorophenyl)-2'-[2,3-difluoro-6-(2-methoxy-ethoxy)-phenyl]spiro[3H-indole-3,3'-piperidine]-2,6'(1H)-dione,
racemic (2'R,3R,4'S)-6-chloro-4'-(3-chlorophenyl)-2'-(1,2-dimethyl-propenyl)spiro[3H-indole-3,3'-piperidine]-2,6'(1H)-dione,
racemic (2'R,3R,4'S)-6-chloro-4'-(3-chlorophenyl)-2'-propionylspiro[3H-indole-3,3'-piperidine]-2,6'(1H)-dione and racemic (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione.

21. A compound of claim 1 selected from the group consisting of
chiral (2'R,3R,4'S)-6-chloro-4'-(3-chlorophenyl)-2'-(2,3-difluoro-6-propoxy-phenyl)spiro[3H-indole-3,3'-piperidine]-2,6'(1H)-dione,
racemic (2'R,3R,4'S)-6-chloro-4'-(3-chlorophenyl)-2'-(1-cyclopropyl-vinyl)spiro[3H-indole-3,3'-piperidine]-2,6'(1H)-dione,
racemic (2'R,3R,4'S)-6-chloro-4'-(3-chlorophenyl)-1'-hydroxycarbonylmethyl-2'-(1-methylene-propyl)spiro[3H-indole-3,3'-piperidine]-2,6'(1H)-dione,
racemic (2'R,3R,4'S)-6-chloro-4'-(3-chlorophenyl)-2'-(1-methylene-propyl)-1'-[(1-methanesulfonyl-piperidin-4-yl)aminocarbonyl-methyl]spiro[3H-indole-3,3'-piperidine]-2,6'(1H)-dione,
racemic (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione,
chiral (2'R,3R,4'S)-6-chloro-4'-(3-chlorophenyl)-2'-(1-methylene-propyl)-1'-(aminocarbonyl-methyl)spiro[3H-indole-3,3'-piperidine]-2,6'(1H)-dione,
racemic (2'R,3R,4'S)-6-chloro-4'-(3-chlorophenyl)-2'-(1-ethyl-2-methyl-propenyl)spiro[3H-indole-3,3'-piperidine]-2,6'(1H)-dione,
racemic (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione,
chiral (2'R,3R,4'S)-6-chloro-4'-(3-chlorophenyl)-2'-[2,3-difluoro-6-(2-hydroxy-ethoxy)-phenyl]spiro[3H-indole-3,3'-piperidine]-2,6'(1H)-dione and
racemic (2'R,3R,4'S)-6-chloro-4'-(3-chlorophenyl)-2'-(2,3-difluoro-6-hydroxy-phenyl)spiro[3H-indole-3,3'-piperidine]-2,6'(1H)-dione.

22. A compound of claim 1 selected from the group consisting of
racemic (2'R,3R,4'S)-6-chloro-4'-(3-chlorophenyl)-2'-(1-ethyl-1-hydroxy-propyl)spiro[3H-indole-3,3'-piperidine]-2,6'(1H)-dione,
racemic (2'R,3R,4'S)-6-chloro-4'-(3-chlorophenyl)-2'-(1-ethyl-3-methyl-oxiranyl)spiro[3H-indole-3,3'-piperidine]-2,6'(1H)-dione,
racemic (2'R,3R,4'S)-6-chloro-4'-(3-chlorophenyl)-2'-(1-fluoro-2-methyl-propenyl)spiro[3H-indole-3,3'-piperidine]-2,6'(1H)-dione,
racemic (2'R,3R,4'S)-6-chloro-4'-(3-chlorophenyl)-2'-isobutyrylspiro[3H-indole-3,3'-piperidine]-2,6'(1H)-dione,
racemic (2'R,3R,4'S)-6-chloro-4'-(3-chlorophenyl)-2'-isopropenyl-1'-hydroxycarbonylmethylspiro[3H-indole-3,3'-piperidine]-2,6'(1H)-dione,
racemic (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione,
racemic (2'R,3R,4'S)-6-chloro-4'-(3-chlorophenyl)-1'-(cyclopropylaminocarbonyl-methyl)-2'-isopropenylspiro[3H-indole-3,3'-piperidine]-2,6'(1H)-dione,
racemic (2'R,3R,4'S)-6-chloro-4'-(3-chlorophenyl)-2'-isopropenyl-1'-[(1-methyl-piperidin-4-yl)aminocarbonyl-methyl]spiro[3H-indole-3,3' piperidine]-2,6'(1H)-dione,
racemic (2'R,3R,4'S)-6-chloro-4'-(3-chlorophenyl)-2'-isopropenyl-1'-[(1-methylsulfonyl-piperidin-4-yl)aminocarbonyl-methyl]spiro[3H-indole-3,3' piperidine]-2,6'(1H)-dione and racemic (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione.

23. A compound of claim 1 selected from the group consisting of racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione, racemic (2'R,3S,4'R)-6-chloro-4'-(3-chloro-phenyl)-4'-cyano-2'-(1-methylene-propyl)spiro[3H-indole-3,3'-piperidine]-2,6'(1H)-dione, racemic (2'R,3R,4'S)-1'-[3-(4-acetylamino-piperidin-1-yl)-propyl]-6-chloro-4'-(3-chlorophenyl)-2'-isopropenylspiro[3H-indole-3,3' piperidine]-2,6'(1H)-dione, racemic (2'R,3R,4'S)-4'-(3-chloro-phenyl)-6'-cyano-2'-(1-methylene-propyl)spiro[3H-indole-3,3'-piperidine]-2,6'(1H)-dione, racemic (2'R,3R,4'S)-4'-(3-chloro-phenyl)-6-cyano-2'-(5-fluoro-2-methyl-phenyl)spiro[3H-indole-3,3'-piperidine]-2,6'(1H)-dione, racemic (2'R,3R,4'S)-1'-[3-(4-acetyl-piperazin-1-yl)-propyl]-6-chloro-4'-(3-chlorophenyl)-2'-isopropenylspiro[3H-indole-3,3'-piperidine]-2,6'(1H)-dione, racemic (2'R,3R,4'S)-6-chloro-4'-(3-chlorophenyl)-2'-isopropenyl-1'-(3-piperidin-1-yl-propyl)spiro[3H-indole-3,3' piperidine]-2,6'(1H)-dione, racemic (2'R,3R,4'S)-2'-[2-(2-acetoxy-ethoxy)-5-methyl-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[6-(2-hydroxy-ethoxy)-3-methyl-phenyl]spiro[3H-indole-3,3'-piperidine]-2,6'(1H)-dione and racemic (2'R,3R,4'S)-6-chloro-4'-(3-chlorophenyl)-2'-[5-cyclopropyl-2-(2-hydroxy-ethoxy)-phenyl]spiro[3H-indole-3,3'-piperidine]-2,6'(1H)-dione.

24. A compound of claim 1 selected from the group consisting of racemic (2'R,3R,4'S)-6-chloro-2'-[5-chloro-2-(2-hydroxy-ethoxy)-phenyl]-4'-(3-chlorophenyl)spiro[3H-indole-3,3'-piperidine]-2,6'(1H)-dione, racemic (2'R,3R,4'S)-6-chloro-2'-[3-chloro-2-fluoro-6-(2-hydroxy-ethoxy)-phenyl]-4'-(3-chlorophenyl)spiro[3H-indole-3,3'-piperidine]-2,6'(1H)-dione, racemic (2'R,3R,4'S)-6-chloro-4'-(3,5-difluoro-phenyl)-2'-(1-methylene-propyl)spiro[3H-indole-3,3'-piperidine]-2,6'(1H)-dione, racemic (2'R,3R,4'S)-6-chloro-4'-(3-cyano-phenyl)-2'-(1-methylene-propyl)spiro[3H-indole-3,3'-piperidine]-2,6'(1H)-dione, racemic (2'R,3R,4'S)-4'-(3-bromo-phenyl)-6-chloro-2'-(1-methylene-propyl)spiro[3H-indole-3,3'-piperidine]-2,6'(1H)-dione, racemic (2'R,3R,4'S)-6-chloro-4'-(3-methoxy-phenyl)-2'-(1-methylene-propyl)spiro[3H-indole-3,3'-piperidine]-2,6'(1H)-dione, racemic (2'R,3R,4'S)-6-chloro-4'-(5-fluoro-2-methyl-phenyl)-2'-(1-methylene-propyl)spiro[3H-indole-3,3'-piperidine]-2,6'(1H)-dione, racemic (2'R,3R,4'S)-6-chloro-4'-(3-fluoro-phenyl)-2'-(1-methylene-propyl)spiro[3H-indole-3,3'-piperidine]-2,6'(1H)-dione, racemic (2'R,3R,4'S)-6-chloro-2'-(1-methylene-propyl)-4'-m-tolylspiro[3H-indole-3,3'-piperidine]-2,6'(1H)-dione and racemic (2'R,3R,4'S)-6-chloro-2'-(1-methylene-propyl)-4'-o-tolylspiro[3H-indole-3,3'-piperidine]-2,6'(1H)-dione.

25. A compound of claim 1 selected from the group consisting of racemic (2'R,3R,4'R)-6-chloro-2'-(1-methylene-propyl)-4'-thiophen-3-ylspiro[3H-indole-3,3'-piperidine]-2,6'(1H)-dione, racemic (2'R,3R,4'S)-6-chloro-4'-(3,5-dichloro-phenyl)-2'-(1-methylene-propyl)spiro[3H-indole-3,3'-piperidine]-2,6'(1H)-dione, racemic (2'R,3R,4'S)-6-chloro-4'-(5-chloro-2-trifluoromethyl-phenyl)-2'-(1-methylene-propyl)spiro[3H-indole-3,3'-piperidine]-2,6'(1H)-dione, racemic (2'R,3R,4'S)-4'-(3-Bromo-phenyl)-6-chloro-2'-isopropenylspiro[3H-indole-3,3'-piperidine]-2,6'(1H)-dione, racemic (2'S,3S,4'R)-6-chloro-2'-(3-chlorophenyl)-4'-(5-fluoro-2-methyl-phenyl)-spiro[3H-indole-3,3'-piperidine]-2,6'(1H)-dione, racemic (2'S,3S,4'R)-6-chloro-2'-(3-chlorophenyl)-4'-(5-fluoro-2-methyl-phenyl)-1'-hydroxycarbonylmethyl-spiro[3H-indole-3,3'-piperidine]-2,6'(1H)-dione, racemic (2'S,3S,4'R)-6-chloro-2'-(3-chlorophenyl)-4'-(5-fluoro-2-methyl-phenyl)-1'-(methylamino-carbonyl-methyl)spiro[3H-indole-3,3'-piperidine]-2,6'(1H)-dione, racemic (2'S,3S,4'R)-6-chloro-2'-(3-chlorophenyl)-1'-(dimethylamino-carbonyl-methyl)-4'-(5-fluoro-2-methyl-phenyl)-spiro[3H-indole-3,3'-piperidine]-2,6'(1H)-dione, racemic (2'S,3S,4'R)-1'-[(4-aminocarbonyl-piperidin-1-yl)carbonyl-methyl]-6-chloro-2'-(3-chlorophenyl)-4'-(5-fluoro-2-methyl-phenyl)spiro[3H-indole-3,3'-piperidine]-2,6'(1H)-dione and racemic (2'S,3S,4'R)-1'-[(3-aminocarbonyl-piperidin-1-yl)carbonyl-methyl]-6-chloro-2'-(3-chlorophenyl)-4'-(5-fluoro-2-methyl-phenyl)-spiro[3H-indole-3,3'-piperidine]-2,6'(1H)-dione.

26. A compound of claim 1 selected from the group consisting of racemic (2'S,3S,4'R)-1'-(aminocarbonyl-methyl)-6-chloro-2'-(3-chlorophenyl)-4'-(5-fluoro-2-methyl-phenyl)spiro[3H-indole-3,3'-piperidine]-2,6'(1H)-dione, racemic (2'S,3S,4'R)-6-chloro-2'-(3-chlorophenyl)-1'-(dimethylamino-propyl)-4'-(5-fluoro-2-methyl-phenyl)-spiro[3H-indole-3,3'-piperidine]-2,6'(1H)-dione, racemic (2'S,3S,4'R)-6-chloro-4'-(3-chlorophenyl)-2'-(5-fluoro-2-methylphenyl)-1'-[(1-methanesulfonyl-piperidine-4-yl)carbonylamino-ethyl]spiro[3H-indole-3,3'-piperidine]-2,6'(1H)-dione, racemic (2'R,3R,4'R)-6-chloro-4'-[2-(4-chloro-2-thiophenyl)]-2'-(5-fluoro-2-methylphenyl)-spiro[3H-indole-3,3'-piperidine]-2,6'(1H)-dione, racemic (2'R,3R,4'R)-6-chloro-4'-[2-(5-chloro-2-thiophenyl)]-2'-(5-fluoro-2-methylphenyl)-spiro[3H-indole-3,3'-piperidine]-2,6'(1H)-dione, racemic (2'R,3R,4'S)-6-chloro-4'-(2,2-dimethylpropyl)-2'-(5-fluoro-2-methylphenyl)-spiro[3H-indole-3,3'-piperidine]-2,6'(1H)-dione, racemic (2'R,3R,4'S)-6-bromo-4'-(3-chlorophenyl)-2'-(2-methylphenyl)spiro[3H-indole-3,3'-piperidine]-2,6'(1H)-dione, racemic (2'R,3R,4'S)-6-bromo-4'-(3-chlorophenyl)-2'-(5-fluoro-2-methylphenyl)spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)spiro[3H-indole-3,3'-piperidine]-2,6'(1H)-dione and racemic (2'R,3R,4'S)-6-bromo-4'-(3-chlorophenyl)-2'-(2,5-dichlorophenyl)spiro[3H-indole-3,3'-piperidine]-2,6'(1H)-dione.

27. A compound of claim 1 selected from the group consisting of racemic (2'R,3R,4'S)-6-bromo-4'-(3-chlorophenyl)-2'-(5-chloro-2-methylphenyl)spiro[3H-indole-3,3'-piperidine]-2,6'(1H)-dione, racemic (2'R,3R,4'S)-6-bromo-4'-(3-chlorophenyl)-2'-(1-methylene-propyl)-spiro[3H-indole-3,3'-piperidine]-2,6'(1H)-dione, chiral (2'R,3R,4'S)-6-bromo-4'-(3-chlorophenyl)-2'-(1-methylene-propyl)-spiro[3H-indole-3,3'-piperidine]-2,6'(1H)-dione, chiral (2'R,3R,4'S)-6-bromo-4'-(3-chlorophenyl)-2'-(1-ethyl-cyclopropyl)spiro[3H-indole-3,3'-piperidine]-2,6'(1H)-dione, racemic (2'R,3R,4'S)-6-cyclopropyl-4'-(3-chlorophenyl)-2'-(1-ethyl-cyclopropyl)-spiro[3H-indole-3,3'-piperidine]-2,6'(1H)-dione, racemic (2'R,3R,4'S)-2'-[2-(4-aminocarbonyl-piperidin-1-yl)methyl-5-fluoro-phenyl]-6-chloro-4'-(3-chlorophenyl)-spiro[3H-indole-3,3'-piperidine]-2,6'(1H)-dione, racemic (2'R,3R,4'S)-6-chloro-4'-(3-chlorophenyl)-2'-[5-fluoro-2-(4-methanesulfonyl-piperazin-1-yl)methyl-phenyl]-spiro[3H-indole-3,3'-piperidine]-2,6'(1H)-dione, racemic (2'R,3R,4'S)-6-chloro-4'-(3-chlorophenyl)-2'-{5-fluoro-2-[(1-methanesulfonyl-piperidin-4-yl)carbonylamino-methyl]-phenyl}-spiro[3H-indole-3,3'-piperidine]-2,6'(1H)-dione, chiral (2'R,3R,4'S)-4'-(3-chlorophenyl)-6-fluoro-2'-(5-fluoro-2-methylphenyl)spiro[3H-indole-3,3'-piperidine]-2,6'(1H)-dione and racemic (2'R,3R,4'S)-4'-(3-chlorophenyl)-2'-(5-fluoro-2-methylphenyl)-6-methoxyspiro[3H-indole-3,3'-piperidine]-2,6'(1H)-dione.

28. A compound of claim 1 selected from the group consisting of racemic (2'R,3R,4'S)-4'-(3-chlorophenyl)-2'-(5-fluoro-2-methylphenyl)spiro[3H-indole-3,3'-piperidine]-2,6'(1H)-dione, racemic (2'R,3R,4'S)-4'-(3-chlorophenyl)-5-fluoro-2'-(5-fluoro-2-methylphenyl)spiro[3H-indole-3,3'-piperidine]-2,6'(1H)-dione, chiral (2'R,3R,4'S)-6-chloro-4'-(3-chloro-phenyl)-2'-(1-methyl-cyclopropyl)spiro[3H-indole-3,3'-piperidine]-2,6'(1H)-dione, racemic (2'R,3R,4'S)-6-bromo-4'-(3-chlorophenyl)-2'-isopropenylspiro[3H-indole-3,3'-piperidine]-2,6'(1H)-dione, chiral (2'R,3R,4'S)-6-bromo-4'-(3-chloro-phenyl)-2'-(1-methyl-cyclopropyl)spiro[3H-indole-3,3'-piperidine]-2,6'(1H)-dione, racemic (2'R,3R,4'S)-4'-(3-chlorophenyl)-6-ethynyl-2'-isopropenylspiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-[(1-methylsulphonyl-4-piperidinyl)aminocarbonyl-methyl]spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-{[4-(1,1-dioxido-2-isothiazolidinyl)ethyl]piperazinyl-carbonyl-methyl}spiro[3H-indole-3,3'-piperidine]-2,6'(1H)-dione, chiral (2'R,3R,4'S)-6-chloro-4'-(3-chlorophenyl)-2'-(5-fluoro-2-methylphenyl)-1'-{[3-(methylsulphonyl)propyl]piperazinyl-carbonyl-methyl}spiro[3H-indole-3,3'-piperidine]-2,6'(1H)-dione and racemic (2'R,3R,4'S)-2'-(2-bromo-5-fluorophenyl)-6-chloro-4'-(3-chlorophenyl)spiro[3H-indole-3,3'-piperidine]-2,6'(1H)-dione.

29. A compound of claim 1 selected from the group consisting of racemic (2'R,3R,4'S)-2'-6-chloro-4'-(3-chlorophenyl)-(2-ethynyl-5-fluorophenyl)spiro[3H-indole-3,3'-piperidine]-2,6'(1H)-dione, racemic (2'R,3R,4'S)-2'-6-chloro-4'-(3-chlorophenyl)-{5-fluoro-2-[3-(methanesulfonyl-methyl-amino)-prop-1-ynyl-phenyl]spiro[3H-indole-3,3'-piperidine]-2,6'(1H)-dione, racemic (2'R,3R,4'S)-2'-[5-bromo-2-(2-hydroxy-ethoxy)-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione, chiral (2'R,3R,4'S)-6-chloro-4'-(3-chlorophenyl)-2'-[5-ethynyl-2-(2-hydroxy-ethoxy)-phenyl]spiro[3H-indole-3,3'-piperidine]-2,6'(1H)-dione, racemic (2'R,3R,4'S)-2'-[3-bromo-2-fluoro-6-(2-hydroxy-ethoxy)-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[2-fluoro-6-(2-hydroxyethoxy)-3-trimethylsilanylethynyl-phenyl]spiro[3H-indole-3,3'-piperidine]-2,6'(1H)-dione, racemic (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione and racemic (2'R,3R,4'S)-6-chloro-4'-(3-chlorophenyl)-2'-[5-ethyl-2-(2-hydroxy-ethoxy)-phenyl]spiro[3H-indole-3,3'-piperidine]-2,6'(1H)-dione.

30. A compound of claim 1 selected from the group consisting of chiral (2'R,3R,4'S)-6-chloro-4'-(3-chlorophenyl)-1'-[(2-hydroxy-ethyl)aminocarbonyl-methyl]-2'-isopropenyl-spiro[3H-indole-3,3'-piperidine]-2,6'(1H)-dione, chiral (2'R,3R,4'S)-1'-(aminocarbonyl-methyl)-6-chloro-4'-(3-chlorophenyl)-2'-isopropenylspiro[3H-indole-3,3'-piperidine]-2,6'(1H)-dione, chiral (2'R,3R,4'S)-6-chloro-4'-(3-chlorophenyl)-1'-(cyclopropylaminocarbonyl-methyl)-2'-isopropenylspiro[3H-indole-3,3'piperidine]-2,6'(1H)-dione, racemic (2'R,3R,4'S)-6-chloro-4'-(3-chlorophenyl)-1'-[(2-hydroxy-1,1-dimethyl-ethyl)aminocarbonyl-methyl]-2'-isopropenyl-spiro[3H-indole-3,3'-piperidine]-2,6'(1H)-dione, racemic (2'R,3R,4'S)-6-chloro-4'-(3-chlorophenyl)-2'-[5-iodo-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-cyano-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-(3-iodophenyl)spiro[3H-indole-3,3'-piperidine]-2,6'(1H)-dione, racemic (2'R,3R,4'S)-6-chloro-4'-(3-chlorophenyl)-2'-(3-ethynyl-phenyl)spiro[3H-indole-3,3'-piperidine]-2,6'(1H)-dione, racemic (2'R,3R,4'S)-6-chloro-4'-(3-chlorophenyl)-2'-(2-fluoro-5-iodophenyl)spiro[3H-indole-3,3'-piperidine]-2,6'(1H)-dione and racemic (2'R,3R,4'S)-6-chloro-4'-(3-chlorophenyl)-2'-(5-ethynyl-2-fluoro-phenyl)spiro[3H-indole-3,3'-piperidine]-2,6'(1H)-dione.

31. A compound of claim 1 selected from the group consisting of racemic (2'R,3R,4'S)-6-chloro-4'-(3-chlorophenyl)-2'-[2-(2-hydroxy-ethoxy)-5-iodo-3-methoxy-phenyl]spiro[3H-indole-3,3'-piperidine]-2,6'(1H)-dione, racemic (2'R,3R,4'S)-6-chloro-4'-(3-chlorophenyl)-2'-[5-ethynyl-2-(2-hydroxy-ethoxy)-3-methoxy-phenyl]spiro[3H-indole-3,3'-piperidine]-2,6'(1H)-dione, racemic (2'R,3R,4'S)-6-chloro-4'-(3-chlorophenyl)-2'-(5-iodo-2-methylphenyl)spiro[3H-indole-3,3'-piperidine]-2,6'(1H)-dione, racemic (2'R,3R,4'S)-6-chloro-4'-(3-chlorophenyl)-2'-(5-ethynyl-2-methylphenyl)spiro[3H-indole-3,3'-piperidine]-2,6'(1H)-dione, chiral (2'R,3R,4'S)-6-chloro-4'-(3-chlorophenyl)-2'-[3-ethynyl-2-fluoro-6-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-(5-iodo-2-nitrophenyl)spiro[3H-indole-3,3'-piperidine]-2,6'(1H)-dione, racemic (2'R,3R,4'S)-6-chloro-4'-(3-chlorophenyl)-2'-(5-ethynyl-2-nitrophenyl)spiro[3H-indole-3,3'-piperidine]-2,6'(1H)-dione, racemic (2'R,3R,4'S)-2'-(2-amino-5-iodophenyl)-6-chloro-4'-(3-chlorophenyl)spiro[3H-indole-3,3'-piperidine]-2,6'(1H)-dione, racemic (2'R,3R,4'S)-2'-(2-amino-5-ethynylphenyl)-6-chloro-4'-(3-chlorophenyl)spiro[3H-indole-3,3'-piperidine]-2,6'(1H)-dione and racemic (2'R,3R,4'S)-2'-(3-bromo-4-fluoro-phenyl)-6-chloro-4'-(3-chlorophenyl)spiro[3H-indole-3,3'-piperidine]-2,6'(1H)-dione.

32. A compound of claim 1 selected from the group consisting of racemic (2'R,3R,4'S)-6-chloro-4'-(3-chlorophenyl)-2'-(3-ethynyl-4-fluoro-phenyl)spiro[3H-indole-3,3'-piperidine]-2,6'(1H)-dione, racemic (2'R,3R,4'S)-2'-(1-benzofuran-5-yl)-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-(5-chloro-2-iodophenyl)spiro[3H-indole-3,3'-piperidine]-2,6'(1H)-dione, racemic (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione, chiral (2'R,3R,4'S)-6-chloro-4'-(3-chlorophenyl)-2'-[2-(2-hydroxy-ethoxy)-5-(1-propynyl)-phenyl]spiro[3H-indole-3,3'-piperidine]-2,6'(1H)-dione, racemic (2'R,3R,4'S)-6-chloro-4'-(3-chlorophenyl)-2'-[5-(3,3-dimethyl-1-butynyl)-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-(3-cyclopropyl-1-butynyl)-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[5-(3-methyl-1-butynyl)-2-(2-hydroxy-ethoxy)-phenyl]spiro[3H-indole-3,3'-piperidine]-2,6'(1H)-dione, racemic (2'R,3R,4'S)-6-chloro-4'-(3-chlorophenyl)-2'-[2-(2-hydroxy-ethoxy)-5-vinyl-phenyl]spiro[3H-indole-3,3'-piperidine]-2,6'(1H)-dione and racemic (2'R,3R,4'S)-6-chloro-4'-(3-chlorophenyl)-2'-[5-ethynyl-2-hydroxy-phenyl]spiro[3H-indole-3,3'-piperidine]-2,6'-dione.

33. A compound of claim 1 selected from the group consisting of chiral (2'R,3R,4'S)-6-chloro-4'-(3-chlorophenyl)-2'-[5-ethynyl-2-hydroxy-phenyl]spiro[3H-indole-3,3'-piperidine]-2,6'-dione, racemic (2'R,3R,4'S)-6-chloro-4'-(3-chlorophenyl)-2'-[5-ethynyl-2-(2,3-dihydroxy-propoxy)-phenyl]-spiro[3H-indole-3,3'-piperidine]-2,6'-dione, racemic (2'R,3R,4'S)-2'-[5-bromo-2-methylsulfanyl-phenyl]-6-chloro-4'-(3-chlorophenyl)spiro[3H-indole-3,3'-piperidine]-2,6'-dione, racemic (2'R,3R,4'S)-2'-[5-bromo-2-methylsulfonyl-phenyl]-6-chloro-4'-(3-chlorophenyl)spiro[3H-indole-3,3'-piperidine]-2,6'-dione, racemic (2'R,3R,4'S)-6-chloro-4'-(3-chlorophenyl)-2'-[5-ethynyl-2-methylsulfonyl-phenyl]spiro[3H-indole-3,3'-piperidine]-2,6'-dione, racemic (2'R,3R,4'S)-2'-[5-bromo-2-methoxy-phenyl]-6-chloro-4'-(3-chlorophenyl)spiro[3H-indole-3,3'-piperidine]-2,6'-dione, racemic (2'R,3R,4'S)-6-chloro-4'-(3-chlorophenyl)-2'-[5-ethynyl-2-methoxy-phenyl]-spiro[3H-indole-3,3'-piperidine]-2,6'-dione, chiral (2'R,3R,4'S)-6-chloro-4'-(3-chlorophenyl)-2'-[2-(2-hydroxy-ethoxy)-5-(3-trifluoroprop-1-ynyl)-phenyl]spiro[3H-indole-3,3'-piperidine]-2,6'-dione, racemic (2'R,3R,4'S)-6-chloro-4'-(3-chlorophenyl)-2'-{5-ethynyl-2-[2-(1-piperidinyl)-ethoxy]-phenyl}spiro[3H-indole-3,3'-piperidine]-2,6'-dione and racemic (2'R,3R,4'S)-2'-[2-(2-azido-ethoxy)-5-ethynyl-phenyl]-6-chloro-4'-(3-chlorophenyl)spiro[3H-indole-3,3'-piperidine]-2,6'-dione.

34. A compound of claim 1 selected from the group consisting of racemic (2'R,3R,4'S)-2'-[2-(2-aminoethyl)-5-ethynyl-phenyl]-6-chloro-4'-(3-chlorophenyl)spiro[3H-indole-3,3'-piperidine]-2,6'-dione, racemic (2'R,3R,4'S)-1'-(aminocarbonyl-methyl)-6-bromo-4'-(3-chlorophenyl)-2'-(1-methylene-propyl)spiro[3H-indole-3,3'-piperidine]-2,6'(1H)-dione, chiral (2'R,3R,4'S)-1'-(aminocarbonyl-methyl)-6-bromo-4'-(3-chlorophenyl)-2'-(1-methylene-propyl)-spiro[3H-indole-3,3'-piperidine]-2,6'(1H)-dione, racemic (2'R,3R,4'S)-6-chloro-4'-(3-chloro-phenyl)-2'-((R)-2,2-difluoro-1-methyl-cyclopropyl)spiro[3H-indole-3,3'-piperidine]-2,6'(1H)-dione, racemic (2'R,3R,4'S)-6-chloro-4'-(3-chloro-phenyl)-2'-((S)-2,2-difluoro-1-methyl-cyclopropyl)spiro[3H-indole-3,3'-piperidine]-2,6'(1H)-dione, racemic (2'R,3R,4'S)-6-chloro-4'-(5-chloro-2-isopropoxy-phenyl)-2'-isopropenylspiro[3H-indole-3,3'-piperidine]-2,6'(1H)-dione, racemic (2'S,3S,4'R)-6-chloro-4'-[5-chloro-2-(2-hydroxy-ethoxy)-phenyl]-2'-[5-fluoro-2-methyl-phenyl]spiro[3H-indole-3,3'-piperidine]-2,6'(1H)-dione, chiral (2'S,3S,4'R)-6-chloro-4'-[5-chloro-2-(2-hydroxy-ethoxy)-phenyl]-2'-[5-fluoro-2-methylphenyl]spiro[3H-indole-3,3'-piperidine]-2,6'(1H)-dione, racemic (2'S,3S,4'R)-6-chloro-4'-[5-chloro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione and chiral (2'S,3S,4'R)-6-chloro-4'-[5-chloro-2-(1-ethoxycarbonyl-1-methyl-ethoxy)-phenyl]-2'-(5-fluoro-2-methyl phenyl)spiro[3H-indole-3,3'-piperidine]-2,6'(1H)-dione.

35. A compound of claim 1 selected from the group consisting of racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2-hydroxy-1,1-dimethyl-ethoxy)-phenyl]-2'-[5-fluoro-2-methylphenyl]spiro[3H-indole-3,3'-piperidine]-2,6'(1H)-dione, racemic (2'R,3R,4'S)-2'-[5-bromo-2-(2,2,2-trifluoro-ethoxy)phenyl]-6-chloro-4'-(3-chlorophenylspiro[3H-indole-3,3'-piperidine]-2,6'(1H)-dione, racemic (2'R,3R,4'S)-6-chloro-4'-(5-chloro-2-methoxycarbonylmethoxy-phenyl)-2'-isopropenylspiro[3H-indole-3,3'-piperidine]-2,6'(1H)-dione, racemic (2'R,3R,4'S)-6-chloro-4'-(5-chloro-2-hydroxycarbonylmethoxy-phenyl)-2'-isopropenylspiro[3H-indole-3,3'-piperidine]-2,6'(1H)-dione, racemic (2'R,3S,4'R)-6-chloro-4'-[5-chloro-2-(1-ethoxycarbonyl-1-methyl-ethoxy)-phenyl]-2'-(2,5-difluoro phenyl)spiro[3H-indole-3,3'-piperidine]-2,6'(1H)-dione, racemic (2'R,3S,4'R)-6-chloro-4'-[5-chloro-2-(1-hydroxycarbonyl-1-methyl-ethoxy)-phenyl]-2'-(2,5-difluoro phenyl)spiro[3H-indole-3,3'-piperidine]-2,6'(1H)-dione, racemic (2'R,3S,4'R)-6-chloro-4'-[5-chloro-2-(2-hydroxy-1,1-dimethyl-ethoxy)-phenyl]-2'-(2,5-difluorophenyl)spiro[3H-indole-3,3'-piperidine]-2,6'(1H)-dione and racemic (2'R,3S,4'R)-4'-[5-bromo-2-(2-methoxycarbonyl-2-methyl-propoxy)-phenyl]-6-chloro 2'-(2,5-dichlorophenyl)spiro[3H-indole-3,3'-piperidine]-2,6'(1H)-dione.

36. A compound of claim 1 selected from the group consisting of racemic (2'R,3S,4'R)-4'-[5-bromo-2-(3-hydroxy-2,2-dimethyl-propoxy)-phenyl]-6-chloro-2'-(2,5-dichlorophenyl)spiro[3H-indole-3,3'-piperidine]-2,6'(1H)-dione, racemic (2'S,3S,4'R)-4'-[5-bromo-2-(2-methoxycarbonyl-2-methyl-propoxy)-phenyl]-6-chloro-2'-(5-fluoro-2-methyl phenyl)spiro[3H-indole-3,3'-piperidine]-2,6'(1H)-dione, racemic (2'S,3S,4'R)-4'-[5-bromo-2-(3-hydroxy-2,2-dimethyl-propoxy)phenyl]-6-chloro-2'-(5-fluoro-2-methyl phenyl)spiro[3H-indole-3,3'-piperidine]-2,6'(1H)-dione, racemic (2'R,3S,4'R)-4'-[5-bromo-2-(2-ethoxycarbonyl-2-methyl-ethoxy)-phenyl]-6-chloro-2'-(2,5-dichloro phenyl)spiro[3H-indole-3,3'-piperidine]-2,6'(1H)-dione, racemic (2'R,3S,4'R)-4'-[5-bromo-2-(2-hydroxycarbonyl-2-methyl-ethoxy)-phenyl]-6-chloro-2'-(2,5-dichloro phenyl)spiro[3H-indole-3,3'-piperidine]-2,6'(1H)-dione, racemic (2'R,3R,4'S)-2'-[5-bromo-2-(2-methoxycarbonyl-2-methyl-propoxy)-phenyl]-6-chloro-4'-(2,5-dichlorophenyl)spiro[3H-indole-3,3'-piperidine]-2,6'(1H)-dione, racemic (2'R,3R,4'S)-2'-[5-bromo-2-(2,2-dimethyl-3-hydroxy propoxy)-phenyl]-6-chloro-4'-(2,5-dichlorophenyl)spiro[3H-indole-3,3'-piperidine]-2,6'(1H)-dione, racemic (2'R,3R,4'S) 4'-[2-(2-amino-ethoxy)-5-chlorophenyl]-6-chloro-2'-(5-fluoro-2-methyl-phenyl)spiro[3H-indole-3,3'-piperidine]-2,6'(1H)-dione, racemic (2'R,3R,4'S)-4'-(3-chlorophenyl)-6-cyclopropyl-2'-isopropenylspiro[3H-indole-3,3'-piperidine]-2,6'(1H)-dione and chiral (2'R,3R,4'S)-6-chloro-4'-(5-chloro-3-pyridinyl)-2'-isopropenylspiro[3H-indole-3,3'-piperidine]-2,6'(1H)-dione.

37. A compound of claim 1 selected from the group consisting of racemic (2'R,3R,4'S)-6-chloro-4'-(5-chloro-2-nitro-phenyl)-2'-isopropenylspiro[3H-indole-3,3'-piperidine]-2,6'(1H)-dione, racemic (2'R,3R,4'S)-4'-(2-amino-5-chloro-phenyl)-6-chloro-2'-isopropenylspiro[3H-indole-3,3'-piperidine]-2,6'(1H)-dione, racemic (2'R,3R,4'S)-4'-(2-acetylamino-5-chloro-phenyl)-6-chloro-2'-isopropenylspiro[3H-indole-3,3'-piperidine]-2,6'(1H)-dione, racemic (2'R,3R,4'S)-6-chloro-4'-(5-chloro-2-methanesulfonylamino-phenyl)-2'-isopropenylspiro[3H-indole-3,3'-piperidine]-2,6'(1H)-dione, racemic (2'R,3R,4'S)-6-chloro-4'-(5-chloro-2-iodophenyl)-2'-(5-fluoro-2-methylphenyl)spiro[3H-indole-3,3'-piperidine]-2,6'(1H)-dione, racemic (2'S,3S,4'R)-6-chloro-4'-[5-chloro-2-(3-hydroxy-2,2-dimethyl-propoxy)-phenyl]-2'-(5-fluoro-2-methyl phenyl)-spiro[3H-indole-3,3'-piperidine]-2,6'(1H)-dione, racemic (2'S,3S,4'R)-6-chloro-4'-(5-chloro-2-(2,2,2-trifluoro-ethoxy)hydroxy-phenyl)-2'-(5-fluoro-2-methylphenyl)spiro[3H-indole-3,3'-piperidine]-2,6'(1H)-dione, racemic (2'S,3S,4'R)-6-chloro-4'-[5-chloro-2-(2-methoxycarbonyl-2-methyl-propoxy)-phenyl]-2'-(5-fluoro-2-methylphenyl)spiro[3H-indole-3,3'-piperidine]-2,6'(1H)-dione, racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione and chiral (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione.

38. A compound of claim 1 selected from the group consisting of racemic (2'R,3R,4'S)-6-chloro-4'-[5-chloro-2-(3-hydroxypropoxyl)-phenyl]-2'-[5-fluoro-2-methylphenyl]spiro[3H-indole-3,3'-piperidine]-2,6'(1H)-dione, racemic (2'R,3S,4'R)-6-chloro-4'-[5-chloro-2-(2-methoxycarbonyl-methoxy)-phenyl]-2'-(2,5-difluorophenyl)spiro[3H-indole-3,3'-piperidine]-2,6'(1H)-dione, racemic (2'R,3S,4'R)-6-chloro-4'-[5-chloro-2-(2-hydroxycarbonyl-methoxy)-phenyl]-2'-(2,5-difluorophenyl)spiro[3H-indole-3,3'-piperidine]-2,6'(1H)-dione, racemic (2'R,3R,4'S)-2'-[5-bromo-2-(2-methoxycarbonyl-2-methyl-propoxy)-phenyl]-6-chloro-4'-(5-chloro-2-methyl-phenyl)spiro[3H-indole-3,3'-piperidine]-2,6'(1H)-dione, racemic (2'R,3R,4'S)-2'-[5-bromo-2-(2-hydroxycarbonyl-2-methyl-propoxy)-phenyl]-6-chloro-4'-(5-chloro-2-methyl-phenyl)spiro[3H-indole-3,3'-piperidine]-2,6'(1H)-dione, racemic (2'S,3S,4'R)-4'-[5-bromo-2-(1-ethoxycarbonyl-1-methyl-ethoxy)-phenyl]-6-chloro-2'-(5-chloro-2-methyl-phenyl)spiro[3H-indole-3,3'-piperidine]-2,6'(1H)-dione, racemic (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione, racemic (2'R,3R,4'S)-2'-[5-bromo-2-(3-hydroxy-2,2-dimethyl-propoxy)-phenyl]-6-chloro-4'-(5-chloro-2-methyl-phenyl)spiro[3H-indole-3,3'-piperidine]-2,6'(1H)-dione, chiral (2'R,3R,4'S)-6-bromo-4'-(3-chlorophenyl)-1'-(2-hydroxy ethyl-2'-isopropenylspiro[3H-indole-3,3'-piperidine]-2,6'(1H)-dione and chiral (2'R,3R,4'S)-1'-(aminocarbonyl-methyl)-6-bromo-4'-(3-chlorophenyl)-2'-isopropenylspiro[3H-indole-3,3'-piperidine]-2,6'(1H)-dione.

39. A compound of claim 1 selected from the group consisting of chiral (2'R,3R,4'S)-1'-(aminocarbonyl-methyl)-6-bromo-4'-(3-chlorophenyl)-2'-(1-methyl cyclopropyl)-spiro[3H-indole-3,3'-piperidine]-2,6'(1H)-dione, racemic (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione, chiral (2'R,3R,4'S)-6-bromo-4'-(3-chlorophenyl)-1'-(2,3-dihydroxy-propyl)-2'-(1-methylcyclopropyl)-spiro[3H-indole-3,3'-piperidine]-2,6'(1H)-dione, racemic (2'R,3R,4'S)-2'-(1-bromo-vinyl)-6-chloro-4'-(3-chlorophenyl)spiro[3H-indole-3,3'-piperidine]-2,6'(1H)-dione, chiral (2'R,3R,4'S)-2'-(1-bromo-vinyl)-6-chloro-4'-(3-chlorophenyl)spiro[3H-indole-3,3'-piperidine]-2,6'(1H)-dione, racemic (2'R,3R,4'S)-6-chloro-4'-(5-chloro-2-methoxycarbonyl-phenyl)-2'-isopropenylspiro[3H-indole-3,3'-piperidine]-2,6'(1H)-dione, racemic (2'R,3R,4'S)-6-chloro-4'-(5-chloro-2-hydroxycarbonyl-phenyl)-2'-isopropenylspiro[3H-indole-3,3'-piperidine]-2,6'(1H)-dione, racemic (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione, chiral (2'R,3R,4'S)-2'-[5-bromo-2-(2-methoxycarbonyl-2-methyl-propoxy)-phenyl]-6-chloro-4'-(3-chlorophenyl)spiro[3H-indole-3,3'-piperidine]-2,6'(1H)-dione and racemic (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione.

40. A compound of claim 1 selected from the group consisting of chiral (2'R,3R,4'S)-2'-[5-bromo-2-(2-hydroxycarbonyl-2-methyl-propoxy)-phenyl]-6-chloro-4'-(3-chlorophenyl)spiro[3H-indole-3,3'-piperidine]-2,6'(1H)-dione, racemic (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione, chiral (2'R,3R,4'S)-2'-[5-bromo-2-(3-hydroxy-2,2-dimethyl-propoxy)-phenyl]-6-chloro-4'-(3-chlorophenyl)spiro[3H-indole-3,3'-piperidine]-2,6'(1H)-dione, racemic (2'R,3R,4'S)-2'-[5-bromo-2-(1-ethoxycarbonyl-1-methyl-ethoxy)-phenyl]-6-chloro-4'-(3-chlorophenyl)spiro[3H-indole-3,3'-piperidine]-2,6'(1H)-dione, racemic (2'R,3R,4'S)-2'-[5-bromo-2-(1-hydroxycarbonyl-1-methyl-ethoxy)-phenyl]-6-chloro-4'-(3-chlorophenyl)spiro[3H-indole-3,3'-piperidine]-2,6'(1H)-dione, racemic (2'R,3R,4'S)-6-chloro-4'-(3-chlorophenyl)-2'-[5-bromo-2-(2-hydroxy-1,1-dimethyl-ethoxy)phenyl]spiro[3H-indole-3,3'-piperidine]-2,6'(1H)-dione, racemic (2'S,3S,4'R)-4'-[5-bromo-2-(1-ethoxycarbonyl-1-methyl-ethoxy)-phenyl]-6-chloro-2'-(5-fluoro-2-methyl-phenyl)spiro[3H-indole-3,3'-piperidine]-2,6'(1H)-dione, racemic (2'S,3S,4'R)-4'-[5-bromo-2-(1-hydroxycarbonyl-1-methyl-ethoxy)-phenyl]-6-chloro-2'-(5-fluoro-2-methyl-phenyl)spiro[3H-indole-3,3'-piperidine]-2,6'(1H)-dione, racemic (2'R,3S,4'R)-4'-[5-bromo-2-(1-ethoxycarbonyl-1-methyl-ethoxy)-phenyl]-6-chloro-2'-(2,5-difluorophenyl)spiro[3H-indole-3,3'-piperidine]-2,6'(1H)-dione and racemic (2'R,3S,4'R)-4'-[5-bromo-2-(1-hydroxycarbonyl-1-methyl-ethoxy)-phenyl]-6-chloro-2'-(2,5-difluorophenyl)spiro[3H-indole-3,3'-piperidine]-2,6'(1H)-dione.

41. A compound of claim 1 selected from the group consisting of racemic (2'S,3S,4'R)-6-chloro-4'-[5-chloro-2-(1-methoxycarbonyl-cyclobutoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-hydroxycarbonyl-cyclobutoxy)-phenyl]-2'-(5-fluoro-2-methyl-phenyl)spiro[3H-indole-3,3'-piperidine]-2,6'(1H)-dione, racemic (2'R,3R,4'S)-6-chloro-4'-[5-chloro-2-(1-hydroxymethyl-cyclobutoxy)-phenyl]-2'-(5-fluoro-2-methyl phenyl)spiro[3H-indole-3,3'-piperidine]-2,6'(1H)-dione, racemic (2'R,3R,4'S)-6-chloro-4'-(5-chloro-2-hydroxyphenyl)-2'-isopropenylspiro[3H-indole-3,3'-piperidine]-2,6'(1H)-dione, racemic (2'R,3R,4'S)-6-chloro-4'-[5-chloro-2-(2-methoxycarbonyl-2-methyl-propoxy)-phenyl]-2'-isopropenylspiro[3H-indole-3,3'-piperidine]-2,6'(1H)-dione, racemic (2'R,3R,4'S)-6-chloro-4'-[5-chloro-2-(2-hydroxycarbonyl-2-methyl-propoxy)-phenyl]-2'-isopropenylspiro[3H-indole-3,3'-piperidine]-2,6'(1H)-dione, racemic (2'R,3R,4'S)-2'-[5-bromo-2-(2-methoxycarbonyl-2-methyl-propoxy)-phenyl]-6-chloro-4'-[5-chloro-2-(methoxycarbonyl-methoxy)-phenyl]spiro[3H-indole-3,3'-piperidine]-2,6'(1H)-dione, racemic (2'R,3R,4'S)-6-chloro-4'-[5-chloro-2-hydroxyethoxy)-phenyl]-2'-[5-bromo-2-(3-hydroxy-2,2-dimethyl-propoxy)-phenyl]spiro[3H-indole-3,3'-piperidine]-2,6'(1H)-dione, racemic (2'S,3S,4'R)-6-chloro-4'-[5-chloro-2-(methoxycarbonyl-methoxy)-phenyl]-2-(5-fluoro-2-methyl-phenyl)spiro[3H-indole-3,3'-piperidine]-2,6'(1H)-dione and racemic (2'S,3S,4'R)-6-chloro-4'-[5-chloro-2-(hydroxycarbonyl-methoxy)-phenyl]-2-(5-fluoro-2-methyl-phenyl)spiro[3H-indole-3,3'-piperidine]-2,6'(1H)-dione.

42. A compound of claim 1 selected from the group consisting of racemic (2'S,3S,4'R)-4'-[5-bromo-2-(2,2,2-trifluoro-ethoxy)-phenyl]-6-chloro-2'-(5-fluoro-2-methylphenyl)spiro[3H-indole-3,3'-piperidine]-2,6'(1H)-dione, racemic (2'R,3S,4'R)-4'-[5-bromo-2-(2,2,2-trifluoro-ethoxy)-phenyl]-6-chloro-2'-(2,5-dichlorophenyl)spiro[3H-indole-3,3'-piperidine]-2,6'(1H)-dione, racemic (2'R,3S,4'R)-6-chloro-4'-[5-chloro-2-(1-ethoxycarbonyl-1-methyl-ethoxy)-phenyl]-2'-(5-chloro-2-fluoro-phenyl)spiro[3H-indole-3,3'-piperidine]-2,6'(1H)-dione, racemic (2'R,3S,4'R)-6-chloro-4'-[5-chloro-2-(1-hydroxycarbonyl-1-methyl-ethoxy)-phenyl]-2'-(5-chloro-2-fluoro-phenyl)spiro[3H-indole-3,3'-piperidine]-2,6'(1H)-dione, chiral (2'S,3S,4'R)-4'-[5-bromo-2-(1-hydroxycarbonyl-1-methyl-ethoxy)-phenyl]-6-chloro-2'-(5-chloro-2-methyl-phenyl)spiro[3H-indole-3,3'-piperidine]-2,6'(1H)-dione, racemic (2'R,3S,4'R)-6-chloro-4'-[5-chloro-2-(1-ethoxycarbonyl-1-methyl-ethoxy)-phenyl]-2'-(2-chloro-5-fluoro-phenyl)spiro[3H-indole-3,3'-piperidine]-2,6'(1H)-dione, racemic (2'S,3S,4'R)-6-chloro-4'-[5-fluoro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-fluoro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-tert-butoxycarbonyl-1-methyl-ethoxy)-phenyl]-2'-(5-fluoro-2-methyl-phenyl)spiro[3H-indole-3,3'-piperidine]-2,6'(1H)-dione and racemic (2'R,3R,4'R)-6-chloro-4'-(3-chloro-2-fluoro-phenyl)-2'-(5-fluoro-2-methyl-phenyl)spiro[3H-indole-3,3'-piperidine]-2,6'(1H)-dione.

43. A pharmaceutical formulation comprising a compound of the formula

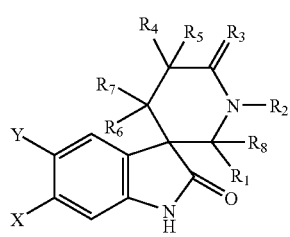

wherein

X is selected from the group consisting of hydrogen, halogen, cyano, nitro, ethynyl, cyclopropyl, methyl, ethyl, isopropyl, methoxy and vinyl, Y is hydrogen or fluorine, $R_4$ and $R_5$ are hydrogen or lower alkyl, one of $R_1$ and $R_8$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, one of $R_6$ and $R_7$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, cyano or lower alkyl, $R_2$ is selected from the group consisting of hydrogen, lower alkyl and substituted lower alkyl, $R_3$ is selected from the group consisting of oxygen, sulfur and NNH(C=O)OR$_9$, $R_9$ is lower alkyl or substituted lower alkyl, and the pharmaceutically acceptable salts carboxylic acid and esters thereof together with a pharmaceutically acceptable carrier or excipient.

44. A process to produce a compound of the formula

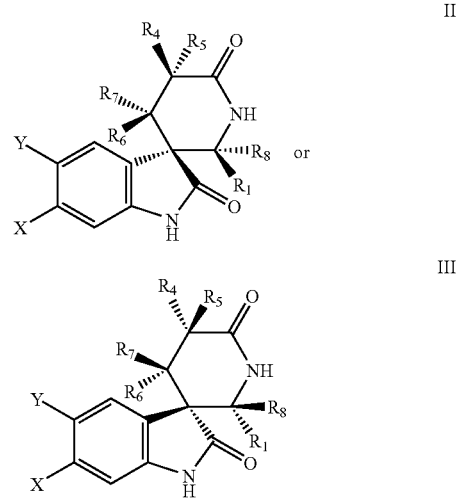

wherein

X is selected from the group consisting of hydrogen, halogen, cyano, nitro, cyclopropyl, methyl, ethyl, and isopropyl Y is hydrogen or fluorine, $R_1$ is hydrogen, $R_4$ and $R_5$ are hydrogen or lower alkyl, $R_8$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl, one of $R_6$ and $R_7$ are selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, cyano or lower alkyl which comprises reacting a compound of the formula

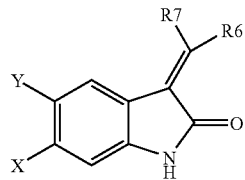

with a compound of the formula

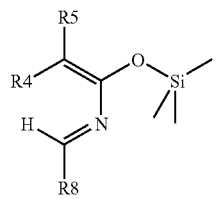

at about 110-160° C. and under anhydrous conditions to produce a compound of formula II or III.

45. A process to produce a compound of the formula

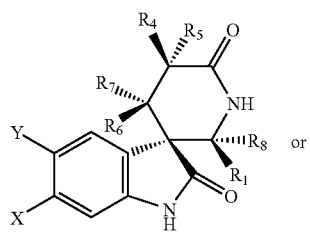 or

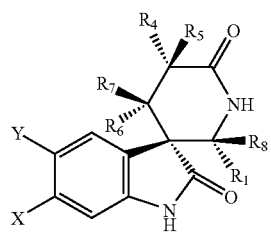

wherein
X is selected from the group consisting of hydrogen, halogen, cyano, nitro, cyclopropyl, methyl, ethyl, and isopropyl,
Y is hydrogen or fluorine,
$R_1$ is hydrogen, $R_4$ and $R_5$ are hydrogen or lower alkyl,
$R_8$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl, one of $R_6$ and $R_7$ are selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, cyano or lower alkyl
which comprises reacting a compound of the formula

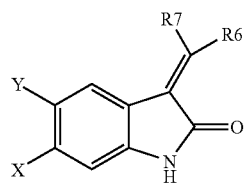

with a suitable protecting group
to provide a compound of the formula

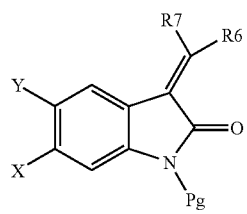

which is thereafter reacted with a compound of the formula

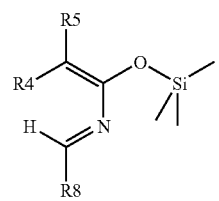

at about 110-160° C. under anhydrous conditions and thereafter deprotecting the resultant product to produce a compound of formula II and III.

* * * * *

UNITED STATES PATENT AND TRADEMARK OFFICE
CERTIFICATE OF CORRECTION

PATENT NO.        : 7,495,007 B2
APPLICATION NO. : 11/846597
DATED             : February 24, 2009
INVENTOR(S)       : Li Chen et al.

It is certified that error appears in the above-identified patent and that said Letters Patent is hereby corrected as shown below:

In Claim 9 at Column 390, Line 19, please delete – "(2'R,3R,4'S)" and
Insert -- (2'S,3R,4'S) --
Line 22, please delete – "(2'R,3R,4'S)" and
Insert -- (2'S,3R,4'S) --
In Claim 13 at Column 392, Line 8, please delete – "(2'R,3R,4'S)" and
Insert -- (2'S,3R,4'S) --
In Claim 14 at Column 392, Line 32, please delete – "(2'R,3R,4'S)" and
Insert -- (2'S,3R,4'S) --
In Claim 15 at Column 393, Line 33, please delete – "(2'R,3R,4'S)" and
Insert -- (2'S,3R,4'S) --
In Claim 16 at Column 393, Line 15, please delete – "(2'R,3R,4'S)" and
Insert -- (2'S,3R,4'S) --
Line 19, please delete – "(2'R,3R,4'S)" and
Insert -- (2'S,3R,4'S) --
Line 26, please delete – "(2'R,3R,4'S)" and
Insert -- (2'S,3R,4'S) --
Line 29, please delete – "(2'R,3R,4'S)" and
Insert -- (2'S,3R,4'S) --
In Claim 19 at Column 395, Line 6, please delete – "(2'R,3R,4'S)" and
Insert -- (2'S,3R,4'S) --
Line 8, please delete – "(2'R,3R,4'S)" and
Insert -- (2'S,3R,4'S) --
In Claim 20 at Column 395, Line 18, please delete – "(2'R,3R,4'S)" and
Insert -- (2'S,3R,4'S) --
Line 21, please delete – "(2'R,3R,4'S)" and
Insert -- (2'S,3R,4'S) --
Line 27, please delete – "(2'R,3R,4'S)" and
Insert -- (2'S,3R,4'S) --
In Claim 20 at Column 396, Line 1, please delete – "(2'R,3R,4'S)" and
Insert -- (2'S,3R,4'S) --
In Claim 21 at Column 396, Line 3, please delete – "(2'R,3R,4'S)" and
Insert -- (2'S,3R,4'S) --
Line 25, please delete – "(2'R,3R,4'S)" and
Insert -- (2'S,3R,4'S) --
Line 28, please delete – "(2'R,3R,4'S)" and
Insert -- (2'S,3R,4'S) --
Line 31, please delete – "(2'R,3R,4'S)" and
Insert -- (2'S,3R,4'S) --

UNITED STATES PATENT AND TRADEMARK OFFICE
CERTIFICATE OF CORRECTION

PATENT NO. : 7,495,007 B2
APPLICATION NO. : 11/846597
DATED : February 24, 2009
INVENTOR(S) : Li Chen et al.

It is certified that error appears in the above-identified patent and that said Letters Patent is hereby corrected as shown below:

In Claim 22 at Column 396, Line 9, please delete – "(2'R,3R,4'S)" and
Insert -- (2'S,3R,4'S) --
Line 12, please delete – "(2'R,3R,4'S)" and
Insert -- (2'S,3R,4'S) --
In Claim 24 at Column 397, Line 6, please delete – "(2'R,3R,4'S)" and
Insert -- (2'S,3R,4'S) --
In Claim 26 at Column 399, Line 4, please delete – "(2'R,3R,4'S)" and
Insert -- (2'S,3R,4'S) --
In Claim 28 at Column 400, Line 7, please delete – "(2'R,3R,4'S)" and
Insert -- (2'S,3R,4'S) --
In Claim 29 at Column 400, Line 19, please delete – "(2'R,3R,4'S)" and
Insert -- (2'S,3R,4'S) --
Line 22, please delete – "(2'R,3R,4'S)" and
Insert -- (2'S,3R,4'S) --
Line 26, please delete – "(2'R,3R,4'S)" and
Insert -- (2'S,3R,4'S) --
In Claim 30 at Column 401, Line 1, please delete – "(2'R,3R,4'S)" and
Insert -- (2'S,3R,4'S) --
Line 4, please delete – "(2'R,3R,4'S)" and
Insert -- (2'S,3R,4'S) --
In Claim 31 at Column 401, Line 15, please delete – "(2'R,3R,4'S)" and
Insert -- (2'S,3R,4'S) --
In Claim 32 at Column 401, Line 9, please delete – "(2'R,3R,4'S)" and
Insert -- (2'S,3R,4'S) --
In Claim 33 at Column 402, Line 6, please delete – "(2'R,3R,4'S)" and
Insert -- (2'S,3R,4'S) --
Line 9, please delete – "(2'R,3R,4'S)" and
Insert -- (2'S,3R,4'S) --
Line 12, please delete – "(2'R,3R,4'S)" and
Insert -- (2'S,3R,4'S) --
In Claim 34 at Column 402, Line 12, please delete – "(2'R,3R,4'S)" and
Insert -- (2'S,3R,4'S) --

UNITED STATES PATENT AND TRADEMARK OFFICE
CERTIFICATE OF CORRECTION

PATENT NO. : 7,495,007 B2  
APPLICATION NO. : 11/846597  
DATED : February 24, 2009  
INVENTOR(S) : Li Chen et al.

Page 3 of 3

It is certified that error appears in the above-identified patent and that said Letters Patent is hereby corrected as shown below:

Line 15, please delete – "(2'R,3R,4'S)" and  
Insert -- (2'S,3R,4'S) --  
In Claim 39 at Column 405, Line 12, please delete – "(2'R,3R,4'S)" and  
Insert -- (2'S,3R,4'S) --  
Line 15, please delete – "(2'R,3R,4'S)" and  
Insert -- (2'S,3R,4'S) --

In Claim 45 at Column 410, Line 25, first line under first formula, after "protecting group" insert -- Pg --

Signed and Sealed this

Fifteenth Day of December, 2009

David J. Kappos  
*Director of the United States Patent and Trademark Office*